US011661403B2

(12) United States Patent
Konradi et al.

(10) Patent No.: US 11,661,403 B2
(45) Date of Patent: May 30, 2023

(54) OXADIAZOLE COMPOUNDS

(71) Applicant: Vivace Therapeutics, Inc., San Mateo, CA (US)

(72) Inventors: Andrei W. Konradi, Burlingame, CA (US); Tracy Tzu-Ling Tang Lin, Redwood City, CA (US)

(73) Assignee: VIVACE THERAPEUTICS, INC., San Mateo, CA (US)

( * ) Notice: Subject to any disclaimer, the term of this patent is extended or adjusted under 35 U.S.C. 154(b) by 171 days.

(21) Appl. No.: 17/054,756

(22) PCT Filed: May 15, 2019

(86) PCT No.: PCT/US2019/032532
§ 371 (c)(1),
(2) Date: Nov. 11, 2020

(87) PCT Pub. No.: WO2019/222431
PCT Pub. Date: Mar. 21, 2019

(65) Prior Publication Data
US 2021/0238154 A1    Aug. 5, 2021

Related U.S. Application Data

(60) Provisional application No. 62/672,370, filed on May 16, 2018.

(51) Int. Cl.
*C07D 271/113* (2006.01)
*C07D 413/04* (2006.01)
*A61K 47/06* (2006.01)

(52) U.S. Cl.
CPC .......... *C07D 271/113* (2013.01); *A61K 47/06* (2013.01); *C07D 413/04* (2013.01)

(58) Field of Classification Search
CPC .......................... C07D 271/113; C07D 413/04
See application file for complete search history.

(56) References Cited

U.S. PATENT DOCUMENTS

| | | | |
|---|---|---|---|
| 3,895,027 A | 7/1975 | Katner | |
| 3,903,106 A | 9/1975 | Katner et al. | |
| 4,010,273 A | 3/1977 | Bormann et al. | |
| 4,492,710 A | 1/1985 | Merkel et al. | |
| 4,962,119 A | 10/1990 | Boschelli et al. | |
| 5,017,467 A | 5/1991 | Masukawa et al. | |
| 5,066,668 A | 11/1991 | Boschelli et al. | |
| 5,114,958 A | 5/1992 | Boschelli et al. | |
| 5,462,952 A | 10/1995 | Boschelli et al. | |
| 5,670,526 A | 9/1997 | Dodd et al. | |
| 6,211,209 B1 | 4/2001 | Baragi et al. | |
| 6,545,030 B1 | 4/2003 | Barrett et al. | |
| 6,972,287 B1 | 12/2005 | Augelli-Szafran et al. | |
| 7,019,033 B2 | 3/2006 | Barrett et al. | |
| 7,956,191 B2 | 6/2011 | Abel et al. | |
| 8,076,486 B2 | 12/2011 | Goutopoulos et al. | |
| 8,198,457 B2 | 6/2012 | Abel et al. | |
| 8,524,911 B2 | 9/2013 | Abel et al. | |
| 8,841,459 B2 | 9/2014 | Deppe et al. | |
| 9,790,229 B2 | 10/2017 | Bui et al. | |
| 2003/0004193 A1 | 1/2003 | Barrett et al. | |
| 2005/0004186 A1 | 1/2005 | Barrett et al. | |
| 2007/0259051 A1 | 11/2007 | Feinmark et al. | |
| 2009/0048301 A1 | 2/2009 | Chen et al. | |
| 2009/0318438 A1 | 12/2009 | Chen et al. | |
| 2015/0111885 A1 | 4/2015 | Bennett et al. | |
| 2015/0157584 A1 | 6/2015 | Guan et al. | |
| 2016/0289171 A1 | 10/2016 | Balog et al. | |
| 2017/0137428 A1 | 5/2017 | Spangenberg | |
| 2020/0062721 A1 | 2/2020 | Konradi et al. | |
| 2020/0354325 A1 | 11/2020 | Konradi et al. | |

FOREIGN PATENT DOCUMENTS

| | | |
|---|---|---|
| JP | 2015523354 A | 8/2015 |
| JP | 2015531787 A | 11/2015 |
| JP | 2016512542 A | 4/2016 |
| WO | WO-0042029 A1 | 7/2000 |
| WO | WO-0105391 A2 | 1/2001 |
| WO | WO-03045912 A1 | 6/2003 |
| WO | WO-2004056789 A1 | 7/2004 |
| WO | WO-2005004818 A2 | 1/2005 |
| WO | WO-2007123936 A1 | 11/2007 |
| WO | WO-2009086163 A2 | 7/2009 |
| WO | WO-2013188138 A1 | 12/2013 |
| WO | WO-2016161269 A1 | 10/2016 |
| WO | WO-2016161279 A1 | 10/2016 |
| WO | WO-2016161286 A1 | 10/2016 |
| WO | WO-2017053706 A1 | 3/2017 |
| WO | WO-2017058716 A1 | 4/2017 |
| WO | WO-2017064277 A1 | 4/2017 |

(Continued)

OTHER PUBLICATIONS

Manbeck et al. Photoluminescent Copper(I) Complexes with Amido-Triazolato Ligands. Inorganic Chemistry 50(8):3431-3441 (2011).
Ouyang et al. Synthesis and structure-activity relationships of 1,2,4-triazoles as a novel class of potent tubulin polymerization inhibitors. Bioorg Med Chem Lett 15(23):5154-5159 (2005).
Berge et al. Pharmaceutical Salts. Journal of Pharmaceutical Sciences 66(1):1-19 (Jan. 1977).
Bundgaard et al. Design of Prodrugs pp. 7-9, 21-24 (1985).
Fleisher et al. Improved oral drug delivery: solubility limitations overcome by the use of prodrugs. Advanced Drug Delivery Reviews 19:115-130 (1996).
Holmes et al., Discovery and structure-activity relationships of novel sulfonamides as potent PTP1B inhibitors. Bioorganic and Medicinal Chemistry Letters 15:4336-4341 (2005).

(Continued)

*Primary Examiner* — Kamal A Saeed
(74) *Attorney, Agent, or Firm* — Wilson Sonsini Goodrich & Rosati

(57) ABSTRACT

Provided herein are compounds and pharmaceutical compositions comprising said compounds that are useful for treating cancers. Specific cancers include those that are mediated by YAP/TAZ or those that are modulated by the interaction between YAP/TAZ and TEAD.

19 Claims, 2 Drawing Sheets

(56) References Cited

FOREIGN PATENT DOCUMENTS

| WO | WO-2018053446 A1 | 3/2018 |
|---|---|---|
| WO | WO-2018204532 A1 | 11/2018 |
| WO | WO-2019040380 A1 | 2/2019 |
| WO | WO-2019113236 A1 | 6/2019 |
| WO | WO-2019222431 A1 | 11/2019 |
| WO | WO-2021102204 A1 | 5/2021 |

OTHER PUBLICATIONS

PCT/US2019/032532 International Invitation to Pay Additional Fees dated Jul. 11, 2019.
PCT/US2019/032532 International Search Report and Written Opinion dated Aug. 30, 2019.
Pobbati et al. Targeting the Central Pocket in Human Transcription Factor TEAD as a Potential Cancer Therapeutic Strategy. Structure 23:2076-2086 (2015).
Pubchem Compound Summary CID 68170056 deposited Nov. 30, 2012.
PUBCHEM Substance record for SID 274578875, available date: Dec. 18, 2015 (retrieved on Jun. 22, 2018). Retrieved from https://pubchem.ncbi.nlm.nih.gov/substance/274578875.
Science IP Report 2017 (1079 pgs).
Yokokawa et al., Discovery of potent non-nucleoside inhibitors of dengue viral RNA-dependent RNA polymerase from a fragment hit using structure-based drug design. Journal of Medicinal Chemistry 59(8):3935-3952 (2016).
PCT/US2020/061387 International Search Report and Written Opinion dated Mar. 18, 2021.
Pubchem CID 90667486 (created Mar. 11, 2015), Date Accessed Mar. 2, 2021.
Sebio et al. Molecular Pathways: Hippo Signaling, a Critical Tumor Suppressor. Clin Cancer Res 21(22):5002-7 (2015).

OXADIAZOLE COMPOUNDS

CROSS-REFERENCE

This application is a § 371 U.S. National Stage Entry of International Application No. PCT/US2019/032532, filed May 15, 2019, which claims benefit of U.S. Provisional Patent Application No. 62/672,370 filed on May 16, 2018, which are incorporated herein by reference in their entirety.

BACKGROUND OF THE DISCLOSURE

YAP and TAZ are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with transcriptional enhancer associate domain (TEAD) transcription factors and coactivate the expression of target genes and promote cell proliferation. Hyperactivation of YAP and TAZ and/or mutations in one or more members of the Hippo pathway network have been implicated in numerous cancers. Described herein are inhibitors associated with one or more members of the Hippo pathway network, such as inhibitors of YAP/TAZ or inhibitors that modulate the interaction between YAP/TAZ and TEAD.

SUMMARY OF THE DISCLOSURE

Provided herein are substituted oxadiazole compounds and pharmaceutical compositions comprising said compounds. In some embodiments, the subject compounds are useful for the treatment of cancer.

Provided in one aspect is a compound of Formula (I), or a pharmaceutically acceptable salt thereof:

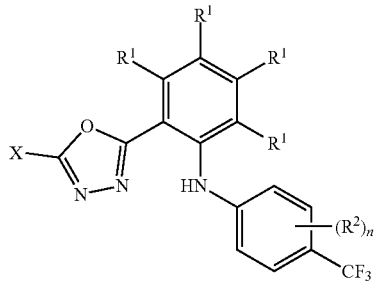

Formula (I)

wherein:
X is H, —CN, halogen, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, -$L^1$-$Y^1$, -$L^2$-$L^3$-$Y^2$-$L^2$-$L^3$-$L^4$-$Y^2$-$L^5$-$L^6$-$L^3$-$Y^2$, or -$L^6$-$L^5$-$L^3$-$Y^2$;

$L^1$ is substituted or unsubstituted $C_1$-$C_6$alkylene;

$Y^1$ is $N_3$, substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;

$L^2$ is absent, substituted or unsubstituted $C_1$-$C_6$alkylene, substituted or unsubstituted $C_3$-$C_{10}$cycloalkylene, or substituted or unsubstituted $C_2$-$C_{10}$heterocycloalkylene;

$L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —O—$NR^3$(C=O)—, —$NR^3$(C=O)—, —$NR^3$(C=O)$NR^3$—, —O(C=O)$NR^3$—, —$NR^3$(C=O)O—, —$NR^3$($SO_2$)$NR^3$—, —$NR^3$($SO_2$)—, —($SO_2$)$NR^3$—, —($SO_2$)$NR^3$—(C=O)—, —(C=O)—$NR^3$($SO_2$)—, —($SO_2$)$NR^3$—(C=O)O—, —O(C=O)—$NR^3$($SO_2$)—, —$NR^3$($SO_2$)—(C=O)—, —(C=O)—$NR^3$($SO_2$)$NR^3$—, —O(C=O)—$NR^3$($SO_2$)—$NR^3$, —$NR^3$($SO_2$)$NR^3$—(C=O)O—, —O—($SO_2$)—, or —($SO_2$)—O—;

each $R^3$ is independently H, —CN, —S(=O)$_2$($C_1$-$C_4$alkyl), or substituted or unsubstituted $C_1$-$C_6$alkyl;

$L^4$ is substituted or unsubstituted $C_1$-$C_6$alkylene;

$L^5$ is substituted or unsubstituted $C_1$-$C_6$alkylene;

$L^6$ is substituted or unsubstituted $C_3$-$C_{10}$cycloalkylene;

$Y^2$ is H, —CN, —$N_3$, halogen, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, —$OR^6$, —(C=O)$OR^6$, —N($R^6$)$_2$, or —(C=O)N($R^6$)$_2$;

or $R^3$ and $Y^2$ on the same N atom are taken together with the N atom to which they are attached to form a substituted or unsubstituted N-containing heterocycle;

each $R^6$ is independently H or substituted or unsubstituted $C_1$-$C_6$alkyl;

or two $R^6$ on the same N atom are taken together with the N atom to which they are attached to form a substituted or unsubstituted N-containing heterocycle;

each $R^1$ is independently H, halogen, —CN, —$OR^4$, —$SR^4$, —N($R^4$)$_2$, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or -$L^7$-$Y^3$;

$L^7$ is substituted or unsubstituted $C_1$-$C_6$alkylene;

$Y^3$ is —Si($R^7$)$_3$;

each $R^7$ is independently substituted or unsubstituted $C_1$-$C_6$alkyl;

n is 0, 1, 2, 3, or 4;

each $R^2$ is independently H, halogen, —$N_3$, —CN, —$OR^5$, —$SR^5$, —($SO_2$)$R^5$, —N(R)$_2$, —$CO_2R^5$, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

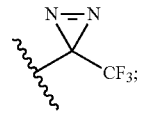 [SMILES: *C1(C(F)(F)F)N=N1]

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

or two $R^4$ on the same N atom are taken together with the N atom to which they are attached to form a substituted or unsubstituted N-containing heterocycle; and each $R^5$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

or two $R^5$ on the same N atom are taken together with the N atom to which they are attached to form a substituted or unsubstituted N-containing heterocycle.

In some embodiments, if X, $L^1$, $L^2$, $L^4$, $L^5$, $L^6$, $L^7$, $Y^1$, $Y^2$, $R^1$, $R^2$, $R^3$, $R^4$, $R^5$, $R^6$, or $R^7$ is substituted, then X, $L^1$, $L^2$, $L^4$, $L^5$, $L^6$, $L^7$, $Y^1$, $Y^2$, $R^1$, $R^2$, $R^3$, $R^4$, $R^5$, $R^6$, or $R^7$ is substituted with 1-5 $R^8$ groups; each $R^8$ is independently selected from halogen, $-N_3$, $-CN$, $-NO_2$, $-OR^9$, $-SR^9$, $-S(=O)R^{10}$, $-S(=O)_2R^{10}$, $-S(=O)_2N(R^9)_2$, $-NR^9S(=O)_2R^{10}$, $-C(=O)R^{10}$, $-OC(=O)R^{10}$, $-CO_2R^9$, $-OCO_2R^{10}$, $-N(R^9)_2$, $-C(=O)N(R^9)_2$, $-OC(=O)N(R^9)_2$, $-NHC(=O)R^{10}$, $-NHC(=O)OR^{10}$, $-(CH_2)r-R^9$, $-(CH_2)r$-halogen, unsubstituted or substituted $C_1$-$C_6$alkyl, unsubstituted or substituted $C_1$-$C_6$fluoroalkyl, unsubstituted or substituted $C_2$-$C_6$alkenyl, unsubstituted or substituted $C_2$-$C_6$alkynyl, unsubstituted or substituted $C_1$-$C_6$heteroalkyl, unsubstituted or substituted $C_3$-$C_{10}$cycloalkyl, unsubstituted or substituted $C_2$-$C_{10}$heterocycloalkyl, unsubstituted or substituted aryl, unsubstituted or substituted aryl, or unsubstituted or substituted heteroaryl; each $R^9$ is independently selected from H, substituted or unsubstituted $C_1$-$C_6$alkyl, unsubstituted or substituted $C_1$-$C_6$fluoroalkyl, unsubstituted or substituted $C_1$-$C_6$heteroalkyl, unsubstituted or substituted $C_3$-$C_{10}$cycloalkyl, unsubstituted or substituted $C_2$-$C_{10}$heterocycloalkyl, unsubstituted or substituted aryl, unsubstituted or substituted aryl, or unsubstituted or substituted heteroaryl; or two $R^9$ on the same N atom are taken together with the N atom to which they are attached to form a N-containing heterocycle; each $R^{10}$ is independently selected from H, substituted or unsubstituted $C_1$-$C_6$alkyl, unsubstituted or substituted $C_1$-$C_6$fluoroalkyl, unsubstituted or substituted $C_1$-$C_6$heteroalkyl, unsubstituted or substituted $C_3$-$C_{10}$cycloalkyl, unsubstituted or substituted $C_2$-$C_{10}$heterocycloalkyl, unsubstituted or substituted aryl, unsubstituted or substituted aryl, or unsubstituted or substituted heteroaryl; and r is 1, 2, 3, or 4.

In some embodiments, X is substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, or substituted or unsubstituted heteroaryl.

In some embodiments, X is substituted or unsubstituted $C_1$-$C_4$alkyl. In some embodiments, X is $-CH_3$, $-CH_2CH_3$, $-CH_2CH_2CH_3$, $-CH(CH_3)_2$, $-CH_2CH_2CH_2CH_3$, $-CH_2CH(CH_3)_2$, or $-C(CH_3)_3$.

In some embodiments, X is substituted or unsubstituted $C_1$-$C_4$haloalkyl. In some embodiments, X is $-CH_2F$, $-CHF_2$, $-CF_3$, or $-CH_2CF_3$.

In some embodiments, X is substituted or unsubstituted $C_3$-$C_6$cycloalkyl. In some embodiments, X is substituted or unsubstituted cyclopropyl, substituted or unsubstituted cyclobutyl, substituted or unsubstituted cyclopentyl, or substituted or unsubstituted cyclohexyl.

In some embodiments, X is substituted or unsubstituted $C_2$-$C_6$heterocycloalkyl. In some embodiments, X is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl.

In some embodiments, X is substituted or unsubstituted heteroaryl. In some embodiments, X is substituted or unsubstituted monocyclic heteroaryl. In some embodiments, X is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, X is -$L^1$-$Y^1$. In some embodiments, $L^1$ is substituted or unsubstituted $C_1$-$C_4$alkylene; and $Y^1$ is substituted or unsubstituted $C_3$-$C_6$cycloalkyl. In some embodiments, $Y^1$ is substituted or unsubstituted cyclopropyl, substituted or unsubstituted cyclobutyl, substituted or unsubstituted cyclopentyl, or substituted or unsubstituted cyclohexyl. In some embodiments, $L^1$ is substituted or unsubstituted $C_1$-$C_4$alkylene; and $Y^1$ is substituted or unsubstituted $C_2$-$C_6$ heterocycloalkyl. In some embodiments, $Y^1$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl. In some embodiments, $L^1$ is substituted or unsubstituted $C_1$-$C_4$alkylene; and $Y^1$ is substituted or unsubstituted phenyl. In some embodiments, $L^1$ is substituted or unsubstituted $C_1$-$C_4$alkylene; and $Y^1$ is substituted or unsubstituted heteroaryl. In some embodiments, $Y^1$ is substituted or unsubstituted monocyclic heteroaryl. In some embodiments, $Y^1$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, X is -$L^2$-$L^3$-$Y^2$. In some embodiments, $L^2$ is substituted or unsubstituted $C_1$-$C_4$alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, —NR$^3$(SO$_2$)NR$^3$—(C=O)O—, or —O—(SO$_2$)—; $Y^2$ is independently H, —CN, —N$_3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, —OR$^6$, —(C=O)OR$^6$, —N(R$^6$)$_2$, or —(C=O)N(R$^6$)$_2$. In some embodiments, $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —NR$^3$(C=O)O—, —NR$^3$(SO$_2$)—, —(SO$_2$)NR$^3$—, or —O—(SO$_2$)—; $Y^2$ is independently H, —CN, —N$_3$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, substituted or unsubstituted monocyclic heteroaryl, —OR$^6$, —(C=O)OR$^6$, —N(R$^6$)$_2$, or —(C=O)N(R$^6$)$_2$; and each R$^6$ is independently H or substituted or unsubstituted $C_1$-$C_4$alkyl.

In some embodiments, $L^2$ is absent; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, —NR$^3$(SO$_2$)NR$^3$—(C=O)O—, or —O—(SO$_2$)—; $Y^2$ is independently H, —CN, —N$_3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, —OR$^6$, —(C=O)OR$^6$, —N(R$^6$)$_2$, or —(C=O)N(R$^6$)$_2$. In some embodiments, $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —NR$^3$(C=O)O—, —NR$^3$(SO$_2$)—, —(SO$_2$)NR$^3$—, or —O—(SO$_2$)—; $Y^2$ is independently H, —CN, —N$_3$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, substituted or unsubstituted monocyclic heteroaryl, —OR$^6$, —(C=O)OR$^6$, —N(R$^6$)$_2$, or —(C=O)N(R$^6$)$_2$; and each R$^6$ is independently H or substituted or unsubstituted $C_1$-$C_4$alkyl.

In some embodiments is

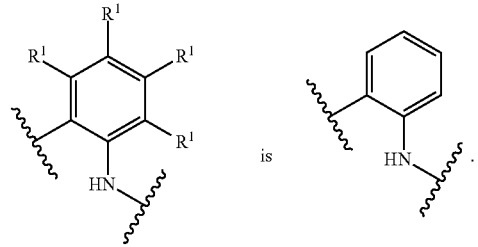

In some embodiments is

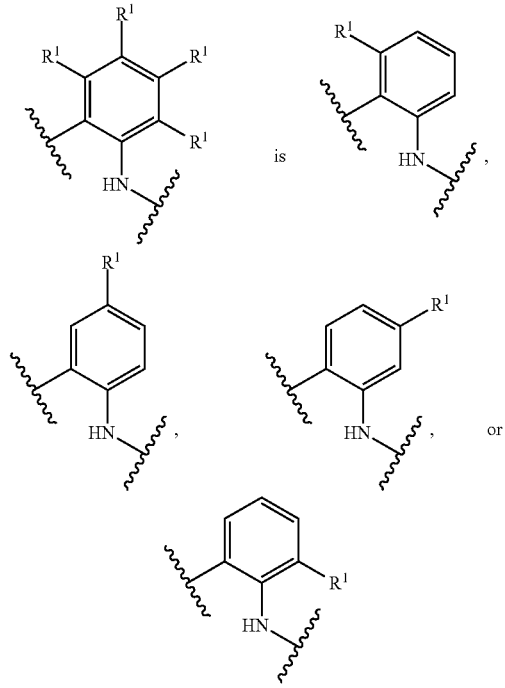

and $R^1$ is halogen, —CN, —OR$^4$, —SR$^4$, —N(R$^4$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, $R^1$ is halogen, —CN, —OR$^4$, —SR$^4$, —N(R$^4$)$_2$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, or substituted or unsubstituted monocyclic heteroaryl. In some embodiments, $R^1$ is halogen, substituted or unsubstituted $C_1$-$C_4$alkyl, or substituted or unsubstituted $C_1$-$C_4$haloalkyl. In some embodiments, $R^1$ is F, Cl, Br, I, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$F, —CHF$_2$, —CF$_3$, or —CH$_2$CF$_3$.

In some embodiments, is

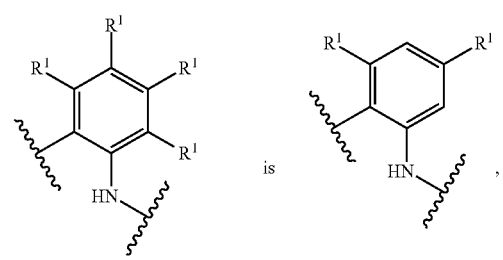

-continued

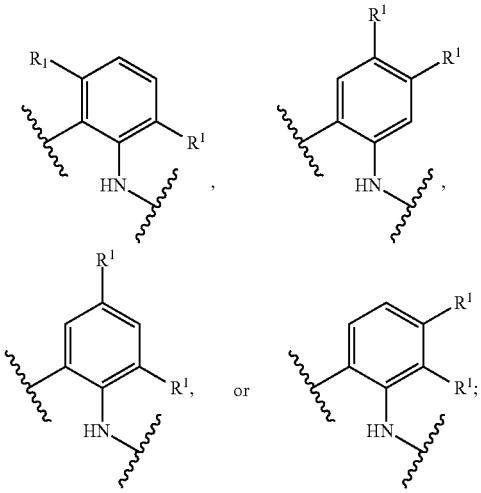

and each $R^1$ is independently halogen, —CN, —OR$^4$, —SR$^4$, —N(R$^4$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, each $R^1$ is independently halogen, —CN, —OR$^4$, —SR$^4$, —N(R$^4$)$_2$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, or substituted or unsubstituted monocyclic heteroaryl. In some embodiments, each $R^1$ is independently halogen, substituted or unsubstituted $C_1$-$C_4$alkyl, or substituted or unsubstituted $C_1$-$C_4$haloalkyl. In some embodiments, each $R^1$ is independently F, Cl, Br, I, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$F, —CHF$_2$, —CF$_3$, or —CH$_2$CF$_3$.

In some embodiments,

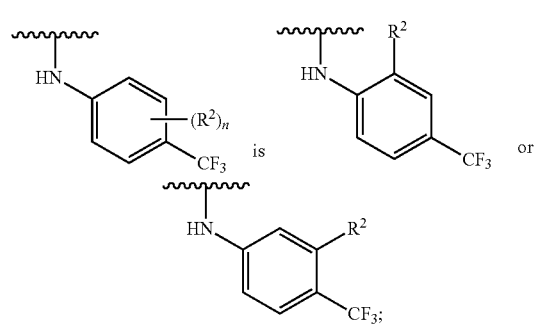

and $R^2$ is halogen, —N$_3$, —CN, —OR$^5$, —SR$^5$, —(SO$_2$)R$^5$, —N(R$^5$)$_2$, —CO$_2$R$^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted aralkyl, substituted or unsubstituted aryl, substituted or unsubstituted heteroaryl, or

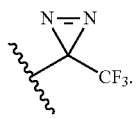 [SMILES: *C1(C(F)(F)F)N=N1]

In some embodiments, R² is halogen, —N₃, —CN, —OR⁵, —SR⁵, —(SO₂)R⁵, —N(R)₂, —CO₂R⁵, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted benzyl, substituted or unsubstituted phenyl, substituted or unsubstituted monocyclic heteroaryl, or

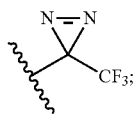 [SMILES: *C1(C(F)(F)F)N=N1]

and each R⁵ is independently H, or substituted or unsubstituted $C_1$-$C_4$alkyl. In some embodiments, R² is halogen, —N₃, —OR⁵, —(SO₂)R⁵, —CO₂R⁵, substituted or unsubstituted $C_1$-$C_4$alkyl, substituted or unsubstituted $C_1$-$C_4$haloalkyl, or

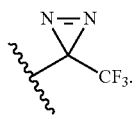

In some embodiments, wherein:

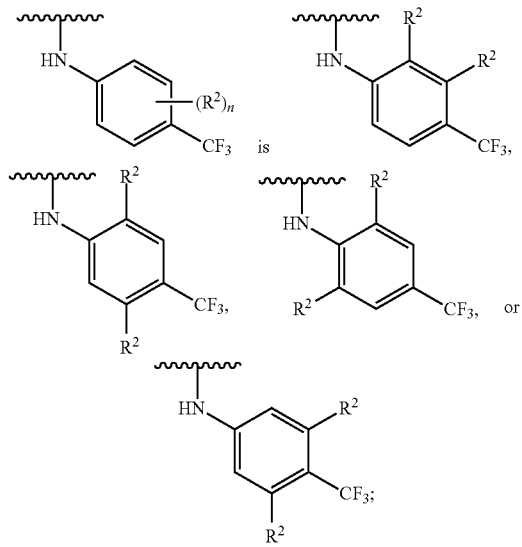 is and each R² is independently halogen, —N₃, —CN, —OR⁵, —SR⁵, —(SO₂)R⁵, —N(R⁵)₂, —CO₂R⁵, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted aralkyl, substituted or unsubstituted aryl, substituted or unsubstituted heteroaryl, or

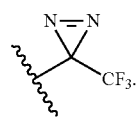 [SMILES: *C1(C(F)(F)F)N=N1]

In some embodiments, each R² is independently halogen, —N₃, —CN, —OR⁵, —SR⁵, —(SO₂)R⁵, —N(R⁵)₂, —CO₂R⁵, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted benzyl, substituted or unsubstituted phenyl, substituted or unsubstituted monocyclic heteroaryl, or

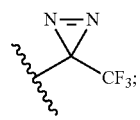

and each R⁵ is independently H, or substituted or unsubstituted $C_1$-$C_4$alkyl. In some embodiments, each R² is independently halogen, —N₃, —OR⁵, —(SO₂)R⁵, —CO₂R⁵, substituted or unsubstituted $C_1$-$C_4$alkyl, substituted or unsubstituted $C_1$-$C_4$haloalkyl, or

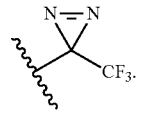

In some embodiments, the compound has the structure of Formula (Ia), or a pharmaceutically acceptable salt thereof:

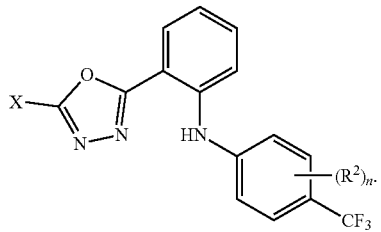

Formula (Ia)

In some embodiments, the compound has the structure of Formula (Ib), or a pharmaceutically acceptable salt thereof:

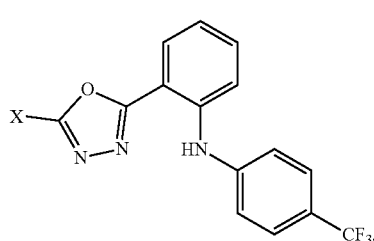

Formula (Ib)

In some embodiments, the compound exhibits an $IC_{50}$ of no more than about 5.000 μM.

Provided in another aspect is a compound, or pharmaceutically acceptable salt thereof, wherein the compound is a compound from Table 1, or a pharmaceutically acceptable salt thereof.

Provided in another aspect is a pharmaceutical composition comprising a pharmaceutically acceptable excipient and any one of the compounds disclosed herein or a pharmaceutically acceptable salt thereof.

Provided herein is a method for treating a cancer in a subject in need thereof comprising administering a therapeutically effective amount of a compound of any one of the compounds disclosed herein or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Certain Terminology

Figure 1:
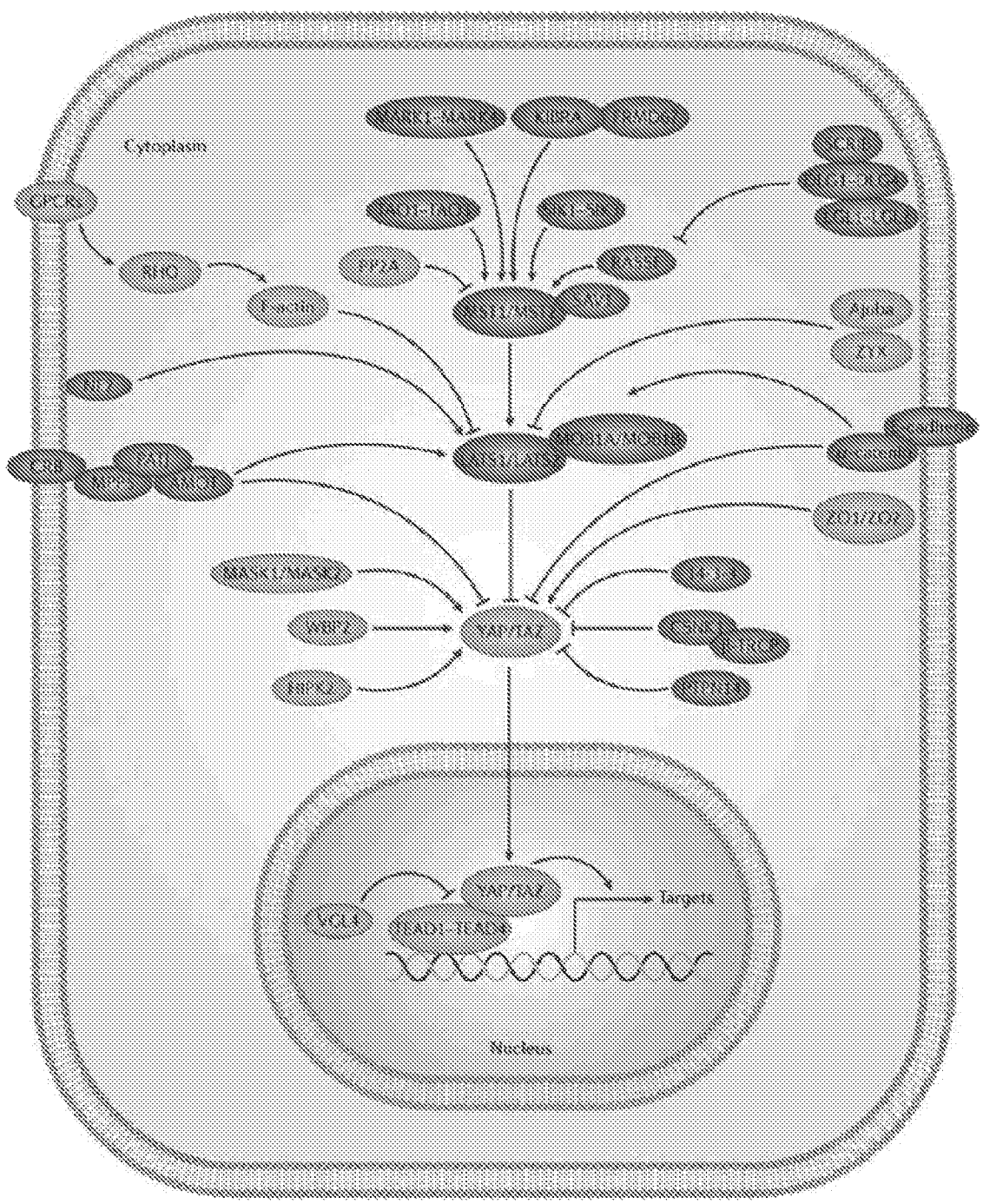
FIG. 1 illustrates a schematic representation of the Hippo signaling network. Hippo pathway components shaded in dark gray indicate components that inhibit YAP/TAZ activity. Hippo pathway components shaded in light gray indicate components that promote YAP/TAZ activity. Pointed and blunt arrowheads indicate activating and inhibitory interactions, respectively. Abbreviations: α-CAT (α-Catenin), AJUB (Ajuba), AMOT (Angiomotin), β-TRCP (β-transducing repeat containing protein), CK1 (Casein Kinase 1), CRB (Crumbs), E-CAD (E-cadherin), EX (Expanded), GPCR (G-protein coupled receptor), HIPK (Homeodomain interacting protein kinase), KIBRA (Kidney brain), LATS (Large tumor suppressor), LGL (Lethal giant larvae), MASK (Multiple ankyrin single KH), MER (Merlin), MOB (Mps one binder), MST (Mammalian sterile 20 like), PALS (Protein Associated with Lin-7), PATJ (Pals-associated tight junction protein), PP2A (Protein phosphatase 2A), PTPN14 (Protein tyrosine phosphatase non-receptor type 14), RASSF (Ras associated factor), SAV (Salvador), SCRIB (Scribble), SIK (Salt inducible kinase), TAO (Thousand and one amino acid protein), TAZ (transcriptional coactivator with PDZ-binding motif), TEAD (TEA domain protein), VGL4 (Vestigial-like 4), WBP2 (WW domain binding protein 2), YAP (Yes associated protein), ZO (Zonula occludens), ZYX (Zyxin).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, in some embodiments, ranges and amounts are expressed as "about" a particular value or range. About also includes the exact amount. Hence "about 5 μL" means "about 5 μL" and also "5 μL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly, or a hospice worker).

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$), —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl. In some embodiments, an alkyl chain is optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)— NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)— NR$^a$R$^f$, —N(R$^a$)C(O)R$^f$, —N(R$^a$)S(O)$_t$R$^f$, (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$), —N(R$^a$)C(O)OR$^f$, —OC(O)— NR$^a$R$^f$, —N(R$^a$)C(O)R, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl. In some embodiments, an alkylene chain is optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R_b$—S(O)$_t OR^a$ (where t is 1 or 2), —$R^b$—S(O)$_t R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$), —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —R-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, and in some embodiments, include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. In some embodiments, the carbocyclyl is saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

The term "cycloalkylene" refers to a divalent cycloalkyl group and is optionally substituted as indicated for the term "cycloalkyl" or "carbocyclyl".

"Carbocyclylalkyl" refers to a radical of the formula —$R^c$-carbocyclyl where $R^o$ is an alkylene chain as defined above. The alkylene chain and the carbocyclyl radical is optionally substituted as defined above.

"Halo" or "halogen" refers to bromo, chloro, fluoro or iodo substituents.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro-, or trifluoro-methyl, -ethyl or -propyl, for example 3,3,3-trifluoropropyl, 2,2-difluoropropyl, 2-fluoroethyl, 2,2,2-trifluoroethyl, fluoromethyl, or trifluoromethyl. Other examples of haloalkyl include, but not limited to, chloromethyl, trichloromethyl, 2-chloroethyl, bromomethyl, and 2-bromoethyl. The term "perhaloalkyl" denotes an alkyl group where all hydrogen atoms of the alkyl group have been replaced by the same or different halogen atoms. In some embodiments, the alkyl part of the haloalkyl radical is optionally substituted as defined above for an alkyl group.

"Heterocyclyl" or "heterocycle" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocyclyl radical is a monocyclic, bicyclic, tricyclic, or tetracyclic ring system, which include fused or bridged ring systems in some embodiments. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). In some embodiments, the heterocyclyl is saturated, (i.e., containing single bonds only) or unsaturated (i.e., containing one or more double bonds or triple bonds.) A fully saturated heterocyclyl radical is also referred to as "heterocycloalkyl." Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—CN, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^o$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^o$ is a straight or branched alkylene or alkenylene chain, and where each of the above substituents is unsubstituted unless otherwise indicated.

"Heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl. In some embodiments, the alkyl part of the heteroalkyl radical is optionally substituted as defined for an alkyl group.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is dioxolanyl, oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In one aspect, a heterocycloalkyl is a $C_2$-$C_6$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "heterocycloalkylene" refers to a divalent heterocycloalkyl group and is optionally substituted as indicated for the term "heterocycloalkyl".

"Heterocyclylalkyl" refers to a radical of the formula —$R^c$-heterocyclyl where $R^o$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^o$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, in some embodiments, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2), and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

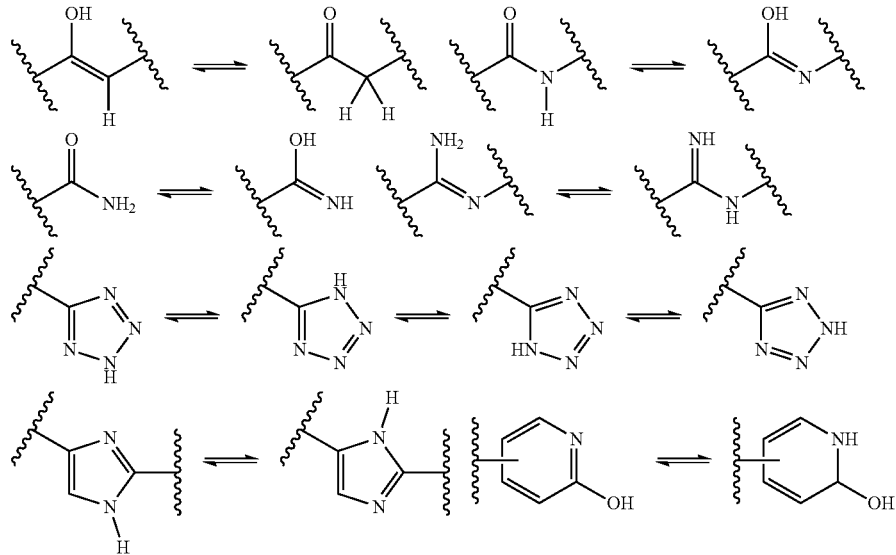

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The term "optionally substituted" or "substituted" means that the referenced group is optionally substituted with one or more additional group(s). In some other embodiments, optional substituents are individually and independently selected from D, halogen, —CN, —NH$_2$, —NH(alkyl), —N(alkyl)$_2$, —OH, —C(=O)OH, —C(=O)Oalkyl, —OC(=O)alkyl, —C(=O)NH$_2$, —C(=O)NH(alkyl), —NHC(=O)alkyl, —N(alkyl)C(=O)alkyl, —C(=O)N(alkyl)$_2$, —S(=O)$_2$NH$_2$, —S(=O)$_2$NH(alkyl), —S(=O)$_2$N(alkyl)$_2$, —CH$_2$CO$_2$H, —CH$_2$CO$_2$alkyl, —CH$_2$C(=O)NH$_2$, —CH$_2$C(=O)NH(alkyl), —CH$_2$C(=O)N(alkyl)$_2$, —CH$_2$S(=O)$_2$NH$_2$, —CH$_2$S(=O)$_2$NH(alkyl), —CH$_2$S(=O)$_2$N(alkyl)$_2$, alkyl, alkenyl, alkynyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups. In some embodiments, an optional substituent on an aliphatic carbon atom (acyclic or cyclic) includes oxo (=O). In some embodiments, an optional substituent on a sulfur atom includes one or two oxo (=O) groups.

"Pharmaceutically acceptable salt" includes both acid and base addition salts. A pharmaceutically acceptable salt of any one of the compounds described herein is intended to encompass any and all pharmaceutically suitable salt forms. Pharmaceutically acceptable salts of the compounds described herein are optionally pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). In some embodiments, acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate, and benzoate derivatives of alcohol or amine functional groups in the active compounds and the like.

Compounds

In some embodiments, the compounds disclosed herein are oxadiazole compounds.

Provided in one aspect is a compound of Formula (I), or a pharmaceutically acceptable salt thereof:

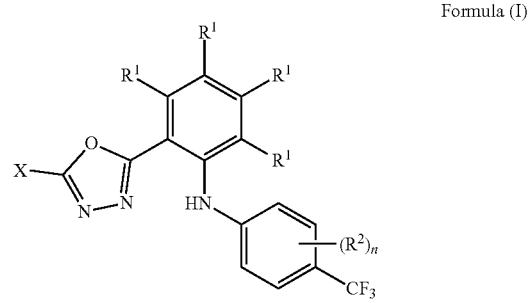

Formula (I)

wherein:
X is H, —CN, halogen, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, -$L^1$-$Y^1$, -$L^2$-$L^3$-$Y^2$-$L^2$-$L^3$-$L^4$-$Y^2$-$L^5$-$L^6$-$L^3$-$Y^2$, or -$L^6$-$L^5$-$L^3$-$Y^2$;
$L^1$ is substituted or unsubstituted $C_1$-$C_6$alkylene;
$Y^1$ is —$N_3$, substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;
$L^2$ is absent, substituted or unsubstituted $C_1$-$C_6$alkylene, substituted or unsubstituted $C_3$-$C_{10}$cycloalkylene, or substituted or unsubstituted $C_2$-$C_{10}$heterocycloalkylene;
$L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—

(C=O)—, —(C=O)—NR$^3$(SO$_2$)NR$^3$—, —O(C=O)—NR$^3$(SO$_2$)—NR$^3$, —NR$^3$(SO$_2$)NR$^3$—(C=O)O—, —O—(SO$_2$)—, or —(SO$_2$)—O—;

each R$^3$ is independently H, —CN, —S(=O)$_2$(C$_1$-C$_4$alkyl), or substituted or unsubstituted C$_1$-C$_6$alkyl;

L$^4$ is substituted or unsubstituted C$_1$-C$_6$alkylene;

L$^5$ is substituted or unsubstituted C$_1$-C$_6$alkylene;

L$^6$ is substituted or unsubstituted C$_3$-C$_{10}$cycloalkylene;

Y$^2$ is H, —CN, —N$_3$, halogen, substituted or unsubstituted C$_1$-C$_6$alkyl, substituted or unsubstituted C$_1$-C$_6$haloalkyl, substituted or unsubstituted C$_2$-C$_6$alkenyl, substituted or unsubstituted C$_2$-C$_6$alkynyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, substituted or unsubstituted heteroaryl, —OR$^6$, —(C=O)OR$^6$, —N(R$^6$)$_2$, or —(C=O)N(R$^6$)$_2$;

or R$^3$ and Y$^2$ on the same N atom are taken together with the N atom to which they are attached to form a substituted or unsubstituted N-containing heterocycle;

each R$^6$ is independently H or substituted or unsubstituted C$_1$-C$_6$alkyl;

or two R$^6$ on the same N atom are taken together with the N atom to which they are attached to form a substituted or unsubstituted N-containing heterocycle;

each R$^1$ is independently H, halogen, —CN, —OR$^4$, —SR$^4$, —N(R$^4$)$_2$, substituted or unsubstituted C$_1$-C$_6$alkyl, substituted or unsubstituted C$_1$-C$_6$haloalkyl, substituted or unsubstituted C$_2$-C$_6$alkenyl, substituted or unsubstituted C$_2$-C$_6$alkynyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, substituted or unsubstituted heteroaryl, or -L$^1$-Y$^3$;

L$^7$ is substituted or unsubstituted C$_1$-C$_6$alkylene;

Y$^3$ is —Si(R$^7$)$_2$;

each R$^7$ is independently substituted or unsubstituted C$_1$-C$_6$alkyl;

n is 0, 1, 2, 3, or 4;

each R$^2$ is independently H, halogen, —N$_3$, —CN, —OR$^5$, —SR$^5$, —(SO$_2$)R$^5$, —N(R$^5$)$^2$, —CO$_2$R$^5$, substituted or unsubstituted C$_1$-C$_6$alkyl, substituted or unsubstituted C$_1$-C$_6$haloalkyl, substituted or unsubstituted C$_2$-C$_6$alkenyl, substituted or unsubstituted C$_2$-C$_6$alkynyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, substituted or unsubstituted heteroaryl, or

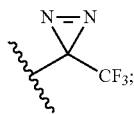 [SMILES: *C1(C(F)(F)F)N=N1]

each R$^4$ is independently H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;

or two R$^4$ on the same N atom are taken together with the N atom to which they are attached to form a substituted or unsubstituted N-containing heterocycle; and each R$^5$ is independently H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;

or two R$^5$ on the same N atom are taken together with the N atom to which they are attached to form a substituted or unsubstituted N-containing heterocycle.

In some embodiments, if X, L$^1$, L$^2$, L$^4$, L$^5$, L$^6$, L$^7$, Y$^1$, Y$^2$, R$^1$, R$^2$, R$^3$, R$^4$, R$^5$, R$^6$, or R$^7$ is substituted, then X, L$^1$L$^2$, L$^4$, L$^5$, L$^6$, L$^7$, Y$^1$, Y$^2$, R$^1$, R$^2$, R$^3$, R$^4$, R$^5$, R$^6$, or R$^7$ is substituted with 1-5 R$^8$ groups; each R$^8$ is independently selected from halogen, —N$_3$, —CN, —NO$_2$, —OR$^9$, —SR$^9$, —S(=O)R$^{10}$, —S(=O)$_2$R$^{10}$, —S(=O)$_2$N(R$^9$)$_2$, —NR$^9$S(=O)$_2$R$^{10}$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NHC(=O)R$^{10}$, —NHC(=O)OR$^{10}$, —(CH$_2$)r-R$^9$, —(CH$_2$)r-halogen, unsubstituted or substituted C$_1$-C$_6$alkyl, unsubstituted or substituted C$_1$-C$_6$fluoroalkyl, unsubstituted or substituted C$_2$-C$_6$alkenyl, unsubstituted or substituted C$_2$-C$_6$alkynyl, unsubstituted or substituted C$_1$-C$_6$heteroalkyl, unsubstituted or substituted C$_3$-C$_{10}$cycloalkyl, unsubstituted or substituted C$_2$-C$_{10}$heterocycloalkyl, unsubstituted or substituted aryl, unsubstituted or substituted aryl, or unsubstituted or substituted heteroaryl; each R$^9$ is independently selected from H, substituted or unsubstituted C$_1$-C$_6$alkyl, unsubstituted or substituted C$_1$-C$_6$fluoroalkyl, unsubstituted or substituted C$_1$-C$_6$heteroalkyl, unsubstituted or substituted C$_3$-C$_{10}$cycloalkyl, unsubstituted or substituted C$_2$-C$_{10}$heterocycloalkyl, unsubstituted or substituted aryl, or unsubstituted or substituted heteroaryl; or two R$^9$ on the same N atom are taken together with the N atom to which they are attached to form a N-containing heterocycle; each R$^{10}$ is independently selected from H, substituted or unsubstituted C$_1$-C$_6$alkyl, unsubstituted or substituted C$_1$-C$_6$fluoroalkyl, unsubstituted or substituted C$_1$-C$_6$heteroalkyl, unsubstituted or substituted C$_3$-C$_{10}$cycloalkyl, unsubstituted or substituted C$_2$-C$_{10}$heterocycloalkyl, unsubstituted or substituted aryl, or unsubstituted or substituted heteroaryl; and r is 1, 2, 3, or 4.

In some embodiments, X is H. In some embodiments, X is —CN. In some embodiments, X is halogen. In some embodiments, X is substituted or unsubstituted C$_1$-C$_6$alkyl. In some embodiments, X is substituted or unsubstituted C$_1$-C$_6$haloalkyl. In some embodiments, X is substituted or unsubstituted C$_2$-C$_6$alkenyl. In some embodiments, X is substituted or unsubstituted C$_2$-C$_6$alkynyl. In some embodiments, X is substituted or unsubstituted C$_3$-C$_{10}$cycloalkyl. In some embodiments, X is substituted or unsubstituted C$_2$-C$_{10}$heterocycloalkyl. In some embodiments, X is substituted or unsubstituted aryl. In some embodiments, X is substituted or unsubstituted heteroaryl. In some embodiments, X is -L$^1$-Y$^1$. In some embodiments, X is -L$^2$-L$^3$-Y$^2$. In some embodiments, X is -L$^2$-L$^3$-L$^4$-Y$^2$. In some embodiments, X is -L$^5$-L$^6$-L$^3$-Y$^2$. In some embodiments, X is -L$^6$-L$^5$-L$^3$-Y$^2$.

In some embodiments, X is substituted or unsubstituted C$_1$-C$_6$alkyl, substituted or unsubstituted C$_1$-C$_6$haloalkyl, substituted or unsubstituted C$_2$-C$_6$alkenyl, substituted or unsubstituted C$_2$-C$_6$alkynyl, substituted or unsubstituted $C_3$-$C_{10}$cycloalkyl, substituted or unsubstituted $C_2$-$C_1$heterocycloalkyl, substituted or unsubstituted aryl, or substituted or unsubstituted heteroaryl.

In some embodiments, X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_1$heterocycloalkyl, substituted or unsubstituted aryl, or substituted or unsubstituted heteroaryl.

In some embodiments, X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, or substituted or unsubstituted heteroaryl.

In some embodiments, X is substituted or unsubstituted $C_1$-$C_4$alkyl. In some embodiments, X is —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$.

In some embodiments, X is substituted or unsubstituted $C_1$-$C_4$haloalkyl. In some embodiments, X is —$CH_2F$, —$CHF_2$, —$CF_3$, or —$CH_2CF_3$.

In some embodiments, X is substituted or unsubstituted $C_3$-$C_6$cycloalkyl. In some embodiments, X is substituted or unsubstituted cyclopropyl, substituted or unsubstituted cyclobutyl, substituted or unsubstituted cyclopentyl, or substituted or unsubstituted cyclohexyl.

In some embodiments, X is substituted or unsubstituted $C_2$-$C_6$heterocycloalkyl. In some embodiments, X is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl.

In some embodiments, X is substituted or unsubstituted heteroaryl. In some embodiments, X is substituted or unsubstituted monocyclic heteroaryl. In some embodiments, X is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, X is -$L^1$-$Y^1$. In some embodiments, $L^1$ is substituted or unsubstituted $C_1$-$C_4$alkylene. In some embodiments, $L^1$ is —$CH_2$—, —$CH_2CH_2$—, —$CH_2CH_2CH_2$—, or —$CH_2CH_2CH_2CH_2$—. In some embodiments, Y is substituted or unsubstituted $C_3$-$C_{10}$cycloalkyl. In some embodiments, $Y^1$ is substituted or unsubstituted $C_3$-$C_6$cycloalkyl. In some embodiments, $Y^1$ is substituted or unsubstituted $C_2$-$C_{10}$ heterocycloalkyl. In some embodiments, $Y^1$ is substituted or unsubstituted $C_2$-$C_6$ heterocycloalkyl. In some embodiments, $Y^1$ is substituted or unsubstituted aryl. In some embodiments, $Y^1$ is or substituted or unsubstituted heteroaryl. In some embodiments, $L^1$ is substituted or unsubstituted $C_1$-$C_4$alkylene; and $Y^1$ is substituted or unsubstituted $C_3$-$C_6$cycloalkyl. In some embodiments, $Y^1$ is substituted or unsubstituted cyclopropyl, substituted or unsubstituted cyclobutyl, substituted or unsubstituted cyclopentyl, or substituted or unsubstituted cyclohexyl. In some embodiments, $L^1$ is substituted or unsubstituted $C_1$-$C_4$alkylene; and $Y^1$ is substituted or unsubstituted $C_2$-$C_6$ heterocycloalkyl. In some embodiments, $Y^1$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl. In some embodiments, $L^1$ is substituted or unsubstituted $C_1$-$C_4$alkylene; and $Y^1$ is substituted or unsubstituted phenyl. In some embodiments, $L^1$ is substituted or unsubstituted $C_1$-$C_4$alkylene; and $Y^1$ is substituted or unsubstituted heteroaryl. In some embodiments, $Y^1$ is substituted or unsubstituted monocyclic heteroaryl. In some embodiments, $Y^1$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, $L^2$ is absent. In some embodiments, $L^2$ is substituted or unsubstituted $C_1$-$C_6$alkylene. In some embodiments, $L^2$ is substituted or unsubstituted $C_1$-$C_4$alkylene. In some embodiments, $L^2$ is —$CH_2$—, —$CH_2CH_2$—, —$CH_2CH_2CH_2$—, or —$CH_2CH_2CH_2CH_2$—. In some embodiments, $L^2$ is substituted or unsubstituted $C_3$-$C_{10}$cycloalkylene. In some embodiments, $L^2$ is substituted or unsubstituted $C_3$-$C_6$cycloalkylene. In some embodiments, $L^2$ is substituted or unsubstituted cyclopropylene, substituted or unsubstituted cyclobutylene, substituted or unsubstituted cyclopentylene, or substituted or unsubstituted cyclohexylene. In some embodiments, $L^2$ is substituted or unsubstituted $C_2$-$C_{10}$heterocycloalkylene. In some embodiments, $L^2$ is substituted or unsubstituted $C_2$-$C_6$heterocycloalkylene. In some embodiments, $L^2$ is substituted or unsubstituted aziridinylene, substituted or unsubstituted azetidinylene, substituted or unsubstituted pyrrolidinylene, substituted or unsubstituted piperidinylene, substituted or unsubstituted oxetanylene, substituted or unsubstituted tetrahydrofuranylene, or substituted or unsubstituted tetrahydropyranylene. In some embodiments, $L^3$ is —O—. In some embodiments, $L^3$ is —S—. In some embodiments, $L^3$ is —(S=O)—. In some embodiments, $L^3$ is —(SO$_2$)—. In some embodiments, $L^3$ is —$NR^3$—. In some embodiments, $L^3$ is —(C=O)—. In some embodiments, $L^3$ is —(C=O)

O—. In some embodiments, $L^3$ is —O(C=O)—. In some embodiments, $L^3$ is —(C=O)NR$^3$—. In some embodiments, $L^3$ is —(C=O)NR$^3$—O—. In some embodiments, $L^3$ is-O—NR$^3$(C=O)—. In some embodiments, $L^3$ is —NR$^3$(C=O)—. In some embodiments, $L^3$ is —NR$^3$(C=O)NR$^3$—. In some embodiments, $L^3$ is —O(C=O)NR$^3$—. In some embodiments, $L^3$ is —NR$^3$(C=O)O—. In some embodiments, $L^3$ is —NR$^3$(SO$_2$)NR$^3$—. In some embodiments, $L^3$ is —NR$^3$(SO$_2$)—. In some embodiments, $L^3$ is —(SO$_2$)NR$^3$—. In some embodiments, $L^3$ is —(SO$_2$)NR$^3$—(C=O)—. In some embodiments, $L^3$ is —(C=O)—NR$^3$(SO$_2$)—. In some embodiments, $L^3$ is —(SO$_2$)NR$^3$—(C=O)O—. In some embodiments, $L^3$ is —O(C=O)—NR$^3$(SO$_2$)—. In some embodiments, $L^3$ is —NR$^3$(SO$_2$)NR$^3$—(C=O)—. In some embodiments, $L^3$ is —(C=O)—NR$^3$(SO$_2$)NR$^3$—. In some embodiments, $L^3$ is —O(C=O)—NR$^3$(SO$_2$)—NR$^3$—. In some embodiments, $L^3$ is —NR$^3$(SO$_2$)NR$^3$—(C=O)O—. In some embodiments, $L^3$ is —O—(SO$_2$)—. In some embodiments, $L^3$ is —(SO$_2$)—O—. In some embodiments, $R^3$ is H. In some embodiments, $R^3$ is substituted or unsubstituted $C_1$-$C_6$alkylene. In some embodiments, $R^3$ is substituted or unsubstituted $C_1$-$C_4$alkylene. In some embodiments, $R^3$ is —CH$_2$—, —CH$_2$CH$_2$—, —CH$_2$CH$_2$CH$_2$—, or —CH$_2$CH$_2$CH$_2$CH$_2$—. In some embodiments, $L^4$ is substituted or unsubstituted $C_1$-$C_6$alkylene. In some embodiments, $L^4$ is substituted or unsubstituted $C_1$-$C_4$alkylene. In some embodiments, $L^4$ is —CH$_2$—, —CH$_2$CH$_2$—, —CH$_2$CH$_2$CH$_2$—, or —CH$_2$CH$_2$CH$_2$CH$_2$—.

In some embodiments, $Y^2$ is H. In some embodiments, $Y^2$ is —CN. In some embodiments, $Y^2$ is —N$_3$. In some embodiments, $Y^2$ is halogen. In some embodiments, $Y^2$ is substituted or unsubstituted $C_1$-$C_6$alkyl. In some embodiments, $Y^2$ is substituted or unsubstituted $C_1$-$C_4$alkyl. In some embodiments, $Y^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —C(CH$_3$)$_3$. In some embodiments, $Y^2$ is substituted or unsubstituted $C_1$-$C_6$haloalkyl. In some embodiments, $Y^2$ is substituted or unsubstituted $C_1$-$C_4$haloalkyl. In some embodiments, $Y^2$ is —CH$_2$F, —CHF$_2$, —CF$_3$, or —CH$_2$CF$_3$. In some embodiments, $Y^2$ is substituted or unsubstituted $C_2$-$C_6$alkenyl. In some embodiments, $Y^2$ is substituted or unsubstituted $C_2$-$C_4$alkenyl. In some embodiments, $Y^2$ is substituted or unsubstituted $C_2$-$C_6$alkynyl. In some embodiments, $Y^2$ is substituted or unsubstituted $C_2$-$C_4$alkynyl. In some embodiments, $Y^2$ is substituted or unsubstituted $C_1$-$C_6$heteroalkyl. In some embodiments, $Y^2$ is substituted or unsubstituted $C_1$-$C_4$heteroalkyl. In some embodiments, $Y^2$ is substituted or unsubstituted $C_3$-$C_{10}$cycloalkyl. In some embodiments, $Y^2$ is substituted or unsubstituted $C_3$-$C_6$cycloalkyl. In some embodiments, $Y^2$ is substituted or unsubstituted cyclopropyl, substituted or unsubstituted cyclobutyl, substituted or unsubstituted cyclopentyl, or substituted or unsubstituted cyclohexyl. In some embodiments, $Y^2$ is substituted or unsubstituted $C_2$-$C_{10}$heterocycloalkyl. In some embodiments, $Y^2$ is substituted or unsubstituted $C_2$-$C_6$heterocycloalkyl. In some embodiments, $Y^2$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl. In some embodiments, $Y^2$ is substituted or unsubstituted aralkyl. In some embodiments, $Y^2$ is substituted or unsubstituted benzyl. In some embodiments, $Y^2$ is substituted or unsubstituted aryl. In some embodiments, $Y^2$ is substituted or unsubstituted phenyl. In some embodiments, $Y^2$ is substituted or unsubstituted heteroaryl. In some embodiments, $Y^2$ is substituted or unsubstituted monocyclic heteroaryl. In some embodiments, $Y^2$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, $Y^2$ is —OR$^6$. In some embodiments, $Y^2$ is —(C=O)OR$^6$. In some embodiments, $Y^2$ is —N(R$^6$)$_2$. In some embodiments, $Y^2$ is —(C=O)N(R$^6$)$_2$. In some embodiments, $R^3$ and $Y^2$ on the same N atom are taken together with the N atom to which they are attached to form a substituted or unsubstituted N-containing heterocycle.

In some embodiments, each $R^6$ is independently H. In some embodiments, each $R^6$ is independently substituted or unsubstituted $C_1$-$C_6$alkyl. In some embodiments, each $R^6$ is independently is substituted or unsubstituted $C_1$-$C_4$alkyl. In some embodiments, each $R^6$ is independently —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —C(CH$_3$)$_3$. In some embodiments, two $R^6$ on the same N atom are taken together with the N atom to which they are attached to form a substituted or unsubstituted N-containing heterocycle;

In some embodiments, X is -L$^2$-L$^3$-Y$^2$. In some embodiments, $L^2$ is substituted or unsubstituted $C_1$-$C_4$alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, —NR$^3$(SO$_2$)NR$^3$—(C=O)O—, or —O—(SO$_2$)—; $Y^2$ is independently H, —CN, —N$_3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, —OR$^6$, —(C=O)OR$^6$, —N(R$^6$)$_2$, or —(C=O)N(R$^6$)$_2$. In some embodiments, $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —NR$^3$(C=O)O—, —NR$^3$(SO$_2$)—, —(SO$_2$)NR$^3$—, or —O—(SO$_2$)—; $Y^2$ is independently H, —CN, —N$_3$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, substituted or unsubstituted monocyclic heteroaryl, —$OR^6$, —(C=O)$OR^6$, —$N(R^6)_2$, or —(C=O)$N(R^6)_2$; and each $R^6$ is independently H or substituted or unsubstituted $C_1$-$C_4$alkyl.

In some embodiments, $L^2$ is absent; $L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —$NR^3$(C=O)—, —$NR^3$(C=O)$NR^3$—, —O(C=O)$NR^3$—, —$NR^3$(C=O)O—, —$NR^3$($SO_2$)$NR^3$—, —$NR^3$($SO_2$)—, —($SO_2$)$NR^3$—, —($SO_2$)$NR^3$—(C=O)—, —($SO_2$)$NR^3$—(C=O)O—, —$NR^3$($SO_2$)$NR^3$—(C=O)—, —$NR^3$($SO_2$)$NR^3$—(C=O)O—, or —O—($SO_2$)—; $Y^2$ is independently H, —CN, —$N_3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, —$OR^6$, —(C=O)$OR^6$, —$N(R^6)_2$, or —(C=O)$N(R^6)_2$. In some embodiments, $L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —$NR^3$(C=O)—, —$NR^3$(C=O)$NR^3$—, —$NR^3$(C=O)O—, —$NR^3$($SO_2$)—, —($SO_2$)$NR^3$—, or —O—($SO_2$)—; $Y^2$ is independently H, —CN, —$N_3$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, substituted or unsubstituted monocyclic heteroaryl, —$OR^6$, —(C=O)$OR^6$, —$N(R^6)_2$, or —(C=O)$N(R^6)_2$; and each $R^6$ is independently H or substituted or unsubstituted $C_1$-$C_4$alkyl.

In some embodiments, X is -$L^2$-$L^3$-$L^4$-$Y^2$. In some embodiments, $L^2$ is substituted or unsubstituted $C_1$-$C_4$alkylene; $L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —$NR^3$(C=O)—, —$NR^3$(C=O)$NR^3$—, —O(C=O)$NR^3$—, —$NR^3$(C=O)O—, —$NR^3$($SO_2$)$NR^3$—, —$NR^3$($SO_2$)—, —($SO_2$)$NR^3$—, —($SO_2$)$NR^3$—(C=O)—, —($SO_2$)$NR^3$—(C=O)O—, —$NR^3$($SO_2$)$NR^3$—(C=O)—, —$NR^3$($SO_2$)$NR^3$—(C=O)O—, or —O—($SO_2$)—; $L^4$ is substituted or unsubstituted $C_1$-$C_4$alkylene; $Y^2$ is independently H, —CN, —$N_3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, —$OR^6$, —(C=O)$OR^6$, —$N(R^6)_2$, or —(C=O)$N(R^6)_2$. In some embodiments, $L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —$NR^3$(C=O)—, —$NR^3$(C=O)$NR^3$—, —$NR^3$(C=O)O—, —$NR^3$($SO_2$)—, —($SO_2$)$NR^3$—, or —O—($SO_2$)—; $Y^2$ is independently H, —CN, —$N_3$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, substituted or unsubstituted monocyclic heteroaryl, —$OR^6$, —(C=O)$OR^6$, —$N(R^6)_2$, or —(C=O)$N(R^6)_2$; and each $R^6$ is independently H or substituted or unsubstituted $C_1$-$C_4$alkyl.

In some embodiments, X is -$L^5$-$L^6$-$L^3$-$Y^2$. In some embodiments, X is -$L^6$-$L^5$-$L^3$-$Y^2$. In some embodiments, $L^5$ is substituted or unsubstituted $C_1$-$C_4$alkylene. In some embodiments, $L^5$ is —$CH_2$—, —$CH_2CH_2$—, —$CH_2CH_2$ $CH_2$—, or —$CH_2CH_2$ $CH_2CH_2$—. In some embodiments, $L^6$ is substituted or unsubstituted $C_3$-$C_6$cycloalkylene. In some embodiments, $L^6$ is substituted or unsubstituted cyclopropylene, substituted or unsubstituted cyclobutylene, substituted or unsubstituted cyclopentylene, or substituted or unsubstituted cyclohexylene.

In some embodiments, each $R^1$ is independently H. In some embodiments, each $R^1$ is independently halogen. In some embodiments, each $R^1$ is independently —CN. In some embodiments, each $R^1$ is independently —$OR^4$. In some embodiments, each $R^1$ is independently —$SR^4$. In some embodiments, each $R^1$ is independently —$N(R^4)_2$. In some embodiments, each $R^1$ is independently substituted or unsubstituted $C_1$-$C_6$alkyl. In some embodiments, each $R^1$ is independently substituted or unsubstituted $C_1$-$C_4$alkyl. In some embodiments, each $R^1$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^1$ is independently substituted or unsubstituted $C_1$-$C_6$haloalkyl. In some embodiments, each $R^1$ is independently substituted or unsubstituted $C_1$-$C_4$haloalkyl. In some embodiments, each $R^1$ is independently —$CH_2F$, —$CHF_2$, —$CF_3$, or —$CH_2CF_3$. In some embodiments, each $R^1$ is independently substituted or unsubstituted $C_2$-$C_6$alkenyl. In some embodiments, each $R^1$ is independently substituted or unsubstituted $C_2$-$C_4$alkenyl. In some embodiments, each $R^1$ is independently substituted or unsubstituted $C_2$-$C_6$alkynyl. In some embodiments, each $R^1$ is independently substituted or unsubstituted $C_2$-$C_4$alkynyl. In some embodiments, each $R^1$ is independently substituted or unsubstituted $C_1$-$C_6$heteroalkyl. In some embodiments, each $R^1$ is independently substituted or unsubstituted $C_1$-$C_4$heteroalkyl. In some embodiments, each $R^1$ is independently substituted or unsubstituted $C_3$-$C_{10}$cycloalkyl. In some embodiments, each $R^1$ is independently substituted or unsubstituted $C_3$-$C_6$cycloalkyl. In some embodiments, each $R^1$ is independently substituted or unsubstituted cyclopropyl, substituted or unsubstituted cyclobutyl, substituted or unsubstituted cyclopentyl, or substituted or unsubstituted cyclohexyl. In some embodiments, each $R^1$ is independently substituted or unsubstituted $C_2$-$C_{10}$heterocycloalkyl. In some embodiments, each $R^1$ is independently substituted or unsubstituted $C_2$-$C_6$heterocycloalkyl. In some embodiments, each $R^1$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl. In some embodiments, each $R^1$ is independently substituted or unsubstituted aralkyl. In some embodiments, each $R^1$ is independently substituted or unsubstituted benzyl. In some embodiments, each $R^1$ is independently substituted or unsubstituted aryl. In some embodiments, each $R^1$ is independently substituted or unsubstituted phenyl. In some embodiments, each $R^1$ is independently substituted or unsubstituted heteroaryl. In some embodiments, each $R^1$ is independently substituted or unsubstituted monocyclic heteroaryl. In some embodiments, each $R^1$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, each $R^1$ is independently -$L^7$-$Y^3$.

In some embodiments, $L^7$ is substituted or unsubstituted $C_1$-$C_6$alkylene. In some embodiments, $L^7$ is substituted or unsubstituted $C_1$-$C_4$alkylene. In some embodiments, $L^7$ is —$CH_2$—, —$CH_2CH_2$—, —$CH_2CH_2CH_2$—, or —$CH_2CH_2CH_2CH_2$—. In some embodiments, $Y^3$ is —$Si(R^7)_2$. In some embodiments, each $R^7$ is independently substituted or unsubstituted $C_1$-$C_6$alkyl. In some embodiments, each $R^7$ is independently substituted or unsubstituted $C_1$-$C_4$alkyl. In some embodiments, each $R^7$ is independently —$CH_3$— $CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$.

In some embodiments,

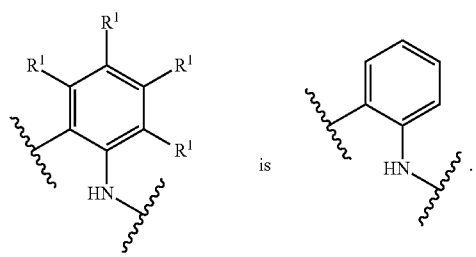

In some embodiments,

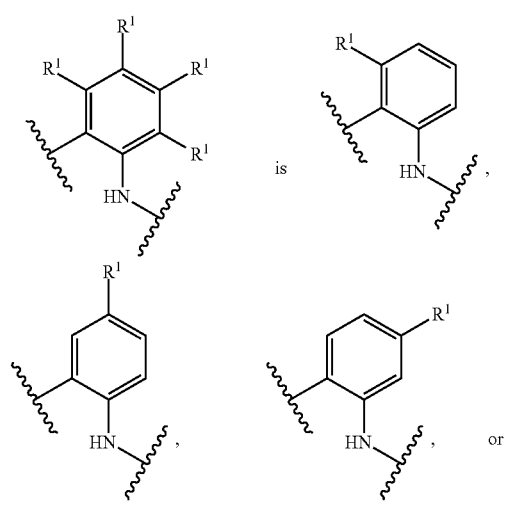

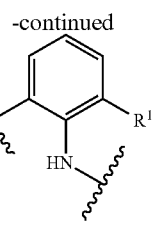

and $R^1$ is halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, $R^1$ is halogen, —CN, —$OR^4$, —$SR^4$, —$N(R^4)_2$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, or substituted or unsubstituted monocyclic heteroaryl. In some embodiments, $R^1$ is halogen, substituted or unsubstituted $C_1$-$C_4$alkyl, or substituted or unsubstituted $C_1$-$C_4$haloalkyl. In some embodiments, $R^1$ is F, Cl, Br, I, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2F$, —$CHF_2$, —$CF_3$, or —$CH_2CF_3$.

In some embodiments,

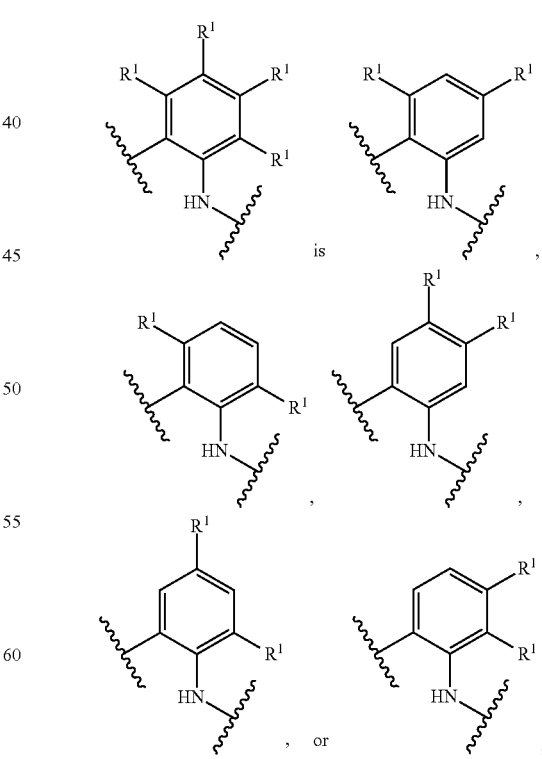

and each $R^1$ is independently halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, each R is independently halogen, —CN, —$OR^4$, —$SR^4$, —$N(R^4)_2$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted benzyl, substituted or unsubstituted phenyl, or substituted or unsubstituted monocyclic heteroaryl. In some embodiments, each $R^1$ is independently halogen, substituted or unsubstituted $C_1$-$C_4$alkyl, or substituted or unsubstituted $C_1$-$C_4$haloalkyl. In some embodiments, each $R^1$ is independently F, Cl, Br, I, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2F$, —$CHF_2$, —$CF_3$, or —$CH_2CF_3$.

In some embodiments, n is 0. In some embodiments, n is 1. In some embodiments, n is 2. In some embodiments, n is 3. In some embodiments, n is 4.

In some embodiments, each $R^2$ is independently H. In some embodiments, each $R^2$ is independently halogen. In some embodiments, each $R^2$ is independently —$N_3$. In some embodiments, each $R^2$ is independently —CN. In some embodiments, each $R^2$ is independently —$OR^5$. In some embodiments, each $R^2$ is independently —$SR^5$. In some embodiments, each $R^2$ is independently —$(SO_2)R^5$. In some embodiments, each $R^2$ is independently —$N(R^5)_2$. In some embodiments, each $R^2$ is independently —$CO_2R^5$. In some embodiments, each $R^2$ is independently substituted or unsubstituted $C_1$-$C_6$alkyl. In some embodiments, each $R^2$ is independently substituted or unsubstituted $C_1$-$C_4$alkyl. In some embodiments, each $R^2$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^2$ is independently substituted or unsubstituted $C_1$-$C_6$haloalkyl. In some embodiments, each $R^2$ is independently substituted or unsubstituted $C_1$-$C_4$haloalkyl. In some embodiments, each $R^2$ is independently —$CH_2F$, —$CHF_2$, —$CF_3$, or —$CH_2CF_3$. In some embodiments, each $R^2$ is independently substituted or unsubstituted $C_2$-$C_6$alkenyl. In some embodiments, each $R^2$ is independently substituted or unsubstituted $C_2$-$C_4$alkenyl. In some embodiments, each $R^2$ is independently substituted or unsubstituted $C_2$-$C_6$alkynyl. In some embodiments, each $R^2$ is independently substituted or unsubstituted $C_2$-$C_4$alkynyl. In some embodiments, each $R^2$ is independently substituted or unsubstituted $C_1$-$C_6$heteroalkyl. In some embodiments, each $R^2$ is independently substituted or unsubstituted $C_1$-$C_4$heteroalkyl. In some embodiments, each $R^2$ is independently substituted or unsubstituted $C_3$-$C_{10}$cycloalkyl. In some embodiments, each $R^2$ is independently substituted or unsubstituted $C_3$-$C_6$cycloalkyl. In some embodiments, each $R^2$ is independently substituted or unsubstituted cyclopropyl, substituted or unsubstituted cyclobutyl, substituted or unsubstituted cyclopentyl, or substituted or unsubstituted cyclohexyl. In some embodiments, each $R^2$ is independently substituted or unsubstituted $C_2$-$C_{10}$heterocycloalkyl. In some embodiments, each $R^2$ is independently substituted or unsubstituted $C_2$-$C_6$heterocycloalkyl. In some embodiments, each $R^2$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl. In some embodiments, each $R^2$ is independently substituted or unsubstituted aralkyl. In some embodiments, each $R^2$ is independently substituted or unsubstituted benzyl. In some embodiments, each $R^2$ is independently substituted or unsubstituted aryl. In some embodiments, each $R^2$ is independently substituted or unsubstituted phenyl. In some embodiments, each $R^2$ is independently substituted or unsubstituted heteroaryl. In some embodiments, each $R^2$ is independently substituted or unsubstituted monocyclic heteroaryl. In some embodiments, each $R^2$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanylIn some embodiments, each $R^2$ is independently

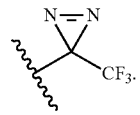 [SMILES: *C1(C(F)(F)F)N=N1]

In some embodiments,

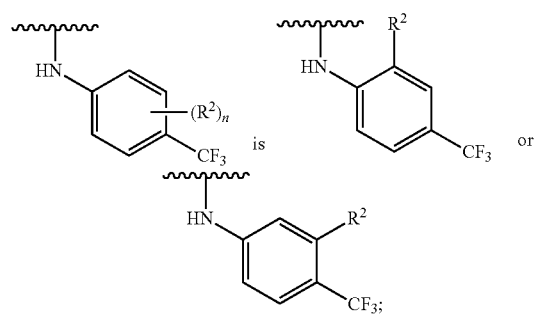

and $R^2$ is halogen, —$N_3$, —CN, —$OR^5$, —$SR^5$, —$(SO_2)R^5$, —$N(R)_2$, —$CO_2R^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted aralkyl, substituted or unsubstituted aryl, substituted or unsubstituted heteroaryl, or

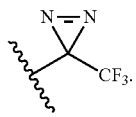 [SMILES: *C1(C(F)(F)F)N=N1]

In some embodiments, $R^2$ is halogen, —$N_3$, —CN, —$OR^5$, —$SR^5$, —$(SO_2)R^5$, —$N(R)_2$, —$CO_2R^5$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted benzyl, substituted or unsubstituted phenyl, substituted or unsubstituted monocyclic heteroaryl, or

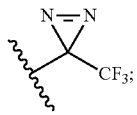 [SMILES: *C1(C(F)(F)F)N=N1]

and each $R^5$ is independently H, or substituted or unsubstituted $C_1$-$C_4$alkyl. In some embodiments, $R^2$ is halogen, —$N_3$, —$OR^5$, —$(SO_2)R^5$, —$CO_2R^5$, substituted or unsubstituted $C_1$-$C_4$alkyl, substituted or unsubstituted $C_1$-$C_4$haloalkyl, or

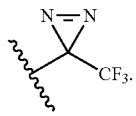 [SMILES: *C1(C(F)(F)F)N=N1]

In some embodiments, wherein:

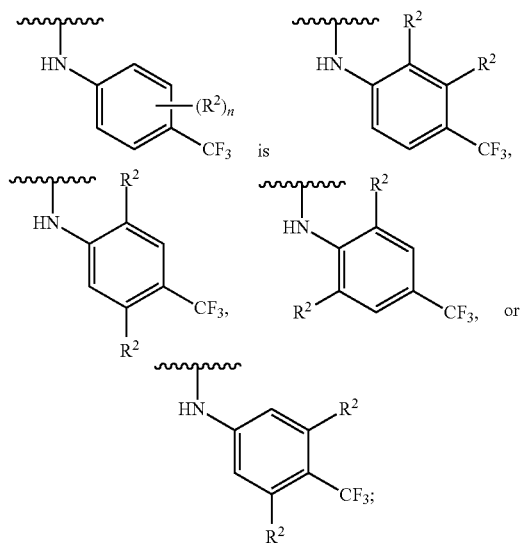

and each $R^2$ is independently halogen, —$N_3$, —CN, —$OR^5$, —$SR^5$, —$(SO_2)R^5$, —$N(R^5)_2$, —$CO_2R^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted aralkyl, substituted or unsubstituted aryl, substituted or unsubstituted heteroaryl, or

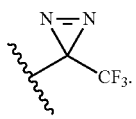

In some embodiments, each $R^2$ is independently halogen, —$N_3$, —CN, —$OR^5$, —$SR^5$, —$(SO_2)R^5$, —$N(R^5)_2$, —$CO_2R^5$, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted benzyl, substituted or unsubstituted phenyl, substituted or unsubstituted monocyclic heteroaryl, or and each $R^5$ is independently H, or substituted or unsubstituted $C_1$-$C_4$alkyl. In some embodiments, each $R^2$ is independently halogen, —$N_3$, —$OR^5$, —$(SO_2)R^5$, —$CO_2R^5$, substituted or unsubstituted $C_1$-$C_4$alkyl, substituted or unsubstituted $C_1$-$C_4$haloalkyl, or In some embodiments, each $R^4$ is independently H. In some embodiments, each $R^4$ is independently substituted or unsubstituted $C_1$-$C_6$alkyl. In some embodiments, each $R^4$ is independently substituted or unsubstituted $C_1$-$C_4$alkyl. In some embodiments, each $R^4$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^4$ is independently substituted or unsubstituted $C_1$-$C_6$haloalkyl. In some embodiments, each $R^4$ is independently substituted or unsubstituted $C_1$-$C_4$haloalkyl. In some embodiments, each $R^4$ is independently —$CH_2F$, —$CHF_2$, —$CF_3$, or —$CH_2CF_3$. In some embodiments, each $R^4$ is independently substituted or unsubstituted $C_1$-$C_6$heteroalkyl. In some embodiments, each $R^4$ is independently substituted or unsubstituted $C_1$-$C_4$heteroalkyl. In some embodiments, each $R^4$ is independently substituted or unsubstituted $C_3$-$C_{10}$cycloalkyl. In some embodiments, each $R^4$ is independently substituted or unsubstituted $C_3$-$C_6$cycloalkyl. In some embodiments, each $R^4$ is independently substituted or unsubstituted cyclopropyl, substituted or unsubstituted cyclobutyl, substituted or unsubstituted cyclopentyl, or substituted or unsubstituted cyclohexyl. In some embodiments, each $R^4$ is independently substituted or unsubstituted $C_2$-$C_{10}$heterocycloalkyl. In some embodiments, each $R^4$ is independently substituted or unsubstituted $C_2$-$C_6$heterocycloalkyl. In some embodiments, each $R^4$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl. In some embodiments, each $R^4$ is independently substituted or unsubstituted aralkyl. In some embodiments, each $R^4$ is independently substituted or unsubstituted benzyl. In some embodiments, each $R^4$ is independently substituted or unsubstituted aryl. In some embodiments, each $R^4$ is independently substituted or unsubstituted phenyl. In some embodiments, each $R^4$ is independently substituted or unsubstituted heteroaryl. In some embodiments, each $R^4$ is independently substituted or unsubstituted monocyclic heteroaryl. In some embodiments, each $R^4$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, two $R^4$ on the same N atom are taken together with the N atom to which they are attached to form a substituted or unsubstituted N-containing heterocycle.

In some embodiments, each $R^5$ is independently H. In some embodiments, each $R^5$ is independently substituted or unsubstituted $C_1$-$C_6$alkyl. In some embodiments, each $R^5$ is independently substituted or unsubstituted $C_1$-$C_4$alkyl. In some embodiments, each $R^5$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^5$ is independently substituted or unsubstituted $C_1$-$C_6$haloalkyl. In some embodiments, each $R^5$ is independently substituted or unsubstituted $C_1$-$C_4$haloalkyl. In some embodiments, each $R^5$ is independently —$CH_2F$, —$CHF_2$, —$CF_3$, or —$CH_2CF_3$. In some embodiments, each $R^5$ is independently substituted or unsubstituted $C_1$-$C_6$heteroalkyl. In some embodiments, each $R^5$ is independently substituted or unsubstituted $C_1$-$C_4$heteroalkyl. In some embodiments, each $R^5$ is independently substituted or unsubstituted $C_3$-$C_{10}$cycloalkyl. In some embodiments, each $R^5$ is independently substituted or unsubstituted $C_3$-$C_6$cycloalkyl. In some embodiments, each $R^5$ is independently substituted or unsubstituted cyclopropyl, substituted or unsubstituted cyclobutyl, substituted or unsubstituted cyclopentyl, or substituted or unsubstituted cyclohexyl. In some embodiments, each $R^5$ is independently substituted or unsubstituted $C_2$-$C_{10}$heterocycloalkyl. In some embodiments, each $R^5$ is independently substituted or unsubstituted $C_2$-$C_6$heterocycloalkyl. In some embodiments, each $R^5$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl. In some embodiments, each $R^5$ is independently substituted or unsubstituted aralkyl. In some embodiments, each $R^5$ is independently substituted or unsubstituted benzyl. In some embodiments, each $R^5$ is independently substituted or unsubstituted aryl. In some embodiments, each $R^5$ is independently substituted or unsubstituted phenyl. In some embodiments, each $R^5$ is independently substituted or unsubstituted heteroaryl. In some embodiments, each $R^5$ is independently substituted or unsubstituted monocyclic heteroaryl. In some embodiments, each $R^5$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, two $R^5$ on the same N atom are taken together with the N atom to which they are attached to form a substituted or unsubstituted N-containing heterocycle.

In some embodiments, the compound has the structure of Formula (Ia), or a pharmaceutically acceptable salt thereof:

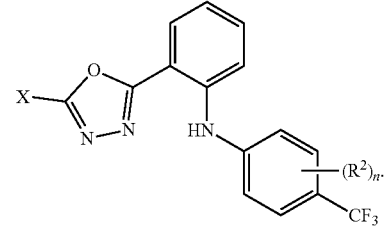

Formula (Ia)

In some embodiments, the compound has the structure of Formula (Ib), or a pharmaceutically acceptable salt thereof:

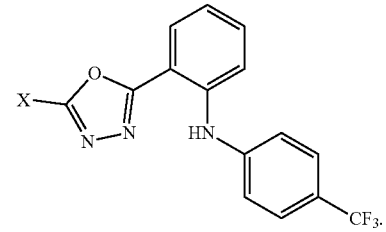

Formula (Ib)

In some embodiments, the compound disclosed herein has the structure provided in Table 1.

TABLE 1

| Compound No. | Structure | Name |
|---|---|---|
| 1 | 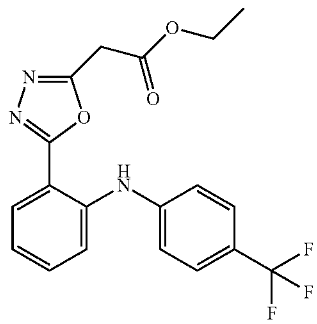 [SMILES: CCOC(=O)Cc1nnc(-c2ccccc2Nc2ccc(C(F)(F)F)cc2)o1] | ethyl 2-(5-(2-((4-(trifluoromethyl)phenyl)amino)phenyl)-1,3,4-oxadiazol-2-yl)acetate |
| 2 | 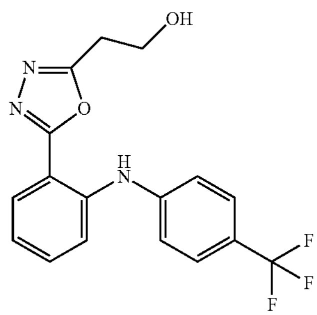 [SMILES: OCCc1nnc(-c2ccccc2Nc2ccc(C(F)(F)F)cc2)o1] | 2-(5-(2-((4-(trifluoromethyl)phenyl)amino)phenyl)-1,3,4-oxadiazol-2-yl)ethan-1-ol |
| 3 | 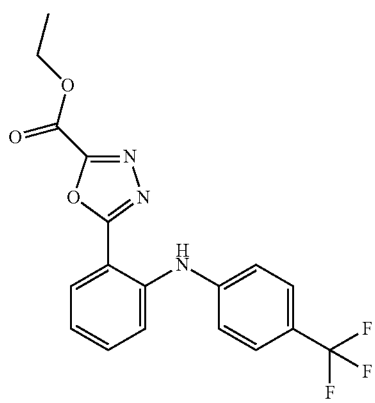 [SMILES: CCOC(=O)c1nnc(-c2ccccc2Nc2ccc(C(F)(F)F)cc2)o1] | ethyl 5-(2-((4-(trifluoromethyl)phenyl)amino)phenyl)-1,3,4-oxadiazole-2-carboxylate |
| 4 | 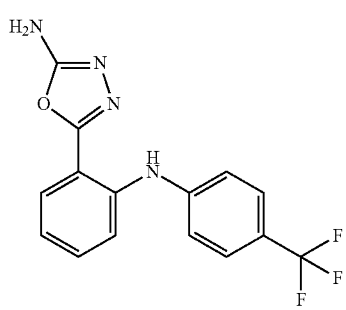 [SMILES: Nc1nnc(-c2ccccc2Nc2ccc(C(F)(F)F)cc2)o1] | 5-(2-((4-(trifluoromethyl)phenyl)amino)phenyl)-1,3,4-oxadiazol-2-amine |

TABLE 1-continued

| Compound No. | Structure | Name |
|---|---|---|
| 5 | 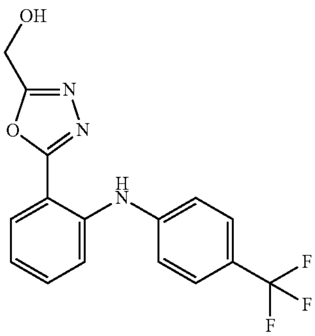 [SMILES: OCc1nnc(-c2ccccc2Nc2ccc(C(F)(F)F)cc2)o1] | (5-(2-((4-(trifluoromethyl)phenyl)amino)phenyl)-1,3,4-oxadiazol-2-yl)methanol |
| 6 | 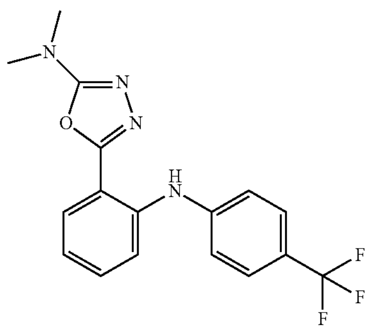 [SMILES: CN(C)c1nnc(-c2ccccc2Nc2ccc(C(F)(F)F)cc2)o1] | N,N-dimethyl-5-(2-((4-(trifluoromethyl)phenyl)amino)phenyl)-1,3,4-oxadiazol-2-amine |
| 8 | 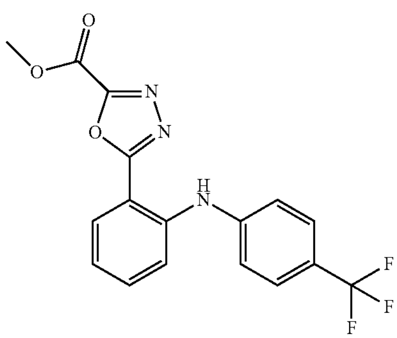 [SMILES: COC(=O)c1nnc(-c2ccccc2Nc2ccc(C(F)(F)F)cc2)o1] | methyl 5-(2-((4-(trifluoromethyl)phenyl)amino)phenyl)-1,3,4-oxadiazole-2-carboxylate |
| 9 | 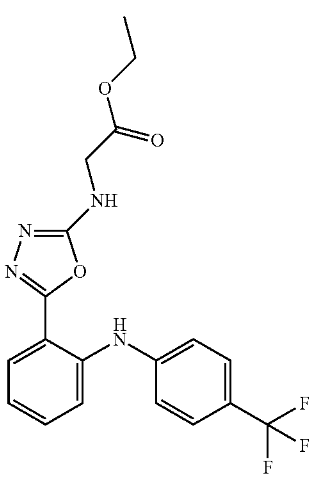 [SMILES: CCOC(=O)CNc1nnc(-c2ccccc2Nc2ccc(C(F)(F)F)cc2)o1] | ethyl (5-(2-((4-(trifluoromethyl)phenyl)amino)phenyl)-1,3,4-oxadiazol-2-yl)glycinate |

TABLE 1-continued

| Compound No. | Structure | Name |
|---|---|---|
| 10 | 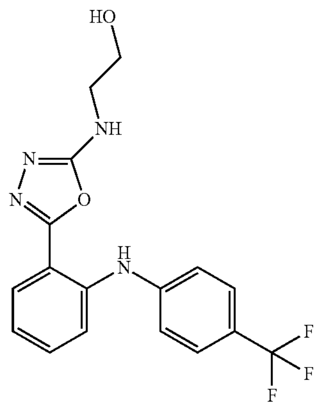 [SMILES: OCCNc1nnc(-c2ccccc2Nc2ccc(C(F)(F)F)cc2)o1] | 2-((5-(2-((4-(trifluoromethyl)phenyl)amino)phenyl)-1,3,4-oxadiazol-2-yl)amino)ethan-1-ol |
| 11 | 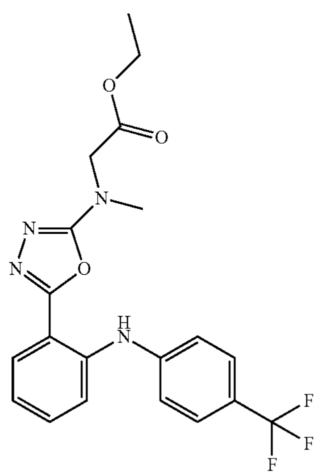 [SMILES: CCOC(=O)CN(C)c1nnc(-c2ccccc2Nc2ccc(C(F)(F)F)cc2)o1] | ethyl N-methyl-N-(5-(2-((4-(trifluoromethyl)phenyl)amino)phenyl)-1,3,4-oxadiazol-2-yl)glycinate |
| 12 | 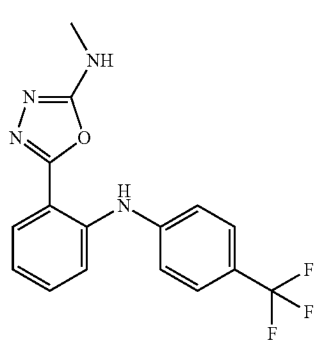 [SMILES: CNc1nnc(-c2ccccc2Nc2ccc(C(F)(F)F)cc2)o1] | N-methyl-5-(2-((4-(trifluoromethyl)phenyl)amino)phenyl)-1,3,4-oxadiazol-2-amine |

TABLE 1-continued

| Compound No. | Structure | Name |
|---|---|---|
| 13 | 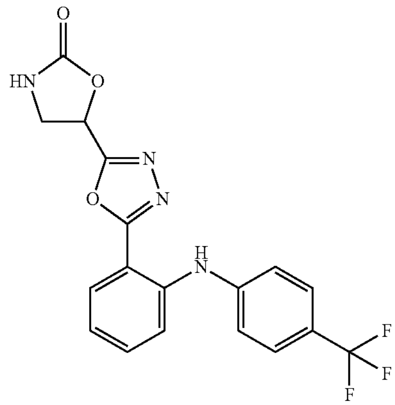 [SMILES: O=C1NCC(c2nnc(-c3ccccc3Nc3ccc(C(F)(F)F)cc3)o2)O1] | 5-(5-(2-((4-(trifluoromethyl)phenyl)amino)phenyl)-1,3,4-oxadiazol-2-yl)oxazolidin-2-one |
| 14 | 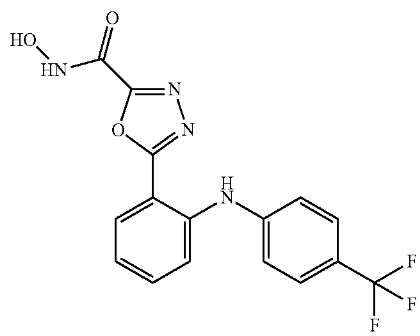 [SMILES: O=C(NO)c1nnc(-c2ccccc2Nc2ccc(C(F)(F)F)cc2)o1] | N-hydroxy-5-(2-((4-(trifluoromethyl)phenyl)amino)phenyl)-1,3,4-oxadiazole-2-carboxamide |
| 15 | 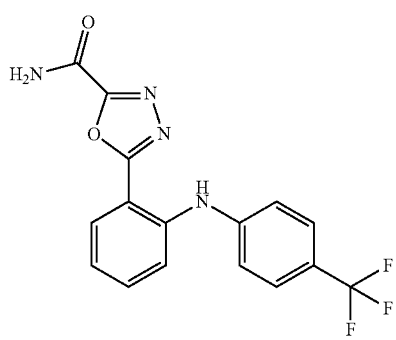 [SMILES: NC(=O)c1nnc(-c2ccccc2Nc2ccc(C(F)(F)F)cc2)o1] | 5-(2-((4-(trifluoromethyl)phenyl)amino)phenyl)-1,3,4-oxadiazole-2-carboxamide |
| 16 | 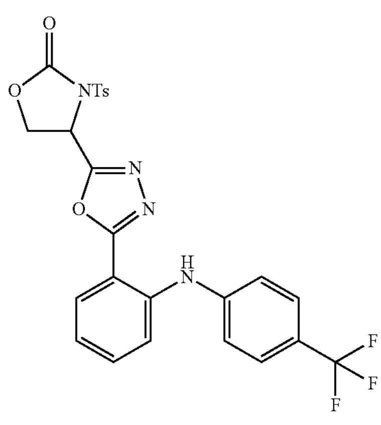 [SMILES: Cc1ccc(S(=O)(=O)N2C(=O)OCC2c2nnc(-c3ccccc3Nc3ccc(C(F)(F)F)cc3)o2)cc1] | 3-tosyl-4-(5-(2-((4-(trifluoromethyl)phenyl)amino)phenyl)-1,3,4-oxadiazol-2-yl)oxazolidin-2-one |

TABLE 1-continued

| Compound No. | Structure | Name |
|---|---|---|
| 17 | 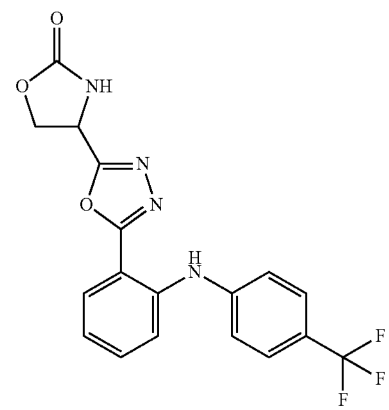 [SMILES: O=C1NC(c2nnc(-c3ccccc3Nc3ccc(C(F)(F)F)cc3)o2)CO1] | 4-(5-(2-((4-(trifluoromethyl)phenyl)amino)phenyl)-1,3,4-oxadiazol-2-yl)oxazolidin-2-one |
| 18 | 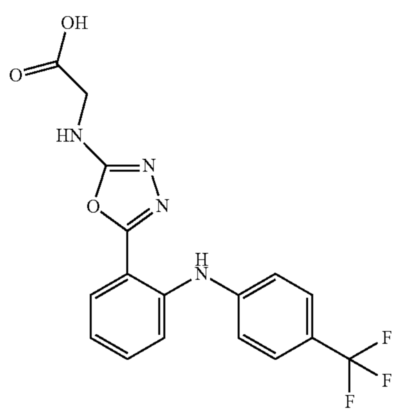 [SMILES: O=C(O)CNc1nnc(-c2ccccc2Nc2ccc(C(F)(F)F)cc2)o1] | (5-(2-((4-(trifluoromethyl)phenyl)amino)phenyl)-1,3,4-oxadiazol-2-yl)glycine |
| 19 | 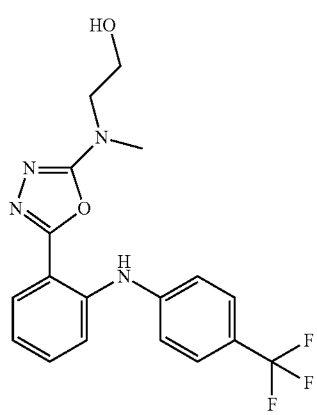 [SMILES: CN(CCO)c1nnc(-c2ccccc2Nc2ccc(C(F)(F)F)cc2)o1] | 2-(methyl(5-(2-((4-(trifluoromethyl)phenyl)amino)phenyl)-1,3,4-oxadiazol-2-yl)amino)ethan-1-ol |
| 20 | 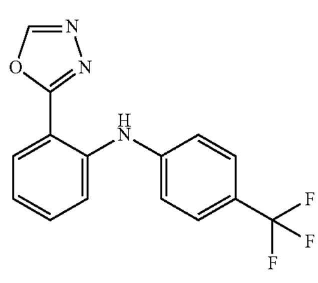 [SMILES: FC(F)(F)c1ccc(Nc2ccccc2-c2nnco2)cc1] | 2-(1,3,4-oxadiazol-2-yl)-N-[4-(trifluoromethyl)phenyl]aniline |

TABLE 1-continued

| Compound No. | Structure | Name |
|---|---|---|
| 21 | 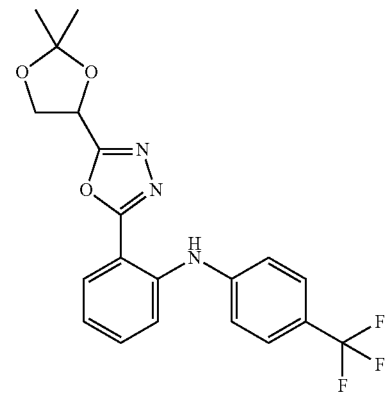 [SMILES: CC1(C)OCC(c2nnc(-c3ccccc3Nc3ccc(C(F)(F)F)cc3)o2)O1] | 2-[5-(2,2-dimethyl-1,3-dioxolan-4-yl)-1,3,4-oxadiazol-2-yl]-N-[4-(trifluoromethyl)phenyl]aniline |
| 22 | 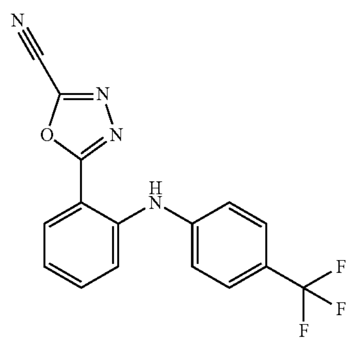 [SMILES: N#Cc1nnc(-c2ccccc2Nc2ccc(C(F)(F)F)cc2)o1] | 5-[2-[4-(trifluoromethyl)anilino]phenyl]-1,3,4-oxadiazole-2-carbonitrile |
| 23 | 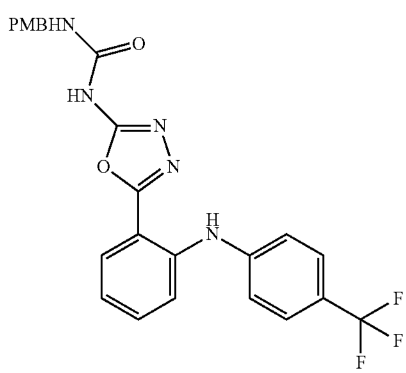 | 1-(4-methoxybenzyl)-3-(5-(2-((4-(trifluoromethyl)phenyl)amino)phenyl)-1,3,4-oxadiazol-2-yl)urea |
| 24 | 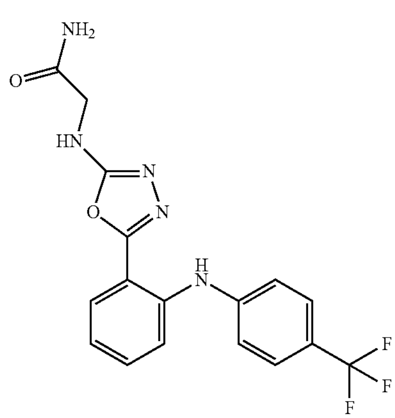 | 2-((5-(2-((4-(trifluoromethyl)phenyl)amino)phenyl)-1,3,4-oxadiazol-2-yl)amino)acetamide |

TABLE 1-continued

| Compound No. | Structure | Name |
|---|---|---|
| 25 | 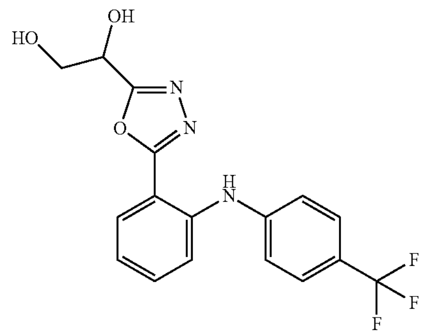 [SMILES: OCC(O)c1nnc(-c2ccccc2Nc2ccc(C(F)(F)F)cc2)o1] | 1-[5-[2-[4-(trifluoromethyl)anilino]phenyl]-1,3,4-oxadiazol-2-yl]ethane-1,2-diol |
| 26 | 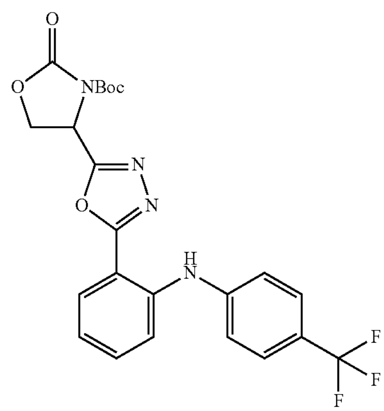 [SMILES: CC(C)(C)OC(=O)N1C(=O)OCC1c1nnc(-c2ccccc2Nc2ccc(C(F)(F)F)cc2)o1] | 2-oxo-4-(5-(2-((4-(trifluoromethyl)phenyl)amino)phenyl)-1,3,4-oxadiazol-2-yl)oxazolidine-3-carboxylate |
| 27 | 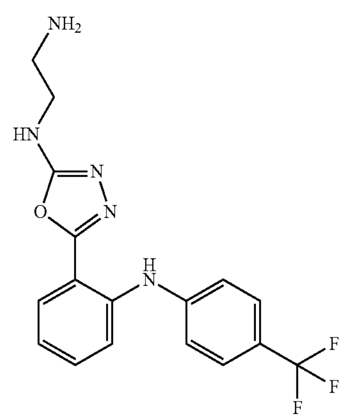 [SMILES: NCCNc1nnc(-c2ccccc2Nc2ccc(C(F)(F)F)cc2)o1] | N1-(5-(2-((4-(trifluoromethyl)phenyl)amino)phenyl)-1,3,4-oxadiazol-2-yl)ethane-1,2-diamine |
| 28 | 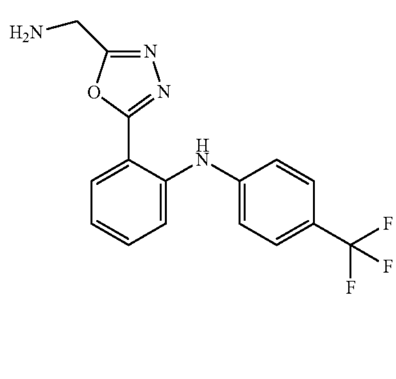 [SMILES: NCc1nnc(-c2ccccc2Nc2ccc(C(F)(F)F)cc2)o1] | 2-[5-(aminomethyl)-1,3,4-oxadiazol-2-yl]-N-[4-(trifluoromethyl)phenyl]aniline |

TABLE 1-continued

| Compound No. | Structure | Name |
|---|---|---|
| 29 | 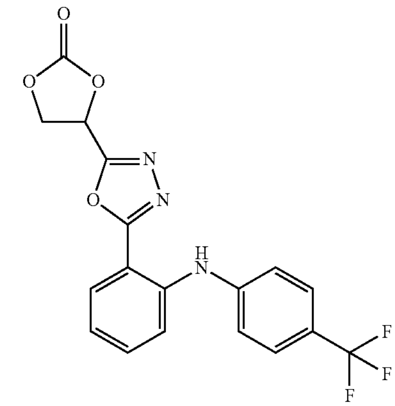 [SMILES: O=C1OCC(c2nnc(-c3ccccc3Nc3ccc(C(F)(F)F)cc3)o2)O1] | 4-[5-[2-[4-(trifluoromethyl)anilino]phenyl]-1,3,4-oxadiazol-2-yl]-1,3-dioxolan-2-one |
| 30 | 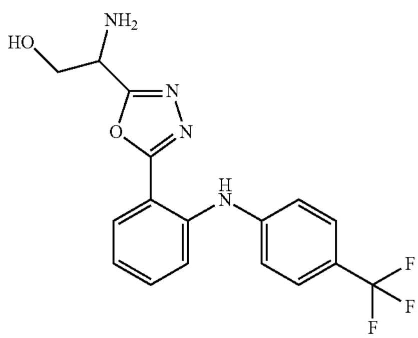 [SMILES: NC(CO)c1nnc(-c2ccccc2Nc2ccc(C(F)(F)F)cc2)o1] | 2-amino-2-(5-(2-((4-(trifluoromethyl)phenyl)amino)phenyl)-1,3,4-oxadiazol-2-yl)ethanol |
| 31 | 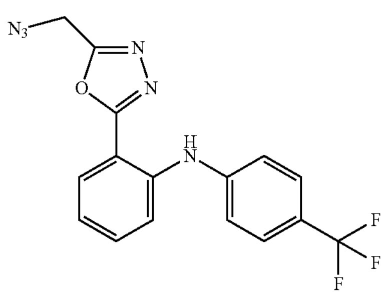 [SMILES: [N-]=[N+]=NCc1nnc(-c2ccccc2Nc2ccc(C(F)(F)F)cc2)o1] | 2-[5-(azidomethyl)-1,3,4-oxadiazol-2-yl]-N-[4-(trifluoromethyl)phenyl]aniline |
| 32 | 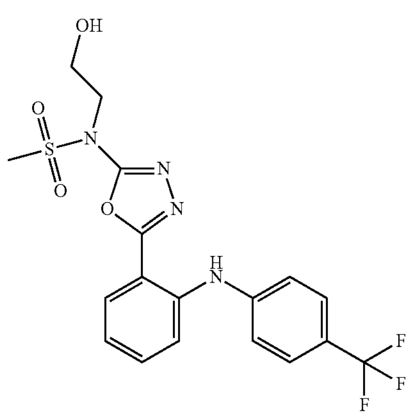 [SMILES: CS(=O)(=O)N(CCO)c1nnc(-c2ccccc2Nc2ccc(C(F)(F)F)cc2)o1] | N-(2-hydroxyethyl)-N-(5-(2-((4-(trifluoromethyl)phenyl)amino)phenyl)-1,3,4-oxadiazol-2-yl)methanesulfonamide |

TABLE 1-continued

| Compound No. | Structure | Name |
|---|---|---|
| 33 | 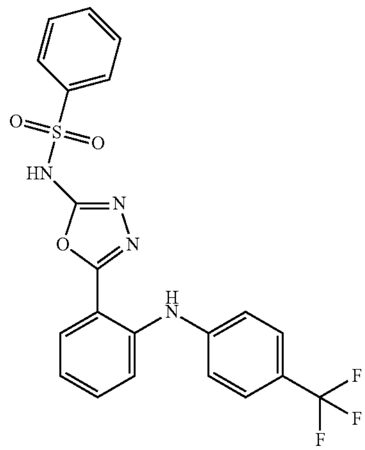 [SMILES: O=S(=O)(Nc1nnc(-c2ccccc2Nc2ccc(C(F)(F)F)cc2)o1)c1ccccc1] | N-(5-(2-((4-(trifluoromethyl)phenyl)amino)phenyl)-1,3,4-oxadiazol-2-yl)benzenesulfonamide |
| 34 | 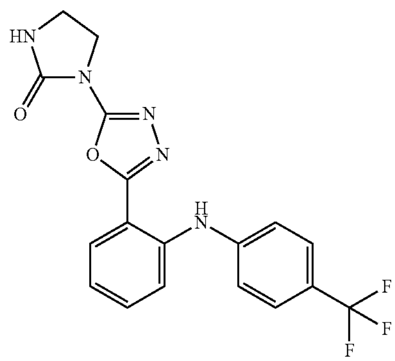 [SMILES: O=C1NCCN1c1nnc(-c2ccccc2Nc2ccc(C(F)(F)F)cc2)o1] | 1-(5-(2-((4-(trifluoromethyl)phenyl)amino)phenyl)-1,3,4-oxadiazol-2-yl)imidazolidin-2-one |
| 35 | 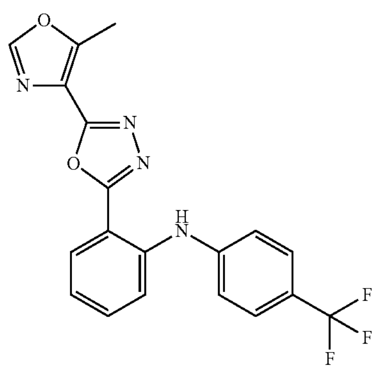 [SMILES: Cc1ocnc1-c1nnc(-c2ccccc2Nc2ccc(C(F)(F)F)cc2)o1] | 2-(5-(5-methyloxazol-4-yl)-1,3,4-oxadiazol-2-yl)-N-(4-(trifluoromethyl)phenyl)aniline |
| 36 | 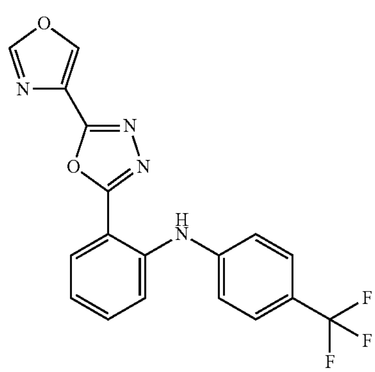 [SMILES: FC(F)(F)c1ccc(Nc2ccccc2-c2nnc(-c3cocn3)o2)cc1] | 2-(5-(oxazol-4-yl)-1,3,4-oxadiazol-2-yl)-N-(4-(trifluoromethyl)phenyl)aniline |

TABLE 1-continued

| Compound No. | Structure | Name |
|---|---|---|
| 37 | 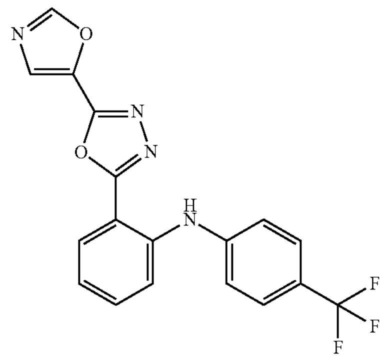 [SMILES: FC(F)(F)c1ccc(Nc2ccccc2-c2nnc(-c3cnco3)o2)cc1] | 2-(5-(oxazol-5-yl)-1,3,4-oxadiazol-2-yl)-N-(4-(trifluoromethyl)phenyl)aniline |
| 38 | 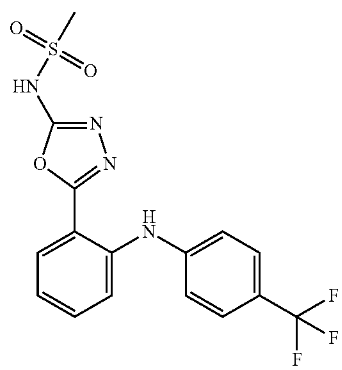 [SMILES: CS(=O)(=O)Nc1nnc(-c2ccccc2Nc2ccc(C(F)(F)F)cc2)o1] | N-(5-(2-((4-(trifluoromethyl)phenyl)amino)phenyl)-1,3,4-oxadiazol-2-yl)methanesulfonamide |
| 39 | 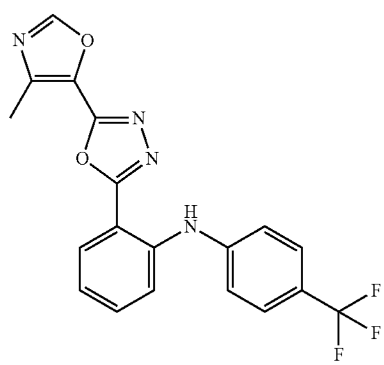 [SMILES: Cc1ncoc1-c1nnc(-c2ccccc2Nc2ccc(C(F)(F)F)cc2)o1] | 2-(5-(4-methyloxazol-5-yl)-1,3,4-oxadiazol-2-yl)-N-(4-(trifluoromethyl)phenyl)aniline |
| 40 | 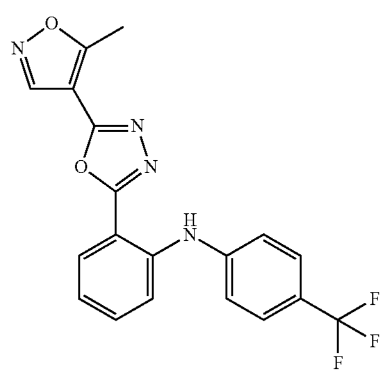 [SMILES: Cc1oncc1-c1nnc(-c2ccccc2Nc2ccc(C(F)(F)F)cc2)o1] | 2-(5-(5-methylisoxazol-4-yl)-1,3,4-oxadiazol-2-yl)-N-(4-(trifluoromethyl)phenyl)aniline |

TABLE 1-continued

| Compound No. | Structure | Name |
|---|---|---|
| 41 | 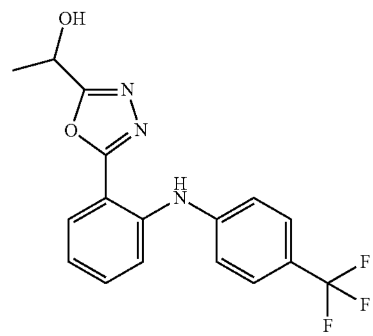 [SMILES: CC(O)c1nnc(-c2ccccc2Nc2ccc(C(F)(F)F)cc2)o1] | 1-(5-(2-((4-(trifluoromethyl)phenyl)amino)phenyl)-1,3,4-oxadiazol-2-yl)ethanol |
| 42 | 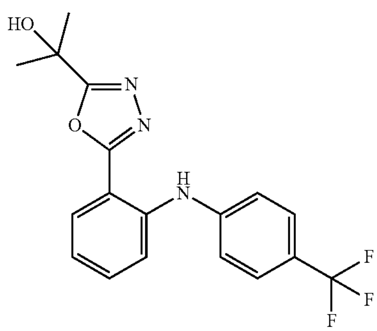 [SMILES: CC(C)(O)c1nnc(-c2ccccc2Nc2ccc(C(F)(F)F)cc2)o1] | 2-(5-(2-((4-(trifluoromethyl)phenyl)amino)phenyl)-1,3,4-oxadiazol-2-yl)propan-2-ol |
| 43 | 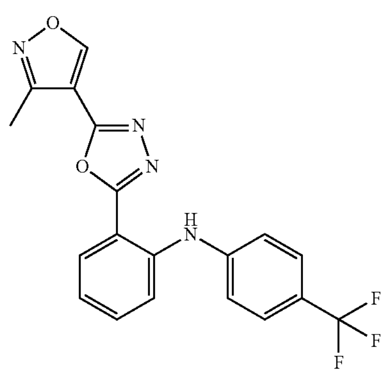 [SMILES: Cc1nocc1-c1nnc(-c2ccccc2Nc2ccc(C(F)(F)F)cc2)o1] | 2-(5-(3-methylisoxazol-4-yl)-1,3,4-oxadiazol-2-yl)-N-(4-(trifluoromethyl)phenyl)aniline |
| 44 | 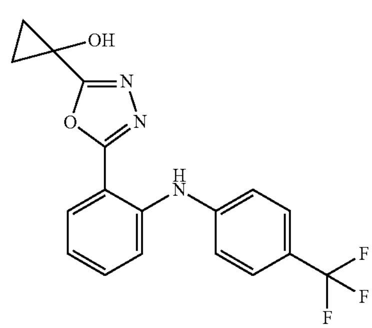 [SMILES: OC1(c2nnc(-c3ccccc3Nc3ccc(C(F)(F)F)cc3)o2)CC1] | 1-(5-(2-((4-(trifluoromethyl)phenyl)amino)phenyl)-1,3,4-oxadiazol-2-yl)cyclopropanol |

TABLE 1-continued

| Compound No. | Structure | Name |
|---|---|---|
| 45 | 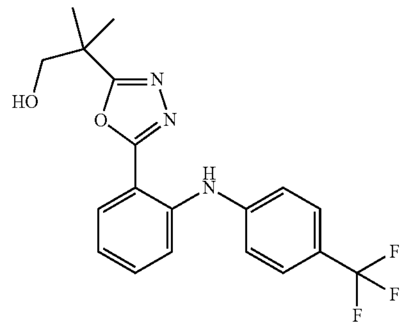 [SMILES: CC(C)(CO)c1nnc(-c2ccccc2Nc2ccc(C(F)(F)F)cc2)o1] | 2-methyl-2-(5-(2-((4-(trifluoromethyl)phenyl)amino)phenyl)-1,3,4-oxadiazol-2-yl)propan-1-ol |
| 46 | 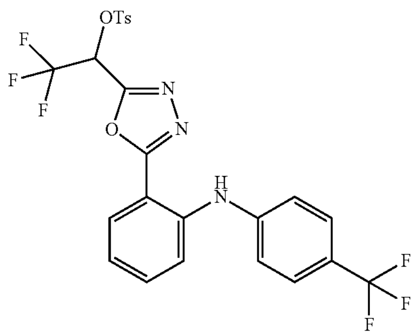 [SMILES: Cc1ccc(S(=O)(=O)OC(c2nnc(-c3ccccc3Nc3ccc(C(F)(F)F)cc3)o2)C(F)(F)F)cc1] | 2,2,2-trifluoro-1-(5-(2-((4-(trifluoromethyl)phenyl)amino)phenyl)-1,3,4-oxadiazol-2-yl)ethyl4-methylbenzenesulfonate |
| 47 | 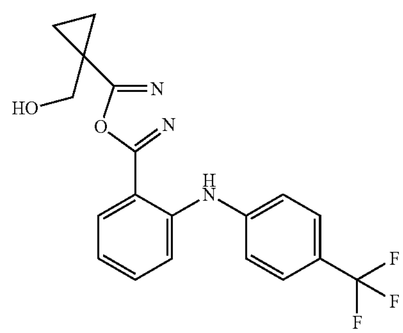 [SMILES: N=C(OC(=N)C1(CO)CC1)c1ccccc1Nc1ccc(C(F)(F)F)cc1] | (1-(5-(2-((4-(trifluoromethyl)phenyl)amino)phenyl)-1,3,4-oxadiazol-2-yl)cyclopropyl)methanol |
| 48 | 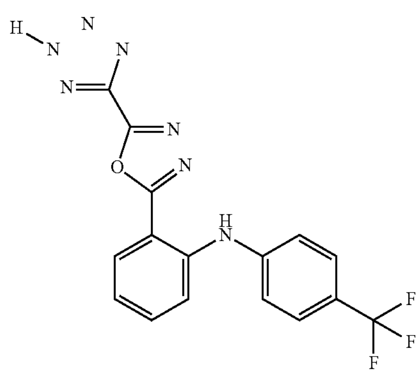 | 2-[5-(2H-tetrazol-5-yl)-1,3,4-oxadiazol-2-yl]-N-[4-(trifluoromethyl)phenyl]aniline |

TABLE 1-continued

| Compound No. | Structure | Name |
|---|---|---|
| 49 | 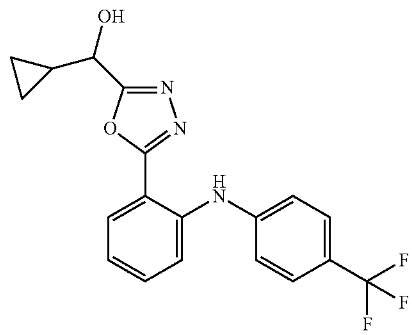 [SMILES: OC(c1nnc(-c2ccccc2Nc2ccc(C(F)(F)F)cc2)o1)C1CC1] | cyclopropyl(5-(2-((4-(trifluoromethyl)phenyl)amino)phenyl)-1,3,4-oxadiazol-2-yl)methanol |
| 50 | 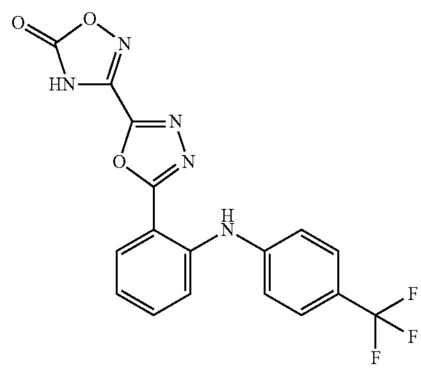 [SMILES: O=c1[nH]c(-c2nnc(-c3ccccc3Nc3ccc(C(F)(F)F)cc3)o2)no1] | 3-[5-[2-[4-(trifluoromethyl)anilino]phenyl]-1,3,4-oxadiazol-2-yl]-4H-1,2,4-oxadiazol-5-one |
| 51 | 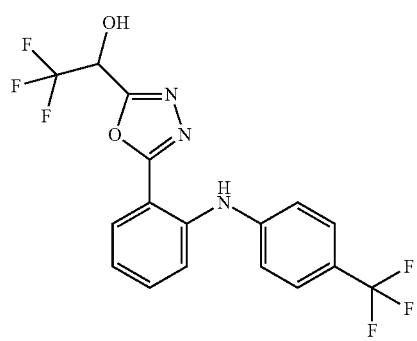 [SMILES: OC(c1nnc(-c2ccccc2Nc2ccc(C(F)(F)F)cc2)o1)C(F)(F)F] | 2,2,2-trifluoro-1-(5-(2-((4-(trifluoromethyl)phenyl)amino)phenyl)-1,3,4-oxadiazol-2-yl)ethanol |
| 52 | 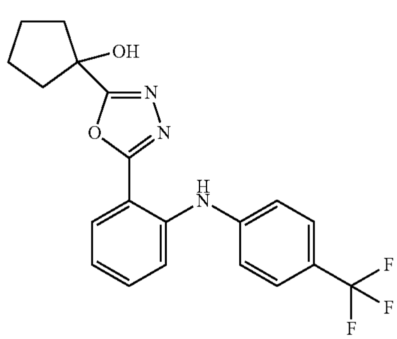 [SMILES: OC1(c2nnc(-c3ccccc3Nc3ccc(C(F)(F)F)cc3)o2)CCCC1] | 1-(5-(2-((4-(trifluoromethyl)phenyl)amino)phenyl)-1,3,4-oxadiazol-2-yl)cyclopentanol |

TABLE 1-continued

| Compound No. | Structure | Name |
|---|---|---|
| 53 | 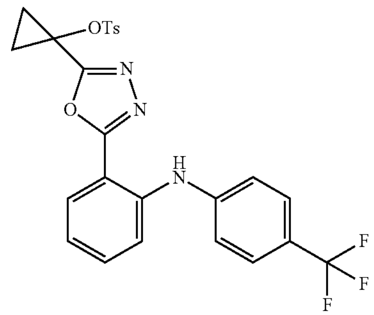 [SMILES: Cc1ccc(S(=O)(=O)OC2(c3nnc(-c4ccccc4Nc4ccc(C(F)(F)F)cc4)o3)CC2)cc1] | 1-(5-(2-((4-(trifluoromethyl)phenyl)amino)phenyl)-1,3,4-oxadiazol-2-yl)cyclopropyl4-methylbenzenesulfonate |
| 54 | 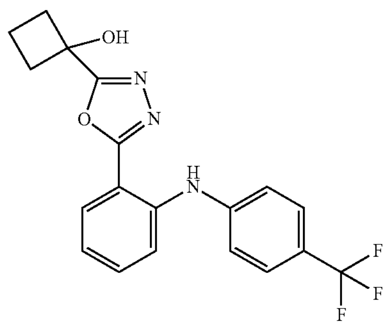 [SMILES: OC1(c2nnc(-c3ccccc3Nc3ccc(C(F)(F)F)cc3)o2)CCC1] | 1-(5-(2-((4-(trifluoromethyl)phenyl)amino)phenyl)-1,3,4-oxadiazol-2-yl)cyclobutanol |
| 55 | 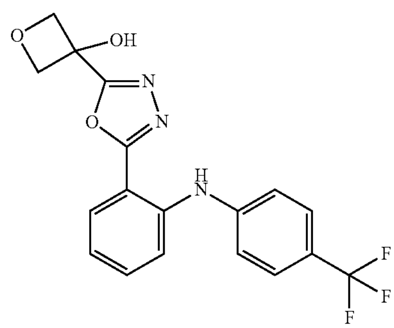 [SMILES: OC1(c2nnc(-c3ccccc3Nc3ccc(C(F)(F)F)cc3)o2)COC1] | 3-(5-(2-((4-(trifluoromethyl)phenyl)amino)phenyl)-1,3,4-oxadiazol-2-yl)oxetan-3-ol |
| 56 | 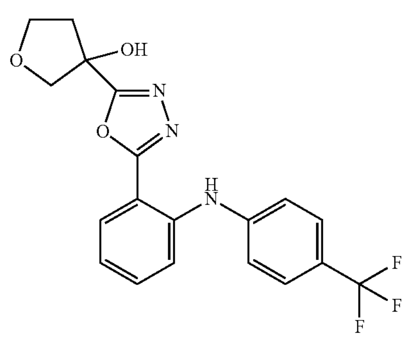 [SMILES: OC1(c2nnc(-c3ccccc3Nc3ccc(C(F)(F)F)cc3)o2)CCOC1] | 3-(5-(2-((4-(trifluoromethyl)phenyl)amino)phenyl)-1,3,4-oxadiazol-2-yl)tetrahydrofuran-3-ol |

TABLE 1-continued

| Compound No. | Structure | Name |
|---|---|---|
| 57 | 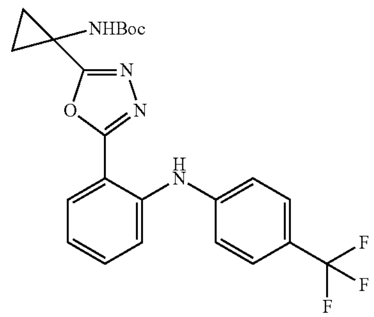 [SMILES: CC(C)(C)OC(=O)NC1(c2nnc(-c3ccccc3Nc3ccc(C(F)(F)F)cc3)o2)CC1] | (1-(5-(2-((4-(trifluoromethyl)phenyl)amino)phenyl)-1,3,4-oxadiazol-2-yl)cyclopropyl)carbamate |
| 58 | 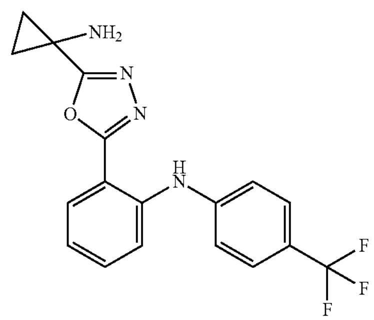 | 2-(5-(1-aminocyclopropyl)-1,3,4-oxadiazol-2-yl)-N-(4-(trifluoromethyl)phenyl)aniline |
| 59 | 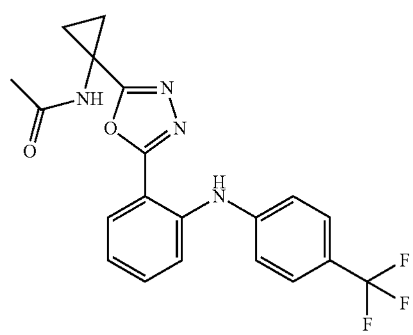 [SMILES: CC(=O)NC1(c2nnc(-c3ccccc3Nc3ccc(C(F)(F)F)cc3)o2)CC1] | N-(1-(5-(2-((4-(trifluoromethyl)phenyl)amino)phenyl)-1,3,4-oxadiazol-2-yl)cyclopropyl)acetamide |
| 60 | 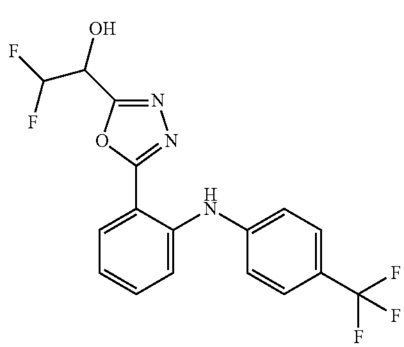 [SMILES: OC(c1nnc(-c2ccccc2Nc2ccc(C(F)(F)F)cc2)o1)C(F)F] | 2,2-difluoro-1-(5-(2-((4-(trifluoromethyl)phenyl)amino)phenyl)-1,3,4-oxadiazol-2-yl)ethanol |

TABLE 1-continued

| Compound No. | Structure | Name |
|---|---|---|
| 61 | 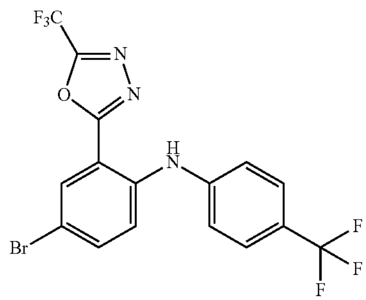 [SMILES: FC(F)(F)c1ccc(Nc2ccc(Br)cc2-c2nnc(C(F)(F)F)o2)cc1] | 4-bromo-2-(5-(trifluoromethyl)-1,3,4-oxadiazol-2-yl)-N-(4-(trifluoromethyl)phenyl)aniline |
| 62 | 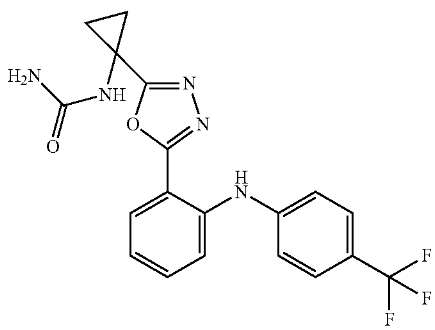 [SMILES: NC(=O)NC1(c2nnc(-c3ccccc3Nc3ccc(C(F)(F)F)cc3)o2)CC1] | 1-(1-(5-(2-((4-(trifluoromethyl)phenyl)amino)phenyl)-1,3,4-oxadiazol-2-yl)cyclopropyl)urea |
| 63 | 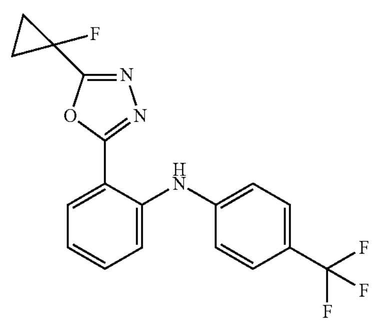 [SMILES: FC(F)(F)c1ccc(Nc2ccccc2-c2nnc(C3(F)CC3)o2)cc1] | 2-(5-(1-fluorocyclopropyl)-1,3,4-oxadiazol-2-yl)-N-(4-(trifluoromethyl)phenyl)aniline |
| 66 | 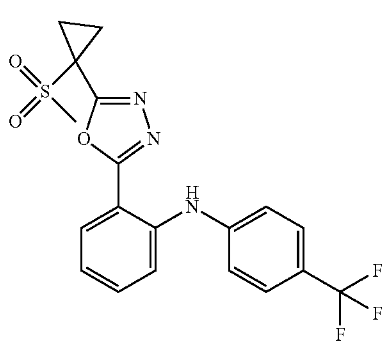 [SMILES: CS(=O)(=O)C1(c2nnc(-c3ccccc3Nc3ccc(C(F)(F)F)cc3)o2)CC1] | 2-[5-(1-methylsulfonylcyclopropyl)-1,3,4-oxadiazol-2-yl]-N-[4-(trifluoromethyl)phenyl]aniline |

TABLE 1-continued

| Compound No. | Structure | Name |
|---|---|---|
| 67 | 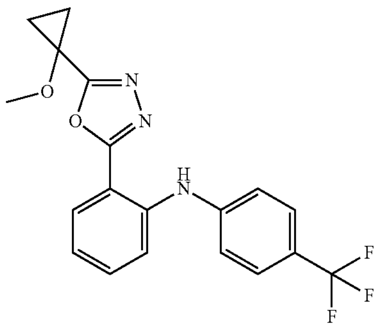 [SMILES: COC1(c2nnc(-c3ccccc3Nc3ccc(C(F)(F)F)cc3)o2)CC1] | 2-(5-(1-methoxycyclopropyl)-1,3,4-oxadiazol-2-yl)-N-(4-(trifluoromethyl)phenyl)aniline |
| 68 | 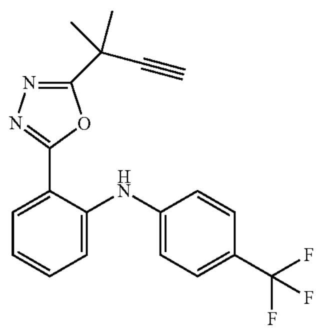 [SMILES: C#CC(C)(C)c1nnc(-c2ccccc2Nc2ccc(C(F)(F)F)cc2)o1] | 2-(5-(2-methylbut-3-yn-2-yl)-1,3,4-oxadiazol-2-yl)-N-(4-(trifluoromethyl)phenyl)aniline |
| 69 | 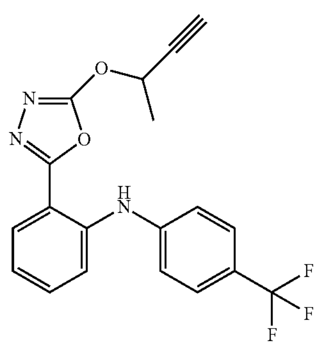 [SMILES: C#CC(C)Oc1nnc(-c2ccccc2Nc2ccc(C(F)(F)F)cc2)o1] | 2-(5-(but-3-yn-2-yloxy)-1,3,4-oxadiazol-2-yl)-N-(4-(trifluoromethyl)phenyl)aniline |
| 70 | 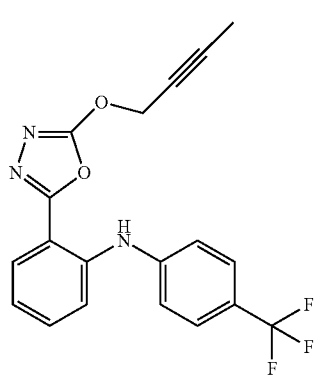 [SMILES: CC#CCOc1nnc(-c2ccccc2Nc2ccc(C(F)(F)F)cc2)o1] | 2-(5-(but-2-yn-1-yloxy)-1,3,4-oxadiazol-2-yl)-N-(4-(trifluoromethyl)phenyl)aniline |

TABLE 1-continued

| Compound No. | Structure | Name |
|---|---|---|
| 71 | 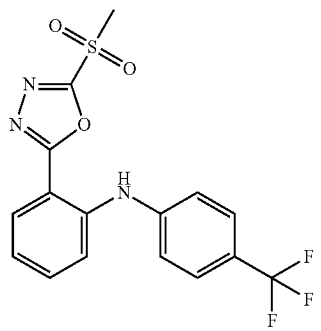 [SMILES: CS(=O)(=O)c1nnc(-c2ccccc2Nc2ccc(C(F)(F)F)cc2)o1] | 2-(5-(methylsulfonyl)-1,3,4-oxadiazol-2-yl)-N-(4-(trifluoromethyl)phenyl)aniline |
| 72 | 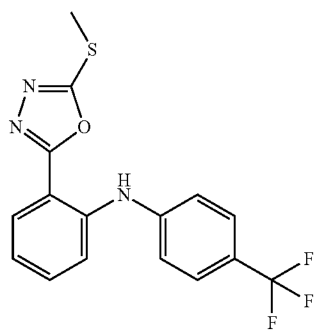 [SMILES: COc1nnc(-c2ccccc2Nc2ccc(C(F)(F)F)cc2)o1] | 2-(5-(methylthio)-1,3,4-oxadiazol-2-yl)-N-(4-(trifluoromethyl)phenyl)aniline |
| 73 | 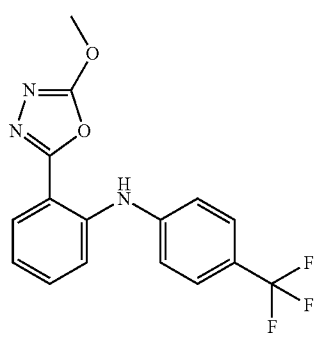 | 2-(5-methoxy-1,3,4-oxadiazol-2-yl)-N-(4-(trifluoromethyl)phenyl)aniline |
| 74 | 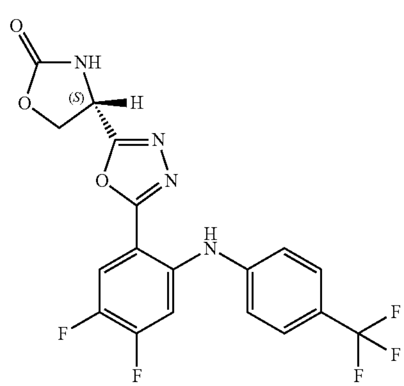 | (S)-4-(5-(4,5-difluoro-2-((4-(trifluoromethyl)phenyl)amino)phenyl)-1,3,4-oxadiazol-2-yl)oxazolidin-2-one |

TABLE 1-continued

| Compound No. | Structure | Name |
|---|---|---|
| 75 | 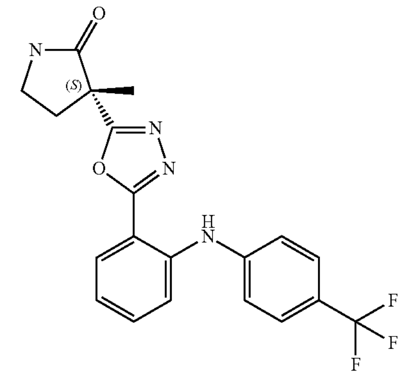 | (S)-3-methyl-3-(5-(2-((4-(trifluoromethyl)phenyl)amino)phenyl)-1,3,4-oxadiazol-2-yl)pyrrolidin-2-one |
| 76 | 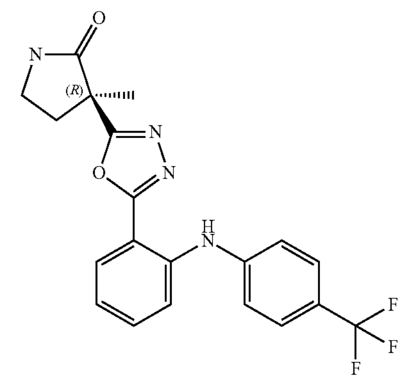 | (R)-3-methyl-3-(5-(2-((4-(trifluoromethyl)phenyl)amino)phenyl)-1,3,4-oxadiazol-2-yl)pyrrolidin-2-one |
| 77 | 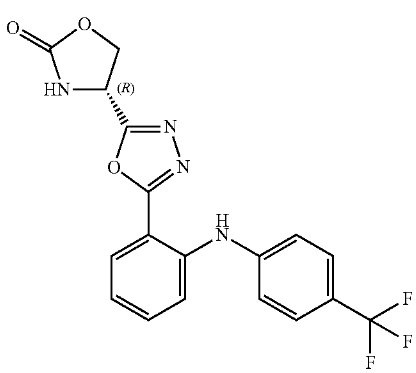 | (R)-4-(5-(2-((4-(trifluoromethyl)phenyl)amino)phenyl)-1,3,4-oxadiazol-2-yl)oxazolidin-2-one |
| 78 | 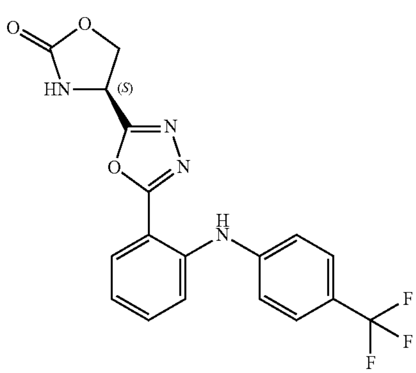 | (S)-4-(5-(2-((4-(trifluoromethyl)phenyl)amino)phenyl)-1,3,4-oxadiazol-2-yl)oxazolidin-2-one |

TABLE 1-continued

| Compound No. | Structure | Name |
|---|---|---|
| 79 | 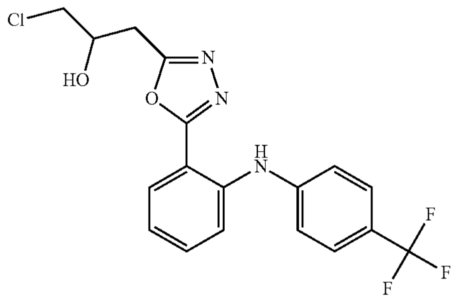 [SMILES: OC(CCl)Cc1nnc(-c2ccccc2Nc2ccc(C(F)(F)F)cc2)o1] | 1-chloro-3-(5-(2-((4-(trifluoromethyl)phenyl)amino)phenyl)-1,3,4-oxadiazol-2-yl)propan-2-ol |
| 80 | 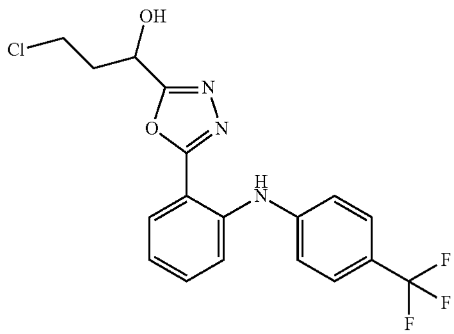 [SMILES: OC(CCCl)c1nnc(-c2ccccc2Nc2ccc(C(F)(F)F)cc2)o1] | 3-chloro-1-(5-(2-((4-(trifluoromethyl)phenyl)amino)phenyl)-1,3,4-oxadiazol-2-yl)propan-1-ol |
| 81 | 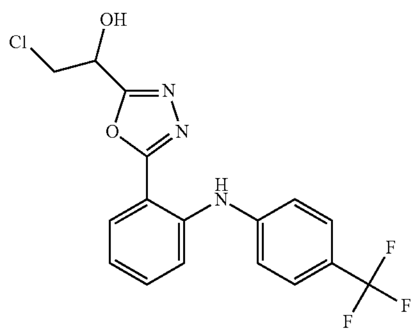 [SMILES: OC(CCl)c1nnc(-c2ccccc2Nc2ccc(C(F)(F)F)cc2)o1] | 2-chloro-1-(5-(2-((4-(trifluoromethyl)phenyl)amino)phenyl)-1,3,4-oxadiazol-2-yl)ethan-1-ol |
| 82 | 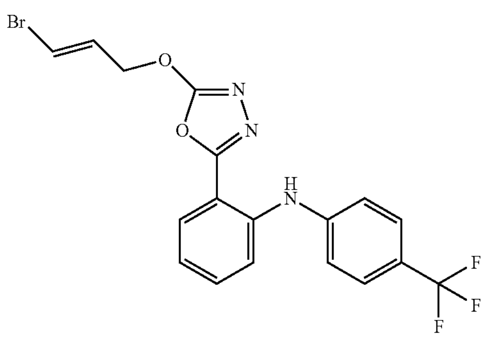 [SMILES: FC(F)(F)c1ccc(Nc2ccccc2-c2nnc(OC/C=C/Br)o2)cc1] | (E)-2-(5-((3-bromoallyl)oxy)-1,3,4-oxadiazol-2-yl)-N-(4-(trifluoromethyl)phenyl)aniline |

TABLE 1-continued

| Compound No. | Structure | Name |
|---|---|---|
| 83 | 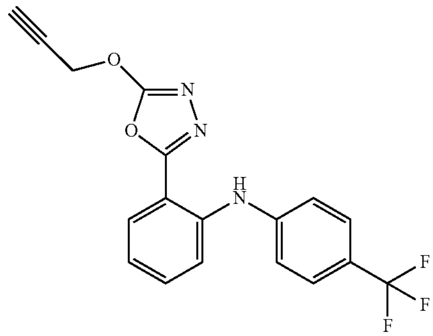 [SMILES: C#CCOc1nnc(-c2ccccc2Nc2ccc(C(F)(F)F)cc2)o1] | 2-(5-(prop-2-yn-1-yloxy)-1,3,4-oxadiazol-2-yl)-N-(4-(trifluoromethyl)phenyl)aniline |
| 84 | 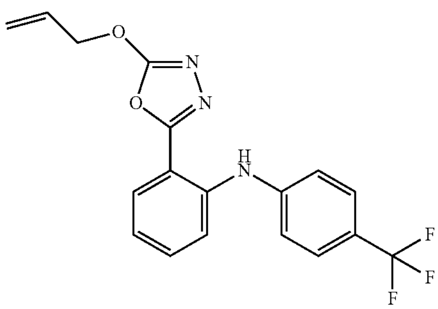 [SMILES: C=CCOc1nnc(-c2ccccc2Nc2ccc(C(F)(F)F)cc2)o1] | 2-(5-(allyloxy)-1,3,4-oxadiazol-2-yl)-N-(4-(trifluoromethyl)phenyl)aniline |
| 85 | 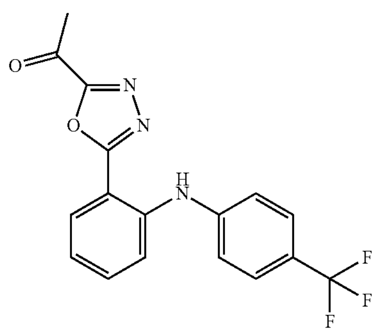 [SMILES: CC(=O)c1nnc(-c2ccccc2Nc2ccc(C(F)(F)F)cc2)o1] | 1-(5-(2-((4-(trifluoromethyl)phenyl)amino)phenyl)-1,3,4-oxadiazol-2-yl)ethan-1-one |
| 86 | 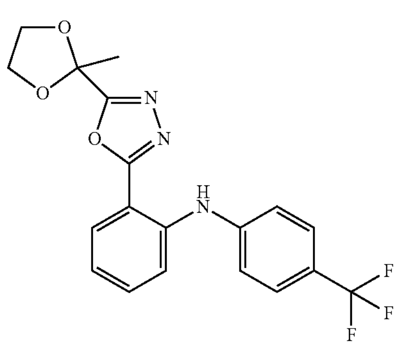 [SMILES: CC1(c2nnc(-c3ccccc3Nc3ccc(C(F)(F)F)cc3)o2)OCCO1] | 2-(5-(2-methyl-1,3-dioxolan-2-yl)-1,3,4-oxadiazol-2-yl)-N-(4-(trifluoromethyl)phenyl)aniline |

TABLE 1-continued

| Compound No. | Structure | Name |
|---|---|---|
| 87 | 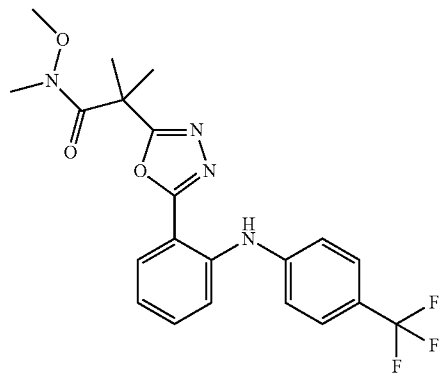 [SMILES: CON(C)C(=O)C(C)(C)c1nnc(-c2ccccc2Nc2ccc(C(F)(F)F)cc2)o1] | N-methoxy-N,2-dimethyl-2-(5-(2-((4-(trifluoromethyl)phenyl)amino)phenyl)-1,3,4-oxadiazol-2-yl)propanamide |
| 88 | 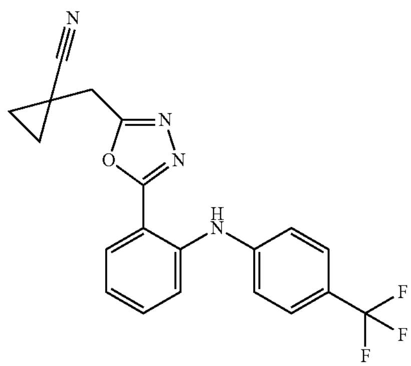 [SMILES: N#CC1(Cc2nnc(-c3ccccc3Nc3ccc(C(F)(F)F)cc3)o2)CC1] | 1-((5-(2-((4-(trifluoromethyl)phenyl)amino)phenyl)-1,3,4-oxadiazol-2-yl)methyl)cyclopropane-1-carbonitrile |
| 89 | 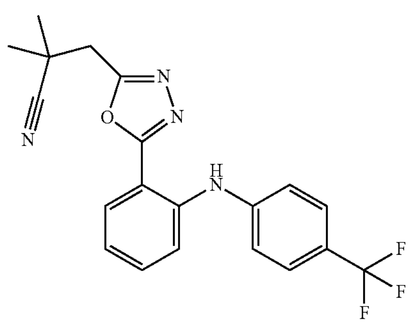 [SMILES: CC(C)(C#N)Cc1nnc(-c2ccccc2Nc2ccc(C(F)(F)F)cc2)o1] | 2,2-dimethyl-3-(5-(2-((4-(trifluoromethyl)phenyl)amino)phenyl)-1,3,4-oxadiazol-2-yl)propanenitrile |
| 90 | 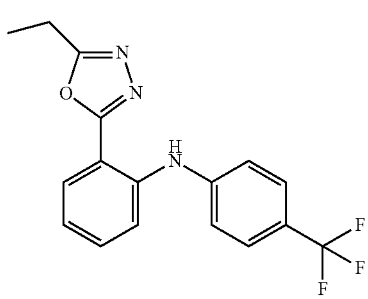 [SMILES: CCc1nnc(-c2ccccc2Nc2ccc(C(F)(F)F)cc2)o1] | 2-(5-ethyl-1,3,4-oxadiazol-2-yl)-N-(4-(trifluoromethyl)phenyl)aniline |

TABLE 1-continued

| Compound No. | Structure | Name |
|---|---|---|
| 91 | 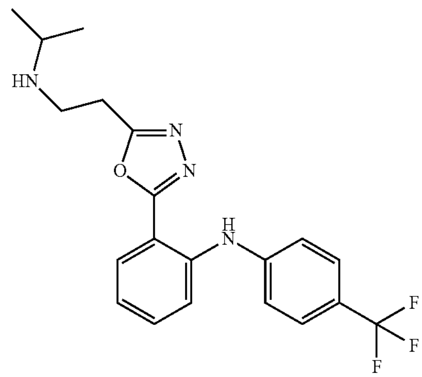 [SMILES: CC(C)NCCc1nnc(-c2ccccc2Nc2ccc(C(F)(F)F)cc2)o1] | 2-(5-(2-(isopropylamino)ethyl)-1,3,4-oxadiazol-2-yl)-N-(4-(trifluoromethyl)phenyl)aniline |
| 92 | 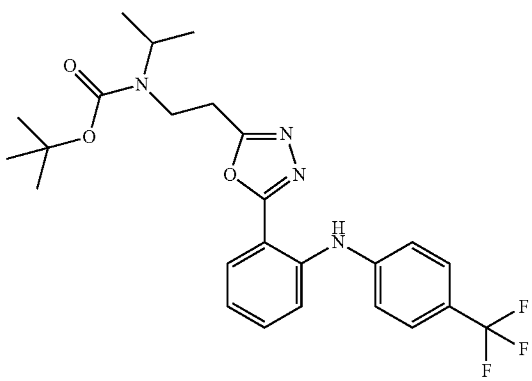 [SMILES: CC(C)N(CCc1nnc(-c2ccccc2Nc2ccc(C(F)(F)F)cc2)o1)C(=O)OC(C)(C)C] | tert-butyl isopropyl(2-(5-(2-((4-(trifluoromethyl)phenyl)amino)phenyl)-1,3,4-oxadiazol-2-yl)ethyl)carbamate |
| 93 | 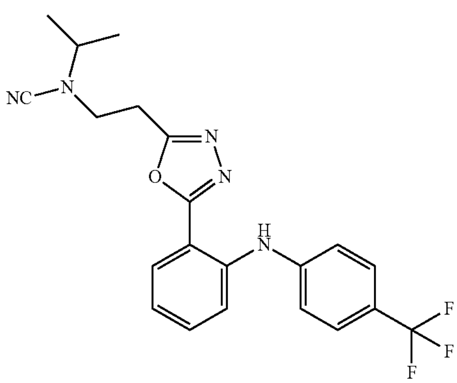 [SMILES: CC(C)N(C#N)CCc1nnc(-c2ccccc2Nc2ccc(C(F)(F)F)cc2)o1] | N-isopropyl-N-(2-(5-(2-((4-(trifluoromethyl)phenyl)amino)phenyl)-1,3,4-oxadiazol-2-yl)ethyl)cyanamide |
| 94 | 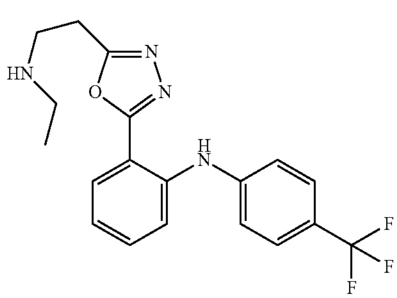 [SMILES: CCNCCc1nnc(-c2ccccc2Nc2ccc(C(F)(F)F)cc2)o1] | 2-(5-(2-(ethylamino)ethyl)-1,3,4-oxadiazol-2-yl)-N-(4-(trifluoromethyl)phenyl)aniline |

TABLE 1-continued

| Compound No. | Structure | Name |
|---|---|---|
| 95 | 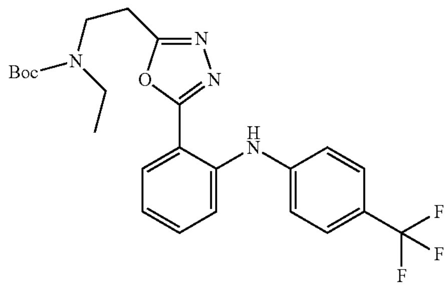 [SMILES: CCN(CCc1nnc(-c2ccccc2Nc2ccc(C(F)(F)F)cc2)o1)C(=O)OC(C)(C)C] | tert-butylethyl(2-(5-(2-((4-(trifluoromethyl)phenyl)amino)phenyl)-1,3,4-oxadiazol-2-yl)ethyl)carbamate |
| 96 | 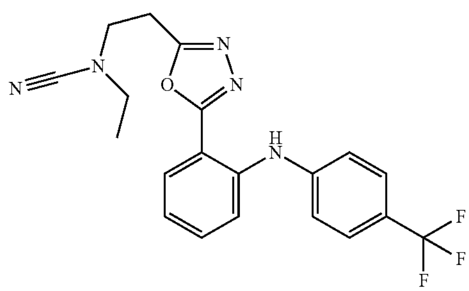 [SMILES: CCN(C#N)CCc1nnc(-c2ccccc2Nc2ccc(C(F)(F)F)cc2)o1] | N-ethyl-N-(2-(5-(2-((4-(trifluoromethyl)phenyl)amino)phenyl)-1,3,4-oxadiazol-2-yl)ethyl)cyanamide |
| 97 | 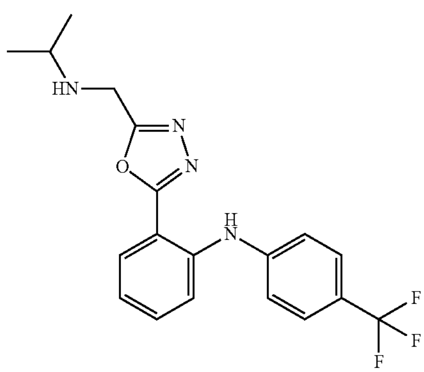 [SMILES: CC(C)NCc1nnc(-c2ccccc2Nc2ccc(C(F)(F)F)cc2)o1] | 2-(5-((isopropylamino)methyl)-1,3,4-oxadiazol-2-yl)-N-(4-(trifluoromethyl)phenyl)aniline |
| 98 | 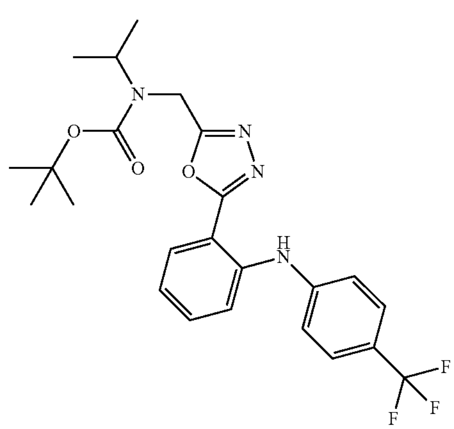 [SMILES: CC(C)N(Cc1nnc(-c2ccccc2Nc2ccc(C(F)(F)F)cc2)o1)C(=O)OC(C)(C)C] | tert-butylisopropyl((5-(2-((4-(trifluoromethyl)phenyl)amino)phenyl)-1,3,4-oxadiazol-2-yl)methyl)carbamate |

TABLE 1-continued

| Compound No. | Structure | Name |
|---|---|---|
| 99 | 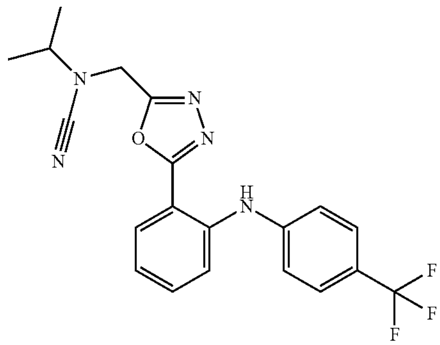 [SMILES: CC(C)N(C#N)Cc1nnc(-c2ccccc2Nc2ccc(C(F)(F)F)cc2)o1] | N-isopropyl-N-((5-(2-((4-(trifluoromethyl)phenyl)amino)phenyl)-1,3,4-oxadiazol-2-yl)methyl)cyanamide |
| 100 | 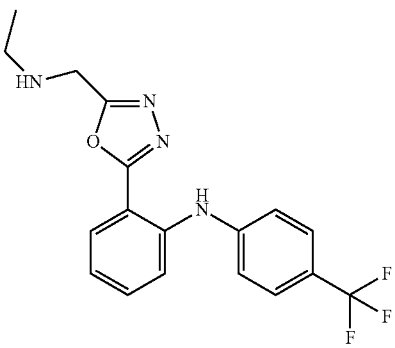 [SMILES: CCNCc1nnc(-c2ccccc2Nc2ccc(C(F)(F)F)cc2)o1] | 2-(5-((ethylamino)methyl)-1,3,4-oxadiazol-2-yl)-N-(4-(trifluoromethyl)phenyl)aniline |
| 101 | 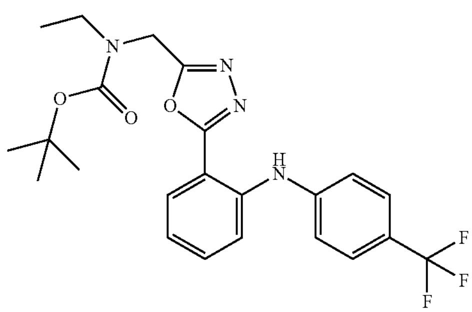 [SMILES: CCN(Cc1nnc(-c2ccccc2Nc2ccc(C(F)(F)F)cc2)o1)C(=O)OC(C)(C)C] | tert-butylethyl((5-(2-((4-(trifluoromethyl)phenyl)amino)phenyl)-1,3,4-oxadiazol-2-yl)methyl)carbamate |
| 102 | 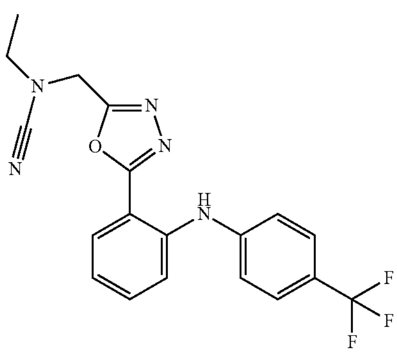 [SMILES: CCN(C#N)Cc1nnc(-c2ccccc2Nc2ccc(C(F)(F)F)cc2)o1] | N-ethyl-N-((5-(2-((4-(trifluoromethyl)phenyl)amino)phenyl)-1,3,4-oxadiazol-2-yl)methyl)cyanamide |

TABLE 1-continued

| Compound No. | Structure | Name |
|---|---|---|
| 103 | 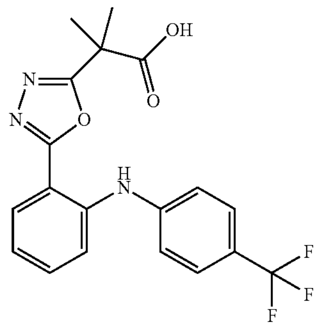 [SMILES: CC(C)(C(=O)O)c1nnc(-c2ccccc2Nc2ccc(C(F)(F)F)cc2)o1] | 2-methyl-2-(5-(2-((4-(trifluoromethyl)phenyl)amino)phenyl)-1,3,4-oxadiazol-2-yl)propanoic acid |
| 104 | 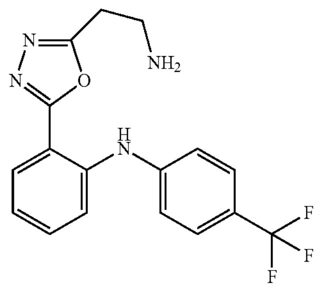 [SMILES: NCCc1nnc(-c2ccccc2Nc2ccc(C(F)(F)F)cc2)o1] | 2-(5-(2-aminoethyl)-1,3,4-oxadiazol-2-yl)-N-(4-(trifluoromethyl)phenyl)aniline |
| 105 | 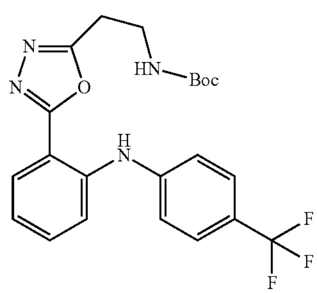 [SMILES: CC(C)(C)OC(=O)NCCc1nnc(-c2ccccc2Nc2ccc(C(F)(F)F)cc2)o1] | tert-butyl(2-(5-(2-((4-(trifluoromethyl)phenyl)amino)phenyl)-1,3,4-oxadiazol-2-yl)ethyl)carbamate |
| 106 | 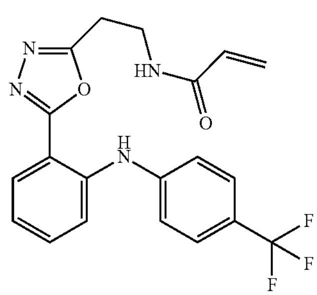 [SMILES: C=CC(=O)NCCc1nnc(-c2ccccc2Nc2ccc(C(F)(F)F)cc2)o1] | N-(2-(5-(2-((4-(trifluoromethyl)phenyl)amino)phenyl)-1,3,4-oxadiazol-2-yl)ethyl)acrylamide |
| 107 | 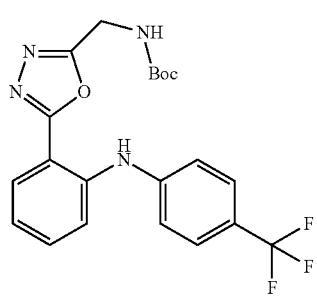 [SMILES: CC(C)(C)OC(=O)NCc1nnc(-c2ccccc2Nc2ccc(C(F)(F)F)cc2)o1] | tert-butyl((5-(2-((4-(trifluoromethyl)phenyl)amino)phenyl)-1,3,4-oxadiazol-2-yl)methyl)carbamate |

TABLE 1-continued

| Compound No. | Structure | Name |
|---|---|---|
| 108 | 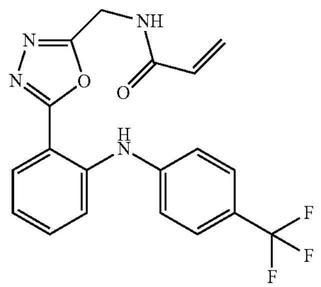 [SMILES: C=CC(=O)NCc1nnc(-c2ccccc2Nc2ccc(C(F)(F)F)cc2)o1] | N-((5-(2-((4-(trifluoromethyl)phenyl)amino)phenyl)-1,3,4-oxadiazol-2-yl)methyl)acrylamide |
| 109 | 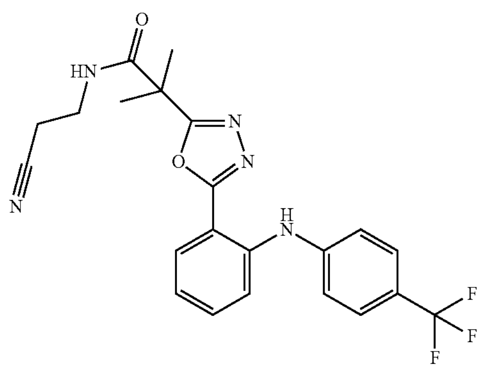 [SMILES: CC(C)(C(=O)NCCC#N)c1nnc(-c2ccccc2Nc2ccc(C(F)(F)F)cc2)o1] | N-(2-cyanoethyl)-2-methyl-2-(5-(2-((4-(trifluoromethyl)phenyl)amino)phenyl)-1,3,4-oxadiazol-2-yl)propanamide |
| 110 | 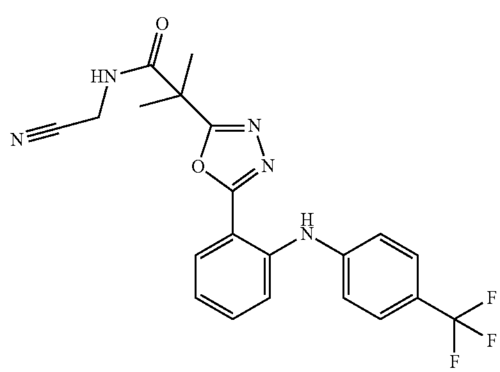 [SMILES: CC(C)(C(=O)NCC#N)c1nnc(-c2ccccc2Nc2ccc(C(F)(F)F)cc2)o1] | N-(cyanomethyl)-2-methyl-2-(5-(2-((4-(trifluoromethyl)phenyl)amino)phenyl)-1,3,4-oxadiazol-2-yl)propanamide |
| 111 | 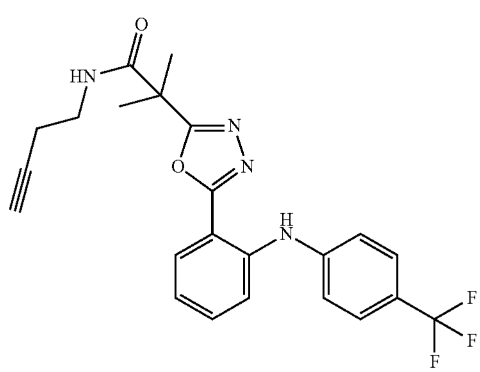 [SMILES: C#CCCNC(=O)C(C)(C)c1nnc(-c2ccccc2Nc2ccc(C(F)(F)F)cc2)o1] | N-(but-3-yn-1-yl)-2-methyl-2-(5-(2-((4-(trifluoromethyl)phenyl)amino)phenyl)-1,3,4-oxadiazol-2-yl)propanamide |

TABLE 1-continued

| Compound No. | Structure | Name |
|---|---|---|
| 112 | 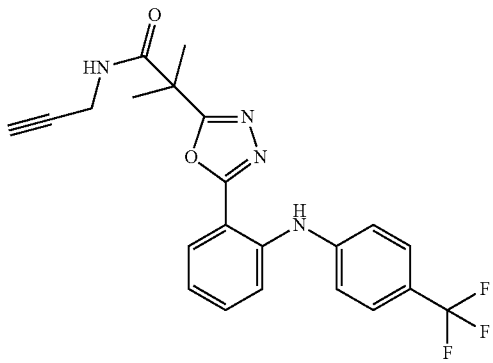 [SMILES: C#CCNC(=O)C(C)(C)c1nnc(-c2ccccc2Nc2ccc(C(F)(F)F)cc2)o1] | 2-methyl-N-(prop-2-yn-1-yl)-2-(5-(2-((4-(trifluoromethyl)phenyl)amino)phenyl)-1,3,4-oxadiazol-2-yl)propanamide |
| 113 | 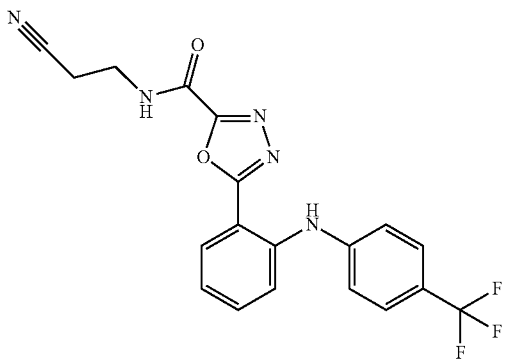 [SMILES: N#CCCNC(=O)c1nnc(-c2ccccc2Nc2ccc(C(F)(F)F)cc2)o1] | N-(2-cyanoethyl)-5-(2-((4-(trifluoromethyl)phenyl)amino)phenyl)-1,3,4-oxadiazole-2-carboxamide |
| 114 | 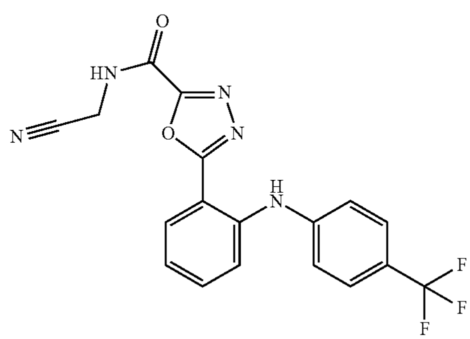 [SMILES: N#CCNC(=O)c1nnc(-c2ccccc2Nc2ccc(C(F)(F)F)cc2)o1] | N-(cyanomethyl)-5-(2-((4-(trifluoromethyl)phenyl)amino)phenyl)-1,3,4-oxadiazole-2-carboxamide |
| 115 | 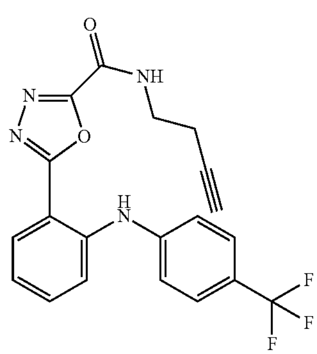 [SMILES: C#CCCNC(=O)c1nnc(-c2ccccc2Nc2ccc(C(F)(F)F)cc2)o1] | N-(but-3-yn-1-yl)-5-(2-((4-(trifluoromethyl)phenyl)amino)phenyl)-1,3,4-oxadiazole-2-carboxamide |

TABLE 1-continued

| Compound No. | Structure | Name |
|---|---|---|
| 116 | 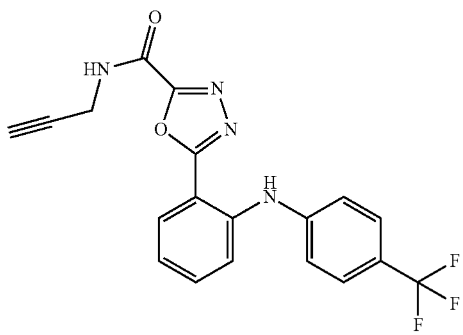 [SMILES: C#CCNC(=O)c1nnc(-c2ccccc2Nc2ccc(C(F)(F)F)cc2)o1] | N-(prop-2-yn-1-yl)-5-(2-((4-(trifluoromethyl)phenyl)amino)phenyl)-1,3,4-oxadiazole-2-carboxamide |
| 117 | 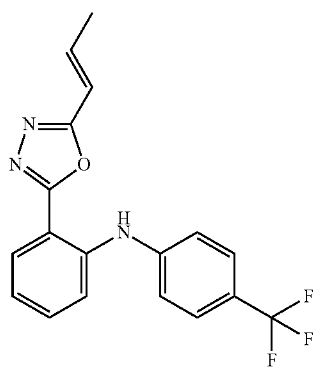 [SMILES: C/C=C/c1nnc(-c2ccccc2Nc2ccc(C(F)(F)F)cc2)o1] | (E)-2-(5-(prop-1-en-1-yl)-1,3,4-oxadiazol-2-yl)-N-(4-(trifluoromethyl)phenyl)aniline |
| 118 | 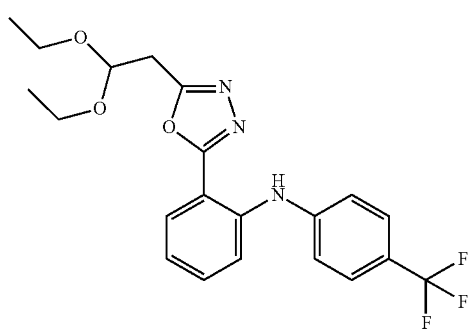 [SMILES: CCOC(Cc1nnc(-c2ccccc2Nc2ccc(C(F)(F)F)cc2)o1)OCC] | 2-(5-(2,2-diethoxyethyl)-1,3,4-oxadiazol-2-yl)-N-(4-(trifluoromethyl)phenyl)aniline |
| 119 | 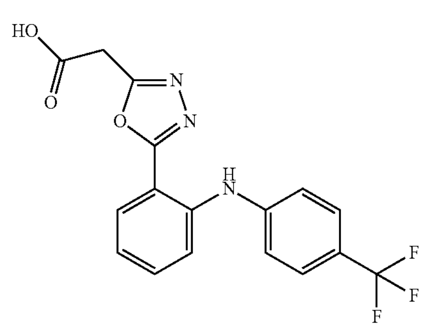 [SMILES: O=C(O)Cc1nnc(-c2ccccc2Nc2ccc(C(F)(F)F)cc2)o1] | 2-(5-(2-((4-(trifluoromethyl)phenyl)amino)phenyl)-1,3,4-oxadiazol-2-yl)acetic acid |

TABLE 1-continued

| Compound No. | Structure | Name |
|---|---|---|
| 120 | 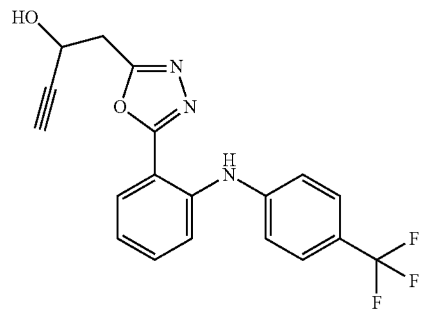 [SMILES: C#CC(O)Cc1nnc(-c2ccccc2Nc2ccc(C(F)(F)F)cc2)o1] | 1-(5-(2-((4-(trifluoromethyl)phenyl)amino)phenyl)-1,3,4-oxadiazol-2-yl)but-3-yn-2-ol |
| 121 | 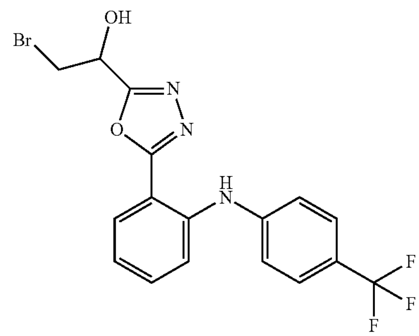 [SMILES: OC(CBr)c1nnc(-c2ccccc2Nc2ccc(C(F)(F)F)cc2)o1] | 2-bromo-1-(5-(2-((4-(trifluoromethyl)phenyl)amino)phenyl)-1,3,4-oxadiazol-2-yl)ethan-1-ol |
| 122 | 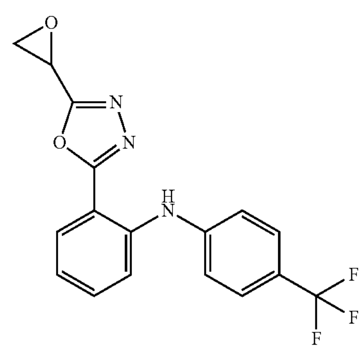 [SMILES: FC(F)(F)c1ccc(Nc2ccccc2-c2nnc(C3CO3)o2)cc1] | 2-(5-(oxiran-2-yl)-1,3,4-oxadiazol-2-yl)-N-(4-(trifluoromethyl)phenyl)aniline |
| 123 | 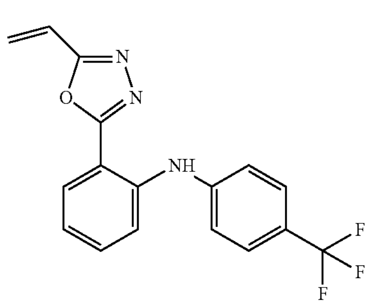 [SMILES: C=Cc1nnc(-c2ccccc2Nc2ccc(C(F)(F)F)cc2)o1] | N-(4-(trifluoromethyl)phenyl)-2-(5-vinyl-1,3,4-oxadiazol-2-yl)aniline |

TABLE 1-continued

| Compound No. | Structure | Name |
|---|---|---|
| 124 | 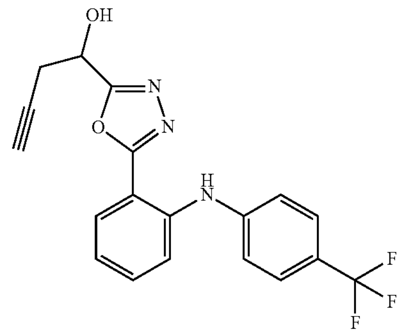 [SMILES: C#CCC(O)c1nnc(-c2ccccc2Nc2ccc(C(F)(F)F)cc2)o1] | 1-(5-(2-((4-(trifluoromethyl)phenyl)amino)phenyl)-1,3,4-oxadiazol-2-yl)but-3-yn-1-ol |
| 125 | 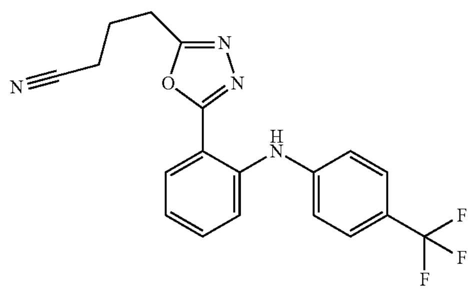 [SMILES: N#CCCCc1nnc(-c2ccccc2Nc2ccc(C(F)(F)F)cc2)o1] | 4-(5-(2-((4-(trifluoromethyl)phenyl)amino)phenyl)-1,3,4-oxadiazol-2-yl)butanenitrile |
| 126 | 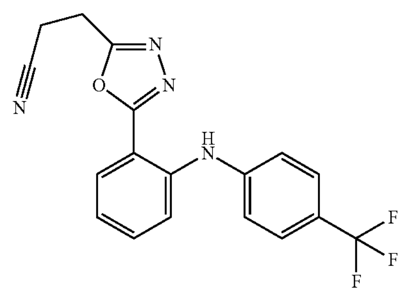 [SMILES: N#CCCc1nnc(-c2ccccc2Nc2ccc(C(F)(F)F)cc2)o1] | 3-(5-(2-((4-(trifluoromethyl)phenyl)amino)phenyl)-1,3,4-oxadiazol-2-yl)propanenitrile |
| 127 | 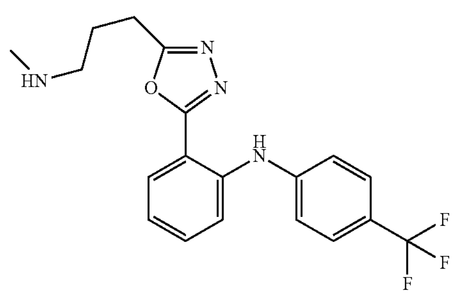 [SMILES: CNCCCc1nnc(-c2ccccc2Nc2ccc(C(F)(F)F)cc2)o1] | 2-(5-(3-(methylamino)propyl)-1,3,4-oxadiazol-2-yl)-N-(4-(trifluoromethyl)phenyl)aniline |
| 128 | 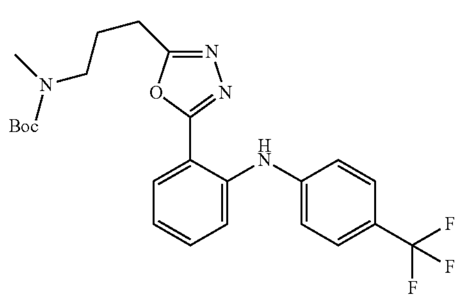 [SMILES: CN(CCCc1nnc(-c2ccccc2Nc2ccc(C(F)(F)F)cc2)o1)C(=O)OC(C)(C)C] | tert-butyl methyl(3-(5-(2-((4-(trifluoromethyl)phenyl)amino)phenyl)-1,3,4-oxadiazol-2-yl)propyl)carbamate |

TABLE 1-continued

| Compound No. | Structure | Name |
|---|---|---|
| 129 | 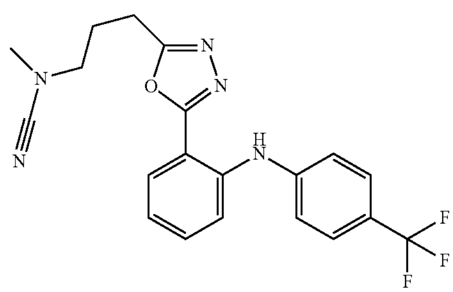 [SMILES: CN(C#N)CCCc1nnc(-c2ccccc2Nc2ccc(C(F)(F)F)cc2)o1] | N-methyl-N-(3-(5-(2-((4-(trifluoromethyl)phenyl)amino)phenyl)-1,3,4-oxadiazol-2-yl)propyl)cyanamide |
| 130 | 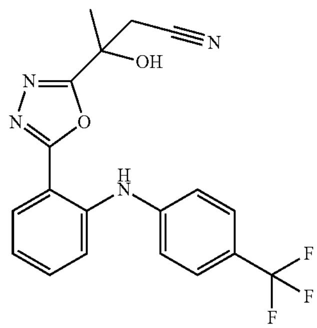 [SMILES: CC(O)(CC#N)c1nnc(-c2ccccc2Nc2ccc(C(F)(F)F)cc2)o1] | 3-hydroxy-3-(5-(2-((4-(trifluoromethyl)phenyl)amino)phenyl)-1,3,4-oxadiazol-2-yl)butanenitrile |
| 131 | 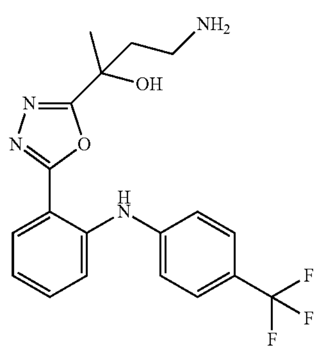 [SMILES: CC(O)(CCN)c1nnc(-c2ccccc2Nc2ccc(C(F)(F)F)cc2)o1] | 4-amino-2-(5-(2-((4-(trifluoromethyl)phenyl)amino)phenyl)-1,3,4-oxadiazol-2-yl)butan-2-ol |
| 132 | 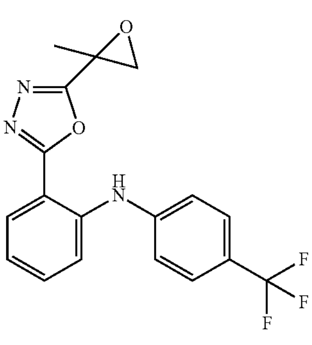 [SMILES: CC1(c2nnc(-c3ccccc3Nc3ccc(C(F)(F)F)cc3)o2)CO1] | 2-(5-(2-methyloxiran-2-yl)-1,3,4-oxadiazol-2-yl)-N-(4-(trifluoromethyl)phenyl)aniline |

TABLE 1-continued

| Compound No. | Structure | Name |
|---|---|---|
| 133 | 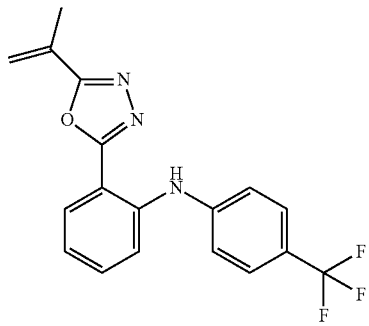 [SMILES: C=C(C)c1nnc(-c2ccccc2Nc2ccc(C(F)(F)F)cc2)o1] | 2-(5-(prop-1-en-2-yl)-1,3,4-oxadiazol-2-yl)-N-(4-(trifluoromethyl)phenyl)aniline |
| 134 | 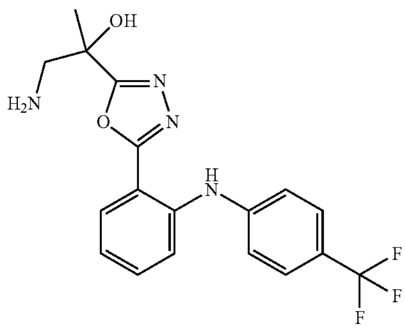 [SMILES: CC(O)(CN)c1nnc(-c2ccccc2Nc2ccc(C(F)(F)F)cc2)o1] | 1-amino-2-(5-(2-((4-(trifluoromethyl)phenyl)amino)phenyl)-1,3,4-oxadiazol-2-yl)propan-2-ol |
| 135 | 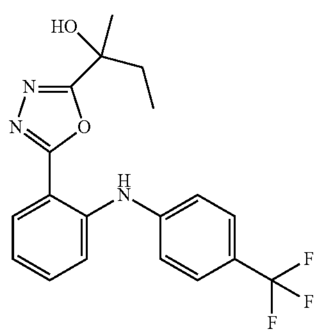 [SMILES: CCC(C)(O)c1nnc(-c2ccccc2Nc2ccc(C(F)(F)F)cc2)o1] | 2-(5-(2-((4-(trifluoromethyl)phenyl)amino)phenyl)-1,3,4-oxadiazol-2-yl)butan-2-ol |
| 136 | 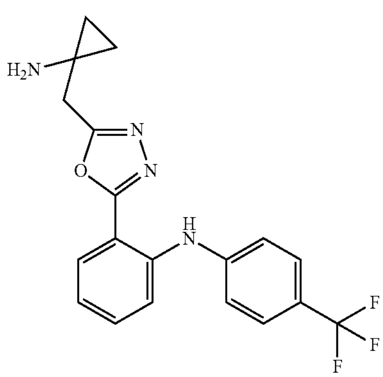 [SMILES: NC1(Cc2nnc(-c3ccccc3Nc3ccc(C(F)(F)F)cc3)o2)CC1] | 2-(5-((1-aminocyclopropyl)methyl)-1,3,4-oxadiazol-2-yl)-N-(4-(trifluoromethyl)phenyl)aniline |

TABLE 1-continued

| Compound No. | Structure | Name |
|---|---|---|
| 137 | 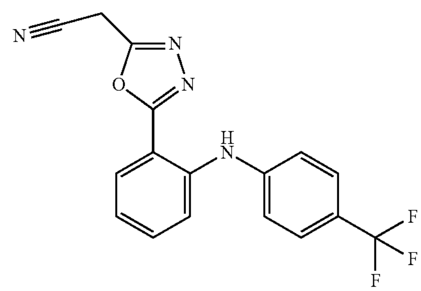 [SMILES: N#CCc1nnc(-c2ccccc2Nc2ccc(C(F)(F)F)cc2)o1] | 2-(5-(2-((4-(trifluoromethyl)phenyl)amino)phenyl)-1,3,4-oxadiazol-2-yl)acetonitrile |
| 138 | 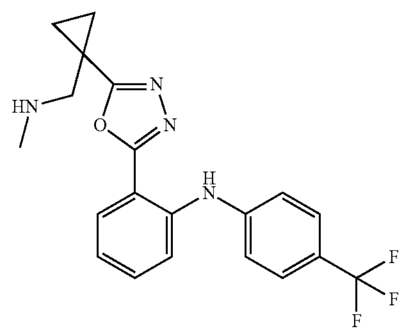 [SMILES: CNCC1(c2nnc(-c3ccccc3Nc3ccc(C(F)(F)F)cc3)o2)CC1] | 2-(5-(1-((methylamino)methyl)cyclopropyl)-1,3,4-oxadiazol-2-yl)-N-(4-(trifluoromethyl)phenyl)aniline |
| 139 | 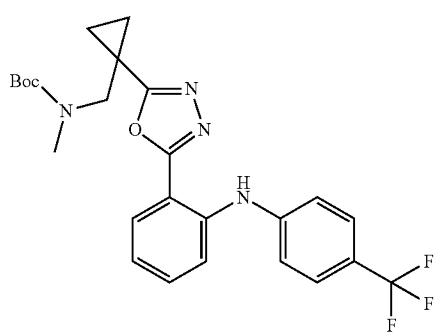 [SMILES: CN(CC1(c2nnc(-c3ccccc3Nc3ccc(C(F)(F)F)cc3)o2)CC1)C(=O)OC(C)(C)C] | tert-butylmethyl((1-(5-(2-((4-(trifluoromethyl)phenyl)amino)phenyl)-1,3,4-oxadiazol-2-yl)cyclopropyl)methyl)carbamate |
| 140 | 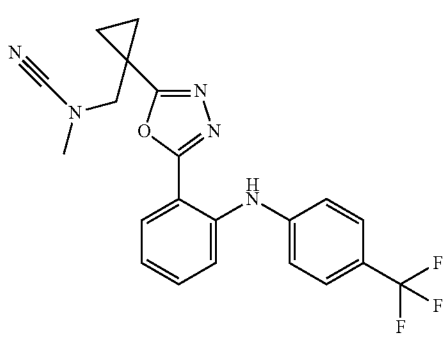 [SMILES: CN(C#N)CC1(c2nnc(-c3ccccc3Nc3ccc(C(F)(F)F)cc3)o2)CC1] | N-methyl-N-((1-(5-(2-((4-(trifluoromethyl)phenyl)amino)phenyl)-1,3,4-oxadiazol-2-yl)cyclopropyl)methyl)cyanamide |

TABLE 1-continued

| Compound No. | Structure | Name |
|---|---|---|
| 141 | 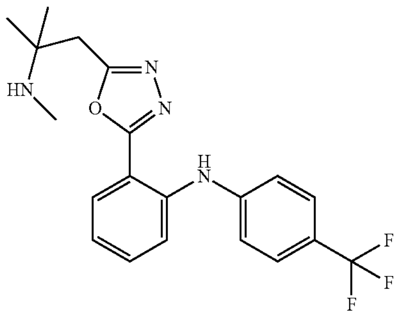 [SMILES: CNC(C)(C)Cc1nnc(-c2ccccc2Nc2ccc(C(F)(F)F)cc2)o1] | 2-(5-(2-methyl-2-(methylamino)propyl)-1,3,4-oxadiazol-2-yl)-N-(4-(trifluoromethyl)phenyl)aniline |
| 142 | 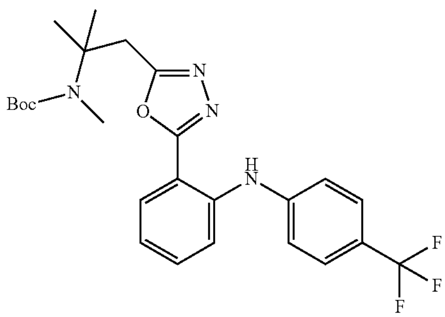 [SMILES: CN(C(=O)OC(C)(C)C)C(C)(C)Cc1nnc(-c2ccccc2Nc2ccc(C(F)(F)F)cc2)o1] | tert-butylmethyl(2-methyl-1-(5-(2-((4-(trifluoromethyl)phenyl)amino)phenyl)-1,3,4-oxadiazol-2-yl)propan-2-yl)carbamate |
| 143 | 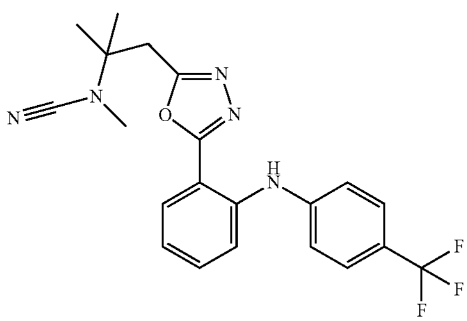 [SMILES: CN(C#N)C(C)(C)Cc1nnc(-c2ccccc2Nc2ccc(C(F)(F)F)cc2)o1] | N-methyl-N-(2-methyl-1-(5-(2-((4-(trifluoromethyl)phenyl)amino)phenyl)-1,3,4-oxadiazol-2-yl)propan-2-yl)cyanamide |
| 144 | 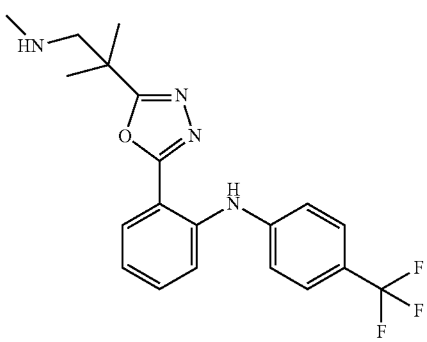 [SMILES: CNCC(C)(C)c1nnc(-c2ccccc2Nc2ccc(C(F)(F)F)cc2)o1] | 2-(5-(2-methyl-1-(methylamino)propan-2-yl)-1,3,4-oxadiazol-2-yl)-N-(4-(trifluoromethyl)phenyl)aniline |

TABLE 1-continued

| Compound No. | Structure | Name |
|---|---|---|
| 145 | 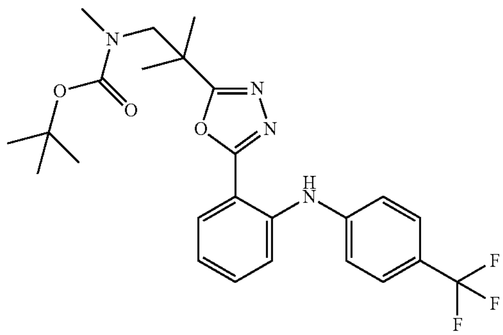 [SMILES: CN(CC(C)(C)c1nnc(-c2ccccc2Nc2ccc(C(F)(F)F)cc2)o1)C(=O)OC(C)(C)C] | tert-butylmethyl(2-methyl-2-(5-(2-((4-(trifluoromethyl)phenyl)amino)phenyl)-1,3,4-oxadiazol-2-yl)propyl)carbamate |
| 146 | 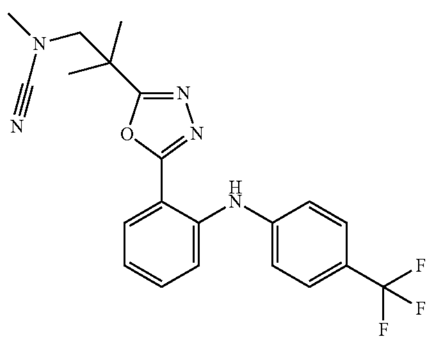 [SMILES: CN(C#N)CC(C)(C)c1nnc(-c2ccccc2Nc2ccc(C(F)(F)F)cc2)o1] | N-methyl-N-(2-methyl-2-(5-(2-((4-(trifluoromethyl)phenyl)amino)phenyl)-1,3,4-oxadiazol-2-yl)propyl)cyanamide |
| 147 | 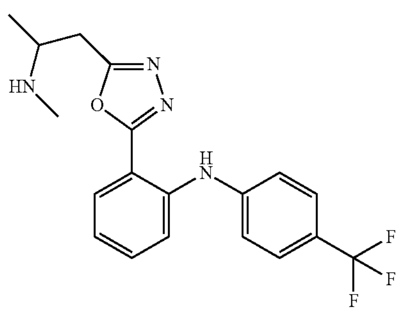 [SMILES: CNC(C)Cc1nnc(-c2ccccc2Nc2ccc(C(F)(F)F)cc2)o1] | 2-(5-(2-(methylamino)propyl)-1,3,4-oxadiazol-2-yl)-N-(4-(trifluoromethyl)phenyl)aniline |
| 148 | 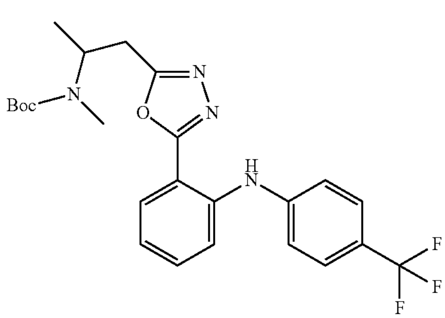 [SMILES: CC(Cc1nnc(-c2ccccc2Nc2ccc(C(F)(F)F)cc2)o1)N(C)C(=O)OC(C)(C)C] | tert-butyl methyl(1-(5-(2-((4-(trifluoromethyl)phenyl)amino)phenyl)-1,3,4-oxadiazol-2-yl)propan-2-yl)carbamate |

TABLE 1-continued

| Compound No. | Structure | Name |
|---|---|---|
| 149 | 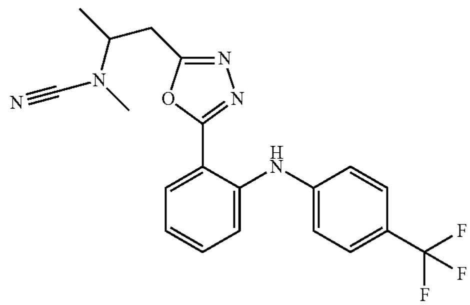 [SMILES: CC(Cc1nnc(-c2ccccc2Nc2ccc(C(F)(F)F)cc2)o1)N(C)C#N] | N-methyl-N-(1-(5-(2-((4-(trifluoromethyl)phenyl)amino)phenyl)-1,3,4-oxadiazol-2-yl)propan-2-yl)cyanamide |
| 150 | 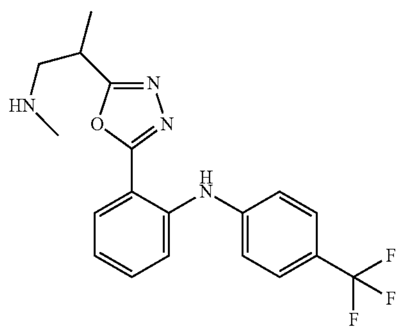 [SMILES: CNCC(C)c1nnc(-c2ccccc2Nc2ccc(C(F)(F)F)cc2)o1] | 2-(5-(1-(methylamino)propan-2-yl)-1,3,4-oxadiazol-2-yl)-N-(4-(trifluoromethyl)phenyl)aniline |
| 151 | 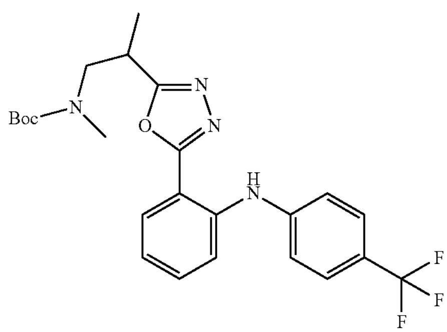 [SMILES: CC(CN(C)C(=O)OC(C)(C)C)c1nnc(-c2ccccc2Nc2ccc(C(F)(F)F)cc2)o1] | tert-butylmethyl(2-(5-(2-((4-(trifluoromethyl)phenyl)amino)phenyl)-1,3,4-oxadiazol-2-yl)propyl)carbamate |
| 152 | 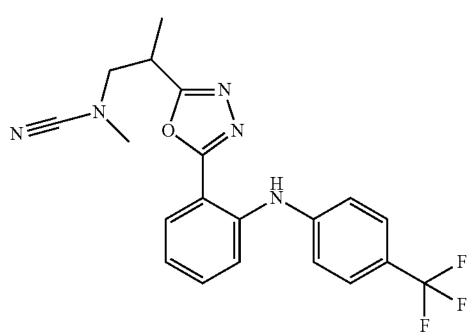 [SMILES: CC(CN(C)C#N)c1nnc(-c2ccccc2Nc2ccc(C(F)(F)F)cc2)o1] | N-methyl-N-(2-(5-(2-((4-(trifluoromethyl)phenyl)amino)phenyl)-1,3,4-oxadiazol-2-yl)propyl)cyanamide |

TABLE 1-continued

| Compound No. | Structure | Name |
|---|---|---|
| 153 | 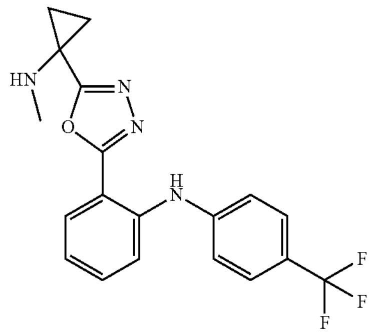 [SMILES: CNC1(c2nnc(-c3ccccc3Nc3ccc(C(F)(F)F)cc3)o2)CC1] | 2-(5-(1-(methylamino)cyclopropyl)-1,3,4-oxadiazol-2-yl)-N-(4-(trifluoromethyl)phenyl)aniline |
| 154 | 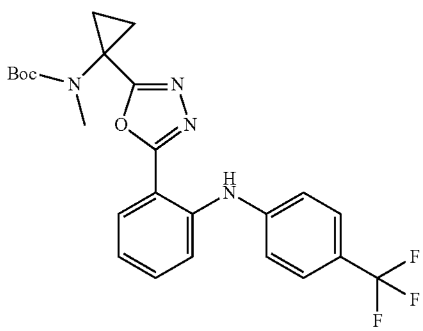 [SMILES: CN(C(=O)OC(C)(C)C)C1(c2nnc(-c3ccccc3Nc3ccc(C(F)(F)F)cc3)o2)CC1] | tert-butyl methyl(1-(5-(2-((4-(trifluoromethyl)phenyl)amino)phenyl)-1,3,4-oxadiazol-2-yl)cyclopropyl)carbamate |
| 155 | 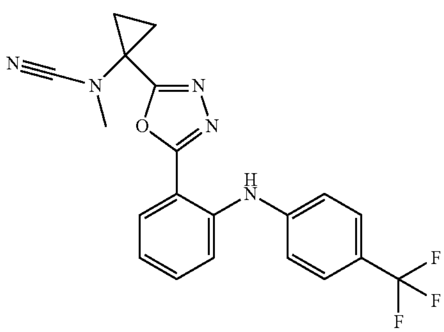 [SMILES: CN(C#N)C1(c2nnc(-c3ccccc3Nc3ccc(C(F)(F)F)cc3)o2)CC1] | N-methyl-N-(1-(5-(2-((4-(trifluoromethyl)phenyl)amino)phenyl)-1,3,4-oxadiazol-2-yl)cyclopropyl)cyanamide |
| 156 | 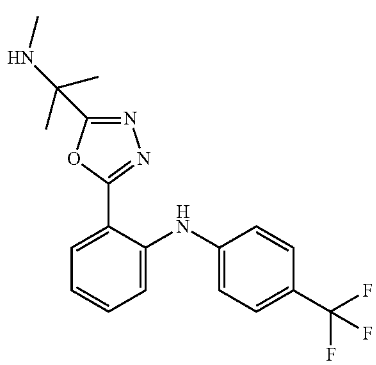 [SMILES: CNC(C)(C)c1nnc(-c2ccccc2Nc2ccc(C(F)(F)F)cc2)o1] | 2-(5-(2-(methylamino)propan-2-yl)-1,3,4-oxadiazol-2-yl)-N-(4-(trifluoromethyl)phenyl)aniline |

TABLE 1-continued

| Compound No. | Structure | Name |
|---|---|---|
| 157 | 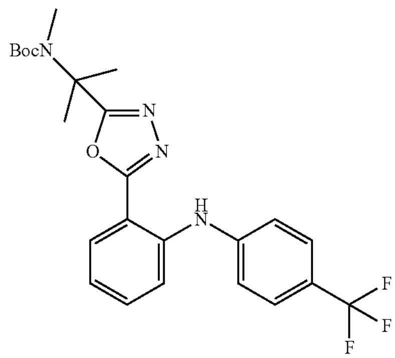 [SMILES: CN(C(=O)OC(C)(C)C)C(C)(C)c1nnc(-c2ccccc2Nc2ccc(C(F)(F)F)cc2)o1] | tert-butylmethyl(2-(5-(2-((4-(trifluoromethyl)phenyl)amino)phenyl)-1,3,4-oxadiazol-2-yl)propan-2-yl)carbamate |
| 158 | 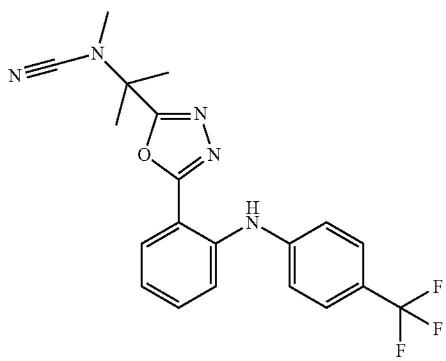 [SMILES: CN(C#N)C(C)(C)c1nnc(-c2ccccc2Nc2ccc(C(F)(F)F)cc2)o1] | N-methyl-N-(2-(5-(2-((4-(trifluoromethyl)phenyl)amino)phenyl)-1,3,4-oxadiazol-2-yl)propan-2-yl)cyanamide |
| 159 | 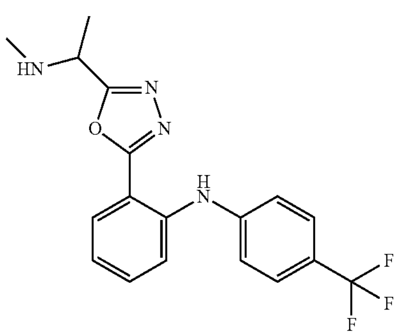 [SMILES: CNC(C)c1nnc(-c2ccccc2Nc2ccc(C(F)(F)F)cc2)o1] | 2-(5-(1-(methylamino)ethyl)-1,3,4-oxadiazol-2-yl)-N-(4-(trifluoromethyl)phenyl)aniline |
| 160 | 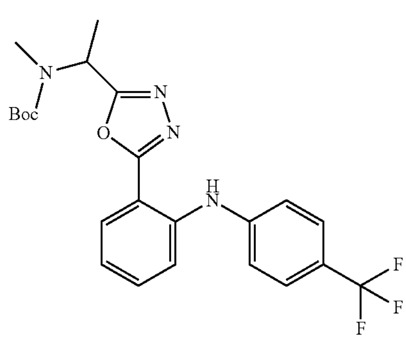 [SMILES: CC(c1nnc(-c2ccccc2Nc2ccc(C(F)(F)F)cc2)o1)N(C)C(=O)OC(C)(C)C] | tert-butylmethyl(1-(5-(2-((4-(trifluoromethyl)phenyl)amino)phenyl)-1,3,4-oxadiazol-2-yl)ethyl)carbamate |

TABLE 1-continued

| Compound No. | Structure | Name |
| --- | --- | --- |
| 161 | 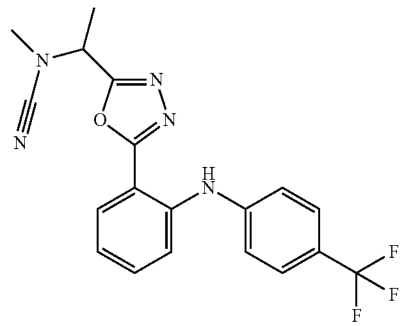 [SMILES: CC(c1nnc(-c2ccccc2Nc2ccc(C(F)(F)F)cc2)o1)N(C)C#N] | N-methyl-N-(1-(5-(2-((4-(trifluoromethyl)phenyl)amino)phenyl)-1,3,4-oxadiazol-2-yl)ethyl)cyanamide |
| 162 | 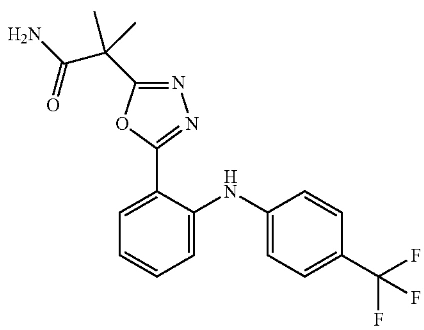 [SMILES: CC(C)(C(N)=O)c1nnc(-c2ccccc2Nc2ccc(C(F)(F)F)cc2)o1] | 2-methyl-2-(5-(2-((4-(trifluoromethyl)phenyl)amino)phenyl)-1,3,4-oxadiazol-2-yl)propanamide |
| 163 | 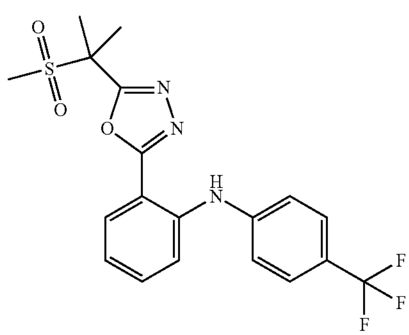 [SMILES: CC(C)(c1nnc(-c2ccccc2Nc2ccc(C(F)(F)F)cc2)o1)S(C)(=O)=O] | 2-(5-(2-(methylsulfonyl)propan-2-yl)-1,3,4-oxadiazol-2-yl)-N-(4-(trifluoromethyl)phenyl)aniline |
| 164 | 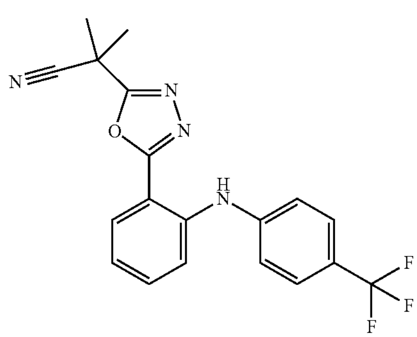 [SMILES: CC(C)(C#N)c1nnc(-c2ccccc2Nc2ccc(C(F)(F)F)cc2)o1] | 2-methyl-2-(5-(2-((4-(trifluoromethyl)phenyl)amino)phenyl)-1,3,4-oxadiazol-2-yl)propanenitrile |

TABLE 1-continued

| Compound No. | Structure | Name |
|---|---|---|
| 165 | 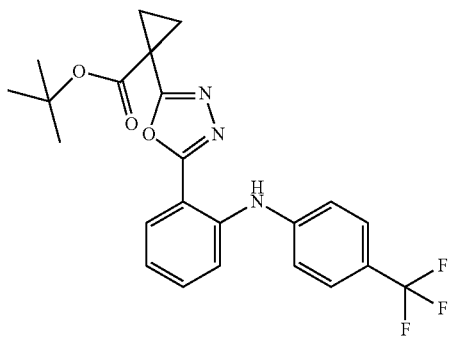 [SMILES: CC(C)(C)OC(=O)C1(c2nnc(-c3ccccc3Nc3ccc(C(F)(F)F)cc3)o2)CC1] | tert-butyl 1-(5-(2-((4-(trifluoromethyl)phenyl)amino)phenyl)-1,3,4-oxadiazol-2-yl)cyclopropane-1-carboxylate |
| 166 | 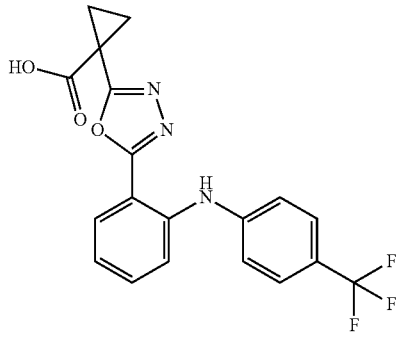 [SMILES: O=C(O)C1(c2nnc(-c3ccccc3Nc3ccc(C(F)(F)F)cc3)o2)CC1] | 1-(5-(2-((4-(trifluoromethyl)phenyl)amino)phenyl)-1,3,4-oxadiazol-2-yl)cyclopropane-1-carboxylic acid |
| 167 | 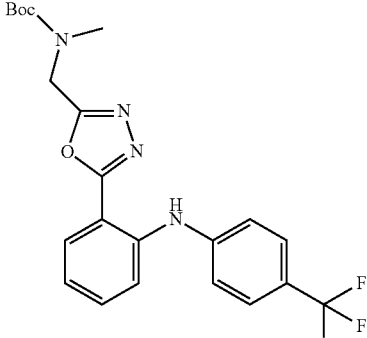 | tert-butyl methyl((5-(2-((4-(trifluoromethyl)phenyl)amino)phenyl)-1,3,4-oxadiazol-2-yl)methyl)carbamate |
| 168 | 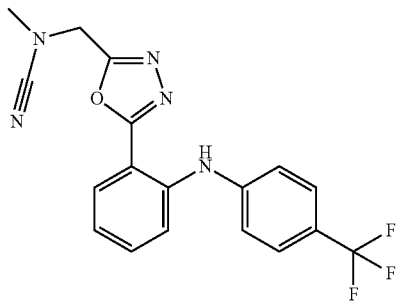 [SMILES: CN(C#N)Cc1nnc(-c2ccccc2Nc2ccc(C(F)(F)F)cc2)o1] | N-methyl-N-((5-(2-((4-(trifluoromethyl)phenyl)amino)phenyl)-1,3,4-oxadiazol-2-yl)methyl)cyanamide |

TABLE 1-continued

| Compound No. | Structure | Name |
|---|---|---|
| 169 | 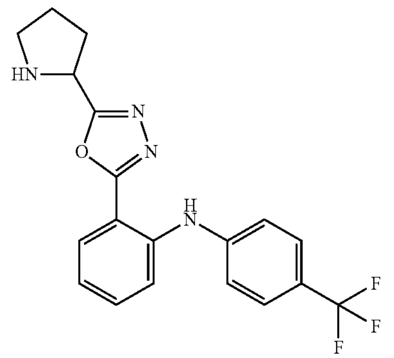 [SMILES: FC(F)(F)c1ccc(Nc2ccccc2-c2nnc(C3CCCN3)o2)cc1] | 2-(5-(pyrrolidin-2-yl)-1,3,4-oxadiazol-2-yl)-N-(4-(trifluoromethyl)phenyl)aniline |
| 170 | 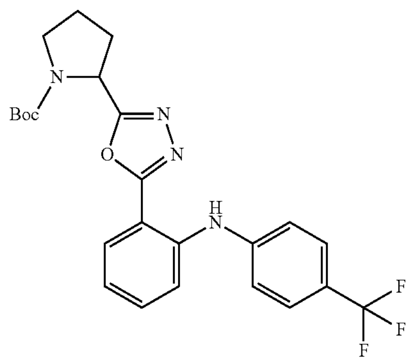 [SMILES: CC(C)(C)OC(=O)N1CCCC1c1nnc(-c2ccccc2Nc2ccc(C(F)(F)F)cc2)o1] | tert-butyl 2-(5-(2-((4-(trifluoromethyl)phenyl)amino)phenyl)-1,3,4-oxadiazol-2-yl)pyrrolidine-1-carboxylate |
| 171 | 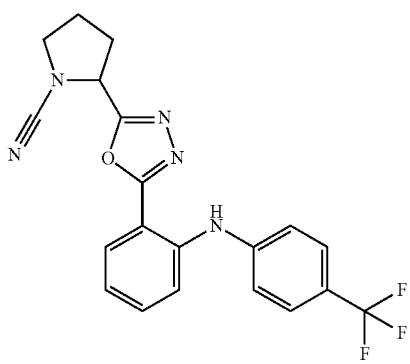 [SMILES: N#CN1CCCC1c1nnc(-c2ccccc2Nc2ccc(C(F)(F)F)cc2)o1] | 2-(5-(2-((4-(trifluoromethyl)phenyl)amino)phenyl)-1,3,4-oxadiazol-2-yl)pyrrolidine-1-carbonitrile |
| 172 | 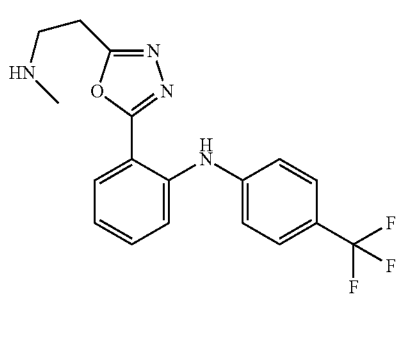 [SMILES: CNCCc1nnc(-c2ccccc2Nc2ccc(C(F)(F)F)cc2)o1] | 2-(5-(2-(methylamino)ethyl)-1,3,4-oxadiazol-2-yl)-N-(4-(trifluoromethyl)phenyl)aniline |

TABLE 1-continued

| Compound No. | Structure | Name |
|---|---|---|
| 173 | 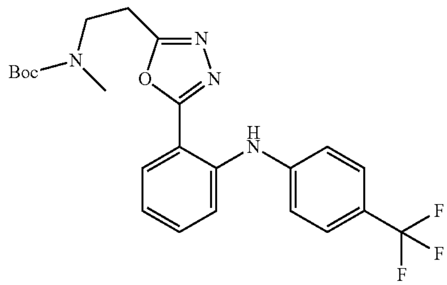 [SMILES: CN(CCc1nnc(-c2ccccc2Nc2ccc(C(F)(F)F)cc2)o1)C(=O)OC(C)(C)C] | tert-butylmethyl(2-(5-(2-((4-(trifluoromethyl)phenyl)amino)phenyl)-1,3,4-oxadiazol-2-yl)ethyl)carbamate |
| 174 | 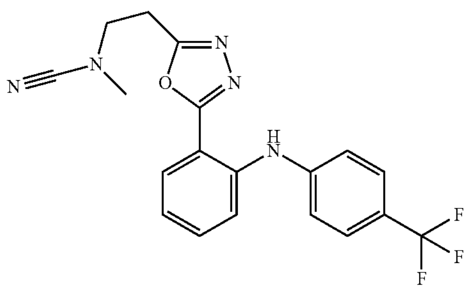 [SMILES: CN(C#N)CCc1nnc(-c2ccccc2Nc2ccc(C(F)(F)F)cc2)o1] | N-methyl-N-(2-(5-(2-((4-(trifluoromethyl)phenyl)amino)phenyl)-1,3,4-oxadiazol-2-yl)ethyl)cyanamide |
| 175 | 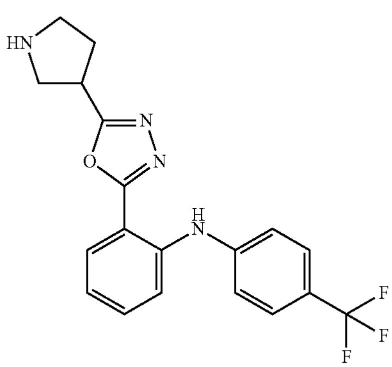 [SMILES: FC(F)(F)c1ccc(Nc2ccccc2-c2nnc(C3CCNC3)o2)cc1] | 2-(5-(pyrrolidin-3-yl)-1,3,4-oxadiazol-2-yl)-N-(4-(trifluoromethyl)phenyl)aniline |
| 176 | 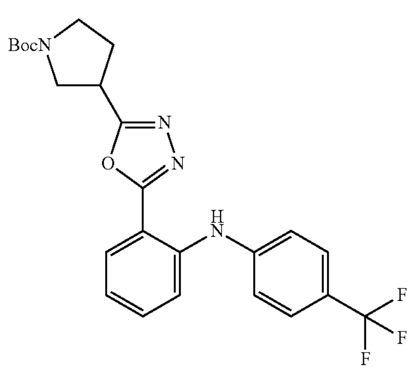 [SMILES: CC(C)(C)OC(=O)N1CCC(c2nnc(-c3ccccc3Nc3ccc(C(F)(F)F)cc3)o2)C1] | tert-butyl3-(5-(2-((4-(trifluoromethyl)phenyl)amino)phenyl)-1,3,4-oxadiazol-2-yl)pyrrolidine-1-carboxylate |

TABLE 1-continued

| Compound No. | Structure | Name |
|---|---|---|
| 177 | 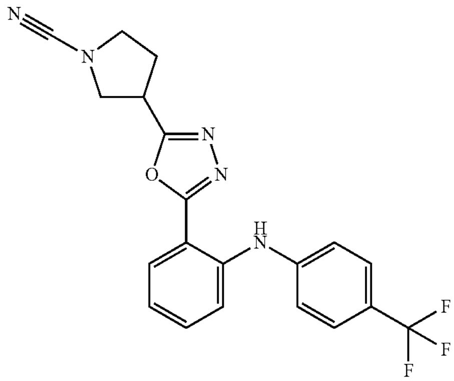 [SMILES: N#CN1CCC(c2nnc(-c3ccccc3Nc3ccc(C(F)(F)F)cc3)o2)C1] | 3-(5-(2-((4-(trifluoromethyl)phenyl)amino)phenyl)-1,3,4-oxadiazol-2-yl)pyrrolidine-1-carbonitrile |
| 178 | 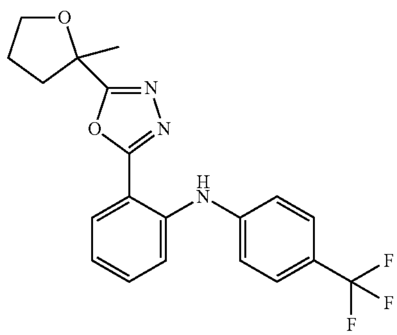 | 2-(5-(2-methyltetrahydrofuran-2-yl)-1,3,4-oxadiazol-2-yl)-N-(4-(trifluoromethyl)phenyl)aniline |
| 179 | 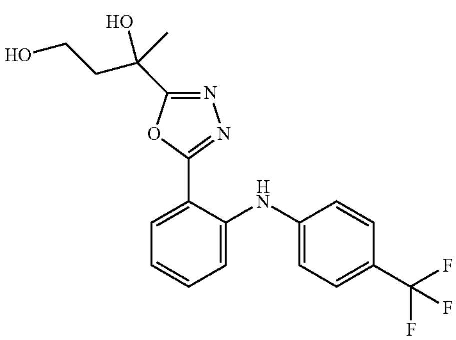 [SMILES: CC(O)(CCO)c1nnc(-c2ccccc2Nc2ccc(C(F)(F)F)cc2)o1] | 3-(5-(2-((4-(trifluoromethyl)phenyl)amino)phenyl)-1,3,4-oxadiazol-2-yl)butane-1,3-diol |
| 180 | 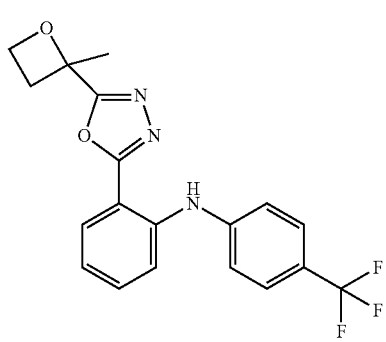 [SMILES: CC1(c2nnc(-c3ccccc3Nc3ccc(C(F)(F)F)cc3)o2)CCO1] | 2-(5-(2-methyloxetan-2-yl)-1,3,4-oxadiazol-2-yl)-N-(4-(trifluoromethyl)phenyl)aniline |

TABLE 1-continued

| Compound No. | Structure | Name |
|---|---|---|
| 181 | 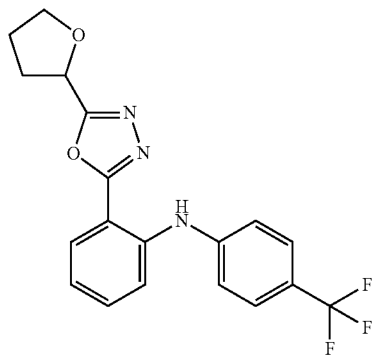 [SMILES: FC(F)(F)c1ccc(Nc2ccccc2-c2nnc(C3CCCO3)o2)cc1] | 2-(5-(tetrahydrofuran-2-yl)-1,3,4-oxadiazol-2-yl)-N-(4-(trifluoromethyl)phenyl)aniline |
| 182 | 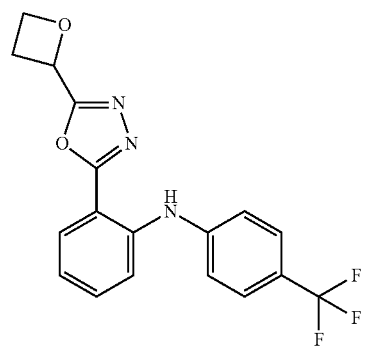 [SMILES: FC(F)(F)c1ccc(Nc2ccccc2-c2nnc(C3CCO3)o2)cc1] | 2-(5-(oxetan-2-yl)-1,3,4-oxadiazol-2-yl)-N-(4-(trifluoromethyl)phenyl)aniline |
| 183 | 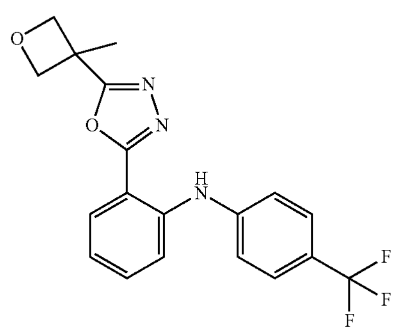 [SMILES: CC1(c2nnc(-c3ccccc3Nc3ccc(C(F)(F)F)cc3)o2)COC1] | 2-(5-(3-methyloxetan-3-yl)-1,3,4-oxadiazol-2-yl)-N-(4-(trifluoromethyl)phenyl)aniline |
| 184 | 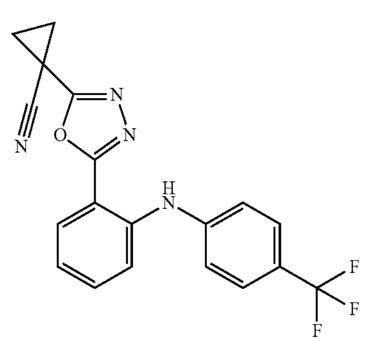 [SMILES: N#CC1(c2nnc(-c3ccccc3Nc3ccc(C(F)(F)F)cc3)o2)CC1] | 1-(5-(2-((4-(trifluoromethyl)phenyl)amino)phenyl)-1,3,4-oxadiazol-2-yl)cyclopropane-1-carbonitrile |

TABLE 1-continued

| Compound No. | Structure | Name |
|---|---|---|
| 185 | 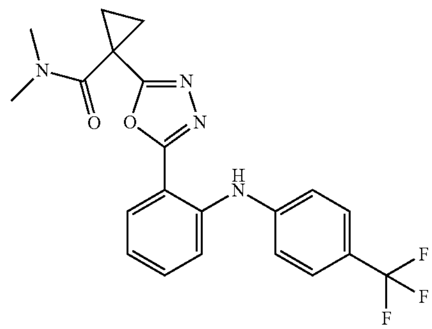 [SMILES: CN(C)C(=O)C1(c2nnc(-c3ccccc3Nc3ccc(C(F)(F)F)cc3)o2)CC1] | N,N-dimethyl-1-(5-(2-((4-(trifluoromethyl)phenyl)amino)phenyl)-1,3,4-oxadiazol-2-yl)cyclopropane-1-carboxamide |
| 186 | 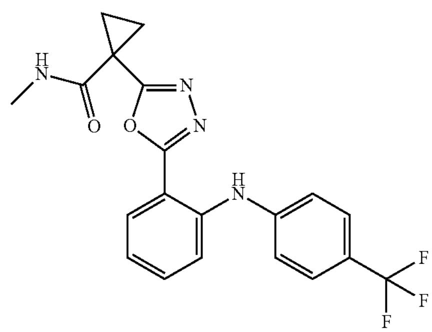 [SMILES: CNC(=O)C1(c2nnc(-c3ccccc3Nc3ccc(C(F)(F)F)cc3)o2)CC1] | N-methyl-1-(5-(2-((4-(trifluoromethyl)phenyl)amino)phenyl)-1,3,4-oxadiazol-2-yl)cyclopropane-1-carboxamide |
| 187 | 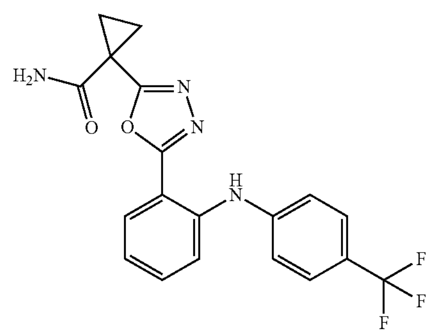 [SMILES: NC(=O)C1(c2nnc(-c3ccccc3Nc3ccc(C(F)(F)F)cc3)o2)CC1] | 1-(5-(2-((4-(trifluoromethyl)phenyl)amino)phenyl)-1,3,4-oxadiazol-2-yl)cyclopropane-1-carboxamide |
| 188 | 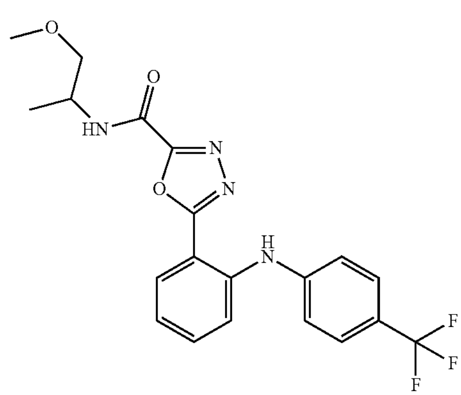 [SMILES: COCC(C)NC(=O)c1nnc(-c2ccccc2Nc2ccc(C(F)(F)F)cc2)o1] | N-(1-methoxypropan-2-yl)-5-(2-((4-(trifluoromethyl)phenyl)amino)phenyl)-1,3,4-oxadiazole-2-carboxamide |

TABLE 1-continued

| Compound No. | Structure | Name |
|---|---|---|
| 189 | 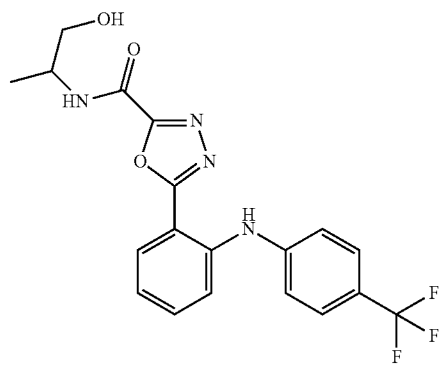 [SMILES: CC(CO)NC(=O)c1nnc(-c2ccccc2Nc2ccc(C(F)(F)F)cc2)o1] | N-(1-hydroxypropan-2-yl)-5-(2-((4-(trifluoromethyl)phenyl)amino)phenyl)-1,3,4-oxadiazole-2-carboxamide |
| 190 | 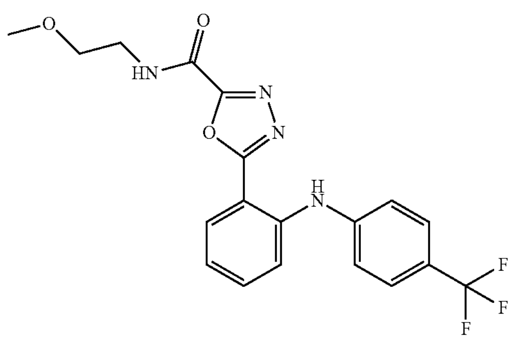 [SMILES: COCCNC(=O)c1nnc(-c2ccccc2Nc2ccc(C(F)(F)F)cc2)o1] | N-(2-methoxyethyl)-5-(2-((4-(trifluoromethyl)phenyl)amino)phenyl)-1,3,4-oxadiazole-2-carboxamide |
| 191 | 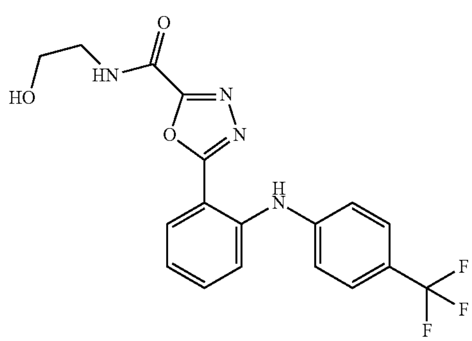 [SMILES: O=C(NCCO)c1nnc(-c2ccccc2Nc2ccc(C(F)(F)F)cc2)o1] | N-(2-hydroxyethyl)-5-(2-((4-(trifluoromethyl)phenyl)amino)phenyl)-1,3,4-oxadiazole-2-carboxamide |
| 192 | 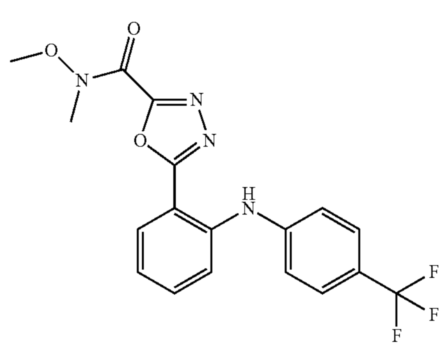 [SMILES: CON(C)C(=O)c1nnc(-c2ccccc2Nc2ccc(C(F)(F)F)cc2)o1] | N-methoxy-N-methyl-5-(2-((4-(trifluoromethyl)phenyl)amino)phenyl)-1,3,4-oxadiazole-2-carboxamide |

TABLE 1-continued

| Compound No. | Structure | Name |
|---|---|---|
| 193 | 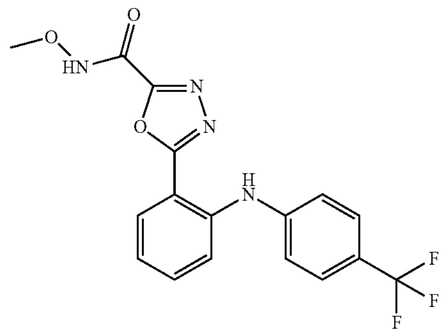 [SMILES: CONC(=O)c1nnc(-c2ccccc2Nc2ccc(C(F)(F)F)cc2)o1] | N-methoxy-5-(2-((4-(trifluoromethyl)phenyl)amino)phenyl)-1,3,4-oxadiazole-2-carboxamide |
| 194 | 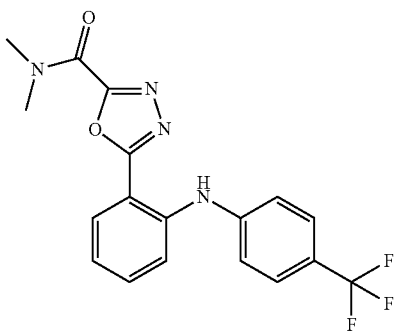 [SMILES: CN(C)C(=O)c1nnc(-c2ccccc2Nc2ccc(C(F)(F)F)cc2)o1] | N,N-dimethyl-5-(2-((4-(trifluoromethyl)phenyl)amino)phenyl)-1,3,4-oxadiazole-2-carboxamide |
| 195 | 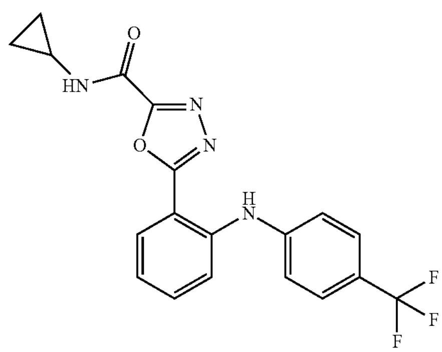 [SMILES: O=C(NC1CC1)c1nnc(-c2ccccc2Nc2ccc(C(F)(F)F)cc2)o1] | N-cyclopropyl-5-(2-((4-(trifluoromethyl)phenyl)amino)phenyl)-1,3,4-oxadiazole-2-carboxamide |
| 196 | 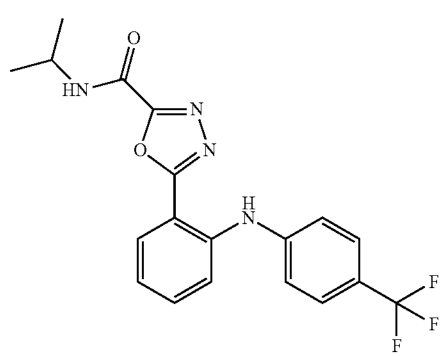 [SMILES: CC(C)NC(=O)c1nnc(-c2ccccc2Nc2ccc(C(F)(F)F)cc2)o1] | N-isopropyl-5-(2-((4-(trifluoromethyl)phenyl)amino)phenyl)-1,3,4-oxadiazole-2-carboxamide |

TABLE 1-continued

| Compound No. | Structure | Name |
|---|---|---|
| 197 | 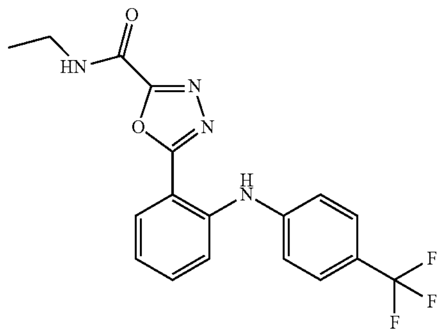 | N-ethyl-5-(2-((4-(trifluoromethyl)phenyl)amino)phenyl)-1,3,4-oxadiazole-2-carboxamide |
| 198 | 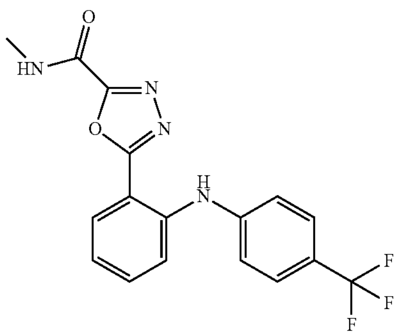 [SMILES: CNC(=O)c1nnc(-c2ccccc2Nc2ccc(C(F)(F)F)cc2)o1] | N-methyl-5-(2-((4-(trifluoromethyl)phenyl)amino)phenyl)-1,3,4-oxadiazole-2-carboxamide |
| 199 | 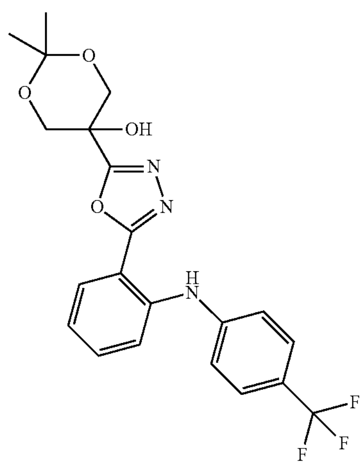 [SMILES: CC1(C)OCC(O)(c2nnc(-c3ccccc3Nc3ccc(C(F)(F)F)cc3)o2)CO1] | 2,2-dimethyl-5-(5-(2-((4-(trifluoromethyl)phenyl)amino)phenyl)-1,3,4-oxadiazol-2-yl)-1,3-dioxan-5-ol |
| 200 | 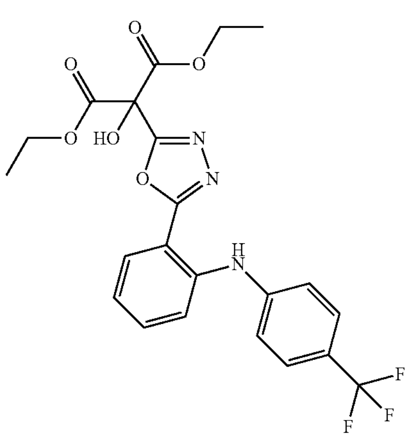 [SMILES: CCOC(=O)C(O)(C(=O)OCC)c1nnc(-c2ccccc2Nc2ccc(C(F)(F)F)cc2)o1] | diethyl 2-hydroxy-2-(5-(2-((4-(trifluoromethyl)phenyl)amino)phenyl)-1,3,4-oxadiazol-2-yl)malonate |

TABLE 1-continued

| Compound No. | Structure | Name |
|---|---|---|
| 201 | 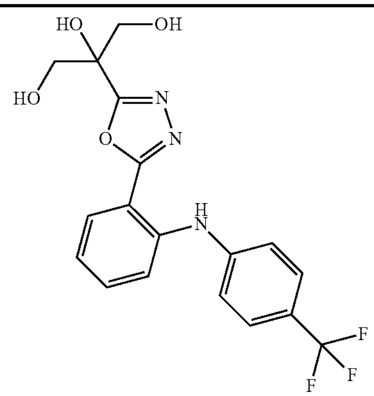 | 2-(5-(2-((4-(trifluoromethyl)phenyl)amino)phenyl)-1,3,4-oxadiazol-2-yl)propane-1,2,3-triol |
| 202 | 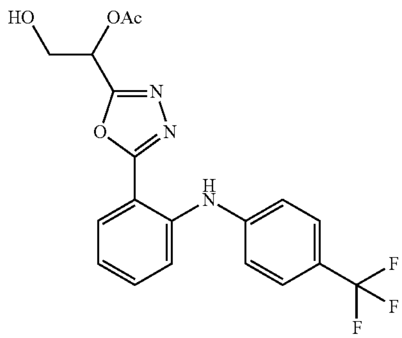 [SMILES: CC(=O)OC(CO)c1nnc(-c2ccccc2Nc2ccc(C(F)(F)F)cc2)o1] | 2-hydroxy-1-(5-(2-((4-(trifluoromethyl)phenyl)amino)phenyl)-1,3,4-oxadiazol-2-yl)ethyl acetate |
| 203 | 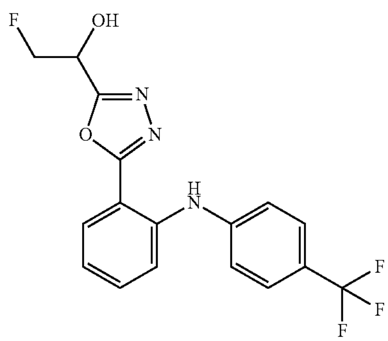 [SMILES: OC(CF)c1nnc(-c2ccccc2Nc2ccc(C(F)(F)F)cc2)o1] | 2-fluoro-1-(5-(2-((4-(trifluoromethyl)phenyl)amino)phenyl)-1,3,4-oxadiazol-2-yl)ethan-1-ol |
| 204 | 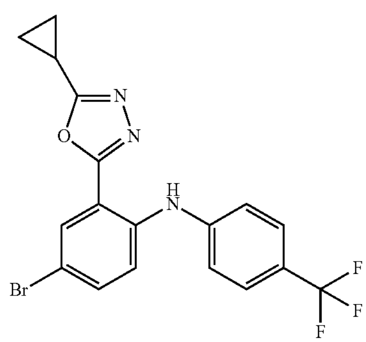 [SMILES: FC(F)(F)c1ccc(Nc2ccc(Br)cc2-c2nnc(C3CC3)o2)cc1] | 4-bromo-2-(5-cyclopropyl-1,3,4-oxadiazol-2-yl)-N-(4-(trifluoromethyl)phenyl)aniline |

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some instances, specific and analogous reactants are identified through the indices of known chemicals prepared by the Chemical Abstract Service of the American Chemical Society, which are available in most public and university libraries, as well as through on-line databases (the American Chemical Society, Washington, D.C., is contacted for more details). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds disclosed herein are prepared as described in the Examples section.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. In some embodiments, examples of isotopes that are incorporated into compounds of the disclosure include isotopes of hydrogen, carbon, nitrogen, oxygen, phosphorous, sulfur, fluorine, and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}$, and $^{36}Cl$, respectively. Compounds described herein, and the metabolites, pharmaceutically acceptable salts, esters, prodrugs, solvates, hydrates or derivatives thereof which contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays. Tritiated, i. e., ³H and carbon-14, i. e., ¹C, isotopes are particularly preferred for their ease of preparation and detectability. Further, substitution with heavy isotopes such as deuterium, i.e., ²H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In some embodiments, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e. g., two, three or four) amino acid residues is covalently joined through an amide or ester bond to a free amino, hydroxy, or carboxylic acid group of compounds of the present disclosure. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, metal salts and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including but not limited to ether, amine, and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, sulfonate esters, sulfate esters and disulfide containing esters; ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to, the following groups and combinations of groups:

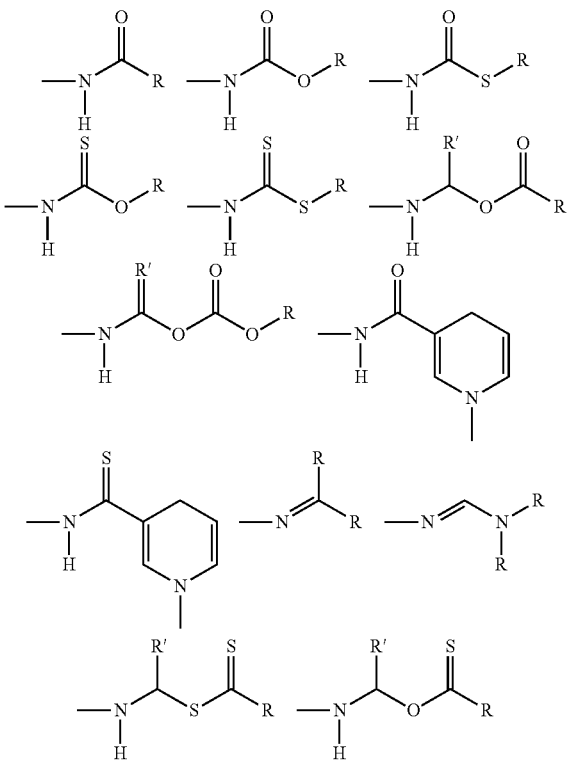

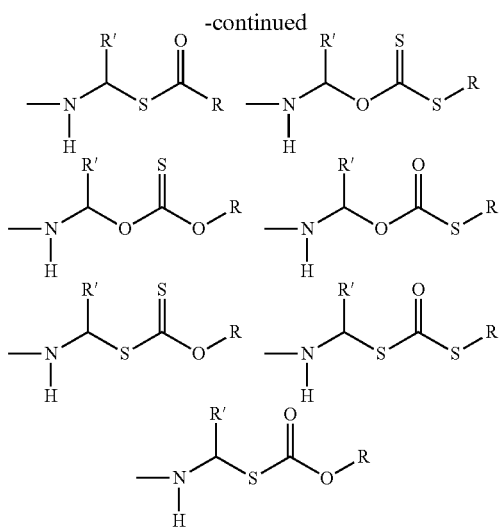

as well as sulfonamides and phosphonamides.

In certain instances, sites on any aromatic ring portions are susceptible to various metabolic reactions, therefore incorporation of appropriate substituents on the aromatic ring structures, reduce, minimize, or eliminate this metabolic pathway.

Metabolites

In some embodiments, compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds described herein are metabolized upon administration to an organism in need to produce a metabolite that is then used to produce a desired effect, including a desired therapeutic effect.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one compound described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used.

For example, disclosed compositions are formulated as a unit dose, and/or are formulated for oral or subcutaneous administration.

In some instances, exemplary pharmaceutical compositions are used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets in some instances, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions also comprise buffering agents in some embodiments. Solid compositions of a similar type are also employed as fillers in soft and hard-filled gelatin capsules using such excipients as lactose or milk sugars, as well as high molecular weight polyethylene glycols and the like.

In some instances, a tablet is made by compression or molding, optionally with one or more accessory ingredients. Compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets are made by molding in a suitable machine a mixture of the subject composition moistened with an inert liquid diluent. Tablets, and other solid dosage forms, such as dragees, capsules, pills and granules, are optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms contain optionally inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, optionally contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component is optionally mixed under sterile conditions with a pharmaceutically acceptable carrier, and with any preservatives, buffers, or propellants which are required in some embodiments.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. Sprays additionally contain customary propellants, such as chlorofluorohydrocarbons and volatile unsubstituted hydrocarbons, such as butane and propane.

Compositions and compounds disclosed herein are alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are used because they minimize exposing the agent to shear, which result in degradation of the compounds contained in the subject compositions in some embodiments. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which optionally contain antioxidants, buffers, bacteriostats, solutes which render the formulation isotonic with the blood of the intended recipient or suspending or thickening agents.

Examples of suitable aqueous and non-aqueous carriers employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. In some embodiments, proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

In some embodiments, the dose of the composition comprising at least one compound as described herein differ, depending upon the patient's (e.g., human) condition, that is, stage of the disease, general health status, age, and other factors that a person skilled in the medical art will use to determine dose.

In some instances, pharmaceutical compositions are administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

In some embodiments, oral doses typically range from about 1.0 mg to about 1000 mg, one to four times, or more, per day.

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional co-activator with PDZ-binding motif (TAZ; also known as WWTR1) (FIG. 1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST1/2 (homologues of Hippo/Hpo in *Drosophila*), Lats1/2 (homologues of Warts/Wts), and their adaptor proteins Sav1 (homologue of Salvador/Sav) and Mob (MOBKL1A and MOBKL1B; homologues of Mats), respectively (FIG. 1). In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] consensus motifs. YAP comprises five [HXRXXS] consensus motifs, wherein X denotes any amino acid residue. In some instances, Lats1/2 phosphorylates YAP at one or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ primes both proteins for further phosphorylation events by CK1δ/p in the degradation motif, which then signals for interaction with the β-TRCP E3 ubiquitin ligase, leading to polyubiquitination and degradation of YAP.

In some instances, Lats1/2 phosphorylates TAZ at the [HXRXXS] consensus motifs. TAZ comprises four [HXRXXS] consensus motifs, wherein X denotes any amino acid residues. In some instances, Lats1/2 phosphorylates TAZ at one or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cytoplasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes $SCF^{\beta\text{-}TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g. Cdc4), Skp1, a bridging protein, and RBX1 which contains a small RING Finger domain which interacts with E2-ubiquitin conjugating enzyme. In some cases, the F-box family comprises more than 40 members, in which exemplary members include F-box/WD repeat-containing protein 1A (FBXW1A, PTrCP1, Fbxw1, hsSlimb, plkappaBalpha-E3 receptor subunit) and S-phase kinase-associated proteins 2 (SKP2). In some embodiments, the SCF complex (e.g. $SCP^{\beta TrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, UBA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE2I, UBE2J, UBE2J2, UBE2K, UBE2L3, UBE2L6, UBE2M, UBE2N, UBE2O, UBE2Q, UBE2Q2, UBE2R1, UBE2R2, UBE2S, UBE2T, UBE2U, UBE2V1, UBE2V2, UBE2Z, ATG2, BIRC5, and UFC1. In some embodiments, the ubiquitinated YAP/TAZ further undergoes the degradation process through the 26S proteasome.

In some embodiments, the Hippo pathway is regulated upstream by several different families of regulators (FIG. 1). In some instances, the Hippo pathway is regulated by the G-protein and its coupled receptors, the Crumbs complex, regulators upstream of the MST kinases, and the adherens junction.

YAP/TAZ Interaction with TEAD

In some embodiments, un-phosphorylated and/or dephosphorylated YAP/TAZ accumulates in the nucleus. Within the nucleus, YAP/TAZ interacts with the TEAD family of transcription factors (e.g. TEAD1, TEAD2, TEAD3, or TEAD4) to activate genes involved in anti-apoptosis and proliferation, such as for example CTFG, Cyr61, and FGF1.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

YAP/TAZ Regulation Mediated by G-Proteins/GPCRs

Figure 2:
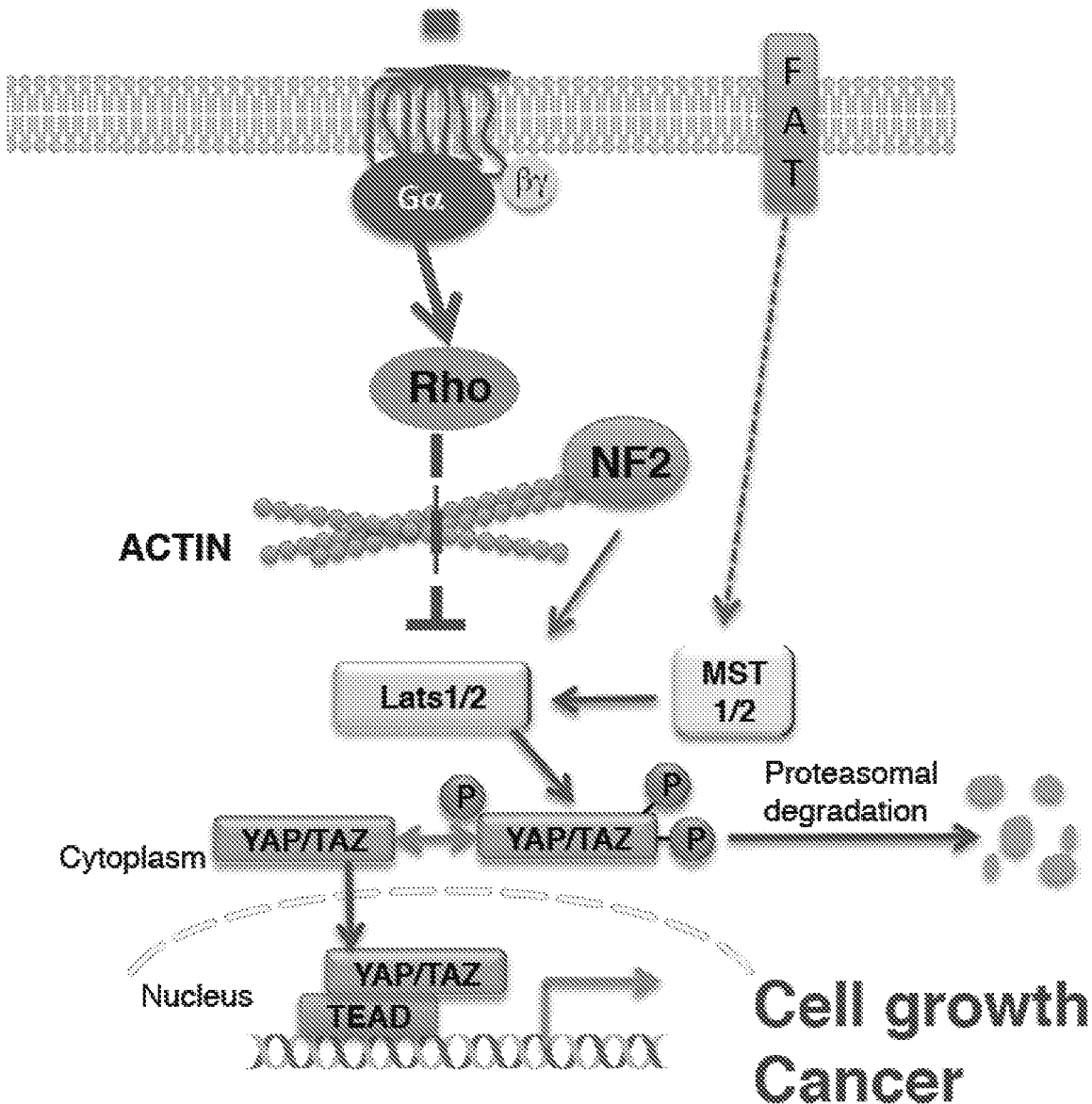
FIG. 2 illustrates a schematic representation of the Hippo signaling pathway regulated by G alpha proteins.

In some embodiments, the Hippo pathway is regulated by the G protein-coupled receptor (GPCR) and G protein (also known as guanine nucleotide-binding proteins) family of proteins (FIG. 2). G proteins are molecular switches that transmit extracellular stimuli into the cell through GPCRs. In some instances, there are two classes of G proteins: monomeric small GTPases; and heterotrimeric G protein complexes. In some instances, the latter class of complexes comprise of alpha ($G_\alpha$), beta ($G_\beta$), and gamma ($G_\gamma$) subunits. In some cases, there are several classes of Ga subunits: $G_{q/11}\alpha$, $G_{12/13}\alpha$, $G_{i/o}\alpha$ (G inhibitory, G other), and Ga (G stimulatory).

In some instances, $G_i\alpha$ (G inhibitory), $G_o\alpha$ (G other), $G_{q/11}\alpha$, and $G_{12/13}\alpha$ coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s\alpha$, in some embodiments, induces Lats1/2 activity, thereby promoting YAP/TAZ degradation.

$G_q$ Family $G_q\alpha$ (also known as $G_{q/11}$ protein), participates in the inositol trisphosphate ($IP_3$) signal transduction pathway and calcium ($Ca^{2+}$) release from intracellular storage through the activation of phospholipase C (PLC). The activated PLC hydrolyzes phosphatidylinositol 4,5-bisphosphate ($PIP_2$) to diacyl glycerol (DAG) and $IP_3$. In some instances, $IP_3$ then diffuses through the cytoplasm into the ER or the sarcoplasmic reticulum (SR) in the case of muscle cells, and then binds to inositol trisphosphate receptor (InsP3R), which is a $Ca^{2+}$ channel. In some cases, the binding triggers the opening of the $Ca^{2+}$ channel, and thereby increases the release of $Ca^{2+}$ into the cytoplasm.

In some embodiments, the GPCRs that interact with $G_q\alpha$ include, but are not limited to, 5-hydroxytryptamine receptor (5-HT receptor) types $5-HT_2$ and $5-HT_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors $M_1$, $M_3$, and $M_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q$a genes have been associated with cancer. Indeed, studies have shown that mutations in $G_q$a promote uveal melanoma (UM) tumorigenesis. In some instances, about 80% of UM cases have been detected to contain a mutation in GNAQ and/or GNA11.

In some instances, mutations or modifications of the $G_q$a genes have been associated with congenital diseases. In some instances, mutations of $G_q$a have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

$G_{12/13}$ Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g. Rho family such as Cdc42), which is involved in cell differentiation, proliferation, cytoskeletal organization, vesicle trafficking, and nuclear transport.

In some embodiments, the GPCRs that interact with $G_{12/13}\alpha$ include, but are not limited to, purinergic receptors (e.g. $P2Y_1$, $P2Y_2$, $P2Y_4$, $P2Y_6$); muscarinic acetylcholine receptors M1 and M3; receptors for thrombin [protease-activated receptor (PAR)-1, PAR-2]; thromboxane (TXA2); sphingosine 1-phosphate (e.g. $S1P_2$, $S1P_3$, $S1P_4$ and $SP_5$); lysophosphatidic acid (e.g. $LPA_1$, $LPA_2$, $LPA_3$); angiotensin II (AT1); serotonin ($5-HT_{2c}$ and $5-HT_4$); somatostatin ($sst_5$); endothelin ($ET_A$ and $ET_B$); cholecystokinin ($CCK_1$); $V_{1a}$ vasopressin receptors; $D_5$ dopamine receptors; fMLP formyl peptide receptors; $GAL_2$ galanin receptors; $EP_3$ prostanoid receptors; $A_1$ adenosine receptors; $\alpha_1$ adrenergic receptors; $BB_2$ bombesin receptors; $B_2$ bradykinin receptors; calcium-sensing receptors; KSHV-ORF74 chemokine receptors; $NK_1$ tachykinin receptors; and thyroid-stimulating hormone (TSH) receptors.

In some instances, $G_{12/13}\alpha$ is further subdivided into $G_{12}$ and $G_{13}$ types which are encoded by GNA12 and GNA13, respectively.

$G_{i/o}$ Family $G_{i/o}\alpha$ (G inhibitory, G other) (also known as $G_i/G_o$ or $G_i$ protein) that suppresses the production of 3',5'-cyclic AMP (cAMP) from adenosine triphosphate (ATP) through an inhibition of adenylate cyclase activity, which converts ATP to cAMP.

In some embodiments, the GPCRs that interact with $G_i\alpha$ include, but are not limited to, 5-hydroxytryptamine receptor (5-HT receptor) types $5-HT_1$ and $5-HT_5$; muscarinic acetylcholine receptors such as $M_2$ and $M_4$; adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as δ, κ, μ, and nociceptin receptors; prostaglandin receptors such as prostaglandin E receptor 1 ($EP_1$), prostaglandin E receptor 3 ($EP_3$), prostaglandin F receptor (FP), and thromboxane receptor (TP); somatostatin receptors sst1, sst2, sst3, sst4, and sst5; and trace amine-associated receptor 8.

In some instances, there are several types of $G_i\alpha$: $G_i\alpha 1$, $G_i\alpha 2$, $G_i\alpha 3$, $G_i\alpha 4$, $G_o\alpha$, $G_t$, $G_{gust}$, and $G_z$. $G_i\alpha 1$ is encoded by GNAI1. $G_i\alpha 2$ is encoded by GNAI2. $G_i\alpha 3$ is encoded by GNAI3. $G_o\alpha$, the $a_o$ subunit, is encoded by GNAO1. $G_t$ is encoded by GNAT1 and GNAT2. $G_{gust}$ is encoded by GNAT3. $G_z$ is encoded by GNAZ.

$G_s$ Family $G_s\alpha$ (also known as G stimulatory, $G_s$ alpha subunit, or $G_s$ protein) activates the cAMP-dependent pathway through the activation of adenylate cyclase, which convers adenosine triphosphate (ATP) to 3′,5′-cyclic AMP (cAMP) and pyrophosphate. In some embodiments, the GPCRs that interact with $G_s\alpha$ include, but are not limited to, 5-hydroxytryptamine receptor (5-HT receptor) types $5\text{-}HT_4$, $5\text{-}HT_6$, and $5\text{-}HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $\beta_1$, $\beta_2$, and $\beta_3$; calcitonin receptor; calcitonin gene-related peptide receptor; corticotropin-releasing hormone receptor; dopamine receptor $D_1$-like family receptors such as $D_1$ and $D_5$; follicle-stimulating hormone receptor (FSH-receptor); gastric inhibitory polypeptide receptor; glucagon receptor; histamine $H_2$ receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein α-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

In some embodiments, the compounds described herein are inhibitors of transcriptional coactivator with PDZ binding motif/Yes—associated protein transcriptional coactivator (TAZ/YAP). In some embodiments, the compounds described herein increase the phosphorylation of transcriptional coactivator with PDZ binding motif/Yes—associated protein transcriptional coactivator (TAZ/YAP) or decrease the dephosphorylation of transcriptional coactivator with PDZ binding motif/Yes—associated protein transcriptional coactivator (TAZ/YAP). In some embodiments, the compounds increase the ubiquitination of transcriptional coactivator with PDZ binding motif/Yes—associated protein transcriptional coactivator (TAZ/YAP) or decrease the deubiquitination of transcriptional coactivator with PDZ binding motif/Yes—associated protein transcriptional coactivator (TAZ/YAP).

In some embodiments, the compounds disclosed herein are inhibitors of one or more of the proteins encompassed by, or related to, the Hippo pathway. In some instances, the one or more proteins comprise a protein shown in FIGS. 1 and/or 2. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha 1$, $G_i\alpha 2$, $G_i\alpha 3$, $G_i\alpha 4$, $G_o\alpha$, $G_t$, $G_{gust}$, and $G_z$. In some embodiments, an inhibitor of the Hippo pathway is an inhibitor of $G_q$. In some embodiments, an inhibitor of the Hippo pathway is an inhibitor of $G_q/i$. In some embodiments, an inhibitor of the Hippo pathway is an inhibitor of $G_{14}$. In some embodiments, an inhibitor of the Hippo pathway is an inhibitor of $G_{q/15}$. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha 1$. In some embodiments, an inhibitor of the Hippo pathway is an inhibitor of $G_i\alpha 2$. In some embodiments, an inhibitor of the Hippo pathway is an inhibitor of $G_i\alpha 3$. In some embodiments, an inhibitor of the Hippo pathway is an inhibitor of $G_i\alpha 4$. In some embodiments, an inhibitor of the Hippo pathway is an inhibitor of Goa. In some embodiments, an inhibitor of the Hippo pathway is an inhibitor of $G_t$. In some embodiments, an inhibitor of the Hippo pathway is an inhibitor of $G_{gust}$. In some embodiments, an inhibitor of the Hippo pathway is an inhibitor of $G_z$.

In some embodiments, an inhibitor of the Hippo pathway is an inhibitor of a core protein of the Hippo pathway. In some embodiments, an inhibitor of the Hippo pathway is an inhibitor of Sav. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g. 26S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

Further embodiments provided herein include combinations of one or more of the particular embodiments set forth above.

Diseases

Cancer

In some embodiments, the compounds disclosed herein are useful for treating cancer. In some embodiments, the cancer is mediated by activation of transcriptional coactivator with PDZ binding motif/Yes—associated protein transcription coactivator (TAZ/YAP). In some embodiments, the cancer is mediated by modulation of the interaction of YAP/TAZ with TEAD. In some embodiments, the cancer is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the cancer is a solid tumor. In some instances, the cancer is a hematologic malignancy. In some instances, the solid tumor is a sarcoma or carcinoma. In some instances, the solid tumor is a sarcoma. In some instances, the solid tumor is a carcinoma.

Exemplary sarcoma includes, but is not limited to, alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, and telangiectatic osteosarcoma.

Exemplary carcinoma includes, but is not limited to, adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer. In some instances, the liver cancer is primary liver cancer.

In some instances, the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma.

In some cases, the cancer is uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the cancer is uveal melanoma, mesothelioma, esophageal cancer, or liver cancer. In some cases, the cancer is uveal melanoma. In some cases, the cancer is mesothelioma. In some cases, the cancer is esophageal cancer. In some cases, the cancer is liver cancer. In some cases, the cancer is primary liver cancer.

In some instances, the cancer is a hematologic malignancy. In some embodiments, a hematologic malignancy is a leukemia, a lymphoma, a myeloma, a non-Hodgkin's lymphoma, a Hodgkin's lymphoma, a T-cell malignancy, or a B-cell malignancy. In some instances, a hematologic malignancy is a T-cell malignancy. Exemplary T-cell malignancy includes, but is not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, and treatment-related T-cell lymphomas.

In some instances, a hematologic malignancy is a B-cell malignancy. Exemplary B-cell malignancy includes, but is not limited to, chronic lymphocytic leukemia (CLL), small lymphocytic lymphoma (SLL), high risk CLL, and a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a relapsed or refractory cancer. In some embodiments, the relapsed or refractory cancer is a relapsed or refractory solid tumor. In some embodiments, the relapsed or refractory solid tumor is a relapsed or refractory sarcoma or a relapsed or refractory carcinoma. In some embodiments, the relapsed or refractory carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the relapsed or refractory cancer is selected from relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the relapsed or refractory cancer is relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the relapsed or refractory cancer is relapsed or refractory uveal melanoma, mesothelioma, esophageal cancer, or liver cancer. In some cases, the relapsed or refractory cancer is relapsed or refractory uveal melanoma. In some cases, the relapsed or refractory cancer is relapsed or refractory mesothelioma. In some cases, the relapsed or refractory cancer is relapsed or refractory esophageal cancer. In some cases, the relapsed or refractory cancer is relapsed or refractory liver cancer. In some cases, the relapsed or refractory cancer is relapsed or refractory primary liver cancer.

In some instances, the relapsed or refractory cancer is a relapsed or refractory hematologic malignancy. In some embodiments, a relapsed or refractory hematologic malignancy is a relapsed or refractory leukemia, a relapsed or refractory lymphoma, a relapsed or refractory myeloma, a relapsed or refractory non-Hodgkin's lymphoma, a relapsed or refractory Hodgkin's lymphoma, a relapsed or refractory T-cell malignancy, or a relapsed or refractory B-cell malignancy. In some instances, a relapsed or refractory hematologic malignancy is a relapsed or refractory T-cell malignancy. In some instances, a relapsed or refractory hematologic malignancy is a relapsed or refractory B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a metastasized cancer. In some instances, the metastasized cancer is a metastasized solid tumor. In some instances, the metastasized solid tumor is a metastasized sarcoma or a metastasized carcinoma. In some embodiments, the metastasized carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the metastasized cancer is metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the metastasized cancer is metastasized uveal melanoma, mesothelioma, esophageal cancer, or liver cancer. In some cases, the metastasized cancer is metastasized uveal melanoma. In some cases, the metastasized cancer is metastasized mesothelioma. In some cases, the metastasized cancer is metastasized esophageal cancer. In some cases, the metastasized cancer is metastasized liver cancer. In some cases, the metastasized cancer is metastasized primary liver cancer.

In some instances, the metastasized cancer is a metastasized hematologic malignancy. In some embodiments, the metastasized hematologic malignancy is a metastasized leukemia, a metastasized lymphoma, a metastasized myeloma, a metastasized non-Hodgkin's lymphoma, a metastasized Hodgkin's lymphoma, a metastasized T-cell malignancy, or a metastasized B-cell malignancy. In some instances, a metastasized hematologic malignancy is a metastasized T-cell malignancy. In some instances, a metastasized hematologic malignancy is a metastasized B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Congenital Diseases

In some embodiments, the compounds disclosed herein are useful for treating a congenital disease. In some embodiments, the congenital disease is mediated by activation of transcriptional coactivator with PDZ binding motif/Yes—associated protein transcription coactivator (TAZ/YAP).

In some embodiments, the congenital disease is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the congenital disease is the result of a genetic abnormality, an intrauterine environment, errors related to morphogenesis, infection, epigenetic modifications on a parental germline, or a chromosomal abnormality. Exemplary congenital diseases include, but are not limited to, Sturge-Weber Syndrome, Port-Wine stain, Holt-Oram syndrome, abdominal wall defects, Becker muscular dystrophy (BMD), biotinidase deficiency, Charcot-Marie-Tooth (CMT), cleft lip, cleft palate, congenital adrenal hyperplasia, congenital heart defects, congenital hypothyroidism, congenital muscular dystrophy, cystic fibrosis, Down syndrome, Duchenne muscular dystrophy, Fragile X syndrome, Friedreich's ataxia, galactosemia, hemoglobinopathies, Krabbe disease, limb-girdle muscular dystrophy, medium chain acyl-CoA dehydrogenase definiency, myasthenia gravis, neural tube defects, phenylketonuria, Pompe disease, severe combined immunodeficiency (SCID), Stickler syndrome (or hereditary progressive arthro-ophthalmopathy), spinal muscular atrophy, and trisomy 18. In some embodiments, the congenital disease is Sturge-Weber Syndrome or Port-Wine stain. In some embodiments, the congenital disease is Sturge-Weber Syndrome. In some embodiments, the congenital disease is Port-Wine stain.

EXAMPLES

These examples are provided for illustrative purposes only and not to limit the scope of the claims provided herein.

List of Abbreviations

As used above, and throughout the disclosure, the following abbreviations, unless otherwise indicated, shall be understood to have the following meanings:
ACN or MeCN acetonitrile
Bn benzyl
BOC or Boc tert-butyl carbamate
t-Bu tert-butyl Cy cyclohexyl
DBA dibenzylideneacetone
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
eq equivalent(s)
Et ethyl
$Et_2O$ diethyl ether
EtOH ethanol
EtOAc ethyl acetate
HPLC high performance liquid chromatography
LAH lithium aluminum anhydride
LCMS liquid chromatography mass spectrometry
Me methyl
MeOH methanol
MS mass spectroscopy
NMM N-methyl-morpholine
NMP N-methyl-pyrrolidin-2-one
NMR nuclear magnetic resonance
RP-HPLC reverse phase-high pressure liquid chromatography
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times were approximate and were not optimized. Column chromatography and thin layer chromatography (TLC) were performed on silica gel unless otherwise noted. Same reagents might have different assigned numbers throughout Examples.

Example 1: ethyl 2-(5-(2-((4-(trifluoromethyl)phenyl)amino)phenyl)-1,3,4-oxadiazol-2-yl) acetate (Compound 1)

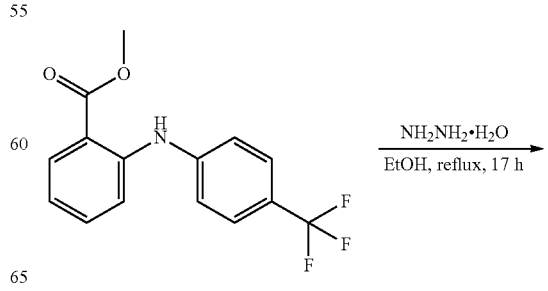

1-1

161
-continued

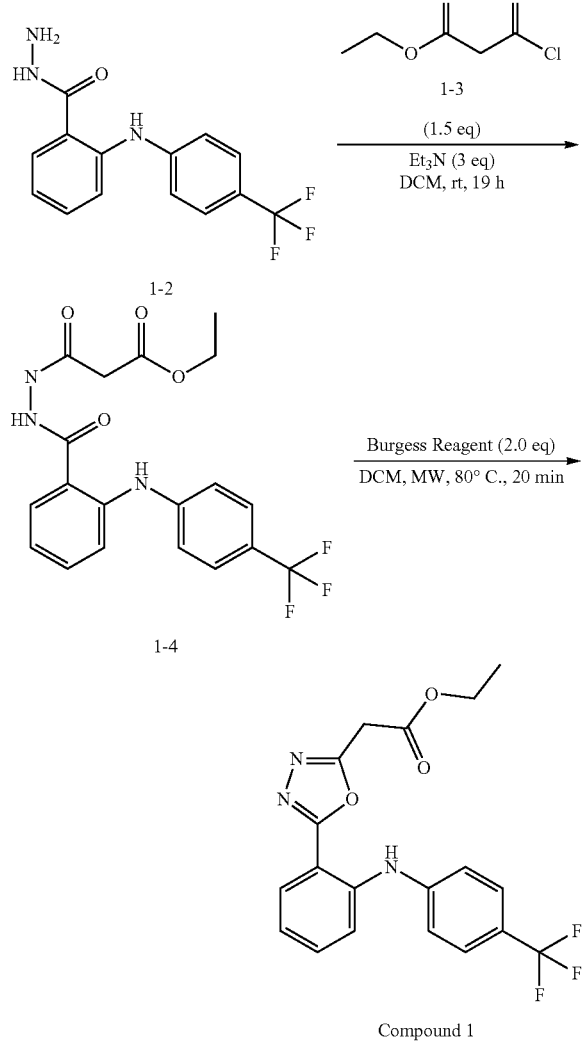

Step 1:
2-((4-(trifluoromethyl)phenyl)amino)benzohydrazide

To a mixture of 1-1 (2.0 g, 6.8 mmol, 1 eq) in EtOH (20 mL) was added NH$_2$NH$_2$.H$_2$O (4.1 g, 70.0 mmol, 4 mL, 85% purity, 10.33 eq). The resulted mixture was stirred at 80° C. for 17 h. LCMS and TLC showed the reaction was completed. The mixture was concentrated in vacuum. The residue was purified by silica gel chromatography. 1-2 (1.8 g, 6.0 mmol, 89.1% yield) was obtained.

Step 2: ethyl 3-oxo-3-(2-(2-((4-(trifluoromethyl) phenyl)amino)benzoyl)hydrazinyl)propanoate To a mixture of 1-2 (500 mg, 1.7 mmol, 1 eq) and TEA (514.1 mg, 5.1 mmol, 0.7 mL, 3 eq) in DCM (6 mL) was added 1-3 (382.4 mg, 2.5 mmol, 0.3 mL, 1.5 eq) dropwise. The resulting mixture was stirred at 15° C. for 19 h. LCMS showed the reaction was complete. The mixture was diluted with water (30 mL) and extracted with EA (30 mL*3). The organic layer was dried over anhydrous Na$_2$SO$_4$, concentrated in vacuum. The residue was purified by silica gel chromatography. 1-4 (0.6 g, 1.2 mmol, 70.1% yield) was obtained.

162

Step 3: ethyl 2-(5-(2-((4-(trifluoromethyl)phenyl) amino)phenyl)-1,3,4-oxadiazol-2-yl)acetate To a mixture of 1-4 (50 mg, 0.12 mmol, 1 eq) in DCM (3 mL) was added Burgess reagent (58.2 mg, 0.24 mmol, 2 eq). The resulted mixture was stirred at 80° C. under microwave condition for 20 min. LCMS and HPLC showed about 34% desired compound was detected, and 42% starting material was remained. The mixture was concentrated in vacuum. The residue was purified by prep-HPLC. Compound 1 (4.33 mg, 11.1 umol, 9.1% yield) was obtained. LCMS (ESI): RT=0.876 min, mass calcd. for C$_{19}$H$_{16}$F$_3$N$_3$O$_3$ 391.11, m/z found 392.0 [M+H]$^+$; $^1$H NMR (400 MHz, CDCl$_3$) δ 9.48 (s, 1H), 7.90 (dd, J=1.1, 7.9 Hz, 1H), 7.59 (d, J=8.5 Hz, 2H), 7.51 (d, J=8.3 Hz, 1H), 7.43-7.35 (m, 3H), 6.97 (t, J=7.5 Hz, 1H), 4.27 (q, J=7.2 Hz, 2H), 4.06 (s, 2H), 1.32 (t, J=7.2 Hz, 3H).

Example 2: 2-(5-(2-((4-(trifluoromethyl)phenyl) amino)phenyl)-1,3,4-oxadiazol-2-yl)ethan-1-ol (Compound 2)

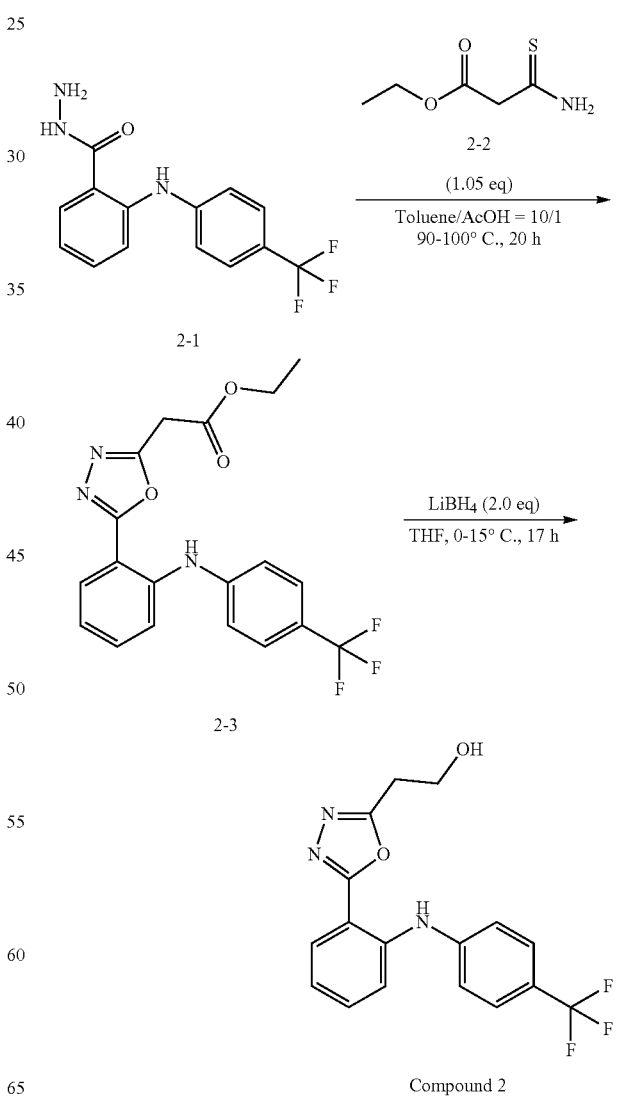

Step 1: ethyl 2-(5-(2-((4-(trifluoromethyl)phenyl)amino)phenyl)-1,3,4-oxadiazol-2-yl)acetate To a mixture of 2-1 (50 mg, 0.17 mmol, 1 eq) in toluene (3 mL) and AcOH (0.3 mL) was added 2-2 (26.2 mg, 0.18 mmol, 1.05 eq). The resulted mixture was stirred at 90° C. for 17 h. LCMS showed the starting material was consumed completed, and 9% desired compound was detected. The mixture was stirred at 100° C. for 3 h. LCMS showed there's no obvious change. The mixture was concentrated in vacuum. The residue was checked by HPLC. The residue was purified by prep-HPLC. 2-3 (10 mg, 25.6 umol, 15.1% yield) was obtained.

Step 2: 2-(5-(2-((4-(trifluoromethyl)phenyl)amino)phenyl)-1,3,4-oxadiazol-2-yl)ethanol To a mixture of 2-3 (10 mg, 25.6 umol, 1 eq) in THF (2 mL) was added LiBH$_4$ (1.1 mg, 51.1 umol, 2 eq) at 0° C. The resulted mixture was stirred at 15° C. for 17 h. LCMS showed there's about 42% desired compound. The mixture was diluted with MeOH (3 mL), concentrated in vacuum. The residue was purified by prep-HPLC. Compound 2 (3.9 mg, 11.2 umol, 43.7% yield) was obtained. LCMS (ESI): RT=0.788 min, mass calcd. for $C_{17}H_{14}F_3N_3O_2$ 349.10, m/z found 349.9 [M+H]$^+$. $^1$H NMR (400 MHz, CDCl$_3$) δ 9.48 (s, 1H), 7.89 (d, J=8.0 Hz, 1H), 7.59 (d, J=8.3 Hz, 2H), 7.52 (d, J=8.5 Hz, 1H), 7.43-7.35 (m, 3H), 6.98 (t, J=7.5 Hz, 1H), 4.17 (t, J=5.8 Hz, 2H), 3.21 (t, J=5.8 Hz, 2H).

Example 3: ethyl 5-(2-((4-(trifluoromethyl)phenyl)amino)phenyl)-1,3,4-oxadiazole-2-carboxylate (Compound 3)

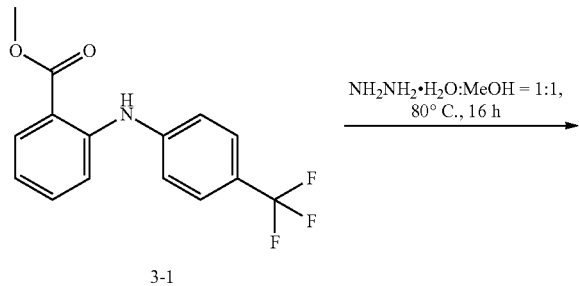

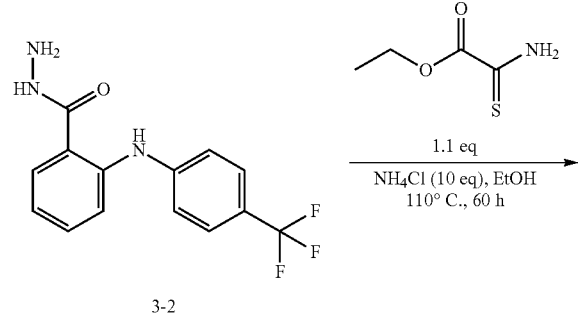

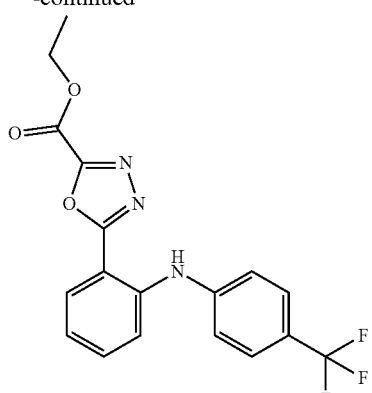

Compound 3

Step 1: 2-((4-(trifluoromethyl)phenyl)amino)benzohydrazide

To a solution of 3-1 (2.2 g, 7.45 mmol, 1 eq) in MeOH (5.5 mL) were added hydrazine-hydrate (5.7 g, 96.87 mmol, 5.5 mL, 13 eq) at 25° C. The resulting solution was stirred at 80° C. for 16 h and cooled to 25° C., along with lots of solid formed. LCMS showed no starting material was remained and 90% of desired product was detected. TLC (PE:EA=2:1 UV) showed the reaction was complete. The mixture was filtered. The filter cake was washed with water (20 mL) and dried to give 1.9 g of residue. The filtrate was concentrated to remove most of methanol and extracted with EA (30 mL) twice, dried by anhydrous Na$_2$SO$_4$, filtered and concentrated to give a residue. The residue was combined with 1.9 g of filter cake to give 3-2 (2.1 g, 7.11 mmol, 95.4% yield), which was used directly without purification. $^1$H NMR (400 MHz, CDCl$_3$) δ 9.25 (s, 1H), 7.52 (d, J=9.0 Hz, 2H), 7.49-7.34 (m, 4H), 7.22 (d, J=8.5 Hz, 2H), 6.94-6.86 (m, 1H), 4.38-3.78 (m, 2H).

Step 2: ethyl 5-(2-((4-(trifluoromethyl)phenyl)amino)phenyl)-1,3,4-oxadiazole-2-carboxylate A flask containing 3-2 (2.1 g, 7.11 mmol, 1 eq), NH$_4$Cl (3.8 g, 71.12 mmol, 2.5 mL, 10 eq) and ethyl 2-amino-2-thioxo-acetate (1.04 g, 7.82 mmol, 1.1 eq) in EtOH (60 mL) was heated at 110° C. for 60 h. (Note: ethyl 2-amino-2-thioxo-acetate was forgotten to add at the beginning, it was added after heating for about 1 h.) LCMS showed 34% of starting material was remained and 16% of desired product was formed. TLC (PE:EA=2:1 UV) showed starting material was remained and new spots were formed. The mixture was filtered and the filter cake was washed with EA (30 mL). The filtrate was concentrated to give a residue. The residue was purified by column chromatography to give Compound 3 (0.2 g) and recovery compound 3-2 (0.64 g, 2.17 mmol, 30.5% yield). Compound 3 (0.2 g) was purified by prep-HPLC to give the title compound (112.8 mg, 0.30 mmol, 4.2% yield). LCMS (ESI): RT=2.054 min, mass calc. for $C_{18}H_{14}F_3N_3O_3$ 377.10, m/z found 377.9[M+1]$^+$; $^1$H NMR (400 MHz, CDCl$_3$) δ 10.27 (s, 1H), 9.44 (s, 1H), 8.07-7.97 (m, 1H), 7.61 (d, J=8.0 Hz, 2H), 7.52-7.31 (m, 4H), 6.99 (t, J=7.5 Hz, 1H), 4.61-4.52 (m, 2H), 1.50 (t, J=7.3 Hz, 3H).

Example 4: 5-(2-((4-(trifluoromethyl)phenyl)amino)phenyl)-1,3,4-oxadiazol-2-amine (Compound 4)

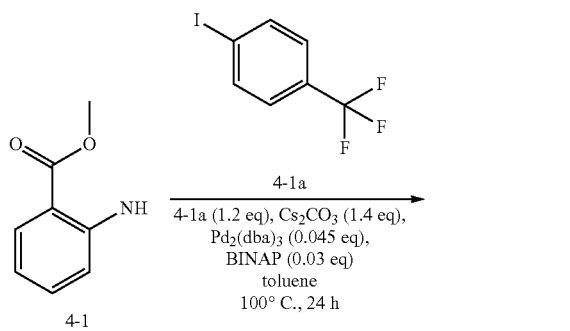

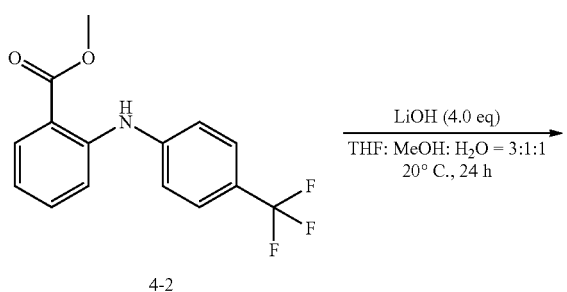

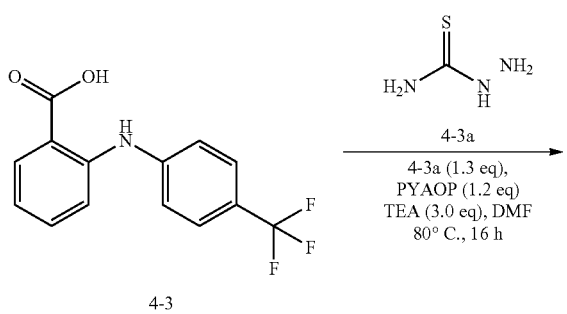

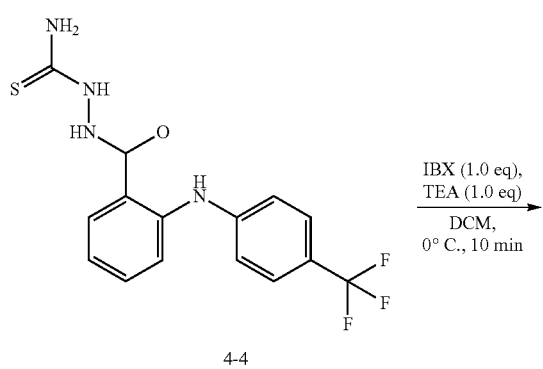

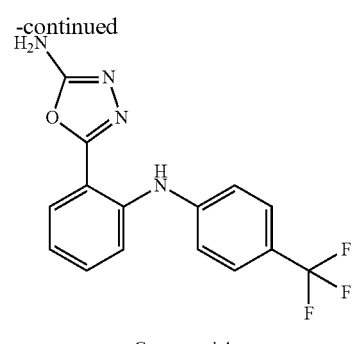

Compound 4

Step 1: methyl 2-[4-(trifluoromethyl)anilino]benzoate

A mixture of 4-1 (2.32 g, 15.3 mmol, 2 mL, 1.0 eq), 4-1a (5.0 g, 18.4 mmol, 2.7 mL, 1.2 eq), $Cs_2CO_3$ (7.0 g, 21.4 mmol, 1.4 eq), $Pd_2(dba)_3$ (631.1 mg, 0.7 mmol, 0.1 eq) and BINAP (286.1 mg, 0.5 mmol, 0.03 eq) in toluene (80 mL) was degassed and purged with $N_2$ for 3 times, and then the mixture was stirred at 100° C. for 24 hr under $N_2$ atmosphere. TLC (Petroleum ether:Ethyl acetate=10:1) indicated that 4-1 remained and three major new spots were detected. LCMS showed 4-1 was consumed completely and desired MS (m/z=295.9; RT=0.888 min) was detected. The reaction mixture was filtered and concentrated under reduced pressure to give a residue. The residue was purified by column chromatography ($SiO_2$) to give 4-2 (1.3 g, 4.3 mmol, 28.1% yield). LCMS showed the desired MS (m/z=295.9; RT=0.888 min) was detected. LCMS (ESI): RT=0.888 min, mass calc. for: $C_{15}H_{12}F_3NO_2$ 295.08, m/z found 295.8 [M+H]+; $^1$H NMR (400 MHz, $CDCl_3$) δ 3.90-3.96 (m, 3H), 6.86 (ddd, J=8.09, 5.58, 2.64 Hz, 1H), 7.26-7.33 (m, 2H), 7.36-7.43 (m, 2H), 7.56 (d, J=8.53 Hz, 2H), 7.94-8.14 (m, 1H), 9.58-9.81 (m, 1H).

Step 2: 2-[4-(trifluoromethyl)anilino]benzoic acid

To a solution of 4-2 (1.1 g, 3.73 mmol, 1.0 eq) in THF (10 mL) and methanol (1 mL) was added LiOH (356.9 mg, 14.9 mmol, 4.0 eq) dissolved in $H_2O$ (1 mL). The mixture was stirred at 20° C. for 16 hr. TLC (Petroleum ether:Ethyl acetate=1:1, UV) indicated compound 4-2 was remained, and one major new spot was detected. The mixture was concentrated to give a residue. The residue was diluted with $H_2O$ (30 mL) and extracted with ethyl acetate (30 mL). The aqueous phase was adjusted to pH~2 from 8 with HCl (2 M), along with lots of solid formed. 4-3 (0.7 g, crude) was obtained. $^1$H NMR (400 MHz, DMSO-d6) δ 6.96 (t, J=7.40 Hz, 1H), 7.39 (d, J=8.28 Hz, 2H), 7.43-7.53 (m, 2H), 7.63 (d, J=8.78 Hz, 2H), 7.95 (dd, J=7.91, 1.38 Hz, 1H), 9.72-9.82 (s, 1H), 13.23-13.32 (s, 1H).

Step 3: [[2-[4-(trifluoromethyl)anilino]benzoyl]amino]thiourea

To a solution of 4-3 (30 mg, 0.1 mmol, 1.0 eq) in DMF (2 mL) was added PYAOP (66.7 mg, 0.1 mmol, 1.2 eq) and TEA (32.4 mg, 0.3 mmol, 0.1 mL, 3.0 eq). Then 4-3a (12.6 mg, 0.1 mmol, 1.3 eq) was added to the mixture. The mixture was stirred at 80° C. for 16 hr. TLC (Petroleum ether:Ethyl acetate=5:1, UV) indicated 4-3 was consumed and one new spot formed. LCMS showed 4-3 was consumed and 47% of desired MS (m/z=354.9; RT=0.720 min). The reaction mixture was concentrated under reduced pressure. The residue was diluted with H$_2$O (15 mL) and extracted with ethyl acetate (30 mL). The combined organic layers were washed with brine (15 mL), dried over Na$_2$SO$_4$, filtered and concentrated under reduced pressure. The residue was purified by prep-TLC (SiO$_2$) to give 4-4. LCMS (ESI): RT=0.724 min, mass calc. for: C$_{15}$H$_{12}$F$_3$NO$_2$ 354.08, m/z found 354.9 [M+H]$^+$; $^1$H NMR (400 MHz, DMSO-d$_6$) δ 2.33 (s, 1H), 6.94-7.03 (t, J=7.28 Hz, 1H), 7.22-7.31 (d, J=8.53 Hz, 2H), 7.38-7.50 (m, 3H), 7.59 (d, J=8.53 Hz, 3H), 7.62-7.73 (m, 1H), 7.78-7.85 (d, J=7.53 Hz, 1H), 9.24-9.34 (s, 1H), 9.44-9.53 (s, 1H), 10.41-10.51 (s, 1H).

Step 4: 5-[2-[4-(trifluoromethyl)anilino]phenyl]-1,3, 4-oxadiazol-2-amine

To a solution of 4-4 (40 mg, 0.1 mmol, 1.0 eq) in DCM (2 mL) was added IBX (31.6 mg, 0.1 mmol, 1.0 eq) and TEA (11.4 mg, 0.1 mmol, 1.0 eq). The mixture was stirred at 0° C. for 10 min. TLC (Petroleum ether:Ethyl acetate=3:1, UV) indicated 4-4 remained and one major new spot was detected. LCMS showed 4-4 was consumed and desired product (m/z=320.9; RT=0.783 min) was detected. The reaction mixture was filtered and concentrated under reduced pressure. The residue was purified by prep-HPLC to give Compound 4 (6.5 mg, 19.7 umol, 17.4% yield). LCMS (ESI): RT=0.769 min, mass calc. for: C$_{15}$H$_{11}$F$_3$N$_4$O 320.09, m/z found 320.9 [M+H]+; $^1$H NMR (400 MHz, DMSO-d$_6$) δ 7.08 (t, J=7.53 Hz, 1H), 7.35-7.41 (m, 4H), 7.41-7.46 (m, 1H), 7.54 (d, J=8.03 Hz, 1H), 7.64 (d, J=8.53 Hz, 2H), 7.70 (d, J=8.03 Hz, 1H), 9.34 (s, 1H).

Example 5: (5-(2-((4-(trifluoromethyl)phenyl) amino)phenyl)-1,3,4-oxadiazol-2-yl)methanol (Compound 5)

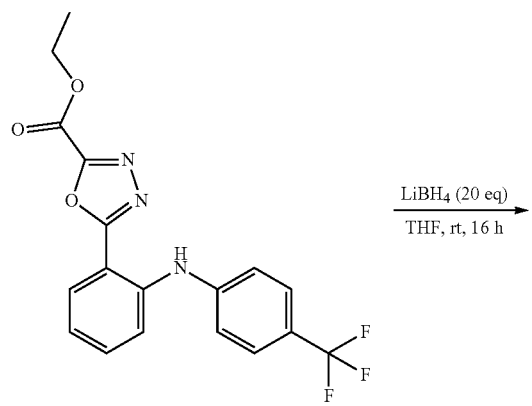

5-1

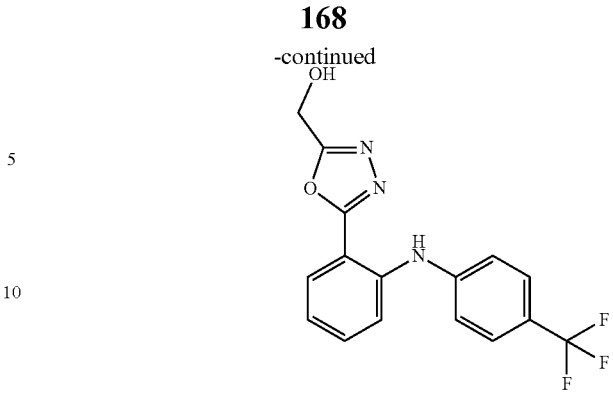

Compound 5

To a solution of 5-1 (64 mg, 0.17 mmol, 1 eq) in THF (4 mL) was added LiBH$_4$ (73.9 mg, 3.4 mmol, 20 eq) at 0° C. Then the mixture was stirred at 25° C. for 16 hr. TLC indicated that 5-1 was consumed completely and four new spots formed. The reaction mixture was quenched by addition water 5 mL at 25° C. and the aqueous phase was extracted with ethyl acetate 40 mL (10 mL*4). The combined organic layers were washed with brine (5 mL), dried over Na$_2$SO$_4$, filtered and concentrated under reduced pressure to give 64 mg crude product. The crude product was purified by prep-TLC to give Compound 5 (8 mg, 23.9 umol, 14.1% yield). LCMS (ESI): RT=0.773 min, mass calcd. for C$_{16}$H$_{12}$N$_3$F$_3$O$_2$, 335.09 m/z found 335.9[M+H]$^+$. $^1$H NMR (400 MHz, CDCl$_3$) δ 9.46 (s, 1H), 7.92 (dd, J=7.9, 1.4 Hz, 1H), 7.59 (d, J=8.5 Hz, 2H), 7.51 (d, J=8.5 Hz, 1H), 7.36-7.44 (m, 3H), 6.98 (t, J=7.2 Hz, 1H), 4.99 (s, 2H), 2.51 (brs, 1H).

Example 6: N,N-dimethyl-5-(2-((4-(trifluoromethyl) phenyl)amino)phenyl)-1,3,4-oxadiazol-2-amine (Compound 6)

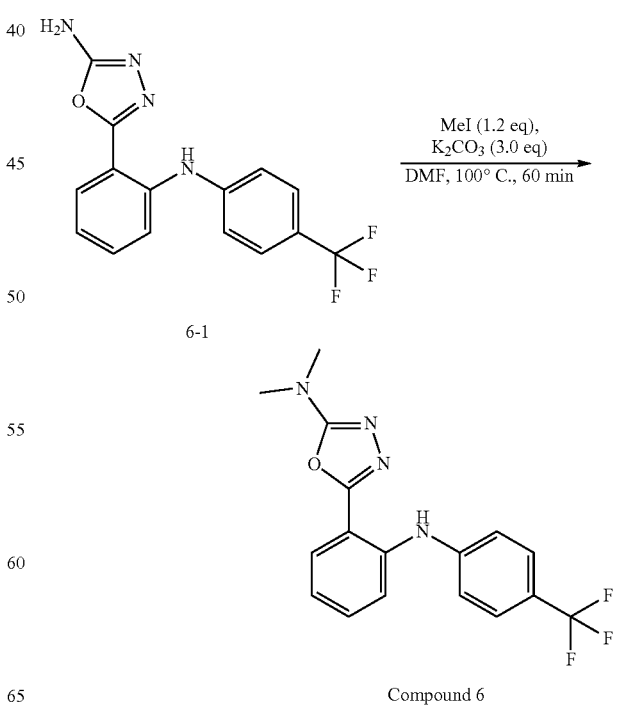

To a solution of 6-1 (40 mg, 0.1 mmol, 1.0 eq) in DMF (2 mL) were added $K_2CO_3$ (51.8 mg, 0.4 mmol, 3.0 eq) and MeI (35.5 mg, 0.3 mmol, 0.01 mL, 2.0 eq). The mixture was stirred under microwave tube at 100° C. for 60 min. LCMS showed 6-1 was consumed completely and two main peaks with desired mass was detected. TLC (Petroleum ether:Ethyl acetate=1:1, UV) indicated 6-1 was consumed, and two major new spots were detected. The mixture was filtered and concentrated under reduced pressure to give a residue. The residue was purified by prep-HPLC to give Compound 6 (3.5 mg, 0.01 mmol, 7.9% yield). LCMS (ESI): RT=0.844 min, mass calc. for: $C_{17}H_{15}F_3N_4O$ 348.12, m/z found 348.9 [M+H]$^+$; $^1$H NMR (400 MHz, DMSO-d$_6$) δ 3.08-3.15 (m, 1H), 3.11 (s, 5H), 6.87 (t, J=7.28 Hz, 1H), 7.22-7.30 (m, 3H), 7.43 (d, J=8.28 Hz, 1H), 7.48 (d, J=8.53 Hz, 2H), 7.58-7.75 (m, 1H), 9.44 (s, 1H).

Example 7: methyl 5-(2-((4-(trifluoromethyl)phenyl)amino)phenyl)-1,3,4-oxadiazole-2-carboxylate (Compound 8)

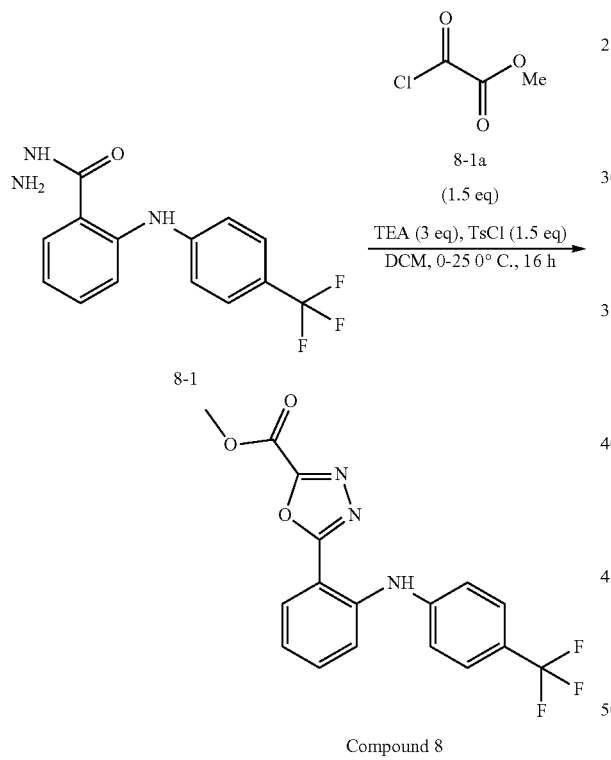

Compound 8

To a solution of 8-1a (207.4 mg, 1.7 mmol, 0.2 mL, 1.0 eq) and TEA (514.1 mg, 5.1 mmol, 0.7 mL, 3.0 eq) in DCM (6.0 mL) was added 8-1 (0.5 g, 1.7 mmol, 1 eq) at 0° C. The mixture was stirred at 25° C. for 16 h. Then TsCl (322.8 mg, 1.7 mmol, 1.0 eq) was added and the mixture was stirred at 25° C. for 5 h. Several new peaks were shown and 47% of desired compound was detected on LC-MS. The reaction mixture was quenched by addition of saturated NaHCO$_3$ (30 mL), and then diluted with EtOAc (100 mL). The organic layers were washed with brine (50 mL*3), dried over Na$_2$SO$_4$, filtered and concentrated under reduced pressure to give Compound 8 (0.4 g, 1.1 mmol, 65.0% yield). 20 mg crude product was purified by prep-HPLC to give Compound 8 (2.40 mg). LCMS (ESI): RT=1.018 min, mass calc. for $C_{17}H_{12}F_3N_3O_3$ 363.08, m/z found 364.2 [M+H]$^+$; $^1$H NMR (400 MHz, DMSO-d$_6$) δ 9.12 (s, 1H), 7.94 (d, J=7.8 Hz, 1H), 7.64 (d, J=8.5 Hz, 2H), 7.58 (d, J=3.3 Hz, 2H), 7.37 (d, J=8.3 Hz, 2H), 7.21-7.12 (m, 1H), 3.99 (s, 3H).

Example 8: ethyl (5-(2-((4-(trifluoromethyl)phenyl)amino)phenyl)-1,3,4-oxadiazol-2-yl)glycinate (Compound 9)

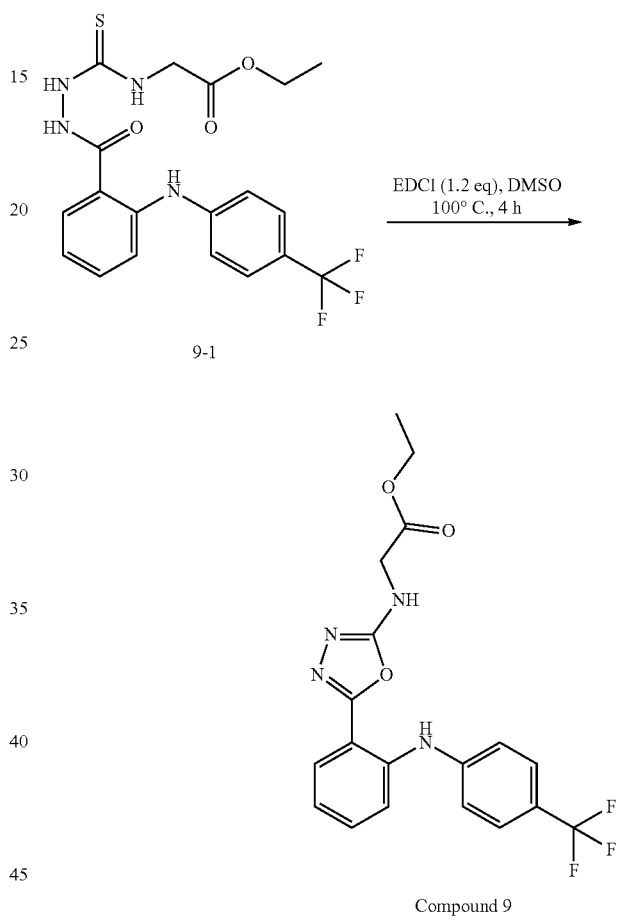

Compound 9

A mixture of 9-1 (1.2 g, 2.72 mmol, 1 eq), EDCI (626.7 mg, 3.27 mmol, 1.2 eq) in DMSO (15 mL) was degassed and purged with N$_2$ for 3 times, and then the mixture was stirred at 100° C. for 4 hr under N$_2$ atmosphere. LCMS showed the reaction was complete and 52% of desired product was formed. The mixture was combined with the another batch and diluted with EA (250 mL) and washed with brine (30 mL*5), dried by anhydrous Na$_2$SO$_4$, filtered and concentrated to give crude Compound 9 (0.9 g, 2.21 mmol, 81.1% yield), which was used directly for next step. 50 mg of crude Compound 9 was purified by prep-HPLC to give the title compound (21.07 mg, 51.8 umol, 1.9% yield). LCMS (ESI): RT=0.821 min, mass calc. for $C_{19}H_{17}F_3N_4O_3$ 406.13, m/z found 406.9 [M+1]$^+$; $^1$H NMR (400 MHz, DMSO-d$_6$) δ 9.27 (s, 1H), 8.42 (t, J=6.4 Hz, 1H), 7.75 (dd, J=1.4, 7.9 Hz, 1H), 7.64 (d, J=8.5 Hz, 2H), 7.55 (d, J=8.0 Hz, 1H), 7.50-7.42 (m, 1H), 7.37 (d, J=8.5 Hz, 2H), 7.10 (t, J=7.2 Hz, 1H), 4.19-4.04 (m, 4H), 1.21 (t, J=7.2 Hz, 3H).

Example 9: 2-((5-(2-((4-(trifluoromethyl)phenyl)amino)phenyl)-1,3,4-oxadiazol-2-yl)amino)ethan-1-ol (Compound 10)

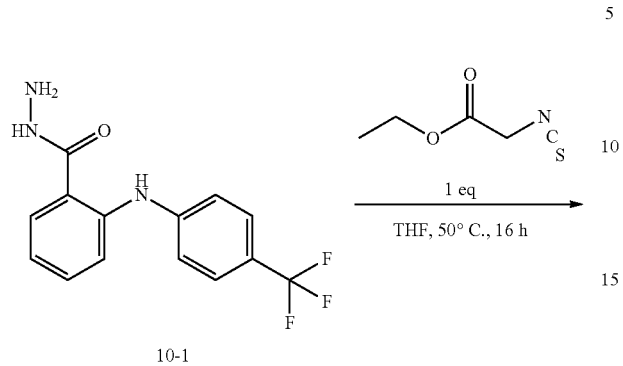

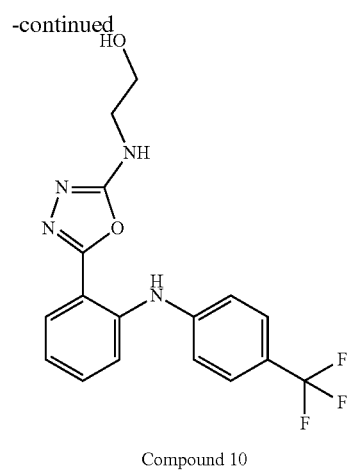

Compound 10

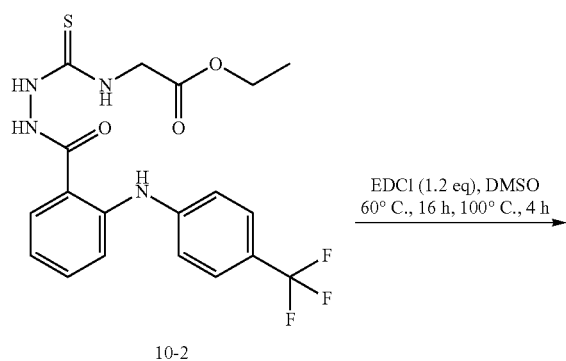

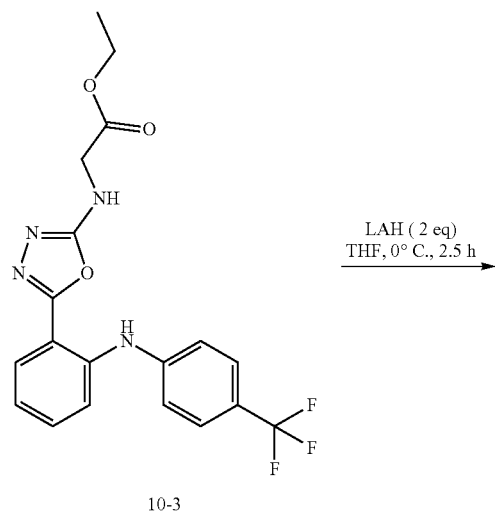

Step 1: 2-(2-(2-((4-(trifluoromethyl)phenyl)amino)benzoyl)hydrazinecarbothioamido)acetate To a solution of 10-1 (813.5 mg, 2.76 mmol, 1 eq) in THF (3.5 mL) was added ethyl 2-isothiocyanatoacetate (400 mg, 2.76 mmol, 0.4 mL, 1 eq). The mixture was stirred at 50° C. for 16 hr. LCMS showed 10-1 was consumed and 65% of desired mass was detected. The residue was concentrated under reduced pressure to give 10-2 (1.4 g, crude), which was used directly. LCMS (ESI): RT=0.769 min, mass calc. for $C_{19}H_{19}F_3N_4O_3S$ 440.11, m/z found 441.0 $[M+1]^+$.

Step 2: 2-((5-(2-((4-(trifluoromethyl)phenyl)amino)phenyl)-1,3,4-oxadiazol-2-yl)amino)acetate A mixture of 10-2 (1.2 g, 2.72 mmol, 1 eq), EDCI (626.7 mg, 3.27 mmol, 1.2 eq) in DMSO (15 mL) was degassed and purged with $N_2$ for 3 times, and then the mixture was stirred at 100° C. for 4 hr under $N_2$ atmosphere. LCMS showed the reaction was complete and 52% of desired product was formed. The mixture was combined with another batch and diluted with EA (250 mL) and washed with brine (30 mL*5), dried by anhydrous $Na_2SO_4$, filtered and concentrated to give crude 10-3 (0.9 g, 2.21 mmol, 81.1% yield), which was used directly for next step. 50 mg of crude 10-3 was purified by prep-HPLC to give 10-3 (21.07 mg, 51.85 umol, 1.90% yield). LCMS (ESI): RT=0.821 min, mass calc. for $C_{19}H_{17}F_3N_4O_3$ 406.13, m/z found 406.9 $[M+1]^+$. $^1$H NMR (400 MHz, DMSO-$d_6$) δ 9.27 (s, 1H), 8.42 (t, J=6.4 Hz, 1H), 7.75 (dd, J=1.4, 7.9 Hz, 1H), 7.64 (d, J=8.5 Hz, 2H), 7.55 (d, J=8.0 Hz, 1H), 7.50-7.42 (m, 1H), 7.37 (d, J=8.5 Hz, 2H), 7.10 (t, J=7.2 Hz, 1H), 4.19-4.04 (m, 4H), 1.21 (t, J=7.2 Hz, 3H).

Step 3: 2-((5-(2-((4-(trifluoromethyl)phenyl)amino)phenyl)-1,3,4-oxadiazol-2-yl)amino)ethanol A solution of 10-3 (0.04 g, 98 umol, 1 eq) in THF (3 mL) was cooled to 0° C. Then LiAlH4 (7.5 mg, 0.20 mmol, 2 eq) was added, along with gas evolved. Then the mixture was stirred at 0° C. for 2.5 h. LCMS showed the reaction was complete and 93% of desired product was formed. The reaction was quenched with water (5 mL) and diluted with EA (50 mL) and separated. The separated organic layer was washed with brine (10 mL) and dried by anhydrous $Na_2SO_4$, filtered and concentrated to give a residue. The residue was purified by prep-HPLC to give Compound 10 (5.21 mg, 14 umol, 14.4% yield). LCMS (ESI): RT=0.747 min, mass calc. for $C_{17}H_{15}F_3N_4O_2$ 364.11, m/z found 364.9 [M+1]$^+$. $^1$H NMR (400 MHz, DMSO-d$_6$) δ 9.32 (s, 1H), 7.92 (br t, J=5.6 Hz, 1H), 7.72 (d, J=7.5 Hz, 1H), 7.64 (br d, J=8.5 Hz, 2H), 7.54 (d, J=8.3 Hz, 1H), 7.46-7.32 (m, 3H), 7.08 (t, J=7.5 Hz, 1H), 4.82 (t, J=5.4 Hz, 1H), 3.62-3.51 (m, 2H), 3.32 (br d, J=5.8 Hz, 2H).

Example 10: ethyl N-methyl-N-(5-(2-((4-(trifluoromethyl)phenyl)amino)phenyl)-1,3,4-oxadiazol-2-yl)glycinate (Compound 11)

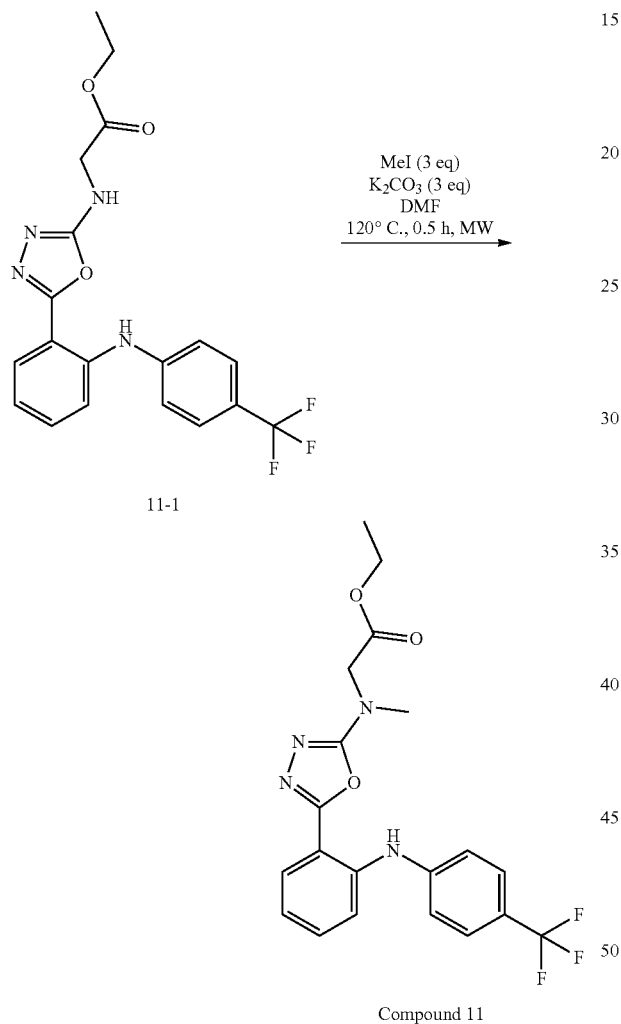

Compound 11

A mixture of 11-1 (200 mg, 0.49 mmol, 1 eq), MeI (209.58 mg, 1.48 mmol, 91.92 uL, 3 eq) and K$_2$CO$_3$ (204.07 mg, 1.48 mmol, 3 eq) in DMF (15 mL) was heated at 120° C. for 0.5 h under microwave. TLC (Petroleum ether:Ethyl acetate=3:1, UV) indicated that 11-1 remained and one main spot was detected. LCMS showed 11-1 was consumed and desired mass (420.9) was detected. The mixture was combined with another batch, filtered and concentrated to give a residue. The residue was purified by column chromatography (SiO$_2$) to give Compound 11 (66.17 mg, 0.15 mmol, 31.5% yield). LCMS (ESI): RT=0.848 min, mass calc. for $C_{20}H_{19}F_3N_4O_3$ 420.14 m/z found 421.0 [M+1]$^+$. $^1$H NMR (400 MHz, DMSO-d$_6$) δ 9.18 (s, 1H), 7.86 (d, J=6.8 Hz, 1H), 7.63 (d, J=8.5 Hz, 2H), 7.56-7.50 (m, 1H), 7.48-7.41 (m, 1H), 7.34 (d, J=8.3 Hz, 2H), 7.11 (t, J=7.5 Hz, 1H), 4.32 (s, 2H), 4.14 (q, J=7.2 Hz, 2H), 3.15 (s, 3H), 1.20 (t, J=7.0 Hz, 3H).

Example 11: N-methyl-5-(2-((4-(trifluoromethyl)phenyl)amino)phenyl)-1,3,4-oxadiazol-2-amine (Compound 12)

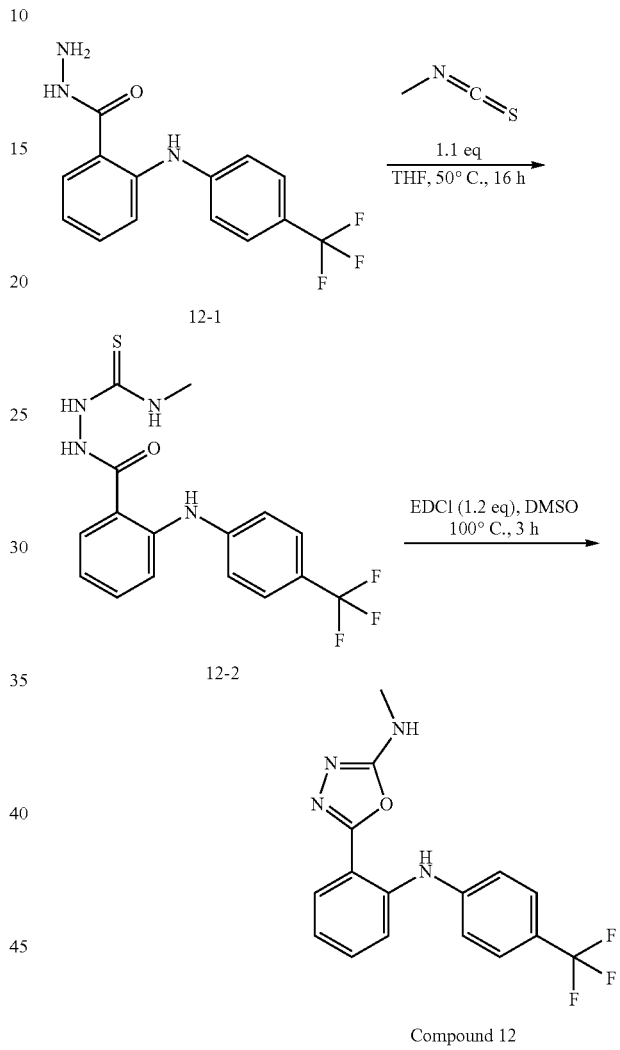

Compound 12

Step 1: N-methyl-2-(2-((4-(trifluoromethyl)phenyl)amino)benzoyl)hydrazinecarbothioamide A tube containing 12-1 (0.2 g, 0.68 mmol, 1 eq) and methylimino(thioxo)methane (54.5 mg, 0.75 mmol, 51 uL, 1.1 eq) in THF (2.5 mL) was heated at 50° C. for 16 hr. LCMS showed the reaction was complete and 82% of desired product was formed. The mixture was concentrated to give crude 12-2 (0.2 g, 0.54 mmol, 80.2% yield). LCMS (ESI): RT=0.742 min, mass calc. for $C_{16}H_{15}F_3N_4OS$ 368.09, m/z found 368.9 [M+1]$^+$.

Step 2: N-methyl-5-(2-((4-(trifluoromethyl)phenyl)amino)phenyl)-1,3,4-oxadiazol-2-amine A tube containing 12-2 (0.15 g, 0.41 mmol, 1 eq) and EDCI (93.67 mg, 0.49 mmol, 1.2 eq) in DMSO (1.5 mL)

was heated at 100° C. for 3 hr. LCMS showed the reaction was complete and 64% of desired product was formed. The mixture was combined with another batch and filtered. The filtrate was purified by prep-HPLC to give Compound 12 (6.54 mg, 19 umol, 4.8% yield). LCMS (ESI): RT=1.366 min, mass calc. for $C_{16}H_{13}F_3N_4O$ 334.10, m/z found 334.9 [M+1]$^+$. $^1$H NMR (400 MHz, DMSO-$d_6$) δ 9.31 (s, 1H), 7.79-7.70 (m, 2H), 7.64 (d, J=8.5 Hz, 2H), 7.56-7.51 (m, 1H), 7.46-7.40 (m, 1H), 7.36 (d, J=8.5 Hz, 2H), 7.08 (t, J=7.3 Hz, 1H), 2.87 (d, J=5.0 Hz, 3H).

Example 12: 5-(5-(2-((4-(trifluoromethyl)phenyl)amino)phenyl)-1,3,4-oxadiazol-2-yl)oxazolidin-2-one (Compound 13)

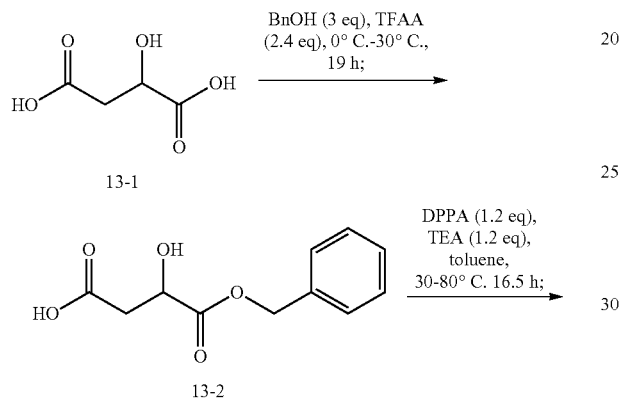

Step 1: 4-(benzyloxy)-3-hydroxy-4-oxobutanoic acid

To a solution of TFAA (18.80 g, 89.49 mmol, 12.5 mL, 2.4 eq) at 0° C. was added 13-1 (5.0 g, 37.29 mmol, 1 eq). The mixture was stirred at 30° C. until the mixture was a clear solution (about 2 h). And then the mixture was concentrated to remove TFAA and the residue was dissolved in phenylmethanol (12.90 g, 119.33 mmol, 12.4 mL, 3.2 eq). The resulting mixture was stirred at 30° C. for 16 h. TLC (DCM:MeOH=10:1, I$_2$) showed starting material was consumed completely and one new spot was formed. The mixture was diluted with EA (20 mL) and extracted with saturated Na$_2$CO$_3$ solution (100 mL). The aqueous layer was separated, then acidified with conc. HCl to pH=1-2 and then extracted with EA (100 mL*3). The combined organic layer was washed with brine (100 mL), dried over anhydrous Na$_2$SO$_4$, filtered and concentrated under reduced pressure to give 13-2 (5.0 g, 22.30 mmol, 59.80% yield). $^1$H NMR (400 MHz, CDCl$_3$) δ 7.44-7.29 (m, 5H), 5.23 (s, 2H), 4.58-4.50 (m, 1H), 2.99-2.79 (m, 2H).

Step 2: benzyl 2-oxooxazolidine-5-carboxylate

To a solution of 13-2 (5.0 g, 22.30 mmol, 1 eq) and TEA (2.71 g, 26.76 mmol, 3.7 mL, 1.2 eq) in toluene (100 mL) at 30° C. was added DPPA (7.36 g, 26.76 mmol, 5.8 mL, 1.2 eq) dropwise. After stirred at 30° C. for 30 min, the mixture was stirred at 80° C. for 16 h. TLC (PE:EA=1:1, I$_2$, plate 1) showed most of starting material still remained but no new spot was formed. TLC (PE:EA=1:1, KMnO$_4$, plate 2) showed most of starting material still remained and two new spots were formed. The mixture was concentrated to remove solvent. And the residue was diluted with saturated Na$_2$CO$_3$ solution (100 mL), and then extracted with EA (100 mL*3).

The combined organic layer was washed with brine (100 mL), dried over anhydrous Na$_2$SO$_4$, filtered and concentrated under reduced pressure to give a residue. The residue was purified by column chromatography (SiO$_2$) to give 13-3 (890 mg, 4.02 mmol, 18.04% yield), which was confirmed by H NMR. $^1$H NMR (400 MHz, CDCl$_3$) δ 7.39 (s, 5H), 5.28 (s, 2H), 5.07 (dd, J=5.6, 9.4 Hz, 1H), 3.90 (t, J=9.4 Hz, 1H), 3.70 (dd, J=5.5, 9.0 Hz, 1H).

Step 3: 2-oxooxazolidine-5-carboxylic acid

To a solution of benzyl 2-oxooxazolidine-5-carboxylate 13-3 (0.89 g, 4.02 mmol, 1 eq) in EtOH (10 mL) was added Pd/C (0.3 g, 0.282 umol, 10% purity, 7.01e-2 eq) under N$_2$. The suspension was degassed under vacuum and purged with H$_2$ several times. The mixture was stirred under H$_2$ (15 psi) at 30° C. for 16 h. TLC (Petroleum ether/Ethyl acetate=1:1 stained by iodine) showed the starting material was consumed completely and new spot was formed. The reaction mixture was filtered and the filtrate was concentrated to give 13-4 (0.47 g, 3.59 mmol, 89.12% yield), which was used directly without purification. $^1$H NMR (400 MHz, CD$_3$OD) δ 5.13-5.08 (m, 1H), 3.91 (t, J=9.4 Hz, 1H), 3.68-3.55 (m, 1H).

Step 4: 2-oxo-N'-(2-((4-(trifluoromethyl)phenyl)amino)benzoyl)oxazolidine-5-carbohydrazide To a solution of 13-4 (20 mg, 0.153 mmol, 1.2 eq) in DMF (1 mL) at 30° C. was added HCTU (68.4 mg, 0.165 mmol, 1.3 eq), and the mixture was stirred at 30° C. for 20 min. And then 13-4a (37.5 mg, 0.127 mmol, 1 eq) and DIPEA (32.9 mg, 0.254 mmol, 44.3 uL, 2 eq) was successively added at 30° C. into the above mixture. The resulting mixture was stirred at 30° C. for 16 h. TLC (DCM:MeOH=10:1, UV) showed some starting material still remained and one new spot was formed. LCMS showed starting material and desired product was included in one peak. The mixture was combined with another batch. The combined sample was purified by prep-HPLC to give 13-5 (18.46 mg, 45.2 umol, 35.56% yield). LCMS (ESI): RT=0.687 min, mass calc. for C$_{18}$H$_{15}$F$_3$N$_4$O$_4$ 408.10, m/z found 431.0[M+23]$^+$. $^1$H NMR (400 MHz, DMSO-d$_6$) δ 10.56 (s, 1H), 10.45 (s, 1H), 9.36 (s, 1H), 7.84 (s, 1H), 7.70 (d, J=7.5 Hz, 1H), 7.59 (d, J=8.5 Hz, 2H), 7.48 (s, 2H), 7.29 (d, J=8.5 Hz, 2H), 7.04 (s, 1H), 5.11 (d, J=3.5 Hz, 1H), 3.79 (t, J=9.3 Hz, 1H), 3.53-3.45 (m, 1H).

Step 5: 5-(5-(2-((4-(trifluoromethyl)phenyl)amino)phenyl)-1,3,4-oxadiazol-2-yl)oxazolidin-2-one To a solution of 13-5 (80 mg, 0.20 mmol, 1 eq) and TEA (59.5 mg, 0.59 mmol, 81.8 uL, 3 eq) in DCM (2 mL) at 30° C. was added TsCl (37.4 mg, 0.20 mmol, 1 eq), and the mixture was stirred at 30° C. for 16 h. TLC (DCM:MeOH=10:1, UV) showed starting material was consumed completely and one new spot was formed. LCMS showed starting material was consumed completely and 54% of desired product was formed. The mixture was concentrated to give a residue. The residue was purified by prep-HPLC to give Compound 13 (13.71 mg, 34.07 umol, 17.39% yield). LCMS (ESI): RT=0.768 min, mass calc. for C$_8$H$_{13}$F$_3$N$_4$O$_3$ 390.09, m/z found 390.9[M+1]$^+$. $^1$H NMR (400 MHz, DMSO-d$_6$) δ 9.13 (s, 1H), 8.09 (s, 1H), 7.93 (d, J=8.0 Hz, 1H), 7.63 (d, J=8.5 Hz, 2H), 7.59-7.52 (m, 2H), 7.35 (d, J=8.5 Hz, 2H), 7.22-7.11 (m, 1H), 6.01 (dd, J=5.5, 9.0 Hz, 1H), 3.99-3.92 (m, 1H), 3.90-3.84 (m, 1H).

Example 13: N-hydroxy-5-(2-((4-(trifluoromethyl)phenyl)amino)phenyl)-1,3,4-oxadiazole-2-carboxamide (Compound 14)

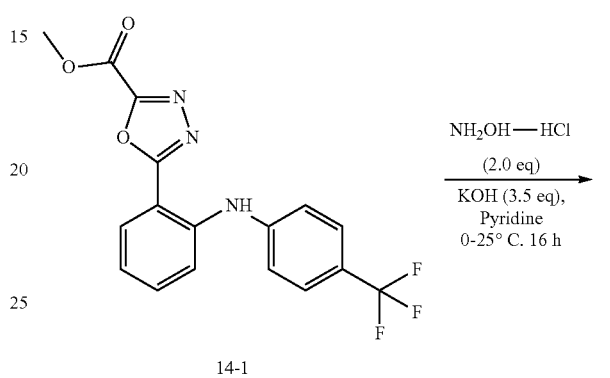

14-1

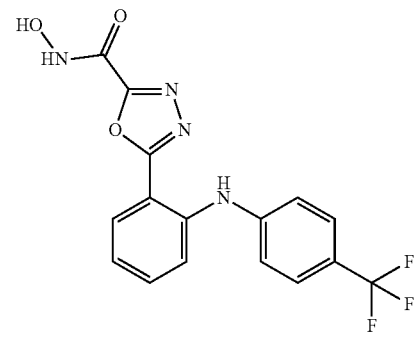

Compound 14

To a solution of NH$_2$OH.HCl (58.3 mg, 0.6 mmol, 2.0 eq, HCl) in pyridine (2 mL) were added KOH (54.1 mg, 1.0 mmol, 3.5 eq) and 14-1 (0.1 g, 0.28 mmol, 1 eq) at 0° C. The mixture was stirred at 25° C. for 16 h. LC-MS showed 16% of 14-1 remained and 39% of desired compound was detected. The reaction mixture was filtered and concentrated under reduced pressure to give a residue. The residue was purified by prep-HPLC to give Compound 14 (13.06 mg, 36 umol, 13.0% yield). LCMS (ESI): RT=0.743 min, mass calc. for C$_{16}$H$_{11}$F$_3$N$_4$O$_3$ 364.08, m/z found 364.9 [M+H]$^+$; $^1$H NMR (400 MHz, CDCl$_3$) δ 12.20 (s, 1H), 9.79 (s, 1H), 9.12 (s, 1H), 8.01 (d, J=7.8 Hz, 1H), 7.64 (d, J=8.5 Hz, 2H), 7.59-7.54 (m, 2H), 7.37 (d, J=8.5 Hz, 2H), 7.18-7.14 (m, J=3.0, 5.1, 7.9 Hz, 1H).

Example 14: 5-(2-((4-(trifluoromethyl)phenyl)amino)phenyl)-1,3,4-oxadiazole-2-carboxamide (Compound 15)

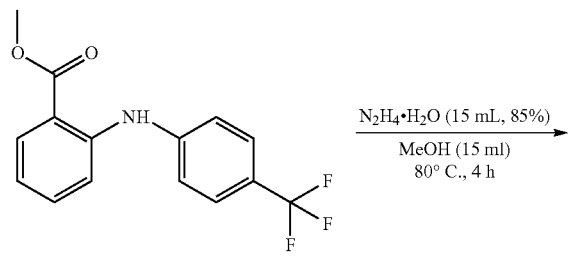

15-1

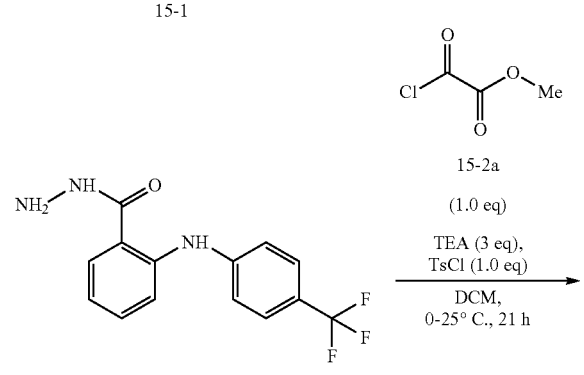

15-2

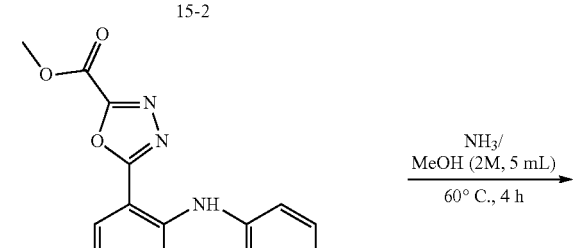

15-3

Compound 15

Step 1: 2-[4-(trifluoromethyl)anilino]benzohydrazide

To a solution of 15-1 (2.0 g, 6.7 mmol, 1.0 eq) in MeOH (15.0 mL) was added N₂H4.H₂O (15.4 g, 262.3 mmol, 15 mL, 38.7 eq). The mixture was stirred at 80° C. for 4 h. TLC (PE:EA=2:1 UV) showed that 15-1 was consumed completely and one new spot formed. The solution was concentrated (lots of solid formed) and then filtered. The filter cake was washed with water (20 mL), triturated with PE (50 mL), filtered and dried under vacuum to give 15-2 (1.9 g, 6.44 mmol, 95.0% yield).

Step 2: methyl 5-[2-[4-(trifluoromethyl)anilino]phenyl]-1,3,4-oxadiazole-2-carboxylate To a solution of 15-2a (207.4 mg, 1.7 mmol, 0.2 mL, 1.0 eq) and TEA (514.1 mg, 5.1 mmol, 0.7 mL, 3.0 eq) in DCM (6.0 mL) was added 15-2 (0.5 g, 1.7 mmol, 1.0 eq) at 0° C. The mixture was stirred at 25° C. for 16 h. Then TsCl (322.8 mg, 1.7 mmol, 1.0 eq) was added and the mixture was stirred at 25° C. for 5 h. Several new peaks were shown and 47% of desired compound was detected on LC-MS. The reaction mixture was quenched by addition of saturated NaHCO₃ (30 mL), and then diluted with EtOAc (100 mL). The organic layer was separated and washed with brine (50 mL*3), dried over Na₂SO₄, filtered and concentrated under reduced pressure to give 15-3 (0.4 g, 1.1 mmol, 65.0% yield). 20 mg crude product was purified by prep-HPLC to give to give desired compound (2.40 mg). LCMS (ESI): RT=1.018 min, mass calc. for $C_{17}H_{12}F_3N_3O_3$ 363.08, m/z found 364.2 [M+H]⁺; ¹H NMR (400 MHz, DMSO-d₆) δ 9.12 (s, 1H), 7.94 (d, J=7.8 Hz, 1H), 7.64 (d, J=8.5 Hz, 2H), 7.58 (d, J=3.3 Hz, 2H), 7.37 (d, J=8.3 Hz, 2H), 7.21-7.12 (m, 1H), 3.99 (s, 3H).

Step 3: methyl 5-[2-[4-(trifluoromethyl)anilino]phenyl]-1,3,4-oxadiazole-2-carboxylate To a solution of NH₃ (46.9 mg, 2.75 mmol, 10 eq) in MeOH (5 mL) was added 15-3 (100.0 mg, 0.3 mmol, 1.0 eq) at 0° C. in seal pot. The mixture was stirred at 60° C. for 4 hr. Several new peaks were shown and 63% of desired compound was detected on LC-MS. The reaction mixture was concentrated under reduced pressure to give Compound 15 (100 mg, crude). 20 mg crude product was purified by prep-HPLC to give Compound 15 (16.37 mg). LCMS (ESI): RT=1.018 min, mass calc. for $C_{16}H_{11}F_3N_4O_2$ 348.08, m/z found 348.9 [M+H]⁺; ¹H NMR (400 MHz, CDCl₃) δ 9.35 (s, 1H), 8.06 (d, J=7.8 Hz, 1H), 7.61 (d, J=8.5 Hz, 2H), 7.53-7.48 (m, 1H), 7.47-7.42 (m, 1H), 7.39 (d, J=8.3 Hz, 2H), 7.07 (s, 1H), 7.00 (t, J=7.5 Hz, 1H), 6.01 (s, 1H).

Example 15: 3-tosyl-4-(5-(2-((4-(trifluoromethyl)phenyl)amino)phenyl)-1,3,4-oxadiazol-2-yl)oxazolidin-2-one (Compound 16) and 4-(5-(2-((4-(trifluoromethyl)phenyl)amino)phenyl)-1,3,4-oxadiazol-2-yl)oxazolidin-2-one (Compound 17)

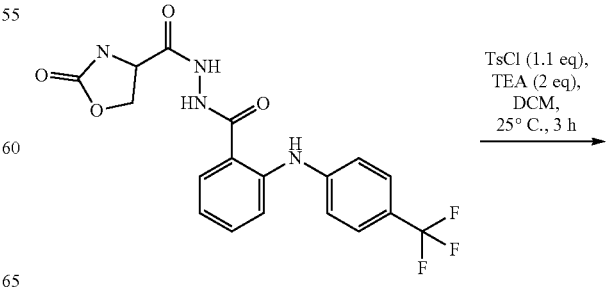

16-1

181
-continued

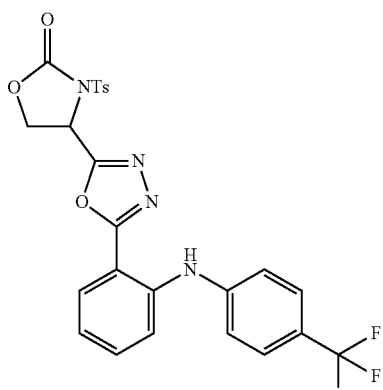

Compound 16

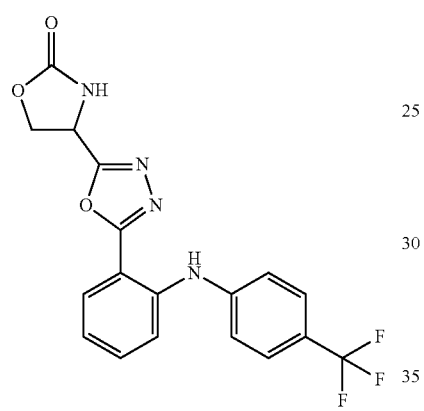

Compound 17

To a mixture of 16-1 (0.15 g, 0.37 mmol, 1 eq) in DCM (9 mL) were added TEA (111.5 mg, 1.10 mmol, 153.39 uL, 3 eq) and TsCl (70.03 mg, 0.37 mmol, 1 eq) at 30° C. After addition, the resulting solution was stirred at 30° C. for 3 h. LCMS showed the reaction was complete and 32% of desired product was formed. TLC (PE:EA=1:1 UV) showed new spots were formed. The mixture was concentrated to give a residue. The residue was combined with another batch and purified by prep-HPLC) to give crude Compound 17 (6 mg) and Compound 16 (3.57 mg, 6.39 umol, 1.74% yield). Then crude Compound 17 was purified by prep-TLC to give Compound 17 (2.6 mg, 6.39 umol, 1.74% yield).

Compound 16: LCMS (ESI): RT=0.880 min, mass calc. for $C_{25}H_{19}F_3N_4O_5S$ 544.10, m/z found 567.0 [M+23]$^+$. $^1$H NMR (400 MHz, DMSO-$d_6$) δ 9.09 (s, 1H), 7.69-7.69 (m, 1H), 7.68-7.65 (m, 1H), 7.68 (s, 1H), 7.64-7.60 (m, 1H), 7.68-7.60 (m, 2H), 7.59-7.55 (m, 2H), 7.48 (d, J=8.3 Hz, 1H), 7.39 (d, J=8.5 Hz, 2H), 7.26 (d, J=8.3 Hz, 2H), 7.12 (br t, J=8.3 Hz, 1H), 6.13 (dd, J=3.1, 8.4 Hz, 1H), 4.83 (t, J=8.5 Hz, 1H), 4.70-4.62 (m, 1H), 2.12 (s, 3H).

Compound 17: LCMS (ESI): RT=0.760 min, mass calc. for $C_8H_{13}F_3N_4O_3$ 390.09, m/z found 391.3 [M+1]$^+$. $^1$H NMR (400 MHz, DMSO-$d_6$) δ 9.16 (s, 1H), 8.57 (s, 1H), 7.92 (d, J=8.3 Hz, 1H), 7.70-7.53 (m, 4H), 7.36 (br d, J=8.3 Hz, 2H), 7.17 (br t, J=6.4 Hz, 1H), 5.37 (dd, J=4.5, 8.5 Hz, 1H), 4.73-4.66 (m, 1H), 4.59 (dd, J=4.4, 8.9 Hz, 1H).

182

Example 16: (5-(2-((4-(trifluoromethyl)phenyl)amino)phenyl)-1,3,4-oxadiazol-2-yl)glycine (Compound 18)

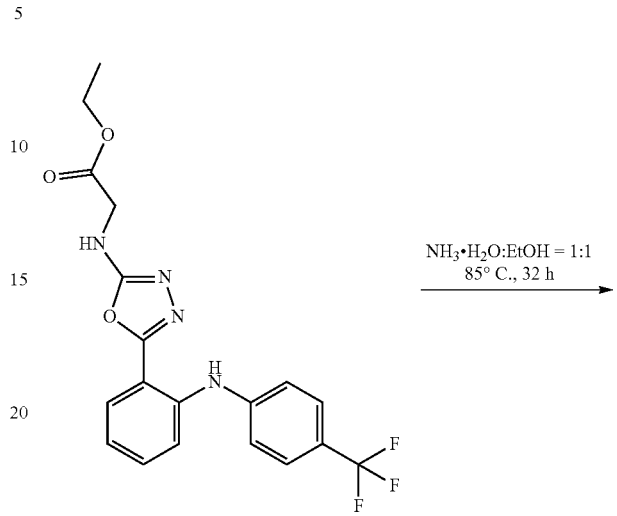

18-1

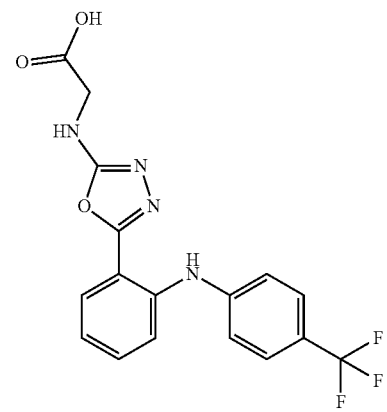

Compound 18

A solution of 18-1 (0.04 g, 98.44 umol, 1 eq) in NH$_3$.H$_2$O (3.45 g, 24.61 mmol, 3.79 mL, 250 eq) was heated at 85° C. for 4 h. TLC (PE:EA=1:1 UV) showed most of starting material remained. Then EtOH (4 mL) was added the mixture was heated at 85° C. for another 4 h. LCMS showed the reaction was complete and 52% of desired product was formed. The reaction mixture was cooled to 25° C. and concentrated under reduced pressure to give a residue. The residue was purified by prep-HPLC to give Compound 18 (6.84 mg, 17.72 umol, 18% yield). LCMS (ESI): RT=0.747 min, mass calc. for $C_{17}H_{13}F_3N_4O_3$ 379.0, m/z found 378.09 [M+23]$^+$. $^1$H NMR (400 MHz, DMSO-$d_6$) δ 9.31 (s, 1H), 8.09 (br s, 1H), 7.74 (br d, J=7.8 Hz, 1H), 7.64 (br d, J=8.5 Hz, 2H), 7.54 (br d, J=8.3 Hz, 1H), 7.47-7.35 (m, 3H), 7.08 (t, J=7.5 Hz, 1H), 3.88 (br s, 2H).

Example 17: 2-(methyl(5-(2-((4-(trifluoromethyl)phenyl)amino)phenyl)-1,3,4-oxadiazol-2-yl)amino)ethan-1-ol (Compound 19)

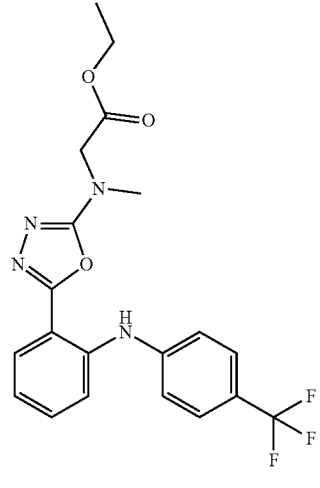

19-1

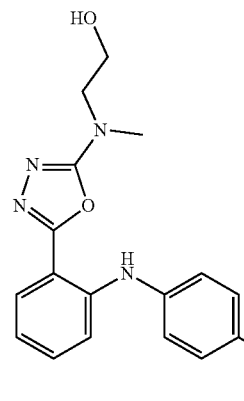

Compound 19

A solution of 19-1 (50 mg, 0.1 mmol, 1.0 eq) in THF (4 mL) was cooled in ice-water bath. Then LiAlH₄ (9.0 mg, 0.2 mmol, 2.0 eq) was added, along with gas evolved. Then the mixture was stirred in ice-water bath for 2.5 hr. LCMS showed 19-1 was consumed and 67% of desired product was detected. Then the mixture was quenched with water (10 mL). The combined mixture was extracted with EA (20 mL*3), dried by anhydrous Na₂SO₄, filtered and concentrated to give a residue. The residue was purified by prep-HPLC to give Compound 19 (40.5 mg, 0.1 mmol, 89.1% yield). LCMS (ESI): RT=0.766 min, mass calc. for: $C_{18}H_{17}F_3N_4O_2$ 378.13, m/z found 378.9 [M+H]⁺; ¹H NMR (400 MHz, CDCl₃) δ 3.27 (s, 3H), 3.69 (t, J=5.27 Hz, 2H), 3.96 (t, J=5.14 Hz, 2H), 6.94 (t, J=7.65 Hz, 1H), 7.30-7.38 (m, 3H), 7.50 (d, J=8.53 Hz, 1H), 7.55 (d, J=8.53 Hz, 2H), 7.73 (d, J=8.03 Hz, 1H), 9.44 (s, 1H).

Example 18: 2-(1,3,4-oxadiazol-2-yl)-N-[4-(trifluoromethyl)phenyl]aniline (Compound 20)

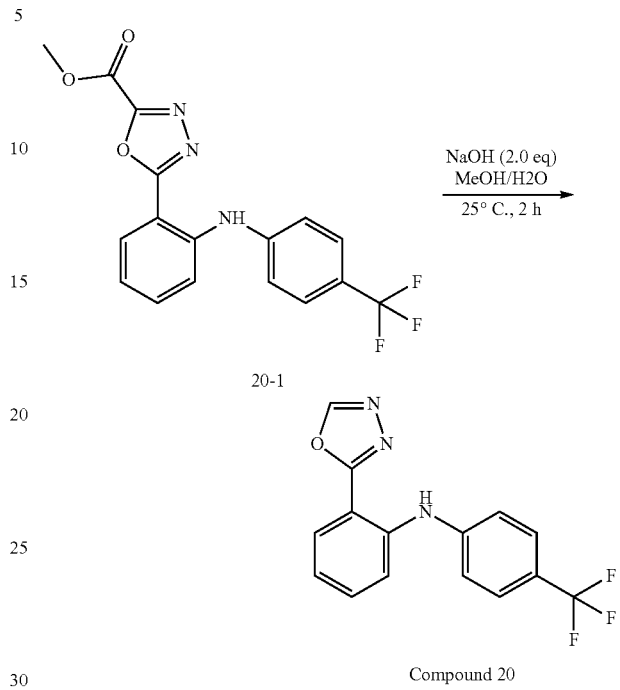

To a solution of 20-1 (0.4 g, 1.1 mmol, 1.0 eq) in MeOH (0.8 mL) was added a solution of NaOH (88.1 mg, 2.2 mmol, 2.0 eq) in H₂O (0.5 mL). The mixture was stirred at 25° C. for 2 h. LC-MS showed 20-1 was consumed completely and 59% of desired mass was detected. The pH of the mixture was adjusted with HCl (1M) to 4-5, and then the mixture was filtered to give a residue. The residue was purified by prep-HPLC to give Compound 20 (7.15 mg, 23.42 umol, 2.13% yield). LCMS (ESI): RT=0.824 min, mass calc. for $C_{15}H_{10}F_3N_3O$ 305.08, m/z found 305.9 [M+H]⁺; ¹H NMR (400 MHz, CDCl₃) δ 9.39 (s, 1H), 9.23 (s, 1H), 7.94 (d, J=7.5 Hz, 1H), 7.63 (d, J=8.5 Hz, 2H), 7.59-7.51 (m, 1H), 7.59-7.51 (m, 1H), 7.36 (d, J=8.3 Hz, 2H), 7.18-7.12 (m, 1H).

Example 19: 2-[5-(2,2-dimethyl-1,3-dioxolan-4-yl)-1,3,4-oxadiazol-2-yl]-N-[4-(trifluoromethyl) phenyl]aniline (Compound 21)

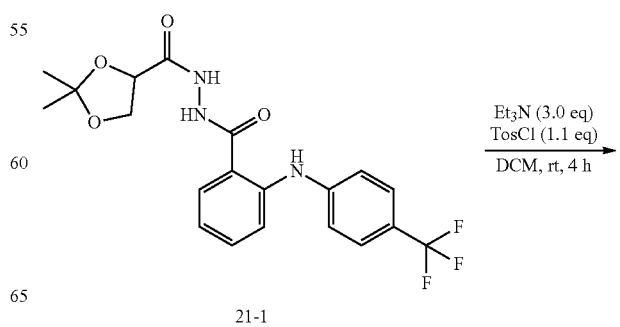

21-1

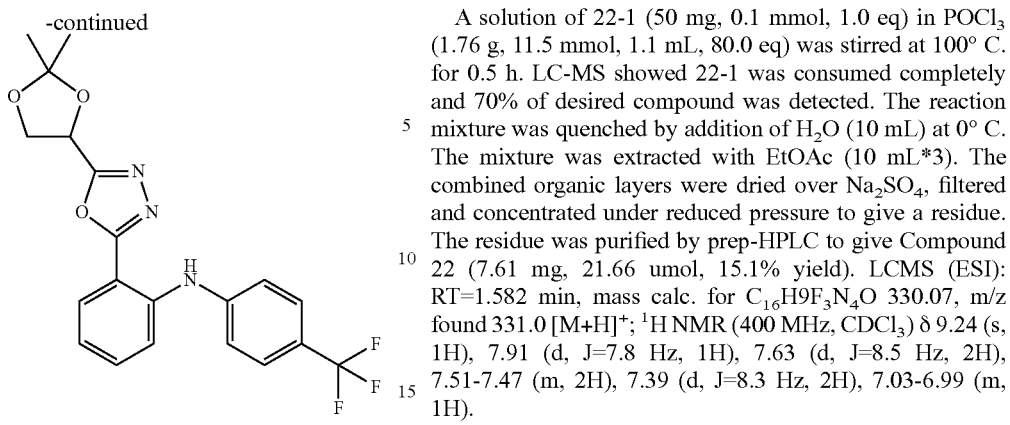

Compound 21

To a solution of 21-1 (62 mg, 0.15 mmol, 1 eq) and TEA (44.4 mg, 0.44 mmol, 61.15 uL, 3 eq) in DCM (2 mL) was added TsCl (29.3 mg, 0.16 mmol, 1.05 eq). The reaction was stirred at 25° C. for 3 hr. LCMS showed that 78% of desired product was detected. HPLC showed that 89% of desired product was detected. The reaction was concentrated. The residue was purified by prep-HPLC to give Compound 21 (18 mg, 44.40 umol, 30.32% yield). LCMS (ESI): RT=0.873 min, mass calcd. for $C_{20}H_{18}F_3N_3O_3$, 405.15 m/z found 406.0[M+H]$^+$. $^1$H NMR (400 MHz, DMSO) δ9.16 (s, 1H), 7.90 (d, J=7.6 Hz, 1H), 7.71-7.49 (m, 4H), 7.34 (d, J=7.6 Hz, 2H), 7.25-7.17 (m, 1H), 5.45 (t, J=5.2 Hz, 1H), 4.50-4.25 (m, 1H), 1.43 (d, J=4.0 Hz, 3H).

Example 20: 5-[2-[4-(trifluoromethyl)anilino]phenyl]-1,3,4-oxadiazole-2-carbonitrile (Compound 22)

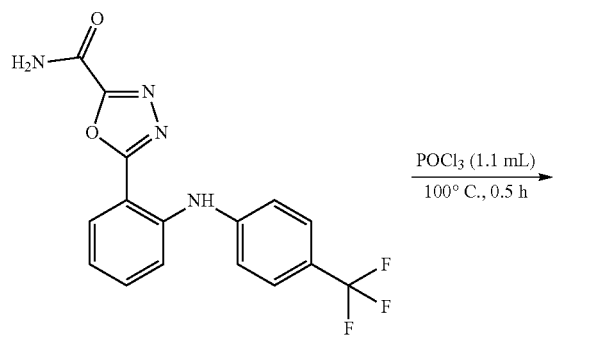

A solution of 22-1 (50 mg, 0.1 mmol, 1.0 eq) in POCl$_3$ (1.76 g, 11.5 mmol, 1.1 mL, 80.0 eq) was stirred at 100° C. for 0.5 h. LC-MS showed 22-1 was consumed completely and 70% of desired compound was detected. The reaction mixture was quenched by addition of H$_2$O (10 mL) at 0° C. The mixture was extracted with EtOAc (10 mL*3). The combined organic layers were dried over Na$_2$SO$_4$, filtered and concentrated under reduced pressure to give a residue. The residue was purified by prep-HPLC to give Compound 22 (7.61 mg, 21.66 umol, 15.1% yield). LCMS (ESI): RT=1.582 min, mass calc. for $C_{16}H9F_3N_4O$ 330.07, m/z found 331.0 [M+H]$^+$; $^1$H NMR (400 MHz, CDCl$_3$) δ 9.24 (s, 1H), 7.91 (d, J=7.8 Hz, 1H), 7.63 (d, J=8.5 Hz, 2H), 7.51-7.47 (m, 2H), 7.39 (d, J=8.3 Hz, 2H), 7.03-6.99 (m, 1H).

Example 21: 1-(4-methoxybenzyl)-3-(5-(2-((4-(trifluoromethyl)phenyl)amino)phenyl)-1,3,4-oxadiazol-2-yl)urea (Compound 23)

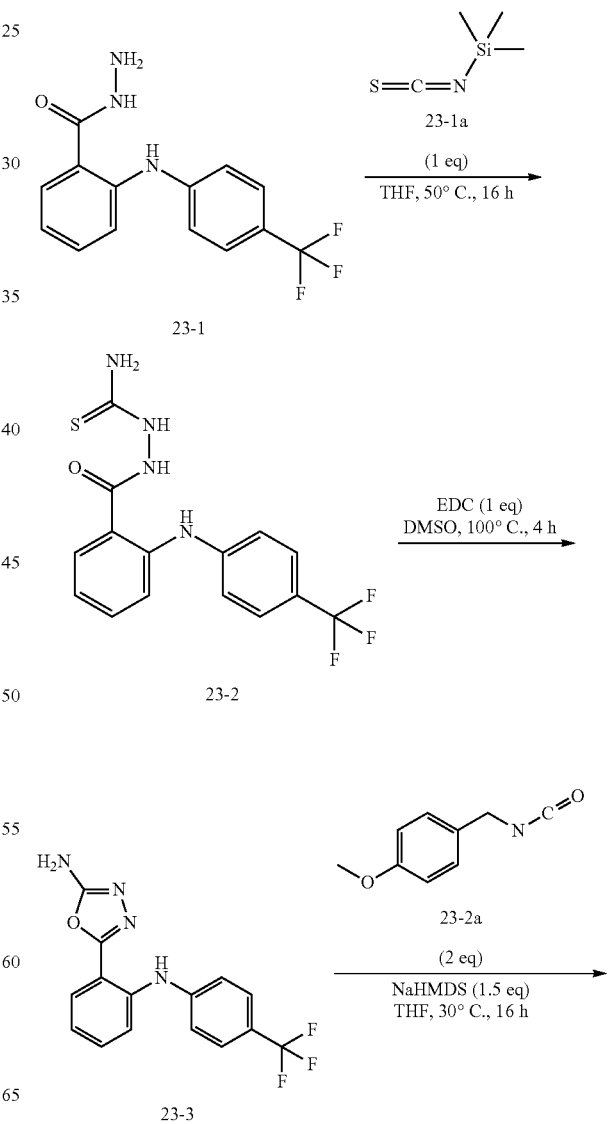

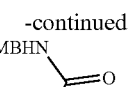

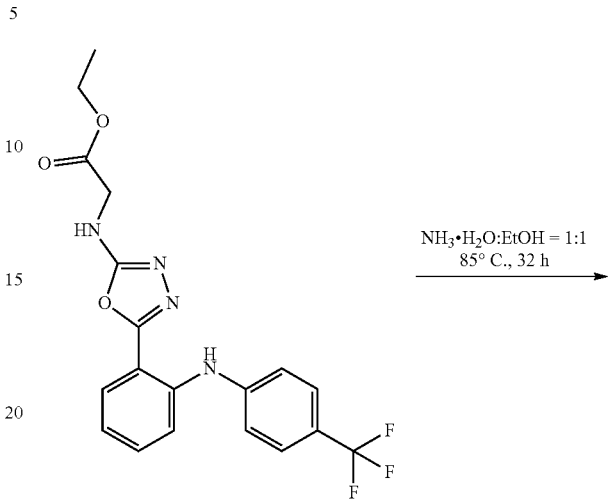

Compound 23

Step 1: 2-(2-((4-(trifluoromethyl)phenyl)amino) benzoyl)hydrazinecarbothioamide To a solution of 23-1 (1.5 g, 5.08 mmol, 1 eq) in THF (25 mL) was added 23-1a (666.9 mg, 5.08 mmol, 63 uL, 1 eq). The mixture was stirred at 50° C. for 16 hr. LCMS showed reactant 23-1 was consumed completely and 69% of desired mass was detected. The solution was concentrated to give compound 23-2 (1.9 g, crude), which was used directly. LCMS (ESI): RT=0.721 min, mass calc. for $C_{15}H_{13}F_3N_4OS$ 354.08, m/z found 354.9 $[M+1]^+$.

Step 2: 5-(2-((4-(trifluoromethyl)phenyl)amino) phenyl)-1,3,4-oxadiazol-2-amine To a solution of compound 23-2 (1.5 g, 4.23 mmol, 1 eq) in DMSO (10 mL) was added EDCI (811.5 mg, 4.23 mmol, 1 eq). The mixture was stirred at 100° C. for 4 hr. LCMS showed the reaction was complete and 52% of desired product was formed. TLC (PE:EA=1:2 UV) showed the reaction was complete. The mixture was diluted with EA (250 mL) and washed with brine (30 mL*3), dried by anhydrous $Na_2SO_4$, filtered and concentrated to give a residue. The residue was purified by column chromatography (SiO$_2$) to give 23-3 (0.7 g, 2.19 mmol, 51.6% yield). $^1$H NMR (400 MHz, DMSO-d$_6$) δ 9.28 (s, 1H), 7.76-7.67 (m, 1H), 7.63 (d, J=8.5 Hz, 2H), 7.55-7.47 (m, 1H), 7.44-7.28 (m, 5H), 7.06 (t, J=7.4 Hz, 1H).

Step 3: 1-(4-methoxybenzyl)-3-(5-(2-((4-(trifluoromethyl)phenyl)amino)phenyl)-1,3,4-oxadiazol-2-yl)urea To a solution of 23-3 (0.1 g, 0.31 mmol, 1 eq) in TH (3 mL) were added NaMDS (1 M, 0.5 mL, 1.5 eq) and 23-2a (101.9 mg, 0.62 mmol, 89 uL, 2 eq) at 30° C. The mixture was stirred at 30° C. for 16 h. LCMS showed no 23-3 was remained and 58% of desired compound was detected. The residue was purified by prep-HPLC to give Compound 23 (105.84 mg, 0.22 mmol, 70.1% yield). LCMS (ESI): RT=0.862 min, mass calc. for $C_{24}H_{20}F_3N_5O_3$ 483.15, m/z found 506.1 $[M+23]^+$. $^1$H NMR (400 MHz, DMSO-d$_6$) δ 11.10 (s, 1H), 9.11 (s, 1H), 7.96 (br t, J=5.5 Hz, 1H), 7.74 (d, J=8.0 Hz, 1H), 7.64 (d, J=8.5 Hz, 2H), 7.60-7.54 (m, 1H), 7.53-7.46 (m, 1H), 7.36 (d, J=8.5 Hz, 2H), 7.27 (d, J=8.5 Hz, 2H), 7.13 (t, J=7.5 Hz, 1H), 6.91 (d, J=8.5 Hz, 2H), 4.35 (d, J=5.8 Hz, 2H), 3.74 (s, 3H), 3.31 (s, 1H).

Example 22: 2-((5-(2-((4-(trifluoromethyl)phenyl)amino)phenyl)-1,3,4-oxadiazol-2-yl)amino)acetamide (Compound 24)

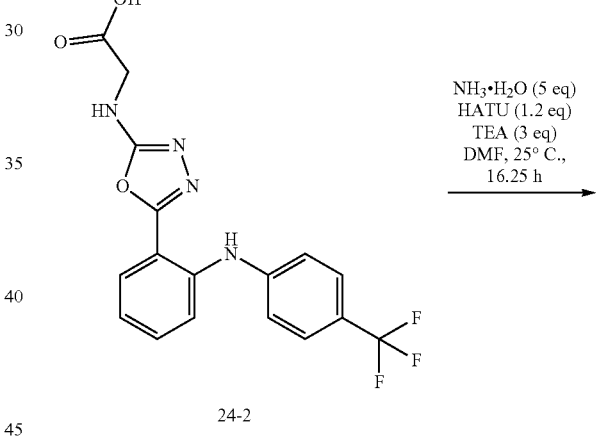

24-1

$NH_3 \cdot H_2O$:EtOH = 1:1
85° C., 32 h 24-2

$NH_3 \cdot H_2O$ (5 eq)
HATU (1.2 eq)
TEA (3 eq)
DMF, 25° C.,
16.25 h

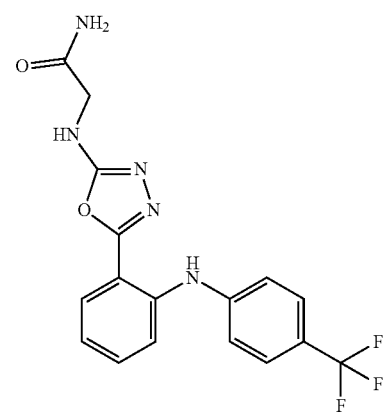

Compound 24

Step 1: 2-((5-(2-((4-(trifluoromethyl)phenyl)amino)phenyl)-1,3,4-oxadiazol-2-yl)amino)acetic Acid A solution of 24-1 (300 mg, 738.27 umol, 1 eq) in NH₃·H₂O (2.59 g, 73.83 mmol, 2.84 mL, 100 eq) was added EtOH (3 mL). The mixture was heated at 85° C. for 16 hr. TLC (PE:EA=1:1 UV) showed most of material was remained. Then EtOH (3 mL) was added and the mixture was heated at 85° C. for another 16 h. LCMS showed 24-1 was consumed, 22% of Compound 24 and 55% of 24-2 were formed. The reaction mixture was concentrated under reduced pressure to give a mixture of Compound 24 and 24-2 (300 mg), which was used into the next step without further purification. $^1$H NMR (400 MHz, DMSO-d₆) δ 9.37 (s, 1H), 9.27 (s, 1H), 7.76-7.69 (m, 3H), 7.64 (br d, J=8.3 Hz, 4H), 7.54 (br dd, J=3.8, 8.3 Hz, 3H), 7.48-7.43 (m, 2H), 7.42-7.35 (m, 5H), 7.08 (q, J=7.9 Hz, 2H), 4.08 (s, 2H), 3.83 (s, 1H), 3.57 (s, 2H).

Step 2: 2-((5-(2-((4-(trifluoromethyl)phenyl)amino)phenyl)-1,3,4-oxadiazol-2-yl)amino) acetamide To a solution of 24-2 (0.3 g, 0.79 mmol, 1 eq) in DMF (10 mL) were added HATU (301.53 mg, 0.79 mmol, 1 eq) and TEA (240.73 mg, 2.38 mmol, 331.13 uL, 3 eq) at 25° C. After stirring for 15 min, NH₃·H₂O (555.8 mg, 3.97 mmol, 610.80 uL, 5 eq) was added and the resulting solution was stirred at 25° C. for 16 h. LCMS showed the reaction was complete and 78% of desired product was formed. TLC (PE:EA=1:1 UV) showed the reaction was complete and new spot was formed. The reaction was diluted with EA (150 mL), washed with brine (20 mL*2) and saturated NaHCO₃ (20 mL*2) in turns, dried by anhydrous Na₂SO₄, filtered and concentrated to give a residue. The residue was purified by column chromatography (SiO₂) and was lyophilized to give Compound 24 (0.025 g, 63.14 umol, 7.96% yield). LCMS (ESI): RT=0.732 min, mass calc. for $C_{17}H_{14}F_3N_5O_2$ 377.11, m/z found 399.9 [M+23]⁺. $^1$H NMR (400 MHz, DMSO-d₆) δ 9.32 (s, 1H), 8.15 (br s, 1H), 7.77-7.68 (m, 1H), 7.65 (br d, J=8.3 Hz, 2H), 7.59-7.48 (m, 2H), 7.44 (br t, J=7.2 Hz, 1H), 7.39 (br d, J=8.3 Hz, 2H), 7.20-7.04 (m, 2H), 4.05-3.98 (m, 1H), 3.82 (br s, 2H), 1.19-1.14 (m, 1H).

Example 23: 1-[5-[2-[4-(trifluoromethyl)anilino]phenyl]-1,3,4-oxadiazol-2-yl]ethane-1,2-diol (Compound 25)

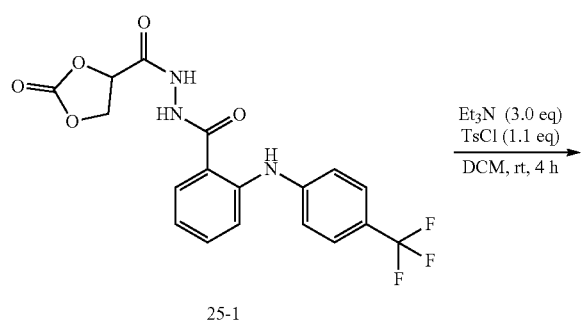

25-1

25-2

Compound 25

Step 1: N'-(2,3-dihydroxypropanoyl)-2-[4-(trifluoromethyl)anilino]benzohydrazide To a solution of 25-1 (0.35 g, 0.83 mmol, 1 eq) and TEA (250.9 mg, 2.48 mmol, 0.34 mL, 3 eq) in DCM (10 mL) was added TsCl (165.4 mg, 0.86 mmol, 1.05 eq). The reaction was stirred at 25° C. for 16 hr. LCMS showed that starting material was remained and 50% of desired product was detected. The reaction was concentrated. Compound 25-2 (300 mg, crude) was used for next step directly.

Step 2: 1-[5-[2-[4-(trifluoromethyl)anilino]phenyl]-1,3,4-oxadiazol-2-yl]ethane-1,2-diol To a solution of compound 25-2 (250 mg, 0.65 mmol, 1 eq) and TEA (197.9 mg, 1.96 mmol, 0.27 mL, 3 eq) in DCM (10 mL) was added TsCl (136.7 mg, 0.72 mmol, 1.1 eq). The reaction was stirred at 25° C. for 16 hr. LCMS showed that 38% of desired product was detected. HPLC showed that 30% of desired product was detected. The reaction was washed with water (2*10 mL). The organic layer was dried over Na₂SO₄ and concentrated. The crude product was purified by prep-HPLC to give Compound 25 (45 mg, 115.79 umol, 17.75% yield). LCMS and HNMR confirmed that desired product was obtained. LCMS (ESI): RT=0.733 min, mass calcd. for $C_{17}H_{14}F_3N_3O_3$, 365.10 m/z found 365.9[M+H]⁺. $^1$H NMR (400 MHz, DMSO) δ9.26 (s, 1H), 7.93 (dd, J=7.6, 1.2 Hz, 1H), 7.65 (d, J=8.4 Hz, 2H), 7.65-7.50 (m, 2H), 7.39 (d, J=8.4 Hz, 2H), 7.15 (t, J=6.8 Hz, 1H), 6.19 (br, 1H), 5.05 (br, 1H), 4.95-4.80 (m, 1H), 3.85-3.70 (m, 2H).

Example 24: 2-oxo-4-(5-(2-((4-(trifluoromethyl)phenyl)amino)phenyl)-1,3,4-oxadiazol-2-yl)oxazolidine-3-carboxylate (Compound 26)

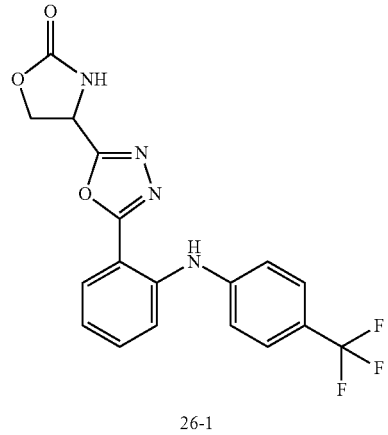

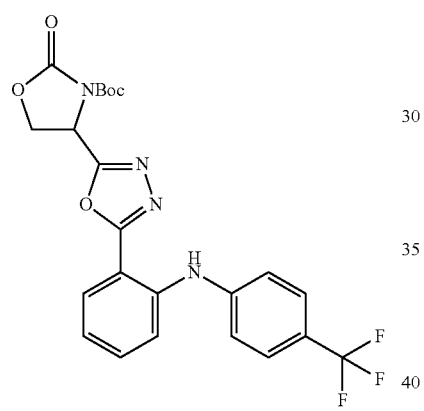

Compound 26

To a solution of 26-1 (0.25 g, 0.64 mmol, 1 eq), TEA (194.4 mg, 1.92 mmol, 0.3 mL, 3 eq) and DMAP (15.6 mg, 0.13 mmol, 0.2 eq) in DCM (5 mL) at 0° C. was added Boc$_2$O (139.8 mg, 0.64 mmol, 0.1 mL, 1 eq). Then the solution was stirred at 25° C. for 16 h. LCMS showed 26-1 was consumed completely and desired product was detected. TLC (Petroleum ether:Ethyl acetate=2:1, UV) indicated 26-1 was consumed and two major new spots were detected. The reaction mixture was quenched with 10 mL of water and concentrated under reduced pressure to remove DCM. The resulting aqueous layer was extracted with ethyl acetate (20 mL*3). The combined organic layer was washed with brine (15 mL), dried by anhydrous Na$_2$SO$_4$, filtered and concentrated to give a residue. The residue was purified by column chromatography (SiO$_2$) to give Compound 26 (15.0 mg, 28.0 umol, 4.36% yield). LCMS (ESI): RT=0.858 min, mass calc. for C$_{23}$H$_{21}$F$_3$N$_4$O$_5$ 490.15, m/z found 513.0 [M+23]$^+$. $^1$H NMR (400 MHz, CDCl$_3$) δ 9.36 (s, 1H), 7.85 (dd, J=1.4, 7.9 Hz, 1H), 7.60 (d, J=8.5 Hz, 2H), 7.54-7.48 (m, 1H), 7.46-7.34 (m, 3H), 7.04-6.92 (m, 1H), 5.72 (dd, J=4.1, 8.9 Hz, 1H), 4.73 (t, J=9.2 Hz, 1H), 4.53 (dd, J=4.0, 9.3 Hz, 1H), 1.52-1.45 (m, 9H).

Example 25: N-(5-(2-((4-(trifluoromethyl)phenyl)amino)phenyl)-1,3,4-oxadiazol-2-yl)ethane-1,2-diamine (Compound 27)

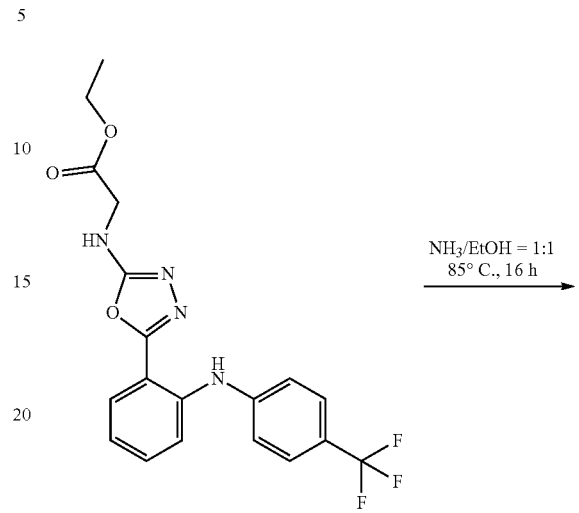

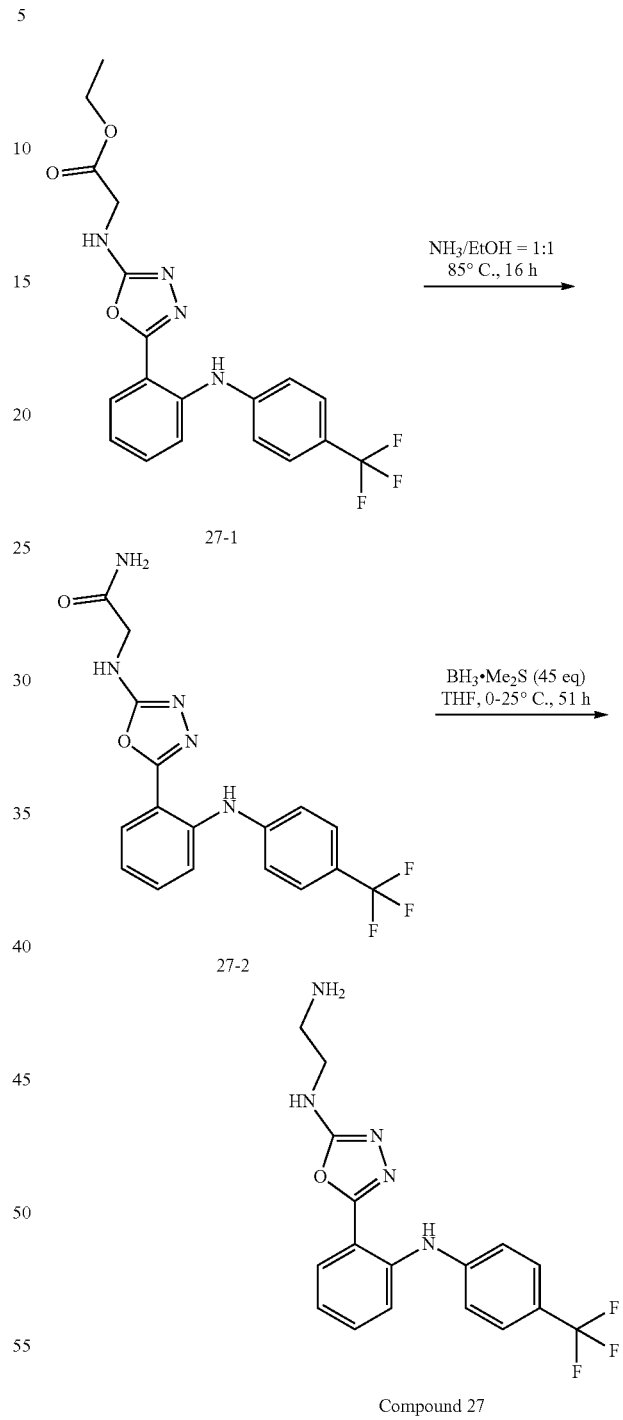

Compound 27

Step 1: 2-((5-(2-((4-(trifluoromethyl)phenyl)amino)phenyl)-1,3,4-oxadiazol-2-yl)amino)acetamide A solution of 27-1 (0.3 g, 0.74 mmol, 1 eq) in EtOH (15 mL) saturated with NH$_3$ (62.87 mg, 3.69 mmol) was stirred at 85° C. for 16 h. LCMS showed 11% of 27-1 was remained and 77% of desired compound was detected. Then the solution was concentrated to give crude 27-2 (180 mg, 0.45 mmol, 61.58% yield), which was used directly without purification.

Step 2: N1-(5-(2-((4-(trifluoromethyl)phenyl)amino) phenyl)-1,3,4-oxadiazol-2-yl)ethane-1,2-diamine To a solution of 27-2 (0.12 g, 0.32 mmol, 1 eq) in THF (5 mL) was added BH$_3$.Me$_2$S (10 M, 0.48 mL, 15 eq) at 0° C. The mixture was stirred at 25° C. for 16 hr under N$_2$ atmosphere. LCMS showed 17% of 27-2 was remained and 57% of desired compound was detected. The mixture was quenched with 5 mL of methanol, stirred at 10 min at 25° C. and concentrated to a residue. The residue was diluted with water (10 mL) and acidified to pH~2 with 1 M HCl and extracted with EA (15 mL*3). The combined organic layers dried by anhydrous Na$_2$SO$_4$, filtered and concentrated to give a residue which was purified by prep-HPLC to give Compound 27 (1.32 mg, 3.55 umol, 1.12% yield). LCMS (ESI): RT=0.639 min, mass calc. for C$_{17}$H$_{16}$F$_3$N$_5$O 363.13, m/z found 364.0 [M+1]$^+$. $^1$H NMR (400 MHz, METHANOL-d$_4$) δ 7.80 (d, J=7.8 Hz, 1H), 7.59 (d, J=8.5 Hz, 2H), 7.56-7.48 (m, 2H), 7.31 (d, J=8.5 Hz, 2H), 7.05-6.99 (m, 1H), 3.82 (s, 4H).

Example 26: 2-[5-(aminomethyl)-1,3,4-oxadiazol-2-yl]-N-[4-(trifluoromethyl)phenyl]aniline (Compound 28)

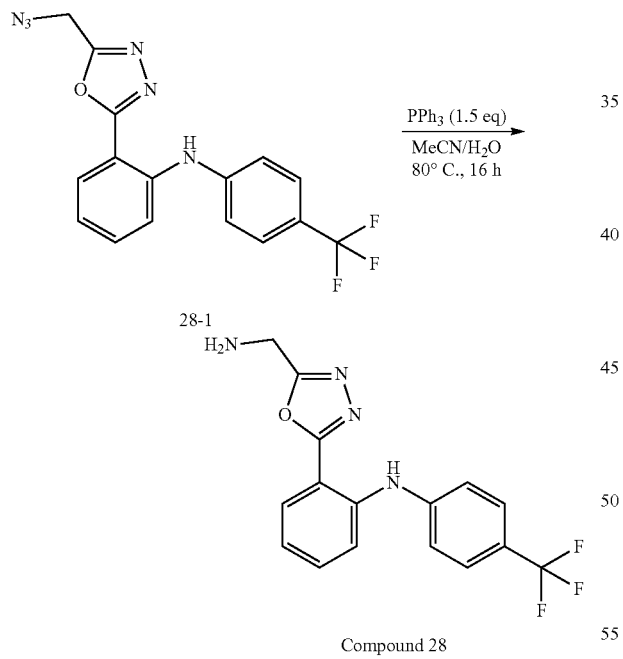

Compound 28

A solvent of 28-1 (50 mg, 0.1 mmol, 1.0 eq) and PPh$_3$ (54.6 mg, 0.2 mmol, 1.5 eq) in MeCN (1 mL) was stirred at 80° C. for 1 h. After H$_2$O (0.2 mL) was added and the mixture was stirred at 80° C. for 3 h. LC-MS showed reactant 28-1 was consumed completely and no desired compound was detected. TLC (Petroleum ether:Ethyl acetate=0:1) indicated reactant 28-1 was consumed completely and one new spot formed. The reaction mixture was concentrated under reduced pressure to give a residue. The residue was purified by column chromatography (SiO$_2$) to give crude Compound 28 (10 mg), which was purified by prep-HPLC to give Compound 28 (2.13 mg, 6 umol, 4.3% yield). LCMS (ESI): RT=0.718 min, mass calc. for C$_{16}$H$_{13}$F$_3$N$_4$O 334.10 m/z found 335.0 [M+H]$^+$; $^1$H NMR (400 MHz, CDCl$_3$) δ 9.50 (s, 1H), 7.90 (d, J=7.8 Hz, 1H), 7.59 (d, J=8.3 Hz, 2H), 7.52 (d, J=8.5 Hz, 1H), 7.44-7.33 (m, 3H), 6.98 (t, J=7.5 Hz, 1H), 4.23-4.02 (m, 2H).

Example 27: 4-[5-[2-[4-(trifluoromethyl)anilino]phenyl]-1,3,4-oxadiazol-2-yl]-1,3-dioxolan-2-one (Compound 29)

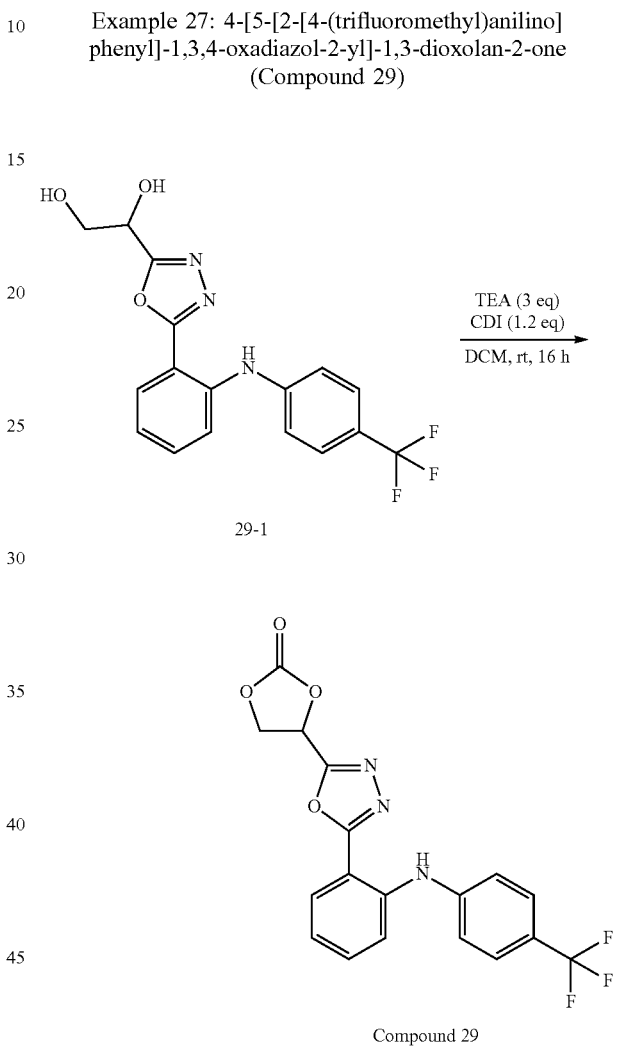

Compound 29

To a solution of 29-1 (20 mg, 54.75 umol, 1 eq) and Et$_3$N (16.6 mg, 0.16 mmol, 22.86 uL, 3 eq) in DCM (1 mL) was added triphosgene (24.3 mg, 82.12 umol, 1.5 eq). The reaction was stirred at 25° C. for 16 hr. LCMS showed that 85% of desired product was detected. The reaction was diluted with DCM (10 mL) and washed with water (2*5 mL). The organic was dried over Na$_2$SO$_4$ and concentrated. The residue was purified by prep-HPLC to give Compound 29 (15 mg, 33.35 umol, 60.92% yield). LCMS (ESI): RT=0.812 min, mass calcd. for C$_{18}$H$_{12}$F$_3$N$_3$O$_4$, 391.08 m/z found 392.0[M+H]$^+$. $^1$H NMR (400 MHz, CDCl$_3$) δ9.32 (s, 1H), 7.92 (dd, J=8.0, 1.2 Hz, 1H), 7.60 (d, J=8.8 Hz, 2H), 7.51 (d, J=8.4 Hz, 1H), 7.50-7.40 (m, 1H), 7.37 (d, J=8.0 Hz, 2H), 7.00 (t, J=8.0 Hz, 1H), 6.05-6.00 (m, 1H), 5.10-5.00 (m, 1H), 5.00-4.85 (m, 1H).

Example 28: 2-amino-2-(5-(2-((4-(trifluoromethyl)phenyl)amino)phenyl)-1,3,4-oxadiazol-2-yl)ethanol (Compound 30)

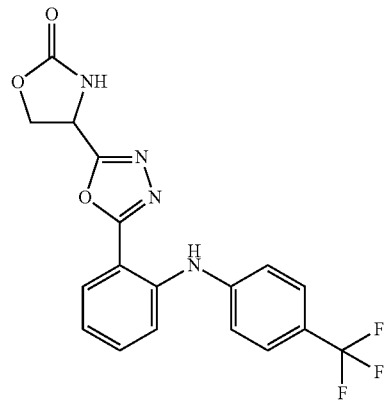

30-1

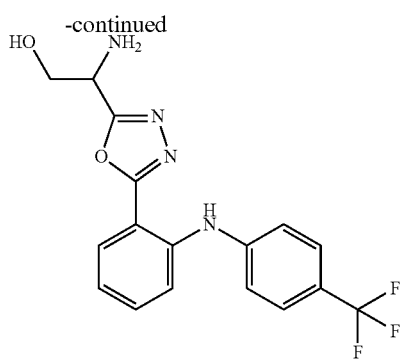

Compound 30

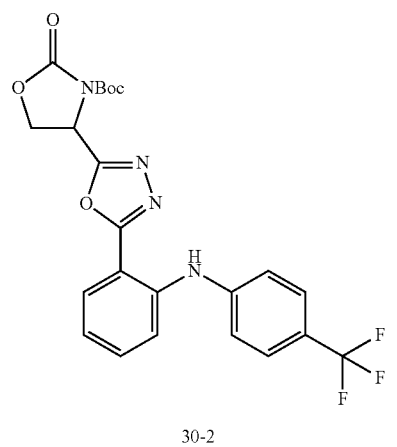

30-2

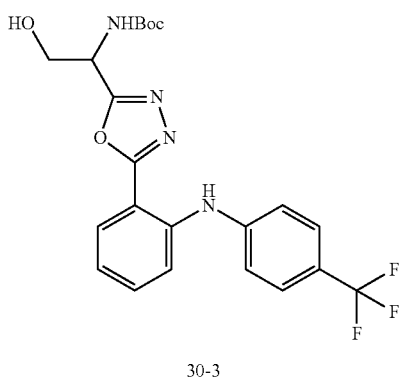

30-3

Step 1: tert-butyl 2-oxo-4-(5-(2-((4-(trifluoromethyl)phenyl)amino)phenyl)-1,3,4-oxadiazol-2-yl)oxazolidine-3-carboxylate To a solution of 30-1 (0.25 g, 0.64 mmol, 1 eq), TEA (194.4 mg, 1.92 mmol, 0.3 mL, 3 eq) and DMAP (15.6 mg, 0.13 mmol, 0.2 eq) in DCM (5 mL) at 0° C. was added Boc$_2$O (139.8 mg, 0.64 mmol, 0.2 mL, 1 eq). Then the solution was stirred at 25° C. for 16 h. LCMS showed 30-1 was consumed completely and desired product was detected. TLC (Petroleum ether:Ethyl acetate=2:1, UV) indicated 30-1 was consumed and two major new spots were detected The reaction mixture was quenched with 10 mL of water and concentrated under reduced pressure to remove DCM. The resulting aqueous layer was extracted with ethyl acetate (20 mL*3). The combined organic layer was washed with brine (15 mL), dried by anhydrous Na$_2$SO$_4$, filtered and concentrated to give a residue. The residue was purified by column chromatography (SiO$_2$) to give 30-2 (15.0 mg, 28 umol, 4.4% yield). LCMS (ESI): RT=0.858 min, mass calc. for C$_{23}$H$_{21}$F$_3$N$_4$O$_5$ 490.15, m/z found 513.0 [M+23]$^+$; $^1$H NMR (400 MHz, CDCl$_3$) δ 9.36 (s, 1H), 7.85 (dd, J=1.4, 7.9 Hz, 1H), 7.60 (d, J=8.5 Hz, 2H), 7.54-7.48 (m, 1H), 7.46-7.34 (m, 3H), 7.04-6.92 (m, 1H), 5.72 (dd, J=4.1, 8.9 Hz, 1H), 4.73 (t, J=9.2 Hz, 1H), 4.53 (dd, J=4.0, 9.3 Hz, 1H), 1.52-1.45 (m, 9H).

Step 2: tert-butyl (2-hydroxy-1-(5-(2-((4-(trifluoromethyl)phenyl)amino)phenyl)-1,3,4-oxadiazol-2-yl)ethyl)carbamate A mixture of 30-2 (0.01 g, 20.4 umol, 1 eq) and K$_2$CO$_3$ (11.3 mg, 81.6 umol, 4 eq) in MeOH (1.5 mL) was stirred at 25° C. for 20 h. LCMS showed 30-2 was consumed and 58% of desired product was detected. The mixture was diluted with EA (50 mL), washed with water (10 mL*2), dried by anhydrous Na$_2$SO$_4$, filtered and concentrated to give compound 30-3 (0.01 g, crude), which was used directly.

Step 3: 2-amino-2-(5-(2-((4-(trifluoromethyl)phenyl)amino)phenyl)-1,3,4-oxadiazol-2-yl)ethanol To a solution of compound 30-3 (10.0 mg, 21.5 umol, 1 eq) in CH$_2$Cl$_2$ (1.6 mL) was added TFA (613.8 mg, 5.38 mmol, 0.4 mL, 250 eq). The mixture was stirred at 25° C. for 2 hr. LCMS showed compound 30-3 was consumed completely and 30% of desired product was formed. The mixture was concentrated at 25° C. to give a crude product and was diluted with water (10 mL), acidified to pH~2 with 1 M HCl and extracted with EA (5 mL*3). The combined organic layer was concentrated to crude product (15 mg), which was purified by prep-HPLC to give Compound 30 (2.13 mg, 5.5 umol, 25.6% yield). LCMS (ESI): RT=0.692 min, mass calc. for $C_{17}H_{15}F_3N_4O_2$ 364.11, m/z found 364.9 [M+1]$^+$; $^1$H NMR (400 MHz, CD$_3$OD) δ 8.03 (dd, J=1.4, 7.9 Hz, 1H), 7.68-7.57 (m, 3H), 7.50 (dt, J=1.5, 7.9 Hz, 1H), 7.42 (d, J=8.5 Hz, 2H), 7.09 (t, J=7.5 Hz, 1H), 4.43-4.32 (m, 1H), 4.02-3.92 (m, 2H).

Example 29: 2-[5-(azidomethyl)-1,3,4-oxadiazol-2-yl]-N-[4-(trifluoromethyl)phenyl]aniline (Compound 31)

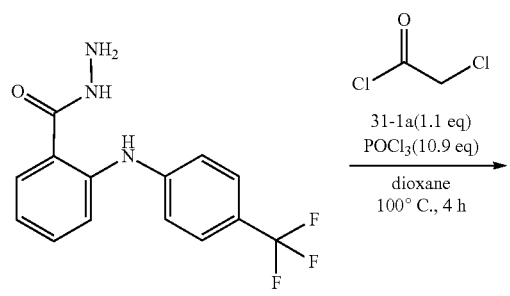

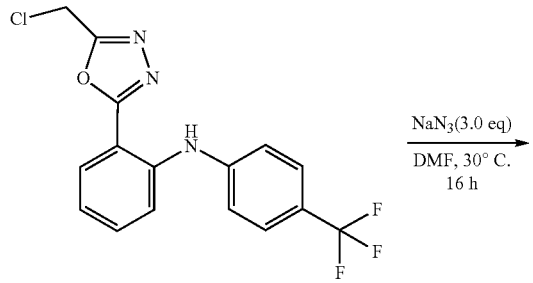

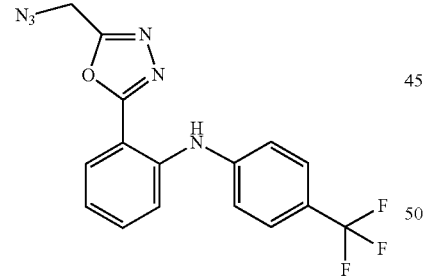

Compound 31

Step 1: 2-[5-(chloromethyl)-1,3,4-oxadiazol-2-yl]-N-[4-(trifluoromethyl)phenyl]aniline 31-1a (84.1 mg, 0.7 mmol, 59 uL, 1.1 eq) was added dropwise to the solution of 31-1 in dioxane (3 mL). The reaction mixture was refluxed 2 hours. POCl$_3$ (18 g, 117.2 mmol, 10.9 mL, 173.2 eq) was added to the reaction mixture, and the reaction was stirred at 100° C. for 2 h. LC-MS showed 31-1 was consumed completely and 43% of desired compound was detected. The mixture was poured into ice water, neutralized with saturated NaHCO$_3$, extracted with EtOAc (20 mL*2). The combined organic layers were dried over Na$_2$SO$_4$, filtered and concentrated under reduced pressure to give a residue. The residue was purified by column chromatography (SiO$_2$) to give 31-2 (100 mg, 0.28 mmol, 41.7% yield). LCMS (ESI): RT=0.853 min, mass calc. for $C_{16}H_{11}ClF_3N_3O$ 353.05 m/z found 353.9 [M+H]$^+$.

Step 2: 2-[5-(azidomethyl)-1,3,4-oxadiazol-2-yl]-N-[4-(trifluoromethyl)phenyl]aniline To a solution of 31-2 (100 mg, 0.3 mmol, 1 eq) in DMF (3 mL) was added NaN$_3$ (55.1 mg, 0.8 mmol, 3.0 eq). The mixture was stirred at 30° C. for 16 h. TLC indicated 31-2 was consumed completely and one new spot formed. The mixture was quenched by addition of H$_2$O (5 mL), and then extracted with EtOAc (5 mL*3). The combined organic layers were washed with brine (10 mL*3), dried over Na$_2$SO$_4$, filtered and concentrated under reduced pressure to give Compound 31 (100 mg, crude). 20 mg of the crude product was purified by prep-HPLC to give Compound 31 (3.41 mg). LCMS (ESI): RT=0.921 min, mass calc. for $C_{16}H_{11}F_3N_6O$ 360.09 m/z found 361.0 [M+H]$^+$; $^1$H NMR (400 MHz, CDCl$_3$) δ 9.43 (s, 1H), 7.91 (dd, J=1.4, 7.9 Hz, 1H), 7.60 (d, J=8.5 Hz, 2H), 7.55-7.49 (m, 1H), 7.46-7.34 (m, 3H), 7.03-6.96 (m, 1H), 4.67 (s, 2H).

Example 30: N-(2-hydroxyethyl)-N-(5-(2-((4-(trifluoromethyl)phenyl)amino)phenyl)-1,3,4-oxadiazol-2-yl)methanesulfonamide (Compound 32)

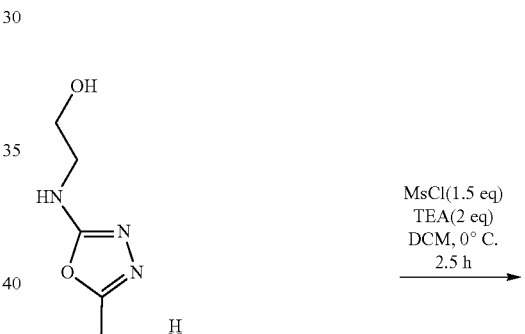

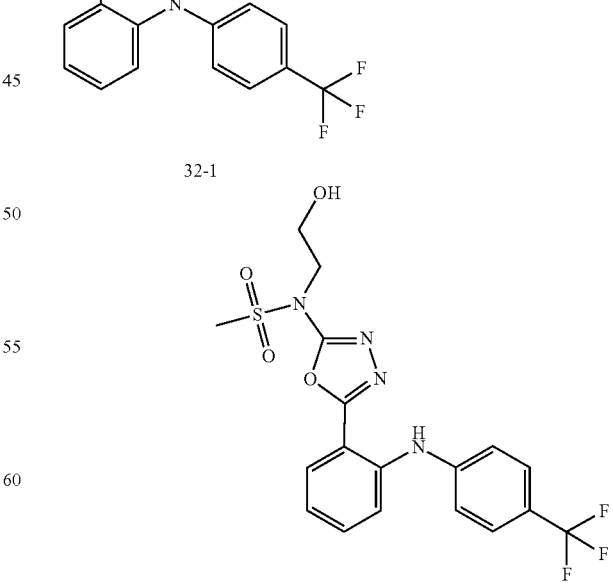

Compound 32

To a stirred solution of 32-1 (0.03 g, 82 umol, 1 eq) and TEA (16.7 mg, 0.16 mmol, 23 uL, 2 eq) in DCM (1 mL) was added MsCl (14.2 mg, 0.12 mmol, 10 uL, 1.5 eq) at 0° C. The mixture was stirred at 0° C. for 2.5 h. LCMS showed the reaction was complete, 38% of Compound 32 was detected. TLC (Petroleum ether:Ethyl acetate=1:1 UV) showed new spots were formed. The mixture was concentrated to give a residue. The residue was purified by prep-TLC to give Compound 32 (2.56 mg, 6 umol, 7.0% yield). LCMS (ESI): RT=0.218 min, mass calc. for $C_{18}H_{17}F_3N_4O_4S$ 442.09, m/z found 443.0 [M+1]$^+$. $^1$H NMR (400 MHz, CDCl$_3$) δ 9.32 (s, 1H), 7.65 (d, J=6.8 Hz, 1H), 7.49 (br d, J=8.5 Hz, 2H), 7.42 (d, J=8.3 Hz, 1H), 7.31-7.23 (m, 3H), 6.87 (t, J=7.5 Hz, 1H), 5.27 (br d, J=5.8 Hz, 1H), 4.45 (t, J=4.9 Hz, 2H), 3.76 (q, J=5.3 Hz, 2H), 3.15-2.84 (m, 3H).

Example 31: N-(5-(2-((4-(trifluoromethyl)phenyl)amino)phenyl)-1,3,4-oxadiazol-2-yl)benzenesulfonamide (Compound 33)

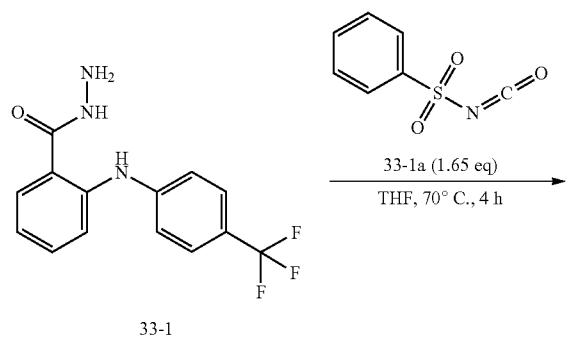

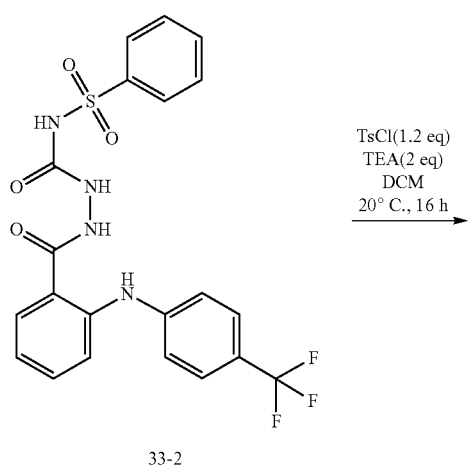

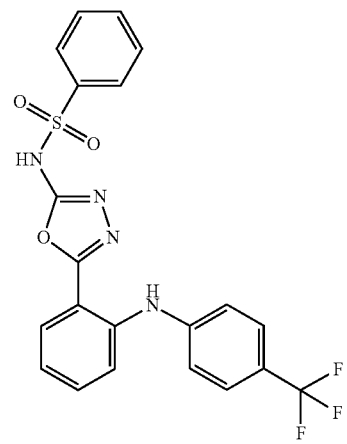

Compound 33

Step 1: N-(phenylsulfonyl)-2-(2-((4-(trifluoromethyl)phenyl)amino)benzoyl)hydrazine carboxamide A mixture of 2-[4-(trifluoromethyl)anilino]benzohydrazide 33-1 (0.20 g, 0.68 mmol, 1 eq) and N-(oxomethylene)benzenesulfonamide 33-1a (136.5 mg, 0.75 mmol, 99 uL, 1.1 eq) in THF (3 mL) was stirred at 70° C. for 2 hr. LCMS showed 19% of starting material was remained and 40% of desired product was formed. Then N-(oxomethylene)benzenesulfonamide 33-1a (68.3 mg, 0.37 mmol, 50 uL, 0.55 eq) was added and the mixture was continuously stirred at 70° C. for another 2 h. LCMS showed starting material was consumed and 11% of desired product was formed. The mixture was concentrated to give a residue. The residue was purified by prep-HPLC to give compound 33-2 (0.15 g, 0.16 mmol, 23.6% yield). LCMS (ESI): RT=0.811 min, mass calc. for $C_{21}H_{17}F_3N_4O_4S$ 478.09, m/z found 501.0 [M+23]$^+$.

Step 2: N-(5-(2-((4-(trifluoromethyl)phenyl)amino)phenyl)-1,3,4-oxadiazol-2-yl)benzene sulfonamide To a mixture of compound 33-2 (0.13 g, 0.27 mmol, 1 eq) and TEA (55.0 mg, 0.54 mmol, 76 uL, 2 eq) in DCM (5 mL) was added TsCl (62.2 mg, 0.33 mmol, 1.2 eq) at 20° C. The resulting mixture was stirred at 20° C. for 16 hr. LCMS showed no starting material was remained and 30% of desired product was formed. The mixture was concentrated at 25° C. to give a residue. The residue was purified by prep-HPLC to give Compound 33 (2.48 mg, 6 umol, 2.0% yield). LCMS (ESI): RT=0.867 min, mass calc. for $C_{21}H_{15}F_3N_4O_3S$ 460.08, m/z found 461.0 [M+1]$^+$; $^1$H NMR (400 MHz, CDCl$_3$) δ 11.13-10.59 (m, 1H), 8.22 (s, 1H), 8.03-7.97 (m, 2H), 7.77 (d, J=7.5 Hz, 1H), 7.63-7.56 (m, 3H), 7.55-7.48 (m, 2H), 7.45-7.38 (m, 2H), 7.29 (d, J=8.5 Hz, 2H), 6.97 (ddd, J=2.1, 6.1, 8.1 Hz, 1H).

Example 32: 1-(5-(2-((4-(trifluoromethyl)phenyl)amino)phenyl)-1,3,4-oxadiazol-2-yl)imidazolidin-2-one (Compound 34)

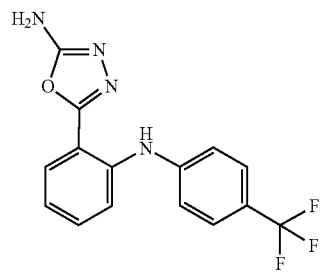

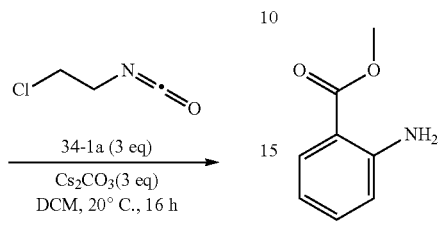

Example 33: 2-(5-(5-methyloxazol-4-yl)-1,3,4-oxadiazol-2-yl)-N-(4-(trifluoromethyl)phenyl) aniline (Compound 35)

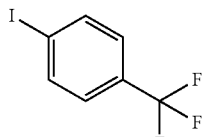

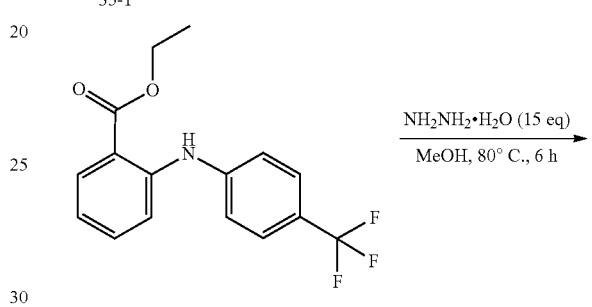

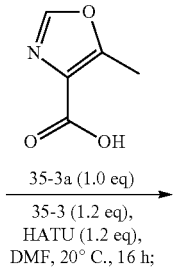

To a stirred solution of 5-[2-[4-(trifluoromethyl)anilino]phenyl]-1,3,4-oxadiazol-2-amine 34-1 (40.0 mg, 0.13 mmol, 1 eq) and Cs$_2$CO$_3$ (122.1 mg, 0.37 mmol, 3 eq) in DCM (3 mL) was added 34-1a (39.5 mg, 0.37 mmol, 3 eq) at 20° C. The mixture was stirred at 20° C. for 16 h. LCMS showed 48% of starting material was remained and 27% of Compound 34 was detected. The mixture was concentrated at 20° C. to give a residue. The residue was purified by prep-HPLC to give Compound 34 (8.65 mg, 21.6 umol, 17.3% yield). LCMS (ESI): RT=0.803 min, mass calc. for C$_{18}$H$_{14}$F$_3$N$_5$O$_2$ 389.11, m/z found 390.0 [M+1]$^+$. $^1$H NMR (400 MHz, CDCl$_3$) δ 9.27 (br s, 1H), 7.89 (br d, J=7.5 Hz, 1H), 7.50 (br d, J=8.0 Hz, 2H), 7.43 (d, J=8.5 Hz, 1H), 7.33-7.25 (m, 3H), 6.90 (t, J=7.3 Hz, 1H), 4.95 (br s, 1H), 4.16 (br s, 2H), 3.68 (br s, 2H).

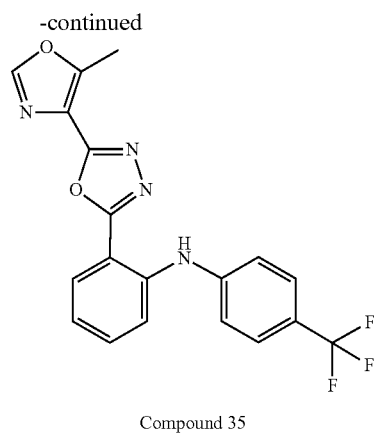

Compound 35

Step 1: ethyl 2-((4-(trifluoromethyl)phenyl)amino)benzoate

The mixture of compound 35-1 (15.00 g, 99.23 mmol, 12.8 mL, 1 eq), compound 35-1a (32.39 g, 119.08 mmol, 17.5 mL, 1.2 eq), $Pd_2(dba)_3$ (2.73 g, 2.98 mmol, 0.03 eq), BINAP (3.71 g, 5.95 mmol, 0.06 eq) and $Cs_2CO_3$ (64.66 g, 198.46 mmol, 2 eq) in toluene (250 mL) at 30° C. was purged and degassed with $N_2$ for 3 times, and the resulting mixture was stirred at 100° C. under $N_2$ for 16 h. TLC (PE:EA=10:1, UV) showed starting material was consumed completely and one new spot was formed. The mixture was concentrated to remove the solvent. The residue was diluted with EA (300 mL), and then filtered to remove the solid. The filtrate was concentrated to give a residue. The residue was purified by column chromatography ($SiO_2$) to give compound 35-2 (21.0 g, 66.54 mmol, 67.1% yield). LCMS (ESI): RT=0.978 min, mass calc. for $C_{16}H_{14}F_3NO_2$ 309.10, m/z found 309.9$[M+1]^+$. $^1H$ NMR (400 MHz, $CDCl_3$) δ 9.69 (s, 1H), 8.05-8.00 (m, 1H), 7.56 (d, J=8.5 Hz, 2H), 7.44-7.36 (m, 2H), 7.30 (d, J=8.5 Hz, 2H), 6.86 (ddd, J=2.5, 5.9, 8.2 Hz, 1H), 4.38 (q, J=7.2 Hz, 2H), 1.42 (t, J=7.0 Hz, 3H).

Step 2: 2-((4-(trifluoromethyl)phenyl)amino)benzohydrazide

To a solution of compound 35-2 (21.00 g, 67.90 mmol, 1 eq) in MeOH (60 mL) at 20° C. was added $NH_2NH_2.H_2O$ (59.98 g, 1.02 mol, 58.2 mL, 15 eq), and the resulting mixture was stirred at 80° C. for 6 h. TLC (PE:EA=10:1, UV) showed starting material was consumed completely and one new spot was formed. LCMS showed starting material was consumed completely and 94% of desired product was formed. The mixture was concentrated to remove the solvent. The residue was diluted with water (100 mL), and then filtered to collect the solid. The filtrate was extracted with EA (100 mL*3) and the combined organic layer was washed with brine (100 mL), dried over anhydrous sodium sulfate, filtered and concentrated under reduced pressure to give a residue. The residue was combined with the filtered solid. The combined solid was purified by washed with PE/EA (200 mL, PE:EA=5:1), filtered and dried in vacuum to give compound 35-3 (19.00 g, 64.35 mmol, 94.8% yield). $^1H$ NMR (400 MHz, $CDCl_3$) δ 9.28 (brs, 1H), 7.54 (d, J=8.5 Hz, 2H), 7.51-7.35 (m, 4H), 7.24 (d, J=8.5 Hz, 2H), 6.96-6.88 (m, 1H), 4.08 (brs, 2H).

Step 3: 5-methyl-N'-(2-((4-(trifluoromethyl)phenyl)amino)benzoyl)oxazole-4-carbohydrazide To a solution of compound 35-3a (200 mg, 1.57 mmol, 1 eq), compound 35-3 (557 mg, 1.89 mmol, 1.2 eq) and HATU (718 mg, 1.89 mmol, 1.2 eq) in DMF (5 mL) at 20° C. was added DIPEA (407 mg, 3.15 mmol, 0.5 mL, 2 eq), and the resulting mixture was stirred at 20° C. for 16 h. LCMS showed starting material was consumed completely and 64% of desired product was formed. The mixture was concentrated to give a residue. The residue was purified by prep-HPLC to give compound 35-4 (400 mg, 0.99 mmol, 62.9% yield). LCMS (ESI): RT=0.797 min, mass calc. for $C_{19}H_{15}F_3N_4O_3$ 404.11, m/z found 405.0$[M+1]^+$. $^1H$ NMR (400 MHz, DMSO-$d_6$) δ 10.50 (s, 1H), 10.19 (s, 1H), 9.45 (s, 1H), 8.41 (s, 1H), 7.72 (d, J=7.6 Hz, 1H), 7.60 (d, J=8.5 Hz, 2H), 7.53-7.44 (m, 2H), 7.30 (d, J=8.5 Hz, 2H), 7.08-7.01 (m, 1H), 2.60 (s, 3H).

Step 4: 2-(5-(5-methyloxazol-4-yl)-1,3,4-oxadiazol-2-yl)-N-(4-(trifluoromethyl)phenyl)aniline To a solution of compound 35-4 (200 mg, 0.49 mmol, 1 eq) and TEA (150.2 mg, 1.48 mmol, 0.2 mL, 3 eq) in DCM (2 mL) at 20° C. was added TsCl (94.3 mg, 0.49 mmol, 1 eq), and the resulting mixture was stirred at 20° C. for 16 h. LCMS showed 7% of starting material still remained and 93% of desired product was formed. The mixture was concentrated to give a residue. The residue was purified by prep-HPLC to give Compound 35 (160.90 mg, 0.42 mmol, 84.2% yield). LCMS (ESI): RT=0.915 min, mass calc. for $C_{19}H_{13}F_3N_4O_2$ 386.10, m/z found 386.9$[M+1]^+$. $^1H$ NMR (400 MHz, DMSO-$d_6$) δ 9.24 (s, 1H), 8.61-8.51 (m, 1H), 7.98 (d, J=7.9 Hz, 1H), 7.64 (d, J=8.5 Hz, 2H), 7.62-7.53 (m, 2H), 7.38 (d, J=8.5 Hz, 2H), 7.18 (t, J=7.4 Hz, 1H), 2.70 (s, 3H).

Example 34: 2-(5-(oxazol-4-yl)-1,3,4-oxadiazol-2-yl)-N-(4-(trifluoromethyl)phenyl)aniline (Compound 36)

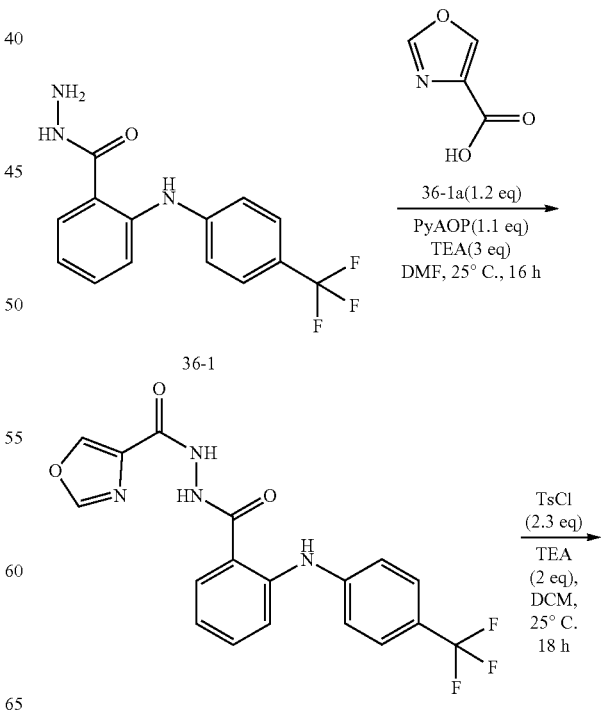

205
-continued

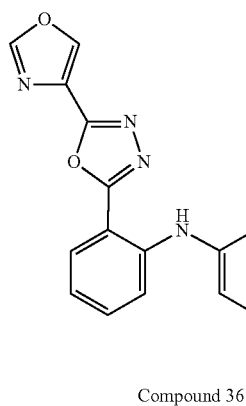

Compound 36

Step 1: N'-(2-((4-(trifluoromethyl)phenyl)amino)benzoyl)oxazole-4-carbohydrazide To a mixture of 36-1a (137.9 mg, 1.22 mmol, 1.2 eq), PYAOP (635.7 mg, 1.22 mmol, 1.2 eq) and TEA (308.4 mg, 3.05 mmol, 424.27 uL, 3 eq) in DMF (3 mL) was added 36-1 (0.3 g, 1.02 mmol, 1 eq) in one portion at 20° C. under $N_2$. The mixture was stirred at 20° C. for 16 h. LCMS showed 7% of starting material was remained and 20% of desired product was detected. The mixture was diluted with EA (50 mL), washed with brine (15 mL) twice, dried by anhydrous $Na_2SO_4$, filtered and concentrated to give a residue. The residue was purified by prep-HPLC to give 36-2 (0.05 g, 0.13 mmol, 12.61% yield). LCMS (ESI): RT=0.767 min, mass calc. for $C_{18}H_{13}F_3N_4O_3$ 390.09, m/z found 390.9 [M+1]$^+$. $^1$H NMR (400 MHz, DMSO-d$_6$) δ 10.57 (s, 1H), 10.40 (s, 1H), 9.43 (s, 1H), 8.78 (s, 1H), 8.60 (s, 1H), 7.73 (d, J=7.5 Hz, 1H), 7.60 (br d, J=8.4 Hz, 2H), 7.53-7.43 (m, 2H), 7.30 (br d, J=8.3 Hz, 2H), 7.05 (br t, J=7.2 Hz, 1H).

Step 2: 2-(5-(oxazol-4-yl)-1,3,4-oxadiazol-2-yl)-N-(4-(trifluoromethyl)phenyl)aniline To a mixture of 36-2 (33 mg, 85 umol, 1 eq) and TEA (17.1 mg, 0.17 mmol, 24 uL, 2 eq) in DCM (3 mL) was added TsCl (16.1 mg, 85 mol, 1 eq) in one portion at 20° C. under $N_2$. The mixture was stirred at 20° C. for 16 h. LCMS showed 78% of starting material was remained and 21% of desired product was detected. Then another batch of TsCl (21 mg, 0.11 mmol, 1.3 eq) was added and the mixture was stirred at 20° C. for 2 h. LCMS showed no starting material was remained and 77% of desired product was detected. The mixture was diluted with DCM (50 mL), washed with brine (15 mL), dried by anhydrous $Na_2SO_4$, filtered and concentrated to give a residue. The residue was purified by prep-HPLC to give Compound 36 (5.52 mg, 15 umol, 17.2% yield). LCMS (ESI): RT=0.875 min, mass calc. for $C_{18}H_{11}F_3N_4O_2$ 372.08 m/z found 372.9 [M+1]$^+$. $^1$H NMR (400 MHz, CDCl$_3$) δ 9.51 (s, 1H), 8.49 (d, J=0.8 Hz, 1H), 8.12 (s, 1H), 8.04 (dd, J=1.4, 8.0 Hz, 1H), 7.60 (d, J=8.5 Hz, 2H), 7.56-7.50 (m, 1H), 7.45-7.37 (m, 3H), 7.27 (s, 1H), 7.04-6.97 (m, 1H).

206

Example 35: 2-(5-(oxazol-5-yl)-1,3,4-oxadiazol-2-yl)-N-(4-(trifluoromethyl)phenyl)aniline (Compound 37)

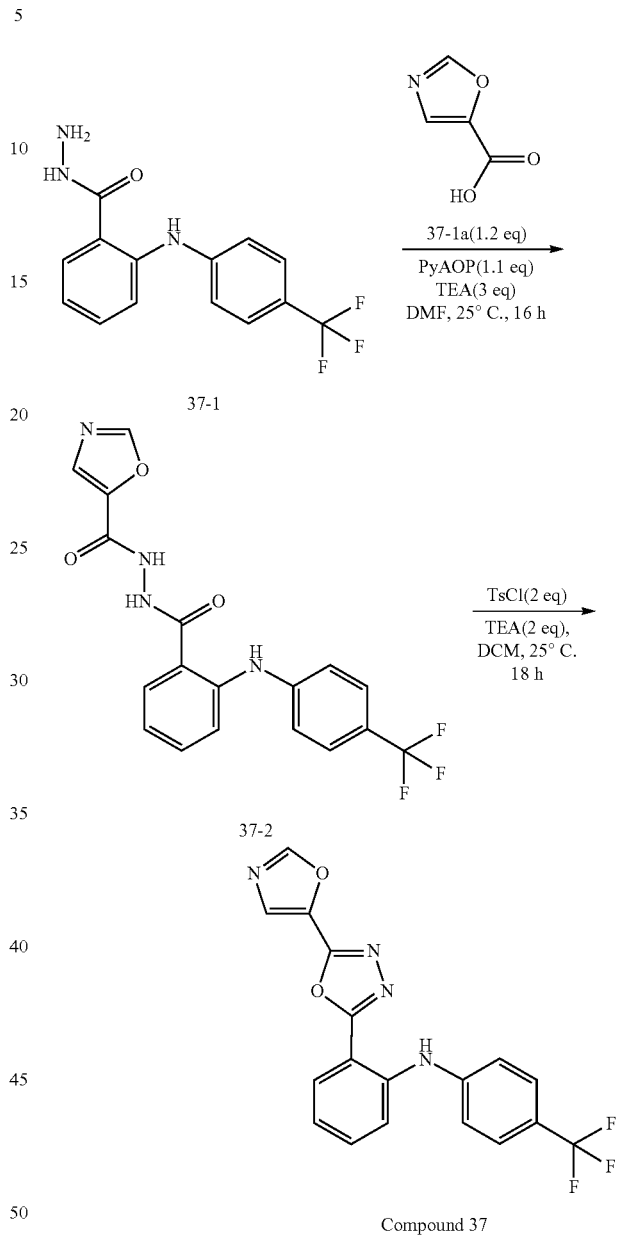

Compound 37

Step 1: N'-(2-((4-(trifluoromethyl)phenyl)amino)benzoyl)oxazole-5-carbohydrazide To a mixture of 37-1a (138.4 mg, 1.22 mmol, 1.2 eq), PYAOP (638.2 mg, 1.22 mmol, 1.2 eq) and TEA (309.6 mg, 3.06 mmol, 425.92 uL, 3 eq) in DMF (3 mL) was added 37-1 (0.3 g, 1.02 mmol, 1 eq) in one portion at 20° C. under $N_2$. The mixture was stirred at 20° C. for 16 h. LCMS showed 9% of starting material and 15% of desired product was detected. The mixture was diluted with EA (50 mL), washed with brine (15 mL) twice, dried by anhydrous $Na_2SO_4$, filtered and concentrated to give a residue. The residue was purified by prep-HPLC to give 37-2 (0.04 g, 0.10 mmol, 10.1% yield). LCMS (ESI): RT=0.749 min, mass calc. for $C_8H_{13}F_3N_4O_3$ 390.09, m/z found 390.9 [M+1]$^+$. $^1$H NMR (400 MHz, DMSO-$d_6$) δ 10.79 (s, 1H), 10.67 (s, 1H), 9.38 (s, 1H), 8.67 (s, 1H), 7.94 (s, 1H), 7.75 (d, J=8.0 Hz, 1H), 7.59 (d, J=8.5 Hz, 2H), 7.53-7.43 (m, 2H), 7.29 (d, J=8.5 Hz, 2H), 7.13-6.99 (m, 1H).

Step 2: 2-(5-(oxazol-5-yl)-1,3,4-oxadiazol-2-yl)-N-(4-(trifluoromethyl)phenyl)aniline To a mixture of 37-2 (23 mg, 59 umol, 1 eq) and TEA (14.9 mg, 0.15 mmol, 21 uL, 2.5 eq) in DCM (2 mL) was added TsCl (11.2 mg, 59 umol, 1 eq) in one portion at 20° C. under N$_2$. The mixture was stirred at 20° C. for 16 h. LCMS showed 51% of starting material was remained and 46% of desired product was detected. Then another batch of TsCl (11.2 mg, 59 umol, 1 eq) was added and the mixture was stirred at 20° C. for 2 h. LCMS showed no starting material was remained and 70% of desired product was detected. The mixture was diluted with DCM (50 mL), washed with brine (15 mL), dried by anhydrous Na$_2$SO$_4$, filtered and concentrated to give a residue. The residue was purified by prep-HPLC to give Compound 37 (2.39 mg, 6 umol, 10.8% yield). LCMS (ESI): RT=0.888 min, mass calc. for $C_{18}H_{11}F_3N_4O_2$ 372.08 m/z found 372.9 [M+1]$^+$. $^1$H NMR (400 MHz, CDCl$_3$) δ 9.46 (s, 1H), 8.21-8.12 (m, 1H), 7.99 (dd, J=1.4, 7.9 Hz, 1H), 7.95-7.90 (m, 1H), 7.61 (d, J=8.5 Hz, 2H), 7.55-7.49 (m, 1H), 7.48-7.36 (m, 3H), 7.07-6.96 (m, 1H).

Example 36: N-(5-(2-((4-(trifluoromethyl)phenyl)amino)phenyl)-1,3,4-oxadiazol-2-yl)methanesulfonamide (Compound 38)

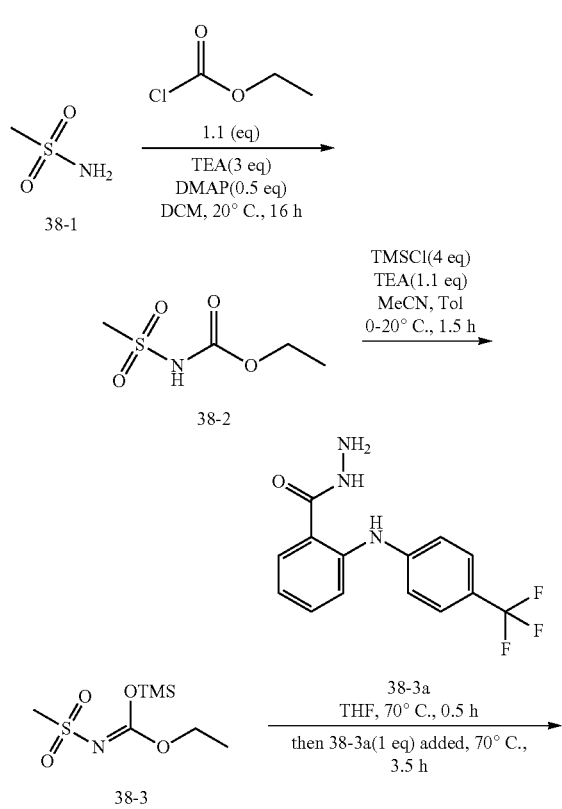

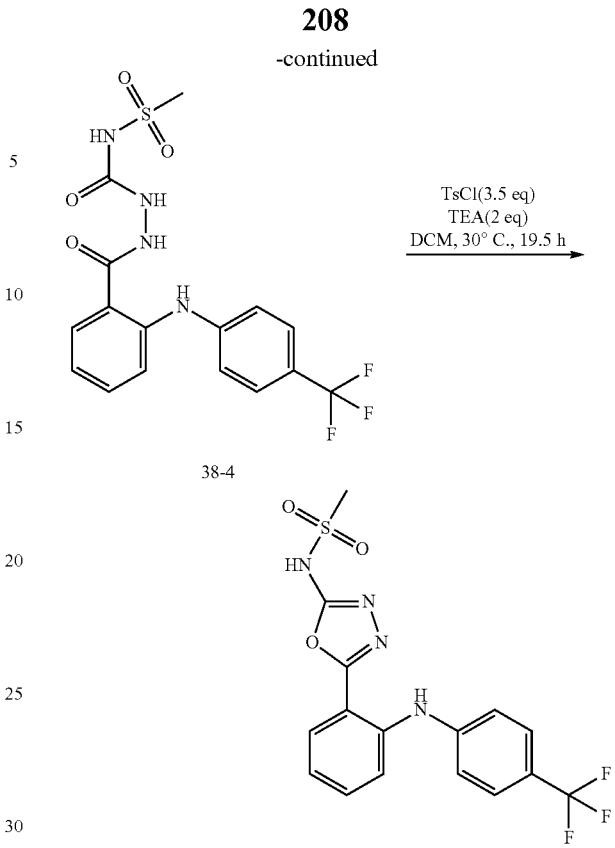

Compound 38

Step 1: Ethyl methylsulfonylcarbamate

To a mixture of 38-1 (5 g, 52.56 mmol, 1 eq), TEA (15.96 g, 157.69 mmol, 22 mL, 3 eq) and DMAP (3.21 g, 26.28 mmol, 0.5 eq) in DCM (20 mL) was added ethyl carbonochloridate (6.27 g, 57.82 mmol, 5.5 mL, 1.1 eq) at 20° C. The resulting mixture was stirred at 20° C. for 16 hr. TLC (Ethyl acetate:Petroleum ether=2:1 I$_2$) showed new spots were formed. The filtrate was concentrated to give a residue. The residue was dissolved in EtOAc (100 mL) and washed with 1 N HCl (30 mL*2), water (30 mL*2), and brine (30 mL*2). The organic layer was dried over anhydrous and concentrated in vacuo to give 38-2 (2.1 g, 12.56 mmol, 23.9% yield), which was used directly. $^1$H NMR (400 MHz, DMSO-$d_6$) δ 11.57 (br s, 1H), 4.15 (q, J=7.2 Hz, 2H), 3.28-3.17 (m, 3H), 1.22 (t, J=7.2 Hz, 3H).

Step 2: (Z)-ethyl (trimethylsilyl) methylsulfonylcarbonimidate

To a solution of 38-2 (0.5 g, 2.99 mmol, 1 eq) in a mixture of MeCN (1 mL) and toluene (6 mL) was added TMSCl (1.30 g, 11.96 mmol, 1.5 mL, 4 eq) and the resulting mixture was cooled in an ice bath. After slowly adding a solution of TEA (332.9 mg, 3.29 mmol, 0.5 mL, 1.1 eq) in Toluene (2 mL), the reaction mixture was stirred at 20° C. for 1.5 hr. The excess trimethylchlorosilane was evaporated in vacuo at 20° C. and diluted with water (15 mL) and extracted with DCM (20 mL) twice. The combined organic layer was dried by anhydrous Na$_2$SO$_4$, filtered and concentrated at 20° C. to give crude product compound 38-3 (0.28 g, 1.17 mmol, 39.1% yield), which was used directly.

Step 3: N-(methylsulfonyl)-2-(2-((4-(trifluoromethyl)phenyl)amino)benzoyl)hydrazine carboxamide A solution of 38-3 (0.14 g, 0.58 mmol, 1 eq) in THF (5 mL) was stirred at 70° C. for 0.5 hr and cooled to 20° C. Then 38-3a (172.7 mg, 0.58 mmol, 1 eq) was added and the resulting mixture was stirred at 70° C. for 3.5 hr. LCMS showed 73% of 38-3a was remained and 21% of desired product was formed. The mixture was concentrated in vacuo to yield a residue. The residue was purified by prep-HPLC to give 38-4 (15 mg, 24 umol, 4.1% yield). LCMS (ESI): RT=0.754 min, mass calc. for $C_{16}H_{15}F_3N_4O_4S$ 416.08, m/z found 438.9 [M+23]$^+$; $^1$H NMR (400 MHz, DMSO-$d_6$) δ 10.46 (br s, 1H), 9.41-9.22 (m, 1H), 7.78-7.56 (m, 2H), 7.48 (br s, 2H), 7.26 (br dd, J=8.3, 17.1 Hz, 2H), 7.14-6.97 (m, 1H), 3.26 (s, 3H).

Step 4: N-(5-(2-((4-(trifluoromethyl)phenyl)amino)phenyl)-1,3,4-oxadiazol-2-yl)methane sulfonamide To a mixture of compound 38-4 (13 mg, 31 umol, 1 eq) and TEA (6.3 mg, 62 umol, 8 uL, 2 eq) in DCM (2 mL) was added TsCl (9 mg, 47 umol, 1.5 eq) at 20° C. Then the mixture was stirred at 30° C. for 1.5 hr. LCMS showed 23% of compound 38-4 was remained and 25% of desired product was formed. Then the mixture was stirred at 30° C. for 16 hr. LCMS showed 21% of compound 38-4 was remained and 29% of desired product was formed. Another batch of TsCl (11.9 mg, 62 umol, 2 eq) was added and the mixture was stirred at 30° C. for 2 hr. LCMS showed no compound 38-4 was remained and 30% of desired product was formed. The mixture was diluted with DCM (50 mL) and washed with brine (10 mL). The organic layer was dried by anhydrous $Na_2SO_4$, filtered and concentrated to give a residue. The residue was purified by prep-HPLC to give Compound 38 (2.78 mg, 7 umol, 22.4% yield). LCMS (ESI): RT=0.801 min, mass calc. for $C_{16}H_{13}F_3N_4O_3S$ 398.07, m/z found 399.0 [M+H]$^+$; $^1$H NMR (400 MHz, $CD_3OD$) δ 7.88 (d, J=7.9 Hz, 1H), 7.62 (d, J=8.5 Hz, 2H), 7.58-7.46 (m, 2H), 7.36 (d, J=8.4 Hz, 2H), 7.11 (t, J=7.5 Hz, 1H), 3.11 (s, 3H).

Example 37: 2-(5-(4-methyloxazol-5-yl)-1,3,4-oxadiazol-2-yl)-N-(4-(trifluoromethyl)phenyl) aniline (Compound 39)

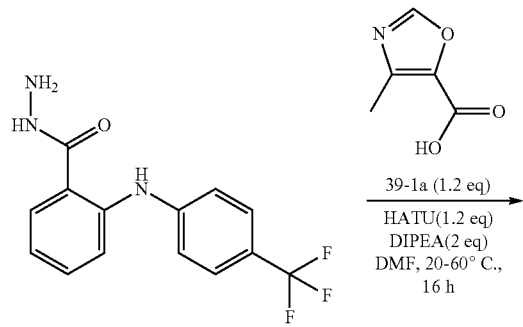

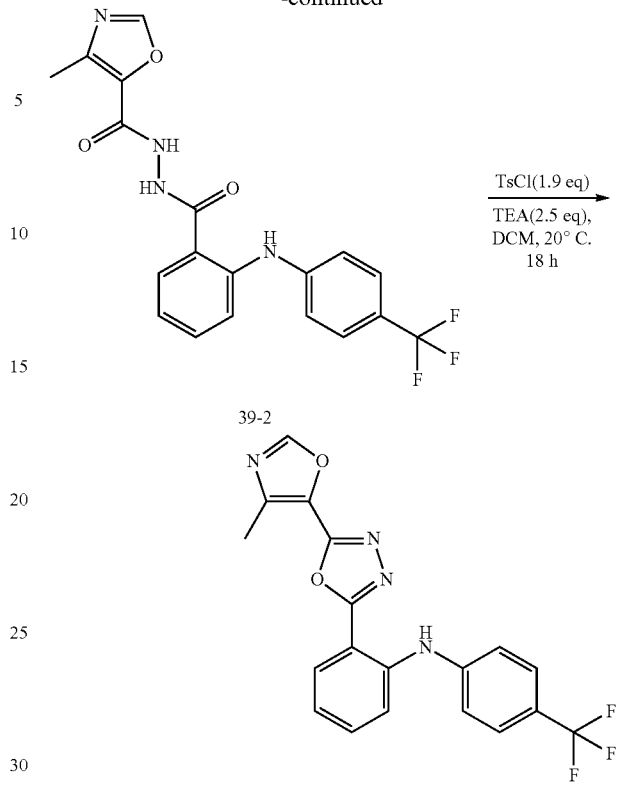

Step 1: 4-methyl-N'-(2-((4-(trifluoromethyl)phenyl)amino)benzoyl)oxazole-5-carbohydrazide To a solution of 39-1 (0.3 g, 1.02 mmol, 1 eq), 39-1a (155.0 mg, 1.22 mmol, 1.2 eq) and HATU (463.6 mg, 1.22 mmol, 1.2 eq) in DMF (4 mL) at 20° C. was added DIPEA (262.6 mg, 2.03 mmol, 0.4 mL, 2 eq), and the resulting mixture was stirred at 60° C. for 16 h. LCMS showed 11% of starting material was remained and 32% of desired product was detected. The mixture was diluted with EA (50 mL), washed with brine (15 mL) twice, dried by anhydrous $Na_2SO_4$, filtered and concentrated to give a residue. The residue was purified by prep-HPLC to give 39-2 (85.05 mg, 0.21 mmol, 20.7% yield). LCMS (ESI): RT=0.766 min, mass calc. for $C_{19}H_{15}F_3N_4O_3$ 404.11, m/z found 405.0 [M+1]$^+$. $^1$H NMR (400 MHz, DMSO-$d_6$) δ 10.56 (d, J=18.0 Hz, 2H), 9.43 (s, 1H), 8.53 (s, 1H), 7.74 (d, J=7.4 Hz, 1H), 7.60 (d, J=8.5 Hz, 2H), 7.54-7.45 (m, 2H), 7.30 (d, J=8.5 Hz, 2H), 7.06 (ddd, J=2.0, 6.3, 7.9 Hz, 1H), 2.41 (s, 3H).

Step 2: 2-(5-(4-methyloxazol-5-yl)-1,3,4-oxadiazol-2-yl)-N-(4-(trifluoromethyl)phenyl)aniline To a mixture of 39-2 (0.08 g, 0.2 mmol, 1 eq) and TEA (50.0 mg, 0.5 mmol, 68 uL, 2.5 eq) in DCM (3 mL) was added TsCl (56.6 mg, 0.3 mol, 1.5 eq) in one portion at 20° C. The mixture was stirred at 20° C. for 16 h. LCMS showed 9% of starting material was remained and 75% of desired product was detected. Then another batch of TsCl (15.1 mg, 79 umol, 0.4 eq) was added and the mixture was stirred at 20° C. for another 2 h. LCMS showed no starting material was remained and 44% of desired product was detected. The mixture was diluted with DCM (50 mL), washed with brine (15 mL) twice, dried by anhydrous Na₂SO₄, filtered and concentrated to give a residue. The residue was purified by prep-HPLC to give Compound 39 (34.15 mg, 88 umol, 44.7% yield). LCMS (ESI): RT=0.922 min, mass calc. for C₁₉H₁₃F₃N₄O₂ 386.10, m/z found 386.9 [M+1]⁺. ¹H NMR (400 MHz, CDCl₃) δ 9.50 (s, 1H), 8.04 (s, 1H), 7.97 (dd, J=1.4, 7.9 Hz, 1H), 7.60 (d, J=8.5 Hz, 2H), 7.54 (d, J=8.1 Hz, 1H), 7.46-7.37 (m, 3H), 7.05-6.98 (m, 1H), 2.67 (s, 3H).

Example 38: 2-(5-(5-methylisoxazol-4-yl)-1,3,4-oxadiazol-2-yl)-N-(4-(trifluoromethyl)phenyl) aniline (Compound 40)

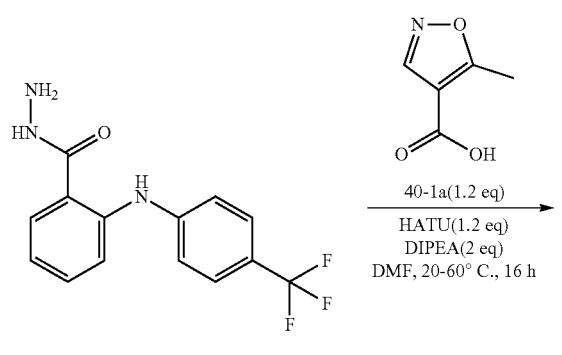

Step 1: 5-methyl-N'-(2-((4-(trifluoromethyl)phenyl)amino)benzoyl)isoxazole-4-carbohydrazide To a solution of 40-1 (0.3 g, 1.02 mmol, 1 eq), 40-1a (155.6 mg, 1.22 mmol, 1.2 eq) and HATU (465.4 mg, 1.22 mmol, 1.2 eq) in DMF (4 mL) at 20° C. was added DIPEA (263.7 mg, 2.04 mmol, 0.4 mL, 2 eq), and the resulting mixture was stirred at 60° C. for 16 h. LCMS showed no starting material was remained and 43% of desired product was detected. The mixture was diluted with EA (50 mL), washed with brine (15 mL) twice, dried by anhydrous Na₂SO₄, filtered and concentrated to give a residue. The residue was purified by prep-HPLC to give 40-2 (0.21 g, 0.52 mmol, 50.9% yield). LCMS (ESI): RT=0.801 min, mass calc. for C₁₉H₁₅F₃N₄O₃ 404.11, m/z found 404.9 [M+1]⁺. ¹H NMR (400 MHz, DMSO-d₆) δ 10.57 (br s, 1H), 9.40 (br s, 1H), 7.69 (d, J=7.8 Hz, 1H), 7.59 (d, J=8.5 Hz, 2H), 7.51-7.43 (m, 3H), 7.30 (d, J=8.6 Hz, 2H), 7.07-6.99 (m, 1H), 2.26 (d, J=2.0 Hz, 3H).

Step 2: 2-(5-(5-methylisoxazol-4-yl)-1,3,4-oxadiazol-2-yl)-N-(4-(trifluoromethyl)phenyl)aniline To a mixture of compound 40-2 (0.21 g, 0.52 mmol, 1 eq) and TEA (131.4 mg, 1.30 mmol, 0.2 mL, 2.5 eq) in DCM (8 mL) was added TsCl (148.5 mg, 0.78 mmol, 1.5 eq) in one portion at 20° C. The mixture was stirred at 20° C. for 16 h. LCMS showed 10% of starting material was remained and 65% of desired product was detected. Then another batch of TsCl (15.8 mg, 83 umol, 0.16 eq) was added and the mixture was stirred at 20° C. for another 2 h. LCMS showed no starting material was remained and 54% of desired product was detected. The mixture was diluted with DCM (50 mL), washed with brine (15 mL) twice, dried by anhydrous Na₂SO₄, filtered and concentrated to give a residue. The residue was purified by prep-HPLC to give Compound 40 (7.8 mg, 20 umol, 3.8% yield). LCMS (ESI): RT=0.922 min, mass calc. for C₁₉H₁₃F₃N₄O₂ 386.10, m/z found 386.9 [M+1]⁺. ¹H NMR (400 MHz, CDCl₃) δ 9.01 (s, 1H), 7.99 (dd, J=1.3, 8.0 Hz, 1H), 7.61 (d, J=8.4 Hz, 2H), 7.54-7.41 (m, 2H), 7.37 (d, J=8.4 Hz, 2H), 7.07-6.98 (m, 1H), 2.51 (s, 3H).

Example 39: 1-(5-(2-((4-(trifluoromethyl)phenyl)amino)phenyl)-1,3,4-oxadiazol-2-yl)ethanol (Compound 41)

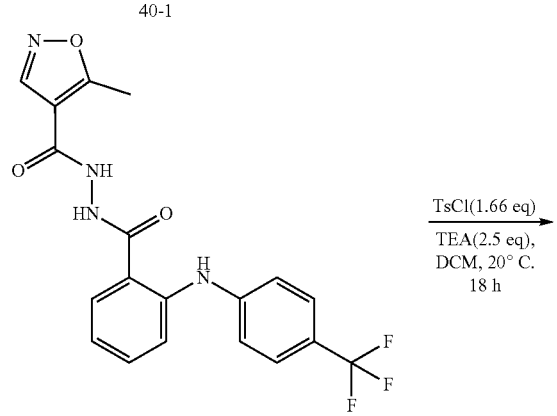

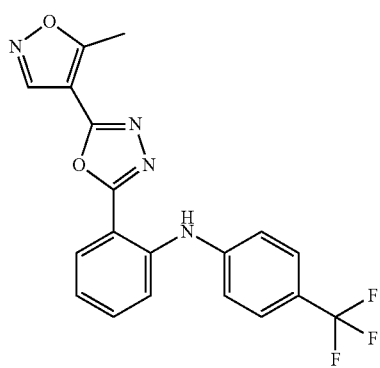

Compound 40

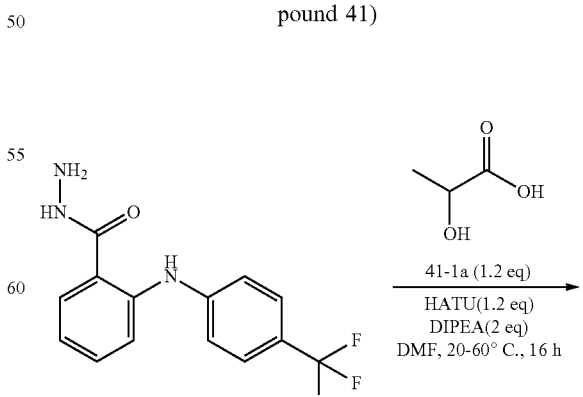

41-1

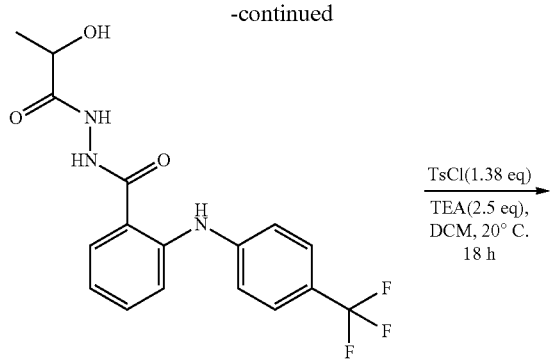

anhydrous Na$_2$SO$_4$, filtered and concentrated to give a residue. The residue was purified by prep-HPLC to give Compound 41 (18.63 mg, 53 umol, 22.6% yield). LCMS (ESI): RT=0.841 min, mass calc. for C$_{17}$H$_{14}$F$_3$N$_3$O$_2$ 349.10, m/z found 349.9 [M+1]$^+$. $^1$H NMR (400 MHz, CDCl$_3$) δ 9.46 (s, 1H), 7.91 (dd, J=1.4, 7.9 Hz, 1H), 7.58 (d, J=8.5 Hz, 2H), 7.53-7.48 (m, 1H), 7.43-7.38 (m, 1H), 7.36 (d, J=8.4 Hz, 2H), 7.02-6.90 (m, 1H), 5.22 (m, 1H), 2.89 (br d, J=5.4 Hz, 1H), 1.76 (d, J=6.8 Hz, 3H).

Example 40: 2-(5-(2-((4-(trifluoromethyl)phenyl)amino)phenyl)-1,3,4-oxadiazol-2-yl)propan-2-ol (Compound 42)

Step 1: N'-(2-hydroxypropanoyl)-2-((4-(trifluoromethyl)phenyl)amino)benzohydrazide To a solution of 41-1 (0.3 g, 1.02 mmol, 1 eq), 41-1a (110.3 mg, 1.22 mmol, 91 uL, 1.2 eq) and HATU (465.4 mg, 1.22 mmol, 1.2 eq) in DMF (4 mL) at 20° C. was added DIPEA (263.7 mg, 2.04 mmol, 0.36 mL, 2 eq), and the resulting mixture was stirred at 60° C. for 16 h. LCMS showed no starting material was remained and 43% of desired product was detected. The mixture was diluted with EA (50 mL), washed with brine (15 mL) twice, dried by anhydrous Na$_2$SO$_4$, filtered and concentrated to give a residue. The residue was purified by prep-HPLC to give 41-2 (92 mg, 0.25 mmol, 24.6% yield). LCMS (ESI): RT=0.727 min, mass calc. for C$_{17}$H$_{16}$F$_3$N$_3$O$_3$ 367.11, m/z found 367.0 [M+1]$^+$. $^1$H NMR (400 MHz, DMSO-d$_6$) δ 10.37 (s, 1H), 9.81 (s, 1H), 9.39 (s, 1H), 7.70-7.65 (m, 1H), 7.59 (d, J=8.5 Hz, 2H), 7.51-7.39 (m, 2H), 7.29 (d, J=8.5 Hz, 2H), 7.08-6.96 (m, 1H), 4.15 (q, J=6.8 Hz, 1H), 1.30 (d, J=6.8 Hz, 3H).

Step 2: 1-(5-(2-((4-(trifluoromethyl)phenyl)amino)phenyl)-1,3,4-oxadiazol-2-yl)ethanol To a mixture of 41-2 (86 mg, 0.23 mmol, 1 eq) and TEA (59.2 mg, 0.58 mmol, 81 uL, 2.5 eq) in DCM (1 mL) was added TsCl (53.6 mg, 0.28 mmol, 1.2 eq) in one portion at 20° C. The mixture was stirred at 20° C. for 16 h. LCMS showed 7% of starting material was remained and 65% of desired product was detected. Then another batch of TsCl (8.0 mg, 42 umol, 0.18 eq) was added and the mixture was stirred at 20° C. for another 2 h. LCMS and HPLC showed no starting material was remained and 59% of desired product was detected. The mixture was diluted with DCM (50 mL), washed with brine (15 mL) twice, dried by

Step 1: N'-(2-hydroxy-2-methylpropanoyl)-2-((4-(trifluoromethyl)phenyl)amino)benzo Hydrazide To a solution of 42-1 (0.3 g, 1.02 mmol, 1 eq), 42-1a (127.4 mg, 1.22 mmol, 91 uL, 1.2 eq) and HATU (465.4 mg, 1.22 mmol, 1.2 eq) in DMF (4 mL) at 20° C. was added DIPEA (263.7 mg, 2.04 mmol, 0.36 mL, 2 eq), and the resulting mixture was stirred at 60° C. for 16 h. LCMS showed no starting material was remained and 31% of desired product was detected. The mixture was diluted with EA (50 mL), washed with brine (15 mL) twice, dried by anhydrous Na$_2$SO$_4$, filtered and concentrated to give a residue. The residue was purified by prep-HPLC to give 42-2 (76.2 mg, 0.2 mmol, 19.6% yield). LCMS (ESI): RT=0.758 min, mass calc. for C$_{18}$H$_{18}$F$_3$N$_3$O$_3$ 381.13, m/z found 382.0 [M+1]$^+$. $^1$H NMR (400 MHz, DMSO-d$_6$) δ 10.36 (s, 1H), 9.67 (s, 1H), 9.40 (s, 1H), 7.67 (d, J=7.5 Hz, 1H), 7.59 (d, J=8.6 Hz, 2H), 7.50-7.41 (m, 2H), 7.29 (d, J=8.5 Hz, 2H), 7.05-6.98 (m, 1H), 1.33 (s, 6H).

Step 2: 2-(5-(2-((4-(trifluoromethyl)phenyl)amino) phenyl)-1,3,4-oxadiazol-2-yl)propan-2-ol To a mixture of 42-2 (71 mg, 0.18 mmol, 1 eq) and TEA (37.7 mg, 0.37 mmol, 51 uL, 2 eq) in DCM (3 mL) was added TsCl (42.6 mg, 0.22 mmol, 1.2 eq) in one portion at 15° C. The mixture was stirred at 15° C. for 2 h. LCMS and HPLC showed 33% of starting material was remained and 65% of desired product was detected. Then another batch of TsCl (8.9 mg, 46 umol, 0.25 eq) was added and the mixture was stirred at 20° C. for another 1 h. LCMS showed 18% starting material was remained and 61% of desired product was detected. The mixture was diluted with DCM (50 mL), washed with brine (15 mL) twice, dried by anhydrous Na$_2$SO$_4$, filtered and concentrated to give a residue. The residue was purified by prep-HPLC to give Compound 42 (19.76 mg, 54 umol, 29.2% yield). LCMS (ESI): RT=0.854 min, mass calc. for C$_{18}$H$_{16}$F$_3$N$_3$O$_2$ 363.12, m/z found 363.9 [M+1]$^+$. $^1$H NMR (400 MHz, CDCl$_3$) δ 9.48 (s, 1H), 7.91 (dd, J=1.4, 7.9 Hz, 1H), 7.58 (d, J=8.5 Hz, 2H), 7.51 (d, J=8.0 Hz, 1H), 7.40 (dt, J=1.5, 7.9 Hz, 1H), 7.35 (d, J=8.5 Hz, 2H), 7.01-6.94 (m, 1H), 2.87 (br s, 1H), 1.80 (s, 6H).

Example 41: 2-(5-(3-methylisoxazol-4-yl)-1,3,4-oxadiazol-2-yl)-N-(4-(trifluoromethyl)phenyl) aniline (Compound 43)

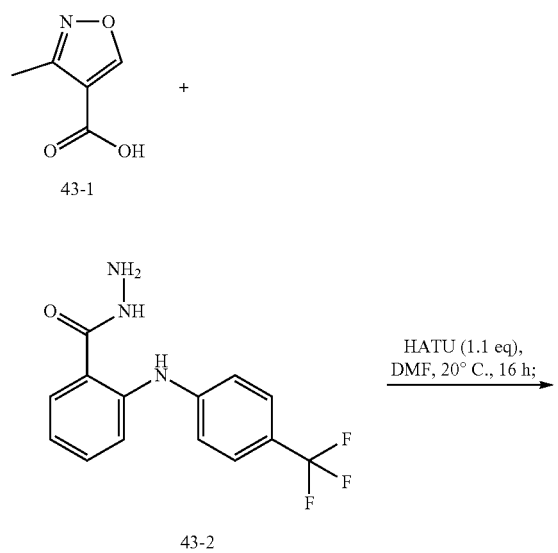

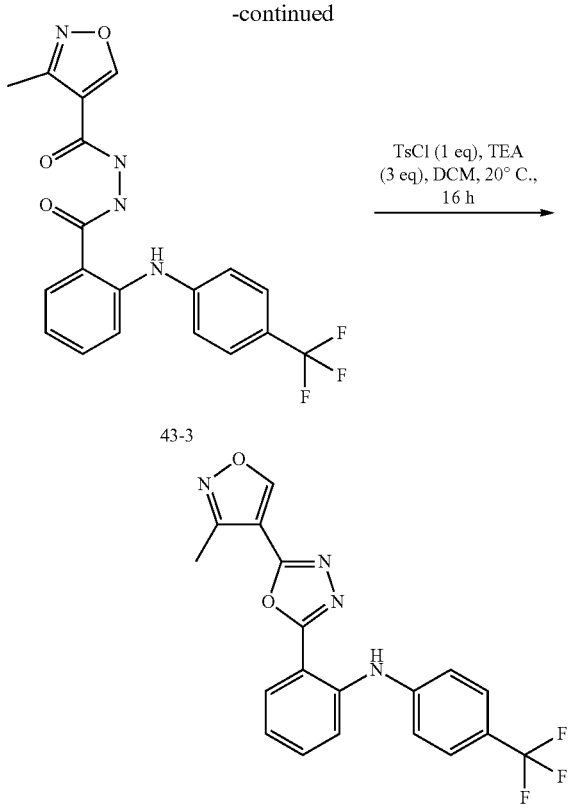

Compound 43

Step 1: 3-methyl-N'-(2-((4-(trifluoromethyl)phenyl) amino)benzoyl)isoxazole-4-carbohydrazide To a solution of compound 43-1 (200 mg, 1.57 mmol, 1 eq) and HATU (658.2 mg, 1.73 mmol, 1.1 eq) in DMF (1 mL) at 20° C. was added compound 43-2 (511.1 mg, 1.73 mmol, 1.1 eq) and DIPEA (406.7 mg, 3.15 mmol, 0.5 mL, 2 eq), and the resulting mixture was stirred at 20° C. for 16 h. LCMS showed starting material was consumed completely, and 29% of guanidine-byproduct and 63% of desired product were formed. The mixture was concentrated to give a residue. The residue was purified by prep-HPLC to give compound 43-3 (334 mg, 0.83 mmol, 52.5% yield). LCMS (ESI): RT=0.781 min, mass calc. for C$_{19}$H$_{15}$F$_3$N$_4$O$_3$ 404.11, m/z found 405.0[M+1]$^+$. $^1$H NMR (400 MHz, DMSO-d$_6$) δ 10.61 (s, 1H), 10.53 (s, 1H), 9.37 (s, 2H), 7.74 (d, J=7.8 Hz, 1H), 7.58 (d, J=8.5 Hz, 2H), 7.52-7.45 (m, 2H), 7.29 (d, J=8.5 Hz, 2H), 7.11-7.02 (m, 1H), 2.41 (s, 3H).

Step 2: 2-(5-(3-methylisoxazol-4-yl)-1,3,4-oxadiazol-2-yl)-N-(4-(trifluoromethyl)phenyl)aniline To a solution of compound 43-3 (230 mg, 0.57 mmol, 1 eq) and TEA (172.7 mg, 1.71 mmol, 0.2 mL, 3 eq) in DCM (3 mL) at 20° C. was added TsCl (108.4 mg, 0.57 mmol, 1 eq), and the resulting mixture was stirred at 20° C. for 16 h. LCMS showed starting material was consumed completely, and 90% of desired product were formed. The mixture was concentrated to give a residue. The residue was purified by prep-HPLC to give Compound 43 (176.96 mg, 0.46 mmol, 80.5% yield). LCMS (ESI): RT=0.946 min, mass calc. for C$_{19}$H$_{13}$F$_3$N$_4$O$_2$ 386.10, m/z found 387.0[M+1]$^+$. $^1$H NMR (400 MHz, DMSO-d$_6$) δ 9.82 (s, 1H), 9.22 (s, 1H), 8.06-8.00 (m, 1H), 7.65 (d, J=8.5 Hz, 2H), 7.62-7.54 (m, 2H), 7.38 (d, J=8.3 Hz, 2H), 7.22-7.15 (m, 1H), 2.57 (s, 3H).

Example 42: 1-(5-(2-((4-(trifluoromethyl)phenyl)amino)phenyl)-1,3,4-oxadiazol-2-yl)cyclopropanol (Compound 44)

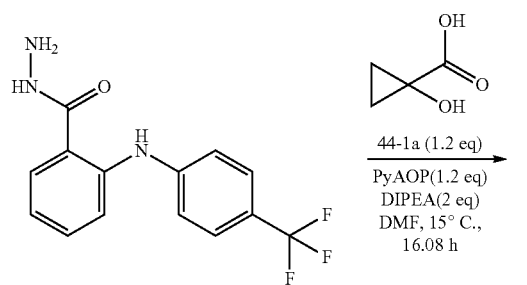

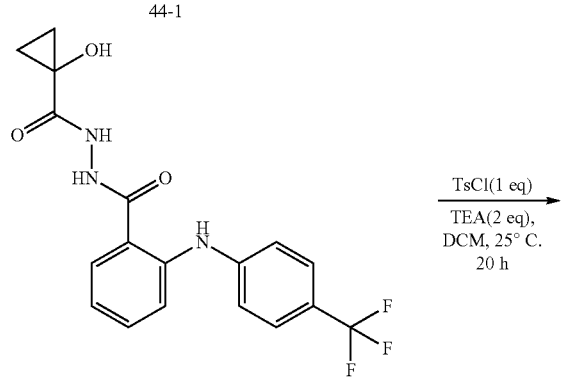

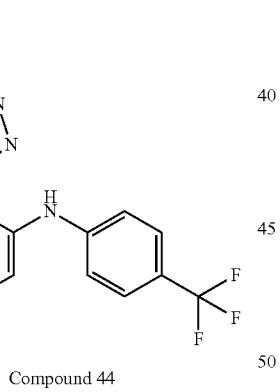

Compound 44

Step 1: N'-(1-hydroxycyclopropanecarbonyl)-2-((4-(trifluoromethyl)phenyl)amino) benzohydrazide To a mixture of 44-1a (207.4 mg, 2.03 mmol, 1.2 eq) and PYAOP (1.07 g, 2.05 mmol, 1.21 eq) in DMF (5 mL) was added DIPEA (547.2 mg, 4.23 mmol, 0.7 mL, 2.5 eq) in one portion at 15° C. After stirring for 5 min, 44-1 (0.5 g, 1.69 mmol, 1 eq) was added and the mixture was stirred at 15° C. for 16 h. LCMS showed no starting material was remained and 43% of desired product was detected. The mixture was diluted with EA (100 mL), washed with brine (15 mL) twice, dried by anhydrous Na$_2$SO$_4$, filtered and concentrated to give a residue. The residue was purified by prep-HPLC to give 44-2 (15 mg, 40 umol, 2.3% yield). LCMS (ESI): RT=0.749 min, mass calc. for C$_{18}$H$_{16}$F$_3$N$_3$O$_3$ 379.11, m/z found 380.0 [M+1]$^+$.

Step 2: 1-(5-(2-((4-(trifluoromethyl)phenyl)amino)phenyl)-1,3,4-oxadiazol-2-yl)cyclopropanol To a mixture of 44-2 (15 mg, 40 umol, 1 eq) and TEA (8 mg, 79 umol, 11 uL, 2 eq) in DCM (2 mL) was added TsCl (11 mg, 59 umol, 1.5 eq) in one portion at 10° C. The mixture was stirred at 10° C. for 16 h. LCMS showed no starting material was remained and 52% of desired product was detected. The mixture was diluted with EA (50 mL), washed with brine (15 mL) twice, dried by anhydrous Na$_2$SO$_4$, filtered and concentrated to give a residue. The residue was purified by prep-HPLC to give Compound 44 (3.41 mg, 9 umol, 23.9% yield). LCMS (ESI): RT=0.850 min, mass calc. for C$_{18}$H$_{14}$F$_3$N$_3$O$_2$ 361.10, m/z found 361.9 [M+1]$^+$. $^1$H NMR (400 MHz, CD$_3$OD) δ 7.94 (dd, J=1.4, 7.9 Hz, 1H), 7.67-7.55 (m, 3H), 7.52-7.45 (m, 1H), 7.40 (d, J=8.3 Hz, 2H), 7.07 (t, J=7.7 Hz, 1H), 1.48-1.32 (m, 4H).

Example 43: 2-methyl-2-(5-(2-((4-(trifluoromethyl)phenyl)amino)phenyl)-1,3,4-oxadiazol-2-yl)propan-1-ol (Compound 45)

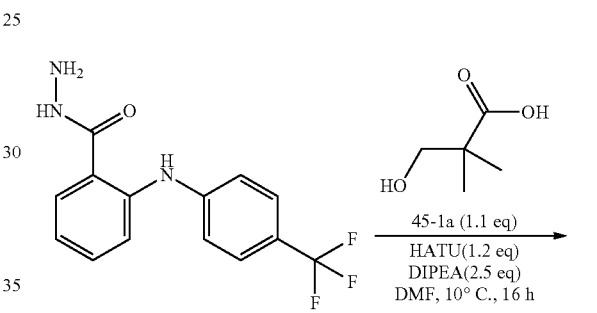

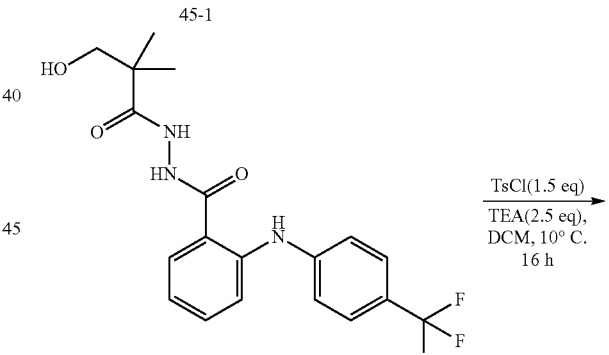

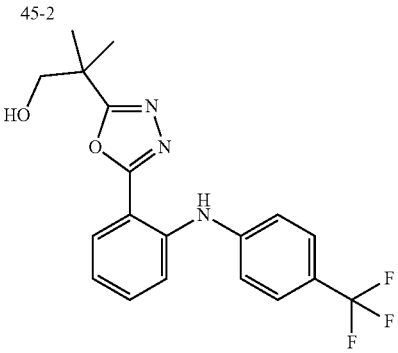

Compound 45

Step 1: N'-(3-hydroxy-2,2-dimethylpropanoyl)-2-((4-(trifluoromethyl)phenyl)amino)benzo hydrazide To a solution of 45-1a (132.5 mg, 1.12 mmol, 1.1 eq) and HATU (465.4 mg, 1.22 mmol, 1.2 eq) in DMF (3 mL) at 10° C. was added DIPEA (329.6 mg, 2.55 mmol, 0.5 mL, 2.5 eq). After stirring for 10 min, 45-1 (0.3 g, 1.02 mmol, 1 eq) was added and the resulting mixture was stirred at 10° C. for 16 h. LCMS showed no starting material was remained and 60% of desired product was detected. TLC (Petroleum ether:Ethyl acetate=1:1, UV) indicated reactant 1 was consumed completely and one new spot formed. The mixture was diluted with EA (50 mL), washed with brine (15 mL) twice, dried by anhydrous $Na_2SO_4$, filtered and concentrated to give a residue. The residue was purified by column chromatography ($SiO_2$) to give compound 45-2 (350 mg, 0.89 mmol, 86.8% yield). LCMS (ESI): RT=0.763 min, mass calc. for $C_{19}H_{20}F_3N_3O_3$ 395.15, m/z found 396.0 $[M+1]^+$.

Step 2: 2-methyl-2-(5-(2-((4-(trifluoromethyl)phenyl)amino)phenyl)-1,3,4-oxadiazol-2-yl)propan-1-ol To a solution of 45-2 (0.25 g, 0.63 mmol, 1 eq) and TEA (160 mg, 1.58 mmol, 0.2 mL, 2.5 eq) in DCM (5 mL) at 10° C. was added TsCl (180.8 mg, 0.95 mmol, 1.5 eq). The resulting mixture was stirred at 10° C. for 16 h. LCMS showed no starting material was remained and 60% of desired product was detected. The mixture was diluted with EA (50 mL), washed with brine (15 mL) twice, dried by anhydrous $Na_2SO_4$, filtered and concentrated to give a residue. The residue was purified by prep-HPLC to give Compound 45 (22.61 mg, 59 umol, 9.4% yield). LCMS (ESI): RT=0.876 min, mass calc. for $C_{19}H_{18}F_3N_3O_2$ 377.14, m/z found 377.9 $[M+1]^+$. $^1$H NMR (400 MHz, $CDCl_3$) δ 9.48 (br s, 1H), 7.88 (d, J=7.8 Hz, 1H), 7.57 (br d, J=8.3 Hz, 2H), 7.51 (d, J=8.5 Hz, 1H), 7.42-7.31 (m, 3H), 6.98 (t, J=7.5 Hz, 1H), 3.85 (s, 2H), 2.83 (br s, 1H), 1.48 (s, 6H).

Example 44: 2,2,2-trifluoro-1-(5-(2-((4-(trifluoromethyl)phenyl)amino)phenyl)-1,3,4-oxadiazol-2-yl) ethyl 4-methylbenzenesulfonate (Compound 46)

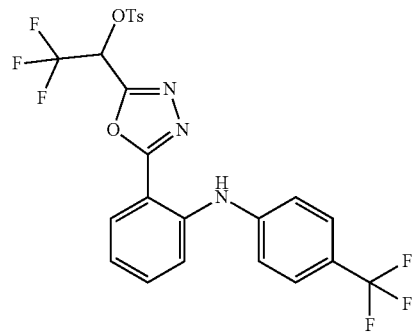

Compound 46

To a solution 46-1 (0.24 g, 0.57 mmol, 1 eq) and TEA (144.1 mg, 1.42 mmol, 0.2 mL, 2.5 eq) in DCM (5 mL) at 10° C. was added TsCl (162.9 mg, 0.85 mmol, 1.5 eq). The resulting mixture was stirred at 10° C. for 16 h. LCMS showed no starting material was remained and 46% of Compound 46 was formed. Then another batch of TsCl (54.3 mg, 0.28 mmol, 0.5 eq) was added and the resulting mixture was stirred at 10° C. for another 1 h. LCMS showed no starting material was remained and 60% of Compound 46 was formed. The mixture was diluted with EA (50 mL), washed with brine (15 mL) twice, dried by anhydrous $Na_2SO_4$, filtered and concentrated to give a residue. The residue was purified by prep-HPLC to give Compound 46 (20 mg, 35 umol, 6.2% yield). LCMS (ESI): RT=1.007 min, mass calc. for $C_{24}H_{17}F_6N_3O_4S$ 557.08, m/z found 558.0 $[M+1]^+$. $^1$H NMR (400 MHz, $CDCl_3$) δ 9.19 (s, 1H), 7.68 (d, J=8.3 Hz, 2H), 7.62 (dd, J=1.4, 7.9 Hz, 1H), 7.54 (d, J=8.5 Hz, 2H), 7.44-7.33 (m, 2H), 7.29 (d, J=8.3 Hz, 2H), 7.16 (s, 2H), 6.93-6.86 (m, 1H), 6.05 (q, J=5.8 Hz, 1H), 2.17 (s, 3H).

Example 45: (1-(5-(2-((4-(trifluoromethyl)phenyl) amino)phenyl)-1,3,4-oxadiazol-2-yl)cyclopropyl) methanol (Compound 47)

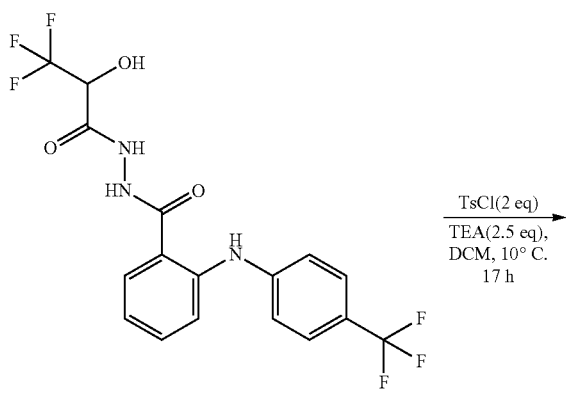

46-1

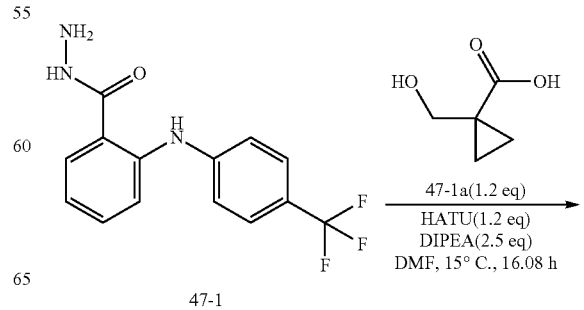

47-1

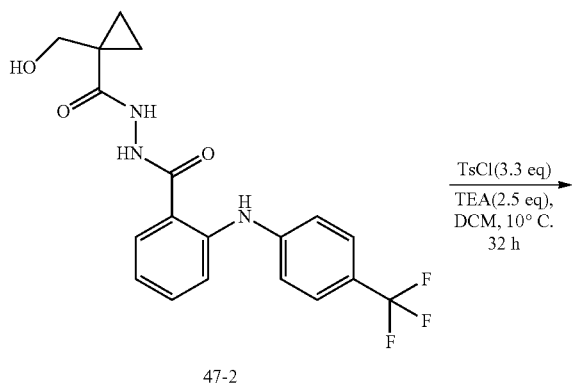

47-2

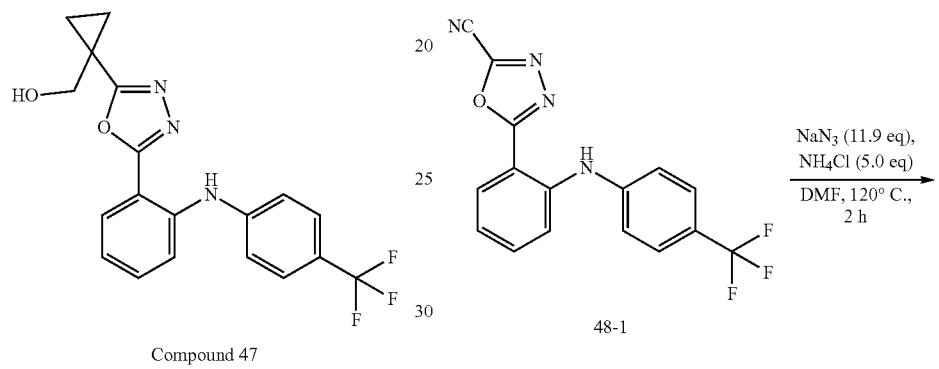

Compound 47

Step 1: N'-(1-(hydroxymethyl)cyclopropanecarbonyl)-2-((4-(trifluoromethyl)phenyl)amino) benzohydrazide To a mixture of 47-1a (70.8 mg, 0.61 mmol, 1.2 eq) and HATU (231.8 mg, 0.61 mmol, 1.2 eq) in DMF (3 mL) was added DIPEA (164.2 mg, 1.27 mmol, 0.2 mL, 2.5 eq) in one portion at 15° C. After stirring for 5 min, 47-1 (0.15 g, 0.51 mmol, 1 eq) was added and the mixture was stirred at 15° C. for 16 h. LCMS and HPLC showed no starting material was remained and 43% of desired product was detected. The mixture was diluted with EA (100 mL), washed with brine (15 mL) twice, dried by anhydrous $Na_2SO_4$, filtered and concentrated to give a residue. The residue was purified by prep-HPLC to give 47-2 (60 mg, 0.15 mmol, 29.4% yield). LCMS (ESI): RT=0.758 min, mass calc. for $C_{19}H_{18}F_3N_3O_3$ 393.13, m/z found 394.0 [M+1]$^+$.

Step 2: (1-(5-(2-((4-(trifluoromethyl)phenyl)amino) phenyl)-1,3,4-oxadiazol-2-yl)cyclopropyl) methanol To a solution of 47-2 (20 mg, 51 umol, 1 eq) and TEA (12.9 mg, 0.13 mmol, 18 uL, 2.5 eq) in DCM (5 mL) at 10° C. was added TsCl (12.6 mg, 66 umol, 1.3 eq). The resulting mixture was stirred at 10° C. for 16 h. LCMS showed 57% of starting material was remained and 14% of desired product was detected. TsCl (29.1 mg, 0.15 mmol, 3 eq) was added to the mixture, and the resulting mixture was stirred at 10° C. for 16 h. LCMS showed 16% of starting material was remained and 30% of desired product was detected. The mixture was diluted with EA (100 mL), washed with brine (15 mL) twice, dried by anhydrous $Na_2SO_4$, filtered and concentrated to give a residue. The residue was purified by prep-HPLC to give Compound 47 (27.56 mg, 73 umol, 36.1% yield). LCMS (ESI): RT=0.849 min, mass calc. for $C_{19}H_{16}F_3N_3O_2$ 375.12, m/z found 376.0 [M+1]$^+$. $^1$H NMR (400 MHz, DMSO-d$_6$) δ 9.21 (s, 1H), 7.93 (d, J=7.5 Hz, 1H), 7.63 (d, J=8.5 Hz, 2H), 7.59-7.49 (m, 2H), 7.32 (d, J=8.3 Hz, 2H), 7.19-7.10 (m, 1H), 5.02 (t, J=5.9 Hz, 1H), 3.79 (d, J=6.0 Hz, 2H), 1.23-1.17 (m, 2H), 1.16-1.09 (m, 2H).

Example 46: 2-[5-(2H-tetrazol-5-yl)-1,3,4-oxadiazol-2-yl]-N-[4-(trifluoromethyl)phenyl]aniline (Compound 48)

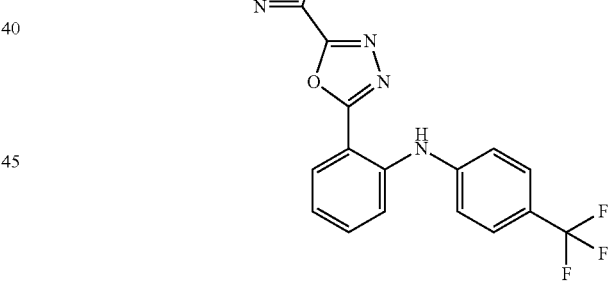

Compound 48

To a solution of 48-1 (30 mg, 90.8 umol, 1 eq) in DMF (0.5 mL) were added $NaN_3$ (0.1 g, 1.1 mmol, 11.9 eq) and $NH_4Cl$ (24.3 mg, 0.5 mmol, 15.9 uL, 5.0 eq). The mixture was stirred at 120° C. for 2 hr. LC-MS showed 48-1 was consumed completely and 98% of desired compound was detected. The reaction mixture was diluted with ($H_2O$ 1 mL). The residue was purified by prep-HPLC to give Compound 48 (2.54 mg, 6.8 umol, 7% yield). LCMS (ESI): RT=0.948 min, mass calc. for $C_{16}H_{10}F_3N_7O$ 373.09, m/z found 374.4 [M+H]$^+$; $^1$H NMR (400 MHz, CDCl$_3$) δ 8.17-8.15 (m, J=1.1, 7.9 Hz, 1H), 7.66-7.57 (m, 3H), 7.54-7.48 (m, 1H), 7.45 (d, J=8.3 Hz, 2H), 7.10 (t, J=7.5 Hz, 1H).

Example 47: cyclopropyl(5-(2-((4-(trifluoromethyl)phenyl)amino)phenyl)-1,3,4-oxadiazol-2-yl)methanol (Compound 49)

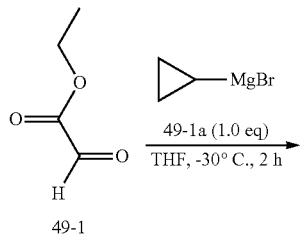

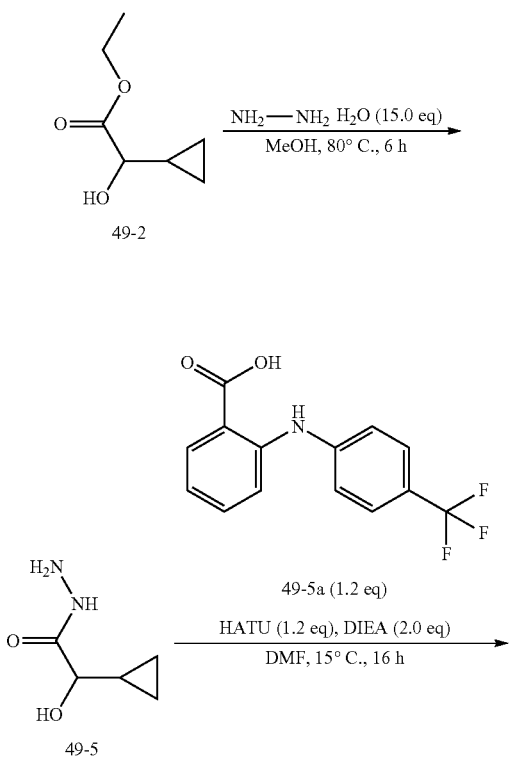

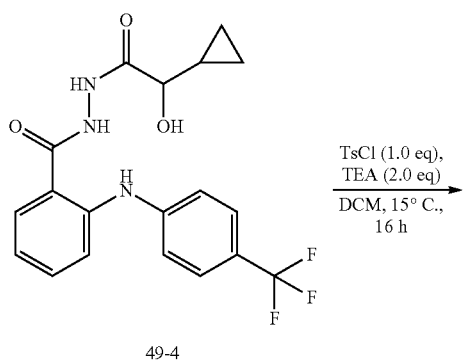

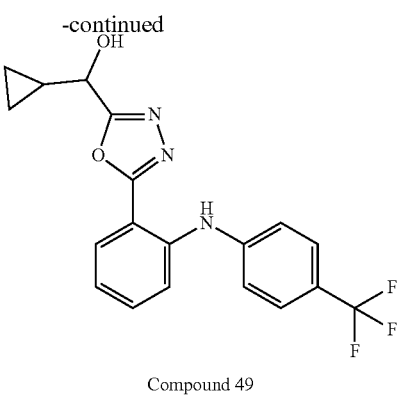

Compound 49

Step 1: Ethyl 2-cyclopropyl-2-hydroxyacetate

To a solution of compound 49-1 (10 g, 48.98 mmol, 1 eq) in THF (100 mL) was added compound 49-1a (0.5 M, 97.9 mL, 1 eq) dropwise at −20~−30° C. bath. The mixture was stirred at −30° C. for 2 hr. TLC (PE/EA=1/1, KMnO$_4$) showed that the starting material was remained and new spots were formed. The reaction mixture was quenched with water (200 mL) dropwise at −20° C. and the aqueous phase was extracted with EA (30 mL*4). The combined organic phase was washed with water (25 mL) and brine (10 mL), dried over Na$_2$SO$_4$, filtered and concentrated in vacuum. The residue was purified by column chromatography (SiO$_2$). 49-2 (1.2 g, 8.32 mmol, 17.0% yield) was obtained. $^1$H NMR (400 MHz, CDCl$_3$) δ 4.24 (m, 2H), 3.76-3.71 (m, 1H), 2.85 (br s, 1H), 1.29 (t, J=7.2 Hz, 3H), 1.13-1.02 (m, 1H), 0.55-0.45 (m, 3H), 0.44-0.35 (m, 1H).

Step 2: 2-cyclopropyl-2-hydroxyacetohydrazide

To a solution of compound 49-2 (100 mg, 0.69 mmol, 1 eq) in MeOH (1 mL) was added NH$_2$NH$_2$.H$_2$O (651 mg, 10.40 mmol, 0.6 mL, 15 eq). The mixture was stirred at 80° C. for 6 hr. TLC (PE/EA=1/1, I2) showed that the starting material was consumed completely. The reaction mixture was concentrated in vacuum. The crude product was used for the next step directly. 49-3 (40 mg, 0.31 mmol, 44.3% yield) was obtained. $^1$H NMR (400 MHz, DMSO-d$_6$) δ 8.79 (br s, 1H), 5.17 (br s, 1H), 4.27 (br s, 2H), 1.07-0.97 (m, 1H), 0.40-0.23 (m, 4H).

Step 3: N'-(2-cyclopropyl-2-hydroxyacetyl)-2-((4-(trifluoromethyl)phenyl)amino)benzo Hydrazide To a solution of compound 49-3a (77.8 mg, 0.28 mmol, 1.2 eq) in DMF (1 mL) were added DIPEA (59.6 mg, 0.46 mmol, 80 uL, 2 eq), HATU (105.2 mg, 0.28 mmol, 1.2 eq) and compound 3 (30 mg, 0.23 mmol, 1 eq). The mixture was stirred at 15° C. for 16 hr. LCMS showed that the starting material was consumed completely and desired product was detected. The reaction mixture was concentrated in vacuum. The crude product was purified by prep-HPLC. 49-4 (30 mg, 76.3 umol, 33.1% yield) was obtained. $^1$H NMR (400 MHz, DMSO-d$_6$) δ 9.93 (br s, 1H), 8.23 (br s, 1H), 7.72 (d, J=7.3 Hz, 1H), 7.57 (d, J=8.5 Hz, 2H), 7.49-7.36 (m, 2H), 7.29 (d, J=8.5 Hz, 2H), 6.98 (t, J=7.4 Hz, 1H), 5.48 (br d, J=4.8 Hz, 1H), 3.65 (br t, J=5.1 Hz, 1H), 1.18-1.06 (m, 1H), 0.52-0.28 (m, 4H).

Step 4: cyclopropyl(5-(2-((4-(trifluoromethyl)phenyl)amino)phenyl)-1,3,4-oxadiazol-2-yl)methanol To a solution of compound 49-4 (25 mg, 63 umol, 1 eq) in DCM (0.5 mL) were added TEA (13 mg, 0.13 mmol, 17.7 uL, 2 eq) and TsCl (12 mg, 63.6 umol, 1 eq). The mixture was stirred at 10° C. for 2 hr. LCMS showed that the starting material was remained and 58% of desired product was detected. The reaction mixture was concentrated in vacuum. The crude product was purified by prep-HPLC. Compound 49 (10 mg, 26.6 umol, 41.9% yield) was obtained. LCMS (ESI): RT=0.885 min, mass calcd. for $C_{19}H_{16}F_3N_3O_2$, 375.12 m/z found 375.9 [M+H]$^+$. $^1$H NMR (400 MHz, CDCl$_3$) δ 8.55 (s, 1H), 8.07 (br d, J=7.78 Hz, 1H), 7.86 (d, J=8.78 Hz, 1H), 7.75 (d, J=8.04 Hz, 2H), 7.64 (d, J=9.04 Hz, 1H), 7.57 (d, J=8.04 Hz, 2H), 7.48 (d, J=8.04 Hz, 1H), 7.13 (br s, 1H), 6.07 (br d, J=8.28 Hz, 1H), 4.36 (dq, J=13.62, 6.76 Hz, 1H), 1.59 (s, 9H), 1.32 (d, J=6.54 Hz, 6H).

Example 48: 3-[5-[2-[4-(trifluoromethyl)anilino]phenyl]-1,3,4-oxadiazol-2-yl]-4H-1,2,4-oxadiazol-5-one (Compound 50)

Step 1: N'-hydroxy-5-[2-[4-(trifluoromethyl)anilino]phenyl]-1,3,4-oxadiazole-2-carboxamidine To a solution of 50-1 (70 mg, 0.2 mmol, 1 eq) and NH$_2$OH—HCl (22.1 mg, 0.2 mmol, 0.98 eq, HCl) in EtOH (2 mL) was added DIPEA (82.2 mg, 0.6 mmol, 0.1 mL, 3.0 eq). The mixture was stirred at 25° C. for 1 hr. LC-MS showed 50-1 was consumed completely and 99% of desired compound was detected. The reaction mixture was filtered to give 50-2 (35 mg, 96.3 umol, 45.4% yield). LCMS (ESI): RT=0.953 min, mass calc. for $C_{16}H_{12}F_3N_5O_2$ 363.09, m/z found 364.4 [M+H]$^+$.

Step 2: 3-[5-[2-[4-(trifluoromethyl)anilino]phenyl]-1,3,4-oxadiazol-2-yl]-4H-1,2,4-oxadiazol-5-one To a solution of 50-2 (35 mg, 96.3 umol, 1 eq) and 50-3a (23.4 mg, 0.1 mmol, 1.5 eq) in THF (1 mL) was added DBU (22.0 mg, 0.1 mmol, 22 uL, 1.5 eq). The mixture was stirred at 25° C. for 2 h. LC-MS showed 30% of 50-2 was remained and 68% of desired compound was detected. The reaction mixture was concentrated under reduced pressure to give a residue. The residue was purified by prep-HPLC to give Compound 50 (8.68 mg, 22.3 umol, 23.1% yield). LCMS (ESI): RT=1.146 min, mass calc. for $C_{12}H_{16}BrN$ 253.05, m/z found 254.3 [M+H]$^+$.

Example 49: 2,2,2-trifluoro-1-(5-(2-((4-(trifluoromethyl)phenyl)amino)phenyl)-1,3,4-oxadiazol-2-yl)ethanol (Compound 51)

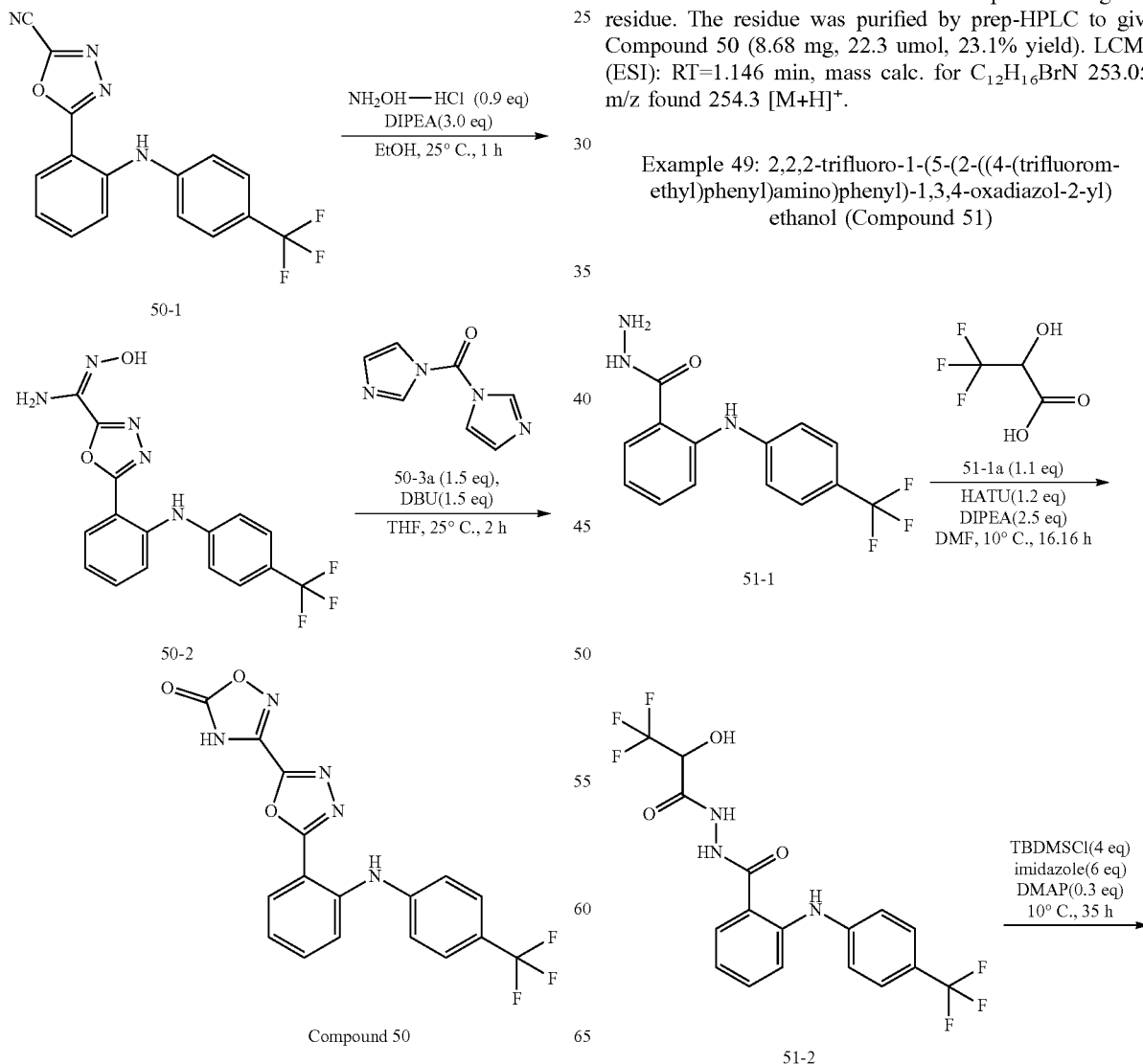

-continued

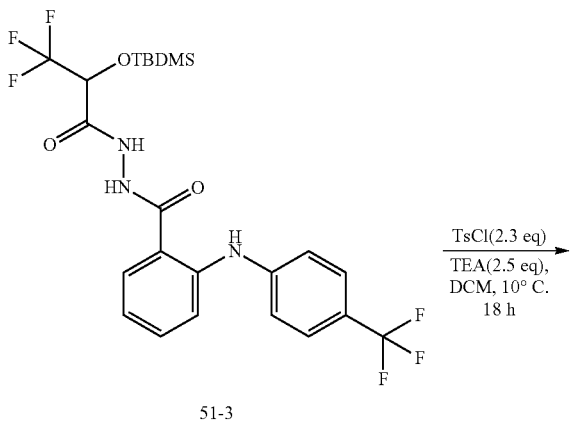

51-3

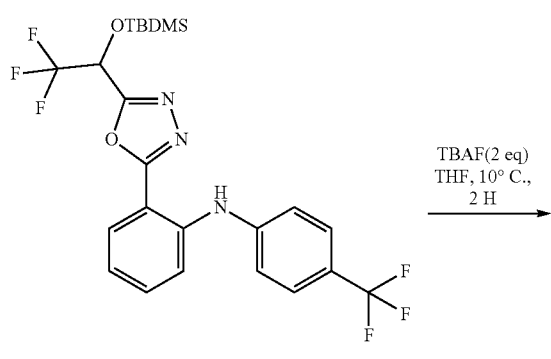

51-4

Compound 51

Step 1: N'-(3,3,3-trifluoro-2-hydroxypropanoyl)-2-((4-(trifluoromethyl)phenyl)amino)benzo Hydrazide To a solution of 51-1a (268.3 mg, 1.86 mmol, 1.1 eq) and HATU (772.7 mg, 2.03 mmol, 1.2 eq) in DMF (5 mL) at 10° C. was added DIPEA (547.2 mg, 4.23 mmol, 0.7 mL, 2.5 eq). After stirring for 10 min, 51-1 (0.5 g, 1.69 mmol, 1 eq) was added and the resulting mixture was stirred at 10° C. for 16 h. LCMS showed no starting material was remained and 14% desired product was detected. The mixture was directly purified by prep-HPLC to give 51-2 (50 mg, 0.11 mmol, 45% yield. LCMS (ESI): RT=0.797 min, mass calc. for $C_{17}H_{13}F_6N_3O_3$ 421.09, m/z found 421.9 [M+1]$^+$. $^1$H NMR (400 MHz, CDCl$_3$) δ 8.98 (br s, 1H), 8.89 (br s, 1H), 8.52 (br s, 1H), 7.53 (d, J=8.0 Hz, 1H), 7.47 (d, J=8.5 Hz, 2H), 7.41-7.31 (m, 2H), 7.16 (d, J=8.3 Hz, 2H), 6.86 (t, J=7.8 Hz, 1H), 4.61 (br d, J=7.0 Hz, 1H), 3.91 (br s, 1H).

Step 2: N'-(2-((tert-butyldimethylsilyl)oxy)-3,3,3-trifluoropropanoyl)-2-((4-(trifluoromethyl)phenyl)amino)benzohydrazide To a solution of 51-2 (40 mg, 95 umol, 1 eq), DMAP (3.5 mg, 28 umol, 0.3 eq) and imidazole (38.8 mg, 0.57 mmol, 6 eq) in DCM (3 mL) at 10° C. was added TBDMSCl (28.6 mg, 0.19 mmol, 23 uL, 2 eq). The resulting mixture was stirred at 10° C. for 16 h. LCMS showed 52% of starting material was remained and 44% desired product was detected. Then another batch of TBDMSCl (14.3 mg, 95 umol, 12 uL, 1 eq) was added and the resulting mixture was stirred at 10° C. for 3 h. LCMS showed 31% of starting material was remained and 65% desired product was detected. Then another batch of TBDMSCl (14.3 mg, 95 umol, 12 uL, 1 eq) was added and the resulting mixture was stirred at 10° C. for another 16 h. LCMS showed no starting material was remained and 89.9% desired product was detected. TLC (Petroleum ether:Ethyl acetate=3:1 UV) showed new spots were formed. The mixture diluted with water (10 mL), extracted with dichloromethane (15 mL*3) and the extracts died over anhydrous Na$_2$SO$_4$, filtered and evaporated to give crude product. The mixture was directly purified-TLC to give 51-3 (34 mg, 60 umol, 63.5% yield).

Step 3: 2-(5-(1-((tert-butyldimethylsilyl)oxy)-2,2,2-trifluoroethyl)-1,3,4-oxadiazol-2-yl)-N-(4-(trifluoromethyl)phenyl)aniline To a solution of compound 51-3 (34 mg, 64 umol, 1 eq) and TEA (16.06 mg, 0.16 mmol, 22 uL, 2.5 eq) in DCM (1 mL) at 10° C. was added TsCl (18.2 mg, 95 umol, 1.5 eq). The resulting mixture was stirred at 10° C. for 2 h. LCMS showed 54% of starting material was remained and 14% of desired product was detected. Then another batch of TsCl (9.68 mg, 51 umol, 0.8 eq) was added and the solution was continuously stirred at 10° C. for 16 h. LCMS showed 18% of starting material was remained and 39% of desired product was detected. TLC (Petroleum ether:Ethyl acetate=5:1 UV) showed some of starting material was remained and new spot was formed. The mixture was directly purified by prep-TLC to give 51-4 (11 mg, 21 umol, 32.8% yield).

Step 4: 2,2,2-trifluoro-1-(5-(2-((4-(trifluoromethyl)phenyl)amino)phenyl)-1,3,4-oxadiazol-2-yl)ethanol To a mixture of 51-4 (9 mg, 17 umol, 1 eq) in THF (1 mL) was added TBAF (1 M, 35 uL, 2 eq). Then the resulting solution was stirred at 10° C. for 2 h. LCMS showed starting material was consumed completely and 100% of desired product was detected. The mixture was diluted with EA (50 mL), washed with brine (15 mL) twice, dried by anhydrous Na$_2$SO$_4$, filtered and concentrated to give a residue. The combined mixture was directly purified by prep-HPLC to give Compound 51 (4.15 mg, 10 umol, 59.2% yield). LCMS (ESI): RT=0.896 min, mass calc. for $C_{17}H_{11}F_6N_3O_2$ 403.08, m/z found 403.9 [M+1]$^+$. $^1$H NMR (400 MHz, CDCl$_3$) δ 9.26 (s, 1H), 7.84 (d, J=6.8 Hz, 1H), 7.53 (d, J=8.3 Hz, 2H), 7.47-7.40 (m, 1H), 7.39-7.33 (m, 1H), 7.30 (d, J=8.5 Hz, 2H), 6.92 (t, J=7.5 Hz, 1H), 5.39 (q, J=5.9 Hz, 1H), 3.63 (br s, 1H).

Example 50: 1-(5-(2-((4-(trifluoromethyl)phenyl) amino)phenyl)-1,3,4-oxadiazol-2-yl)cyclo pentanol (Compound 52)

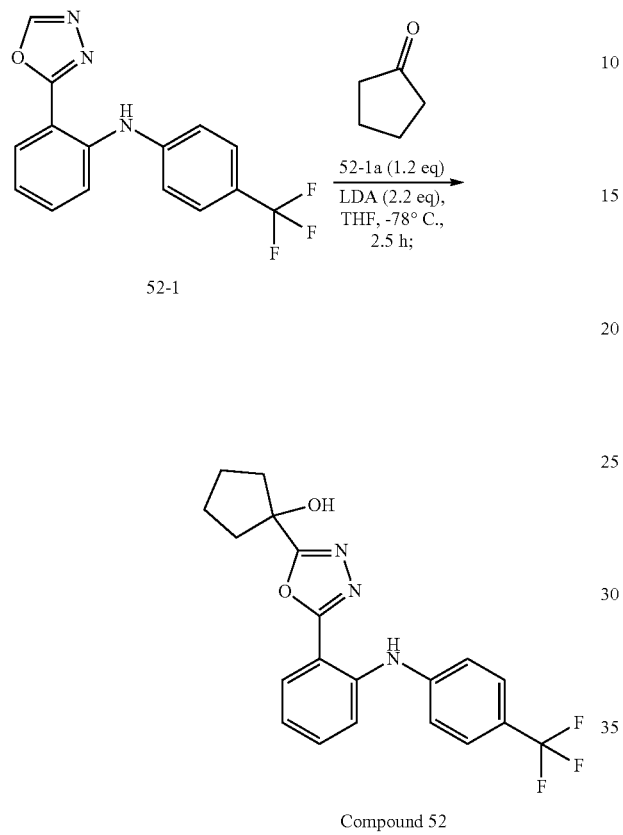

Example 51: 1-(5-(2-((4-(trifluoromethyl)phenyl) amino)phenyl)-1,3,4-oxadiazol-2-yl)cyclo propyl 4-methylbenzenesulfonate (Compound 53)

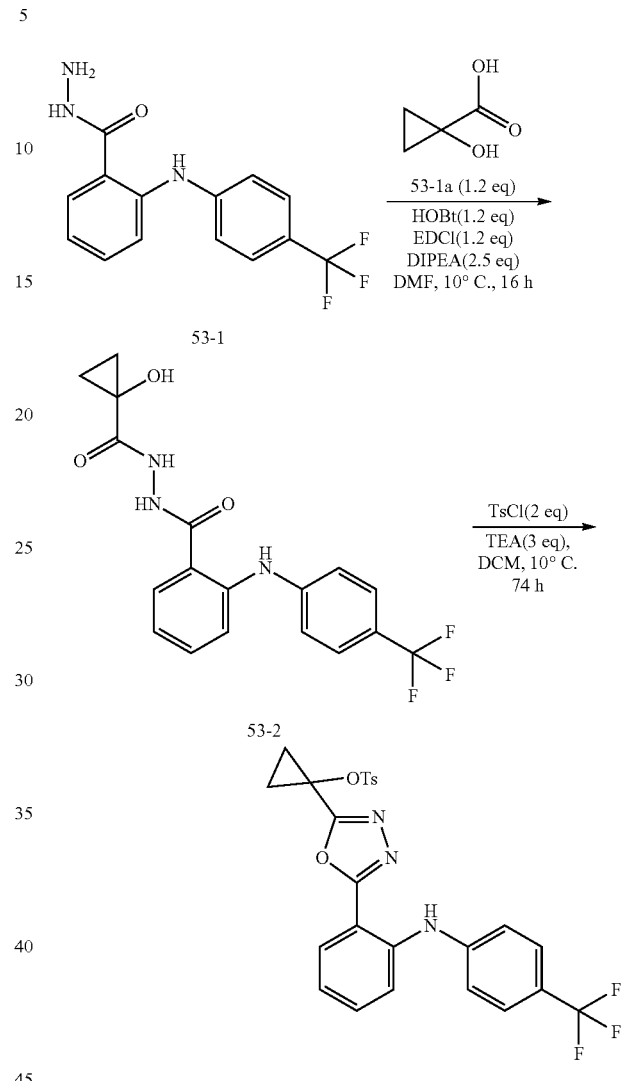

To a solution of 52-1 (100 mg, 0.33 mmol, 1 eq) in THF (2 mL) at −78° C. was added LDA (2 M, 0.4 mL, 2.2 eq) dropwise, and the mixture was stirred at −78° C. for 0.5 h. And then 52-1a (33.1 mg, 0.39 mmol, 35 uL, 1.2 eq) in THF (1 mL) was added dropwise at −78° C. into the above mixture. The resulting mixture was stirred at −78° C. for 2 h. TLC (PE:EA=5:1, UV) showed some starting material still remained and one new spot was formed. LCMS showed 27% of starting material still remained and 68% of desired product was formed. The reaction mixture was quenched with saturated NH$_4$Cl solution (5 mL) at −78° C., and then diluted with water (20 mL) and extracted with EA (20 mL*3). The combined organic layers were washed with brine (20 mL), dried over anhydrous Na$_2$SO$_4$, filtered and concentrated under reduced pressure to give a residue. The residue was purified by prep-TLC to give Compound 52 (66.97 mg, 0.17 mmol, 52.5% yield). LCMS (ESI): RT=0.898 min, mass calc. for $C_{20}H_{18}F_3N_3O_2$ 389.14, m/z found 390.0[M+1]$^+$. $^1$H NMR (400 MHz, CDCl$_3$) δ 9.51 (s, 1H), 7.91 (dd, J=1.4, 7.9 Hz, 1H), 7.58 (d, J=8.5 Hz, 2H), 7.52 (d, J=8.0 Hz, 1H), 7.44-7.38 (m, 1H), 7.36 (d, J=8.3 Hz, 2H), 7.01-6.95 (m, 1H), 2.58 (s, 1H), 2.38-2.28 (m, 2H), 2.21-2.13 (m, 2H), 2.11-2.00 (m, 2H), 1.98-1.86 (m, 2H).

Step 1: N'-(1-hydroxycyclopropanecarbonyl)-2-((4-(trifluoromethyl)phenyl)amino)benzo hydrazide A mixture of 53-1 (450 mg, 1.52 mmol, 1 eq), 53-1a (186.7 mg, 1.83 mmol, 1.2 eq), HOBt (247.1 mg, 1.83 mmol, 1.2 eq), EDCI (350.6 mg, 1.83 mmol, 1.2 eq) and DIPEA (492.4 mg, 3.81 mmol, 0.7 mL, 2.5 eq) in DMF (10 mL) was stirred at 10° C. for 16 h. LCMS showed 35% of starting material was remained and 61% of desired product was detected. The mixture was diluted with EA (100 mL), washed with brine (15 mL), dried with Na$_2$SO$_4$, filtered and concentrated to give a residue. The residue was purified by prep-HPLC to give compound 53-2 (0.5 g, 1.28 mmol, 83.9% yield). $^1$H NMR (400 MHz, DMSO-d$_6$) δ 10.36 (s, 1H), 9.93 (s, 1H), 9.43 (br s, 1H), 7.67 (d, J=7.1 Hz, 1H), 7.59 (d, J=8.6 Hz, 2H), 7.53-7.39 (m, 2H), 7.28 (d, J=8.5 Hz, 2H), 7.02 (t, J=6.7 Hz, 1H), 6.43 (s, 1H), 1.14-1.04 (m, 2H), 0.98-0.90 (m, 2H).

Step 2: 1-(5-(2-((4-(trifluoromethyl)phenyl)amino)phenyl)-1,3,4-oxadiazol-2-yl)cyclopropyl 4-methylbenzenesulfonate To a mixture of 53-2 (0.45 g, 1.19 mmol, 1 eq) and TEA (360.1 mg, 3.56 mmol, 0.5 mL, 3 eq) in DCM (15 mL) was added TsCl (226.2 mg, 1.19 mmol, 1 eq) at 10° C. The resulting mixture was stirred at 10° C. for 1 h. LCMS showed 22% of starting material remained and 15% of 53 was formed. Then another TsCl (113.1 mg, 0.59 mmol, 0.5 eq) was added and the resulting mixture was stirred at 10° C. for 1.5 h. LCMS and HPLC showed 8% of starting material remained, and 30% of 53 was formed. The mixture was directly diluted with EA (20 mL), washed with water (5 mL*3), dried by anhydrous $Na_2SO_4$, filtered and concentrated to give a residue. The residue was purified by prep-HPLC to give Compound 53 (23 mg, 40 umol, 3.4% yield). LCMS (ESI): RT=0.985 min, mass calc. for $C_{25}H_{20}F_3N_3O_4S$ 515.11, m/z found 538.0 [M+23]$^+$. $^1$H NMR (400 MHz, DMSO-d$_6$) δ 9.10 (s, 1H), 7.72 (d, J=8.3 Hz, 2H), 7.66 (dd, J=3.4, 8.1 Hz, 3H), 7.56 (d, J=3.8 Hz, 2H), 7.36 (d, J=8.5 Hz, 2H), 7.32 (d, J=8.1 Hz, 2H), 7.14 (td, J=4.1, 8.1 Hz, 1H), 2.15 (s, 3H), 1.75-1.67 (m, 2H), 1.61-1.52 (m, 2H).

Example 52: 1-(5-(2-((4-(trifluoromethyl)phenyl)amino)phenyl)-1,3,4-oxadiazol-2-yl)cyclo butanol (Compound 54)

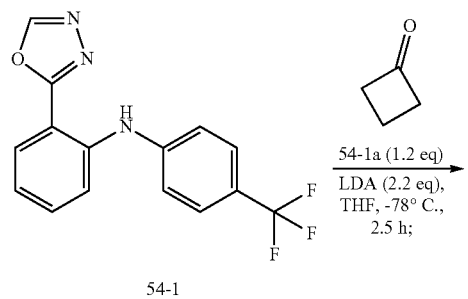

Compound 54

To a solution of 54-1 (100 mg, 0.33 mmol, 1 eq) in THF (2 mL) at −78° C. was added LDA (2 M, 0.4 mL, 2.2 eq) dropwise, and the mixture was stirred at −78° C. for 0.5 h. And then 54-1a (27.6 mg, 0.39 mmol, 29 uL, 1.2 eq) in THF (1 mL) was added dropwise at −78° C. into the above mixture. The resulting mixture was stirred at −78° C. for 2 h. TLC (PE:EA=5:1, UV) showed some starting material still remained and one new spot was formed. LCMS showed starting material was consumed completely and 90% of desired product was formed. The reaction mixture was quenched with saturated $NH_4Cl$ solution (5 mL) at −78° C., and then diluted with water (20 mL) and extracted with EA (20 mL*3). The combined organic layers were washed with brine (20 mL), dried over anhydrous $Na_2SO_4$, filtered and concentrated under reduced pressure to give a residue. The residue was purified by prep-TLC to give Compound 54 (55.89 mg, 0.15 mmol, 45.5% yield). LCMS (ESI): RT=0.881 min, mass calc. for $C_{19}H_{16}F_3N_3O_2$ 375.12, m/z found 376.0[M+1]$^+$. $^1$H NMR (400 MHz, CDCl$_3$) δ 9.51 (s, 1H), 7.94 (dd, J=1.3, 8.0 Hz, 1H), 7.59 (d, J=8.5 Hz, 2H), 7.52 (d, J=8.0 Hz, 1H), 7.44-7.39 (m, 1H), 7.37 (d, J=8.3 Hz, 2H), 7.01-6.96 (m, 1H), 2.97 (s, 1H), 2.87-2.76 (m, 2H), 2.61-2.50 (m, 2H), 2.13-2.04 (m, 1H), 2.03-1.92 (m, 1H).

Example 53: (Compound 55) 3-(5-(2-((4-(trifluoromethyl)phenyl)amino)phenyl)-1,3,4-oxadiazol-2-yl)oxetan-3-ol

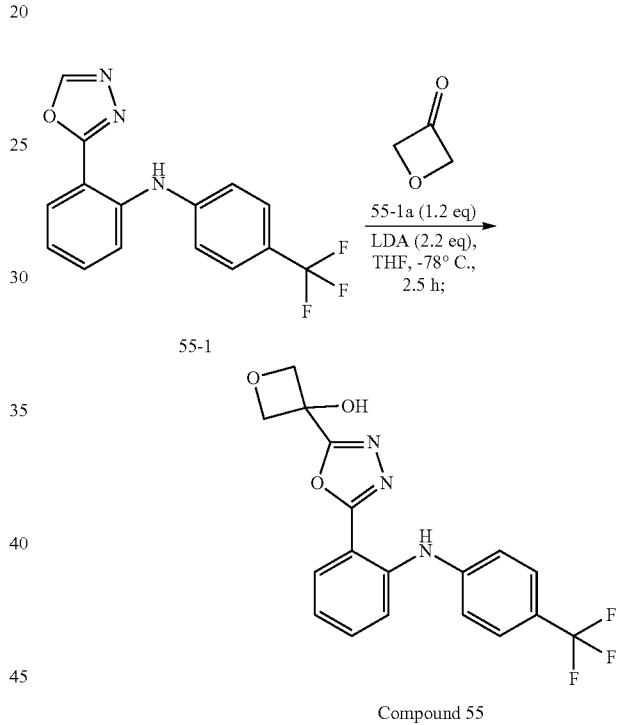

Compound 55

To a solution of 55-1 (100 mg, 0.33 mmol, 1 eq) in THF (2 mL) at −78° C. was added LDA (2 M, 0.4 mL, 2.2 eq) dropwise, and the mixture was stirred at −78° C. for 0.5 h. And then oxetan-3-one (28.3 mg, 0.39 mmol, 29 uL, 1.2 eq) in THF (1 mL) was added dropwise at −78° C. into the above mixture. The resulting mixture was stirred at −78° C. for 2 h. TLC (PE:EA=2:1, UV) showed some starting material still remained and one new spot was formed. LCMS showed 24% of starting material still remained and 76% of desired product was formed. The reaction mixture was quenched with saturated $NH_4Cl$ solution (5 mL) at −78° C., and then diluted with water (20 mL) and extracted with EA (20 mL*3). The combined organic layers were washed with brine (20 mL), dried over anhydrous $Na_2SO_4$, filtered and concentrated under reduced pressure to give a residue. The residue was purified by flash silica gel chromatography to give Compound 55 (69.12 mg, 0.18 mmol, 55.9% yield). LCMS (ESI): RT=0.826 min, mass calc. for $C_{18}H_{14}F_3N_3O_3$ 377.10, m/z found 378.1[M+1]$^+$. $^1$H NMR (400 MHz, CDCl₃) δ 9.38 (s, 1H), 7.97 (dd, J=1.4, 7.9 Hz, 1H), 7.60 (d, J=8.5 Hz, 2H), 7.54-7.50 (m, 1H), 7.47-7.40 (m, 1H), 7.37 (d, J=8.5 Hz, 2H), 7.03-6.97 (m, 1H), 5.14 (d, J=7.8 Hz, 2H), 5.02 (d, J=7.8 Hz, 2H), 3.78 (s, 1H).

Example 54: 3-(5-(2-((4-(trifluoromethyl)phenyl)amino)phenyl)-1,3,4-oxadiazol-2-yl)tetra hydro-furan-3-ol (Compound 56)

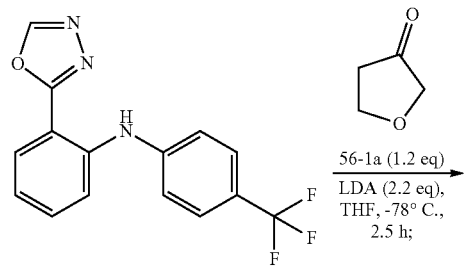

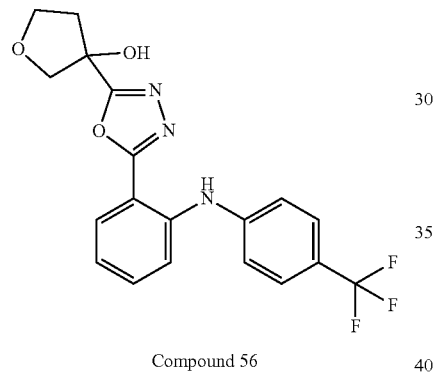

Compound 56

To a solution of 56-1 (100 mg, 0.33 mmol, 1 eq) in THF (2 mL) at −78° C. was added LDA (2 M, 0.4 mL, 2.2 eq) dropwise, and the mixture was stirred at −78° C. for 0.5 h. And then 56-1a (33.8 mg, 0.39 mmol, 35 uL, 1.2 eq) in THF (1 mL) was added dropwise at −78° C. into the above mixture. The resulting mixture was stirred at −78° C. for 2 h. TLC (PE:EA=2:1, UV) showed some starting material still remained and one new spot was formed. LCMS showed 38% of starting material still remained and 62% of desired product was formed. The reaction mixture was quenched with saturated NH₄Cl solution (5 mL) at −78° C., and then diluted with water (20 mL) and extracted with EA (20 mL*3). The combined organic layers were washed with brine (20 mL), dried over anhydrous Na₂SO₄, filtered and concentrated under reduced pressure to give a residue. The residue was purified by flash silica gel chromatography to give Compound 56 (51.73 mg, 0.13 mmol, 38.6% yield). LCMS (ESI): RT=0.828 min, mass calc. for $C_{19}H_{16}F_3N_3O_3$ 391.11, m/z found 391.9[M+1]⁺. ¹H NMR (400 MHz, CDCl₃) δ 9.42 (s, 1H), 7.91 (dd, J=1.3, 8.0 Hz, 1H), 7.59 (d, J=8.5 Hz, 2H), 7.54-7.49 (m, 1H), 7.45-7.39 (m, 1H), 7.36 (d, J=8.5 Hz, 2H), 7.02-6.95 (m, 1H), 4.29-4.12 (m, 4H), 3.17 (s, 1H), 2.71 (td, J=8.6, 13.2 Hz, 1H), 2.51-2.42 (m, 1H).

Example 55: (1-(5-(2-((4-(trifluoromethyl)phenyl)amino)phenyl)-1,3,4-oxadiazol-2-yl)cyclopropyl) carbamate (Compound 57)

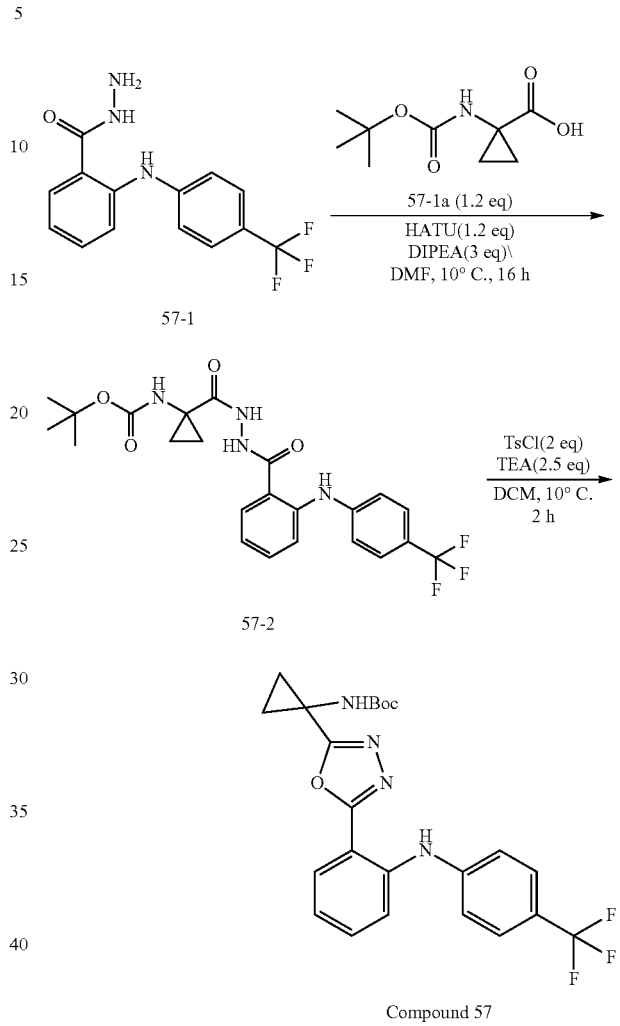

Compound 57

Step 1: Tert-Butyl (1-(2-(2-((4-(trifluoromethyl)phenyl)amino)benzoyl)hydrazinecarbonyl)cyclopropyl)carbamate A mixture of 57-1 (600 mg, 2.03 mmol, 1 eq), 57-1a (490.7 mg, 2.44 mmol, 1.2 eq), DIPEA (787.9 mg, 6.1 mmol, 1.1 mL, 3 eq) and HATU (927.2 mg, 2.44 mmol, 1.2 eq) in DMF (1 mL) was stirred at 10° C. for 16 h. LCMS showed no starting material was remained and 53% of desired product was detected. The mixture was diluted with EA (100 mL), washed with aq. saturated citric acid (15 mL*2), aq. saturated NaHCO₃ (15 mL*2) and brine (15 mL) in turns, dried with Na₂SO₄, filtered and concentrated to give crude compound 57-2 (850 mg, 1.78 mmol, 87.4% yield), which was used directly. ¹H NMR (400 MHz, DMSO-d₆) δ 10.39 (br s, 1H), 10.48-10.28 (m, 1H), 9.84 (s, 1H), 9.43 (s, 1H), 7.96 (s, 1H), 7.67 (d, J=7.4 Hz, 1H), 7.58 (d, J=8.6 Hz, 2H), 7.49-7.40 (m, 3H), 7.28 (br d, J=8.3 Hz, 2H), 7.00 (br t, J=7.1 Hz, 1H), 1.40 (s, 9H), 1.32-1.27 (m, 2H), 1.01-0.95 (m, 2H).

Step 2: Tert-Butyl (1-(5-(2-((4-(trifluoromethyl) phenyl)amino)phenyl)-1,3,4-oxadiazol-2-yl)cyclopropyl)carbamate To a mixture of 57-2 (50 mg, 0.1 mmol, 1 eq) and TEA (26.4 mg, 0.26 mmol, 36 uL, 2.5 eq) in DCM (2 mL) was added TsCl (29.9 mg, 0.16 mmol, 1.5 eq) at 10° C. Then the resulting mixture was stirred at 10° C. for 1 h. LCMS showed 16% of starting material was remained and 48% of desired product was detected. Then another portion of TsCl (9.9 mg, 52 umol, 0.5 eq) was added and the mixture was stirred at 10° C. for another 1 h. LCMS showed 15% of starting material was remained and 56% of desired product was detected. The solution was diluted with EA (100 mL), washed with brine (15 mL), dried with $Na_2SO_4$, filtered and concentrated to give a residue. The residue was purified by prep-HPLC to give Compound 57 (25 mg, 53 umol, 51.3% yield). LCMS (ESI): RT=0.942 min, mass calc. for $C_{23}H_{23}F_3N_4O_3$ 460.17, m/z found 482.9 [M+23]$^+$. $^1$H NMR (400 MHz, DMSO-$d_6$) δ 9.16 (s, 1H), 8.05 (s, 1H), 7.85 (br d, J=7.9 Hz, 1H), 7.63 (d, J=8.6 Hz, 2H), 7.58-7.50 (m, 2H), 7.34 (d, J=8.6 Hz, 2H), 7.14 (t, J=7.3 Hz, 1H), 1.53-1.48 (m, 2H), 1.40 (s, 9H), 1.34-1.30 (m, 2H).

Example 56: 2-(5-(1-aminocyclopropyl)-1,3,4-oxadiazol-2-yl)-N-(4-(trifluoromethyl)phenyl) aniline (Compound 58)

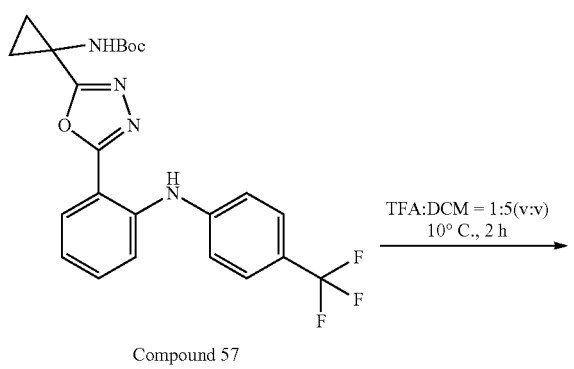

Compound 57

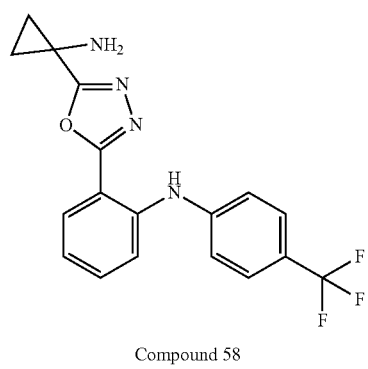

Compound 58

To a solution of Compound 57 (50 mg, 0.11 mmol, 1 eq) in DCM (1 mL) was added TFA (309.5 mg, 2.71 mmol, 0.2 mL, 25 eq) at 10° C. Then the mixture was stirred at 10° C. for 2 h. LCMS showed no starting material was remained and 96% of desired product was formed. The mixture was concentrated at 10° C. to give a residue. The residue was purified by prep-HPLC to give Compound 58 (3.51 mg, 9 umol, 8.9% yield). LCMS (ESI): RT=0.729 min, mass calc. for $C_{18}H_{15}F_3N_4O$ 360.12, m/z found 361.0 [M+1]$^+$. $^1$H NMR (400 MHz, DMSO-$d_6$) δ 9.32-9.12 (m, 1H), 7.93 (d, J=7.5 Hz, 1H), 7.62 (br d, J=8.4 Hz, 2H), 7.57-7.47 (m, 2H), 7.32 (br d, J=8.4 Hz, 2H), 7.19-7.07 (m, 1H), 3.02-2.61 (m, 1H), 1.29-1.20 (m, 2H), 1.14-1.05 (m, 2H).

Example 57: N-(1-(5-(2-((4-(trifluoromethyl)phenyl)amino)phenyl)-1,3,4-oxadiazol-2-yl)cyclopropyl)acetamide (Compound 59)

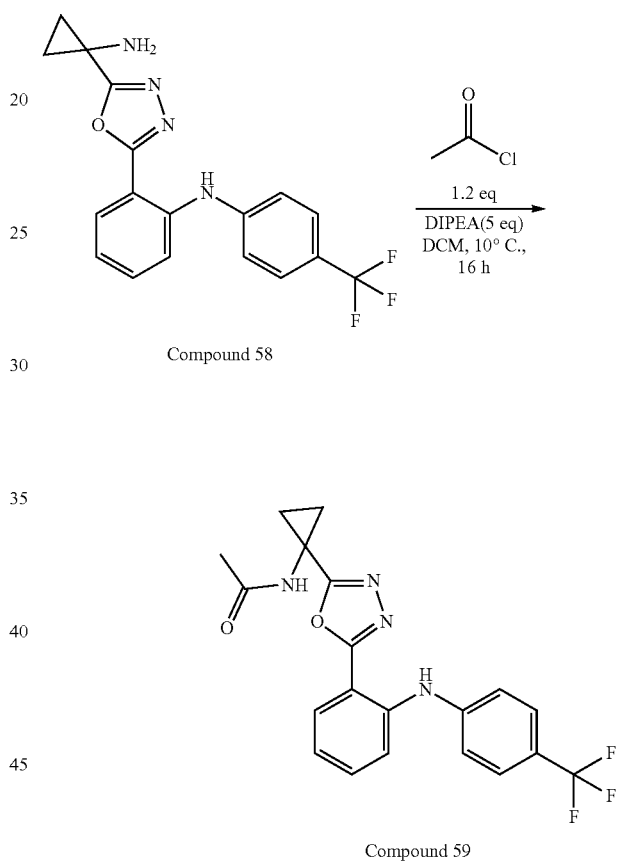

To a mixture of Compound 58 (100 mg, 0.21 mmol, 1 eq, TFA) and DIPEA (136.2 mg, 1.05 mmol, 0.2 mL, 5 eq) in DCM (3 mL) was added a solution of acetyl chloride (19.9 mg, 0.25 mmol, 18 uL, 1.2 eq) in DCM (1 mL) at 10° C. Then the resulting mixture was stirred at 10° C. for 16 h. LCMS showed no starting material was remained and 42% of desired product was detected. The mixture was quenched methanol (0.01 mL) and concentrated to give a residue. The residue was purified by prep-HPLC to give Compound 59 (9.59 mg, 23 umol, 10.8% yield). LCMS (ESI): RT=0.808 min, mass calc. for $C_{20}H_{17}F_3N_4O_2$ 402.13, m/z found 425.0 [M+23]$^+$. $^1$H NMR (400 MHz, CDCl$_3$) δ 9.37 (s, 1H), 7.69 (dd, J=1.5, 7.9 Hz, 1H), 7.49 (d, J=8.5 Hz, 2H), 7.42 (d, J=8.5 Hz, 1H), 7.33-7.24 (m, 3H), 6.87 (t, J=7.6 Hz, 1H), 6.20 (s, 1H), 3.85 (s, 1H), 2.11 (s, 1H), 2.03 (s, 3H), 1.71-1.65 (m, 2H), 1.46-1.41 (m, 2H).

Example 58: 2,2-difluoro-1-(5-(2-((4-(trifluoromethyl)phenyl)amino)phenyl)-1,3,4-oxadiazol-2-yl)ethanol (Compound 60)

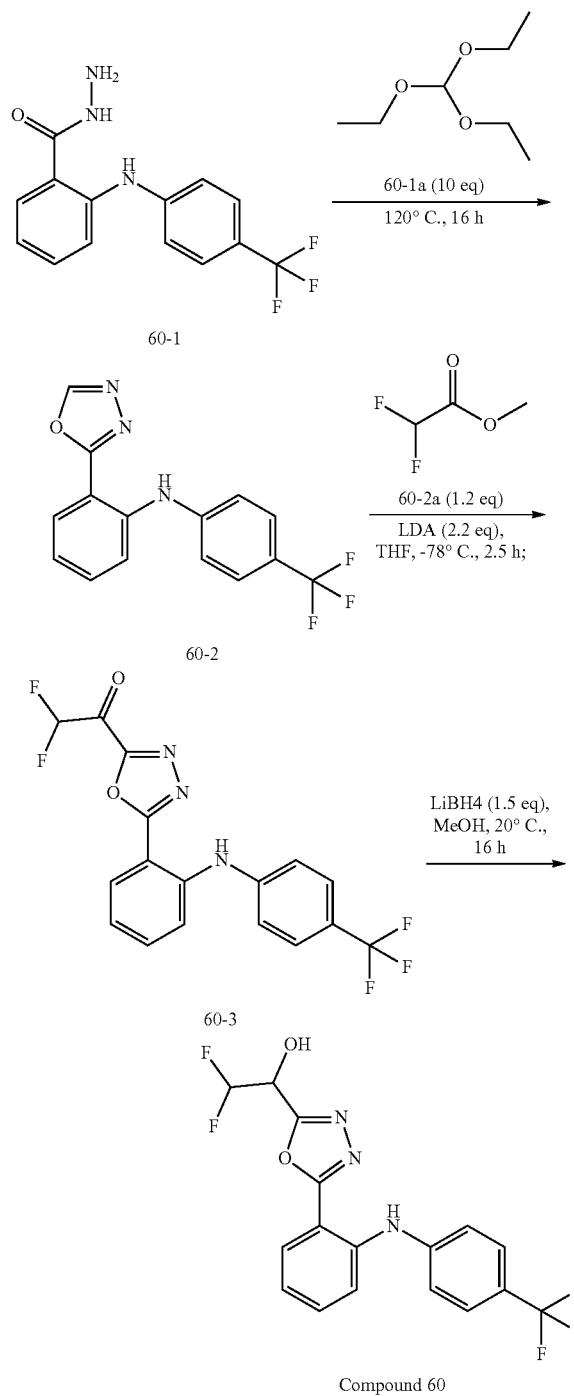

Step 1: 2-(1,3,4-oxadiazol-2-yl)-N-(4-(trifluoromethyl)phenyl)aniline

The mixture of compound 60-1 (1.50 g, 5.08 mmol, 1 eq) and compound 60-1a (7.53 g, 50.8 mmol, 8.5 mL, 10 eq) (neat reaction) was stirred at 120° C. under $N_2$ for 16 h. TLC (PE:EA=1:1, UV) showed starting material was consumed completely, and one new spot was formed. The mixture was concentrated to give a residue. The residue was purified by flash silica gel chromatography to give compound 60-2 (1.40 g, 4.49 mmol, 88.5% yield). LCMS (ESI): RT=0.989 min, mass calc. for $C_{15}H_{10}F_3N_3O$ 305.08, m/z found 306.1 $[M+1]^+$.

Step 2: 2,2-difluoro-1-(5-(2-((4-(trifluoromethyl)phenyl)amino)phenyl)-1,3,4-oxadiazol-2-yl)ethanone To a solution of compound 60-2 (100 mg, 0.33 mmol, 1 eq) in THF (2 mL) at −78° C. was added LDA (2 M, 0.4 mL, 2.2 eq) dropwise, and the mixture was stirred at −78° C. for 0.5 h. And then compound 60-2a (43.3 mg, 0.39 mmol, 35 uL, 1.2 eq) in THF (1 mL) was added dropwise at −78° C. The resulting mixture was stirred at −78° C. for 2 h. TLC (PE:EA=2:1, UV) showed some starting material still remained and one new spot was formed. LCMS showed 40% of starting material still remained and 59% of one new peak was formed. The reaction mixture was quenched with saturated $NH_4Cl$ solution (5 mL) at −78° C., and then diluted with water (20 mL) and extracted with EA (20 mL*3). The combined organic layers were washed with brine (20 mL), dried over anhydrous $Na_2SO_4$, filtered and concentrated under reduced pressure to give a residue. The residue was purified by prep-TLC to give compound 60-3 (40.0 mg, 90.1 umol, 27.5% yield). LCMS (ESI): RT=0.815 min, mass calc. for $C_{17}H_{10}F_5N_3O_2$ 383.07, m/z found 401.9$[M+H_2O+1]^+$. $^1H$ NMR (400 MHz, $CDCl_3$) δ 9.45 (s, 1H), 8.04 (d, J=8.0 Hz, 1H), 7.69-7.57 (m, 2H), 7.54-7.46 (m, 2H), 7.40 (d, J=8.3 Hz, 2H), 7.02 (ddd, J=2.4, 5.8, 8.2 Hz, 1H), 6.86-6.59 (m, 1H).

Step 3: 2,2-difluoro-1-(5-(2-((4-(trifluoromethyl)phenyl)amino)phenyl)-1,3,4-oxadiazol-2-yl)ethanol To a solution of compound 60-3 (20 mg, 52.2 umol, 1 eq) in MeOH (1 mL) at 20° C. was added $LiBH_4$ (1.7 mg, 78.3 umol, 1.5 eq), and the mixture was stirred at 20° C. for 16 h. TLC (PE:EA=2:1, UV) showed starting material was consumed completely and one new spot was formed. LCMS showed starting material was consumed completely and 97% of desired product was formed. The reaction mixture was quenched with water (0.5 mL) at 20° C., and then diluted with water (20 mL) and extracted with EA (20 mL*3). The combined organic layers were washed with brine (20 mL), dried over anhydrous $Na_2SO_4$, filtered and concentrated under reduced pressure to give a residue. The residue was purified by prep-TLC to give Compound 60 (14.63 mg, 38.0 umol, 72.8% yield). LCMS (ESI): RT=0.865 min, mass calc. for $C_{17}H_{12}F_5N_3O_2$ 385.05, m/z found 385.7$[M+1]^+$. $^1H$ NMR (400 MHz, $CDCl_3$) δ 9.39 (s, 1H), 7.93 (d, J=8.0 Hz, 1H), 7.60 (d, J=8.5 Hz, 2H), 7.54-7.49 (m, 1H), 7.43 (t, J=8.4 Hz, 1H), 7.38 (d, J=8.5 Hz, 2H), 7.00 (t, J=7.5 Hz, 1H), 6.34-6.07 (m, 1H), 5.31-5.24 (m, 1H), 3.13 (d, J=7.3 Hz, 1H).

Example 59: 4-bromo-2-(5-(trifluoromethyl)-1,3,4-oxadiazol-2-yl)-N-(4-(trifluoromethyl) phenyl)aniline (Compound 61)

Example 60: 1-(1-(5-(2-((4-(trifluoromethyl)phenyl)amino)phenyl)-1,3,4-oxadiazol-2-yl)cyclopropyl)urea (Compound 62)

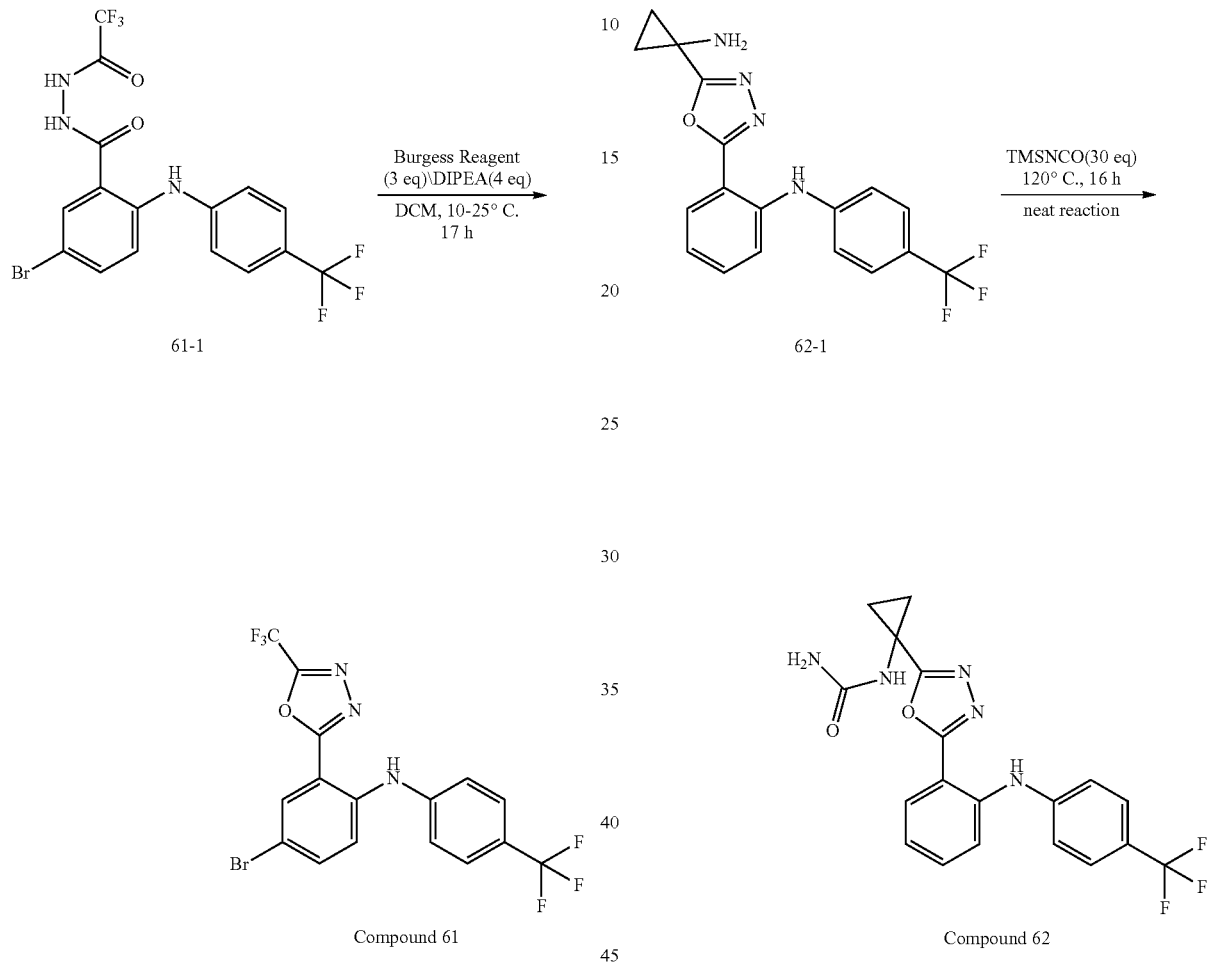

To a mixture of compound 61-1 (10 mg, 21 umol, 1 eq) and DIPEA (11 mg, 85 umol, 15 uL, 4 eq) in DCM (1 mL) was added Burgess reagent (15.2 mg, 64 umol, 3 eq) in one portion at 10° C. The mixture was stirred at 25° C. for 1 h. LCMS showed 65% of compound 61-1 was remained and 26% of desired product was detected. Then the mixture was continuously stirred at 25° C. for 16 h. TLC (Petroleum ether:Ethyl acetate=2:1 UV) showed no compound 61-1 was remained and one main new spot was detected. The mixture was purified by prep-TLC to give Compound 61 (5.84 mg, 13 umol, 58.9% yield). MS (ESI): mass calc. for $C_{16}H_8BrF_6N_3O$ 450.98, m/z found 453.9721 [M+1]$^+$. $^1$H NMR (400 MHz, CDCl$_3$) δ 9.28 (s, 1H), 8.04 (d, J=2.3 Hz, 1H), 7.64 (d, J=8.4 Hz, 2H), 7.53 (dd, J=2.3, 9.1 Hz, 1H), 7.37 (d, J=9.0 Hz, 3H).

A mixture of 62-1 (100 mg, 0.21 mmol, 1 eq, TFA) and isocyanato(trimethyl)silane (728.6 mg, 6.32 mmol, 0.8 mL, 30 eq) was stirred at 120° C. for 16 h. LCMS showed no starting material was remained and 67% of desired product was detected. The mixture was quenched with diluted with DCM (50 mL), washed with brine (15 mL), dried by anhydrous Na$_2$SO$_4$, filtered and concentrated at 10° C. to give a residue. The residue was purified by prep-HPLC to give Compound 62 (11.85 mg, 29.13 umol, 13.82% yield). LCMS (ESI): RT=0.882 min, mass calc. for $C_{19}H_{16}F_3N_5O_2$ 403.13, m/z found 404.1[M+1]$^+$. $^1$H NMR (400 MHz, DMSO-d$_6$) δ 9.18 (s, 1H), 7.85 (d, J=7.1 Hz, 1H), 7.63 (d, J=8.5 Hz, 2H), 7.58-7.48 (m, 2H), 7.34 (d, J=8.4 Hz, 2H), 7.19-7.06 (m, 2H), 5.77 (s, 2H), 1.58-1.43 (m, 2H), 1.37-1.22 (m, 2H).

Example 61: 2-(5-(1-fluorocyclopropyl)-1,3,4-oxadiazol-2-yl)-N-(4-(trifluoromethyl)phenyl) aniline (Compound 63)

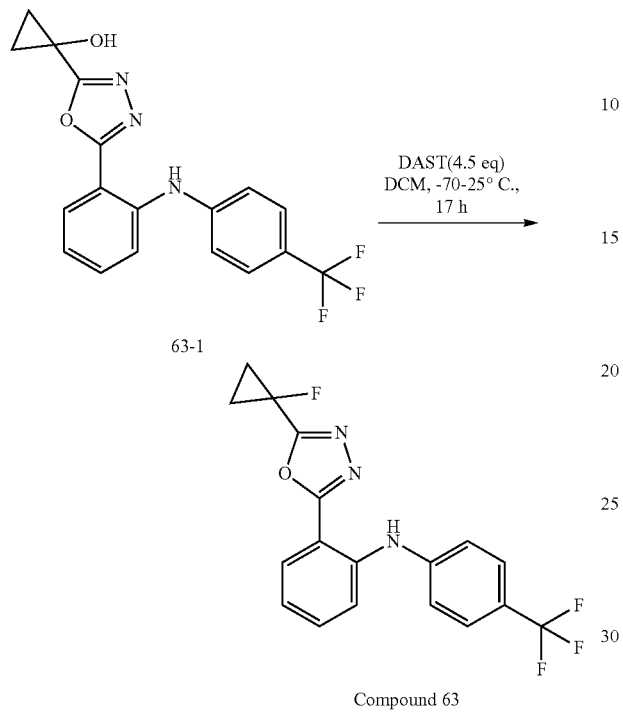

To a mixture of 63-1 (5 mg, 14 umol, 1 eq) in DCM (1 mL) was added DAST (3.3 mg, 21 umol, 3 uL, 1.5 eq) in one portion at −70° C. The mixture was stirred at 25° C. for 1 h. LCMS showed 78% of starting material was remained and no desired product was detected. Then another batch of DAST (6.7 mg, 41 umol, 5 uL, 3 eq) was added and the mixture was continuously stirred at 25° C. for 16 h. LCMS showed the starting material was consumed completely and 52% of desired product was formed. TLC (Petroleum ether: Ethyl acetate=2:1 UV) the starting material was consumed completely and two main new spots were formed. The mixture was purified directly by prep-TLC to give Compound 63 (4.2 mg, 11 umol, 80.6% yield). LCMS (ESI): RT=1.064 min, mass calc. for $C_{18}H_{13}F_4N_3O$ 363.10, m/z found 364.1 [M+1]$^+$. $^1$H NMR (400 MHz, DMSO-d$_6$+CD$_3$OD) δ 7.92 (d, J=7.5 Hz, 1H), 7.60 (d, J=8.5 Hz, 2H), 7.57-7.49 (m, 2H), 7.32 (d, J=8.5 Hz, 2H), 7.13 (t, J=7.3 Hz, 1H), 1.78-1.63 (m, 2H), 1.51-1.41 (m, 2H).

Example 62: 2-[5-(1-methylsulfonylcyclopropyl)-1,3,4-oxadiazol-2-yl]-N-[4-(trifluoromethyl) phenyl] aniline (Compound 66)

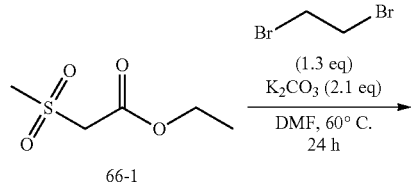

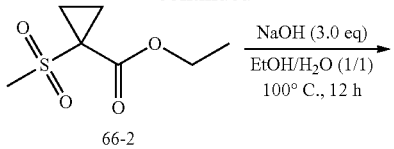

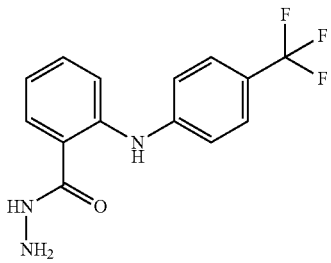

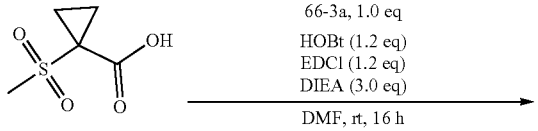

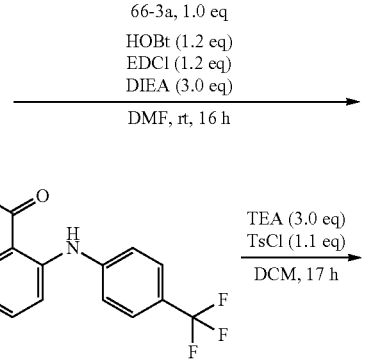

Compound 66

Step 1: ethyl 1-methylsulfonylcyclopropanecarboxylate

To a solution of compound 66-1 (1 g, 6 mmol, 1 eq) in DMF (10 mL) were added 1,2-dibromoethane (1.5 g, 8.4 mmol, 0.6 mL, 1.4 eq) and K2CO3 (1.6 g, 12 mmol, 2 eq). The reaction was heated at 60° C. for 24 hr. TLC (EA:PE=1:5, KMnO4) showed that starting material was consumed completely. The reaction was diluted with EA (50 mL) and washed with brine (2*20 mL). The organic layer was dried over Na$_2$SO$_4$ and concentrated. Compound 66-2 (0.8 g, crude) was used for next step directly. $^1$H NMR (400 MHz, CDCl$_3$) δ 4.35-4.15 (m, 2H), 3.22 (s, 3H), 1.85-1.70 (m, 2H), 1.70-1.60 (m, 2H), 1.35-1.20 (m, 3H).

Step 2: 1-methylsulfonylcyclopropanecarboxylic Acid

To a solution of compound 66-2 (0.8 g, 3.1 mmol, 1 eq) in EtOH (10 mL) and H$_2$O (10 mL) was added NaOH (374.5 mg, 9.3 mmol, 3 eq). The reaction was heated at 100° C. for 12 hr. The reaction was concentrated. The residue was adjusted pH to 5 with 1 N. aq. HCl and extracted with EA (3*15 mL). The organic layer was dried over Na$_2$SO$_4$ and concentrated. Compound 66-3 (0.3 g, 1.8 mmol, 58% yield) was used for next step directly. $^1$H NMR (400 MHz, CDCl$_3$) δ 9.13 (br, 1H), 3.23 (s, 3H), 1.95-1.80 (m, 2H), 1.80-1.70 (m, 2H).

Step 3: N'-(1-methylsulfonylcyclopropanecarbonyl)-2-[4-(trifluoromethyl)anilino]benzo Hydrazide To a mixture of compound 66-3 (0.1 g, 0.6 mmol, 1 eq), HOBt (98 mg, 0.7 mmol, 1.2 eq) and EDCI (140 mg, 0.7 mmol, 1.2 eq) in DMF (4 mL) was added compound 66-3a (179 mg, 0.6 mmol, 1 eq) followed by DIEA (236 mg, 1.8 mmol, 0.3 mL, 3 eq). The reaction was stirred at 20° C. for 16 hr. LCMS showed that 28% of desired product was detected. The reaction was concentrated. The crude product was purified by prep-HPLC to give compound 66-4 (30 mg, 67 umol, 11% yield).

Step 4: 2-[5-(1-methylsulfonylcyclopropyl)-1,3,4-oxadiazol-2-yl]-N-[4-(trifluoromethyl) phenyl]aniline To a solution of compound 66-4 (30 mg, 67 umol, 1 eq) and TsCl (14 mg, 74 umol, 1.1 eq) in DCM (1 mL) was added Et$_3$N (20.6 mg, 0.2 mmol, 28 uL, 3 eq). The reaction was stirred at 20° C. for 16 hr. LCMS showed that 27% of starting material was remained and 29% of desired product was detected. Additional of TsCl (14 mg) was added. The reaction was stirred at 20° C. for 1 hr. LCMS showed that 29% of desired product was detected. The reaction was diluted with DCM (15 mL) and washed with water (2*5 mL). The organic layer was dried over Na$_2$SO$_4$ and concentrated. The residue was purified by prep-HPLC to give Compound 66 (2.01 mg, 4.7 umol, 6.9% yield). LCMS (ESI): RT=0.862 min, mass calc. for: C$_{19}$H$_{16}$F$_3$N$_3$O$_3$S 423.09, m/z found 423.9 [M+H]$^+$; $^1$H NMR (400 MHz, DMSO-d$_6$) δ 9.13 (s, 1H), 7.97 (d, J=8.03 Hz, 1H), 7.63 (d, J=8.53 Hz, 2H), 7.58 (d, J=3.01 Hz, 2H), 7.33 (d, J=8.53 Hz, 2H), 7.18 (ddd, J=7.91, 4.89, 3.26 Hz, 1H), 3.32 (s, 3H), 1.83-1.90 (m, 2H), 1.76-1.82 (m, 2H).

Example 63: 2-(5-(1-methoxycyclopropyl)-1,3,4-oxadiazol-2-yl)-N-(4-(trifluoromethyl)phenyl) aniline (Compound 67)

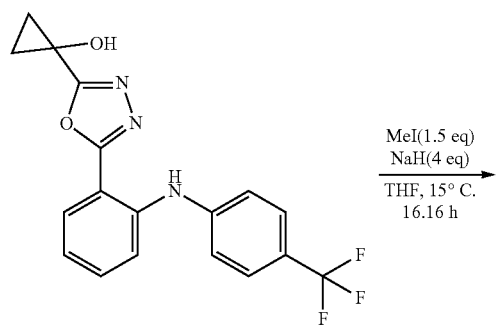

67-1

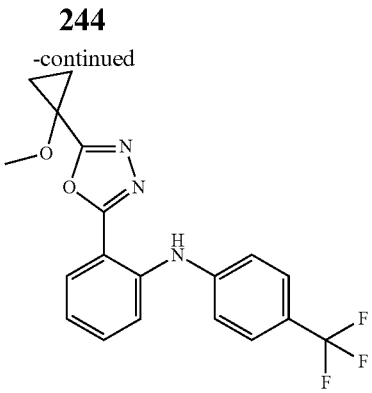

Compound 67

To a mixture of 67-1 (17 mg, 47 umol, 1 eq) in THF (2 mL) was added NaH (7.5 mg, 0.19 mmol, 60% purity, 4 eq) in one portion at 15° C. After stirring for 10 min, a solution of MeI (10 mg, 70.6 umol, 4 uL, 1.5 eq) in THF (1 mL) was added and then the mixture was stirred at 15° C. for 16 h. LCMS showed no starting material was remained and 85% of desired product was detected. The mixture was diluted with EA (50 mL), washed with brine (10 mL*2), dried by anhydrous Na$_2$SO$_4$, filtered and concentrated to give a residue. The residue was purified by prep-HPLC to give Compound 67 (2.48 mg, 6.6 umol, 14.0% yield). LCMS (ESI): RT=1.050 min, mass calc. for C$_{19}$H$_{16}$F$_3$N$_3$O$_2$ 375.34, m/z found 376.1 [M+1]$^+$; $^1$H NMR (400 MHz, DMSO-d$_6$) δ 9.07 (br s, 1H), 7.92 (br d, J=8.0 Hz, 1H), 7.67-7.46 (m, 4H), 7.29 (br d, J=8.3 Hz, 2H), 7.16 (br s, 1H), 3.43 (s, 3H), 1.44-1.25 (m, 4H).

Example 64: 2-(5-(2-methylbut-3-yn-2-yl)-1,3,4-oxadiazol-2-yl)-N-(4-(trifluoromethyl)phenyl)aniline (Compound 68)

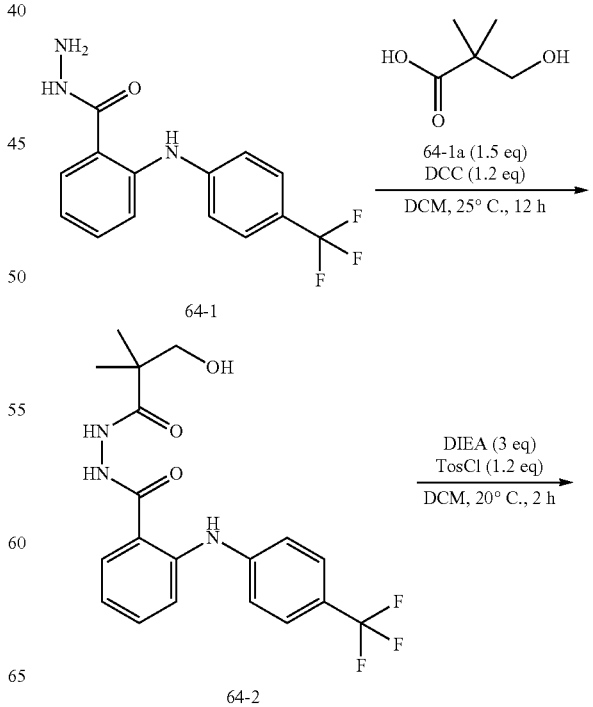

-continued

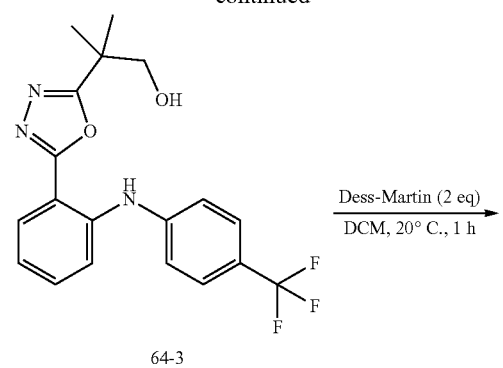

64-3

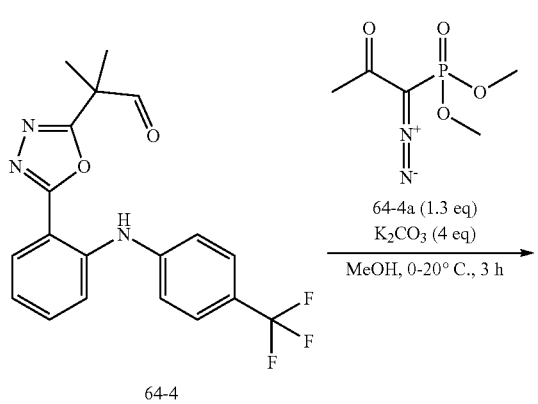

64-4

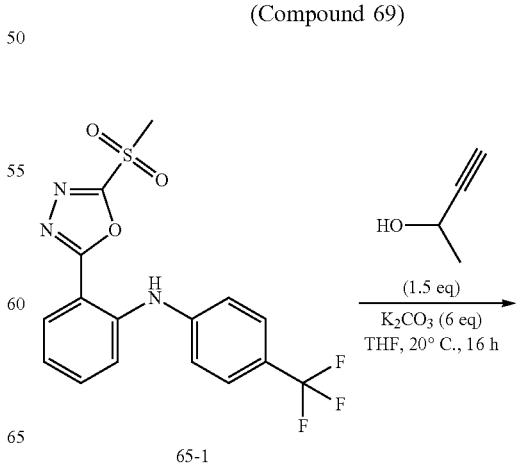

Compound 68

Step 1: N'-(3-hydroxy-2,2-dimethyl-propanoyl)-2-[4-(trifluoromethyl)anilino]benzohydrazide To a solution of 64-1 (50 mg, 0.17 mmol, 1 eq) and 64-1a (30.0 mg, 0.25 mmol, 1.5 eq) in DCM (1 mL) was added DCC (41.9 mg, 0.20 mmol, 41 uL, 1.2 eq). The mixture was stirred at 25° C. for 12 h. The mixture was diluted with H$_2$O (10 mL), extracted with EA (20 mL*3). The combined organic layers were washed with brine (15 mL), dried over Na$_2$SO$_4$, filtered and concentrated under reduced pressure to give a residue. The residue was purified by flash silica gel chromatography to give 64-2 (60 mg, 0.15 mmol, 89.6% yield).

Step 2: 2-methyl-2-[5-[2-[4-(trifluoromethyl)anilino]phenyl]-1,3,4-oxadiazol-2-yl]propan-1-ol To a solution of 64-2 (60 mg, 0.15 mmol, 1 eq) in DCM (1 mL) were added TosCl (34.7 mg, 0.18 mmol, 1.2 eq) and DIEA (58.8 mg, 0.46 mmol, 79 uL, 3 eq). The mixture was stirred at 20° C. for 2 h. The mixture was diluted with H$_2$O (10 mL), extracted with EA (20 mL*3). The combined organic layers were washed with brine (15 mL), dried over Na$_2$SO$_4$, filtered and concentrated under reduced pressure to give a residue. The residue was purified by flash silica gel chromatography to give 64-3 (30 mg, 79.5 umol, 52.4% yield).

Step 3: 2-methyl-2-[5-[2-[4-(trifluoromethyl)anilino]phenyl]-1,3,4-oxadiazol-2-yl]propanal To a mixture of 64-3 (20 mg, 53.0 umol, 1 eq) in DCM (0.5 mL) was added Dess-Martin (45.0 mg, 0.11 mmol, 33 uL, 2 eq). The mixture was stirred at 20° C. for 1 h. The mixture was diluted with NaS$_2$O$_3$ (8 mL), extracted with DCM (15 mL*2). The combined organic layers were washed with NaHCO$_3$ (10 mL), dried over Na$_2$SO$_4$, filtered and concentrated under reduced pressure to give a residue. The residue was purified by prep-TLC to give 64-4 (15 mg, 34.8 umol, 65.6% yield).

Step 4: 2-(5-(2-methylbut-3-yn-2-yl)-1,3,4-oxadiazol-2-yl)-N-(4-(trifluoromethyl)phenyl)aniline To a mixture of 64-4 (10 mg, 26.6 umol, 1 eq) and 64-4a (6.7 mg, 34.6 umol, 1.3 eq) in MeOH (0.5 mL) was added K$_2$CO$_3$ (14.7 mg, 0.11 mmol, 4 eq) at 0° C. The mixture was stirred at 0° C. for 2 h. Then the mixture was stirred at 20° C. for 1 h. The mixture was concentrated. The residue was diluted with H$_2$O (5 mL), extracted with EA (10 mL*3). The combined organic layers were washed with brine (8 mL), dried over Na$_2$SO$_4$, filtered and concentrated under reduced pressure to give a residue. The residue was checked by HPLC. The residue was purified by prep-HPLC to give Compound 68 (3.1 mg, 8.2 umol, 30.8% yield). LCMS (ESI): RT=1.072 min, mass calc. for C$_{20}$H$_{16}$F$_3$N$_3$O 371.12, m/z found 372.0 [M+H]$^+$; $^1$H NMR (400 MHz, CDCl$_3$) δ 9.54 (s, 1H), 7.94 (dd, J=1.3, 7.9 Hz, 1H), 7.58 (d, J=8.5 Hz, 2H), 7.53 (d, J=8.5 Hz, 1H), 7.45-7.32 (m, 3H), 6.99 (t, J=7.6 Hz, 1H), 2.40 (s, 1H), 1.82 (s, 6H).

Example 65: 2-(5-(but-3-yn-2-yloxy)-1,3,4-oxadiazol-2-yl)-N-(4-(trifluoromethyl)phenyl)aniline (Compound 69)

65-1

-continued

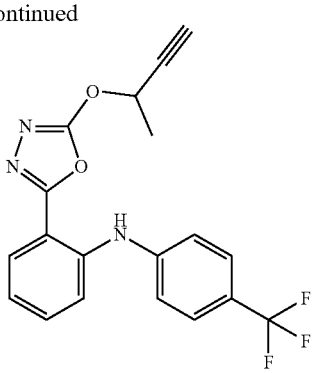

Compound 69

To a solution of but-3-yn-2-ol (8.2 mg, 0.12 mmol, 9 uL, 1.5 eq) in THF (1 mL) was added K$_2$CO$_3$ (64.9 mg, 0.47 mmol, 6 eq) and compound 65-1 (30 mg, 78 umol, 1 eq) at 20° C. The mixture was stirred at 20° C. for 16 hr. The reaction mixture was concentrated to give a residue which was purified by prep-HPLC to give Compound 69 (10 mg, 25 umol, 32.2% yield). LCMS (ESI): RT=1.058 min, mass calc. for C$_{19}$H$_{14}$F$_3$N$_3$O$_2$ 373.3, m/z found 374.0 [M+H]$^+$; $^1$H NMR (400 MHz, CDCl$_3$) δ 9.36 (s, 1H), 7.77 (dd, J=1.4, 8.0 Hz, 1H), 7.57 (d, J=8.5 Hz, 2H), 7.50 (d, J=8.4 Hz, 1H), 7.40-7.36 (m, 1H), 7.34 (d, J=8.5 Hz, 2H), 6.96 (t, J=7.5 Hz, 1H), 5.65-5.59 (m, 1H), 2.68 (d, J=2.1 Hz, 1H), 1.81 (d, J=6.6 Hz, 3H).

Example 66: 2-(5-(but-2-yn-1-yloxy)-1,3,4-oxadiazol-2-yl)-N-(4-(trifluoromethyl)phenyl)aniline (Compound 70)

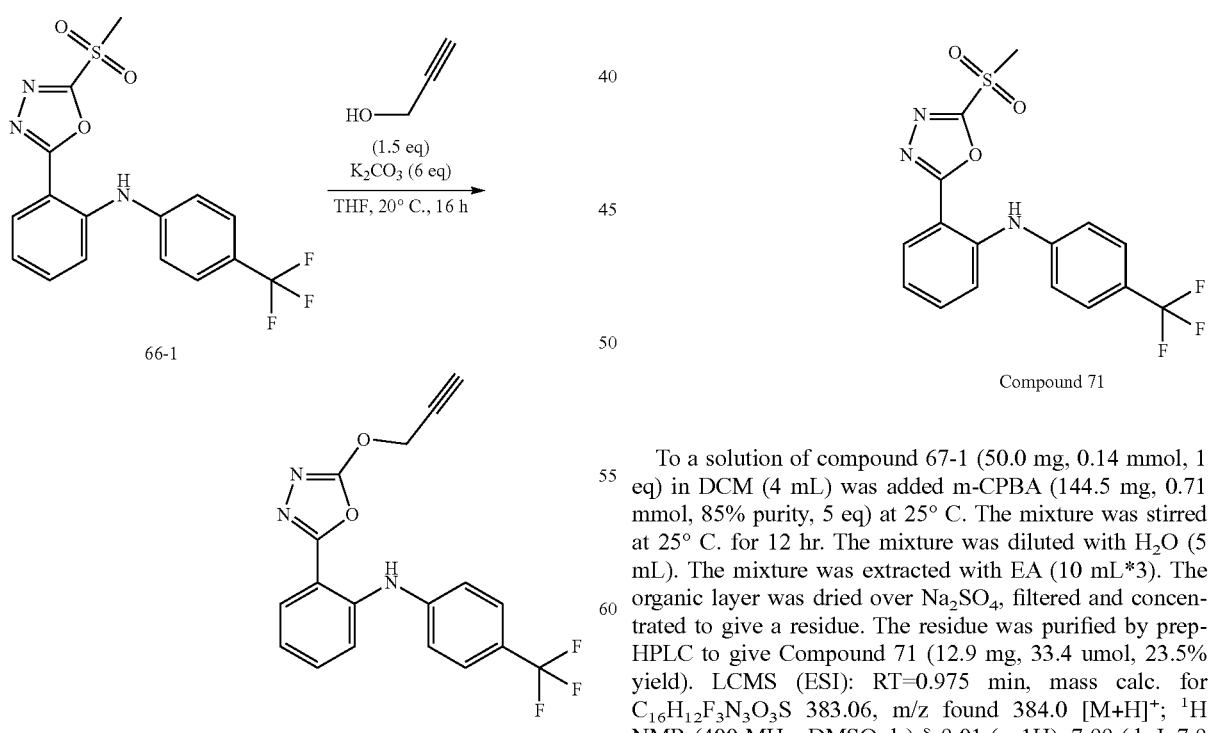

To a solution of but-2-yn-1-ol (13.7 mg, 0.20 mmol, 15 uL, 1.5 eq) in THF (1 mL) was added K$_2$CO$_3$ (108.2 mg, 0.78 mmol, 6 eq) and compound 66-1 (50 mg, 0.13 mmol, 1 eq) at 20° C. The mixture was stirred at 20° C. for 16 hr. The reaction mixture was concentrated to give a residue which was purified by prep-HPLC to give Compound 70 (10 mg, 26 umol, 19.7% yield). LCMS (ESI): RT=1.082 min, mass calc. for C$_{19}$H$_{14}$F$_3$N$_3$O$_2$ 373.3, m/z found 374.0 [M+H]$^+$; $^1$H NMR (400 MHz, CDCl$_3$) δ 8.54 (s, 1H), 7.80 (dd, J=1.3, 7.9 Hz, 1H), 7.59 (d, J=8.5 Hz, 2H), 7.50-7.47 (m, 1H), 7.40 (dt, J=1.4, 7.8 Hz, 1H), 7.30 (s, 2H), 7.02-6.97 (m, 1H), 5.43 (q, J=3.3 Hz, 2H), 2.27 (t, J=3.3 Hz, 3H).

Example 67: 2-(5-(methylsulfonyl)-1,3,4-oxadiazol-2-yl)-N-(4-(trifluoromethyl)phenyl)aniline (Compound 71)

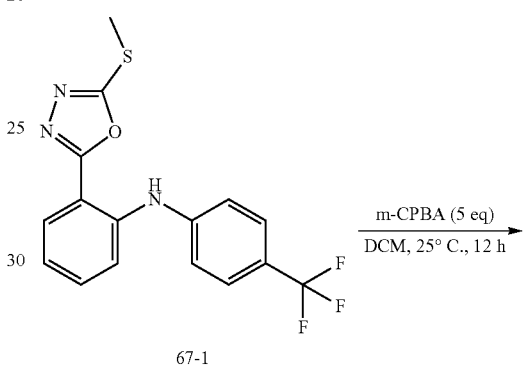

To a solution of compound 67-1 (50.0 mg, 0.14 mmol, 1 eq) in DCM (4 mL) was added m-CPBA (144.5 mg, 0.71 mmol, 85% purity, 5 eq) at 25° C. The mixture was stirred at 25° C. for 12 hr. The mixture was diluted with H$_2$O (5 mL). The mixture was extracted with EA (10 mL*3). The organic layer was dried over Na$_2$SO$_4$, filtered and concentrated to give a residue. The residue was purified by prep-HPLC to give Compound 71 (12.9 mg, 33.4 umol, 23.5% yield). LCMS (ESI): RT=0.975 min, mass calc. for C$_{16}$H$_{12}$F$_3$N$_3$O$_3$S 383.06, m/z found 384.0 [M+H]$^+$; $^1$H NMR (400 MHz, DMSO-d$_6$) δ 9.01 (s, 1H), 7.99 (d, J=7.9 Hz, 1H), 7.67-7.59 (m, 4H), 7.34 (br d, J=8.4 Hz, 2H), 7.21 (br t, J=7.1 Hz, 1H), 3.68 (s, 3H).

Example 68: 2-(5-(methylthio)-1,3,4-oxadiazol-2-yl)-N-(4-(trifluoromethyl)phenyl)aniline (Compound 72)

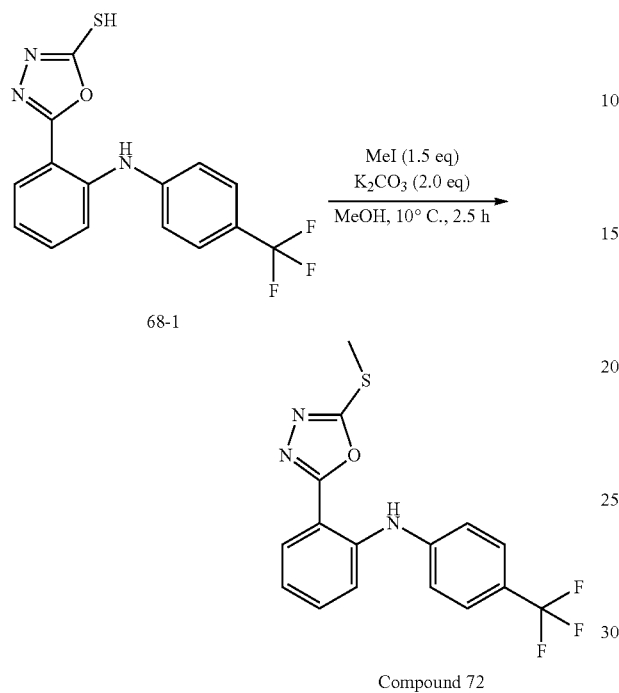

68-1

Compound 72

To a solution of compound 68-1 (50.0 mg, 0.15 mmol, 1 eq) in MeOH (1 mL) was added K$_2$CO$_3$ (41.0 mg, 0.30 mmol, 2 eq). The mixture was stirred at 10° C. for 0.5 hr. MeI (31.6 mg, 0.22 mmol, 14 uL, 1.5 eq) was added. The mixture was stirred at 10° C. for 2 hr. The mixture was diluted with H$_2$O (5 mL). The mixture was extracted with EA (5 mL*3). The organic layer was dried over Na$_2$SO$_4$, filtered and concentrated to give a residue. The residue was purified by prep-HPLC to give Compound 72 (33.1 mg, 93.4 umol, 63.0% yield). LCMS (ESI): RT=1.065 min, mass calc. for C$_{16}$H$_{12}$F$_3$N$_3$OS 351.07, m/z found 352.0 [M+H]$^+$; $^1$H NMR (400 MHz, CDCl$_3$) δ 9.40 (s, 1H), 7.85 (dd, J=1.4, 7.9 Hz, 1H), 7.58 (d, J=8.5 Hz, 2H), 7.51 (d, J=8.1 Hz, 1H), 7.42-7.34 (m, 3H), 7.00-6.94 (m, 1H), 2.80 (s, 3H)

Example 69: 2-(5-methoxy-1,3,4-oxadiazol-2-yl)-N-(4-(trifluoromethyl)phenyl)aniline (Compound 73)

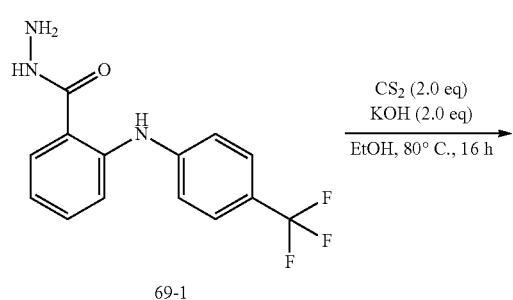

69-1

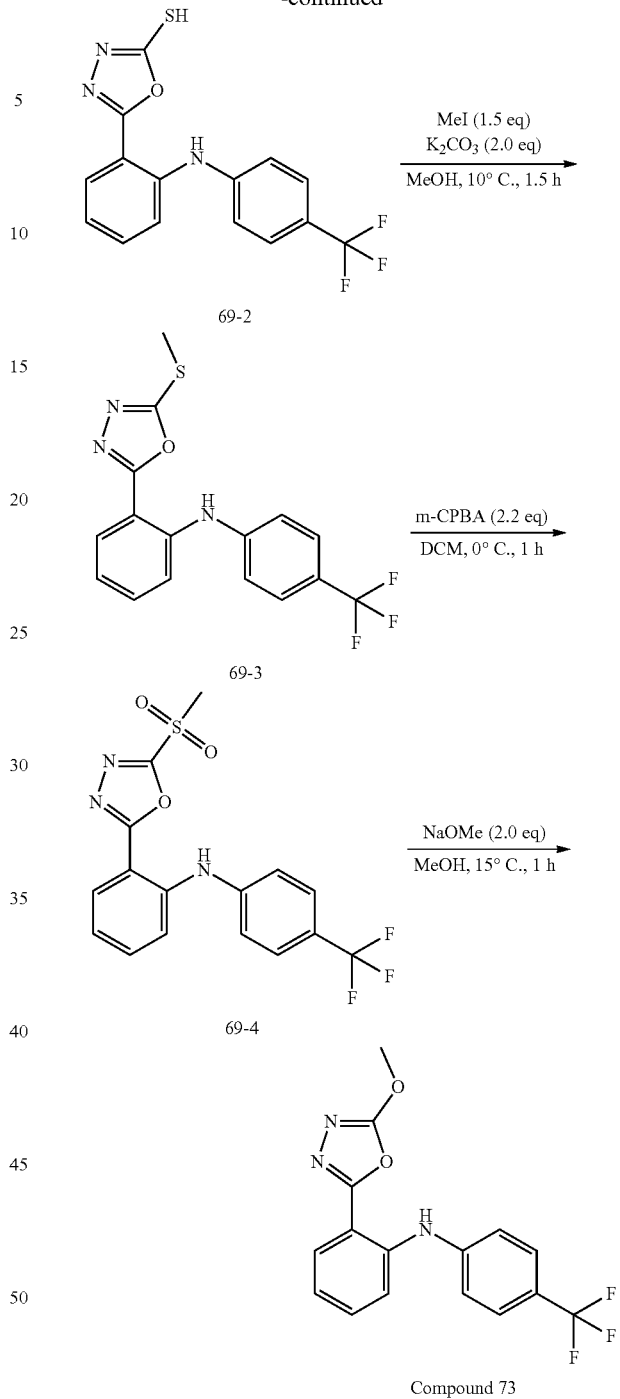

69-2

69-3

69-4

Compound 73

Step 1: 5-(2-((4-(trifluoromethyl)phenyl)amino)phenyl)-1,3,4-oxadiazole-2-thiol To a solution of compound 69-1 (1.00 g, 3.39 mmol, 1 eq) and KOH (380.0 mg, 6.77 mmol, 2 eq) in EtOH (10 mL) was added CS$_2$ (515.8 mg, 6.77 mmol, 0.41 mL, 2 eq). The mixture was stirred at 80° C. for 16 hr. The mixture was concentrated. 1 N HCl was added to the residue until pH=6-7. The mixture was extracted with EA (15 mL*3). The organic layer was dried over Na$_2$SO$_4$, filtered and concentrated to give a residue. The residue was purified by flash silica gel chromatography to give compound 69-2 (700.0 mg, 2.08 mmol, 61.3% yield).

Step 2: 2-(5-(methylthio)-1,3,4-oxadiazol-2-yl)-N-(4-(trifluoromethyl)phenyl)aniline To a solution of compound 69-2 (650.0 mg, 1.93 mmol, 1 eq) in MeOH (10 mL) was added $K_2CO_3$ (532.6 mg, 3.85 mmol, 2 eq). The mixture was stirred at 10° C. for 0.5 hr. Me (410.3 mg, 2.89 mmol, 0.18 mL, 1.5 eq) was added. The mixture was stirred at 10° C. for 1 hr. The mixture was concentrated. The residue was diluted with $H_2O$ (10 mL). The mixture was extracted with EA (15 mL*3). The organic layer was dried over $Na_2SO_4$, filtered and concentrated to give compound 69-3 (500.0 mg, crude).

Step 3: 2-(5-(methylsulfonyl)-1,3,4-oxadiazol-2-yl)-N-(4-(trifluoromethyl)phenyl)aniline To a solution of compound 69-3 (50.0 mg, 0.14 mmol, 1 eq) in DCM (2 mL) was added m-CPBA (63.6 mg, 0.31 mmol, 85% purity, 2.2 eq) at 0° C. The mixture was stirred at 0° C. for 1 hr. The mixture was diluted with $H_2O$ (5 mL). The mixture was extracted with EA (10 mL*3). The organic layer was dried over $Na_2SO_4$, filtered and concentrated to give a residue. The residue was purified by flash silica gel chromatography to give compound 69-4 (35.0 mg, 54.8 umol, 38.5% yield).

Step 4: 2-(5-methoxy-1,3,4-oxadiazol-2-yl)-N-(4-(trifluoromethyl)phenyl)aniline

To a solution of compound 69-4 (35.0 mg, 54.8 umol, 1 eq) in MeOH (1 mL) was added NaOMe (5.9 mg, 0.11 mmol, 2 eq). The mixture was stirred at 15° C. for 1 hr. The mixture was diluted with $H_2O$ (5 mL). The mixture was extracted with EA (10 mL*3). The organic layer was dried over $Na_2SO_4$, filtered and concentrated to give a residue. The residue was purified by prep-HPLC to give Compound 73 (8.4 mg, 25.1 umol, 45.7% yield). LCMS (ESI): RT=1.018 min, mass calc. for $C_{16}H_{12}F_3N_3O_2$ 335.09, m/z found 336.0 $[M+H]^+$; $^1$H NMR (400 MHz, $CDCl_3$) δ 9.35 (br s, 1H), 7.77 (d, J=7.6 Hz, 1H), 7.58 (br d, J=8.4 Hz, 2H), 7.50 (d, J=8.4 Hz, 1H), 7.40-7.32 (m, 3H), 6.96 (t, J=7.5 Hz, 1H), 4.27 (s, 3H).

Example 70: (S)-4-(5-(4,5-difluoro-2-((4-(trifluoromethyl)phenyl)amino)phenyl)-1,3,4-oxadiazol-2-yl)oxazolidin-2-one (Compound 74)

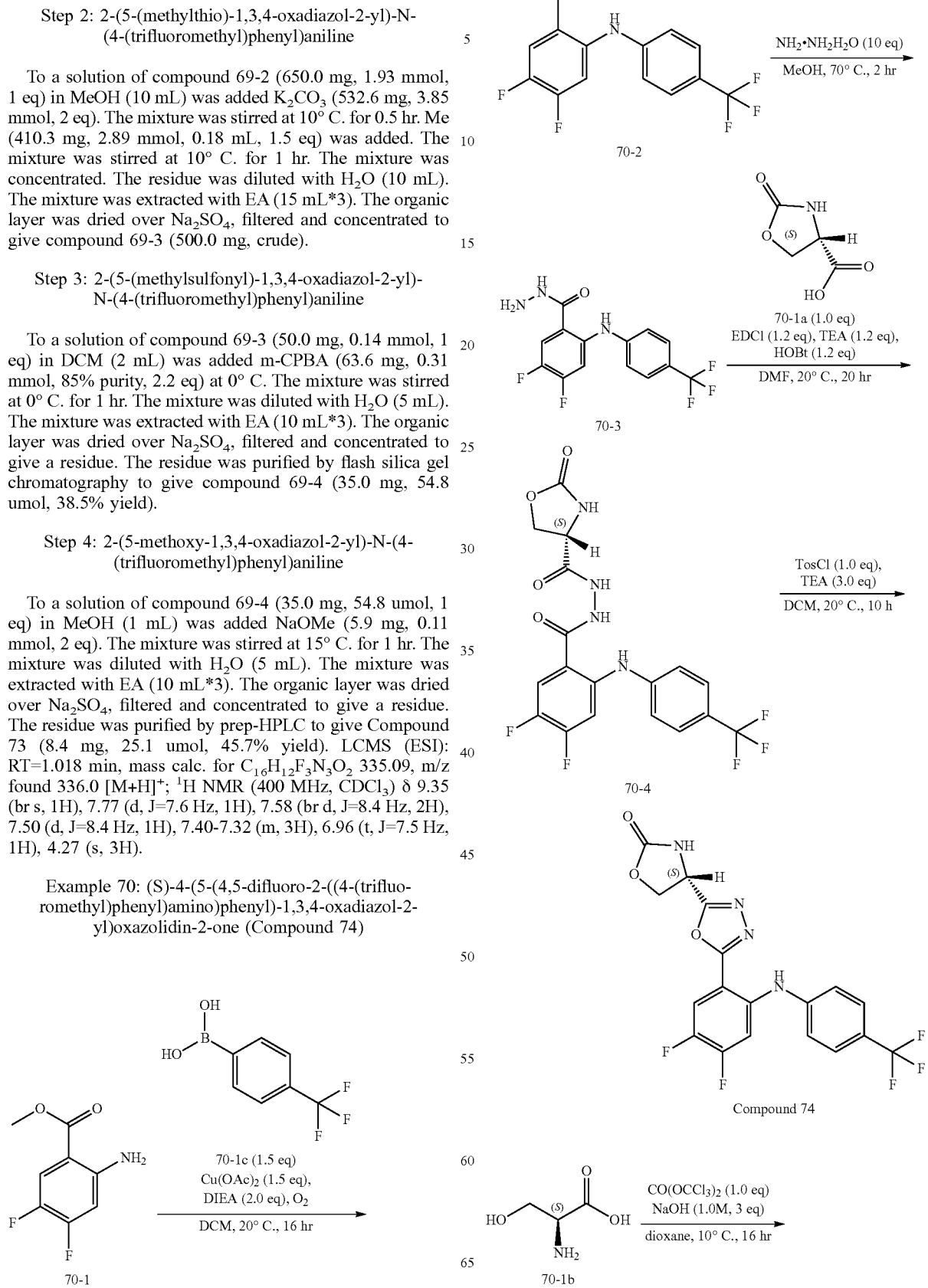

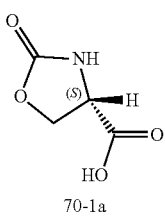

70-1a

Step 1: methyl 4,5-difluoro-2-[4-(trifluoromethyl)anilino]benzoate

To a solution of 70-1 (1.00 g, 5.34 mmol, 1 eq) and 70-1c (1.50 g, 8.02 mmol, 1.5 eq) in DCM (15 mL) were added Cu(OAc)$_2$ (1.40 g, 8.02 mmol, 1.5 eq) and DIEA (1.30 g, 10.69 mmol, 1.8 mL, 2 eq). The mixture was degassed, purged with O$_2$ for 3 times and stirred at 20° C. for 16 hr. The mixture was concentrated. The residue was dissolved in EA (10 mL) and washed with H$_2$O (3 mL*3). The combined organic layers were washed with brine (3 mL*3), dried over Na$_2$SO$_4$, filtered and concentrated under reduced pressure. The residue was purified by flash silica gel chromatography to give 70-2 (650.0 mg, 1.96 mmol, 36.7% yield). $^1$H NMR (400 MHz, CDCl$_3$) δ 9.61 (br s, 1H), 7.79 (dd, J=9.0, 11.1 Hz, 1H), 7.58 (d, J=8.5 Hz, 2H), 7.25 (d, J=2.3 Hz, 1H), 7.10 (dd, J=6.9, 12.8 Hz, 1H), 3.92-3.88 (m, 3H)

Step 2: 4,5-difluoro-2-[4-(trifluoromethyl)anilino]benzohydrazide

To a solution of compound 70-2 (650.0 mg, 1.96 mmol, 1.0 eq) in MeOH (10 mL) was added NH$_2$NH$_2$.H$_2$O (1.16 g, 19.62 mmol, 1.1 mL, 10 eq). The mixture was stirred at 70° C. for 2 hr. The reaction mixture was concentrated in vacuum. The residue was diluted with EA (15 mL), washed with H$_2$O (5 mL) and brine (5 mL), dried over Na$_2$SO$_4$, filtered and concentrated in vacuum. The residue was purified by flash silica gel chromatography to give 70-3 (470.0 mg, 1.42 mmol, 72.3% yield). $^1$H NMR (400 MHz, DMSO-d$_6$) δ 9.91 (s, 1H), 9.71 (s, 1H), 7.68 (dd, J=8.9, 11.3 Hz, 1H), 7.59 (d, J=8.5 Hz, 2H), 7.47-7.39 (m, 1H), 7.28 (d, J=8.5 Hz, 2H), 4.55 (br s, 2H)

Step 3: (4S)-2-oxooxazolidine-4-carboxylic Acid

To a solution of NaOH (1 M, 14.2 mL, 3 eq) was added compound 70-1b (500.0 mg, 4.76 mmol, 1 eq) at 10° C., followed by addition of a solution of bis(trichloromethyl) carbonate (1.40 g, 4.76 mmol, 1 eq) in dioxane (6 mL). The solution was stirred at 10° C. for 16 hr. The reaction was concentrated in vacuum. Then the residue was diluted with MeCN (20 mL), filtered and the filtrate was concentrated in vacuum to give 70-1a (600.0 mg, crude), which was used for the next step directly. $^1$H NMR confirmed that compound. $^1$H NMR (400 MHz, DMSO-d$_6$) δ 8.15 (s, 1H), 4.51-4.43 (m, 1H), 4.36-4.31 (m, 1H), 4.27 (dd, J=4.1, 8.4 Hz, 1H).

Step 4: (4S)—N'-[4,5-difluoro-2-[4-(trifluoromethyl)anilino]benzoyl]-2-oxo-oxazolidine-4-carbohydrazide To a solution of 70-1a (65.9 mg, 0.50 mmol, 1 eq), EDCI (115.7 mg, 0.60 mmol, 1.2 eq) and HOBt (81.5 mg, 0.60 mmol, 1.2 eq) in DMF (2 mL) were added 70-3 (200.0 mg, 0.60 mmol, 1.2 eq) and TEA (61.1 mg, 0.60 mmol, 84 uL, 1.2 eq) at 20° C., The mixture was stirred at 20° C. for 20 hr. The solution was diluted with H$_2$O (2 mL) and extracted with EA (4 mL*3). Then the combined organic layers were washed with brine (4 mL*3) and H$_2$O (4 mL*3). Finally, the organic layer was dried by Na$_2$SO$_4$, filtered and concentrated under reduced pressure to give a residue. The residue was triturated with DCM (5 ml) to give 70-4 (80.0 mg, crude). $^1$H NMR (400 MHz, DMSO-d$_6$) δ 10.84-10.61 (m, 1H), 10.49 (br s, 1H), 9.50 (br s, 1H), 8.15 (s, 1H), 7.88-7.76 (m, 1H), 7.60 (d, J=8.5 Hz, 2H), 7.53-7.40 (m, 1H), 7.31 (br d, J=8.4 Hz, 2H), 4.60-4.51 (m, 1H), 4.48-4.40 (m, 1H), 4.22 (dd, J=4.3, 8.3 Hz, 1H)

Step 5: (S)-4-(5-(4,5-difluoro-2-((4-(trifluoromethyl)phenyl)amino)phenyl)-1,3,4-oxadiazol-2-yl)oxazolidin-2-one To a solution of 70-4 (70.0 mg, 0.16 mmol, 1.0 eq) in DCM (1 mL) were added TosCl (30.0 mg, 0.16 mmol, 1.0 eq) and TEA (47.8 mg, 0.47 mmol, 65 uL, 3.0 eq), the solution was stirred at 20° C. for 10 hr. The solution was diluted with H$_2$O (1 mL) and extracted with EA (1 mL*3). Then the combined organic layers were washed with brine (1 mL*3) and H$_2$O (1 mL*3). Finally, the organic layer was dried by Na$_2$SO$_4$, filtered and concentrated under reduced pressure to give a residue. The residue was purified by prep-HPLC. Then the product was purified by column chromatography. LCMS, MS and $^1$H NMR confirmed that Compound 74 (3.39 mg, 7.1 umol, 4.5% yield) was obtained. LCMS (ESI): RT=1.041 min, mass calc. for C$_{18}$H$_{11}$F$_5$N$_4$O$_3$ 426.08, m/z found 427.0 [M+H]$^+$; $^1$H NMR (400 MHz, CDCl$_3$) δ 9.33 (s, 1H), 7.69 (dd, J=8.4, 10.3 Hz, 1H), 7.64 (d, J=8.4 Hz, 2H), 7.34 (d, J=8.5 Hz, 2H), 7.23 (dd, J=6.8, 12.5 Hz, 1H), 6.19 (s, 1H), 5.39-5.30 (m, 1H), 4.91-4.85 (m, 1H), 4.82-4.77 (m, 1H).

Example 71: (S)-3-methyl-3-(5-(2-((4-(trifluoromethyl)phenyl)amino)phenyl)-1,3,4-oxadiazol-2-yl)pyrrolidin-2-one (Compound 75) and (R)-3-methyl-3-(5-(2-((4-(trifluoromethyl)phenyl)amino)phenyl)-1,3,4-oxadiazol-2-yl)pyrrolidin-2-one (Compound 76)

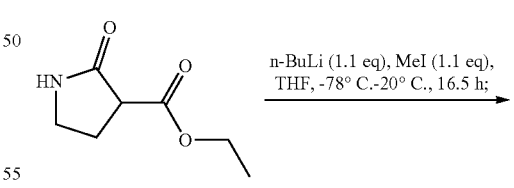

71-1

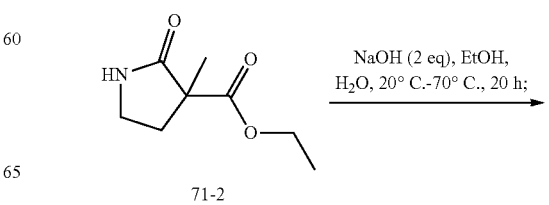

71-2

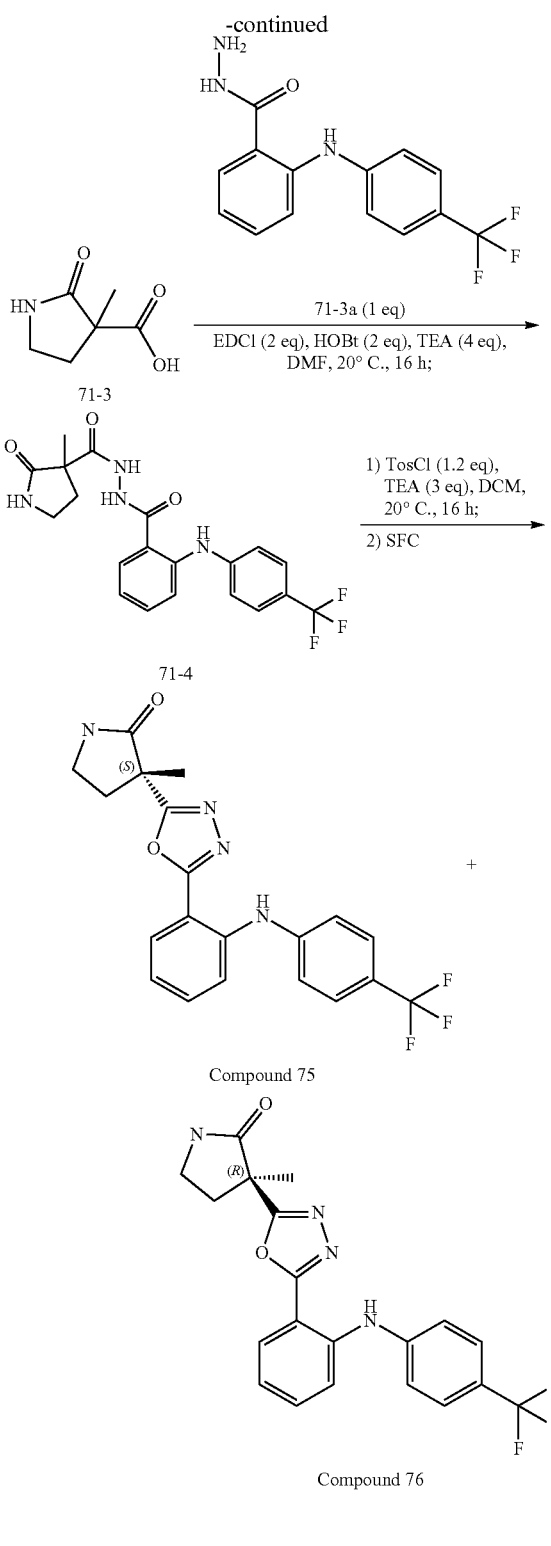

Step 1: ethyl 3-methyl-2-oxopyrrolidine-3-carboxylate PGP-12

To a solution of 71-1 (800 mg, 5.09 mmol, 1 eq) in THF (10 mL) at −78° C. was added n-BuLi (2.5 M, 2.24 mL, 1.1 eq) and the mixture was stirred at −78° C. for 0.5 h. And then Me (794.7 mg, 5.60 mmol, 0.35 mL, 1.1 eq) was added into the above mixture at −78° C., and the mixture was stirred at 20° C. for 16 h. The reaction mixture was quenched with saturated $NH_4Cl$ (20 mL), and then extracted with EA (20 mL*3). The combined organic layers were washed with brine (20 mL), dried over $Na_2SO_4$, filtered and concentrated under reduced pressure to give a residue. The residue was purified by flash silica gel chromatography to give 71-2 (720 mg, 3.79 mmol, 74.4% yield). $^1$H NMR (400 MHz, $CDCl_3$) δ 6.16 (brs, 1H), 4.21 (dq, J=1.8, 7.1 Hz, 2H), 3.54-3.42 (m, 1H), 3.40-3.30 (m, 1H), 2.69-2.59 (m, 1H), 2.04 (ddd, J=7.0, 8.4, 13.0 Hz, 1H), 1.46 (s, 3H), 1.28 (t, J=7.1 Hz, 3H).

Step 2: 3-methyl-2-oxopyrrolidine-3-carboxylic Acid

To a solution of 71-2 (350 mg, 2.04 mmol, 1 eq) in EtOH (2 mL) at 20° C. was added NaOH (2 M, 2.04 mL, 2 eq) and the mixture was stirred at 20° C. for 16 h, and then stirred at 70° C. for 4 h. The reaction mixture was concentrated to remove EtOH. The residue was diluted with water (20 mL), acidified with 2 N HCl to pH=1-2, and then extracted with EA (20 mL*3). The combined organic layers were washed with brine (20 mL), dried over $Na_2SO_4$, filtered and concentrated under reduced pressure to give 30 mg sample. The liquid layer was lyophilized to give a residue, which was dissolved in MeOH and then filtered to remove the precipitate. The filtrate was concentrated to give 350 mg sample. The above two batches were combined to give 71-3 (380 mg, 1.86 mmol, 90.9% yield). $^1$H NMR (400 MHz, DMSO-$d_6$) δ 7.85 (brs, 1H), 3.25-3.18 (m, 2H), 2.43-2.38 (m, 1H), 1.92-1.84 (m, 1H), 1.19 (s, 3H).

Step 3: 3-methyl-2-oxo-N'-(2-((4-(trifluoromethyl)phenyl)amino)benzoyl)pyrrolidine-3-carbohydrazide To a solution of 71-3a (220 mg, 0.75 mmol, 1 eq), 71-3 (304.7 mg, 1.49 mmol, 2 eq), EDCI (285.7 mg, 1.49 mmol, 2 eq) and HOBt (201.4 mg, 1.49 mmol, 2 eq) in DMF (5 mL) at 20° C. was added TEA (301.6 mg, 2.98 mmol, 0.41 mL, 4 eq), and the mixture was stirred at 20° C. for 16 h. The reaction mixture was concentrated to remove DMF. The residue was diluted with water (20 mL), and then extracted with EA (20 mL*3). The combined organic layers were washed with brine (20 mL), dried over $Na_2SO_4$, filtered and concentrated under reduced pressure to give 71-4 (400 mg, 0.67 mmol, 89.4% yield), which was used directly for next step. LCMS (ESI): RT=0.987 min, mass calc. for $C_{20}H_{19}F_3N_4O_3$ 420.14, m/z found 442.9 [M+Na]$^+$.

Step 4: (S)-3-methyl-3-(5-(2-((4-(trifluoromethyl)phenyl)amino)phenyl)-1,3,4-oxadiazol-2-yl)pyrrolidin-2-one (Compound 75) and (R)-3-methyl-3-(5-(2-((4-(trifluoromethyl)phenyl)amino)phenyl)-1,3,4-oxadiazol-2-yl)pyrrolidin-2-one (Compound 76)

To a solution of 71-4 (400 mg, 0.67 mmol, 1 eq) and TEA (202.2 mg, 2.00 mmol, 0.28 mL, 3 eq) in DCM (5 mL) at 20° C. was added TosCl (152.4 mg, 0.80 mmol, 1.2 eq), and the mixture was stirred at 20° C. for 16 h. The mixture was diluted with water (20 mL), and then extracted with EA (20 mL*3). The combined organic layers were washed with brine (20 mL), dried over $Na_2SO_4$, filtered and concentrated under reduced pressure to give a residue. The residue was purified by flash silica gel chromatography to give 170 mg of desired product as a mixture (R/S isomers=1:1 ratio) by LCMS and SFC. The 100 mg of desired product as a mixture (R/S, from the above 170 mg batch) was purified further by SFC to give Compound 75 (24.7 mg, 61.5 umol, 9.2% yield, 99.8% ee) and Compound 76 (19.3 mg, 47.5 umol, 7.1% yield, 99.8% ee). Compound 75: LCMS (ESI): RT=0.944 min, mass calc. for $C_{20}H_{17}F_3N_4O_2$ 402.13, m/z found 402.9 [M+H]$^+$; $^1$H NMR (400 MHz, CDCl$_3$) δ 9.48 (brs, 1H), 7.92 (dd, J=1.4, 7.9 Hz, 1H), 7.58 (d, J=8.5 Hz, 2H), 7.51 (d, J=8.4 Hz, 1H), 7.40 (dt, J=1.5, 7.9 Hz, 1H), 7.35 (d, J=8.5 Hz, 2H), 7.02-6.93 (m, 1H), 5.94 (brs, 1H), 3.72-3.63 (m, 1H), 3.53 (dt, J=4.8, 8.8 Hz, 1H), 3.03 (ddd, J=4.8, 7.9, 12.9 Hz, 1H), 2.39-2.30 (m, 1H), 1.80 (s, 3H). Compound 76: LCMS (ESI): RT=0.942 min, mass calc. for $C_{20}H_{17}F_3N_4O_2$ 402.13, m/z found 402.9 [M+H]$^+$; $^1$H NMR (400 MHz, CDCl$_3$) δ 9.48 (s, 1H), 7.92 (dd, J=1.4, 8.0 Hz, 1H), 7.57 (d, J=8.5 Hz, 2H), 7.51 (d, J=8.0 Hz, 1H), 7.39 (dt, J=1.5, 7.9 Hz, 1H), 7.34 (d, J=8.5 Hz, 2H), 7.01-6.93 (m, 1H), 6.37 (br s, 1H), 3.71-3.62 (m, 1H), 3.53 (dt, J=5.0, 8.8 Hz, 1H), 3.01 (ddd, J=4.9, 7.9, 12.9 Hz, 1H), 2.33 (ddd, J=6.3, 7.8, 13.2 Hz, 1H), 1.79 (s, 3H).

Example 72: (R)-4-(5-(2-((4-(trifluoromethyl)phenyl)amino)phenyl)-1,3,4-oxadiazol-2-yl)oxazolidin-2-one (Compound 77)

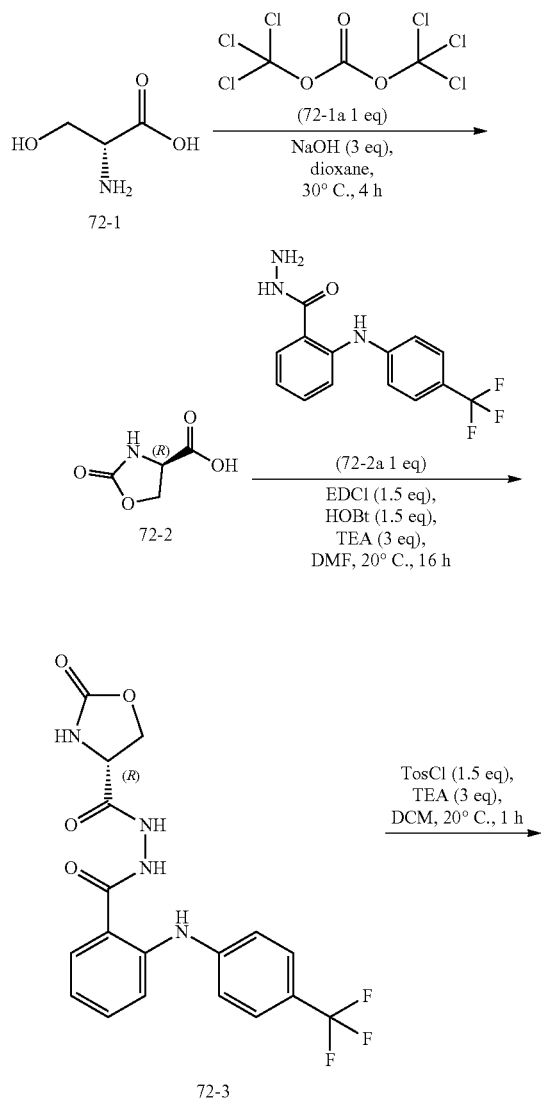

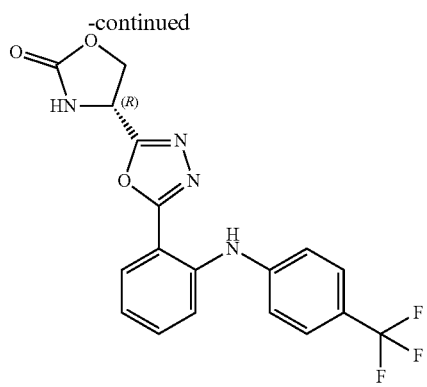

Compound 77

Step 1: (R)-2-oxooxazolidine-4-carboxylic Acid

To a solution of NaOH (1 M, 11.43 mL, 3 eq) was added 72-1 at 30° C., followed by addition of a solution 72-1a (1.1 g, 3.81 mmol, 1 eq) in dioxane (4 mL) along with gas evolved. After stirring for 2 h, the mixture was clear, then the mixture was stirred for another 2 hr at 30° C. The reaction mixture was concentrated under reduced pressure and then extracted with hot acetonitrile (150 mL). The mixture was filtered and concentrated under reduced pressure to give 72-2 (260 mg, 1.79 mmol, 46.9% yield). $^1$H NMR (400 MHz, DMSO-d$_6$) δ 8.14 (brs, 1H), 4.36-4.31 (m, 2H), 4.27 (brdd, J=3.3, 8.3 Hz, 1H).

Step 2: (R)-2-oxo-N'-(2-((4-(trifluoromethyl)phenyl)amino)benzoyl)oxazolidine-4-carbohydrazie To a solution of 72-2, EDCI (288.8 mg, 1.51 mmol, 1.5 eq) and HOBt (203.6 mg, 1.51 mmol, 1.5 eq) in DMF (2 mL) at 20° C. were added 72-2a (296.6 mg, 1.00 mmol, 1 eq) and TEA (304.9 mg, 3.01 mmol, 0.42 mL, 3 eq). The mixture was stirred at 20° C. for 16 h. The reaction mixture was diluted with water (20 mL) and extracted with EA (20 mL*3). The combined organic layers were washed with water (20 mL*2) and brine (20 mL*2), dried over Na$_2$SO$_4$, filtered and concentrated under reduced pressure to give 72-3 (330 mg, 0.59 mmol, 58.7% yield). LCMS (ESI): RT=0.782 min, mass calc. for $C_{18}H_{15}F_3N_4O_4$ 408.33, m/z found 408.9 [M+H]$^+$.

Step 3: (R)-4-(5-(2-((4-(trifluoromethyl)phenyl)amino)phenyl)-1,3,4-oxadiazol-2-yl)oxazolidin-2-one To a solution of 72-3 (300 mg, 0.73 mmol, 1 eq) in DCM (3 mL) were added TEA (223.0 mg, 2.20 mmol, 0.31 mL, 3 eq) and TosCl (210.1 mg, 1.10 mmol, 1.5 eq). The mixture was stirred at 20° C. for 1 h. The reaction mixture was concentrated under reduced pressure to give a residue. The reaction mixture was diluted with water (20 mL) and extracted with EA (20 mL*3). The combined organic layers were washed with water (20 mL) and brine (20 mL), dried over Na$_2$SO$_4$, filtered and concentrated under reduced pressure to give a residue. The residue was purified by flash silica gel chromatography to give Compound 77 (60 mg, 0.15 mmol, 20.1% yield). LCMS (ESI): RT=0.822 min, mass calc. for $C_{18}H_{13}F_3N_4O_3$ 390.32, m/z found 390.9 [M+H]$^+$; $^1$H NMR (400 MHz, CDCl$_3$) δ 9.32 (s, 1H), 7.90 (brd, J=7.9 Hz, 1H), 7.62 (brd, J=8.1 Hz, 2H), 7.53-7.49 (m, 1H), 7.44 (brd, J=7.5 Hz, 1H), 7.36 (brd, J=8.1 Hz, 3H), 6.99 (t, J=7.5 Hz, 1H), 5.42 (brdd, J=4.8, 8.2 Hz, 1H), 4.93-4.88 (m, 1H), 4.84-4.79 (m, 1H).

Example 73: (S)-4-(5-(2-((4-(trifluoromethyl)phenyl)amino)phenyl)-1,3,4-oxadiazol-2-yl)oxazolidin-2-one (Compound 78)

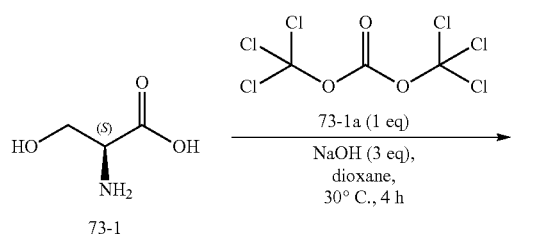

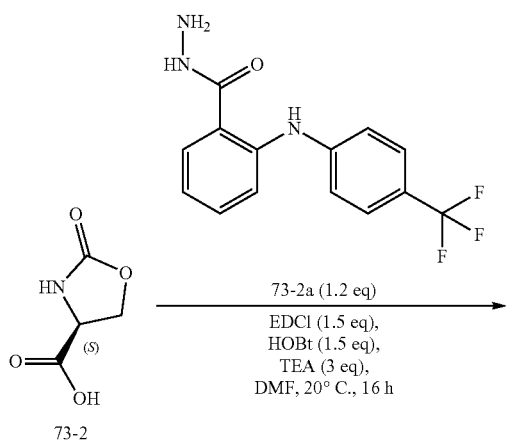

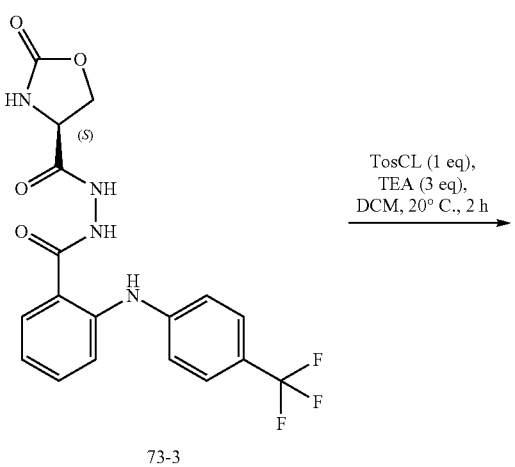

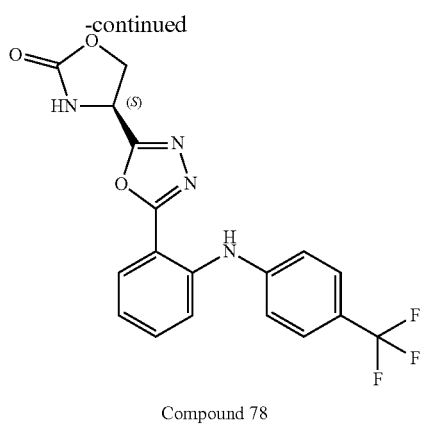

Compound 78

Step 1: (S)-2-oxooxazolidine-4-carboxylic Acid

To a solution of NaOH (1 M, 11.43 mL, 3 eq) was added 73-1 at 30° C., followed by addition of a solution 73-1a (1.1 g, 3.81 mmol, 1 eq) in dioxane (4 mL) along with gas evolved. After stirring for 2 h, the mixture was clear, then the mixture was stirred for another 2 hr at 30° C. The reaction mixture was concentrated under reduced pressure and then extracted with hot acetonitrile (150 mL). The mixture was filtered and concentrated under reduced pressure to give 73-2 (664 mg, 2.76 mmol, 94.0% yield). $^1$H NMR (400 MHz, DMSO-$d_6$) δ 8.14 (s, 1H), 4.52-4.42 (m, 1H), 4.37-4.24 (m, 2H).

Step 2: (S)-2-oxo-N'-(2-((4-(trifluoromethyl)phenyl)amino)benzoyl)oxazolidine-4-carbohydrazie To a solution of 73-2 (300 mg, 2.29 mmol, 1 eq), EDCI (658.1 mg, 3.43 mmol, 1.5 eq) and HOBt (463.9 mg, 3.43 mmol, 1.5 eq) in DMF (3 mL) at 30° C. was added 73-2a (810.9 mg, 2.75 mmol, 1.2 eq) and TEA (694.8 mg, 6.87 mmol, 1 mL, 3 eq). The mixture was stirred at 20° C. for 16 h. The reaction mixture was diluted with water (20 mL) and extracted with EA (20 mL*3). The combined organic layers were washed with water (20 mL*2) and brine (20 mL*2), dried over $Na_2SO_4$, filtered and concentrated under reduced pressure to give 73-3 (900 mg, 1.81 mmol, 79% yield). LCMS (ESI): RT=0.768 min, mass calc. for $C_{18}H_{15}F_3N_4O_4$ 408.33, m/z found 430.9 [M+Na]$^+$; $^1$H NMR (400 MHz, DMSO-$d_6$) δ 9.85 (brs, 1H), 9.58 (s, 1H), 7.95 (s, 2H), 7.55 (s, 3H), 7.44-7.42 (m, 2H), 7.23 (s, 2H), 6.99 (s, 1H), 4.52 (br s, 1H), 4.41 (dd, J=4.4, 9.2 Hz, 1H), 4.23 (dd, J=4.5, 8.3 Hz, 1H).

Step 3: (S)-4-(5-(2-((4-(trifluoromethyl)phenyl)amino)phenyl)-1,3,4-oxadiazol-2-yl)oxazolidin-2-one To a solution of 73-3 (100 mg, 0.24 mmol, 1 eq) in DCM (1 mL) were added TEA (74.3 mg, 0.73 mmol, 0.1 mL, 3 eq) and TosCl (46.7 mg, 0.24 mmol, 1 eq). The mixture was stirred at 20° C. for 2 h. The reaction mixture was concentrated under reduced pressure to give a residue. The reaction mixture was diluted with water (20 mL) and extracted with EA (20 mL*3). The combined organic layers were washed with water (20 mL) and brine (20 mL), dried over $Na_2SO_4$, filtered and concentrated under reduced pressure to give a residue. The residue was purified by flash silica gel chromatography to give Compound 78 (20 mg, 0.50 mmol, 20.1% yield). LCMS (ESI): RT=0.850 min, mass calc. for $C_{18}H_{13}F_3N_4O_3$ 390.32, m/z found 390.9 [M+H]$^+$; $^1$H NMR (400 MHz, CDCl$_3$) δ 9.33 (brs, 1H), 7.88 (brd, J=7.9 Hz, 1H), 7.60 (brd, J=8.3 Hz, 2H), 7.52-7.48 (m, 1H), 7.45-7.40 (m, 1H), 7.36 (br d, J=8.1 Hz, 2H), 6.98 (t, J=7.5 Hz, 1H), 5.99 (brs, 1H), 5.35 (br s, 1H), 4.91-4.85 (m, 1H), 4.82-4.77 (m, 1H).

Example 74: 1-chloro-3-(5-(2-((4-(trifluoromethyl)phenyl)amino)phenyl)-1,3,4-oxadiazol-2-yl)propan-2-ol (Compound 79)

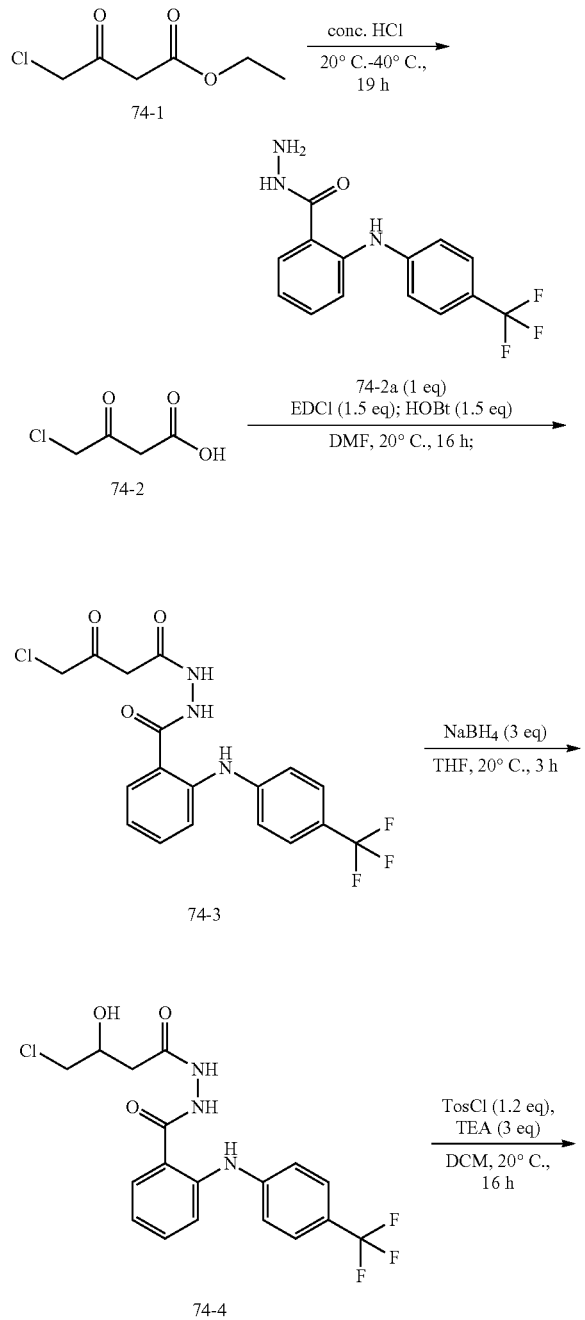

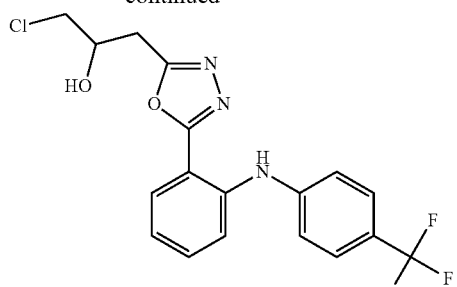

Compound 79

Step 1: 4-chloro-3-oxobutanoic Acid

The solution of 74-1 (300 mg, 1.82 mmol, 0.25 mL, 1 eq) in conc. HCl (2 mL) was stirred at 20° C. for 16 h, and then stirred at 40° C. for another 3 h. The reaction mixture was diluted with water (20 mL) and extracted with EA (10 mL). The combined organic layers were washed with brine (20 mL), dried over Na$_2$SO$_4$, filtered and concentrated under reduced pressure to give 74-2 (190 mg, 1.39 mmol, 76.5% yield), which was used directly for next step. $^1$H NMR (400 MHz, CDCl$_3$) δ 4.24 (s, 2H), 3.76 (s, 2H).

Step 2: N'-(4-chloro-3-oxobutanoyl)-2-((4-(trifluoromethyl)phenyl)amino)benzohydrazide To a solution of 74-2a (180 mg, 0.61 mmol, 1 eq), 74-2 (99.9 mg, 0.73 mmol, 1.2 eq) and HOBt (123.6 mg, 0.91 mmol, 1.5 eq) in DMF (1 mL) at 20° C. was added EDCI (175.3 mg, 0.91 mmol, 1.5 eq), and the mixture was stirred at 20° C. for 16 h. The reaction mixture was diluted with water (10 mL) and extracted with EA (10 mL*3). The combined organic layers were washed with water (10 mL*2) and brine (10 mL), dried over anhydrous Na$_2$SO$_4$, filtered and concentrated under reduced pressure to give 74-3 (180 mg, 0.21 mmol, 34.3% yield), which was used directly for next step. LCMS (ESI): RT=0.981 min, mass calc. for $C_{18}H_{15}ClF_3N_3O_3$ 413.08, m/z found 435.9 [M+Na]$^+$.

Step 3: N'-(4-chloro-3-hydroxybutanoyl)-2-((4-(trifluoromethyl)phenyl)amino)benzohydrazide To a solution of 74-3 (160 mg, 0.19 mmol, 1 eq) in THF (1 mL) at 20° C. was added NaBH$_4$ (21.1 mg, 0.56 mmol, 3 eq), and the mixture was stirred at 20° C. for 3 h. The reaction mixture was quenched with water (20 mL) at 20° C., and then extracted with EA (10 mL*3). The combined organic layers were washed with brine (20 mL), dried over Na$_2$SO$_4$, filtered and concentrated under reduced pressure to give 74-4 (80 mg, 0.13 mmol, 70.5% yield), which was used directly for next step. LCMS (ESI): RT=0.980 min, mass calc. for $C_{18}H_{17}CF_3N_3O_3$ 415.09, m/z found 437.9 [M+Na]$^+$.

Step 4: 1-chloro-3-(5-(2-((4-(trifluoromethyl)phenyl)amino)phenyl)-1,3,4-oxadiazol-2-yl)propan-2-ol To a solution of 74-4 (70 mg, 0.11 mmol, 1 eq) and TEA (34.8 mg, 0.34 mmol, 48 uL, 3 eq) in DCM (1 mL) at 20° C. was added TosCl (26.2 mg, 0.14 mmol, 1.2 eq), and the mixture was stirred at 20° C. for 16 h. The residue was concentrated to give a residue. The residue was purified by flash silica gel chromatography and prep-HPLC to give Compound 79 (4.4 mg, 11.1 umol, 9.7% yield). LCMS (ESI): RT=0.986 min, mass calc. for $C_{18}H_{15}ClF_3N_3O_2$ 397.08, m/z found 398.0 [M+H]$^+$; $^1$H NMR (400 MHz, CDCl$_3$) δ 9.45 (s, 1H), 7.89 (dd, J=1.4, 8.0 Hz, 1H), 7.59 (d, J=8.5 Hz, 2H), 7.52 (d, J=8.4 Hz, 1H), 7.44-7.39 (m, 1H), 7.37 (d, J=8.5 Hz, 2H), 7.02-6.95 (m, 1H), 4.49 (br d, J=4.4 Hz, 1H), 3.78 (dd, J=4.0, 5.1 Hz, 2H), 3.35-3.21 (m, 2H), 3.06 (d, J=4.8 Hz, 1H).

Example 75: 3-chloro-1-(5-(2-((4-(trifluoromethyl)phenyl)amino)phenyl)-1,3,4-oxadiazol-2-yl)propan-1-ol (Compound 80)

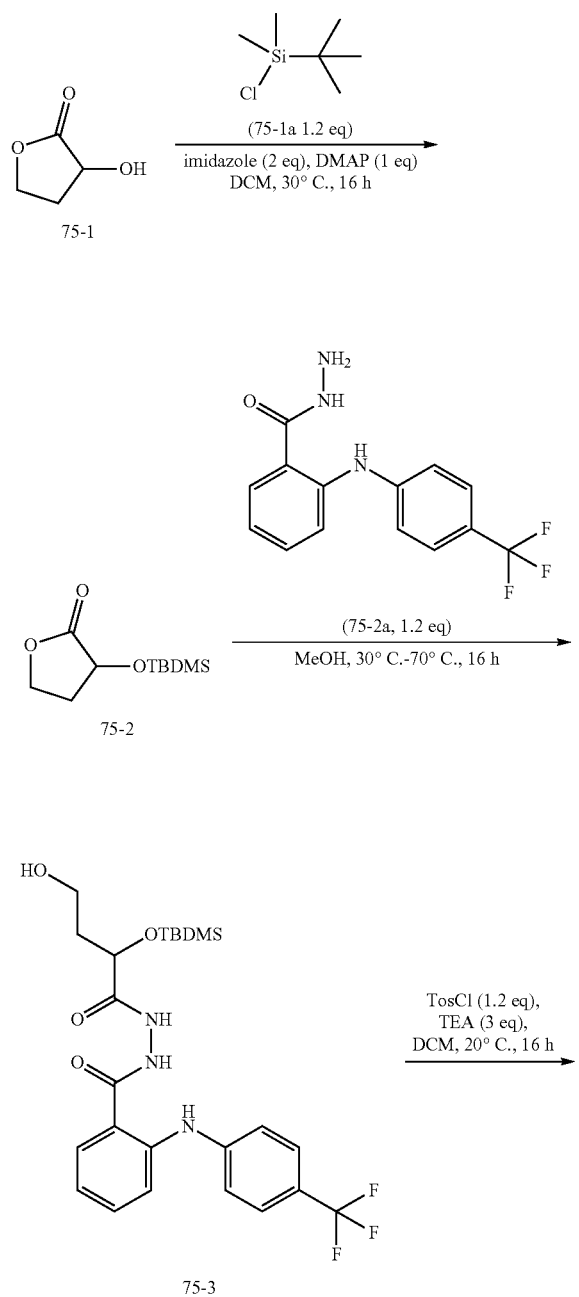

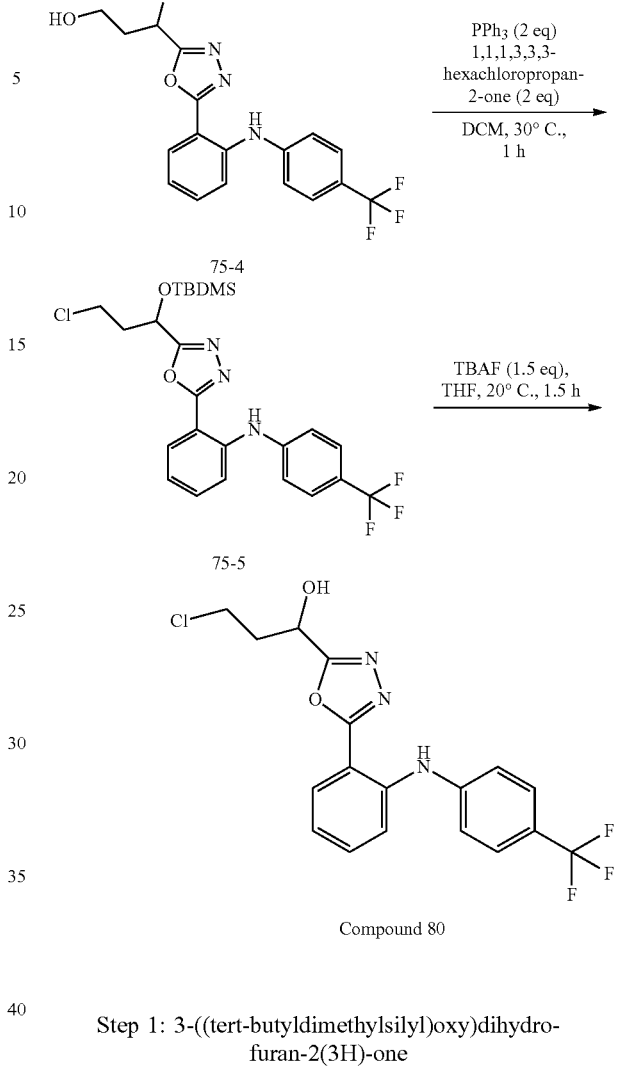

Step 1: 3-((tert-butyldimethylsilyl)oxy)dihydrofuran-2(3H)-one

To a solution of 75-1 (300 mg, 2.94 mmol, 0.23 mL, 1 eq) in DCM (3 mL) were added imidazole (400.1 mg, 5.88 mmol, 2 eq), DMAP (359.0 mg, 2.94 mmol, 1 eq) and 75-1a (531.5 mg, 3.53 mmol, 0.43 mL, 1.2 eq). The mixture was stirred at 30° C. for 16 h. The reaction mixture was diluted with water (20 mL) and extracted with EA (20 mL*3). The combined organic layers were washed with water (20 mL*2) and brine (20 mL*2), dried over Na$_2$SO$_4$, filtered and concentrated under reduced pressure give 75-2 (664 mg, 2.76 mmol, 94.0% yield). $^1$H NMR (400 MHz, CDCl$_3$) δ 4.44-4.33 (m, 2H), 4.18 (dt, J=6.4, 9.2 Hz, 1H), 2.50-2.42 (m, 1H), 2.21 (qd, J=8.8, 12.6 Hz, 1H), 0.90 (s, 9H), 0.15 (d, J=9.3 Hz, 6H)

Step 2: N'-(2-((tert-butyldimethylsilyl)oxy)-4-hydroxybutanoyl)-2-((4-(trifluoromethyl)phenyl)amino)benzohydrazide To a solution of 75-2 (300 mg, 1.11 mmol, 1 eq) in MeOH (3 mL) at 30° C. was added 75-2a (393.0 mg, 1.33 mmol, 1.2 eq). The mixture was stirred at 70° C. for 16 h. The reaction mixture was diluted with water (20 mL) and extracted with EA (20 mL*3). The combined organic layers were washed with water (20 mL*2) and brine (20 mL*2), dried over Na₂SO₄, filtered and concentrated under reduced pressure to give 75-3 (600 mg, 0.56 mmol, 50.8% yield). LCMS (ESI): RT=0.906 min, mass calc. for $C_{23}H_{30}F_3N_3O_3Si$ 511.21, m/z found 534.1 [M+Na]⁺.

Step 3: 3-((tert-butyldimethylsilyl)oxy)-3-(5-(2-((4-(trifluoromethyl)phenyl)amino)phenyl)-1,3,4-oxadiazol-2-yl)propan-1-ol To a solution of 75-3 (600 mg, 1.17 mmol, 1 eq) in DCM (7 mL) at 30° C. were added TEA (356.0 mg, 3.52 mmol, 0.49 mL, 3 eq) and TosCl (268.3 mg, 1.41 mmol, 1.2 eq). The mixture was stirred at 30° C. for 16 h. The reaction mixture was concentrated under reduced pressure to give a residue. The residue was purified by flash silica gel chromatography to give 75-4 (192 mg, 0.23 mmol, 19.9% yield). LCMS (ESI): RT=1.042 min, mass calc. for $C_{24}H_{30}F_3N_3O_3Si$ 493.59, m/z found 494.1 [M+H]⁺; ¹H NMR (400 MHz, CDCl₃) δ 9.52 (s, 1H), 7.91 (d, J=7.9 Hz, 1H), 7.59 (br d, J=8.4 Hz, 2H), 7.52 (d, J=8.5 Hz, 1H), 7.44-7.40 (m, 1H), 7.38 (brd, J=8.4 Hz, 2H), 6.99 (t, J=7.5 Hz, 1H), 5.31 (t, J=6.3 Hz, 1H), 4.46 (t, J=5.6 Hz, 1H), 3.89 (brd, J=5.1 Hz, 2H), 3.79 (brd, J=4.4 Hz, 1H), 3.75 (s, 1H), 2.25 (quin, J=6.1 Hz, 2H), 2.12-1.89 (m, 2H), 0.93 (s, 13H), 0.19 (s, 3H), 0.09 (s, 4H).

Step 4: 2-(5-(1-((tert-butyldimethylsilyl)oxy)-3-chloropropyl)-1,3,4-oxadiazol-2-yl)-N-(4-(trifluoromethyl)phenyl)aniline To a solution of 75-4 (160 mg, 0.32 mmol, 1 eq) and PPh₃ (170.0 mg, 0.65 mmol, 2 eq) in DCM (2 mL) at 30° C. was added 1,1,1,3,3,3-hexachloropropan-2-one (171.6 mg, 0.65 mmol, 98 uL, 2 eq). The mixture was stirred at 30° C. for 1 h. The reaction mixture was concentrated under reduced pressure to give a residue. The reaction mixture was concentrated under reduced pressure to give a residue. The residue was purified by flash silica gel chromatography to give to give 75-5 (120 mg, 0.14 mmol, 43.38% yield). LCMS (ESI): RT=1.152 min, mass calc. for $C_{24}H_{29}CF_3N_3O_2Si$ 512.04, m/z found 512.1 [M+H]⁺; ¹H NMR (400 MHz, CDCl₃) δ 7.90 (d, J=7.8 Hz, 1H), 7.59 (d, J=8.4 Hz, 2H), 7.52 (d, J=8.4 Hz, 1H), 7.44-7.36 (m, 3H), 6.99 (t, J=7.5 Hz, 1H), 5.32 (dd, J=4.3, 8.7 Hz, 1H), 3.84-3.76 (m, 2H), 3.75 (s, 1H), 3.70-3.64 (m, 1H), 2.50 (tdd, J=4.7, 9.1, 14.0 Hz, 1H), 2.35 (tdd, J=4.8, 9.4, 14.3 Hz, 1H), 2.22-2.08 (m, 1H), 0.92 (s, 12H), 0.21 (s, 3H), 0.13-0.07 (m, 6H).

Step 5: 3-chloro-1-(5-(2-((4-(trifluoromethyl)phenyl)amino)phenyl)-1,3,4-oxadiazol-2-yl)propan-1-ol To a solution of 75-5 (50 mg, 97 umol, 1 eq) in THF (1 mL) at 30° C. was added TBAF (1 M, 0.15 mL, 1.5 eq). The mixture was stirred at 30° C. for 1.5 h. The reaction mixture was concentrated under reduced pressure to remove solvent and then extracted with petroleum ether (5 mL*2) to give the residue. The residue was diluted with water (5 mL), then acidified with 2N HCl at 30° C. to pH=7, and then extracted with EA (5 mL*3). The combined organic layers were washed with water (5 mL) and brine (5 mL), dried over anhydrous Na₂SO₄, filtered and concentrated under reduced pressure to give a residue. The residue was purified by prep-HPLC to give Compound 80 (10 mg, 25 umol, 25.5% yield). LCMS (ESI): RT=0.910 min, mass calc. for $C_{18}H_{15}ClF_3N_3O_2$ 397.78, m/z found 398.0 [M+H]⁺; ¹H NMR (400 MHz, CDCl₃) δ 9.43 (s, 1H), 7.91 (d, J=7.9 Hz, 1H), 7.59 (d, J=8.3 Hz, 2H), 7.51 (d, J=8.4 Hz, 1H), 7.44-7.33 (m, 3H), 6.98 (t, J=7.6 Hz, 1H), 5.40-5.31 (m, 1H), 3.95-3.87 (m, 1H), 3.84-3.76 (m, 1H), 2.98 (brd, J=5.4 Hz, 1H), 2.57-2.40 (m, 2H).

Example 76: 2-chloro-1-(5-(2-((4-(trifluoromethyl)phenyl)amino)phenyl)-1,3,4-oxadiazol-2-yl)ethan-1-ol (Compound 81)

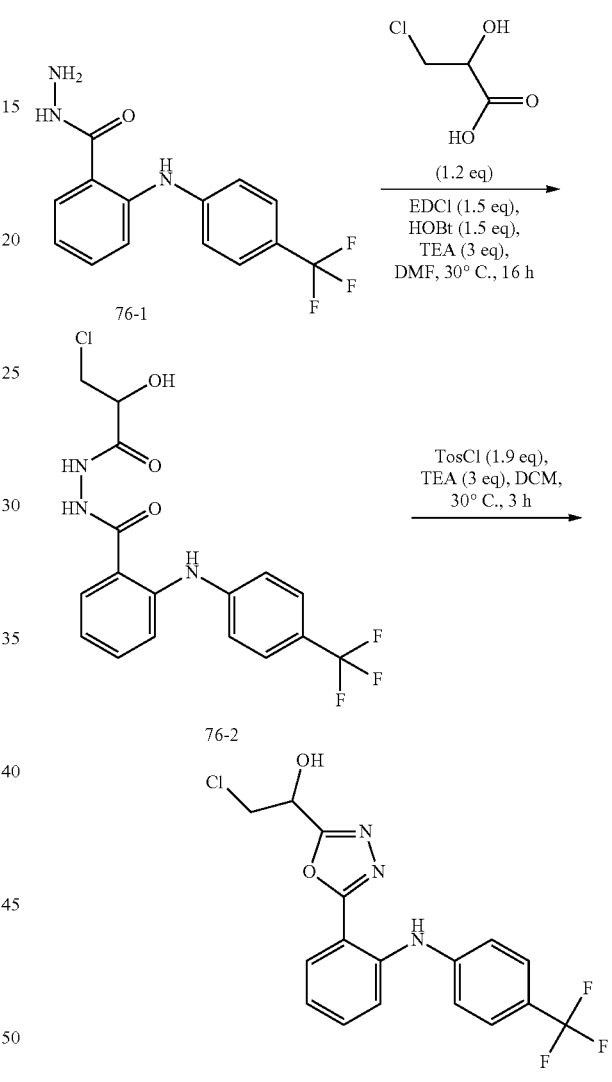

Step 1: 2-((4-(trifluoromethyl) phenyl)amino)benzohydrazide

To a solution of 76-1a (101.2 mg, 0.81 mmol, 1.2 eq), EDCI (194.8 mg, 1.02 mmol, 1.5 eq) and HOBt (137.3 mg, 1.02 mmol, 1.5 eq) in DMF (2 mL) at 30° C. were added 76-1 (200 mg, 0.68 mmol, 1 eq) and TEA (205.6 mg, 2.03 mmol, 0.28 mL, 3 eq). The mixture was stirred at 30° C. for 16 h. The reaction mixture was diluted with water (30 mL) and extracted with EA (30 mL*3). The combined organic layers were washed with water (20 mL*2) and brine (20 mL*2), dried over Na₂SO₄, filtered and concentrated under reduced pressure to give to give 76-2 (484 mg, 0.89 mmol, 87.1% yield). LCMS (ESI): RT=0.755 min, mass calc. for C$_{17}$H$_{15}$ClF$_3$N$_3$O$_3$ 401.08, m/z found 401.9 [M+H]+

Step 2: 2-chloro-1-(5-(2-((4-(trifluoromethyl)phenyl)amino)phenyl)-1,3,4-oxadiazol-2-yl)ethan-1-ol To a solution of 76-2 (262 mg, 0.65 mmol, 1 eq) in DCM (3 mL) at 30° C. were added TEA (198 mg, 1.96 mmol, 0.27 mL, 3 eq) and TosCl (236.2 mg, 1.24 mmol, 1.9 eq). The mixture was stirred at 30° C. for 3 h. The reaction mixture was diluted with water (30 mL) and extracted with EA (30 mL*3). The combined organic layers were washed with water (20 mL*2) and brine (20 mL*2), dried over Na$_2$SO$_4$, filtered and concentrated under reduced pressure to give a residue. The residue was purified by flash silica gel chromatography, prep-HPLC and prep-TLC to give Compound 81 (10 mg, 26 umol, 4.00% yield). Compound 81: LCMS (ESI): RT=0.871 min, mass calc. for C$_{17}$H$_{13}$ClF$_3$N$_3$O$_2$ 383.06, m/z found 384.0 [M+H]$^+$; $^1$H NMR (400 MHz, CDCl$_3$) δ 9.43 (brs, 1H), 7.92 (brd, J=7.8 Hz, 1H), 7.60 (brd, J=8.5 Hz, 2H), 7.51 (brd, J=8.0 Hz, 1H), 7.43 (brd, J=8.3 Hz, 1H), 7.37 (brd, J=7.5 Hz, 2H), 6.99 (brt, J=6.9 Hz, 1H), 5.33 (brs, 1H), 4.13-4.03 (m, 2H), 3.16 (brs, 1H).

Example 77: (E)-2-(5-((3-bromoallyl)oxy)-1,3,4-oxadiazol-2-yl)-N-(4-(trifluoromethyl)phenyl)aniline (Compound 82) and 2-(5-(prop-2-yn-1-yloxy)-1,3,4-oxadiazol-2-yl)-N-(4-(trifluoromethyl)phenyl)aniline (Compound 83)

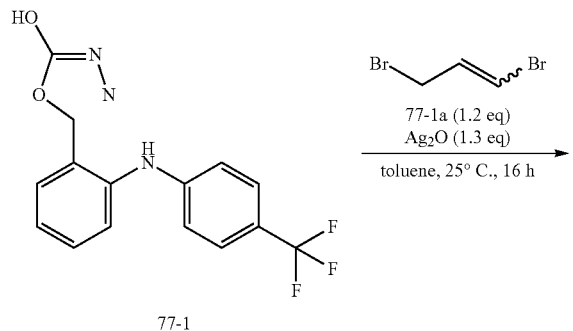

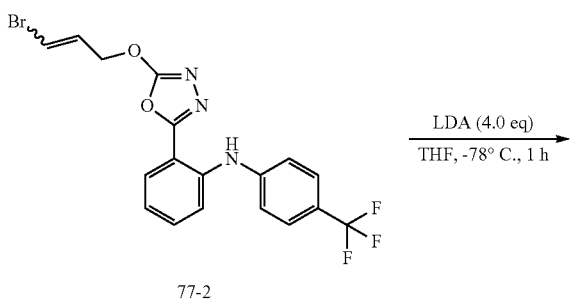

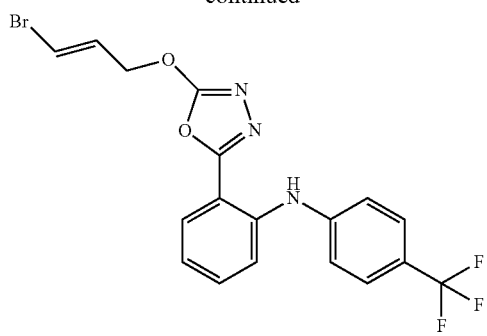

Compound 82

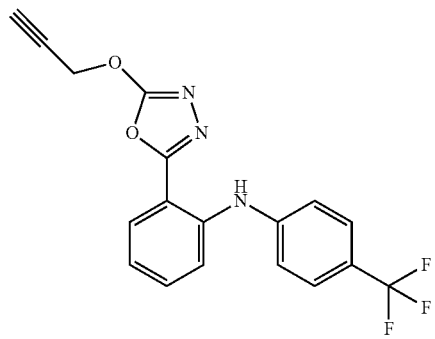

Compound 83

Step 1: 2-[5-[(Z)-3-bromoallyloxy]-1,3,4-oxadiazol-2-yl]-N-[4-(trifluoromethyl)phenyl]aniline To a solution of compound 77-1 (0.4 g, 1.25 mmol, 1 eq) and compound 77-1a (298.6 mg, 1.49 mmol, 1.2 eq) in toluene (6 mL) was added Ag$_2$O (375.1 mg, 1.62 mmol, 1.3 eq). The reaction was stirred at 25° C. for 16 hr. The reaction was filtered and concentrated. The crude product was purified by column chromatography on silica gel to give compound 77-2 (120 mg, 0.27 mmol, 21.8% yield).

Step 2: (E)-2-(5-((3-bromoallyl)oxy)-1,3,4-oxadiazol-2-yl)-N-(4-(trifluoromethyl)phenyl)aniline (Compound 82) and 2-(5-(prop-2-yn-1-yloxy)-1,3,4-oxadiazol-2-yl)-N-(4-(trifluoromethyl)phenyl)aniline (Compound 83)

To a solution of compound 77-2 (40 mg, 90.8 umol, 1 eq) in THF (2 mL) was added LDA (2 M, 0.18 mL, 4 eq) at −78° C. The reaction was stirred at −78° C. for 1 hr. The reaction was quenched by sat. NH$_4$Cl (5 mL) and extracted with EA (2*10 mL). The organic layer was dried over Na$_2$SO$_4$ and concentrated. The residue was purified by prep-HPLC to give Compound 82 (6.8 mg, 14.8 umol, 16.2% yield) LCMS (ESI): RT=1.115 min, mass calcd. for C$_8$H$_{13}$BrF$_3$N$_3$O$_2$ 439.01, m/z found 439.9 [M+H]$^+$; $^1$H NMR (400 MHz, CDCl$_3$) δ 9.30 (s, 1H), 7.76 (dd, J=1.3, 7.9 Hz, 1H), 7.58 (d, J=8.4 Hz, 2H), 7.50 (d, J=8.3 Hz, 1H), 7.39-7.33 (m, 3H), 6.96 (t, J=7.8 Hz, 1H), 6.76 (d, J=13.8 Hz, 1H), 6.53 (td, J=6.8, 13.6 Hz, 1H), 4.99 (d, J=6.9 Hz, 2H); and Compound 83 (1.6 mg, 4.4 umol, 4.8% yield) LCMS (ESI): RT=1.049 min, mass calcd. for $C_{18}H_{12}F_3N_3O_2$ 359.09, m/z found 359.9 [M+H]+; 1H NMR (400 MHz, CDCl3) δ 9.32 (s, 1H), 7.78 (dd, J=1.4, 8.0 Hz, 1H), 7.58 (d, J=8.5 Hz, 2H), 7.50 (d, J=8.4 Hz, 1H), 7.40-7.31 (m, 3H), 7.00-6.91 (m, 1H), 5.16 (d, J=2.5 Hz, 2H), 2.72 (t, J=2.4 Hz, 1H).

Example 78: 2-(5-(allyloxy)-1,3,4-oxadiazol-2-yl)-N-(4-(trifluoromethyl)phenyl)aniline (Compound 84)

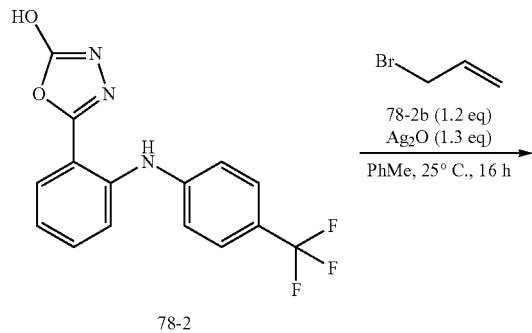

Example 79: 1-(5-(2-((4-(trifluoromethyl)phenyl)amino)phenyl)-1,3,4-oxadiazol-2-yl)ethan-1-one (Compound 85) and 2-(5-(2-methyl-1,3-dioxolan-2-yl)-1,3,4-oxadiazol-2-yl)-N-(4-(trifluoromethyl)phenyl)aniline (Compound 86)

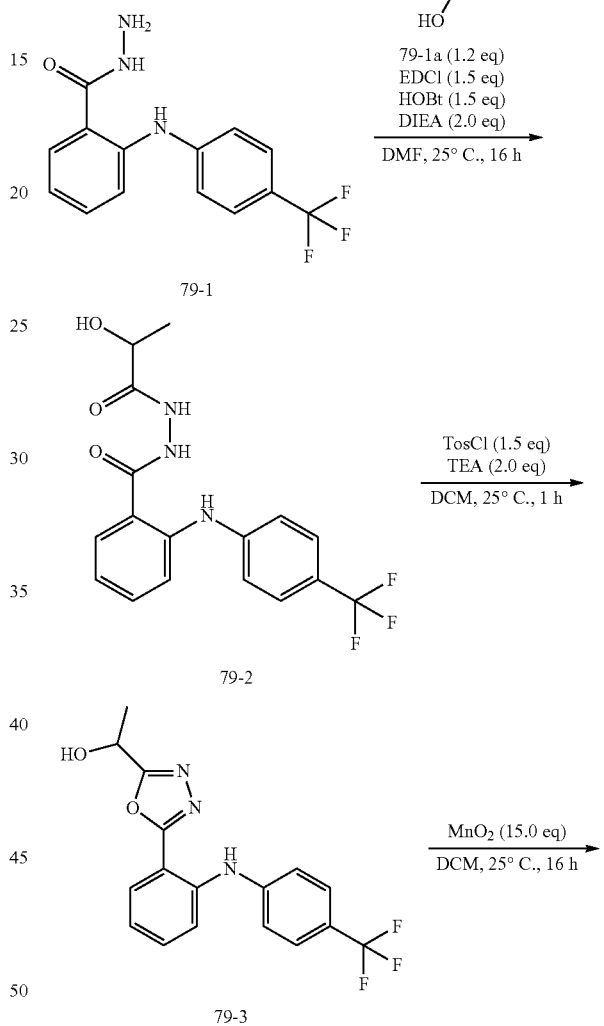

To a solution of compound 78-2 (50 mg, 0.15 mmol, 1 eq) and compound 78-2b (22.5 mg, 0.18 mmol, 16 uL, 1.2 eq) in toluene (1 mL) was added Ag2O (46.8 mg, 0.20 mmol, 9 uL, 1.3 eq) at 25° C. The reaction was stirred at 25° C. for 16 hr. The reaction was diluted with EA (20 mL), filtered and concentrated. The residue was purified by prep-HPLC to give Compound 84 (3.4 mg, 8.8 umol, 5.6% yield). LCMS (ESI): RT=1.078 min, mass calcd. For $C_{18}H_{14}F_3N_3O_2$, 361.10 m/z found 362.0 [M+H]+. 1H NMR (400 MHz, CDCl3) δ 9.35 (s, 1H), 7.77 (dd, J=1.5, 8.0 Hz, 1H), 7.57 (d, J=8.4 Hz, 2H), 7.50 (d, J=8.1 Hz, 1H), 7.39-7.33 (m, 3H), 6.99-6.93 (m, 1H), 6.18-6.05 (m, 1H), 5.62-5.52 (m, 1H), 5.45 (dd, J=1.0, 10.4 Hz, 1H), 5.04 (td, J=1.1, 6.0 Hz, 2H).

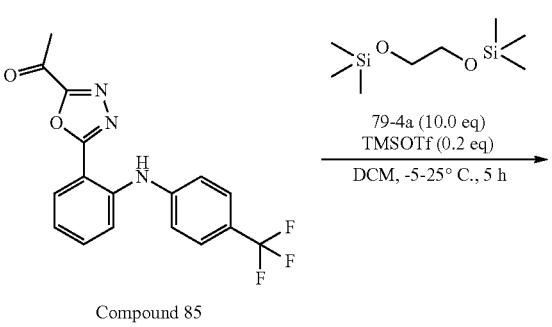

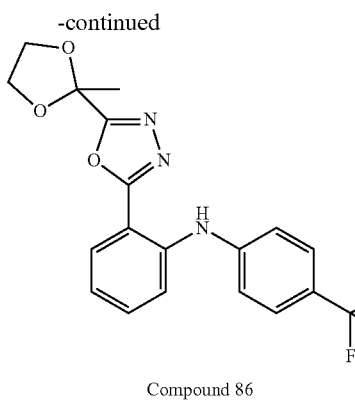

Compound 86

Step 1: N'-(2-hydroxypropanoyl)-2-[4-(trifluoromethyl)anilino]benzohydrazide To a solution of compound 79-1 (500 mg, 1.69 mmol, 1 eq) and compound 79-1a (183.0 mg, 2.03 mmol, 0.15 mL, 1.2 eq) in DMF (8 mL) were added HOBt (343.2 mg, 2.54 mmol, 1.5 eq), EDCI (486.9 mg, 2.54 mmol, 1.5 eq) and DIEA (437.7 mg, 3.39 mmol, 0.59 mL, 2 eq). The mixture was stirred at 25° C. for 16 hr. The reaction mixture was quenched with H$_2$O (15 mL), extracted with EA (15 mL*3). The combined organic phase was washed with H$_2$O (10 mL) and brine (10 mL*3), dried over Na$_2$SO$_4$, filtered and concentrated in vacuum. The crude product was used for the next step directly. LCMS confirmed that compound 79-2 (310 mg, 0.82 mmol, 48.3% yield) was obtained.

Step 2: 1-[5-[2-[4-(trifluoromethyl)anilino]phenyl]-1,3,4-oxadiazol-2-yl]ethanol To a solution of compound 79-2 (310 mg, 0.84 mmol, 1 eq) in DCM (2 mL) were added TEA (170.8 mg, 1.69 mmol, 0.23 mL, 2 eq) and TosCl (241.3 mg, 1.27 mmol, 1.5 eq). The mixture was stirred at 25° C. for 1 hr. The reaction mixture was concentrated in vacuum. The residue was diluted with EA (20 mL), washed with H$_2$O (5 mL) and brine (5 mL), dried over Na$_2$SO$_4$, filtered and concentrated in vacuum. The residue was purified by flash silica gel chromatography. LCMS confirmed that the compound 79-3 (135 mg, 0.14 mmol, 16.9% yield) was obtained.

Step 3: 1-(5-(2-((4-(trifluoromethyl)phenyl)amino)phenyl)-1,3,4-oxadiazol-2-yl)ethan-1-one (Compound 85)

To a solution of compound 79-3 (135 mg, 0.39 mmol, 1 eq) in DCM (5 mL) was added MnO$_2$ (504 mg, 5.80 mmol, 15 eq). The mixture was stirred at 25° C. for 16 hr. The reaction mixture was filtered and the filtrate was concentrated in vacuum. The crude product was purified by prep-TLC. LCMS and $^1$HNMR confirmed that Compound 85 (80 mg, 0.22 mmol, 57.2% yield) was obtained. LCMS (ESI): RT=0.939 min, mass calcd. For C$_{17}$H$_{12}$F$_3$N$_3$O$_2$, 347.09 m/z found 347.9 [M+H]$^+$. $^1$H NMR (400 MHz, CDCl$_3$) δ 9.48 (s, 1H), 8.03 (dd, J=1.5, 8.0 Hz, 1H), 7.61-7.60 (m, 1H), 7.62 (d, J=8.5 Hz, 1H), 7.53-7.48 (m, 1H), 7.48-7.42 (m, 1H), 7.39 (d, J=8.3 Hz, 2H), 7.00 (ddd, J=1.3, 6.9, 7.9 Hz, 1H), 2.83 (s, 3H).

Step 4: 2-(5-(2-methyl-1,3-dioxolan-2-yl)-1,3,4-oxadiazol-2-yl)-N-(4-(trifluoromethyl)phenyl)aniline (Compound 86)

To a solution of Compound 85 (50 mg, 0.14 mmol, 1 eq) and compound 79-4a (297.2 mg, 1.44 mmol, 10 eq) in DCM (1 mL) was added TMSOTf (6.4 mg, 28 umol, 5 uL, 0.2 eq) at −5° C. Then the mixture was warmed to 25° C. and stirred at 25° C. for 5 hr. The reaction mixture was quenched with TEA (5 drops), concentrated in vacuum. The residue was diluted with EA (20 mL), washed with H$_2$O (5 mL) and brine (5 mL), dried over Na$_2$SO$_4$, filtered and concentrated in vacuum. The crude product was purified by prep-TLC. LCMS, HPLC and $^1$HNMR confirmed that Compound 86 (17.4 mg, 42 umol, 29.6% yield) was obtained. LCMS (ESI): RT=1.037 min, mass calcd. For C$_{19}$H$_{13}$F$_3$N$_4$O, 391.34 m/z found 392.0 [M+H]$^+$. $^1$H NMR (400 MHz, CDCl$_3$) δ 9.62-9.37 (m, 1H), 7.90 (d, J=8.0 Hz, 1H), 7.59 (br d, J=8.3 Hz, 2H), 7.52 (d, J=8.5 Hz, 1H), 7.44-7.33 (m, 3H), 6.98 (t, J=7.6 Hz, 1H), 4.30-4.18 (m, 1H), 4.24 (br d, J=5.3 Hz, 3H), 1.96 (s, 3H).

Example 80: N-methoxy-N,2-dimethyl-2-(5-(2-((4-(trifluoromethyl)phenyl)amino)phenyl)-1,3,4-oxadiazol-2-yl)propanamide (Compound 87)

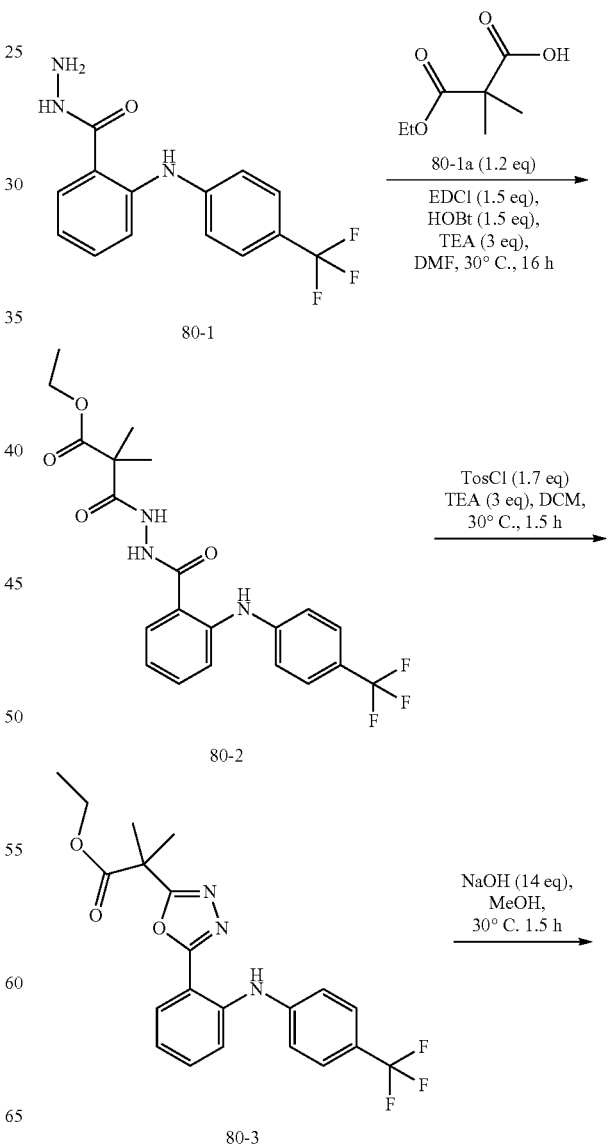

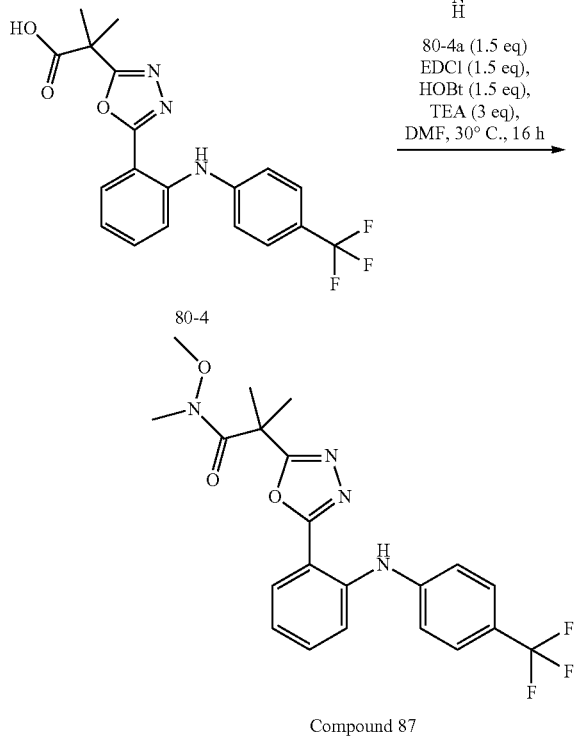

80-4

Compound 87

Step 1: Ethyl 2,2-dimethyl-3-oxo-3-(2-(2-((4-(trifluoromethyl)phenyl)amino)benzoyl)hydrazinyl)propanoate To a solution of 80-1a (195.3 mg, 1.22 mmol, 1.2 eq), EDCI (292.2 mg, 1.52 mmol, 1.5 eq) and HOBt (205.9 mg, 1.52 mmol, 1.5 eq) in DMF (20 mL) at 30° C. were added 80-1 (300 mg, 1.02 mmol, 1 eq) and TEA (308.4 mg, 3.05 mmol, 0.42 mL, 3 eq). The mixture was stirred at 30° C. for 16 h. The reaction mixture was diluted with water (30 mL) and extracted with EA (30 mL*3). The combined organic layers were washed with water (20 mL*2) and brine (20 mL), dried over $Na_2SO_4$, filtered and concentrated under reduced pressure to give 80-2 (484 mg, 0.89 mmol, 87.1% yield). LCMS (ESI): RT=0.835 min, mass calc. for $C_{21}H_{22}F_3N_3O_4$ 437.41, m/z found 438.0 $[M+H]^+$.

Step 2: ethyl2-methyl-2-(5-(2-((4-(trifluoromethyl)phenyl)amino)phenyl)-1,3,4-oxadiazol-2-yl)propanoate To a solution of 80-2 (480 mg, 1.10 mmol, 1 eq) in DCM (6 mL) at 30° C. were added TEA (333.1 mg, 3.29 mmol, 0.46 mL, 3 eq) and TosCl (355.7 mg, 1.87 mmol, 1.7 eq). The mixture was stirred at 30° C. for 1.5 h. The reaction mixture was diluted with water (20 mL), and then extracted with EA (20 mL*3). The combined organic layers were washed with brine (20 mL), dried over anhydrous $Na_2SO_4$, filtered and concentrated under reduced pressure to give a residue. The residue was purified by flash silica gel chromatography to give 80-3 (375 mg, 0.82 mmol, 75.0% yield). LCMS (ESI): RT=0.976 min, mass calc. for $C_2H_{20}F_3N_3O_3$ 419.40, m/z found 420.0 $[M+H]^+$.

Step 3: 2-methyl-2-(5-(2-((4-(trifluoromethyl)phenyl)amino)phenyl)-1,3,4-oxadiazol-2-yl)propanoic Acid To a solution of 80-3 (370 mg, 0.88 mmol, 1 eq) in MeOH (12 mL) at 30° C. was added NaOH (2 M, 6.18 mL, 14 eq). The mixture was stirred at 30° C. for 1.5 h. The reaction mixture was concentrated under reduced pressure to remove solvent. The residue was diluted with water (20 mL), then acidified with 2N HCl at 0° C. to pH=2-3, and then extracted with EA (20 mL*3). The combined organic layers were washed with brine (20 mL), dried over anhydrous $Na_2SO_4$, filtered and concentrated under reduced pressure to give 80-4 (340 mg, 0.78 mmol, 88.6% yield). LCMS (ESI): RT=0.875 min, mass calc. for $C_{19}H_{16}F_3N_3O_3$ 391.34, m/z found 392.0 $[M+H]^+$;

Step 4: N-methoxy-N,2-dimethyl-2-(5-(2-((4-(trifluoromethyl)phenyl)amino)phenyl)-1,3,4-oxadiazol-2-yl)propanamide To a solution of 80-4 (51 mg, 0.13 mmol, 1 eq) and HATU (74.3 mg, 0.20 mmol, 1.5 eq) in DMF (10 mL) at 30° C. were added 80-4a (19.1 mg, 0.20 mmol, 1.5 eq) and TEA (66.0 mg, 0.65 mmol, 91 uL, 5 eq). The mixture was stirred at 30° C. for 16 h. The reaction mixture was diluted with water (40 mL) and extracted with EA (20 mL*3). The combined organic layers were washed with water (10 mL*2) and brine (20 ml*2), dried over anhydrous $Na_2SO_4$, filtered and concentrated under reduced pressure to give a residue. The residue was purified by flash silica gel chromatography and prep-HPLC to give Compound 87 (24 mg, 52 umol, 39.9% yield). LCMS (ESI): RT=0.912 min, mass calc. for $C_{21}H_{21}F_3N_4O_3$ 434.41, m/z found 435.1 $[M+H]^+$; $^1$H NMR (400 MHz, $CDCl_3$) δ 9.58 (s, 1H), 7.87 (d, J=7.8 Hz, 1H), 7.59 (d, J=8.4 Hz, 2H), 7.53 (d, J=8.4 Hz, 1H), 7.43-7.35 (m, 3H), 7.02-6.95 (m, 1H), 3.32 (s, 3H), 3.23 (s, 3H), 1.75 (s, 6H)

Example 81: 1-((5-(2-((4-(trifluoromethyl)phenyl)amino)phenyl)-1,3,4-oxadiazol-2-yl)methyl)cyclopropane-1-carbonitrile (Compound 88)

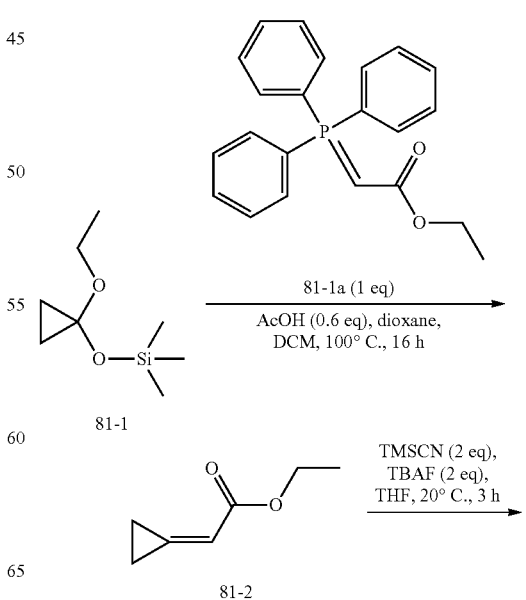

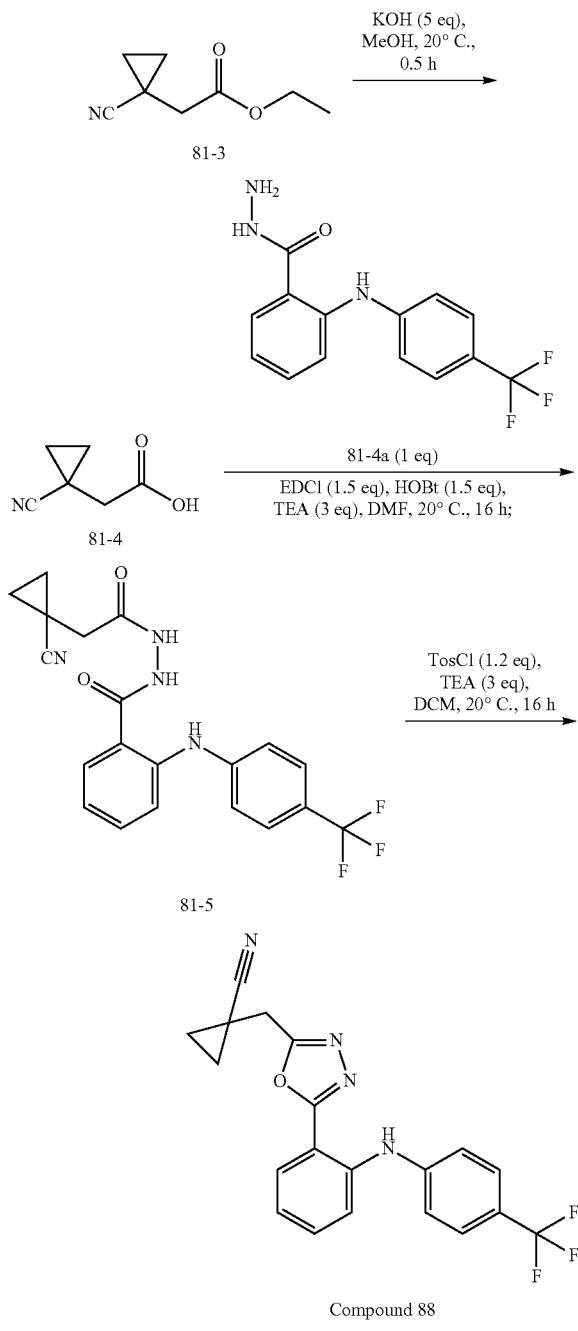

Step 1: Ethyl 2-cyclopropylideneacetate

To a solution of 81-1 (2 g, 11.47 mmol, 2.31 mL, 1.1 eq) and AcOH (375.7 mg, 6.26 mmol, 0.36 mL, 0.6 eq) in dioxane (30 mL) at 100° C. was added 81-1a (3.63 g, 10.43 mmol, 1 eq) in DCM (10 mL) drop-wise, and the mixture was stirred at 100° C. for 16 h. The mixture was concentrated to give a residue. The residue was purified by flash silica gel chromatography to give 81-2 (450 mg, 3.57 mmol, 34.2% yield) (volatile). $^1$H NMR (400 MHz, CDCl$_3$) δ 6.23 (quin, J=1.9 Hz, 1H), 4.22 (q, J=7.1 Hz, 2H), 1.49-1.42 (m, 2H), 1.31 (t, J=7.2 Hz, 3H), 1.26-1.21 (m, 2H).

Step 2: Ethyl 2-(1-cyanocyclopropyl)acetate

To a solution of TBAF (1 M, 1.59 mL, 2 eq) at 20° C. was added TMSCN (157.3 mg, 1.59 mmol, 0.20 mL, 2 eq). And then the mixture was stirred at 20° C. for 0.5 h. And then a solution of 81-2 (100 mg, 0.79 mmol, 1 eq) in THF (0.5 mL) was added at 20° C. into the above mixture. The resulting mixture was stirred at 20° C. for 2.5 h. The reaction mixture was concentrated under reduced pressure to give a residue. The residue was purified by flash silica gel chromatography to give 81-3 (110 mg, 0.72 mmol, 90.6% yield). $^1$H NMR (400 MHz, CDCl$_3$) δ 4.23 (q, J=7.1 Hz, 2H), 2.49 (s, 2H), 1.40-1.35 (m, 2H), 1.31 (t, J=7.0 Hz, 3H), 0.98-0.93 (m, 2H).

Step 3: 2-(1-cyanocyclopropyl)acetic Acid

To a solution of KOH (201.5 mg, 3.59 mmol, 5 eq) in MeOH (4 mL) at 20° C. was added 81-3 (110 mg, 0.72 mmol, 1 eq). And then the mixture was stirred at 20° C. for 0.5 h. The reaction mixture was concentrated under reduced pressure to give a residue. The residue was diluted with water (10 mL), then acidified with 2 N HCl to pH=1-2, and then extracted with EA (20 mL*3). The combined organic layers were washed with brine (20 mL), dried over Na$_2$SO$_4$, filtered and concentrated under reduced pressure to give 81-4 (86 mg, 0.69 mmol, 95.7% yield). $^1$H NMR (400 MHz, CDCl$_3$) δ 2.58 (s, 2H), 1.45-1.37 (m, 2H), 1.02-0.95 (m, 2H).

Step 4: N'-(2-(1-cyanocyclopropyl)acetyl)-2-((4-(trifluoromethyl)phenyl)amino)benzohydrazide To a solution of 81-4 (81.4 mg, 0.65 mmol, 1.2 eq), EDCI (155.8 mg, 0.81 mmol, 1.5 eq), HOBt (109.8 mg, 0.81 mmol, 1.5 eq) and 81-4a (160 mg, 0.54 mmol, 1 eq) in DMF (2 mL) at 20° C. was added TEA (164.5 mg, 1.63 mmol, 0.23 mL, 3 eq). And then the mixture was stirred at 20° C. for 16 h. The reaction mixture was concentrated under reduced pressure to give a residue. The residue was diluted with water (20 mL), and then extracted with EA (20 mL*3). The combined organic layers were washed with brine (20 mL), dried over Na$_2$SO$_4$, filtered and concentrated under reduced pressure to give 81-5 (240 mg, 0.45 mmol, 83.7% yield), which was used directly for next step. LCMS (ESI): RT=0.788 min, mass calc. for C$_{20}$H$_{17}$F$_3$N$_4$O$_2$ 402.13, m/z found 403.0 [M+H]$^+$.

Step 5: 1-((5-(2-((4-(trifluoromethyl)phenyl)amino) phenyl)-1,3,4-oxadiazol-2-yl)methyl)cyclopropane-1-carbonitrile To a solution of 81-5 (140 mg, 0.26 mmol, 1 eq) and TEA (80.3 mg, 0.79 mmol, 0.11 mL, 3 eq) in DCM (1 mL) at 20° C. was added TosCl (60.5 mg, 0.32 mmol, 1.2 eq). And then the mixture was stirred at 20° C. for 16 h. The reaction mixture was concentrated under reduced pressure to give a residue. The residue was purified by flash silica gel chromatography to give Compound 88 (55 mg, 0.14 mmol, 54.1% yield). LCMS (ESI): RT=0.876 min, mass calc. for C$_{20}$H$_{15}$F$_3$N$_4$O 384.12, m/z found 385.0 [M+H]$^+$; $^1$H NMR (400 MHz, CDCl$_3$) δ 9.45 (s, 1H), 7.93 (dd, J=1.4, 7.9 Hz, 1H), 7.59 (d, J=8.3 Hz, 2H), 7.54-7.49 (m, 1H), 7.44-7.39 (m, 1H), 7.38 (d, J=8.3 Hz, 2H), 7.00 (t, J=7.7 Hz, 1H), 3.19 (s, 2H), 1.52-1.46 (m, 2H), 1.20-1.14 (m, 2H).

Example 82: 2,2-dimethyl-3-(5-(2-((4-(trifluoromethyl)phenyl)amino)phenyl)-1,3,4-oxadiazol-2-yl)propanenitrile (Compound 89)

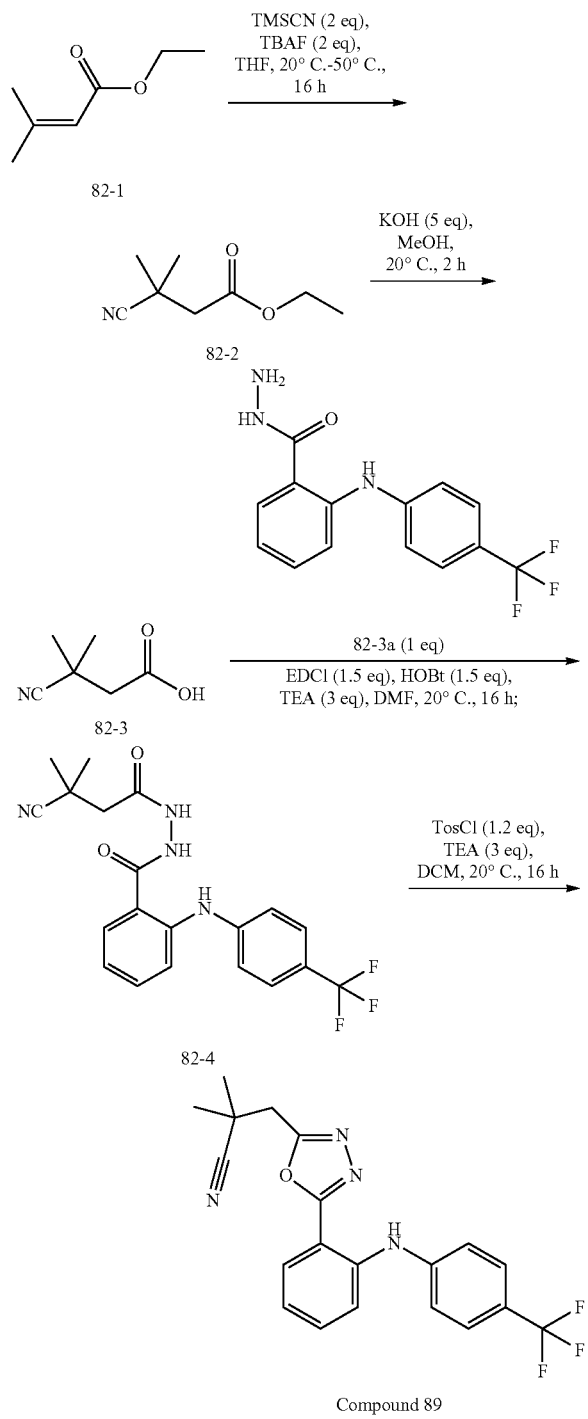

Step 1: Ethyl 3-cyano-3-methylbutanoate

To a solution of TBAF (1 M, 3.12 mL, 2 eq) in THF (0.5 mL) at 20° C. was added TMSCN (309.6 mg, 3.12 mmol, 0.39 mL, 2 eq). And then the mixture was stirred at 20° C. for 0.5 h. And then ethyl 82-1 (200 mg, 1.56 mmol, 0.22 mL, 1 eq) was added at 20° C. into the above mixture. The resulting mixture was stirred at 50° C. for 16 h. The reaction mixture was concentrated under reduced pressure to give a residue. The residue was purified by flash silica gel chromatography to give 82-2 (130 mg, 0.84 mmol, 53.7% yield) was obtained. $^1$H NMR (400 MHz, CDCl$_3$) δ 4.21 (q, J=6.9 Hz, 2H), 2.57 (s, 2H), 1.48 (s, 6H), 1.30 (t, J=7.1 Hz, 3H).

Step 2: 3-cyano-3-methylbutanoic Acid

To a solution of KOH (235.0 mg, 4.19 mmol, 5 eq) in MeOH (3 mL) at 20° C. was added 82-2 (130 mg, 0.84 mmol, 1 eq). And then the mixture was stirred at 20° C. for 2 h. The reaction mixture was concentrated under reduced pressure to give a residue. The residue was diluted with water (10 mL), then acidified with 2 N HCl to pH=1-2, and then extracted with EA (20 mL*3). The combined organic layers were washed with brine (20 mL), dried over Na$_2$SO$_4$, filtered and concentrated under reduced pressure to give 82-3 (105 mg, 0.83 mmol, 98.6% yield), which was used directly for next step. $^1$H NMR (400 MHz, CDCl$_3$) δ 2.65 (s, 2H), 1.51 (s, 6H).

Step 3: N'-(3-cyano-3-methylbutanoyl)-2-((4-(trifluoromethyl)phenyl)amino)benzohydrazide To a solution of 82-3 (103.4 mg, 0.81 mmol, 1.2 eq), EDCI (194.8 mg, 1.02 mmol, 1.5 eq), HOBt (137.3 mg, 1.02 mmol, 1.5 eq) and 82-3a (200 mg, 0.68 mmol, 1 eq) in DMF (2 mL) at 20° C. was added TEA (205.6 mg, 2.03 mmol, 0.28 mL, 3 eq). And then the mixture was stirred at 20° C. for 16 h. The reaction mixture was concentrated under reduced pressure to give a residue. The residue was diluted with water (20 mL), and then extracted with EA (20 mL*3). The combined organic layers were washed with brine (20 mL), dried over Na$_2$SO$_4$, filtered and concentrated under reduced pressure to give 82-4 (320 mg, 0.58 mmol, 85.3% yield), which was used directly for next step. LCMS (ESI): RT=0.841 min, mass calc. for C$_{20}$H$_{19}$F$_3$N$_4$O$_2$ 404.15, m/z found 405.0 [M+H]$^+$.

Step 4: 2,2-dimethyl-3-(5-(2-((4-(trifluoromethyl)phenyl)amino)phenyl)-1,3,4-oxadiazol-2-yl)propanenitrile To a solution of 82-4 (180 mg, 0.32 mmol, 1 eq) and TEA (98.6 mg, 0.97 mmol, 0.14 mL, 3 eq) in DCM (1 mL) at 20° C. was added TosCl (74.3 mg, 0.39 mmol, 1.2 eq). And then the mixture was stirred at 20° C. for 16 h. The reaction mixture was concentrated under reduced pressure to give a residue. The residue was purified by flash silica gel chromatography to give Compound 89 (45 mg, 0.11 mmol, 34.1% yield). LCMS (ESI): RT=0.895 min, mass calc. for C$_{20}$H$_{17}$F$_3$N$_4$O 386.14, m/z found 387.0 [M+H]$^+$; $^1$H NMR (400 MHz, CDCl$_3$) δ 9.44 (s, 1H), 7.93 (dd, J=1.3, 8.0 Hz, 1H), 7.59 (d, J=8.5 Hz, 2H), 7.51 (d, J=8.0 Hz, 1H), 7.44-7.39 (m, 1H), 7.38 (d, J=8.8 Hz, 2H), 7.01-6.97 (m, 1H), 3.27 (s, 2H), 1.57 (s, 6H).

Example 83: 2-(5-ethyl-1,3,4-oxadiazol-2-yl)-N-(4-(trifluoromethyl)phenyl)aniline (Compound 90)

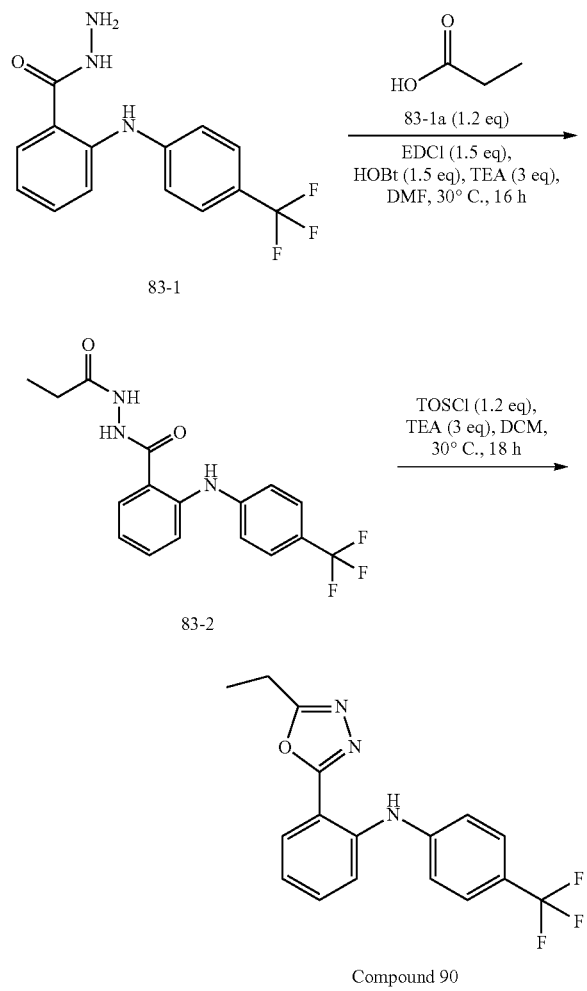

Step 1: N'-propionyl-2-((4-(trifluoromethyl)phenyl)amino)benzohydrazide

To a solution of 83-1a (30.1 mg, 0.41 mmol, 30 uL, 1.2 eq), EDCI (97.4 mg, 0.51 mmol, 1.5 eq) and HOBt (68.7 mg, 0.51 mmol, 1.5 eq) in DMF (1 mL) at 30° C. were added 83-1 (100 mg, 0.34 mmol, 1 eq) and TEA (102.8 mg, 1.02 mmol, 0.14 mL, 3 eq). The mixture was stirred at 30° C. for 16 h. The reaction mixture was diluted with water (20 mL) and extracted with EA (20 mL*3). The combined organic layers were washed with water (20 mL) and brine (20 mL), dried over $Na_2SO_4$, filtered and concentrated under reduced pressure to give 83-2 (140 mg, 0.20 mmol, 58.8% yield). LCMS (ESI): RT=0.764 min, mass calc. for $C_{17}H_{16}F_3N_3O_2$ 351.12, m/z found 351.9 $[M+H]^+$.

Step 2: 2-(5-ethyl-1,3,4-oxadiazol-2-yl)-N-(4-(trifluoromethyl)phenyl)aniline

To a solution of 83-2 (134 mg, 0.19 mmol, 1 eq) in DCM (2 mL) at 30° C. were added TEA (57.9 mg, 0.57 mmol, 80 uL, 3 eq) and TosCl (43.6 mg, 0.23 mmol, 1.2 eq). The mixture was stirred at 30° C. for 18 h. The reaction mixture was concentrated under reduced pressure to give the residue which was purified by prep-HPLC to give Compound 90 (32 mg, 96.0 umol, 50.3% yield). LCMS (ESI): RT=0.935 min, mass calc. for $C_{17}H_{14}F_3N_3O$ 333.11, m/z found 333.9 $[M+H]^+$; $^1H$ NMR (400 MHz, $CDCl_3$) δ 9.56 (s, 1H), 7.89 (dd, J=1.4, 7.9 Hz, 1H), 7.58 (d, J=8.3 Hz, 2H), 7.52 (d, J=8.5 Hz, 1H), 7.41-7.35 (m, 3H), 7.00-6.95 (m, 1H), 2.99 (q, J=7.5 Hz, 2H), 1.47 (t, J=7.5 Hz, 3H).

Example 84: 2-(5-(2-(isopropylamino)ethyl)-1,3,4-oxadiazol-2-yl)-N-(4-(trifluoromethyl)phenyl)aniline (Compound 91), tert-butyl isopropyl(2-(5-(2-((4-(trifluoromethyl)phenyl)amino)phenyl)-1,3,4-oxadiazol-2-yl)ethyl)carbamate (Compound 92), and N-isopropyl-N-(2-(5-(2-((4-(trifluoromethyl)phenyl)amino)phenyl)-1,3,4-oxadiazol-2-yl)ethyl)cyanamide (Compound 93)

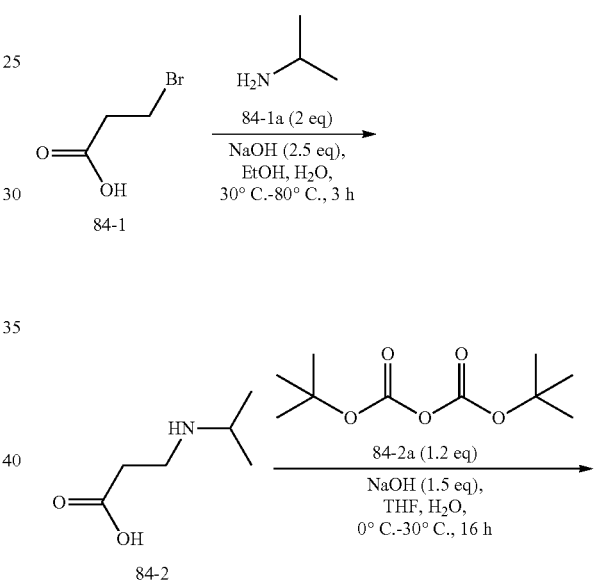

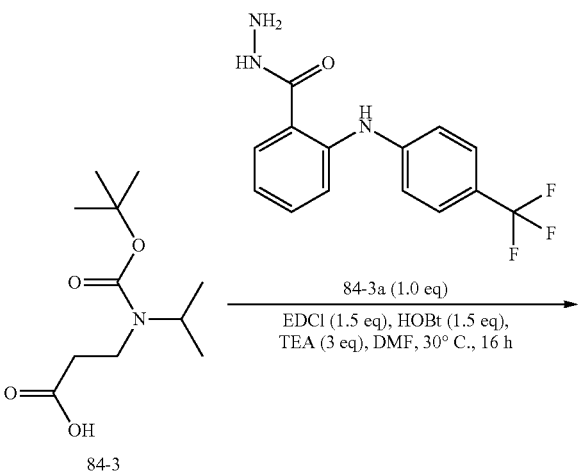

-continued

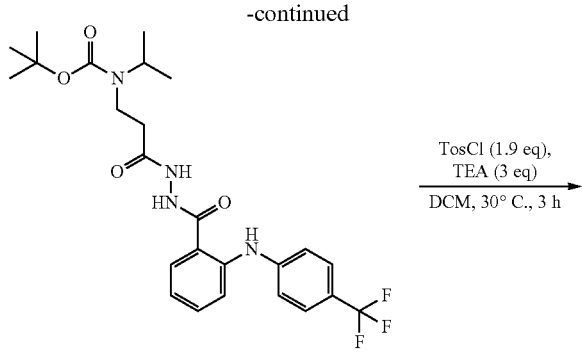

84-4

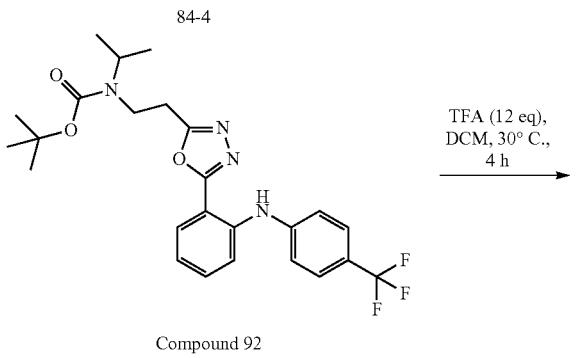

Compound 92

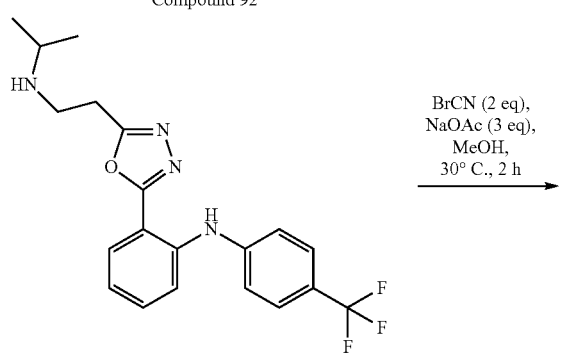

Compound 91

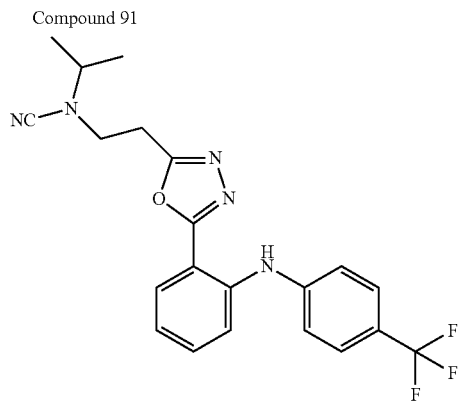

Compound 93

Step 1: 3-(isopropylamino)propanoic Acid

To a solution of 84-1 (1.6 g, 10.72 mmol, 1.11 mL, 1 eq) in EtOH (30 mL) at 30° C. was added 84-1a (1.3 g, 21.44 mmol, 1.84 mL, 2 eq). The mixture was stirred at 80° C. for 3 h. To the resulting mixture was added the solution of NaOH (1.1 g, 26.80 mmol, 2.5 eq) in water (10 mL). The reaction mixture was concentrated under reduced pressure to give 84-2 (2.05 g, 10.71 mmol, 99.9% yield) was obtained. Crude $^1$H NMR (400 MHz, DMSO-$d_6$) δ 2.70-2.61 (m, 1H), 2.56 (t, J=6.6 Hz, 2H), 2.04-2.00 (m, 2H), 0.93 (d, J=6.1 Hz, 6H).

Step 2: 3-((tert-butoxycarbonyl)(isopropyl)amino)propanoic Acid Compound

To a solution 84-2 (2.1 g, 10.71 mmol, 1 eq) and NaOH (642.4 mg, 16.06 mmol, 1.5 eq) in THF (10 mL) and water (10 mL) at 0° C. was added 84-2a (2.8 g, 12.85 mmol, 2.95 mL, 1.2 eq). The mixture stirred at 30° C. for 16 h. The reaction mixture was concentrated under reduced pressure to remove solvent and then extracted with petroleum ether (20 mL*2) to give the residue. The residue was diluted with water (20 mL), then acidified with 2N HCl at 0° C. to pH=2.5, and then extracted with EA (20 mL*3). The combined organic layers were washed with water (20 mL) and brine (20 mL), dried over anhydrous Na$_2$SO$_4$, filtered and concentrated under reduced pressure to give 84-3 (920 mg, 3.58 mmol, 33.4% yield). Crude $^1$H NMR (400 MHz, DMSO-$d_6$) δ 12.22 (brs, 1H), 4.18-3.92 (m, 1H), 3.27-3.21 (m, 2H), 2.44-2.36 (m, 2H), 1.39 (s, 9H), 1.06 (brd, J=6.8 Hz, 6H).

Step 3: Tert-Butyl Isopropyl(3-oxo-3-(2-(2-((4-(trifluoromethyl)phenyl)amino)benzoyl)hydrazinyl)propyl)carbamate To a solution of 84-3 (188.0 mg, 0.81 mmol, 1.2 eq), EDCI (194.8 mg, 1.02 mmol, 1.5 eq) and HOBt (137.3 mg, 1.02 mmol, 1.5 eq) in DMF (4 mL) at 30° C. were added 84-3a (200 mg, 0.68 mmol, 1 eq) and TEA (205.6 mg, 2.03 mmol, 0.28 mL, 3 eq). The mixture was stirred at 30° C. for 16 h. The reaction mixture was diluted with water (20 mL) and extracted with EA (20 mL*3). The combined organic layers were washed with water (20 mL) and brine (20 mL), dried over Na$_2$SO$_4$, filtered and concentrated under reduced pressure to give 84-4 (370 mg, 0.51 mmol, 75.2% yield). LCMS (ESI): R=0.877 min, mass calcd. For C$_{25}$H$_{31}$F$_3$N$_4$O$_4$ 508.23 m/z found 531.1 [M+Na]$^+$.

Step 4: Tert-Butyl Isopropyl(2-(5-(2-((4-(trifluoromethyl)phenyl)amino)phenyl)-1,3,4-oxadiazol-2-yl)ethyl)carbamate (Compound 92)

To a solution of 84-4 (338 mg, 0.47 mmol, 1 eq) in DCM (3 mL) at 30° C. were added TEA (141.2 mg, 1.40 mmol, 0.19 mL, 3 eq) and TosCl (168.5 mg, 0.88 mmol, 1.9 eq). The mixture was stirred at 30° C. for 3 h. The reaction mixture was concentrated under reduced pressure to give a residue. The residue was purified by flash silica gel chromatography to give Compound 92 (180 mg, 0.34 mmol, 74.1% yield). LCMS (ESI): RT=1.017 min, mass calc. for C$_{25}$H$_{29}$F$_3$N$_4$O$_3$ 490.22, m/z found 491.1 [M+H]$^+$; $^1$H NMR (400 MHz, CDCl$_3$) δ 9.52 (s, 1H), 7.87 (brd, J=7.5 Hz, 1H), 7.58 (d, J=8.5 Hz, 2H), 7.51 (d, J=8.4 Hz, 1H), 7.42-7.35 (m, 3H), 6.97 (t, J=7.2 Hz, 1H), 4.45-4.08 (m, 1H), 3.57 (brd, J=7.0 Hz, 2H), 3.23 (brd, J=8.6 Hz, 2H), 1.47 (s, 9H), 1.16 (d, J=6.9 Hz, 6H).

Step 5: 2-(5-(2-(isopropylamino)ethyl)-1,3,4-oxadiazol-2-yl)-N-(4-(trifluoromethyl)phenyl)aniline (Compound 91)

To a solution of Compound 92 (160 mg, 0.33 mmol, 1 eq) in DCM (3 mL) at 30° C. was added TFA (446.3 mg, 3.91 mmol, 0.29 mL, 12 eq). The mixture was stirred at 30° C. for 4 h. The reaction mixture was concentrated under reduced pressure to give a residue. The residue was diluted with water (20 mL), Na$_2$CO$_3$ (20 mL) and extracted with EA (20 mL*3). The combined organic layers were washed with brine (20 mL), dried over Na$_2$SO$_4$, filtered and concentrated under reduced pressure to give a residue. The residue was purification by prep-HPLC to give Compound 91 (90 mg, 0.23 mmol, 70.0% yield). LCMS (ESI): RT=0.750 min, mass calc. for C$_{20}$H2F$_3$N$_4$O 390.17, m/z found 391.0 [M+H]$^+$; $^1$H NMR (400 MHz, CDCl$_3$) δ 9.49 (s, 1H), 7.89-7.84 (m, 1H), 7.58 (d, J=8.5 Hz, 2H), 7.51 (d, J=8.0 Hz, 1H), 7.42-7.35 (m, 3H), 6.97 (t, J=7.5 Hz, 1H), 3.24 (s, 4H), 3.06-2.96 (m, 1H), 1.18 (d, J=6.3 Hz, 6H)

Step 6: N-isopropyl-N-(2-(5-(2-((4-(trifluoromethyl)phenyl)amino)phenyl)-1,3,4-oxadiazol-2-yl)ethyl)cyanamide (Compound 93)

To a solution of Compound 91 (40.0 mg, 0.10 mmol, 1 eq) and NaOAc (25.2 mg, 0.31 mmol, 3 eq) in MeOH (1 mL) at 30° C. was added cyanogen bromide (21.7 mg, 0.20 mmol, 15 uL, 2 eq), and the resulting mixture was stirred at 30° C. for 2 h. The reaction mixture was diluted with water (20 mL), and then extracted with EA (20 mL*3). The combined organic layers were washed with brine (20 mL), dried over anhydrous Na$_2$SO$_4$, filtered and concentrated under reduced pressure to give a residue. The residue was purified by prep-HPLC to give Compound 93 (14.9 mg, 36 umol, 35.0% yield). LCMS (ESI): RT=0.896 min, mass calc. for C$_{21}$H$_{20}$F$_3$N$_5$O 415.16, m/z found 438.0 [M+Na]$^+$; $^1$H NMR (400 MHz, CDCl$_3$) δ 9.44 (s, 1H), 7.89 (dd, J=1.4, 7.9 Hz, 1H), 7.58 (d, J=8.3 Hz, 2H), 7.51 (d, J=8.5 Hz, 1H), 7.43-7.34 (m, 3H), 6.98 (t, J=7.5 Hz, 1H), 3.60-3.55 (m, 2H), 3.33 (t, J=7.0 Hz, 2H), 3.30-3.25 (m, 1H), 1.30 (d, J=6.5 Hz, 6H).

Example 85: 2-(5-(2-(ethylamino)ethyl)-1,3,4-oxadiazol-2-yl)-N-(4-(trifluoromethyl)phenyl)aniline (Compound 94), tert-butyl ethyl(2-(5-(2-((4-(trifluoromethyl)phenyl)amino)phenyl)-1,3,4-oxadiazol-2-yl)ethyl)carbamate (Compound 95), and N-ethyl-N-(2-(5-(2-((4-(trifluoromethyl)phenyl)amino)phenyl)-1,3,4-oxadiazol-2-yl)ethyl)cyanamide (Compound 96)

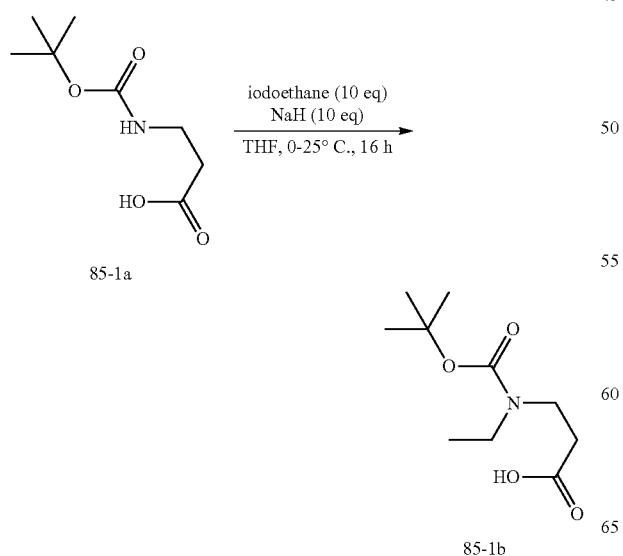

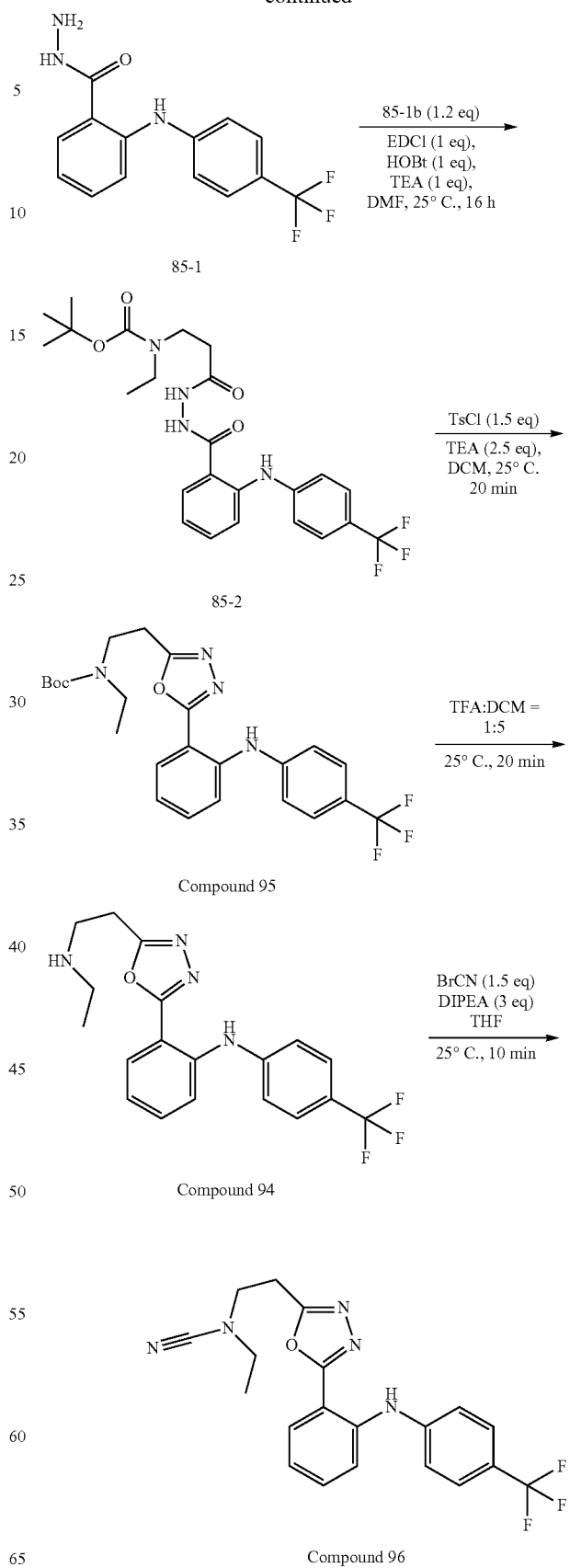

Step 1: 3-((tert-butoxycarbonyl)(ethyl)amino)propanoic Acid

To a solution of 3-(tert-butoxycarbonylamino)propanoic acid 85-1a (500 mg, 2.64 mmol, 1 eq) and iodoethane (4.12 g, 26.43 mmol, 2.11 mL, 10 eq) in THF (20 mL) was added NaH (1.06 g, 26.43 mmol, 60% purity, 10 eq) slowly in portions (gas evolved) over a period of 1 hr at 0° C. Then the mixture was stirred at 25° C. for 16 h. The mixture was quenched with water (20 mL) at 0° C. and extracted with EA (20 mL) twice. The separated aqueous layer was cooled in ice-water bath and adjusted to pH~3 with 1 M HCl and then extracted with EA (30 mL) twice. The combined organic layer was washed with brine (15 mL), dried by anhydrous $Na_2SO_4$, filtered and concentrated to give 3-[tert-butoxycarbonyl(ethyl)amino]propanoic acid 85-1b (500 mg, 2.30 mmol, 87.1% yield). No purification and used directly for next step. $^1$H NMR (400 MHz, DMSO-$d_6$) δ 3.39-3.29 (m, 2H), 3.21-3.13 (m, 2H), 2.46-2.38 (m, 2H), 1.92 (s, 1H), 1.42-1.38 (m, 9H), 1.06-0.97 (m, 3H).

Step 2: Tert-Butyl Ethyl(3-oxo-3-(2-(2-((4-(trifluoromethyl)phenyl)amino)benzoyl)hydrazinyl)propyl)carbamate To a solution of 85-1 (250 mg, 0.85 mmol, 1 eq) and 3-[tert-butoxycarbonyl(ethyl)amino]propanoic acid (220.7 mg, 1.02 mmol, 1.2 eq), HOBt (114.4 mg, 0.85 mmol, 1 eq) and EDCI (162.3 mg, 0.85 mmol, 1 eq) in DMF (3 mL) was added TEA (85.7 mg, 0.85 mmol, 0.12 mL, 1 eq) at 25° C. Then the mixture was stirred at 25° C. for 16 hr. The mixture was diluted with EA (100 mL), washed with saturated aq. $NH_4Cl$ (15 mL*2) and brine (15 mL*2) in turns, dried by anhydrous $Na_2SO_4$, filtered and concentrated to give 85-2 (600 mg, crude). No purification and used directly for next step. LCMS (ESI): R=0.979 min, mass calcd. For $C_{24}H_{29}F_3N_4O_4$ 494.21 m/z found 517 [M+23]$^+$.

Step 3: Tert-Butyl Ethyl(2-(5-(2-((4-(trifluoromethyl)phenyl)amino)phenyl)-1,3,4-oxadiazol-2-yl)ethyl)carbamate (Compound 95)

To a solution of 85-2 (500 mg, 1.01 mmol, 1 eq) and TosCl (289.1 mg, 1.52 mmol, 1.5 eq) in DCM (15 mL) was added TEA (255.8 mg, 2.53 mmol, 0.35 mL, 2.5 eq) at 25° C. Then the mixture was stirred at 25° C. for 20 min. The reaction mixture was quenched with water (5 mL) and diluted with DCM (100 mL), washed with saturated aq. $NH_4Cl$ (15 mL*2) and brine (15 mL*2) in turns, dried by anhydrous $Na_2SO_4$, filtered and concentrated to give a residue (500 mg). The residue was purified by prep-HPLC to give Compound 95 (140 mg, 0.29 mmol, 28.5% yield). LCMS (ESI): R=1.112 min, mass calcd. For $C_{24}H_{27}F_3N_4O_3$ 476.20 m/z found 477.1 [M+1]$^+$. $^1$H NMR (400 MHz, DMSO-$d_6$) δ 9.24 (br d, J=16.1 Hz, 1H), 7.89 (d, J=7.5 Hz, 1H), 7.64 (d, J=8.5 Hz, 2H), 7.60-7.48 (m, 2H), 7.36 (d, J=8.5 Hz, 2H), 7.19-7.10 (m, 1H), 3.56 (t, J=6.5 Hz, 2H), 3.27-3.06 (m, 4H), 1.38-1.10 (m, 9H), 1.04 (br t, J=6.9 Hz, 3H).

Step 4: 2-(5-(2-(ethylamino)ethyl)-1,3,4-oxadiazol-2-yl)-N-(4-(trifluoromethyl)phenyl)aniline (Compound 94)

To a solution of Compound 95 (130 mg, 0.27 mmol, 1 eq) in DCM (3 mL) was added TFA (933.3 mg, 8.18 mmol, 0.61 mL, 30 eq) at 25° C. Then the resulting mixture was stirred at 25° C. for 20 min. The mixture was concentrated at 25° C. to give a residue. The residue was lyophilized to give Compound 94 (130 mg, 0.26 mmol, 93.9% yield, TFA). LCMS (ESI): R=0.845 min, mass calcd. For $C_{19}H_{19}F_3N_4O$ 376.15 m/z found 377.1 [M+1]$^+$; $^1$H NMR (400 MHz, DMSO-$d_6$) δ 9.24 (s, 1H), 8.64 (br s, 2H), 7.94 (dd, J=1.1, 7.9 Hz, 1H), 7.65 (d, J=8.6 Hz, 2H), 7.62-7.51 (m, 2H), 7.38 (d, J=8.5 Hz, 2H), 7.20-7.12 (m, 1H), 3.47-3.35 (m, 4H), 3.05 (q, J=7.3 Hz, 2H), 1.20 (t, J=7.3 Hz, 3H).

Step 5: N-ethyl-N-(2-(5-(2-((4-(trifluoromethyl)phenyl)amino)phenyl)-1,3,4-oxadiazol-2-yl)ethyl)cyanamide (Compound 96)

To a solution of Compound 94 (50 mg, 0.1 mmol, 1 eq, TFA) and DIPEA (39.5 mg, 0.3 mmol, 53 uL, 3 eq) in THF (2 mL) was added BrCN (16.2 mg, 0.15 mmol, 11 uL, 1.5 eq) at 25° C. Then the resulting mixture was stirred at 25° C. for 10 min. The mixture was quenched with water (5 mL) and diluted with EA (100 mL), washed with saturated aq. $NH_4C$ (15 mL*2) and brine (15 mL*2) in turns, dried by anhydrous $Na_2SO_4$, filtered and concentrated to give a residue. The residue was purified by prep-HPLC to give Compound 96 (20.3 mg, 50 umol, 49.3% yield). LCMS (ESI): R=0.992 min, mass calcd. For $C_{20}H_{18}F_3N_5O$ 401.15 m/z found 402.0 [M+1]$^+$; $^1$H NMR (400 MHz, DMSO-$d_6$) δ 9.24 (s, 1H), 7.95 (br d, J=7.5 Hz, 1H), 7.64 (br d, J=8.5 Hz, 2H), 7.60-7.45 (m, 2H), 7.38 (br d, J=8.3 Hz, 2H), 7.14 (br t, J=7.0 Hz, 1H), 3.54 (br t, J=6.7 Hz, 2H), 3.27 (br t, J=6.5 Hz, 2H), 3.10 (q, J=7.3 Hz, 2H), 1.14 (t, J=7.2 Hz, 3H).

Example 86: 2-(5-((isopropylamino)methyl)-1,3,4-oxadiazol-2-yl)-N-(4-(trifluoromethyl)phenyl)aniline (Compound 97), tert-butyl isopropyl((5-(2-((4-(trifluoromethyl)phenyl)amino)phenyl)-1,3,4-oxadiazol-2-yl)methyl)carbamate (Compound 98), and N-isopropyl-N-((5-(2-((4-(trifluoromethyl)phenyl)amino)phenyl)-1,3,4-oxadiazol-2-yl)methyl)cyanamide (Compound 99)

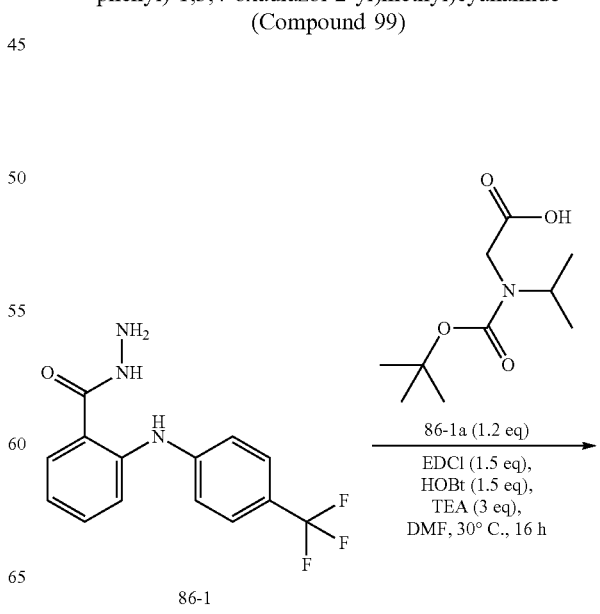

287
-continued

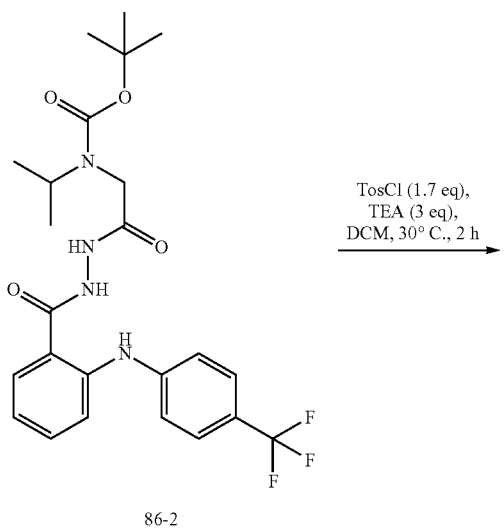

86-2

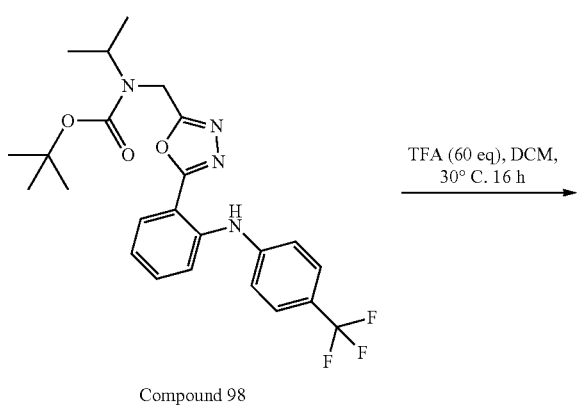

Compound 98

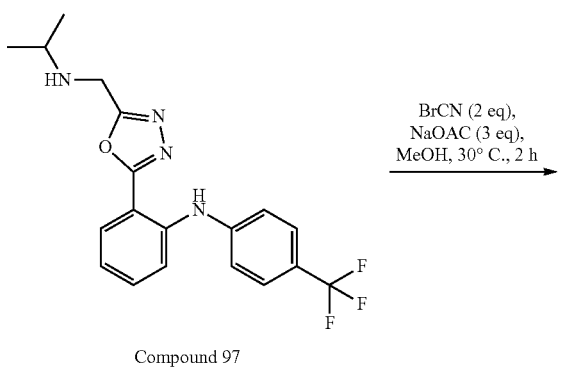

Compound 97

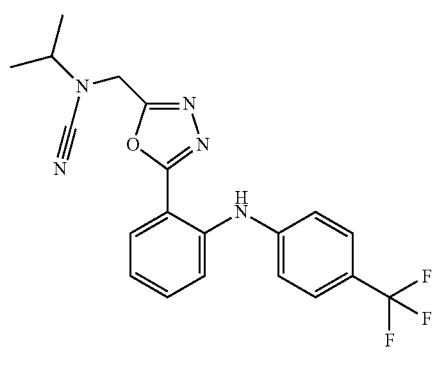

Compound 99

288

Step 1: Tert-Butyl Isopropyl(2-oxo-2-(2-(2-((4-(trifluoromethyl)phenyl)amino)benzoyl)hydrazinyl)ethyl)carbamate To a solution of 86-1 (200.0 mg, 0.68 mmol, 1.0 eq), EDCI (194.8 mg, 1.02 mmol, 1.5 eq) and HOBt (137.3 mg, 1.02 mmol, 1.5 eq) in DMF (3 mL) at 30° C. were added 86-1a (176.6 mg, 0.81 mmol, 1.2 eq) and TEA (205.6 mg, 2.03 mmol, 0.28 mL, 3 eq). The mixture was stirred at 30° C. for 16 h. The reaction mixture was diluted with water (20 mL) and extracted with EA (20 mL*3). The combined organic layers were washed with water (20 mL*2) and brine (20 mL), dried over $Na_2SO_4$, filtered and concentrated under reduced pressure to give to give 86-2 (230 mg, 0.39 mmol, 57.7% yield). LCMS (ESI): RT=0.861 min, mass calc. for $C_{24}H_{29}F_3N_4O_4$ 494.21, m/z found 517.1 [M+Na]+.

Step 2: Tert-Butyl Isopropyl((5-(2-((4-(trifluoromethyl)phenyl)amino)phenyl)-1,3,4-oxadiazol-2-yl)methyl)carbamate (Compound 98)

To a solution of 86-2 (220 mg, 0.44 mmol, 1 eq) in DCM (3 mL) at 30° C. were added TEA (135.1 mg, 1.33 mmol, 0.19 mL, 3 eq) and TosCl (144.2 mg, 0.76 mmol, 1.7 eq), and the mixture was stirred at 30° C. for 2 h. The reaction mixture was diluted with water (20 mL), and then extracted with EA (20 mL*3). The combined organic layers were washed with brine (20 mL), dried over anhydrous $Na_2SO_4$, filtered and concentrated under reduced pressure to give a residue. The residue was purified by flash silica gel chromatography to give Compound 98 (150 mg, 0.31 mmol, 70.8% yield). LCMS (ESI): RT=1.002 min, mass calc. for $C_{24}H_{27}F_3N_4O_3$ 476.20, m/z found 499.0 [M+Na]+; $^1$H NMR (400 MHz, CDCl$_3$) δ 9.50 (s, 1H), 7.84 (brs, J=8.3 Hz, 1H), 7.59 (d, J=8.3 Hz, 2H), 7.51 (d, J=8.3 Hz, 1H), 7.42-7.36 (m, 3H), 6.96 (t, J=7.5 Hz, 1H), 4.58 (brs, 3H), 1.44 (brs, 9H), 1.22 (d, J=6.8 Hz, 6H).

Step 3: 2-(5-((isopropylamino)methyl)-1,3,4-oxadiazol-2-yl)-N-(4-(trifluoromethyl)phenyl)aniline (Compound 97)

To a solution of Compound 98 (140 mg, 0.29 mmol, 1 eq) in DCM (3 mL) at 30° C. was added TFA (2.0 g, 17.63 mmol, 1.31 mL, 60 eq) and the mixture was stirred at 30° C. for 16 h. The reaction mixture was diluted with saturation $Na_2CO_3$ solution (20 mL) and then extracted with EA (20 mL*3). The combined organic layers were washed with brine (20 mL), dried over anhydrous $Na_2SO_4$, filtered and concentrated under reduced pressure to give Compound 97 (70 mg, 0.19 mmol, 63.3% yield). LCMS (ESI): RT=0.745 min, mass calc. for $C_{18}H_{17}F_3N_4O$ 376.15, m/z found 377 [M+H]+; $^1$H NMR (400 MHz, CDCl$_3$) δ 9.51 (s, 1H), 7.91 (dd, J=1.5, 80 Hz, 1H), 7.59 (d, J=8.5 Hz, 2H), 7.51 (d, J=8.3 Hz, 1H), 7.42-7.36 (m, 3H), 6.98 (t, J=7.1 Hz, 1H), 4.16 (s, 2H), 4.16 (s, 2H), 2.96 (quin, J=6.2 Hz, 1H), 1.15 (d, J=6.3 Hz, 6H).

Step 4: N-isopropyl-N-((5-(2-((4-(trifluoromethyl)phenyl)amino)phenyl)-1,3,4-oxadiazol-2-yl)methyl)cyanamide (Compound 99)

To a solution of Compound 97 (25.0 mg, 66 umol, 1 eq) and NaOAc (16.4 mg, 0.20 mmol, 3 eq) in MeOH (1 mL) at 30° C. was added cyanogen bromide (14.1 mg, 0.13 mmol, 10 uL, 2 eq), and the resulting mixture was stirred at 30° C. for 2 h. The reaction mixture was diluted with water (20 mL)

and extracted with EA (20 mL*3). The combined organic layers were washed with water (10 mL*2) and brine (20 ml), dried over anhydrous Na$_2$SO$_4$, filtered and concentrated under reduced pressure to give a residue. The residue was purified by prep-HPLC to give Compound 99 (13.0 mg, 32 umol, 48.8% yield). LCMS (ESI): RT=0.888 min, mass calc. for C$_{20}$H$_8$F$_3$N$_5$O 401.15, m/z found 402.0 [M+H]$^+$; $^1$H NMR (400 MHz, CDCl$_3$) δ 9.39 (s, 1H), 7.94 (dd, J=1.5, 8.0 Hz, 1H), 7.60 (d, J=8.5 Hz, 2H), 7.54-7.49 (m, 1H), 7.46-7.41 (m, 1H), 7.38 (d, J=8.5 Hz, 2H), 7.03-6.98 (m, 1H), 4.57 (s, 2H), 3.37 (spt, J=6.5 Hz, 1H), 1.33 (d, J=6.5 Hz, 6H).

Example 87: 2-(5-((ethylamino)methyl)-1,3,4-oxadiazol-2-yl)-N-(4-(trifluoromethyl)phenyl)aniline (Compound 100), and tert-butyl ethyl((5-(2-((4-(trifluoromethyl)phenyl)amino)phenyl)-1,3,4-oxadiazol-2-yl)methyl)carbamate (Compound 101), and N-ethyl-N-((5-(2-((4-(trifluoromethyl)phenyl)amino)phenyl)-1,3,4-oxadiazol-2-yl)methyl)cyanamide (Compound 102)

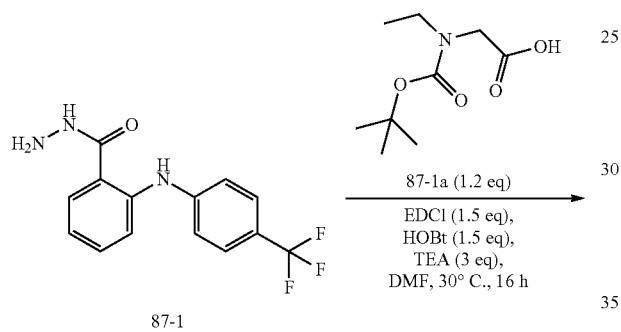

Step 1: Tert-Butyl Ethyl(2-oxo-2-(2-(2-((4-(trifluoromethyl)phenyl)amino)benzoyl)hydrazinyl)ethyl)carbamate To a solution of 87-1a (123.9 mg, 0.61 mmol, 1.2 eq), EDCI (146.1 mg, 0.76 mmol, 1.5 eq) and HOBt (103 mg, 0.76 mmol, 1.5 eq) in DMF (3 mL) at 30° C. was added 87-1 (150 mg, 0.51 mmol, 1 eq) and TEA (154.2 mg, 1.52 mmol, 0.21 mL, 3 eq). The mixture was stirred at 30° C. for 16 h. The reaction mixture was diluted with water (20 mL) and extracted with EA (20 mL*3). The combined organic layers were washed with water (20 mL*2) and brine (20 mL), dried over Na$_2$SO$_4$, filtered and concentrated under reduced pressure to give a residue. The residue was purified by flash silica gel chromatography to give 87-2 (170 mg, 0.34 mmol, 67.3% yield) was obtained. LCMS (ESI): R=0.846 min, mass calcd. For C$_{23}$H$_{27}$F$_3$N$_4$O$_4$ 480.20 m/z found 503.0 [M+23]$^+$.

Step 2: Tert-Butyl Ethyl((5-(2-((4-(trifluoromethyl)phenyl)amino)phenyl)-1,3,4-oxadiazol-2-yl)methyl)carbamate (Compound 101)

To a solution of 87-2 (170 mg, 0.35 mmol, 1 eq) in DCM (3 mL) at 30° C. was added TEA (107.4 mg, 1.06 mmol, 0.15 mL, 3 eq) and TosCl (80.9 mg, 0.42 mmol, 1.2 eq), and the mixture was stirred at 30° C. for 2 h. The reaction mixture was diluted with water (20 mL), and then extracted with EA (20 mL*3). The combined organic layers were washed with water (10 mL*2) and brine (20 mL), dried over anhydrous Na$_2$SO$_4$, filtered and concentrated under reduced pressure to give a residue. The residue was purified by flash silica gel chromatography to give Compound 101 (150 mg, 0.32 mmol, 91.7% yield). LCMS (ESI): RT=0.988 min, mass calc. for C$_{23}$H$_{25}$F$_3$N$_4$O$_3$ 462.19, m/z found 485.0 [M+23]+; $^1$H NMR (400 MHz, CDCl$_3$) δ 9.49 (s, 1H), 7.86 (brs, 1H), 7.59 (d, J=8.5 Hz, 2H), 7.51 (d, J=8.5 Hz, 1H), 7.43-7.34 (m, 3H), 6.97 (t, J=7.5 Hz, 1H), 4.82-4.64 (m, 2H), 3.40 (brs, 2H), 1.50 (brs, 9H), 1.18 (brs, 3H).

Step 3: 2-(5-((ethylamino)methyl)-1,3,4-oxadiazol-2-yl)-N-(4-(trifluoromethyl)phenyl)aniline (Compound 100)

To a solution of Compound 101 (140 mg, 0.35 mmol, 1 eq) in DCM (3 mL) at 30° C. was added TFA (517.8 mg, 4.54 mmol, 0.34 mL, 15 eq) and the mixture was stirred at 30° C. for 1 h. The reaction mixture was diluted with water (20 mL), saturated Na$_2$CO$_3$ solution (20 mL) and then extracted with EA (20 mL*3). The combined organic layers were washed with brine (20 mL), dried over anhydrous Na$_2$SO$_4$, filtered and concentrated under reduced pressure to give Compound 100 (70.0 mg, 0.19 mmol, 61.1% yield). LCMS (ESI): RT=0.722 min, mass calc. for C$_{18}$H$_{17}$F$_3$N$_4$O 362.14, m/z found 363 [M+H]$^+$; $^1$H NMR (400 MHz, CDCl$_3$) δ 9.51 (s, 1H), 7.91 (dd, J=1.4, 7.9 Hz, 1H), 7.59 (d, J=8.5 Hz, 2H), 7.51 (d, J=8.4 Hz, 1H), 7.42-7.36 (m, 3H), 7.00-6.94 (m, 1H), 4.45 (brs, 1H), 4.15 (s, 2H), 2.80 (q, J=7.1 Hz, 2H), 1.18 (t, J=7.1 Hz, 3H).

Step 4: N-ethyl-N-((5-(2-((4-(trifluoromethyl)phenyl)amino)phenyl)-1,3,4-oxadiazol-2-yl)methyl)cyanamide (Compound 102)

To a solution of Compound 100 (30 mg, 82.8 umol, 1 eq) and TEA (25.1 mg, 0.25 mmol, 35 uL, 3 eq) in THF (2 mL) at 30° C. was added cyanogen bromide (17.5 mg, 0.17 mmol, 12 uL, 2 eq), and the resulting mixture was stirred at 30° C. for 4 h. The reaction mixture was diluted with water (30 mL) and extracted with EA (30 mL*3). The combined organic layers were washed with brine (30 mL), dried over anhydrous Na$_2$SO$_4$, filtered and concentrated under reduced pressure to give a residue. The residue was purified by prep-HPLC to give Compound 102 (5.0 mg, 12.9 umol, 15.6% yield). LCMS (ESI): RT=0.869 min, mass calc. for C$_{18}$H$_{17}$F$_3$N$_4$O 387.36, m/z found 388.0 [M+H]$^+$; $^1$H NMR (400 MHz, CDCl$_3$) δ 9.39 (s, 1H), 7.94 (dd, J=1.3, 7.9 Hz, 1H), 7.60 (d, J=8.4 Hz, 2H), 7.54-7.49 (m, 1H), 7.46-7.41 (m, 1H), 7.38 (d, J=8.4 Hz, 2H), 7.04-6.97 (m, 1H), 4.56 (s, 2H), 3.22 (q, J=7.3 Hz, 2H), 1.36 (t, J=7.3 Hz, 3H).

Example 88: 2-methyl-2-(5-(2-((4-(trifluoromethyl)phenyl)amino)phenyl)-1,3,4-oxadiazol-2-yl)propanoic Acid (Compound 103)

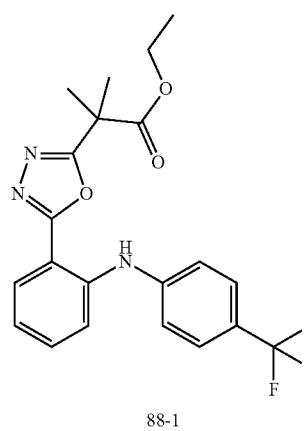

88-1

NaOH (10 eq), MeOH, 30° C., 1.5 h

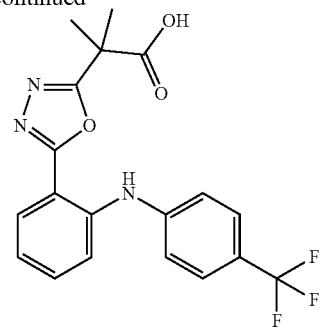

Compound 103

To a solution of 88-1 (250 mg, 0.60 mmol, 1 eq) in MeOH (6 mL) at 30° C. was added NaOH (2 M, 2.98 mL, 10 eq), and the mixture was stirred at 30° C. for 1.5 h. The reaction mixture was concentrated under reduced pressure to remove solvent. The residue was diluted with water (20 mL), then acidified withe 2N HCl at 0° C. to pH=2-3, and then extracted with EA (20 mL*3). The combined organic layers were washed with brine (20 mL), dried over anhydrous Na$_2$SO$_4$, filtered and concentrated under reduced pressure to give Compound 103 (220 mg, 0.55 mmol, 91.8% yield). LCMS (ESI): RT=0.988 min, mass calc. for C$_{19}$H$_{16}$F$_3$N$_3$O$_3$ 391.11, m/z found 392 [M+1]$^+$; $^1$H NMR (400 MHz, CDCl$_3$) δ 9.51 (s, 1H), 7.89 (dd, J=1.4, 7.9 Hz, 1H), 7.58 (d, J=8.5 Hz, 2H), 7.52 (d, J=8.3 Hz, 1H), 7.43-7.38 (m, 1H), 7.35 (d, J=8.5 Hz, 2H), 7.00-6.94 (m, 1H), 1.83 (s, 6H).

Example 89: 2-(5-(2-aminoethyl)-1,3,4-oxadiazol-2-yl)-N-(4-(trifluoromethyl)phenyl)aniline (Compound 104)

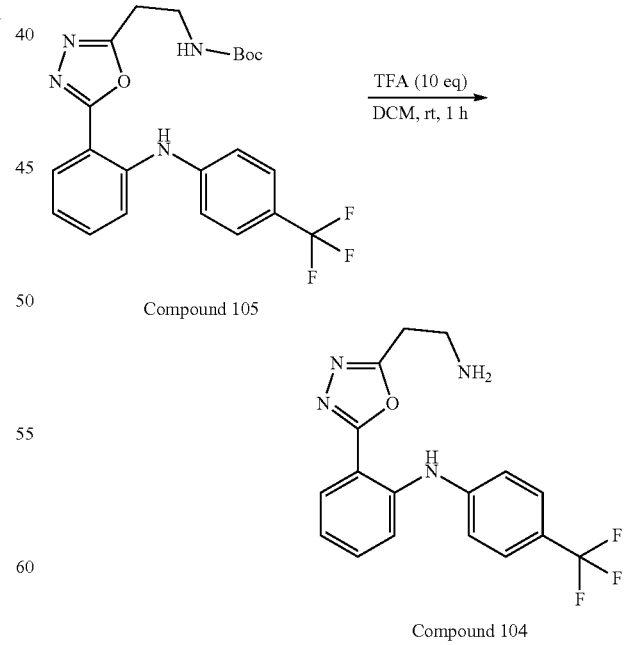

To a solution of Compound 105 (100 mg, 0.22 mmol, 1 eq) in DCM (2 mL) was added TFA (254.2 mg, 2.23 mmol, 0.16 mL, 10 eq). The reaction was stirred at 25° C. for 1 hr.

The reaction was neutralized with sat.Na$_2$CO$_3$ and extracted with DCM (3*10 mL). The organic layer was dried over Na$_2$SO$_4$ and concentrated. Compound 104 (70 mg, 0.19 mmol, 87% yield) was used for next step without further purification. LCMS (ESI): RT=0.825 min, mass calc. for C$_{17}$H$_{15}$F$_3$N$_4$O 348.12, m/z found 349.0 [M+1]$^+$; $^1$H NMR (400 MHz, CDCl$_3$) δ 9.51 (s, 1H), 7.88 (dd, J=1.3, 8.0 Hz, 1H), 7.58 (d, J=8.5 Hz, 2H), 7.51 (d, J=8.3 Hz, 1H), 7.43-7.32 (m, 3H), 7.01-6.94 (m, 1H), 4.59 (br s, 1H), 3.26 (br s, 2H), 3.13-3.06 (m, 2H).

Example 90: Tert-Butyl (2-(5-(2-((4-(trifluoromethyl)phenyl)amino)phenyl)-1,3,4-oxadiazol-2-yl)ethyl)carbamate (Compound 105)

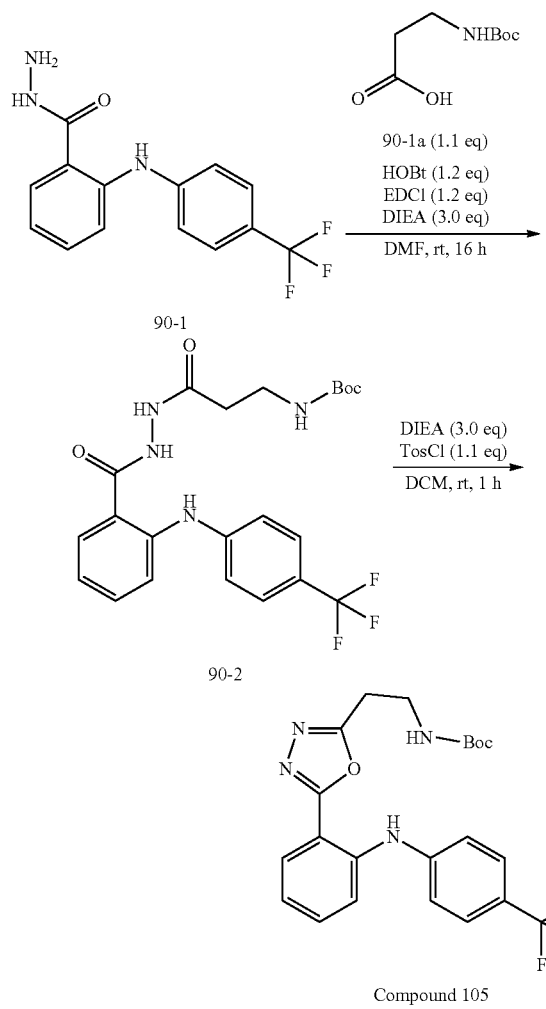

Step 1: Tert-Butyl N-[3-oxo-3-[2-[2-[4-(trifluoromethyl)anilino]benzoyl]hydrazino]propyl]carbamate To a mixture of compound 90-1 (0.2 g, 0.67 mmol, 1 eq), compound 90-1a (140.9 mg, 0.74 mmol, 1.1 eq), HOBt (109.8 mg, 0.81 mmol, 1.2 eq) and EDCI (155.8 mg, 0.81 mmol, 1.2 eq) in DMF (4 mL) was added DIEA (262.6 mg, 2 mmol, 0.35 mL, 3 eq) at 25° C. under N$_2$. The mixture was stirred at 25° C. for 16 hr. The reaction was diluted with EA (30 mL) and washed with brine (2*10 mL). The organic layer was dried over Na$_2$SO$_4$ and concentrated. The compound 90-2 (0.3 g, crude) was used for next step directly.

Step 2: Tert-Butyl (2-(5-(2-((4-(trifluoromethyl)phenyl)amino)phenyl)-1,3,4-oxadiazol-2-yl)ethyl)carbamate To a solution of compound 90-2 (0.3 g, 0.64 mmol, 1 eq) and DIEA (249.3 mg, 1.9 mmol, 0.33 mL, 3 eq) in DCM (4 mL) was added TosCl (134.8 mg, 0.7 mmol, 1.1 eq). The reaction was stirred at 25° C. for 1 hr. The reaction was diluted with DCM (30 mL) and washed with water (2*10 mL). The organic layer was dried over Na$_2$SO$_4$ and concentrated. The crude product was purified by column chromatography on silica gel to give Compound 105 (130 mg, 0.28 mmol, 45% yield). LCMS (ESI): RT=1.048 min, mass calc. for C$_{22}$H$_{23}$F$_3$N$_4$O$_3$ 448.16, m/z found 449.1 [M+1]$^+$; $^1$H NMR (400 MHz, CDCl$_3$) δ 9.47 (s, 1H), 7.88 (dd, J=1.3, 7.8 Hz, 1H), 7.58 (d, J=8.5 Hz, 2H), 7.51 (d, J=8.3 Hz, 1H), 7.54-7.47 (m, 1H), 7.44-7.33 (m, 3H), 7.02-6.95 (m, 1H), 3.69 (q, J=6.0 Hz, 2H), 3.16 (t, J=6.3 Hz, 2H), 1.44 (s, 9H).

Example 91: N-(2-(5-(2-((4-(trifluoromethyl)phenyl)amino)phenyl)-1,3,4-oxadiazol-2-yl)ethyl)acrylamide (Compound 106)

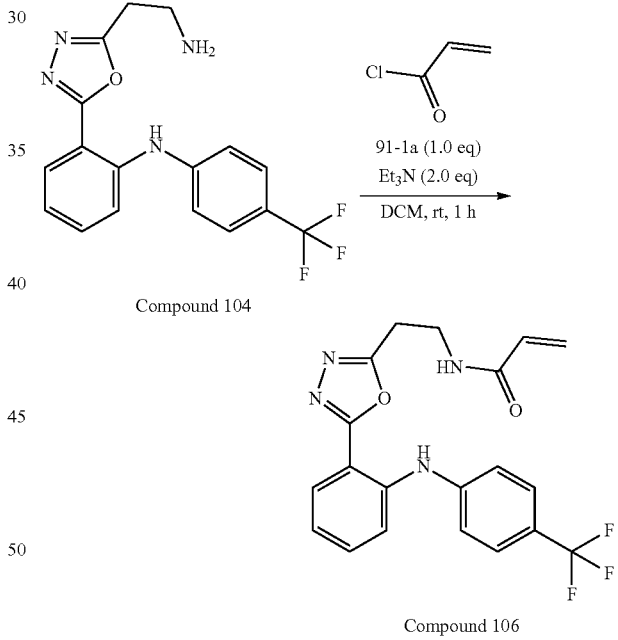

To a solution of Compound 104 (60 mg, 0.17 mmol, 1 eq) and Et$_3$N (34.8 mg, 0.34 mmol, 47.9 uL, 2 eq) in DCM (2 mL) was added 91-1a (15.5 mg, 0.17 mmol, 14 uL, 1 eq). The reaction was stirred at 25° C. for 1 hr. The reaction was diluted with DCM (20 mL) and washed with H$_2$O (2*5 mL). The organic layer was dried over Na$_2$SO$_4$ and concentrated. The residue was purified by prep-HPLC to give Compound 106 (11.2 mg, 27 umol, 16% yield). LCMS (ESI): RT=0.942 min, mass calc. for C$_{20}$H$_{17}$F$_3$N$_4$O$_2$ 402.13, m/z found 403.0 [M+1]$^+$; $^1$H NMR (400 MHz, CDCl$_3$) δ 9.45 (s, 1H), 7.89 (dd, J=1.4, 7.9 Hz, 1H), 7.60 (d, J=8.5 Hz, 2H), 7.53 (d, J=8.4 Hz, 1H), 7.47-7.34 (m, 3H), 7.03-6.91 (m, 1H), 6.33

(dd, J=1.3, 16.9 Hz, 2H), 6.18-6.06 (m, 1H), 5.69 (dd, J=1.3, 10.3 Hz, 1H), 3.93 (q, J=6.1 Hz, 2H), 3.23 (t, J=6.0 Hz, 2H).

Example 92: tert-butyl ((5-(2-((4-(trifluoromethyl)phenyl)amino)phenyl)-1,3,4-oxadiazol-2-yl)methyl)carbamate (Compound 107)

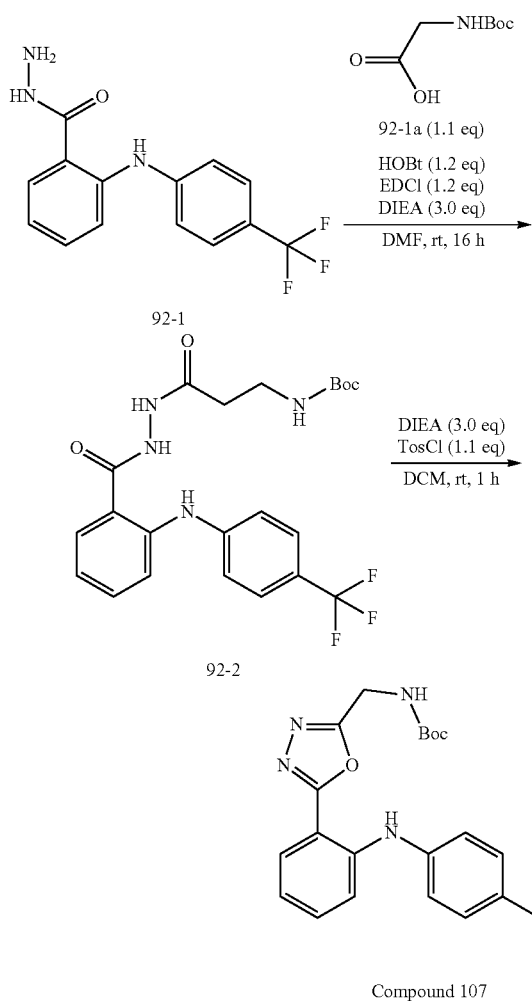

Compound 107

Step 1: Tert-Butyl N-[2-oxo-2-[2-[2-[4-(trifluoromethyl)anilino]benzoyl]hydrazino]ethyl]carbamate To a mixture of compound 92-1 (0.2 g, 0.67 mmol, 1 eq), compound 92-1a (130.5 mg, 0.74 mmol, 1.1 eq), HOBt (109.8 mg, 0.81 mmol, 1.2 eq) and EDCI (155.8 mg, 0.81 mmol, 1.2 eq) in DMF (4 mL) was added DIEA (262.6 mg, 2 mmol, 0.35 mL, 3 eq) at 25° C. under N$_2$. The mixture was stirred at 25° C. for 16 hr. The reaction was diluted with EA (30 mL) and washed with brine (2*10 mL). The organic layer was dried over Na$_2$SO$_4$ and concentrated. The compound 92-2 (0.3 g, crude) was used for next step directly.

Step 2: tert-butyl ((5-(2-((4-(trifluoromethyl)phenyl)amino)phenyl)-1,3,4-oxadiazol-2-yl)methyl)carbamate To a solution of compound 92-2 (0.3 g, 0.66 mmol, 1 eq) and DIEA (257 mg, 1.99 mmol, 0.34 mL, 3 eq) in DCM (4 mL) was added TosCl (139 mg, 0.72 mmol, 1.1 eq). The reaction was stirred at 25° C. for 1 hr. The reaction was diluted with DCM (30 mL) and washed with water (2*10 mL). The organic layer was dried over Na$_2$SO$_4$ and concentrated. The crude product was purified by column chromatography on silica gel to give Compound 107 (120 mg, 0.26 mmol, 40.7% yield). LCMS (ESI): RT=1.040 min, mass calc. for C$_{21}$H$_{21}$F$_3$N$_4$O$_3$ 434.16, m/z found 435.0 [M+1]$^+$; $^1$H NMR (400 MHz, CDCl$_3$) δ 9.45 (s, 1H), 7.88 (dd, J=1.3, 8.0 Hz, 1H), 7.59 (d, J=8.5 Hz, 2H), 7.51 (d, J=8.5 Hz, 1H), 7.43-7.33 (m, 3H), 7.01-6.93 (m, 1H), 5.24-5.12 (m, 1H), 4.67 (d, J=5.8 Hz, 2H), 1.49 (s, 9H).

Example 93: N-((5-(2-((4-(trifluoromethyl)phenyl)amino)phenyl)-1,3,4-oxadiazol-2-yl)methyl)acrylamide (Compound 108)

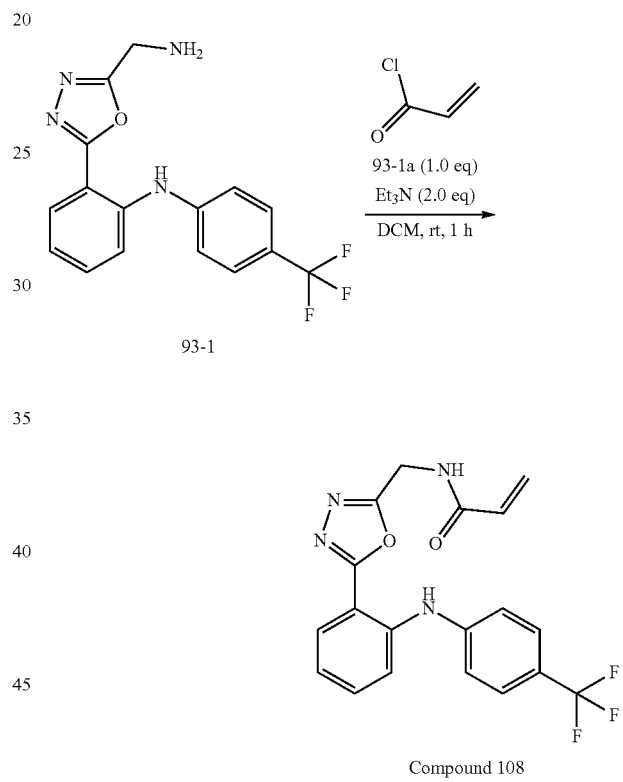

Compound 108

To a solution of 93-1 (60 mg, 0.17 mmol, 1 eq) and Et$_3$N (36.3 mg, 0.35 mmol, 49.9 uL, 2 eq) in DCM (2 mL) was added 93-1a (16.2 mg, 0.17 mmol, 14.6 uL, 1 eq). The reaction was stirred at 25° C. for 1 hr. The reaction was diluted with DCM (20 mL) and washed with H$_2$O (2*5 mL). The organic layer was dried over Na$_2$SO$_4$ and concentrated. The residue was purified by prep-HPLC to give Compound 108 (17.3 mg, 44 umol, 24.6% yield). LCMS (ESI): RT=0.942 min, mass calc. for C$_{19}$H$_{15}$F$_3$N$_4$O$_2$ 388.11, m/z found 349.0 [M+1]$^+$; $^1$H NMR (400 MHz, CDCl$_3$) δ=9.42 (s, 1H), 7.90 (dd, J=1.4, 7.9 Hz, 1H), 7.60 (d, J=8.5 Hz, 2H), 7.57-7.49 (m, 1H), 7.45-7.33 (m, 2H), 7.45-7.33 (m, 1H), 7.05-6.95 (m, 1H), 6.43 (dd, J=1.0, 17.1 Hz, 1H), 6.33-6.14 (m, 2H), 5.80 (dd, J=1.3, 10.3 Hz, 1H), 4.90 (d, J=5.8 Hz, 2H).

Example 94: N-(2-cyanoethyl)-2-methyl-2-(5-(2-((4-(trifluoromethyl)phenyl)amino)phenyl)-1,3,4-oxadiazol-2-yl)propanamide (Compound 109)

Example 95: N-(cyanomethyl)-2-methyl-2-(5-(2-((4-(trifluoromethyl)phenyl)amino)phenyl)-1,3,4-oxadiazol-2-yl)propanamide (Compound 110)

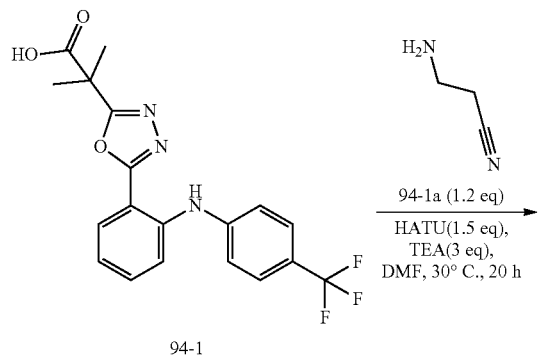

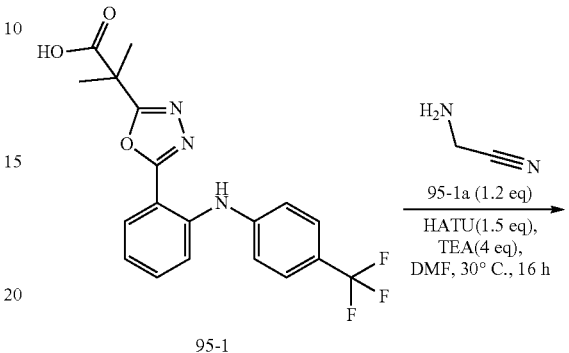

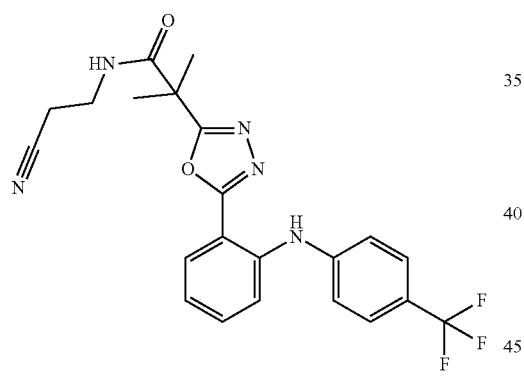

Compound 109

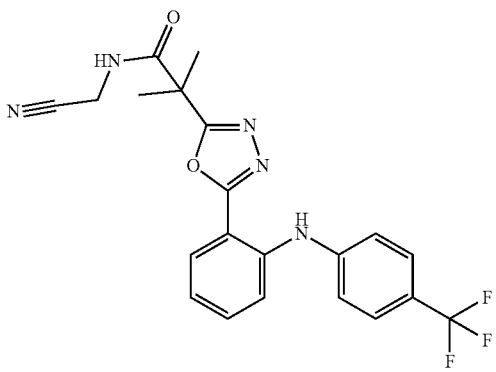

Compound 110

To a solution of 94-1 (40 mg, 0.10 mmol, 1 eq) and HATU (58.3 mg, 0.15 mmol, 1.5 eq) in DMF (1 mL) at 30° C. were added 94-1a (8.6 mg, 0.12 mmol, 9 uL, 1.2 eq) and TEA (31.0 mg, 0.31 mmol, 43 uL, 3 eq). The mixture was stirred at 30° C. for 20 h. The reaction mixture was concentrated under reduced pressure to give the residue which was purified by prep-HPLC to give Compound 109 (20 mg, 45.1 umol, 44.1% yield). LCMS (ESI): RT=0.853 min, mass calc. for $C_{22}H_{20}F_3N_5O_2$ 443.16, m/z found 444.0 [M+H]$^+$; $^1$H NMR (400 MHz, CDCl$_3$) δ 9.37 (s, 1H), 7.88 (dd, J=1.3, 7.9 Hz, 1H), 7.59 (d, J=8.4 Hz, 2H), 7.52-7.48 (m, 1H), 7.43-7.38 (m, 1H), 7.35 (d, J=8.4 Hz, 2H), 7.31 (brd, J=5.9 Hz, 1H), 7.01-6.95 (m, 1H), 3.54 (q, J=6.3 Hz, 2H), 2.66 (t, J=6.4 Hz, 2H), 1.79 (s, 6H).

To a solution of 95-1 (40 mg, 0.1 mmol, 1 eq) and HATU (58.3 mg, 0.15 mmol, 1.5 eq) in DMF (1 mL) at 30° C. were added 95-1a (15.8 mg, 0.12 mmol, 1.2 eq, HCl) and TEA (41.4 mg, 0.41 mmol, 57 uL, 4 eq). The mixture was stirred at 30° C. for 16 h. The reaction mixture was concentrated under reduced pressure to give a residue which was purified by prep-HPLC to give Compound 110 (13 mg, 30 umol, 29.3% yield). LCMS (ESI): RT=0.860 min, mass calc. for $C_{21}H_{18}F_3N_5O_2$ 429.14, m/z found 430.0 [M+H]$^+$; $^1$H NMR (400 MHz, CDCl$_3$) δ 9.32 (s, 1H), 7.87 (dd, J=1.4, 7.9 Hz, 1H), 7.74 (brs, 1H), 7.60 (d, J=8.3 Hz, 2H), 7.52-7.49 (m, 1H), 7.44-7.40 (m, 1H), 7.35 (d, J=8.3 Hz, 2H), 7.02-6.97 (m, 1H), 4.22 (d, J=5.5 Hz, 2H), 1.80 (s, 6H).

Example 96: N-(but-3-yn-1-yl)-2-methyl-2-(5-(2-((4-(trifluoromethyl)phenyl)amino)phenyl)-1,3,4-oxadiazol-2-yl)propanamide (Compound 111)

Example 97: 2-methyl-N-(prop-2-yn-1-yl)-2-(5-(2-((4-(trifluoromethyl)phenyl)amino)phenyl)-1,3,4-oxadiazol-2-yl)propanamide (Compound 112)

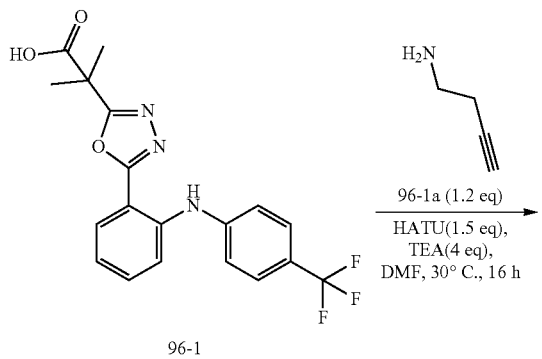

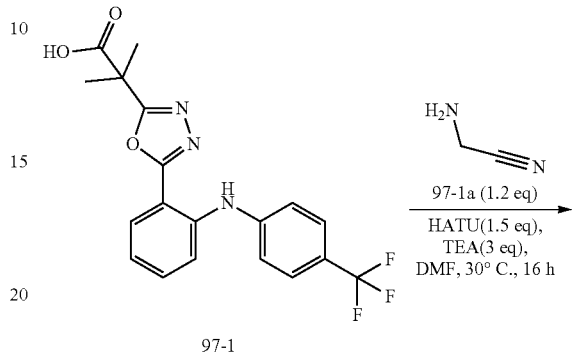

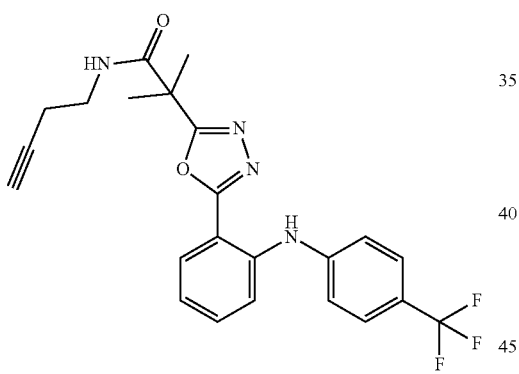

Compound 111

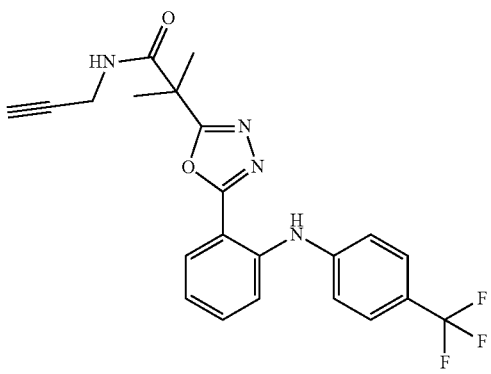

Compound 112

To a solution of 96-1 (40 mg, 0.10 mmol, 1 eq) and HATU (58.3 mg, 0.15 mmol, 1.5 eq) in DMF (1 mL) at 30° C. were added 96-1a (17.4 mg, 0.12 mmol, 1.2 eq, HCl) and TEA (41.4 mg, 0.41 mmol, 57 uL, 4 eq). The mixture was stirred at 30° C. for 16 h. The reaction mixture was concentrated under reduced pressure to give the residue which was purified by prep-HPLC to give Compound 111 (32 mg, 72.3 umol, 70.8% yield). LCMS (ESI): RT=0.891 min, mass calc. for $C_{23}H_{21}F_3N_4O_2$ 442.16, m/z found 443.0 [M+H]$^+$; $^1$H NMR (400 MHz, CDCl$_3$) δ 9.44 (s, 1H), 7.89 (dd, J=1.4, 7.9 Hz, 1H), 7.59 (d, J=8.5 Hz, 2H), 7.52 (d, J=8.3 Hz, 1H), 7.44-7.38 (m, 1H), 7.36 (d, J=8.5 Hz, 2H), 7.01-6.96 (m, 1H), 6.72 (brs, 1H), 3.42 (q, J=6.3 Hz, 2H), 2.42 (dt, J=2.6, 6.4 Hz, 2H), 1.91 (t, J=2.6 Hz, 1H), 1.79 (s, 6H)

To a solution of 97-1 (30 mg, 76.7 umol, 1 eq) and HATU (43.7 mg, 0.11 mmol, 1.5 eq) in DMF (1 mL) at 30° C. were added 97-1a (5.1 mg, 92.0 umol, 5.9 uL, 1.2 eq) and TEA (23.3 mg, 0.23 mmol, 32 uL, 3 eq). The mixture was stirred at 30° C. for 16 h. The reaction mixture was concentrated under reduced pressure to give a residue which was purified by prep-HPLC to give Compound 112 (13.0 mg, 30.4 umol, 39.6% yield). LCMS (ESI): RT=0.884 min, mass calc. for $C_{22}H_{19}F_3N_4O_2$ 428.15, m/z found 429.0 [M+H]$^+$; $^1$H NMR (400 MHz, CDCl$_3$) δ=9.41 (s, 1H), 7.88 (dd, J=1.4, 8.0 Hz, 1H), 7.59 (d, J=8.5 Hz, 2H), 7.53-7.50 (m, 1H), 7.44-7.39 (m, 1H), 7.36 (d, J=8.4 Hz, 2H), 7.01-6.97 (m, 1H), 6.92 (brs, 1H), 4.07 (dd, J=2.6, 5.1 Hz, 2H), 2.24 (t, J=2.6 Hz, 1H), 1.79 (s, 6H)

Example 98: N-(2-cyanoethyl)-5-(2-((4-(trifluoromethyl)phenyl)amino)phenyl)-1,3,4-oxadiazole-2-carboxamide (Compound 113)

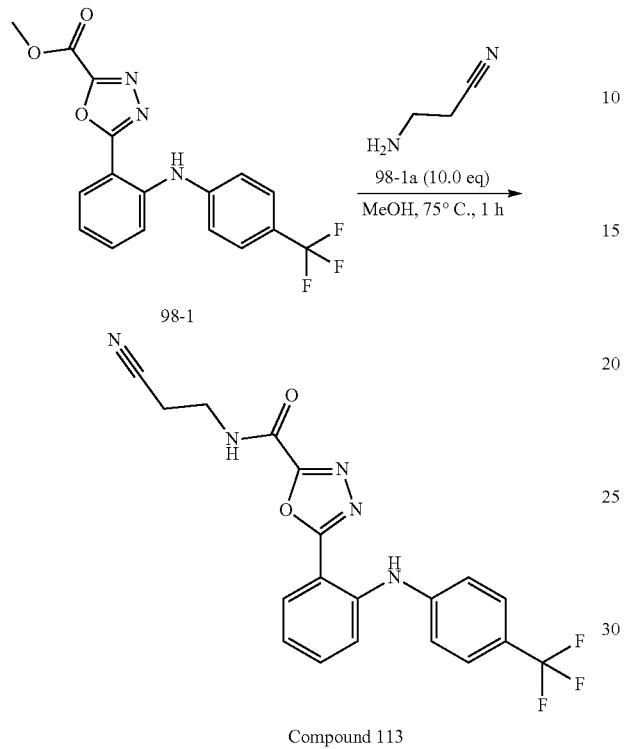

Compound 113

To a solution of compound 98-1 (50 mg, 0.14 mmol, 1 eq) in MeOH (1 mL) was added compound 98-1a (96.4 mg, 1.38 mmol, 0.1 mL, 10 eq). The mixture was stirred at 75° C. for 1 hr. The reaction mixture was filtered and the solid was collected to give Compound 113 (39 mg, 97 umol, 70.6% yield). LCMS (ESI): RT=0.841 min, mass calcd. For $C_{19}H_{14}F_3N_5O_2$, 401.11 m/z found 402.0 [M+H]$^+$; $^1$H NMR (400 MHz, DMSO-d$_6$) δ 9.64 (t, J=5.8 Hz, 1H), 9.11 (s, 1H), 7.99 (d, J=7.8 Hz, 1H), 7.64 (d, J=8.5 Hz, 2H), 7.57 (d, J=3.5 Hz, 2H), 7.37 (d, J=8.5 Hz, 2H), 7.23-7.14 (m, 1H), 3.56 (q, J=6.4 Hz, 2H), 2.82 (t, J=6.5 Hz, 2H).

Example 99: N-(cyanomethyl)-5-(2-((4-(trifluoromethyl)phenyl)amino)phenyl)-1,3,4-oxadiazole-2-carboxamide (Compound 114)

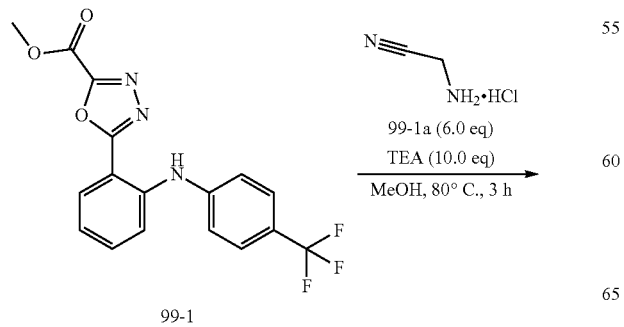

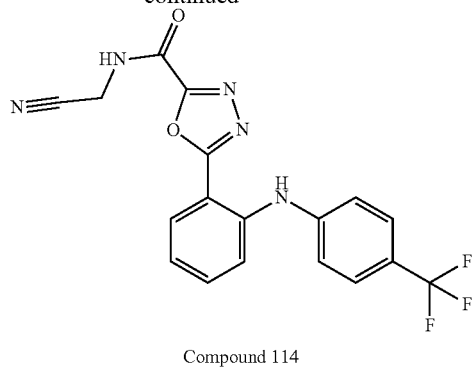

Compound 114

To a solution of compound 99-1 (50 mg, 0.14 mmol, 1 eq) in MeOH (1 mL) were added compound 99-1a (77.1 mg, 0.83 mmol, 6 eq, HCl) and TEA (139.2 mg, 1.38 mmol, 0.19 mL, 10 eq). The mixture was stirred at 80° C. for 3 hr. The reaction mixture was concentrated in vacuum. The crude product was purified by prep-HPLC. LCMS and $^1$HNMR confirmed that Compound 114 (24.1 mg, 62.4 umol, 45.3% yield) was obtained. LCMS (ESI): RT=0.834 min, mass calcd. For $C_{18}H_{12}F_3N_5O_2$, 387.09 m/z found 388.0 [M+H]$^+$; $^1$H NMR (400 MHz, CDCl$_3$) δ 9.27 (s, 1H), 8.05 (d, J=7.8 Hz, 1H), 7.76 (br s, 1H), 7.62 (d, J=8.5 Hz, 2H), 7.52-7.42 (m, 2H), 7.39 (d, J=8.3 Hz, 2H), 7.05-6.97 (m, 1H), 4.47 (d, J=6.0 Hz, 2H).

Example 100: N-(but-3-yn-1-yl)-5-(2-((4-(trifluoromethyl)phenyl)amino)phenyl)-1,3,4-oxadiazole-2-carboxamide (Compound 115)

Compound 115

To a solution of compound 100-1 (50 mg, 0.14 mmol, 1 eq) in MeOH (2 mL) were added K$_2$CO$_3$ (95.1 mg, 0.69 mmol, 5 eq) and compound 100-1a (145.2 mg, 1.38 mmol, 10 eq). The mixture was stirred at 75° C. for 2 hr. The reaction mixture was concentrated in vacuum. The residue was diluted with H₂O (10 mL), extracted with EA (15 mL*3). The combined organic phase was washed with H₂O (5 mL) and brine (5 mL), dried over Na₂SO₄, filtered and concentrated in vacuum. The residue was purified by prep-TLC. LCMS and ¹HNMR confirmed that Compound 115 (4.33 mg, 10.8 umol, 7.8% yield) was obtained. LCMS (ESI): RT=0.881 min, mass calcd. For C₂₀H₁₅F₃N₄O₂, 400.11 m/z found 400.9 [M+H]⁺; ¹H NMR (400 MHz, CDCl₃) δ 9.29 (s, 1H), 7.99 (dd, J=1.2, 8.1 Hz, 1H), 7.53 (d, J=8.5 Hz, 2H), 7.45-7.33 (m, 3H), 7.30 (d, J=8.5 Hz, 2H), 6.93 (t, J=7.5 Hz, 1H), 3.62 (q, J=6.4 Hz, 2H), 2.51 (dt, J=2.6, 6.4 Hz, 2H), 2.02 (t, J=2.6 Hz, 1H).

Example 101: N-(prop-2-yn-1-yl)-5-(2-((4-(trifluoromethyl)phenyl)amino)phenyl)-1,3,4-oxadiazole-2-carboxamide (Compound 116)

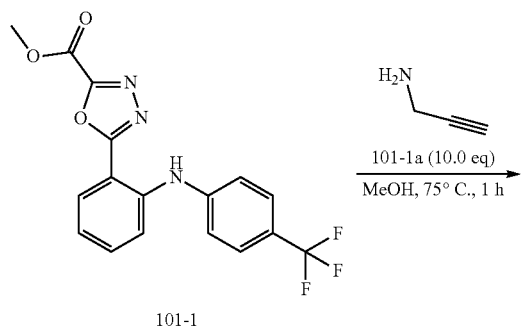

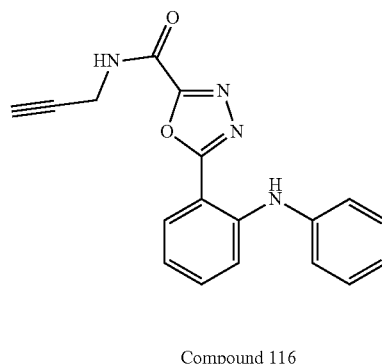

Compound 116

To a solution of compound 101-1 (50 mg, 0.14 mmol, 1 eq) in MeOH (1 mL) was added compound 101-1a (75.8 mg, 1.38 mmol, 88 uL, 10 eq). The mixture was stirred at 75° C. for 1 hr. The reaction mixture was filtered and the solid was collected to give Compound 116 (27 mg, 69 umol, 50.7% yield). LCMS (ESI): RT=0.862 min, mass calcd. For C₁₉H₁₃F₃N₄O₂, 386.10 m/z found 386.9 [M+H]⁺; ¹H NMR (400 MHz, CDCl₃) δ 9.34 (s, 1H), 8.10-8.01 (m, 1H), 7.61 (d, J=8.5 Hz, 2H), 7.52-7.47 (m, 1H), 7.47-7.42 (m, 1H), 7.39 (d, J=8.4 Hz, 2H), 7.36-7.29 (m, 1H), 7.00 (t, J=7.4 Hz, 1H), 4.33 (dd, J=2.5, 5.5 Hz, 2H), 2.36 (t, J=2.5 Hz, 1H).

Example 102: (E)-2-(5-(prop-1-en-1-yl)-1,3,4-oxadiazol-2-yl)-N-(4-(trifluoromethyl)phenyl)aniline (Compound 117)

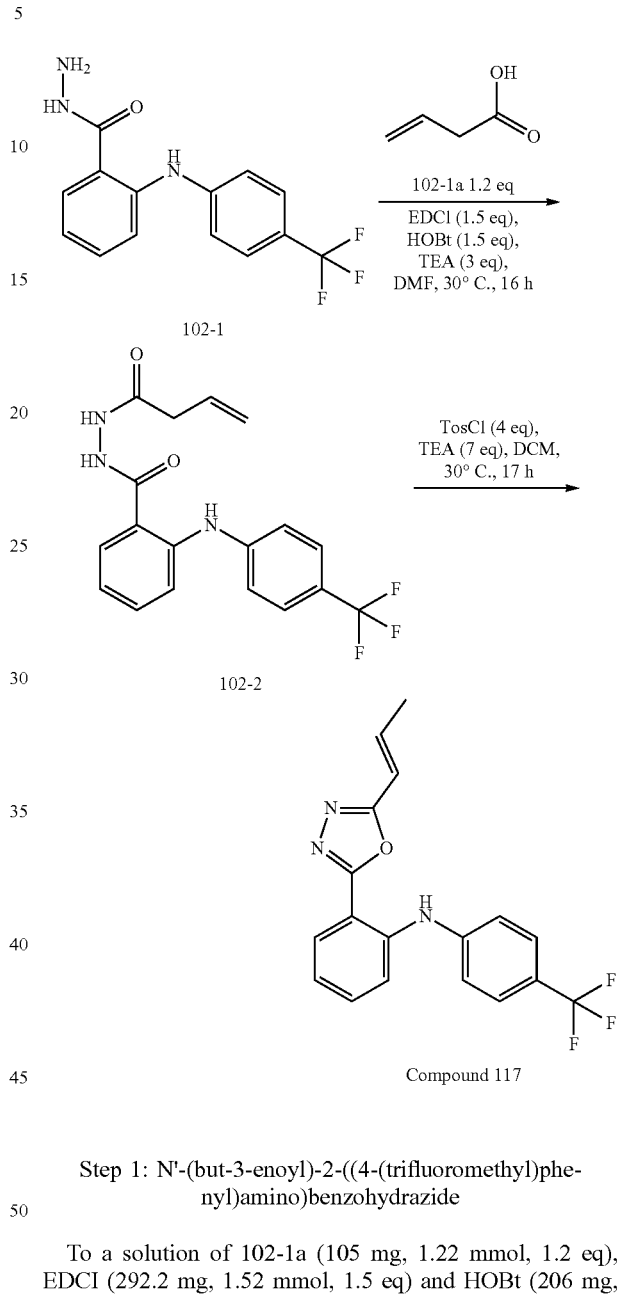

Step 1: N'-(but-3-enoyl)-2-((4-(trifluoromethyl)phenyl)amino)benzohydrazide

To a solution of 102-1a (105 mg, 1.22 mmol, 1.2 eq), EDCI (292.2 mg, 1.52 mmol, 1.5 eq) and HOBt (206 mg, 1.52 mmol, 1.5 eq) in DMF (3 mL) at 30° C. were added 102-1 (300 mg, 1.02 mmol, 1 eq) and TEA (308.4 mg, 3.05 mmol, 0.42 mL, 3 eq). The mixture was stirred at 30° C. for 16 h. The reaction mixture was diluted with water (20 mL) and extracted with EA (20 mL*3). The combined organic layers were washed with water (20 mL*2) and brine (20 mL), dried over Na₂SO₄, filtered and concentrated under reduced pressure to give a residue. The residue was purified by flash silica gel chromatography to give 102-2 (175 mg, 0.45 mmol, 44.6% yield). LCMS (ESI): RT=0.775 min, mass calc. for C₁₈H₁₆F₃N₃O₂ 363.12, m/z found 363.9 [M+H]⁺; ¹H NMR (400 MHz, CDCl₃) δ 9.18 (brs, 1H), 7.61 (t, J=7.1 Hz, 1H), 7.53 (d, J=8.5 Hz, 1H), 7.46-7.43 (m, 1H), 7.39 (d, J=8.0 Hz, 1H), 7.22 (d, J=8.5 Hz, 3H), 7.07-6.95 (m, 1H), 6.92-6.89 (m, 1H), 6.03-5.92 (m, 1H), 5.36-5.31 (m, 1H), 3.17 (d, J=7.0 Hz, 1H), 1.91 (dd, J=1.2, 6.9 Hz, 2H)

Step 2: (E)-2-(5-(prop-1-en-1-yl)-1,3,4-oxadiazol-2-yl)-N-(4-(trifluoromethyl)phenyl)aniline To a solution of 102-2 (120 mg, 0.33 mmol, 1 eq) in DCM (2 mL) at 30° C. were added TEA (234.0 mg, 2.31 mmol, 0.32 mL, 7 eq) and TosCl (251.9 mg, 1.32 mmol, 4 eq). The mixture was stirred at 30° C. for 17 h. The reaction mixture was diluted with water (20 mL), and then extracted with EA (20 mL*3). The combined organic layers were washed with water (20 mL*2) and brine (20 mL*2), dried over anhydrous Na₂SO₄, filtered and concentrated under reduced pressure to give a residue. The residue was purified by flash silica gel chromatography and prep-HPLC to give Compound 117 (40 mg, 0.11 mmol, 34.4% yield). LCMS (ESI): RT=0.968 min, mass calc. for $C_{18}H_{14}F_3N_3O$ 345.11, m/z found 345.9 [M+H]⁺; ¹H NMR (400 MHz, CDCl₃) δ 9.58 (s, 1H), 7.91 (dd, J=1.3, 7.9 Hz, 1H), 7.58 (d, J=8.4 Hz, 2H), 7.51 (d, J=8.4 Hz, 1H), 7.41-7.36 (m, 3H), 7.01-6.91 (m, 2H), 6.51 (dd, J=1.7, 15.9 Hz, 1H), 2.05 (dd, J=1.7, 6.9 Hz, 3H)

Example 103: 2-(5-(2,2-diethoxyethyl)-1,3,4-oxadiazol-2-yl)-N-(4-(trifluoromethyl)phenyl)aniline (Compound 118)

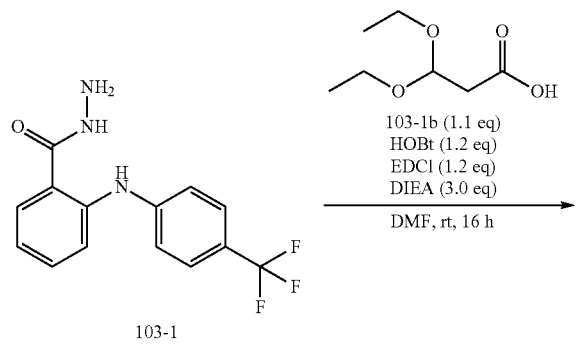

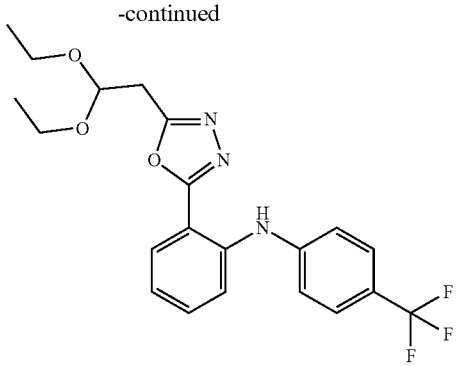

Compound 118

Step 1: N'-(3,3-diethoxypropanoyl)-2-[4-(trifluoromethyl)anilino]benzohydrazide

To a solution of 103-1b (301.5 mg, 1.86 mmol, 1.1 eq), EDCI (388.7 mg, 2.03 mmol, 1.2 eq) and HOBt (274.0 mg, 2.03 mmol, 1.2 eq) in DMF (5 mL) was added compound 103-1 (0.5 g, 1.69 mmol, 1 eq) followed by DIEA (655.2 mg, 5.07 mmol, 0.88 mL, 3 eq). The reaction mixture was stirred at 25° C. for 16 hours. The reaction was diluted with EA (30 mL) and washed with brine (2*10 mL). The organic layer was dried over Na₂SO₄ and concentrated. The residue was purified by column chromatography on silica gel to give compound 103-2 (0.45 g, 0.94 mmol, 55.7% yield).

Step 2: 2-(5-(2,2-diethoxyethyl)-1,3,4-oxadiazol-2-yl)-N-(4-(trifluoromethyl)phenyl)aniline To a solution of compound 103-2 (0.35 g, 0.79 mmol, 1 eq) and DIEA (308.8 mg, 2.39 mmol, 0.41 mL, 3 eq) in DCM (6 mL) was added TosCl (182.2 mg, 0.95 mmol, 1.2 eq). The reaction was stirred at 25° C. for 1 hr. The reaction was diluted with DCM (10 mL) and washed with water (2*5 mL). The organic layer was dried over Na₂SO₄ and concentrated. The crude product was purified by column chromatography on silica gel to give Compound 118 (250 mg, 0.58 mmol, 73.6% yield). LCMS (ESI): RT=1.075 min, mass calc. for $C_{21}H_{22}F_3N_3O_3$ 421.16, m/z found 422.1 [M+1]⁺; ¹H NMR (400 MHz, CDCl₃) δ 9.54 (s, 1H), 7.89 (d, J=7.9 Hz, 1H), 7.58 (d, J=8.4 Hz, 2H), 7.52 (d, J=8.6 Hz, 1H), 7.44-7.31 (m, 3H), 6.97 (t, J=7.6 Hz, 1H), 5.06 (t, J=5.8 Hz, 1H), 3.81-3.72 (m, 2H), 3.66-3.55 (m, 2H), 3.31 (d, J=5.8 Hz, 2H), 1.22 (t, J=7.0 Hz, 6H).

Example 104: 2-(5-(2-((4-(trifluoromethyl)phenyl)amino)phenyl)-1,3,4-oxadiazol-2-yl)acetic acid (Compound 119)

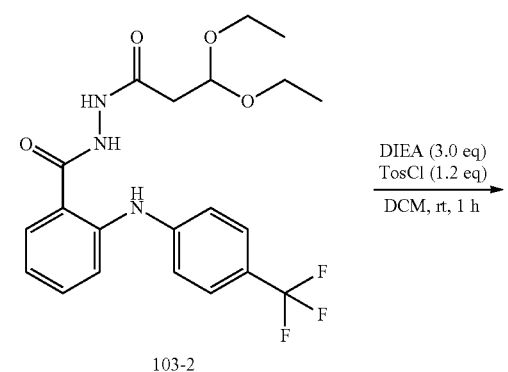

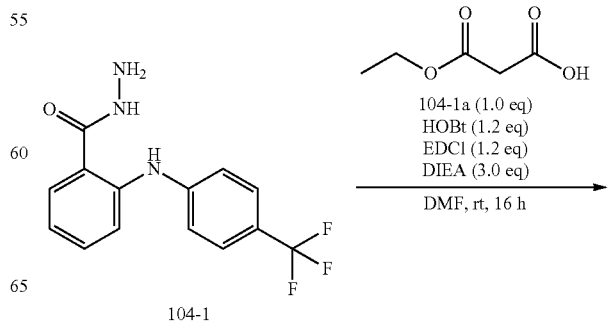

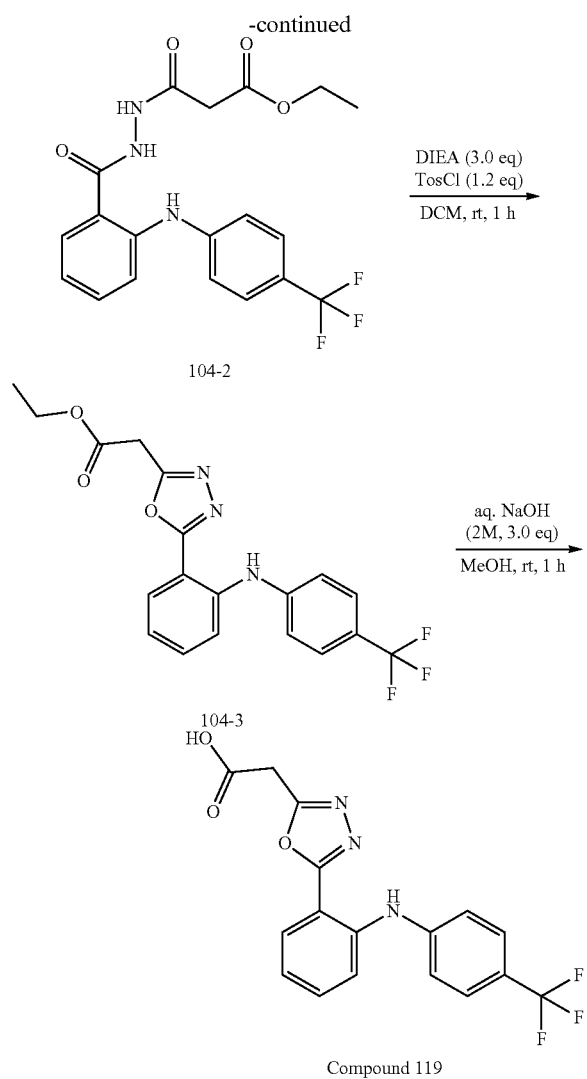

104-2

104-3

Compound 119

Step 1: Ethyl 3-oxo-3-[2-[2-[4-(trifluoromethyl)anilino]benzoyl]hydrazino]propanoate To a solution of compound 104-1a (223.2 mg, 1.6 mmol, 1 eq), EDCI (388.7 mg, 2.0 mmol, 1.2 eq) and HOBt (274.0 mg, 2.0 mmol, 1.2 eq) in DMF (5 mL) was added compound 104-1 (0.5 g, 1.6 mmol, 1 eq) followed by DIEA (655.2 mg, 5.0 mmol, 0.88 mL, 3 eq). The reaction mixture was stirred at 25° C. for 16 hours. The reaction was diluted with EA (30 mL) and washed with brine (2*10 mL). The organic layer was dried over Na₂SO₄ and concentrated to give compound 104-2 (700 mg, crude), which was used for next step directly.

Step 2: Ethyl 2-[5-[2-[4-(trifluoromethyl)anilino]phenyl]-1,3,4-oxadiazol-2-yl]acetate To a solution of compound 104-2 (700 mg, 1.7 mmol, 1 eq) and DIEA (663.0 mg, 5.1 mmol, 0.89 mL, 3 eq) in DCM (10 mL) was added TosCl (391.2 mg, 2.0 mmol, 1.2 eq). The reaction was stirred at 25° C. for 1 hr. The reaction was diluted with DCM (30 mL) and washed with water (2*10 mL). The organic layer was dried over Na₂SO₄ and concentrated. The crude product was purified by column chromatography on silica gel to give compound 104-3 (410 mg, 0.99 mmol, 58.2% yield).

Step 3: 2-(5-(2-((4-(trifluoromethyl)phenyl)amino)phenyl)-1,3,4-oxadiazol-2-yl)acetic Acid To a solution of compound 104-3 (310 mg, 0.79 mmol, 1 eq) in MeOH (1 mL) was added NaOH (2 M, 1.19 mL, 3 eq). The reaction was stirred at 25° C. for 1 hr. Another batch was combined. The reaction was concentrated. The aqueous layer was adjusted pH to 3-4 with 2N aq. HCl and filtered. Compound 119 (350 mg, 0.94 mmol, 79.4% yield) was obtained and then used for next step directly. LCMS (ESI): RT=0.936 min, mass calc. for $C_{17}H_{12}F_3N_3O_3$ 363.08, m/z found 363.9 [M+1]⁺; ¹H NMR (400 MHz, DMSO-d₆) δ 13.44-12.87 (m, 1H), 9.22 (s, 1H), 7.89 (dd, J=1.3, 8.0 Hz, 1H), 7.65 (d, J=8.5 Hz, 2H), 7.60-7.50 (m, 2H), 7.40 (d, J=8.6 Hz, 2H), 7.19-7.09 (m, 1H), 4.17 (s, 2H).

Example 105: 1-(5-(2-((4-(trifluoromethyl)phenyl)amino)phenyl)-1,3,4-oxadiazol-2-yl)but-3-yn-2-ol (Compound 120)

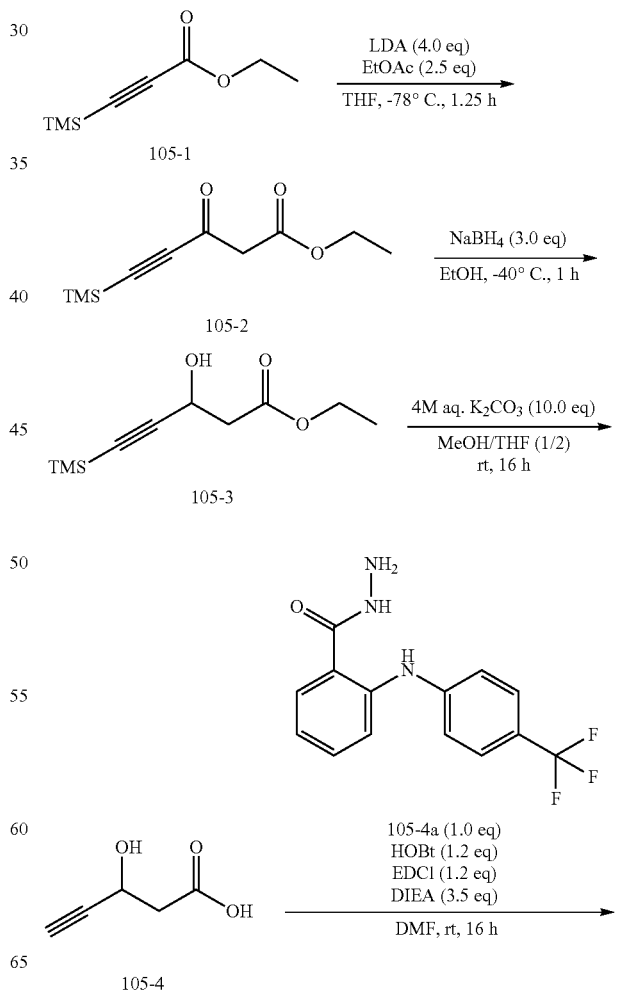

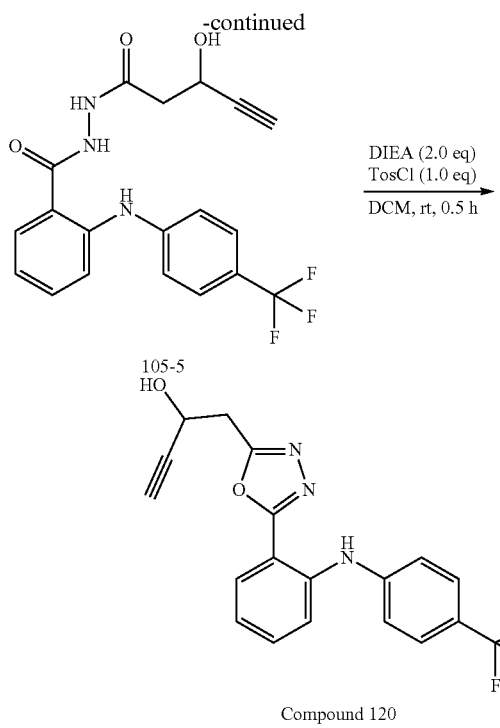

Step 1: Ethyl 3-oxo-5-trimethylsilyl-pent-4-ynoate

To a solution of EtOAc (1.29 g, 14.6 mmol, 1.4 mL, 2.5 eq) in THF (20 mL) was added drop-wise LDA (2 M, 11.7 mL, 4 eq) at −78° C. After 15 min, compound 105-1 (1 g, 5.8 mmol, 1.1 mL, 1 eq) in THF (5 mL) was added drop-wise at −78° C. The reaction was stirred at −78° C. for 1 hr. AcOH (1 mL) was added to the solution. The reaction was poured into ice/water slurry with 2N aq. HCl maintaining aqueous layer at the pH 3 and extracted with EA (2*50 mL). The organic layer was dried over Na$_2$SO$_4$ and concentrated. The crude product was purified by column chromatography on silica gel to give compound 105-2 (100 mg, 0.47 mmol, 8% yield).

Step 2: Ethyl 3-hydroxy-5-trimethylsilyl-pent-4-ynoate

To a solution of compound 105-2 (0.1 g, 0.47 mmol, 1 eq) in EtOH (3 mL) was added NaBH$_4$ (53.4 mg, 1.4 mmol, 3 eq) at −40° C. and the reaction was stirred at this temperature for 1 hr. The reaction was quenched by 2M aq. HCl (5 mL) and washed with EA (2*20 mL). The organic layer was dried over Na$_2$SO$_4$ and concentrated. The residue was purified by column chromatography on silica gel to give compound 105-3 (20 mg, 93.3 umol, 19.8% yield).

Step 3: 3-hydroxypent-4-ynoic Acid

A solution of K$_2$CO$_3$ (128.9 mg, 0.93 mmol, 10 eq) in H$_2$O (1 mL) was added to the solution of compound 105-3 (20 mg, 93.3 umol, 1 eq) in MeOH (1 mL) and THF (2 mL). The reaction was stirred at 25° C. for 16 hr. The reaction was concentrated. EtOH (5 mL) was added and the solution was filtered. The filtrate was concentrated to give compound 105-4 (10 mg, crude), which was used for next step directly.

Step 4: N'-(3-hydroxypent-4-ynoyl)-2-[4-(trifluoromethyl)anilino]benzohydrazide

To a solution of compound 105-4 (10 mg, 87.6 umol, 1 eq), HOBt (14.2 mg, 0.1 mmol, 1.2 eq) and EDCI (20.1 mg, 0.1 mmol, 1.2 eq) in DMF (1 mL) was added compound 105-4a (25.8 mg, 87.6 umol, 1 eq) followed by DIEA (28.3 mg, 0.21 mmol, 38 uL, 2.5 eq). The reaction was stirred at 25° C. for 16 hr. The reaction was diluted with EA (15 mL) and washed with brine (2*5 mL). The organic layer was dried over Na$_2$SO$_4$ and concentrated to give compound 105-5 (25 mg, crude), which was used for next step directly.

Step 5: 1-(5-(2-((4-(trifluoromethyl)phenyl)amino)phenyl)-1,3,4-oxadiazol-2-yl)but-3-yn-2-ol To a solution of compound 105-5 (25 mg, 63.8 umol, 1 eq) and TosCl (12.1 mg, 63.8 umol, 1.0 eq) in DCM (1 mL) was added DIEA (16.5 mg, 0.12 mmol, 22 uL, 2.0 eq). The reaction was stirred at 25° C. for 30 min. The reaction was diluted with DCM (10 mL) and washed with H$_2$O (2*5 mL). The organic layer was dried over Na$_2$SO$_4$ and concentrated. The reaction was purified by prep-HPLC to give Compound 120 (1.3 mg, 3.5 umol, 5.5% yield). LCMS (ESI): RT=0.961 min, mass calc. for C$_{19}$H$_{14}$F$_3$N$_3$O$_2$ 373.14, m/z found 374.0 [M+1]$^+$; $^1$H NMR (400 MHz, DMSO-d$_6$) δ 9.48 (br s, 1H), 7.89 (br d, J=8.1 Hz, 1H), 7.59 (br d, J=8.0 Hz, 2H), 7.52 (br d, J=8.3 Hz, 1H), 7.42 (br d, J=7.3 Hz, 1H), 7.37 (br d, J=8.6 Hz, 2H), 6.98 (t, J=7.4 Hz, 1H), 5.03-4.94 (m, 1H), 3.41 (br d, J=5.5 Hz, 2H), 2.57 (s, 1H).

Example 106: 2-bromo-1-(5-(2-((4-(trifluoromethyl)phenyl)amino)phenyl)-1,3,4-oxadiazol-2-yl)ethan-1-ol (Compound 121)

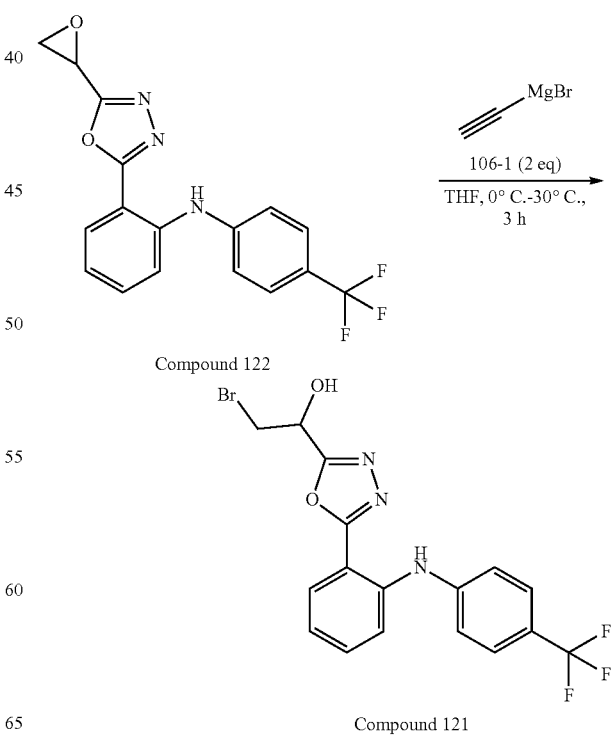

To a solution of Compound 122 (15.0 mg, 43.2 umol, 1 eq) in THF (1 mL) at 0° C. was added 106-1 (0.5 M, 0.17 mL, 2 eq), and the mixture was stirred at 30° C. for 3 h. The reaction mixture was quenched with saturated NH₄Cl (10 mL), diluted with water (10 mL) and then extracted with EA (20 mL*3). The combined organic layers were washed with brine (20 mL), dried over anhydrous Na₂SO₄, filtered and concentrated under reduced pressure to give Compound 121 (10.4 mg, 23.7 umol, 54.8% yield). LCMS (ESI): RT=0.867 min, mass calc. for $C_{17}H_{13}BrF_3N_3O_2$ 427.01, m/z found 429.8 [M+H]⁺; ¹H NMR (400 MHz, CDCl₃) δ 9.43 (s, 1H), 7.92 (dd, J=1.5, 8.0 Hz, 1H), 7.60 (d, J=8.5 Hz, 2H), 7.51 (d, J=8.5 Hz, 1H), 7.45-7.39 (m, 1H), 7.37 (d, J=8.5 Hz, 2H), 7.01-6.96 (m, 1H), 5.38-5.29 (m, 1H), 3.98-3.88 (m, 2H), 3.18 (d, J=6.8 Hz, 1H).

Example 107: 2-(5-(oxiran-2-yl)-1,3,4-oxadiazol-2-yl)-N-(4-(trifluoromethyl)phenyl)aniline (Compound 122), N-(4-(trifluoromethyl)phenyl)-2-(5-vinyl-1,3,4-oxadiazol-2-yl)aniline (Compound 123), and 1-(5-(2-((4-(trifluoromethyl)phenyl)amino)phenyl)-1,3,4-oxadiazol-2-yl)but-3-yn-1-ol (Compound 124)

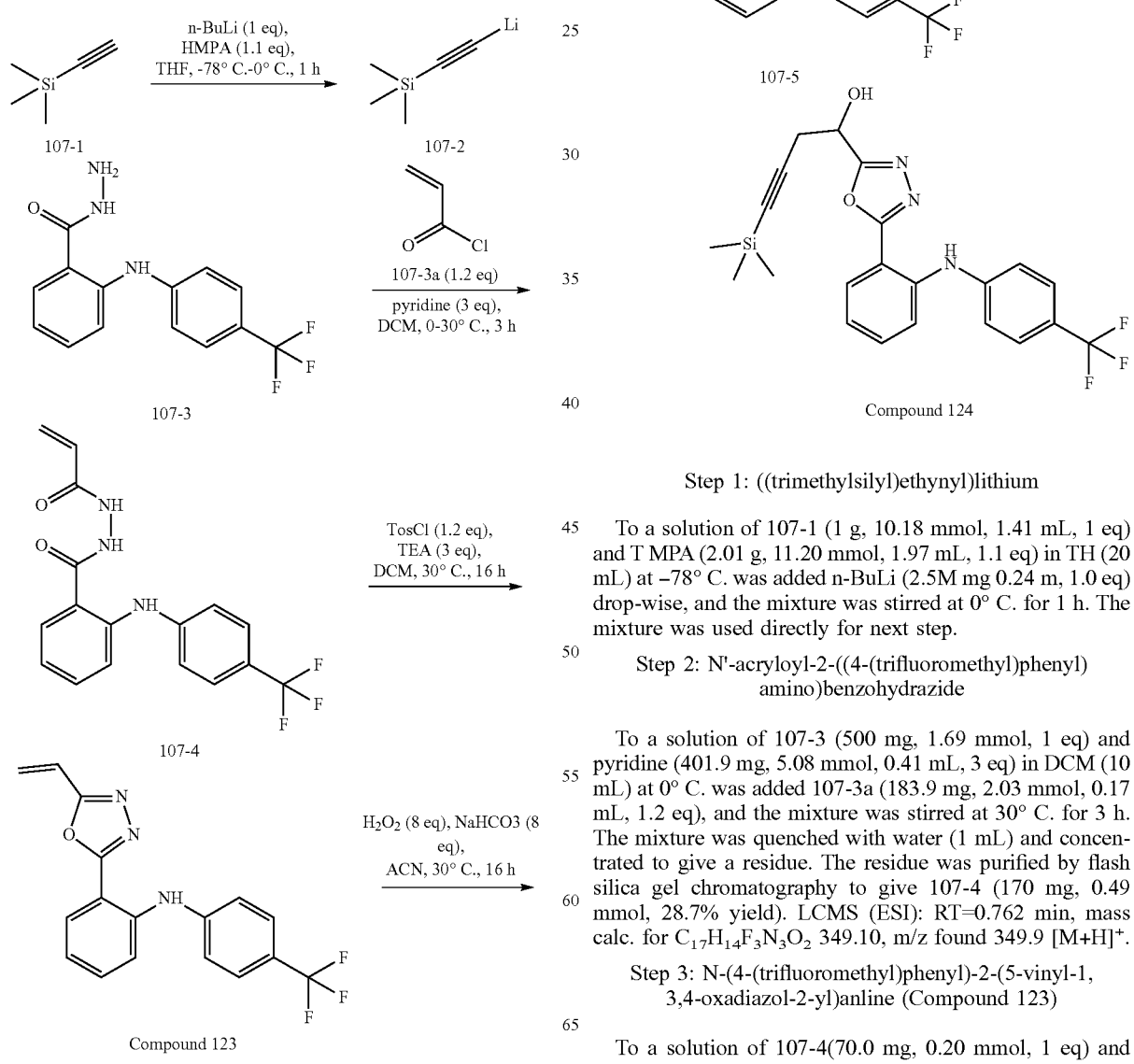

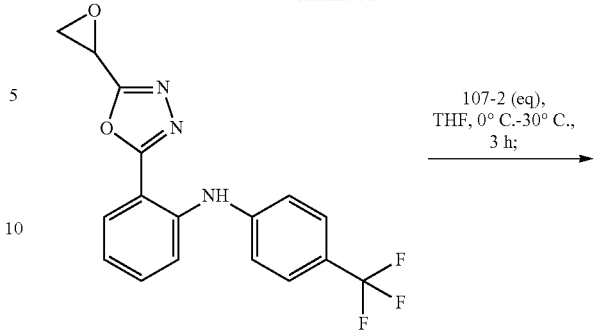

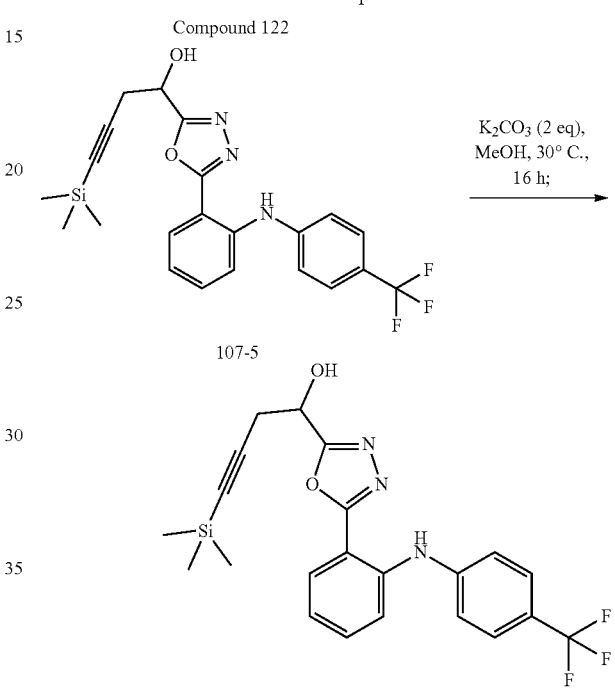

Step 1: ((trimethylsilyl)ethynyl)lithium

To a solution of 107-1 (1 g, 10.18 mmol, 1.41 mL, 1 eq) and T MPA (2.01 g, 11.20 mmol, 1.97 mL, 1.1 eq) in TH (20 mL) at −78° C. was added n-BuLi (2.5M mg 0.24 m, 1.0 eq) drop-wise, and the mixture was stirred at 0° C. for 1 h. The mixture was used directly for next step.

Step 2: N'-acryloyl-2-((4-(trifluoromethyl)phenyl)amino)benzohydrazide

To a solution of 107-3 (500 mg, 1.69 mmol, 1 eq) and pyridine (401.9 mg, 5.08 mmol, 0.41 mL, 3 eq) in DCM (10 mL) at 0° C. was added 107-3a (183.9 mg, 2.03 mmol, 0.17 mL, 1.2 eq), and the mixture was stirred at 30° C. for 3 h. The mixture was quenched with water (1 mL) and concentrated to give a residue. The residue was purified by flash silica gel chromatography to give 107-4 (170 mg, 0.49 mmol, 28.7% yield). LCMS (ESI): RT=0.762 min, mass calc. for $C_{17}H_{14}F_3N_3O_2$ 349.10, m/z found 349.9 [M+H]⁺.

Step 3: N-(4-(trifluoromethyl)phenyl)-2-(5-vinyl-1,3,4-oxadiazol-2-yl)anline (Compound 123)

To a solution of 107-4(70.0 mg, 0.20 mmol, 1 eq) and TEA (60.8 mg, 0.60 mmol, 84 uL, 3 eq) in DCM (3 mL) at 30° C. was added TosCl (45.8 mg, 0.24 mmol, 1.2 eq), and the mixture was stirred at 30° C. for 16 h. The mixture was concentrated to give a residue. The residue was purified by prep-HPLC to give Compound 123 (30 mg, 90.6 umol, 45.2% yield). LCMS (ESI): RT=0.933 min, mass calc. for $C_{17}H_{12}F_3N_3O$ 331.09, m/z found 331.9 [M+H]$^+$; $^1$H N/R (400 MHz, CDCl$_3$) δ 9.55 (s, 1H), 7.94 (dd, J=1.5, 8.0 Hz, 1H), 7.59 (d, J=8.5 Hz, 2H), 7.52 (d, J=7.8 Hz, 1H), 7.44-7.35 (m, 3H), 7.02-6.96 (m, 1H), 6.81 (dd, J=11.3, 17.6 Hz, 1H), 6.40 (d, J=17.8 Hz, 1H), 5.95-5.89 (m, 1H), 5.92 (d, J=11.8 Hz, 1H).

Step 4: 2-(5-(oxiran-2-yl)-1,3,4-oxadiazol-2-yl)-N-(4-(trifluoromethyl)phenyl)aniline (Compound 122)

To a solution of Compound 123 (120 mg, 0.36 mmol, 1 eq) in ACN (4 mL) at 30° C. were added H$_2$O$_2$ (328.6 mg, 2.90 mmol, 0.28 mL, 30% purity, 8 eq) and NaHCO$_3$ (243.4 mg, 2.90 mmol, 8 eq), and the mixture was stirred at 30° C. for 16 h. The reaction mixture was quenched with saturated Na$_2$SO$_3$ (30 mL), concentrated under reduced pressure to remove ACN. The residue was extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography to give Compound 122 (19.0 mg, 53.1 umol, 14.7% yield). LCMS (ESI): RT=0.877 min, mass calc. for $C_{17}H_{12}F_3N_3O_2$ 347.09, m/z found 347.9 [M+H]$^+$; $^1$H NMR (400 MHz, CDCl$_3$) δ 9.42 (s, 1H), 7.86 (dd, J=1.3, 8.0 Hz, 1H), 7.59 (d, J=8.5 Hz, 2H), 7.52-7.48 (m, 1H), 7.44-7.39 (m, 1H), 7.37 (d, J=8.5 Hz, 2H), 7.00-6.94 (m, 1H), 4.26 (dd, J=2.4, 4.1 Hz, 1H), 3.46 (dd, J=2.4, 5.4 Hz, 1H), 3.36 (dd, J=4.1, 5.4 Hz, 1H).

Step 5: 1-(5-(2-((4-(trifluoromethyl)phenyl)amino) phenyl)-1,3,4-oxadiazol-2-yl)-4-(trimethylsilyl)but-3-yn-1-ol To a solution of Compound 122 (20 mg, 57.6 umol, 1 eq) in THF (0.5 mL) at 0° C. was added compound 107-2 (0.37 M, 0.47 mL, 3 eq), and the resulting mixture was stirred at 30° C. for 3 h. The reaction mixture was quenched with saturated NH$_4$Cl solution (5 mL), then diluted with water (5 mL) and extracted with EA (10 mL*3). The combined organic layers were washed with brine (10 mL), dried over anhydrous Na$_2$SO$_4$, filtered and concentrated under reduced pressure to give 107-5 (25.0 mg, 56.1 umol, 97.4% yield) as crude, which was used directly for next step. LCMS (ESI): RT=0.975 min, mass calc. for $C_{22}H_{22}F_3N_3O_2Si$ 445.14, m/z found 446.2 [M+H]$^+$.

Step 6: 1-(5-(2-((4-(trifluoromethyl)phenyl)amino) phenyl)-1,3,4-oxadiazol-2-yl)but-3-yn-1-ol (Compound 124)

To a solution of 107-5 (23.0 mg, 51.6 umol, 1 eq) in MeOH (1 mL) at 30° C. was added K$_2$CO$_3$ (14.3 mg, 0.10 mmol, 2 eq), and the resulting mixture was stirred at 30° C. for 16 h. The reaction mixture was filtered to remove the solid. The filtrate was concentrated under reduced pressure to give a residue. The residue was purified by flash silica gel chromatography to give Compound 124 (6.5 mg, 17.4 umol, 33.7% yield). LCMS (ESI): RT=0.855 min, mass calc. for $C_{19}H_{14}F_3N_3O_2$ 373.10, m/z found 373.9 [M+H]$^+$; $^1$H NMR (400 MHz, CDCl$_3$) δ 9.46 (s, 1H), 7.92 (dd, J=1.3, 8.0 Hz, 1H), 7.59 (d, J=8.4 Hz, 2H), 7.54-7.49 (m, 1H), 7.44-7.39 (m, 1H), 7.37 (d, J=8.4 Hz, 2H), 6.98 (t, J=7.6 Hz, 1H), 5.23 (t, J=5.8 Hz, 1H), 3.08 (brs, 1H), 3.04-2.97 (m, 2H), 2.16 (t, J=2.6 Hz, 1H).

Example 108: 4-(5-(2-((4-(trifluoromethyl)phenyl) amino)phenyl)-1,3,4-oxadiazol-2-yl)butanenitrile (Compound 125)

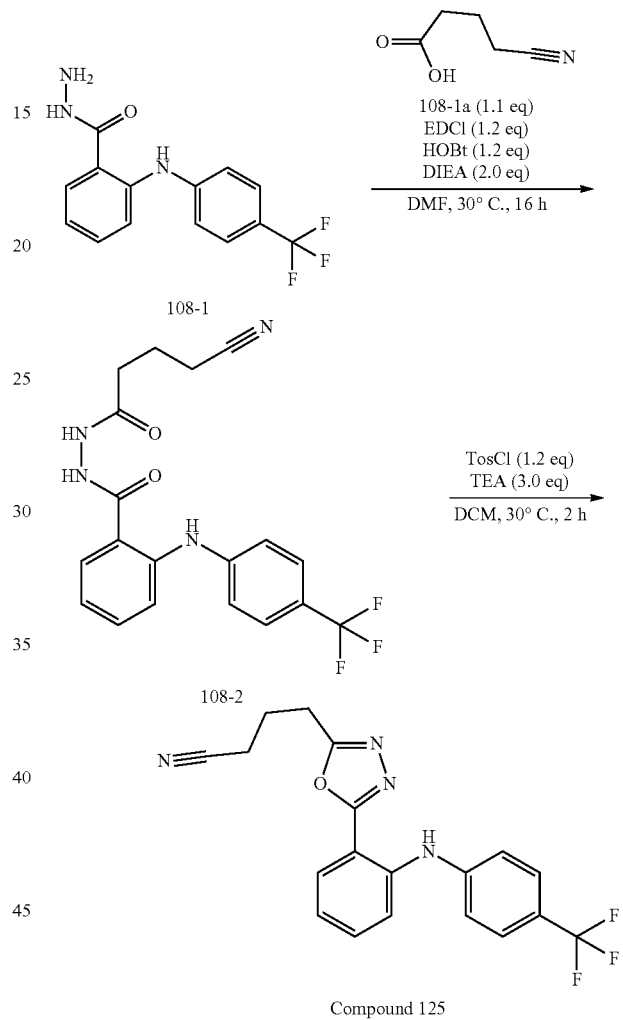

Compound 125

Step 1: N'-(4-cyanobutanoyl)-2-[4-(trifluoromethyl) anilino]benzohydrazide

To a solution of compound 108-1 (200 mg, 0.68 mmol, 1 eq) and compound 108-1a (84 mg, 0.75 mmol, 1.1 eq) in DMF (3 mL) were added EDCI (155 mg, 0.71 mmol, 1.2 eq), HOBt (110 mg, 0.81 mmol, 1.2 eq) and DIEA (175 mg, 1.35 mmol, 0.24 mL, 2 eq). The mixture was stirred at 30° C. for 16 hr. The reaction mixture was quenched with H$_2$O (10 mL), extracted with EA (15 mL*3). The combined organic phase was washed with H$_2$O (5 mL*2) and brine (5 mL*3), dried over Na$_2$SO$_4$, filtered and concentrated in vacuum. The crude product was purified by column chromatography. Compound 108-2 (165 mg, 0.42 mmol, 62% yield) was obtained.

Step 2: 4-(5-(2-((4-(trifluoromethyl)phenyl)amino)phenyl)-1,3,4-oxadiazol-2-yl)butanenitrile To a solution of compound 108-2 (100 mg, 0.26 mmol, 1 eq) in DCM (1 mL) were added TosCl (73 mg, 0.38 mmol, 1.5 eq) and TEA (78 mg, 0.77 mmol, 0.1 mL, 3 eq). The mixture was stirred at 30° C. for 2 hr. The reaction mixture was concentrated in vacuum. The residue was diluted with EA (20 mL), washed with H$_2$O (5 mL) and brine (5 mL), dried over Na$_2$SO$_4$, filtered and concentrated in vacuum. The crude product was purified by prep-HPLC. LCMS and $^1$HNMR confirmed that Compound 125 (47.8 mg, 0.13 mmol, 50% yield) was obtained. LCMS (ESI): RT=0.879 min, mass calcd. For C$_{19}$H$_{15}$F$_3$N$_4$O, 372.12 m/z found 372.9 [M+H]$^+$. $^1$H NMR (400 MHz, CDCl$_3$) δ 9.47 (s, 1H), 7.89 (dd, J=1.4, 7.9 Hz, 1H), 7.60 (d, J=8.5 Hz, 2H), 7.53 (d, J=8.3 Hz, 1H), 7.45-7.40 (m, 1H), 7.38 (d, J=8.5 Hz, 2H), 7.06-6.94 (m, 1H), 3.17 (t, J=7.2 Hz, 2H), 2.66 (t, J=7.0 Hz, 2H), 2.31 (quin, J=7.2 Hz, 2H).

Example 109: 3-(5-(2-((4-(trifluoromethyl)phenyl)amino)phenyl)-1,3,4-oxadiazol-2-yl)propanenitrile (Compound 126)

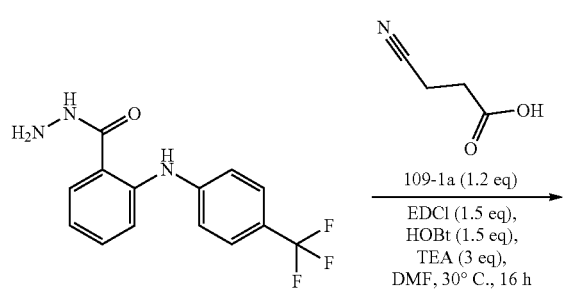

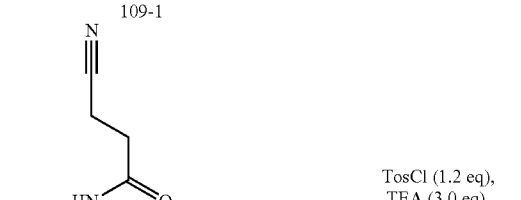

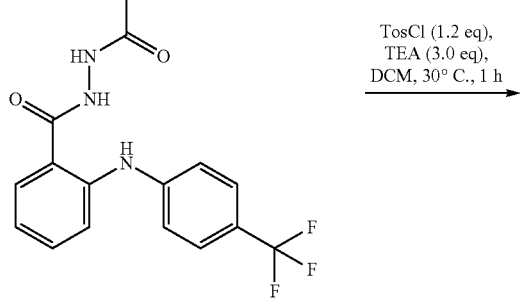

Compound 126

Step 1: N'-(3-cyanopropanoyl)-2-((4-(trifluoromethyl)phenyl)amino)benzohydrazide To a solution of 109-1a (40.3 mg, 0.41 mmol, 1.2 eq), EDCI (97.4 mg, 0.51 mmol, 1.5 eq) and HOBt (68.7 mg, 0.51 mmol, 1.5 eq) in DMF (2 mL) at 30° C. was added 109-1 (100 mg, 0.34 mmol, 1 eq) and then TEA (102.8 mg, 1.02 mmol, 0.14 mL, 3 eq), and the resulting mixture was stirred at 30° C. for 16 h. The reaction mixture was diluted with water (20 mL) and extracted with EA (20 mL*3). The combined organic layers were washed with water (10 mL*2) and brine (20 ml), dried over anhydrous Na$_2$SO$_4$, filtered and concentrated under reduced pressure to give 109-2 (160 mg, 0.29 mmol, 86.2% yield), which was used directly for next step. LCMS (ESI): RT=0.749 min, mass calc. for C$_{18}$H$_{15}$F$_3$N$_4$O$_2$ 376.11, m/z found 399.0 [M+23]$^+$.

Step 2: 3-(5-(2-((4-(trifluoromethyl)phenyl)amino)phenyl)-1,3,4-oxadiazol-2-yl)propanenitrile To a solution of 109-2 (150 mg, 0.27 mmol, 1 eq) and TEA (83.1 mg, 0.82 mmol, 0.11 mL, 3 eq) in DCM (1 mL) at 30° C. was added TosCl (62.7 mg, 0.33 mmol, 1.2 eq), and the resulting mixture was stirred at 30° C. for 1 h. The mixture was concentrated to give a residue. The residue was purified by flash silica gel chromatography to give 50 mg sample. The 50 mg sample was purified further by prep-HPLC to give Compound 126 (14.0 mg, 39.1 umol, 14.3% yield). LCMS (ESI): RT=0.862 min, mass calc. for C$_{18}$H$_{13}$F$_3$N$_4$O 358.10, m/z found 358.9 [M+1]$^+$; $^1$H NMR (400 MHz, CDCl$_3$) δ 9.42 (s, 1H), 7.88 (dd, J=1.5, 8.0 Hz, 1H), 7.59 (d, J=8.3 Hz, 2H), 7.54-7.49 (m, 1H), 7.44-7.39 (m, 1H), 7.37 (d, J=8.5 Hz, 2H), 7.02-6.95 (m, 1H), 3.36 (t, J=7.3 Hz, 2H), 3.00 (t, J=7.4 Hz, 2H).

Example 110: 2-(5-(3-(methylamino)propyl)-1,3,4-oxadiazol-2-yl)-N-(4-(trifluoromethyl)phenyl)aniline (Compound 127), tert-butyl methyl(3-(5-(2-((4-(trifluoromethyl)phenyl)amino)phenyl)-1,3,4-oxadiazol-2-yl)propyl)carbamate (Compound 128), and N-methyl-N-(3-(5-(2-((4-(trifluoromethyl)phenyl)amino)phenyl)-1,3,4-oxadiazol-2-yl)propyl)cyanamide (Compound 129)

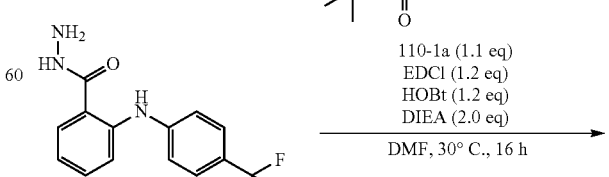

110-1

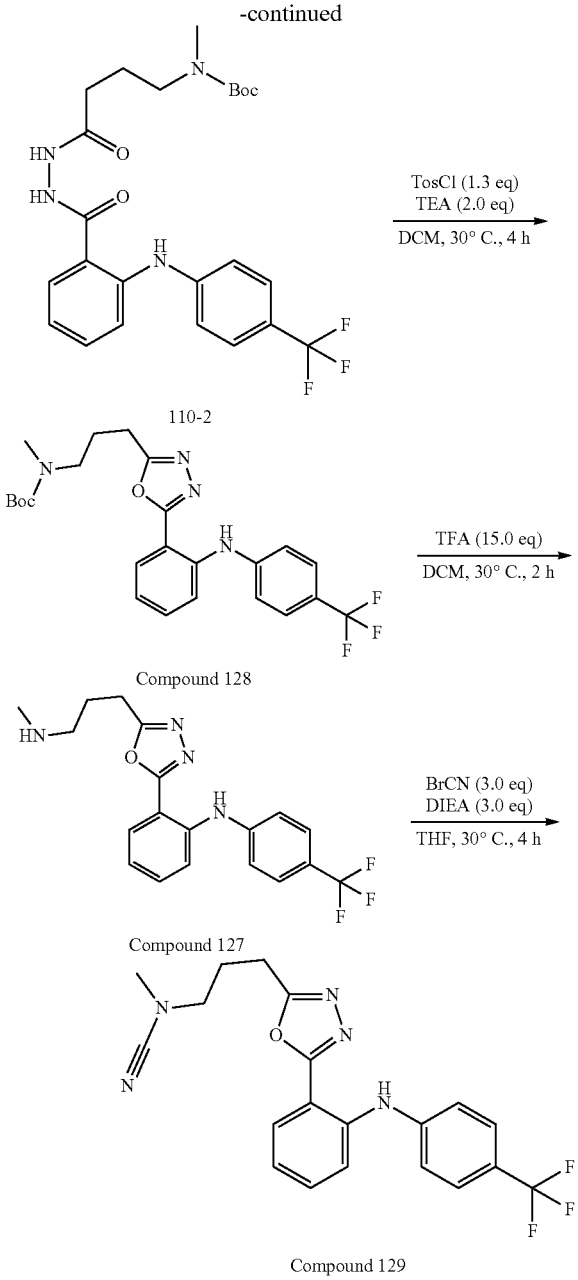

Step 2: Tert-Butyl Methyl(3-(5-(2-((4-(trifluoromethyl)phenyl)amino)phenyl)-1,3,4-oxadiazol-2-yl)propyl)carbamate (Compound 128)

To a solution of compound 110-2 (260 mg, 0.53 mmol, 1 eq) in DCM (3 mL) were added TEA (106 mg, 1.05 mmol, 0.15 mL, 2 eq) and TosCl (130 mg, 0.68 mmol, 1.3 eq). The mixture was stirred at 30° C. for 4 hr. The reaction mixture was concentrated in vacuum. The residue was diluted with EA (20 mL), washed with H$_2$O (5 mL) and brine (5 mL), dried over Na$_2$SO$_4$, filtered and concentrated in vacuum. The crude product was purified by column chromatography. LCMS and $^1$HNMR confirmed that Compound 128 (162 mg, 0.33 mmol, 63% yield) was obtained. LCMS (ESI): RT=0.973 min, mass calcd. For C$_{24}$H$_{27}$F$_3$N$_4$O$_3$, 476.20 m/z found 499.0 [M+Na]$^+$. $^1$H NMR (400 MHz, CDCl$_3$) δ 9.53 (s, 1H), 7.88 (dd, J=1.3, 7.8 Hz, 1H), 7.58 (d, J=8.3 Hz, 2H), 7.51 (d, J=8.3 Hz, 1H), 7.42-7.33 (m, 3H), 6.97 (t, J=7.2 Hz, 1H), 3.41 (br t, J=6.7 Hz, 2H), 2.96 (t, J=7.5 Hz, 2H), 2.90 (s, 3H), 2.12 (quin, J=7.3 Hz, 2H), 1.45 (s, 9H).

Step 3: 2-(5-(3-(methylamino)propyl)-1,3,4-oxadiazol-2-yl)-N-(4-(trifluoromethyl)phenyl)aniline (Compound 127)

To a solution of Compound 128 (150 mg, 0.31 mmol, 1 eq) in DCM (2 mL) was added TFA (538 mg, 4.72 mmol, 0.35 mL, 15 eq). The mixture was stirred at 30° C. for 2 hr. The reaction mixture was concentrated in vacuum. The residue was diluted with EA (20 mL), washed with saturated aq.Na$_2$CO$_3$ (10 mL) and brine (10 mL), dried over Na$_2$SO$_4$, filtered and concentrated in vacuum. The crude product was used for the next step directly. LCMS and $^1$HNMR confirmed that Compound 127 (110 mg, 0.29 mmol, 91% yield) was obtained. LCMS (ESI): RT=2.008 min, mass calcd. For C$_{19}$H$_{19}$F$_3$N$_4$O, 376.15 m/z found 377.1 [M+H]$^+$. $^1$H NMR (400 MHz, CDCl$_3$) δ 9.46 (br s, 1H), 7.56-7.44 (m, 4H), 7.37-7.30 (m, 1H), 7.19 (d, J=8.5 Hz, 2H), 6.90 (t, J=7.2 Hz, 1H), 3.41 (t, J=7.0 Hz, 2H), 2.96 (s, 3H), 2.74-2.63 (m, 2H), 2.08-1.94 (m, 2H).

Step 4: N-methyl-N-(3-(5-(2-((4-(trifluoromethyl)phenyl)amino)phenyl)-1,3,4-oxadiazol-2-yl)propyl)cyanamide (Compound 129)

To a solution of Compound 128 (70 mg, 0.19 mmol, 1 eq) in THF (1 mL) were added BrCN (59 mg, 0.56 mmol, 41 uL, 3 eq) and DIEA (72 mg, 0.56 mmol, 97 uL, 3 eq). The mixture was stirred at 30° C. for 2 hr. The reaction mixture was concentrated in vacuum. The residue was diluted with EA (20 mL), washed with H$_2$O (5 mL) and brine (5 mL), dried over Na$_2$SO$_4$, filtered and concentrated in vacuum. The crude product was purified by prep-HPLC. LCMS and $^1$HNMR confirmed that Compound 129 (4.5 mg, 11 umol, 6% yield) was obtained. LCMS (ESI): RT=2.008 min, mass calcd. For C$_{20}$H$_{18}$F$_3$N$_5$O, 401.15 m/z found 402.0 [M+H]$^+$. $^1$H NMR (400 MHz, CDCl$_3$) δ 9.47 (s, 1H), 7.89 (dd, J=1.4, 7.9 Hz, 1H), 7.59 (d, J=8.5 Hz, 2H), 7.51 (d, J=8.0 Hz, 1H), 7.45-7.34 (m, 3H), 7.03-6.93 (m, 1H), 3.20 (t, J=6.9 Hz, 2H), 3.09 (t, J=7.3 Hz, 2H), 2.93 (s, 3H), 2.27 (quin, J=7.0 Hz, 2H).

Step 1: Tert-Butyl N-methyl-N-[4-oxo-4-[2-[2-[4-(trifluoromethyl)anilino]benzoyl]hydrazino]butyl]carbamate To a solution of compound 110-1 (200 mg, 0.68 mmol, 1 eq) and compound 110-1a (161 mg, 0.75 mmol, 1.1 eq) in DMF (3 mL) were added EDCI (155 mg, 0.81 mmol, 1.2 eq), HOBt (109 mg, 0.81 mmol, 1.2 eq) and DIEA (175 mg, 1.35 mmol, 0.24 mL, 2 eq). The mixture was stirred at 30° C. for 16 hr. The reaction mixture was quenched with H$_2$O (10 mL), extracted with EA (15 mL*3). The combined organic phase was washed with H$_2$O (5 mL*2) and brine (5 mL*3), dried over Na$_2$SO$_4$, filtered and concentrated in vacuum. The crude product was purified by column chromatography. LCMS confirmed that compound 110-2 (260 mg, 0.49 mmol, 72% yield) was obtained.

Example 111: 3-hydroxy-3-(5-(2-((4-(trifluoromethyl)phenyl)amino)phenyl)-1,3,4-oxadiazol-2-yl)butanenitrile (Compound 130) and 4-amino-2-(5-(2-((4-(trifluoromethyl)phenyl)amino)phenyl)-1,3,4-oxadiazol-2-yl)butan-2-ol (Compound 131)

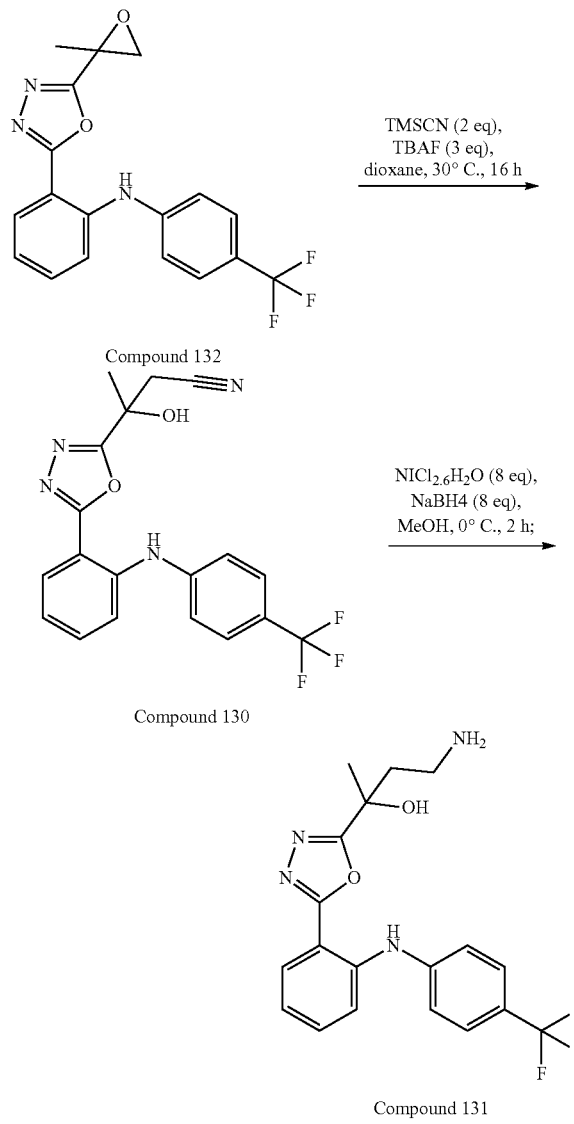

Step 1: 3-hydroxy-3-(5-(2-((4-(trifluoromethyl)phenyl)amino)phenyl)-1,3,4-oxadiazol-2-yl)butanenitrile (Compound 130)

To a solution of Compound 132 (25 mg, 69.2 umol, 1 eq) in dioxane (2 mL) at 30° C. was added TMSCN (13.7 mg, 0.14 mmol, 17 uL, 2 eq) and then TBAF (1 M, 0.21 mL, 3 eq), and the resulting mixture was stirred at 30° C. for 16 h. The mixture was concentrated to give a residue. The residue was purified by flash silica gel chromatography to give Compound 130 (20.0 mg, 50.2 umol, 72.5% yield). LCMS (ESI): RT=0.841 min, mass calc. for $C_{19}H_{15}F_3N_4O_2$ 388.11, m/z found 388.9 [M+1]$^+$; $^1$H NMR (400 MHz, CDCl$_3$) δ 9.36 (s, 1H), 7.91 (dd, J=1.4, 7.9 Hz, 1H), 7.60 (d, J=8.5 Hz, 2H), 7.53-7.49 (m, 1H), 7.42 (dt, J=1.4, 7.8 Hz, 1H), 7.36 (d, J=8.5 Hz, 2H), 7.02-6.97 (m, 1H), 3.44 (brs, 1H), 3.17 (q, J=16.8 Hz, 2H), 1.95 (s, 3H).

Step 2: 4-amino-2-(5-(2-((4-(trifluoromethyl)phenyl)amino)phenyl)-1,3,4-oxadiazol-2-yl)butan-2-ol (Compound 131)

To a solution of Compound 130 (140 mg, 0.36 mmol, 1 eq) in MeOH (3 mL) at 0° C. was added NiCl$_2$.6H$_2$O (685.5 mg, 2.88 mmol, 8 eq) and then NaBH$_4$ (109.1 mg, 2.88 mmol, 8 eq), and the resulting mixture was stirred at 0° C. for 2 h. After quenched with saturated NH$_4$Cl solution (20 mL) at 0° C., it was stirred at 30° C. for 16 h. The mixture was concentrated to give a residue. The residue was diluted with water (30 mL) and extracted with EA (30 mL*3). The combined organic layers were washed with brine (30 mL), dried over anhydrous Na$_2$SO$_4$, filtered and concentrated under reduced pressure to give a residue. The residue was purified by prep-HPLC. The collected pure fractions was basified with saturated NaHCO$_3$ solution to pH=8-9, then concentrated to remove ACN and then extracted with EA (50 mL*3). The combined organic layers were washed with brine (30 mL), dried over anhydrous Na$_2$SO$_4$, filtered and concentrated under reduced pressure to give Compound 131 (45.0 mg, 0.11 mmol, 31.8% yield). LCMS (ESI): RT=0.705 min, mass calc. for $C_{19}H_{19}F_3N_4O_2$ 392.15, m/z found 393.0 [M+1]$^+$; $^1$H NMR (400 MHz, CD$_3$OD) δ 7.73 (d, J=6.9 Hz, 1H), 7.51 (d, J=8.6 Hz, 2H), 7.48-7.44 (m, 1H), 7.42-7.36 (m, 1H), 7.21 (d, J=8.5 Hz, 2H), 6.99 (t, J=7.3 Hz, 1H), 3.48 (brs, 1H), 3.40-3.32 (m, 1H), 2.12 (d, J=6.4 Hz, 2H), 1.50 (s, 3H).

Example 112: 2-(5-(2-methyloxiran-2-yl)-1,3,4-oxadiazol-2-yl)-N-(4-(trifluoromethyl)phenyl)aniline (Compound 132), 2-(5-(prop-1-en-2-yl)-1,3,4-oxadiazol-2-yl)-N-(4-(trifluoromethyl)phenyl)aniline (Compound 133), and 1-amino-2-(5-(2-((4-(trifluoromethyl)phenyl)amino)phenyl)-1,3,4-oxadiazol-2-yl)propan-2-ol (Compound 134)

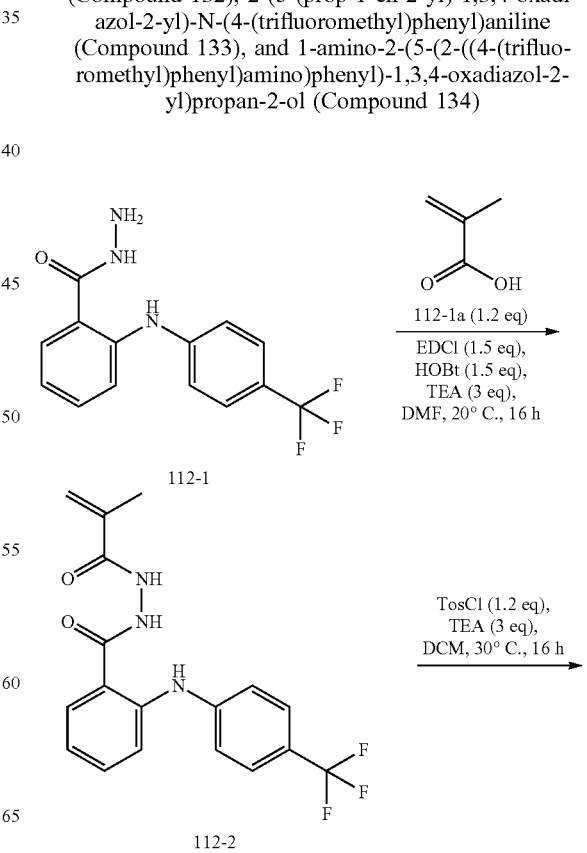

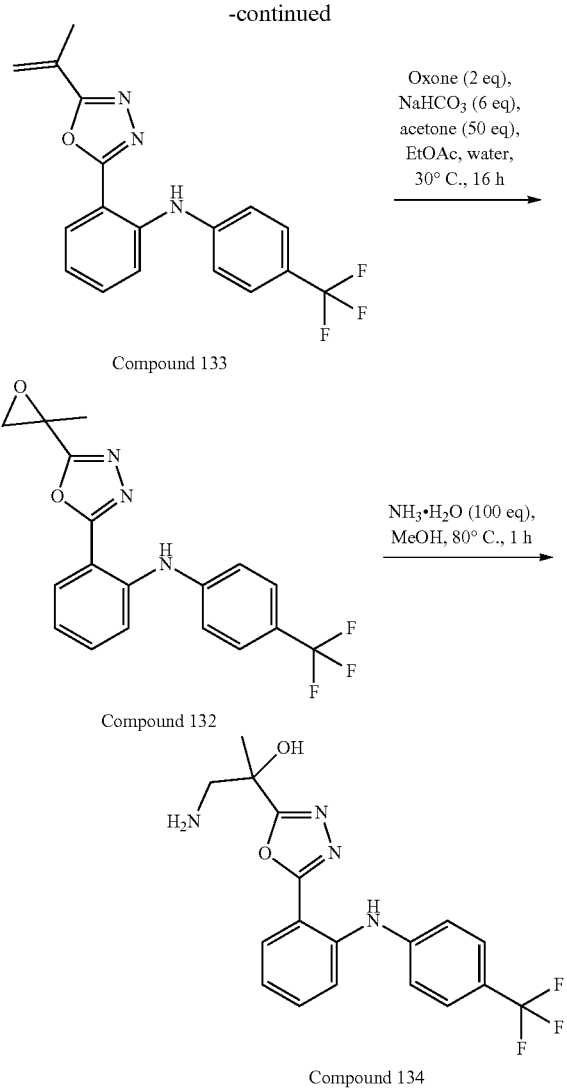

Step 1: N'-methacryloyl-2-((4-(trifluoromethyl)phenyl)amino)benzohydrazide

To a solution of 112-1a (174.9 mg, 2.03 mmol, 0.17 mL, 1.2 eq), EDCI (487.0 mg, 2.54 mmol, 1.5 eq) and HOBt (343.2 mg, 2.54 mmol, 1.5 eq) in DMF (10 mL) at 20° C. was added 112-1 (500 mg, 1.69 mmol, 1 eq) and then TEA (514.1 mg, 5.08 mmol, 0.71 mL, 3 eq), and the mixture was stirred at 20° C. for 16 h. The reaction mixture was diluted with water (20 mL), and then extracted with EA (20 mL*3). The combined organic layers were washed with water (10 mL*2) and brine (20 mL), dried over anhydrous $Na_2SO_4$, filtered and concentrated under reduced pressure to give a residue. The residue was purified by flash silica gel chromatography to give 112-2 (440 mg, 1.17 mmol, 69.2% yield). LCMS (ESI): RT=0.783 min, mass calc. for $C_8H_{16}F_3N_3O_2$ 363.12, m/z found 363.9 [M+1]$^+$; $^1$H NMR (400 MHz, CDCl$_3$) δ 9.18 (s, 1H), 9.02 (brs, 1H), 8.72 (brs, 1H), 7.61 (d, J=8.0 Hz, 1H), 7.54 (d, J=8.5 Hz, 2H), 7.48-7.44 (m, 1H), 7.43-7.38 (m, 1H), 7.24 (d, J=8.3 Hz, 2H), 6.94 (t, J=7.5 Hz, 1H), 5.95 (s, 1H), 5.53 (s, 1H), 2.06 (s, 3H).

Step 2: 2-(5-(prop-1-en-2-yl)-1,3,4-oxadiazol-2-yl)-N-(4-(trifluoromethyl)phenyl)aniline (Compound 133)

To a solution of 112-2 (200 mg, 0.55 mmol, 1 eq) and TEA (167.1 mg, 1.65 mmol, 0.23 mL, 3 eq) in DCM (3 mL) at 30° C. was added TosCl (125.9 mg, 0.66 mmol, 1.2 eq), and the mixture was stirred at 30° C. for 16 h. The reaction mixture was diluted with water (20 mL), and then extracted with EA (20 mL*3). The combined organic layers were washed with water (10 mL*2) and brine (20 mL), dried over anhydrous $Na_2SO_4$, filtered and concentrated under reduced pressure to give a residue. The residue was purified by flash silica gel chromatography to give Compound 133 (120 mg, 0.34 mmol, 61.2% yield). LCMS (ESI): RT=0.978 min, mass calc. for $C_{18}H_{14}F_3N_3O$ 345.11, m/z found 345.9 [M+1]$^+$; $^1$H NMR (400 MHz, CDCl$_3$) δ 9.62 (s, 1H), 7.94 (dd, J=1.4, 7.9 Hz, 1H), 7.59 (d, J=8.5 Hz, 2H), 7.53 (d, J=8.0 Hz, 1H), 7.44-7.39 (m, 1H), 7.37 (d, J=8.8 Hz, 2H), 7.03-6.95 (m, 1H), 6.13 (s, 1H), 5.63 (d, J=0.6 Hz, 1H), 2.30 (s, 3H).

Step 3: 2-(5-(2-methyloxiran-2-yl)-1,3,4-oxadiazol-2-yl)-N-(4-(trifluoromethyl)phenyl)aniline (Compound 132)

To a solution of Compound 133 (120 mg, 0.35 mmol, 1 eq) and NaHCO$_3$ (175.2 mg, 2.09 mmol, 81 uL, 6 eq) in water (2 mL) and EtOAc (2 mL) at 30° C. was added acetone (1.01 g, 17.38 mmol, 1.28 mL, 50 eq) and then Oxone (427.3 mg, 0.70 mmol, 2 eq), and the mixture was stirred at 30° C. for 16 h. The reaction mixture was diluted with water (20 mL), and then extracted with EA (20 mL*3). The combined organic layers were washed with water (10 mL*2) and brine (20 mL), dried over anhydrous Na$_2$SO$_4$, filtered and concentrated under reduced pressure to give a residue. The residue was purified by flash silica gel chromatography to give Compound 132 (35.0 mg, 95.3 umol, 27.4% yield). LCMS (ESI): RT=0.914 min, mass calc. for $C_{18}H_{14}F_3N_3O_2$ 361.10, m/z found 361.9 [M+1]$^+$; $^1$H NMR (400 MHz, CDCl$_3$) δ 9.45 (s, 1H), 7.85 (dd, J=1.4, 7.9 Hz, 1H), 7.59 (d, J=8.5 Hz, 2H), 7.51 (d, J=7.8 Hz, 1H), 7.40 (dt, J=1.5, 7.9 Hz, 1H), 7.36 (d, J=8.3 Hz, 2H), 6.97 (ddd, J=1.1, 7.2, 8.0 Hz, 1H), 3.54 (d, J=5.5 Hz, 1H), 3.16 (d, J=5.0 Hz, 1H), 1.94 (s, 3H).

Step 4: 1-amino-2-(5-(2-((4-(trifluoromethyl)phenyl)amino)phenyl)-1,3,4-oxadiazol-2-yl)propan-2-ol (Compound 134)

To a solution of Compound 132 (30 mg, 83.0 umol, 1 eq) in MeOH (1 mL) at 30° C. was added NH$_3$·H$_2$O (1.16 g, 8.30 mmol, 1.28 mL, 25% solution, 100 eq), and the mixture was stirred at 80° C. for 1 h. The reaction mixture was concentrated under reduced pressure to give Compound 134 (23.0 mg, 60.8 umol, 73.2% yield). LCMS (ESI): RT=0.718 min, mass calc. for $C_{18}H_{17}F_3N_4O_2$ 378.13, m/z found 379.0 [M+1]$^+$; $^1$H NMR (400 MHz, CDCl$_3$) δ 9.43 (s, 1H), 7.93 (d, J=7.0 Hz, 1H), 7.56 (d, J=8.3 Hz, 2H), 7.49 (d, J=8.3 Hz, 1H), 7.41-7.36 (m, 1H), 7.33 (d, J=8.5 Hz, 2H), 6.96 (t, J=7.4 Hz, 1H), 3.59 (d, J=12.5 Hz, 1H), 2.89 (d, J=12.5 Hz, 1H), 2.72 (brs, 3H), 1.66 (s, 3H).

Example 113: 2-(5-(2-((4-(trifluoromethyl)phenyl)amino)phenyl)-1,3,4-oxadiazol-2-yl)butan-2-ol (Compound 135)

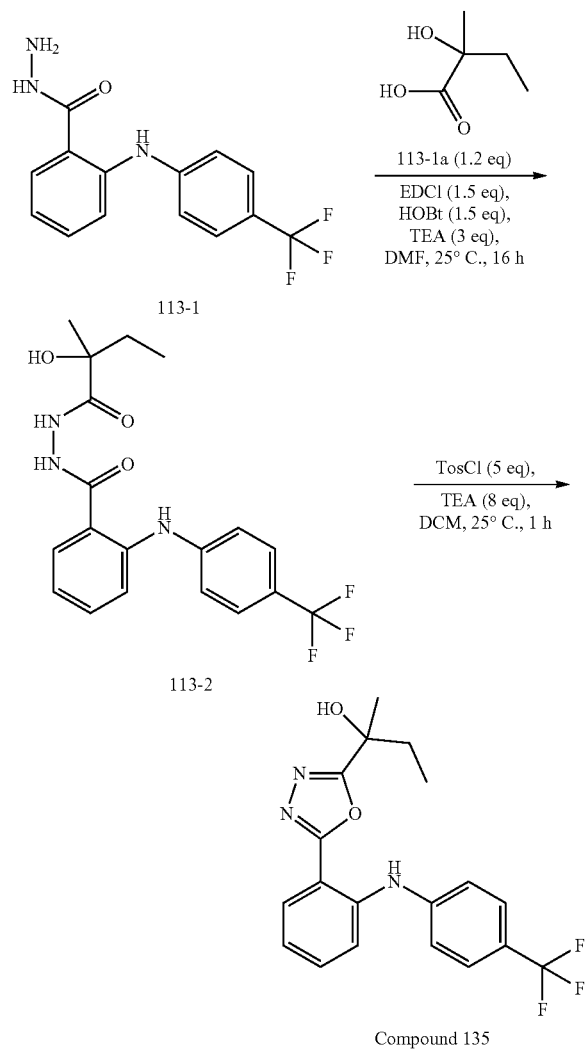

Step 1: N'-(2-hydroxy-2-methylbutanoyl)-2-((4-(trifluoromethyl)phenyl)amino)benzohydrazide To a solution of 2-hydroxy-2-methyl-butanoic acid 113-1a (48.0 mg, 0.41 mmol, 1.2 eq), EDCI (97.39 mg, 508.04 umol, 1.5 eq) and TEA (102.8 mg, 1.02 mmol, 0.14 mL, 3 eq) in DMF (1.5 mL) at 25° C. were added 113-1 (100 mg, 0.34 mmol, 1 eq) and then HOBt (68.6 mg, 0.51 mmol, 1.5 eq) and the resulting mixture was stirred at 25° C. for 16 h. The mixture was directly purified by prep-HPLC to give 113-2 (30 mg, 75.88 umol, 22.40% yield). LCMS (ESI): R=0.775 min, mass calcd. For $C_{19}H_{20}F_3N_3O_3$ 418.0 found [M+23]$^+$.

Step 2: 2-(5-(2-((4-(trifluoromethyl)phenyl)amino)phenyl)-1,3,4-oxadiazol-2-yl)butan-2-ol To a solution of compound 113-2 (25 mg, 63.2 umol, 1 eq) and TosCl (60.3 mg, 0.32 mmol, 5 eq) in DCM (3 mL) was added TEA (51.2 mg, 0.51 mmol, 70 uL, 8 eq) at 25° C. and the resulting mixture was stirred at 25° C. for 1 h. The mixture was diluted with water (5 mL) and then diluted with EA (30 mL) and separated. The separated organic layer was washed with brine (10 mL) twice, dried by anhydrous Na$_2$SO$_4$, filtered and concentrated under pressure to give a residue. The residue was directly purified by prep-HPLC to give Compound 135 (7.7 mg, 20.54 umol, 32.48% yield). LCMS (ESI): R=0.898 min, mass calcd. For $C_{19}H_{18}F_3N_3O_2$ 377.14 m/z found 377.9 [M+1]$^+$; $^1$H NMR (400 MHz, DMSO-d$_6$) δ 9.24 (s, 1H), 7.94 (d, J=7.9 Hz, 1H), 7.63 (d, J=8.6 Hz, 2H), 7.59-7.51 (m, 2H), 7.33 (d, J=8.5 Hz, 2H), 7.22-7.11 (m, 1H), 5.97-5.79 (m, 1H), 1.96-1.80 (m, 2H), 1.63-1.45 (m, 3H), 0.83 (t, J=7.4 Hz, 3H).

Example 114: 2-(5-((1-aminocyclopropyl)methyl)-1,3,4-oxadiazol-2-yl)-N-(4-(trifluoromethyl)phenyl)aniline (Compound 136)

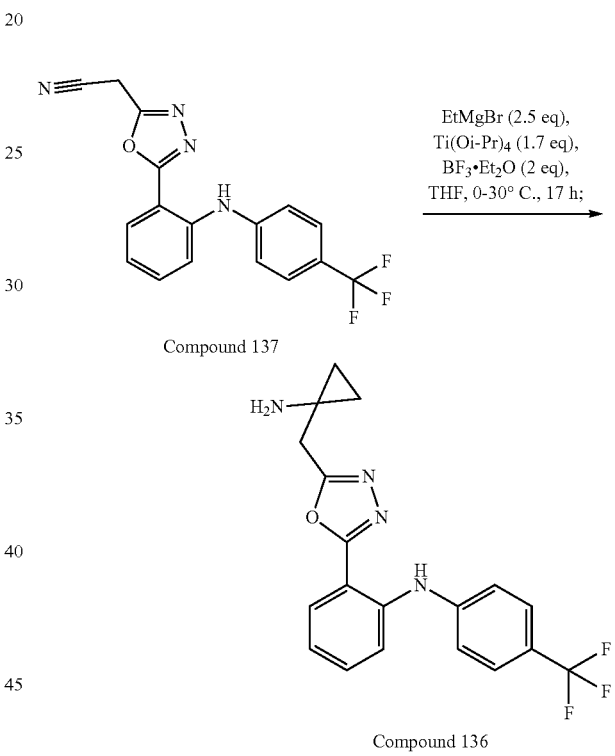

To a solution of Compound 137 (50 mg, 0.15 mmol, 1 eq) in THF (1 mL) at 0° C. were added Ti(i-PrO)$_4$ (70.2 mg, 0.25 mmol, 73 uL, 1.7 eq) and then EtMgBr (3.0 M, 0.12 mL, 2.5 eq), and the mixture was stirred at 30° C. for 1 h. After BF$_3$.Et$_2$O (137.4 mg, 0.29 mmol, 0.12 mL, 30% solution, 2 eq) was added at 0° C. into the above mixture, the resulting mixture was stirred at 30° C. for 16 h. The mixture was quenched with water (1 mL), diluted with saturated Na$_2$CO$_3$ solution (20 mL), and then extracted with EA (20 mL*3). The combined organic layers were washed with brine (20 mL), dried over anhydrous Na$_2$SO$_4$, filtered and concentrated under reduced pressure to give a residue. The residue was purified by prep-HPLC to give Compound 136 (5.0 mg, 12.6 umol, 8.6% yield). LCMS (ESI): RT=0.739 min, mass calc. for $C_{19}H_{17}F_3N_4O$ 374.14, m/z found 375.0 [M+H]$^+$; $^1$H NMR (400 MHz, CDCl$_3$) δ 9.56 (s, 1H), 7.91 (s, 1H), 7.60 (d, J=7.0 Hz, 2H), 7.54 (d, J=8.3 Hz, 1H), 7.45-7.36 (m, 3H), 7.02 (s, 1H), 3.08 (brs, 2H), 0.83 (brs, 4H).

Example 115: 2-(5-(2-((4-(trifluoromethyl)phenyl) amino)phenyl)-1,3,4-oxadiazol-2-yl)acetonitrile (Compound 137)

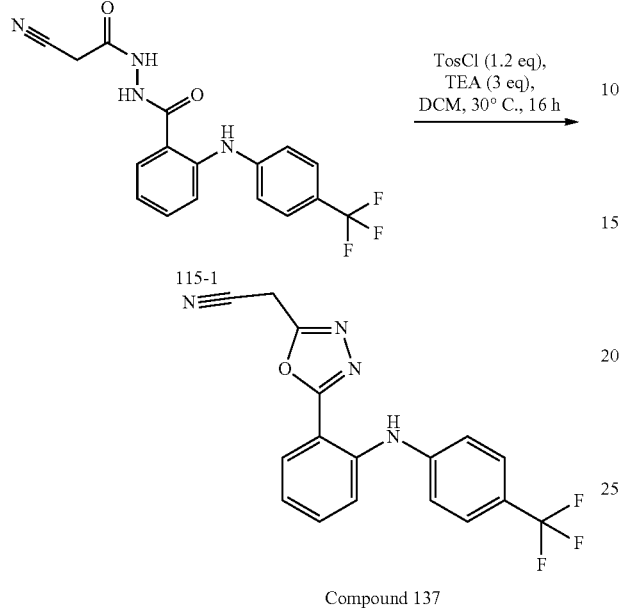

Compound 137

To a solution of 115-1 (350 mg, 0.97 mmol, 1 eq) and TEA (293.3 mg, 2.90 mmol, 0.40 mL, 3 eq) in DCM (5 mL) at 30° C. was added TosCl (221.0 mg, 1.16 mmol, 1.2 eq), and the resulting mixture was stirred at 30° C. for 16 h. The mixture was concentrated under reduced pressure to give a residue. The residue was purified by flash silica gel chromatography to give Compound 137 (160 mg, 0.46 mmol, 48.1% yield). LCMS (ESI): RT=0.857 min, mass calc. for $C_{17}H_{11}F_3N_4O$ 344.09, m/z found 344.9 [M+H]$^+$; $^1$H NMR (400 MHz, CDCl$_3$) δ 9.33 (s, 1H), 7.90 (dd, J=1.3, 7.9 Hz, 1H), 7.60 (d, J=8.4 Hz, 2H), 7.53-7.49 (m, 1H), 7.46-7.41 (m, 1H), 7.38 (d, J=8.4 Hz, 2H), 7.03-6.97 (m, 1H), 4.17 (s, 2H).

Example 116: 2-(5-(1-((methylamino)methyl)cyclopropyl)-1,3,4-oxadiazol-2-yl)-N-(4-(trifluoromethyl)phenyl)aniline (Compound 138)

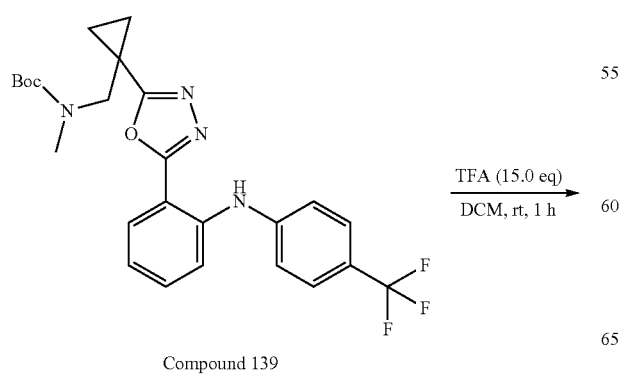

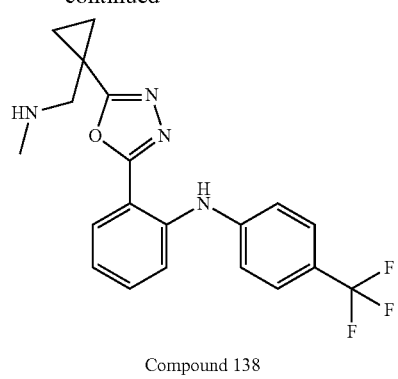

Compound 138

To a solution of Compound 139 (0.2 g, 0.4 mmol, 1 eq) in DCM (2 mL) was added TFA (700 mg, 6.14 mmol, 0.45 mL, 15 eq). The reaction was stirred at 25° C. for 1 hr. The reaction was diluted with DCM (30 mL) adjusted pH to 8-9 with Sat.Na$_2$CO$_3$ and washed with H$_2$O (2*5 mL). The organic layer was dried over Na$_2$SO$_4$ and concentrated. Compound 138 (120 mg, 0.3 mmol, 74% yield) was obtained without further purification. LCMS (ESI): RT=0.836 min, mass calc. for $C_{20}H_{19}F_3N_4O$ 388.15, m/z found 389.0 [M+1]$^+$; $^1$H NMR (400 MHz, CDCl$_3$) δ 9.43 (s, 1H), 7.71 (dd, J=1.3, 7.9 Hz, 1H), 7.49 (d, J=8.5 Hz, 2H), 7.43 (d, J=8.4 Hz, 1H), 7.34-7.24 (m, 3H), 6.88 (t, J=7.6 Hz, 1H), 2.94 (s, 2H), 2.46-2.39 (m, 3H), 1.40-1.31 (m, 2H), 1.12-1.04 (m, 2H).

Example 117: tert-butyl methyl((1-(5-(2-((4-(trifluoromethyl)phenyl)amino)phenyl)-1,3,4-oxadiazol-2-yl)cyclopropyl)methyl)carbamate (Compound 139)

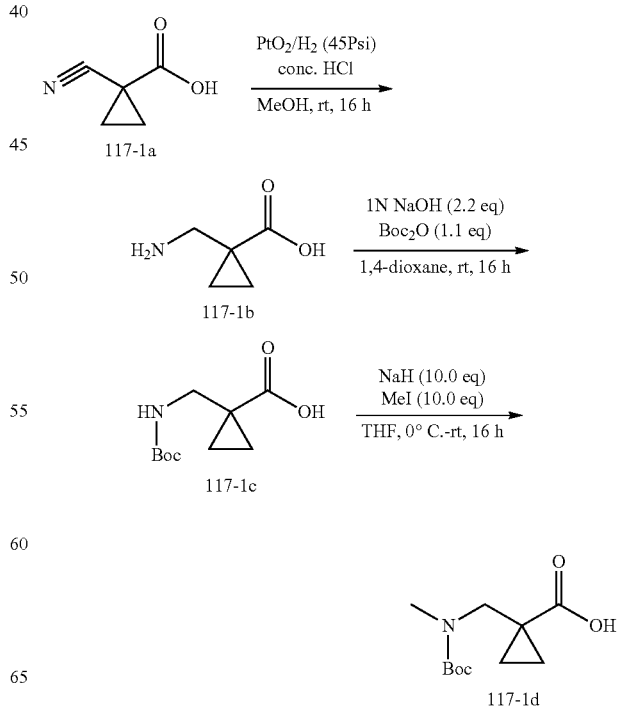

-continued

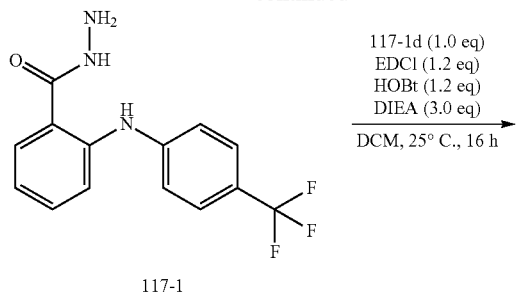

117-1

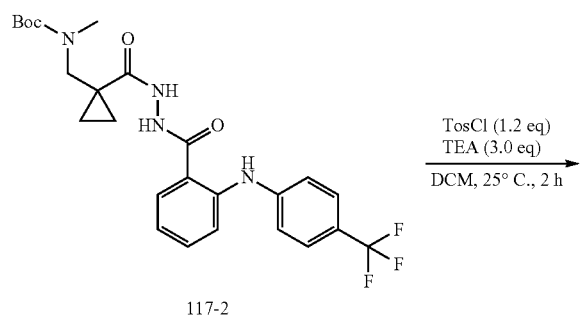

117-2

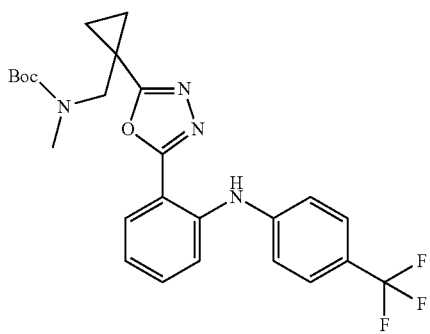

Compound 139

Step 1: 1-(aminomethyl)cyclopropanecarboxylic Acid

To a solution of compound 117-1a (1 g, 9 mmol, 1 eq) and HCl (12 M, 0.5 mL) in MeOH (40 mL) was added PtO$_2$ (0.3 g, 0.26 mmol, 2.94e-2 eq) under N$_2$. The suspension was degassed under vacuum and purged with H$_2$ several times. The mixture was stirred under H$_2$ (45 psi) at 25° C. for 16 hours. The reaction was filtered and concentrated. Compound 117-1b (1.2 g, 7.92 mmol, 87.9% yield, HCl) was used for next step directly. $^1$H NMR (400 MHz, CD$_3$OD) δ 3.33 (td, J=1.6, 3.3 Hz, 2H), 3.04 (s, 3H), 1.32-1.25 (m, 3H), 0.93-0.84 (m, 3H).

Step 2: 1-[(tert-butoxycarbonylamino)methyl]cyclopropanecarboxylic Acid

A solution of compound 117-1b (1.2 g, 7.9 mmol, 1 eq, HCl) and NaOH (1 M, 17 mL, 2.2 eq) in 1,4-dioxane (25 mL) was stirred at 25° C. for 15 min. Boc$_2$O (1.9 g, 8.7 mmol, 2 mL, 1.1 eq) was added to the solution. The reaction was stirred at 25° C. for 16 hr. 1,4-dioxane was removed. The aqueous layer was adjusted pH to 3 with Sat. citric acid and extracted with EA (2*40 mL). The organic layer was dried over Na$_2$SO$_4$ and concentrated. Compound 117-1c (1.5 g, 6.97 mmol, 88% yield) was used for next step directly. $^1$HNMR (400 MHz, CD$_3$OD) δ 3.30 (s, 2H), 1.45 (s, 9H), 1.21-1.13 (m, 2H), 0.95-0.90 (m, 2H).

Step 3: 1-[[tert-butoxycarbonyl(methyl)amino]methyl]cyclopropanecarboxylic Acid To a solution of compound 117-1c (0.7 g, 3.2 mmol, 1 eq) and MeI (4.6 g, 32.5 mmol, 2 mL, 10 eq) in THF (15 mL) was added NaH (1.30 g, 32.52 mmol, 60% purity, 10 eq) in portions at 0° C. The reaction was stirred at 25° C. for 16 hr. The precipitate was formed. PE (15 mL) was added. The reaction was washed with water (2*20 mL). The aqueous layer was adjusted pH to 4 with Sat. citric acid and extracted with EA (2*30 mL). The organic layer was dried over Na$_2$SO$_4$ and concentrated. The compound 117-1d (0.45 g, 1.9 mmol, 60% yield) was used for next step directly. $^1$H NMR (400 MHz, CDCl$_3$) δ 3.58 (s, 2H), 2.92 (s, 3H), 1.46 (s, 9H), 1.40-1.25 (m, 2H), 1.10-1.00 (m, 2H).

Step 4: tert-butyl N-methyl-N-[[1-[[[2-[4-(trifluoromethyl)anilino]benzoyl]amino]carbamoyl]cyclopropyl]methyl]carbamate To a solution of compound 117-1 (300 mg, 1 mmol, 1 eq), HOBt (164.7 mg, 1.2 mmol, 1.2 eq) and EDCI (233.7 mg, 1.22 mmol, 1.2 eq) in DMF (5 mL) was added compound 117-1d (232.9 mg, 1 mmol, 1 eq) followed by DIEA (393.9 mg, 3.05 mmol, 0.53 mL, 3 eq). The reaction was stirred at 25° C. for 16 hr. The reaction was diluted with EA (60 mL) and washed with brine (2*20 mL). The organic layer was dried over Na$_2$SO$_4$ and concentrated. The residue was purified by column chromatography on silica gel to give compound 117-2 (360 mg, 0.68 mmol, 67% yield). LCMS confirmed that desired product was obtained. LCMS (ESI): RT=1.018 min, mass calc. for C$_{25}$H$_{29}$F$_3$N$_4$O$_4$ 506.21, m/z found 507.1 [M+1]$^+$.

Step 5: Tert-Butyl Methyl((1-(5-(2-((4-(trifluoromethyl)phenyl)amino)phenyl)-1,3,4-oxadiazol-2-yl)cyclopropyl)methyl)carbamate To a solution of compound 117-2 (0.36 g, 0.71 mmol, 1 eq) and TosCl (162.6 mg, 0.85 mmol, 1.2 eq) in DCM (8 mL) was added DIEA (275.5 mg, 2.13 mmol, 0.37 mL, 3 eq). The reaction was stirred at 25° C. for 2 hr. The reaction was diluted with DCM (30 mL) and washed with brine (2*10 mL). The organic layer was dried over Na$_2$SO$_4$ and concentrated. The reaction was purified by column chromatography on silica gel to give Compound 139 (0.27 g, 0.55 mmol, 76.9% yield). LCMS (ESI): RT=1.131 min, mass calc. for C$_{25}$H$_{27}$F$_3$N$_4$O$_3$ 488.20, m/z found 489.0 [M+1]$^+$; $^1$H NMR (400 MHz, CDCl$_3$) δ 9.49 (br s, 1H), 7.88 (br s, 1H), 7.59 (d, J=8.5 Hz, 2H), 7.55-7.50 (m, 1H), 7.44-7.33 (m, 3H), 6.98 (t, J=7.4 Hz, 1H), 3.90-3.79 (m, 2H), 2.99 (s, 3H), 1.44 (s, 11H), 1.31-1.19 (m, 2H).

Example 118: N-methyl-N-((1-(5-(2-((4-(trifluoromethyl)phenyl)amino)phenyl)-1,3,4-oxadiazol-2-yl)cyclopropyl)methyl)cyanamide (Compound 140)

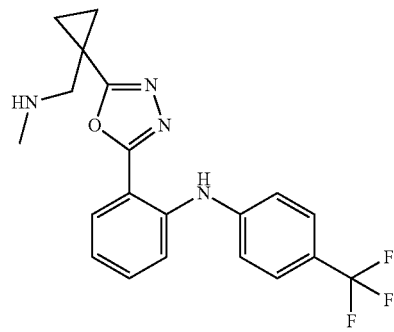

Compound 138

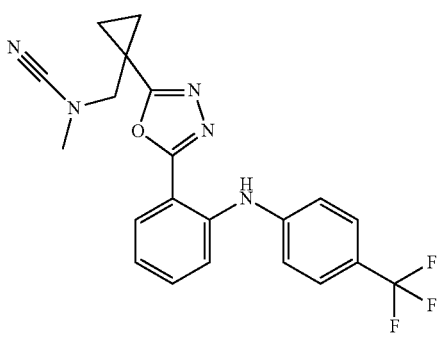

Compound 140

To a solution of Compound 138 (0.1 g, 0.25 mmol, 1 eq) and DIEA (99.8 mg, 0.77 mmol, 0.13 mL, 3 eq) in THF (2 mL) was added BrCN (50 mg, 0.47 mmol, 34 uL, 1.83 eq). The reaction was stirred at 25° C. for 1 hr. The reaction was diluted with EA (30 mL) and washed with brine (3*10 mL). The organic layer was dried over Na$_2$SO$_4$ and concentrated. The crude product was triturated with EA (3 mL) and PE (10 mL), filtered to give Compound 140 (60.5 mg, 0.14 mmol, 54.5% yield). LCMS (ESI): RT=1.002 min, mass calc. for C$_{21}$H$_{18}$F$_3$N$_5$O 413.15, m/z found 414.0 [M+1]$^+$; $^1$H NMR (400 MHz, CDCl$_3$) δ 9.36 (s, 1H), 7.76 (dd, J=1.2, 7.9 Hz, 1H), 7.50 (d, J=8.5 Hz, 2H), 7.43 (d, J=8.5 Hz, 1H), 7.35-7.25 (m, 3H), 6.90 (t, J=7.4 Hz, 1H), 3.44 (s, 2H), 2.99 (s, 3H), 1.50-1.40 (m, 2H), 1.31-1.18 (m, 2H).

Example 119: 2-(5-(2-methyl-2-(methylamino)propyl)-1,3,4-oxadiazol-2-yl)-N-(4-(trifluoromethyl)phenyl)aniline (Compound 141)

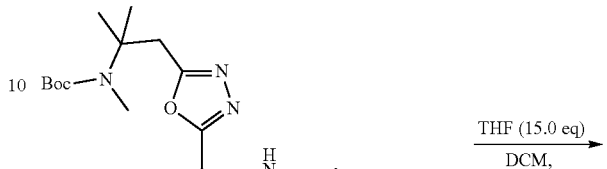

Compound 142

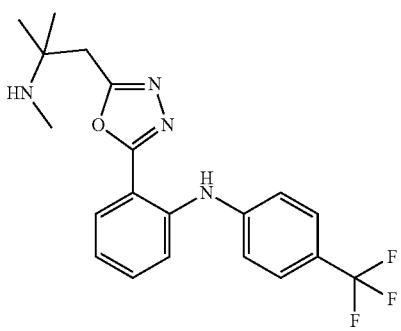

Compound 141

To a solution of Compound 142 (70 mg, 0.14 mmol, 1 eq) in DCM (2 mL) was added TFA (244 mg, 2.1 mmol, 0.15 mL, 15 eq). The reaction was stirred at 25° C. for 1 hr. The reaction was diluted with DCM (5 mL) and washed with water (10 mL). The aqueous layer was adjusted pH to 8-9 with Sat.Na$_2$CO$_3$ and extracted with EA (2*10 mL). The organic layer was dried over Na$_2$SO$_4$ and concentrated. 60 mg of crude Compound 141 was obtained. 20 mg of crude product was purified by prep-HPLC to give pure Compound 141 (1.9 mg, 4.8 umol, 3% yield). LCMS (ESI): RT=0.847 min, mass calc. for C$_{20}$H$_{21}$F$_3$N$_4$O 390.17, m/z found 391.0 [M+1]$^+$; $^1$HNMR (400 MHz, CDCl$_3$) δ 9.56 (s, 1H), 7.89 (d, J=6.8 Hz, 1H), 7.60 (d, J=8.5 Hz, 2H), 7.53 (d, J=8.0 Hz, 1H), 7.44-7.36 (m, 3H), 6.99 (t, J=7.2 Hz, 1H), 3.09 (s, 2H), 2.47 (s, 3H), 1.27 (s, 6H). 40 mg of remained crude product was used directly in the synthesis of Compound 143.

Example 120: tert-butylmethyl(2-methyl-1-(5-(2-((4-(trifluoromethyl)phenyl)amino)phenyl)-1,3,4-oxadiazol-2-yl)propan-2-yl)carbamate (Compound 142)

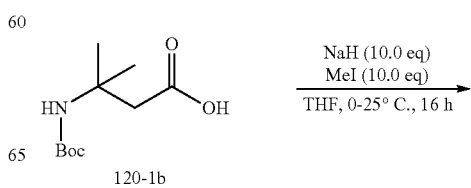

120-1b

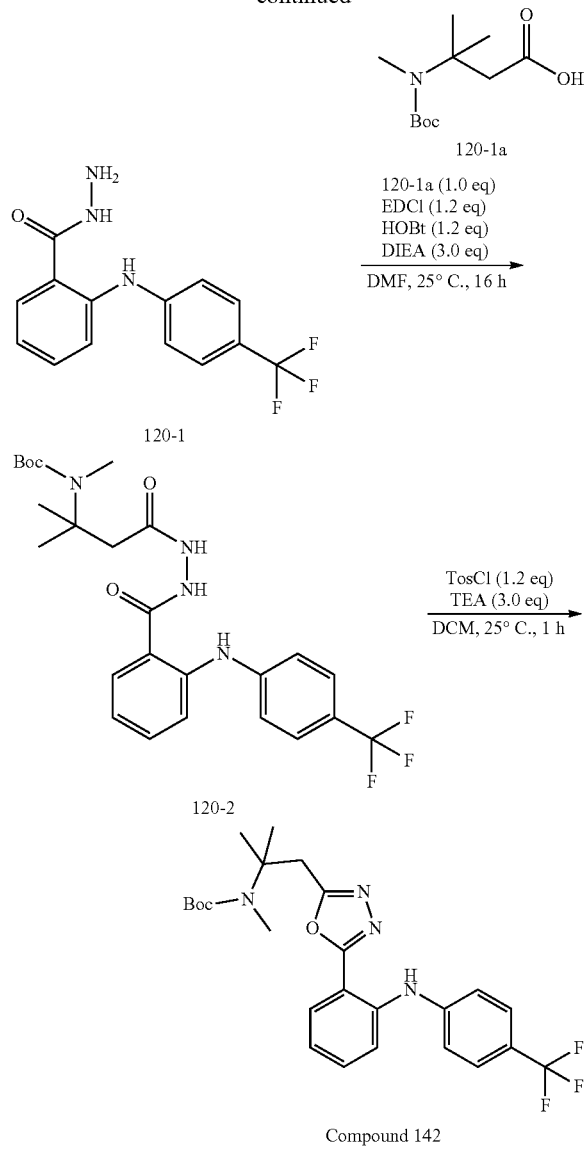

eq) and HOBt (98 mg, 0.72 mmol, 1.2 eq) in DMF (5 mL) was added DIEA (234 mg, 1.82 mmol, 0.31 mL, 3 eq). The reaction was stirred at 25° C. for 16 hr. The reaction was diluted with EA (30 mL) and washed with brine (2*10 mL). The organic layer was dried over $Na_2SO_4$ and concentrated. The residue was purified by column chromatography on silica gel to give 120-2 (170 mg, 0.29 mmol, 49% yield). LCMS (ESI): RT=1.018 min, mass calc. for $C_{25}H_{31}F_3N_4O_4$ 508.23, m/z found 509.1 [M+1]$^+$.

Step 3: Tert-Butyl Methyl(2-methyl-1-(5-(2-((4-(trifluoromethyl)phenyl)amino)phenyl)-1,3,4-oxadiazol-2-yl)propan-2-yl)carbamate To a solution of 120-2 (170 mg, 0.33 mmol, 1 eq) and TosCl (76.4 mg, 0.4 mmol, 1.2 eq) in DCM (4 mL) was added $Et_3N$ (101 mg, 1 mmol, 0.13 mL, 3 eq). The reaction was stirred at 25° C. for 1 hr. The reaction was diluted with DCM (30 mL) and washed with H2O (2*10 mL). The organic layer was dried over $Na_2SO_4$ and concentrated. The residue was purified by column chromatography on silica gel to give crude Compound 142 (90 mg). 20 mg of crude product was re-purified by prep-HPLC to give Compound 142 (10.2 mg, 20.7 umol, 6.2% yield). LCMS (ESI): RT=1.148 min, mass calc. for $C_{25}H_{29}F_3N_4O_3$ 490.22, m/z found 491.1 [M+1]$^+$; $^1$H NMR (400 MHz, CDCl$_3$) δ 9.54 (s, 1H), 7.89 (dd, J=1.4, 7.9 Hz, 1H), 7.58 (d, J=8.5 Hz, 2H), 7.51 (d, J=8.3 Hz, 1H), 7.43-7.32 (m, 3H), 6.96 (t, J=7.2 Hz, 1H), 3.60 (s, 2H), 2.78 (s, 3H), 1.54 (s, 6H), 1.53 (s, 9H).

Example 121: N-methyl-N-(2-methyl-1-(5-(2-((4-(trifluoromethyl)phenyl)amino)phenyl)-1,3,4-oxadiazol-2-yl)propan-2-yl)cyanamide (Compound 143)

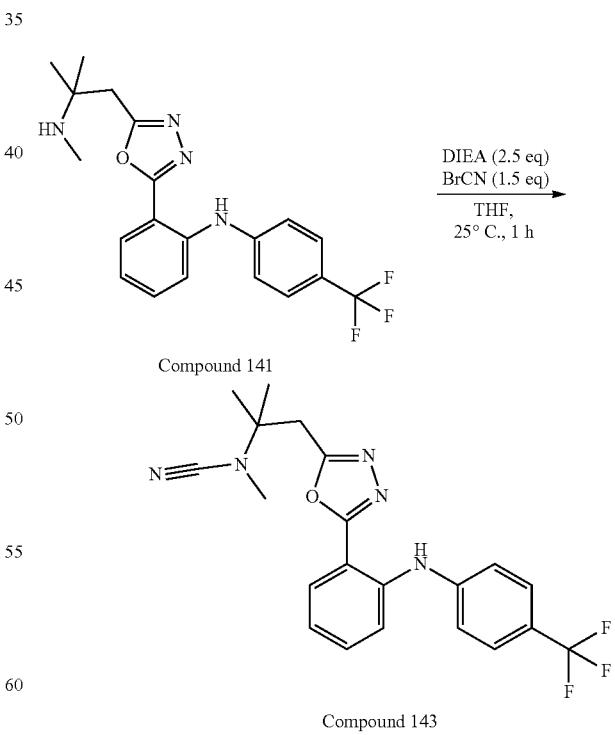

Step 1: 3-[tert-butoxycarbonyl(methyl)amino]-3-methyl-butanoic Acid

To a solution of 120-1b (0.3 g, 1.3 mmol, 1 eq) and MeI (1.9 g, 13 mmol, 0.86 mL, 10 eq) in THF (8 mL) was added NaH (551.9 mg, 13.8 mmol, 60% purity, 10 eq) at 0° C. The reaction was warmed to 25° C. and stirred at 25° C. for 16 hr. PE (10 mL) was added to the solution. The reaction was washed with water (2*10 mL). The aqueous layer was adjusted pH to 4-5 with Sat. citric acid solution and extracted with EA (2*15 mL). The organic layer was dried over $Na_2SO_4$ and concentrated. Compound 120-1a (140 mg, 0.6 mmol, 43% yield) was used for next step directly. $^1$H NMR (400 MHz, CDCl$_3$) δ 2.88 (s, 2H), 2.79 (s, 3H), 1.37 (s, 9H), 1.37 (s, 6H).

Step 2: tert-butyl N-[1,1-dimethyl-3-oxo-3-[2-[2-[4-(trifluoromethyl)anilino]benzoyl]hydrazino]propyl]-N-methyl-carbamate To a solution of 120-1 (178.7 mg, 0.6 mmol, 1 eq), 120-1a (140 mg, 0.6 mmol, 1 eq), EDCI (139.2 mg, 0.72 mmol, 1.2

To a solution of Compound 141 (30 mg, 76 umol, 1 eq) and DIEA (24.8 mg, 0.19 mmol, 33 uL, 2.5 eq) in THF (2 mL) was added BrCN (12 mg, 0.11 mmol, 8 uL, 1.5 eq). The reaction was stirred at 25° C. for 1 hr. The reaction was diluted with EA (20 mL) and washed with H₂O (2*10 mL). The organic layer was dried over Na₂SO₄ and concentrated. The residue was triturated with MeOH (5 mL) and filtered to give Compound 143 (16.8 mg, 40 umol, 52% yield). LCMS (ESI): RT=0.993 min, mass calc. for $C_{21}H_{20}F_3N_5O$ 415.16, m/z found 416.1 [M+1]⁺; ¹H NMR (400 MHz, CDCl₃) δ 9.46 (s, 1H), 7.91 (d, J=8.0 Hz, 1H), 7.59 (d, J=8.5 Hz, 2H), 7.51 (d, J=8.3 Hz, 1H), 7.44-7.32 (m, 3H), 6.99 (t, J=7.7 Hz, 1H), 3.24 (s, 2H), 2.95 (s, 3H), 1.50 (s, 6H).

Example 122: 2-(5-(2-methyl-1-(methylamino)propan-2-yl)-1,3,4-oxadiazol-2-yl)-N-(4-(trifluoromethyl)phenyl)aniline (Compound 144), tert-butyl methyl(2-methyl-2-(5-(2-((4-(trifluoromethyl)phenyl)amino)phenyl)-1,3,4-oxadiazol-2-yl)propyl)carbamate (Compound 145), and N-methyl-N-(2-methyl-2-(5-(2-((4-(trifluoromethyl)phenyl)amino)phenyl)-1,3,4-oxadiazol-2-yl)propyl)cyanamide (Compound 146)

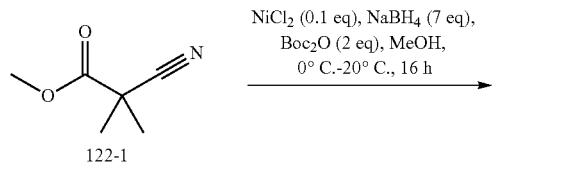

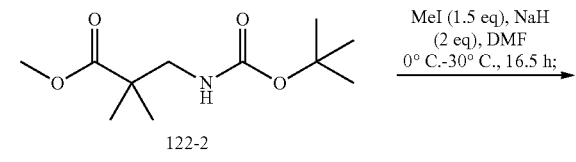

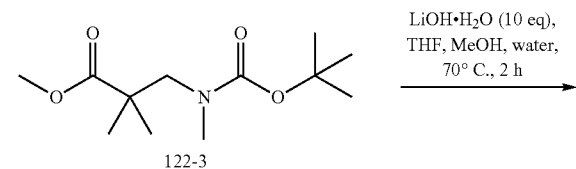

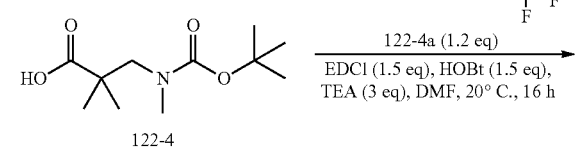

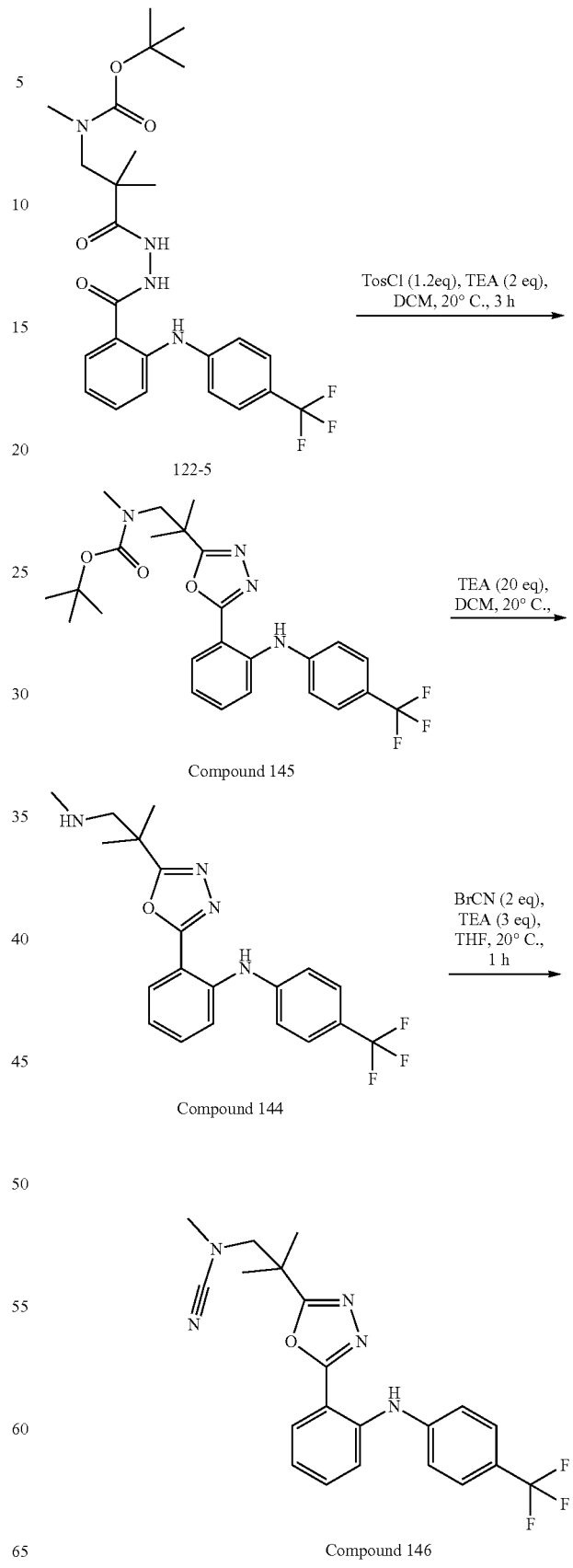

Step 1: Methyl 3-((tert-butoxycarbonyl)amino)-2,2-dimethylpropanoate

To a solution of 122-1 (2.0 g, 15.73 mmol, 1 eq), (Boc)$_2$O (6.87 g, 31.46 mmol, 7.23 mL, 2 eq) and NiCl$_2$ (203.9 mg, 1.57 mmol, 0.1 eq) in MeOH (40 mL) at 0° C. was added NaBH$_4$ (4.17 g, 110.11 mmol, 7 eq) slowly portion-wise, and the resulting mixture was stirred at 20° C. for 16 h. The reaction mixture was quenched with NH$_4$.H$_2$O (10 mL), and then concentrated to remove solvent. And the residue was diluted with water (50 mL), and then extracted with EA (50 mL*3). The combined organic layers were washed with brine (50 mL), dried over anhydrous Na$_2$SO$_4$, filtered and concentrated under reduced pressure to give a residue. The residue was purified by flash silica gel chromatography to give 122-2 (600 mg, 2.59 mmol, 16.5% yield). $^1$H NMR (400 MHz, CDCl$_3$) δ 4.97 (brs, 1H), 3.69 (s, 3H), 3.24 (d, J=6.6 Hz, 2H), 1.44 (s, 9H), 1.19 (s, 6H).

Step 2: Methyl 3-((tert-butoxycarbonyl)(methyl)amino)-2,2-dimethylpropanoate To a solution of 122-2 (300 mg, 1.30 mmol, 1 eq) in DMF (3 mL) at 0° C. was added NaH (103.8 mg, 2.59 mmol, 60% purity, 2 eq) slowly portion-wise, and then the mixture was stirred at 0° C. for 0.5 h. And then iodomethane (276.2 mg, 1.95 mmol, 0.12 mL, 1.5 eq) was added drop-wise into the above mixture at 0° C., and the resulting mixture was stirred at 30° C. for 16 h. The reaction mixture was quenched with water (20 mL), and then extracted with EA (20 mL*3). The combined organic layers were washed with water (10 mL*2) and brine (20 mL), dried over anhydrous Na$_2$SO$_4$, filtered and concentrated under reduced pressure to give a residue. The residue was purified by flash silica gel chromatography to give 122-3 (120 mg, 0.44 mmol, 33.9% yield). $^1$H NMR (400 MHz, CDCl$_3$) δ 3.69 (s, 3H), 3.45 (s, 2H), 2.80 (s, 3H), 1.45 (s, 9H), 1.19 (s, 6H).

Step 3: 3-((tert-butoxycarbonyl)(methyl)amino)-2,2-dimethylpropanoic Acid

To a solution of 122-3 (120 mg, 0.49 mmol, 1 eq) in THF (2 mL) and MeOH (2 mL) at 20° C. was added LiOH.H$_2$O (205.3 mg, 4.89 mmol, 10 eq) in water (2 mL), and then the mixture was stirred at 70° C. for 2 h. The reaction mixture was quenched with water (20 mL), and then extracted with EA (20 mL*3). The combined organic layers were washed with water (10 mL*2) and brine (20 mL), dried over anhydrous Na$_2$SO$_4$, filtered and concentrated under reduced pressure to give a residue. The residue was purified by flash silica gel chromatography to give 122-4 (110 mg, 0.43 mmol, 87.5% yield). $^1$H NMR (400 MHz, CDCl$_3$) δ 3.48 (s, 2H), 2.88 (s, 3H), 1.45 (s, 9H), 1.22 (s, 6H).

Step 4: Tert-Butyl (2,2-dimethyl-3-oxo-3-(2-(2-((4-(trifluoromethyl)phenyl)amino)benzoyl)hydrazinyl)propyl)(methyl)carbamate To a solution of 122-4 (100 mg, 0.43 mmol, 1 eq), EDCI (124.3 mg, 0.65 mmol, 1.5 eq) and HOBt (87.6 mg, 0.65 mmol, 1.5 eq) in DMF (2 mL) at 20° C. was added 122-4a (153.2 mg, 0.52 mmol, 1.2 eq) and then TEA (131.3 mg, 1.30 mmol, 0.18 mL, 3 eq), and the mixture was stirred at 20° C. for 16 h. The reaction mixture was diluted with water (20 mL), and then extracted with EA (20 mL*3). The combined organic layers were washed with water (10 mL*2) and brine (20 mL), dried over anhydrous Na$_2$SO$_4$, filtered and concentrated under reduced pressure to give 122-5 (310 mg, 0.41 mmol, 95.9% yield), which was used directly for next step. LCMS (ESI): RT=0.875 min, mass calc. for C$_{25}$H$_{31}$F$_3$N$_4$O$_4$ 508.23, m/z found 531.1 [M+23]$^+$.

Step 5: Tert-Butyl Methyl(2-methyl-2-(5-(2-((4-(trifluoromethyl)phenyl)amino)phenyl)-1,3,4-oxadiazol-2-yl)propyl)carbamate (Compound 145)

To a solution of 122-5 (300 mg, 0.40 mmol, 1 eq) and TEA (81.2 mg, 0.80 mol, 0.11 mL, 2 eq) in DCM (1 mL) at 20° C. was added TosCl (91.8 mg, 0.48 mmol, 1.2 eq), and the mixture was stirred at 20° C. for 3 h. The reaction mixture was combined with that of ES8223-478, and then was concentrated under reduced pressure to give a residue. The residue was purified by prep-TLC (PE:EA=5:1, UV) to give Compound 145 (140 mg, 0.28 mmol, 70.4% yield). LCMS (ESI): RT=1.008 min, mass calc. for C$_{25}$H$_{29}$F$_3$N$_4$O$_3$ 490.22, m/z found 513.0 [M+23]$^+$; $^1$H NMR (400 MHz, CDCl$_3$) δ 9.56 (brs, 1H), 7.89 (brs, 1H), 7.57 (d, J=8.0 Hz, 2H), 7.52 (d, J=7.8 Hz, 1H), 7.39 (t, J=7.9 Hz, 1H), 7.34 (d, J=8.0 Hz, 2H), 6.99 (t, J=7.0 Hz, 1H), 3.60 (s, 2H), 2.81-2.74 (m, 3H), 1.53 (s, 6H), 1.36 (s, 9H).

Step 6: 2-(5-(2-methyl-1-(methylamino)propan-2-yl)-1,3,4-oxadiazol-2-yl)-N-(4-(trifluoromethyl)phenyl)aniline (Compound 144)

To a solution of Compound 145 (130 mg, 0.27 mmol, 1 eq) in DCM (2 mL) at 20° C. was added TFA (604.4 mg, 5.30 mmol, 0.39 mL, 20 eq), and the mixture was stirred at 20° C. for 1 h. The mixture was concentrated to remove solvent. The residue was diluted with saturated Na$_2$CO$_3$ solution (20 mL) and extracted with EA (20 mL*3). The combined organic layers were washed with brine (20 mL), dried over anhydrous Na$_2$SO$_4$, filtered and concentrated under reduced pressure to give Compound 144 (100 mg, 0.25 mmol, 93.9% yield), which was used directly for next step. LCMS (ESI): RT=0.752 min, mass calc. for C$_{20}$H$_{21}$F$_3$N$_4$O 390.17, m/z found 391.0 [M+1]$^+$; $^1$H NMR (400 MHz, CDCl$_3$) δ 9.44 (s, 1H), 7.88 (dd, J=1.4, 7.9 Hz, 1H), 7.58 (d, J=8.5 Hz, 2H), 7.51 (d, J=8.3 Hz, 1H), 7.40 (t, J=7.9 Hz, 1H), 7.35 (d, J=8.3 Hz, 2H), 6.98 (t, J=7.5 Hz, 1H), 3.14 (s, 2H), 2.63 (s, 3H), 1.56 (s, 6H).

Step 7: N-methyl-N-(2-methyl-2-(5-(2-((4-(trifluoromethyl)phenyl)amino)phenyl)-1,3,4-oxadiazol-2-yl)propyl)cyanamide (Compound 146)

To a solution of Compound 144 (50 mg, 0.13 mmol, 1 eq) and TEA (38.9 mg, 0.38 mmol, 53 uL, 3 eq) in THF (2 mL) at 20° C. was added BrCN (27.1 mg, 0.26 mmol, 19 uL, 2 eq), and the mixture was stirred at 20° C. for 1 h. The residue was diluted with water (20 mL) and extracted with EA (20 mL*3). The combined organic layers were washed with brine (20 mL), dried over anhydrous Na$_2$SO$_4$, filtered and concentrated under reduced pressure to give a residue. The residue was purified by prep-HPLC to give Compound 146 (13.0 mg, 31.3 umol, 24.4% yield). LCMS (ESI): RT=0.895 min, mass calc. for C$_{21}$H$_{20}$F$_3$N$_5$O 415.16, m/z found 437.9 [M+23]$^+$; $^1$H NMR (400 MHz, CDCl$_3$) δ 9.49 (s, 1H), 7.90 (dd, J=1.4, 7.9 Hz, 1H), 7.58 (d, J=8.5 Hz, 2H), 7.52 (d, J=8.1 Hz, 1H), 7.44-7.38 (m, 1H), 7.36 (d, J=8.5 Hz, 2H), 7.02-6.96 (m, 1H), 3.44 (s, 2H), 2.89 (s, 3H), 1.60 (s, 6H).

Example 123: 2-(5-(2-(methylamino)propyl)-1,3,4-oxadiazol-2-yl)-N-(4-(trifluoromethyl)phenyl)aniline (Compound 147)

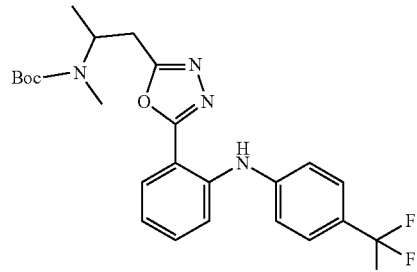

Compound 148

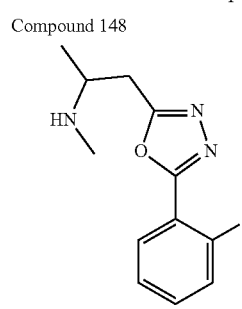

Compound 147

To a solution of Compound 148 (130 mg, 0.27 mmol, 1 eq) in DCM (3 mL) was added TFA (155.5 mg, 1.36 mmol, 0.1 mL, 5 eq). The reaction was stirred at 25° C. for 2 hr. The reaction was adjusted pH to 8-9 with sat. Na$_2$CO$_3$ and extracted with DCM (2*15 mL). The organic layer was dried over Na$_2$SO$_4$ and concentrated. 80 mg of crude product was obtained. Crude Compound 147 (60 mg, 0.14 mmol, 52% yield) was used for next step directly. 20 mg of crude product was purified by prep-HPLC to give Compound 147 (4.2 mg, 11 umol, 4% yield). LCMS and $^1$HNMR confirmed that desired product was obtained. LCMS (ESI): RT=0.831 min, mass calc. for C$_{19}$H$_{19}$F$_3$N$_4$O 376.18, m/z found 377.1 [M+1]$^+$; $^1$H NMR (400 MHz, CDCl$_3$) δ 9.53 (s, 1H), 7.88 (d, J=7.03 Hz, 1H), 7.58 (d, J=8.53 Hz, 2H), 7.52 (d, J=8.53 Hz, 1H), 7.32-7.43 (m, 3H), 6.98 (t, J=7.40 Hz, 1H), 3.15-3.24 (m, 1H), 2.97-3.13 (m, 2H), 1.24 (d, J=6.27 Hz, 3H).

Example 124: Tert-Butyl Methyl(1-(5-(2-((4-(trifluoromethyl)phenyl)amino)phenyl)-1,3,4-oxadiazol-2-yl)propan-2-yl)carbamate (Compound 148)

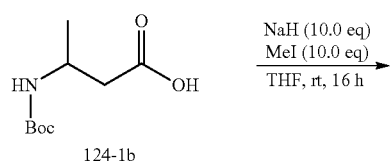

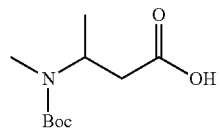

124-1a

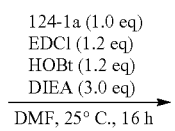

124-1

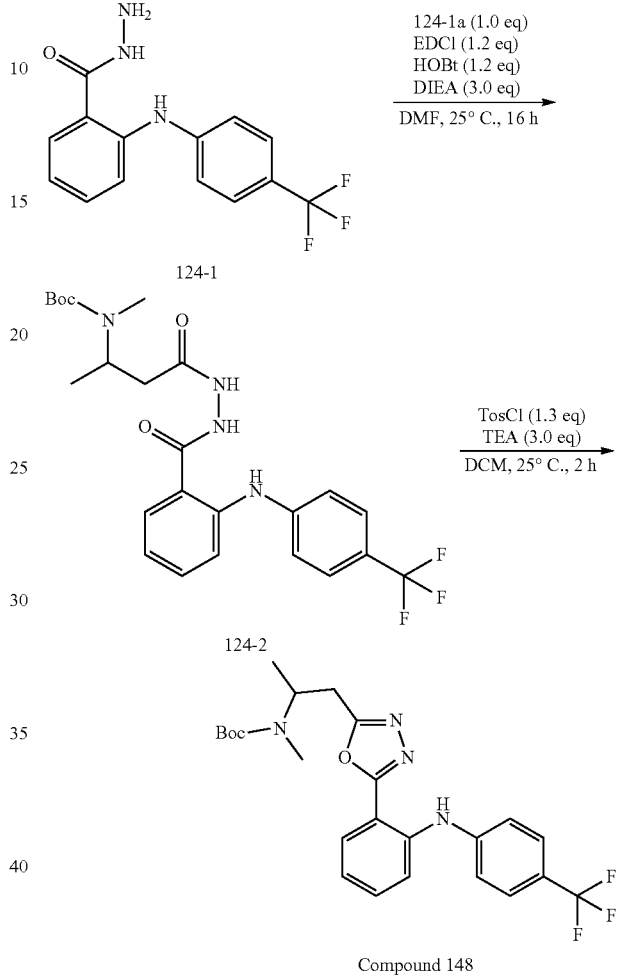

Compound 148

Step 1: 3-[tert-butoxycarbonyl(methyl)amino]butanoic Acid

To a solution of compound 124-1b (0.2 g, 1 mmol, 1 eq) and MeI (1.4 g, 10.3 mmol, 0.64 mL, 10 eq) in THF (8 mL) was added NaH (411.9 mg, 10.3 mmol, 60% purity, 10 eq) at 0° C. The reaction was warmed to 25° C. and stirred at 25° C. for 16 hr. The reaction was quenched by PE (10 mL). The aqueous layer was adjusted pH to 4-5 with Sat. Citric acid and extracted with EA (2*20 mL). The organic layer was dried over Na$_2$SO$_4$ and concentrated to give 124-1a (0.22 g, 1 mmol, 98% yield), which was used for next step directly. $^1$H NMR (400 MHz, CDCl$_3$) δ 4.44 (br, 1H), 2.66 (s, 3H), 2.51 (dd, J=15.06, 8.03 Hz, 1H), 2.35 (dd, J=15.06, 6.53 Hz, 1H), 1.36 (s, 9H), 1.11 (d, J=6.78 Hz, 3H).

Step 2: Tert-Butyl N-methyl-N-[1-methyl-3-oxo-3-[2-[2-[4-(trifluoromethyl)anilino]benzoyl]hydrazino]propyl]carbamate To a mixture of compound 124-1 (300 mg, 1 mmol, 1 eq) and compound 124-1a (220.7 mg, 1.0 mmol, 1 eq) and EDCI (233.7 mg, 1.2 mmol, 1.2 eq) in DMF (6 mL) was added HOBt (164.7 mg, 1.2 mmol, 1.2 eq), followed by DIEA (393.9 mg, 3 mmol, 0.53 mL, 3 eq). The mixture was stirred at 25° C. for 16 hr. The reaction was diluted with EA (30 mL) and washed with brine (2*10 mL). The organic layer was dried over $Na_2SO_4$ and concentrated. The residue was purified by column chromatography on silica gel to give compound 124-2 (340 mg, 0.6 mmol, 62% yield). LCMS (ESI): RT=0.962 min, mass calc. for $C_{24}H_{29}F_3N_4O_4$ 494.21, m/z found 495.1 [M+1]$^+$.

Step 3: Tert-Butyl Methyl(1-(5-(2-((4-(trifluoromethyl)phenyl)amino)phenyl)-1,3,4-oxadiazol-2-yl)propan-2-yl)carbamate To a solution of compound 124-2 (200 mg, 0.4 mmol, 1 eq) in DCM (3 mL) was added TEA (122.7 mg, 1.2 mmol, 0.17 mL, 3 eq) followed by TosCl (100 mg, 0.5 mmol, 1.3 eq). The reaction was stirred at 25° C. for 2 hr. The reaction was diluted with DCM (20 mL) and washed with H2O (2*5 mL). The organic layer was dried over $Na_2SO_4$ and concentrated to give Compound 148 (130 mg, 0.25 mmol, 62% yield), which was used for next step directly. LCMS (ESI): RT=1.091 min, mass calc. for $C_{24}H_{27}F_3N_4O_3$ 476.20, m/z found 477.1 [M+1]$^+$; $^1$H NMR (400 MHz, $CDCl_3$) δ 9.46 (br s, 1H), 7.90 (br s, 1H), 7.58 (d, J=8.53 Hz, 2H), 7.50 (d, J=8.28 Hz, 1H), 7.31-7.43 (m, 3H), 6.94-7.01 (m, 1H), 4.44-4.93 (m, 1H), 3.11-3.23 (m, 1H), 3.00-3.09 (m, 1H), 2.82 (br d, J=19.58 Hz, 3H), 1.57 (s, 9H), 1.34-1.36 (m, 3H).

Example 125: N-methyl-N-(1-(5-(2-((4-(trifluoromethyl)phenyl)amino)phenyl)-1,3,4-oxadiazol-2-yl)propan-2-yl)cyanamide (Compound 149)

To a solution of Compound 147 (60 mg, 0.16 mmol, 1 eq) and DIEA (51 mg, 0.39 mmol, 69 uL, 2.5 eq) in THF (2 mL) was added BrCN (25.3 mg, 0.23 mmol, 17 uL, 1.5 eq). The reaction was stirred at 25° C. for 1 hr. The reaction was diluted with EA (10 mL) and washed with H$_2$O (2*3 mL). The organic layer was dried over $Na_2SO_4$ and concentrated. The residue was purified by prep-HPLC to give Compound 149 (5.5 mg, 13.5 umol, 8.5% yield). LCMS (ESI): RT=0.991 min, mass calc. for $C_{20}H_{18}F_3N_5O$ 401.15, m/z found 402.1 [M+1]$^+$; $^1$H NMR (400 MHz, $CDCl_3$) δ 9.45 (s, 1H), 7.90 (dd, J=7.88, 1.38 Hz, 1H), 7.59 (d, J=8.50 Hz, 2H), 7.51 (d, J=8.13 Hz, 1H), 7.35-7.44 (m, 3H), 6.93-7.02 (m, 1H), 3.59-3.68 (m, 1H), 3.27-3.36 (m, 1H), 3.10-3.19 (m, 1H), 1.47 (d, J=6.63 Hz, 3H).

Example 126: 2-(5-(1-(methylamino)propan-2-yl)-1,3,4-oxadiazol-2-yl)-N-(4-(trifluoromethyl)phenyl) aniline (Compound 150), tert-butyl methyl(2-(5-(2-((4-(trifluoromethyl)phenyl)amino)phenyl)-1,3,4-oxadiazol-2-yl)propyl)carbamate (Compound 151), and N-methyl-N-(2-(5-(2-((4-(trifluoromethyl)phenyl)amino)phenyl)-1,3,4-oxadiazol-2-yl)propyl)cyanamide (Compound 152)

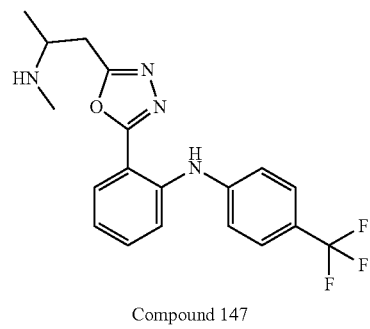

Compound 147

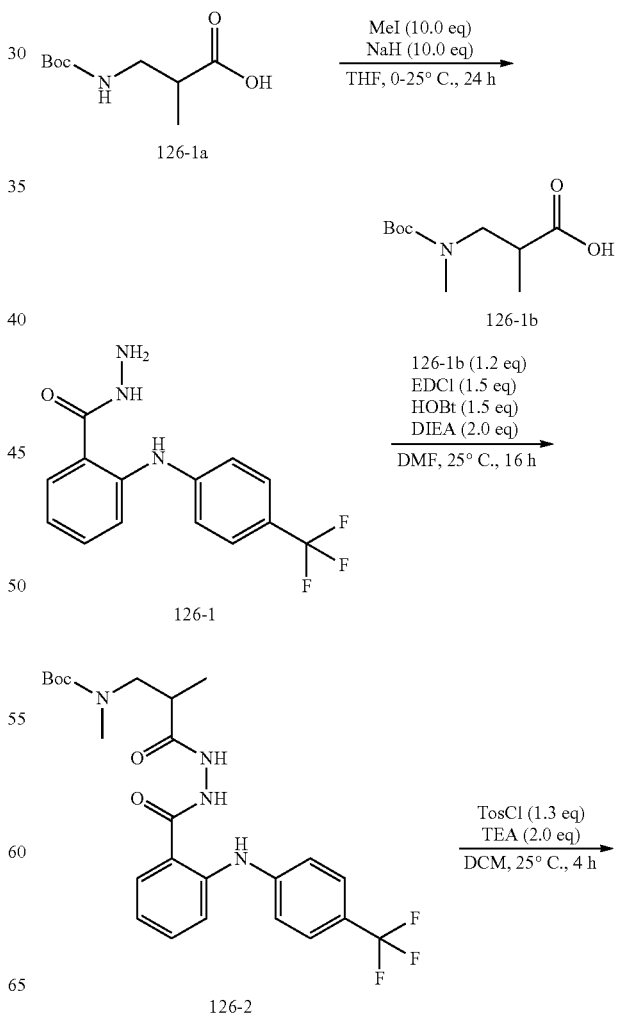

Compound 149

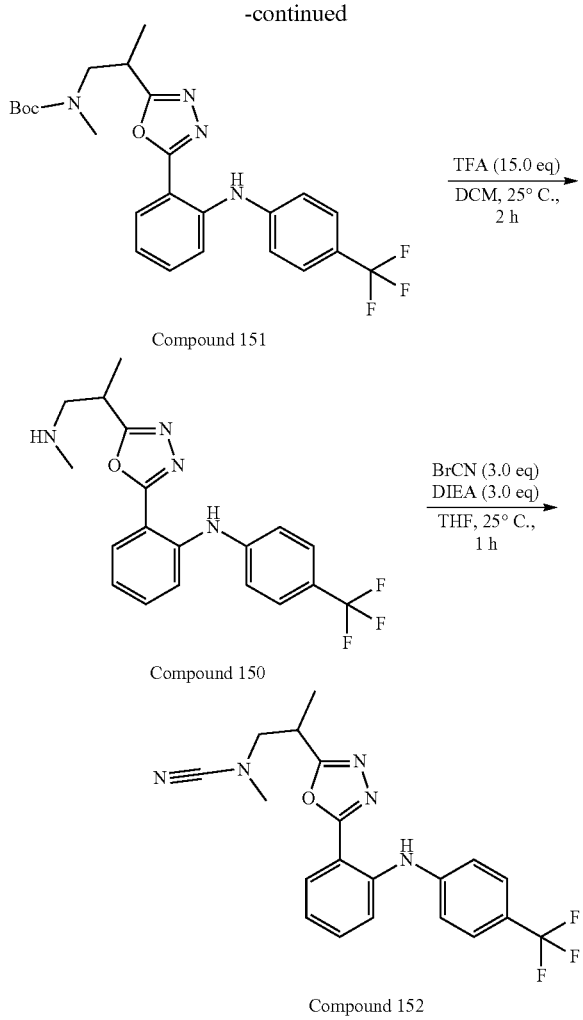

Compound 151

Compound 150

Compound 152

Step 1: 3-[tert-butoxycarbonyl(methyl)amino]-2-methyl-propanoic Acid

To a solution of compound 126-1a (200 mg, 0.98 mmol, 1 eq) and MeI (1.40 g, 9.84 mmol, 0.6 mL, 10 eq) in THF (2 mL) was added NaH (393 mg, 9.84 mmol, 60% purity, 10 eq) slowly in portions over a period of 1 hr at 0° C. Then the mixture was stirred at 20° C. for 23 hr. The reaction mixture was diluted with petro ether (5 mL). Then the organic phase was removed, the aqueous phase was adjusted pH=3 with aqueous solution of citric acid and extracted with EA (15 mL*3). The combined organic phase was washed with $H_2O$ (5 mL) and brine (5 mL), dried over $Na_2SO_4$, filtered and concentrated in vacuum. The crude product was used for the next step directly. $^1$HNMR showed that compound 126-1b (155 mg, 0.71 mmol, 72.5% yield) was obtained. $^1$H NMR (400 MHz, CDCl$_3$) δ 3.44-3.34 (m, 1H), 3.28 (br dd, J=6.9, 13.3 Hz, 1H), 2.83-2.69 (m, 4H), 1.41-1.35 (m, 9H), 1.11 (d, J=7.1 Hz, 3H)

Step 2: Tert-Butyl N-methyl-N-[2-methyl-3-oxo-3-[2-[2-4-(trifluoromethyl)anilino]benzoyl]hydrazino]propyl]carbamate To a solution of compound 126-1 (170 mg, 0.57 mmol, 1 eq) and compound 126-1b (150 mg, 0.69 mmol, 1.2 eq) in DMF (2 mL) were added HOBt (116 mg, 0.86 mmol, 1.5 eq), EDCI (165 mg, 0.86 mmol, 1.5 eq) and DIEA (148 mg, 1.15 mmol, 0.2 mL, 2 eq). The mixture was stirred at 25° C. for 16 hr. The reaction mixture was quenched with $H_2O$ (10 mL), extracted with EA (15 mL*3). The combined organic phase was washed with $H_2O$ (5 mL) and brine (5 mL), dried over $Na_2SO_4$, filtered and concentrated in vacuum. The crude product was purified by column chromatography. Compound 126-2 (120 mg, 0.22 mmol, 38% yield) was obtained. $^1$H NMR (400 MHz, CDCl$_3$) δ 9.40-8.43 (m, 3H), 7.59 (dd, J=1.1, 7.9 Hz, 1H), 7.52 (d, J=8.5 Hz, 2H), 7.45-7.41 (m, 1H), 7.39-7.33 (m, 1H), 7.21 (d, J=8.3 Hz, 2H), 6.88 (t, J=7.4 Hz, 1H), 3.67-3.16 (m, 2H), 2.88 (s, 4H), 1.46 (s, 9H), 1.21 (d, J=7.0 Hz, 3H).

Step 3: Tert-Butyl Methyl(2-(5-(2-((4-(trifluoromethyl)phenyl)amino)phenyl)-1,3,4-oxadiazol-2-yl)propyl)carbamate (Compound 151)

To a solution of compound 126-2 (120 mg, 0.22 mmol, 1 eq) in DCM (3 mL) were added TEA (44 mg, 0.44 mmol, 61 uL, 2 eq) and TosCl (54 mg, 0.28 mmol, 1.3 eq). The mixture was stirred at 25° C. for 4 hr. The reaction mixture was concentrated in vacuum. The residue was diluted with EA (20 mL), washed with $H_2O$ (5 mL) and brine (5 mL), dried over $Na_2SO_4$, filtered and concentrated in vacuum. The crude product was purified by column chromatography. Compound 151 (95 mg, 0.19 mmol, 88% yield) was obtained. LCMS (ESI): RT=0.976 min, mass calcd. For $C_{24}H_{27}F_3N_4O_3$, 476.20 m/z found 499.0 [M+Na]$^+$. $^1$H NMR (400 MHz, CDCl$_3$) δ 9.52 (br d, J=11.4 Hz, 1H), 7.93-7.85 (m, 1H), 7.58 (d, J=8.5 Hz, 2H), 7.51 (d, J=8.4 Hz, 1H), 7.43-7.33 (m, 3H), 7.01-6.95 (m, 1H), 3.73-3.46 (m, 3H), 2.98-2.84 (m, 3H), 1.46 (br s, 3H), 1.39 (s, 9H).

Step 4: 2-(5-(1-(methylamino)propan-2-yl)-1,3,4-oxadiazol-2-yl)-N-(4-(trifluoromethyl)phenyl)aniline (Compound 150)

To a solution of Compound 151 (90 mg, 0.19 mmol, 1 eq) in DCM (2 mL) was added TFA (323 mg, 2.83 mmol, 0.2 mL, 15 eq). The mixture was stirred at 25° C. for 2 hr. The reaction mixture was concentrated in vacuum. The residue was diluted with EA (20 mL), washed with saturated aq.$Na_2CO_3$ (5 mL) and brine (5 mL), dried over $Na_2SO_4$, filtered and concentrated in vacuum. The crude product was used for the next step directly. LCMS and $^1$H NMR confirmed that Compound 150 (65 mg, 0.16 mmol, 87% yield) was obtained. LCMS (ESI): RT=0.736 min, mass calcd. For $C_{19}H_{19}F_3N_4O$, 376.15 m/z found 377.0 [M+H]$^+$. $^1$H NMR (400 MHz, CDCl$_3$) δ 9.54 (s, 1H), 7.89 (dd, J=1.4, 7.9 Hz, 1H), 7.58 (d, J=8.5 Hz, 2H), 7.52 (d, J=8.4 Hz, 1H), 7.43-7.33 (m, 3H), 7.01-6.95 (m, 1H), 3.43 (qd, J=7.1, 13.9 Hz, 1H), 3.11 (dd, J=8.2, 12.1 Hz, 1H), 2.93 (dd, J=5.6, 12.1 Hz, 1H), 2.50 (s, 3H), 1.47 (d, J=7.0 Hz, 3H).

Step 5: N-methyl-N-(2-(5-(2-((4-(trifluoromethyl)phenyl)amino)phenyl)-1,3,4-oxadiazol-2-yl)propyl)cyanamide (Compound 152)

To a solution of Compound 150 (60 mg, 0.16 mmol, 1 eq) in THF (2 mL) were added DIEA (61 mg, 0.48 mmol, 83 uL, 3 eq) and BrCN (50 mg, 0.48 mmol, 35 uL, 3 eq). The mixture was stirred at 25° C. for 1 hr. The reaction mixture was diluted with EA (15 mL), washed with $H_2O$ (5 mL) and brine (5 mL), dried over $Na_2SO_4$, filtered and concentrated in vacuum. The crude product was purified by prep-HPLC.

LCMS and ¹HNMR confirmed that Compound 152 (19 mg, 47 umol, 29% yield) was obtained. LCMS (ESI): RT=0.875 min, mass calcd. For $C_{20}H8F_3N5O$, 401.15 m/z found 401.9 [M+H]⁺. ¹H NMR (400 MHz, CDCl₃) δ 9.48 (s, 1H), 7.92 (dd, J=1.4, 7.9 Hz, 1H), 7.60 (d, J=8.3 Hz, 2H), 7.53 (d, J=8.3 Hz, 1H), 7.45-7.36 (m, 3H), 7.01 (t, J=7.3 Hz, 1H), 3.63-3.53 (m, 2H), 3.45-3.36 (m, 1H), 2.98 (s, 3H), 1.56 (d, J=6.8 Hz, 3H).

Example 127: 2-(5-(1-(methylamino)cyclopropyl)-1,3,4-oxadiazol-2-yl)-N-(4-(trifluoromethyl)phenyl)aniline (Compound 153), tert-butyl methyl(1-(5-(2-((4-(trifluoromethyl)phenyl)amino)phenyl)-1,3,4-oxadiazol-2-yl)cyclopropyl)carbamate (Compound 154), and N-methyl-N-(1-(5-(2-((4-(trifluoromethyl)phenyl)amino)phenyl)-1,3,4-oxadiazol-2-yl)cyclopropyl)cyanamide (Compound 155)

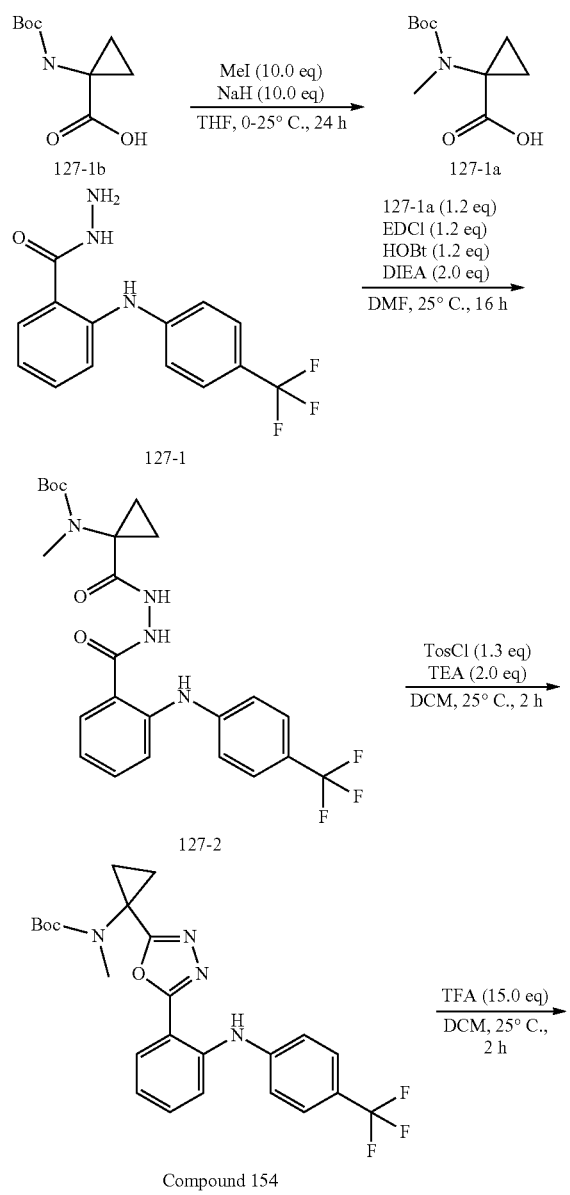

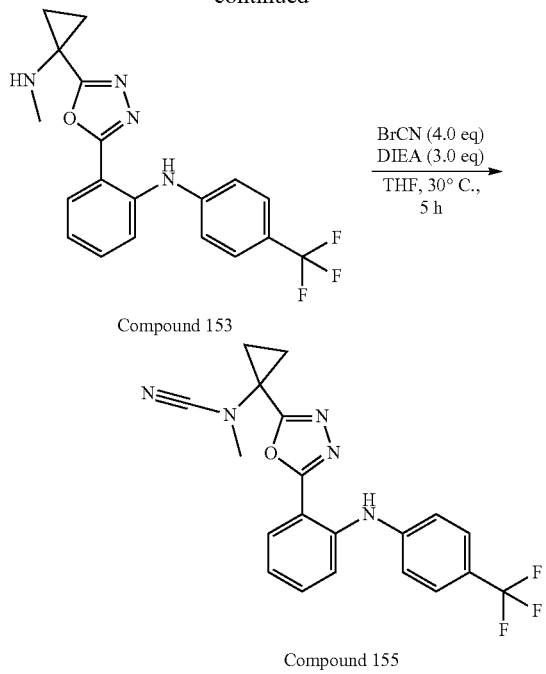

Step 1: 1-[tert-butoxycarbonyl(methyl)amino]cyclopropanecarboxylic Acid

To a solution of compound 127-1b (300 mg, 1.49 mmol, 1 eq) and MeI (2.12 g, 14.91 mmol, 0.93 mL, 10 eq) in THF (5 mL) was added a mixture of NaH (596 mg, 14.91 mmol, 60% purity, 10 eq) in THF (5 mL) slowly at 0° C. Then the mixture was stirred at 25° C. for 24 hr. The reaction mixture was diluted with petro ether (5 mL). Then the organic phase was removed, the aqueous phase was adjusted pH=3 with aqueous solution of citric acid and extracted with EA (15 mL*3). The combined organic phase was washed with H₂O (5 mL) and brine (5 mL), dried over Na₂SO₄, filtered and concentrated in vacuum. The crude product was used for the next step directly. ¹HNMR confirmed that compound 127-1a (303 mg, 1.41 mmol, 94% yield) was obtained. ¹H NMR (400 MHz, DMSO-d₆) δ 12.48 (br s, 1H), 2.75 (s, 3H), 1.35 (s, 8H), 1.37-1.34 (m, 1H), 1.28-1.07 (m, 4H).

Step 2: Tert-Butyl N-methyl-N-[1-[[[2-[4-(trifluoromethyl)anilino]benzoyl]amino]carbamoyl]cyclopropyl]carbamate To a solution of compound 127-1 (228 mg, 0.77 mmol, 1 eq) and compound 127-1a (200 mg, 0.93 mmol, 1.2 eq) in DMF (5 mL) were added HOBt (125 mg, 0.93 mmol, 1.2 eq), EDCI (178 mg, 0.93 mmol, 1.2 eq) and DIEA (200 mg, 1.55 mmol, 0.3 mL, 2 eq). The mixture was stirred at 25° C. for 16 hr. The reaction mixture was quenched with H₂O (10 mL), extracted with EA (15 mL*3). The combined organic phase was washed with H₂O (5 mL) and brine (5 mL*3), dried over Na₂SO₄, filtered and concentrated in vacuum. The crude product was purified by column chromatography. Compound 127-2 (235 mg, 0.45 mmol, 58% yield) was obtained. ¹H NMR (400 MHz, CDCl₃) δ 9.20 (br s, 1H), 8.91-8.62 (m, 2H), 7.59 (br d, J=7.8 Hz, 1H), 7.53 (d, J=8.3 Hz, 2H), 7.47-7.43 (m, 1H), 7.41-7.35 (m, 1H), 7.23 (d, J=8.5 Hz, 2H), 6.91 (t, J=7.4 Hz, 1H), 2.99 (s, 3H), 1.69-1.64 (m, 2H), 1.51 (s, 9H), 1.22 (br s, 2H).

Step 3: Tert-Butyl Methyl(1-(5-(2-((4-(trifluoromethyl)phenyl)amino)phenyl)-1,3,4-oxadiazol-2-yl)cyclopropyl)carbamate (Compound 154)

To a solution of compound 127-2 (150 mg, 0.30 mmol, 1 eq) in DCM (2 mL) were added TEA (92 mg, 0.91 mmol, 0.13 mL, 3 eq) and TosCl (75 mg, 0.4 mmol, 1.3 eq). The mixture was stirred at 25° C. for 2 hr. The reaction mixture was concentrated in vacuum. The residue was diluted with EA (20 mL), washed with H₂O (5 mL) and brine (5 mL), dried over Na₂SO₄, filtered and concentrated in vacuum. The crude product was purified by column chromatography. Compound 154 (134 mg, 0.27 mmol, 90% yield) was obtained. LCMS (ESI): RT=0.997 min, mass calcd. For C$_{24}$H$_{25}$F$_3$N$_4$O$_3$, 474.19 m/z found 497.1 [M+Na]⁺. ¹H NMR (400 MHz, CDCl₃) δ 9.50 (br s, 1H), 7.79 (br s, 1H), 7.57 (br d, J=8.3 Hz, 2H), 7.51 (br d, J=8.3 Hz, 1H), 7.42-7.32 (m, 3H), 6.96 (br t, J=7.2 Hz, 1H), 3.08 (s, 3H), 1.73 (br s, 2H), 1.57-1.40 (m, 11H).

Step 4: 2-(5-(1-(methylamino)cyclopropyl)-1,3,4-oxadiazol-2-yl)-N-(4-(trifluoromethyl)phenyl)aniline (Compound 153)

To a solution of Compound 154 (120 mg, 0.25 mmol, 1 eq) in DCM (2 mL) was added TFA (432 mg, 3.79 mmol, 0.28 mL, 15 eq). The mixture was stirred at 25° C. for 2 hr. The reaction mixture was concentrated in vacuum. The residue was diluted with EA (20 mL), washed with saturated aq.Na₂CO₃ (10 mL) and brine (5 mL), dried over Na₂SO₄, filtered and concentrated in vacuum. The product was used for the next step directly. LCMS and ¹HNMR showed that Compound 153 (88 mg, 0.23 mmol, 92% yield) was obtained. LCMS (ESI): RT=0.736 min, mass calcd. For C$_{19}$H$_{17}$F$_3$N$_4$O, 374.14 m/z found 374.9 [M+H]⁺. ¹H NMR (400 MHz, CDCl₃) δ 9.45 (s, 1H), 7.73 (dd, J=1.5, 8.0 Hz, 1H), 7.50 (d, J=8.5 Hz, 2H), 7.44 (d, J=8.0 Hz, 1H), 7.34-7.26 (m, 3H), 6.89 (t, J=7.5 Hz, 1H), 2.56-2.53 (m, 1H), 2.55 (s, 2H), 1.35-1.30 (m, 2H), 1.25-1.19 (m, 2H).

Step 5: N-methyl-N-(1-(5-(2-((4-(trifluoromethyl)phenyl)amino)phenyl)-1,3,4-oxadiazol-2-yl)cyclopropyl)cyanamide (Compound 155)

To a solution of Compound 153 (80 mg, 0.21 mmol, 1 eq) in THF (2 mL) were added DIEA (82 mg, 0.64 mmol, 0.11 mL, 3 eq) and BrCN (90 mg, 0.85 mmol, 62 uL, 4 eq). The mixture was stirred at 30° C. for 5 hr. The reaction mixture was concentrated in vacuum. The residue was diluted with EA (20 mL), washed with H₂O (5 mL) and brine (5 mL), dried over Na₂SO₄, filtered and concentrated in vacuum. The crude product was purified by prep-HPLC. LCMS and ¹HNMR confirmed that Compound 155 (52 mg, 0.13 mmol, 60% yield) was obtained. LCMS (ESI): RT=0.897 min, mass calcd. For C$_{20}$H$_{16}$F$_3$N$_5$O, 399.13 m/z found 399.9 [M+H]⁺. ¹H NMR (400 MHz, CDCl₃) δ 9.40 (s, 1H), 7.85 (dd, J=1.3, 8.0 Hz, 1H), 7.59 (d, J=8.5 Hz, 2H), 7.54-7.49 (m, 1H), 7.45-7.39 (m, 1H), 7.36 (d, J=8.3 Hz, 2H), 7.01-6.96 (m, 1H), 3.12 (s, 3H), 1.76-1.71 (m, 2H), 1.69-1.64 (m, 2H).

Example 128: 2-(5-(2-(methylamino)propan-2-yl)-1,3,4-oxadiazol-2-yl)-N-(4-(trifluoromethyl)phenyl)aniline (Compound 156), tert-butyl methyl(2-(5-(2-((4-(trifluoromethyl)phenyl)amino)phenyl)-1,3,4-oxadiazol-2-yl)propan-2-yl)carbamate (Compound 157), and N-methyl-N-(2-(5-(2-((4-(trifluoromethyl)phenyl)amino)phenyl)-1,3,4-oxadiazol-2-yl)propan-2-yl)cyanamide (Compound 158)

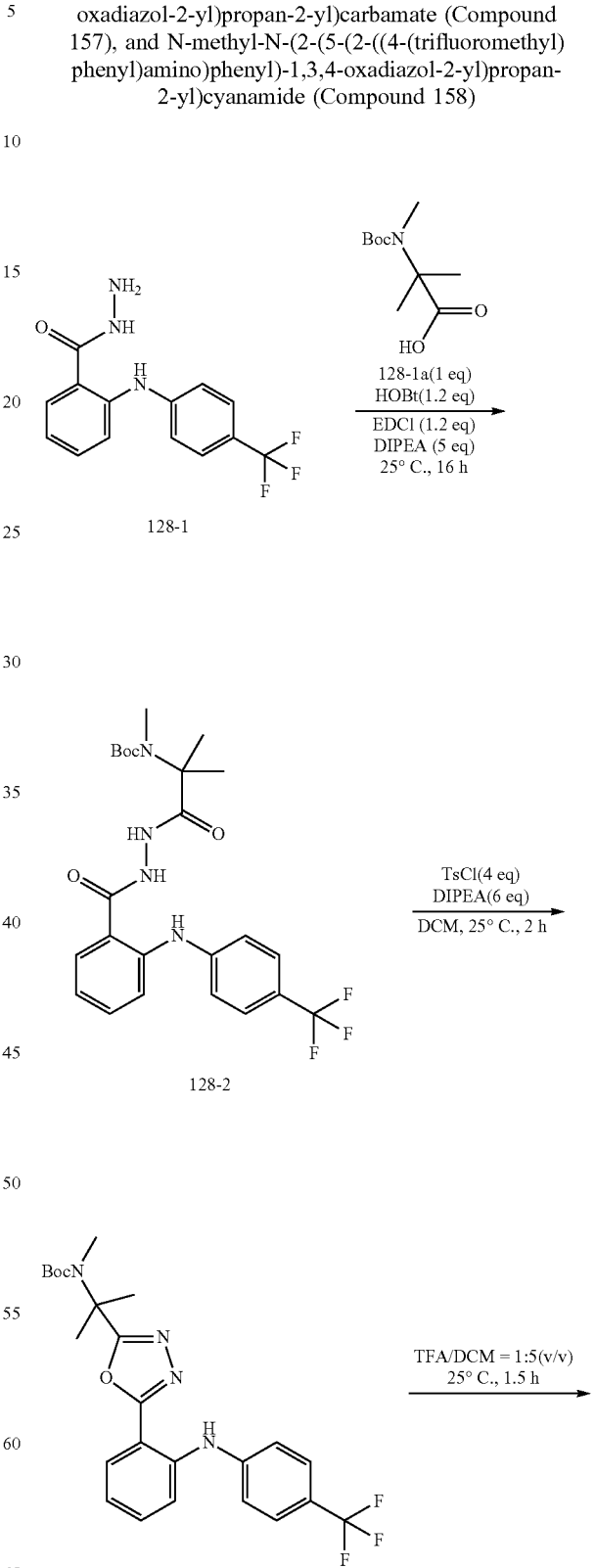

-continued

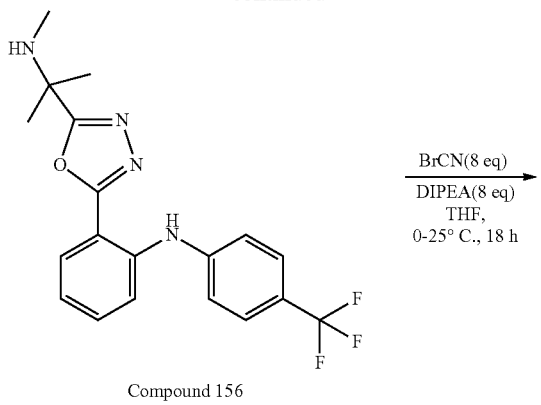

Compound 156

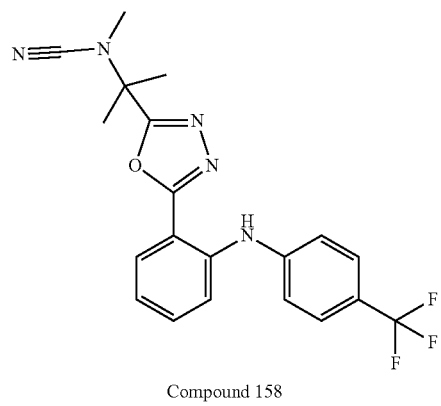 [SMILES: CN(C#N)C(C)(C)c1nnc(-c2ccccc2Nc2ccc(C(F)(F)F)cc2)o1]

Compound 158

Step 1: Tert-Butyl Methyl(2-methyl-1-oxo-1-(2-(2-((4-(trifluoromethyl)phenyl)amino)benzoyl)hydrazinyl)propan-2-yl)carbamate To a solution of 128-1a (200 mg, 0.92 mmol, 1 eq), 128-1 (271.8 mg, 0.92 mmol, 1 eq), HOBt (149.3 mg, 1.10 mmol, 1.2 eq) and EDCI (211.8 mg, 1.10 mmol, 1.2 eq) was added DIPEA (594.9 mg, 4.60 mmol, 0.8 mL, 5 eq) at 25° C. Then the resulting mixture was stirred at 25° C. for 16 h. The mixture was directly purified by prep-HPLC to give 128-2 (130 mg, 0.26 mmol, 28.6% yield). LCMS (ESI): RT=0.852 min, mass calcd. For $C_{24}H_{29}F_3N_4O_4$ 494.21 m/z found 517.0 [M+23]$^+$.

Step 2: Tert-Butyl Methyl(2-(5-(2-((4-(trifluoromethyl)phenyl)amino)phenyl)-1,3,4-oxadiazol-2-yl)propan-2-yl)carbamate (Compound 157)

To a solution of 128-2 (125 mg, 0.25 mmol, 1 eq) and TosCl (192.8 mg, 1.01 mmol, 4 eq) in DCM (4 mL) was added DIPEA (196.0 mg, 1.52 mmol, 0.3 mL, 6 eq) at 25° C. Then the resulting mixture was stirred at 25° C. for 2 h. The solution was concentrated to give a residue. The residue was purified by column chromatography to give Compound 157 (95 mg, 0.20 mmol, 78.5% yield). LCMS (ESI): RT=0.993 min, mass calcd. For $C_{24}H_{27}F_3N_4O_3$ 476.20 m/z found 477.0 [M+1]$^+$; $^1$H NMR (400 MHz, CDCl$_3$) δ 9.62 (s, 1H), 7.87 (dd, J=1.4, 7.9 Hz, 1H), 7.62-7.50 (m, 3H), 7.42-7.33 (m, 3H), 7.00-6.93 (m, 1H), 3.09 (s, 3H), 1.78 (s, 6H), 1.26 (s, 9H).

Step 3: 2-(5-(2-(methylamino)propan-2-yl)-1,3,4-oxadiazol-2-yl)-N-(4-(trifluoromethyl)phenyl)aniline (Compound 156)

To a solution of Compound 157 (80 mg, 0.17 mmol, 1 eq) in DCM (4 mL) was added TFA (0.8 mL) at 25° C. Then the resulting mixture was stirred at 25° C. for 1.5 h. The solution was concentrated at 20° C. to give a residue. The residue was diluted with 20 mL of water and lyophilized to give Compound 156 (82 mg, 0.16 mmol, 97.1% yield, TFA). LCMS (ESI): RT=0.739 min, mass calcd. For $C_{19}H_{19}F_3N_4O$ 376.15 m/z found 376.9 [M+1]$^+$. $^1$H NMR (400 MHz, DMSO-d$_6$) δ 9.53 (br s, 1H), 9.03 (s, 1H), 7.92 (d, J=7.5 Hz, 1H), 7.59-7.46 (m, 4H), 7.22 (d, J=8.5 Hz, 2H), 7.15-7.07 (m, 1H), 2.48 (s, 3H), 1.64 (s, 6H).

Step 4: N-methyl-N-(2-(5-(2-((4-(trifluoromethyl)phenyl)amino)phenyl)-1,3,4-oxadiazol-2-yl)propan-2-yl)cyanamide (Compound 158)

To a solution of Compound 156 (60 mg, 0.16 mmol, 1 eq) and DIPEA (82.4 mg, 0.64 mmol, 0.1 mL, 4 eq) in THF (3 mL) was added cyanogen bromide (33.8 mg, 0.32 mmol, 24 uL, 2 eq) at 0° C. The mixture was stirred at 25° C. for 2 hr. Then another batch of cyanogen bromide (101.3 mg, 0.96 mmol, 70 uL, 6 eq) and DIPEA (82.4 mg, 0.64 mmol, 0.1 mL, 4 eq) was added and the resulting mixture was stirred for another 16 h at 25° C. The solution was quenched with water (10 mL) and then diluted with EA (50 mL), washed with brine (15 mL*3). The combined organic layer was dried by anhydrous Na$_2$SO$_4$, filtered and concentrated to give a residue. The residue was purified by column chromatography to give Compound 158 (14 mg, 35 umol, 21.9% yield). LCMS (ESI): R=0.885 min, mass calcd. For $C_{20}H_{18}F_3N_5O$ 401.15 m/z found 401.9 [M+1]$^+$; $^1$H NMR (400 MHz, CDCl$_3$) δ 9.42 (s, 1H), 7.94 (dd, J=1.4, 7.9 Hz, 1H), 7.59 (d, J=8.3 Hz, 2H), 7.55-7.49 (m, 1H), 7.43 (dt, J=1.5, 7.8 Hz, 1H), 7.36 (d, J=8.5 Hz, 2H), 7.05-6.98 (m, 1H), 2.86 (s, 3H), 1.94-1.84 (m, 6H).

Example 129: 2-(5-(1-(methylamino)ethyl)-1,3,4-oxadiazol-2-yl)-N-(4-(trifluoromethyl)phenyl)aniline (Compound 159), tert-butyl methyl(1-(5-(2-((4-(trifluoromethyl)phenyl)amino)phenyl)-1,3,4-oxadiazol-2-yl)ethyl)carbamate (Compound 160), and N-methyl-N-(1-(5-(2-((4-(trifluoromethyl)phenyl)amino)phenyl)-1,3,4-oxadiazol-2-yl)ethyl)cyanamide (Compound 161)

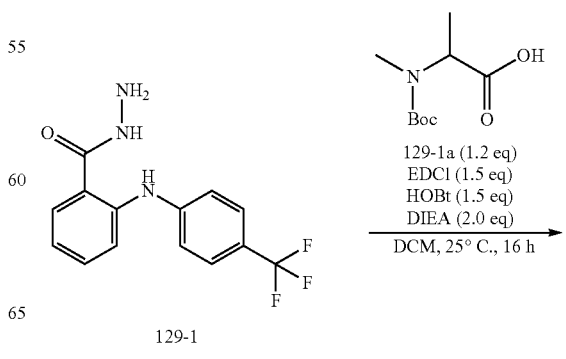

-continued

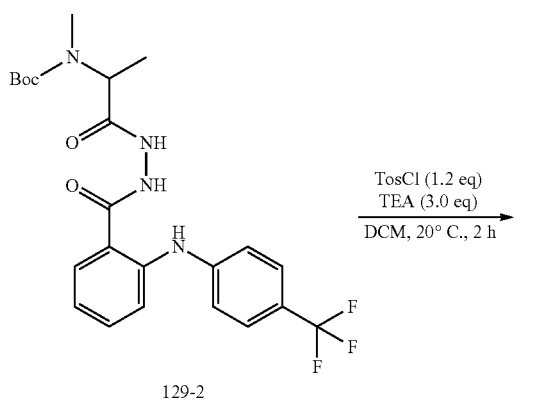

129-2

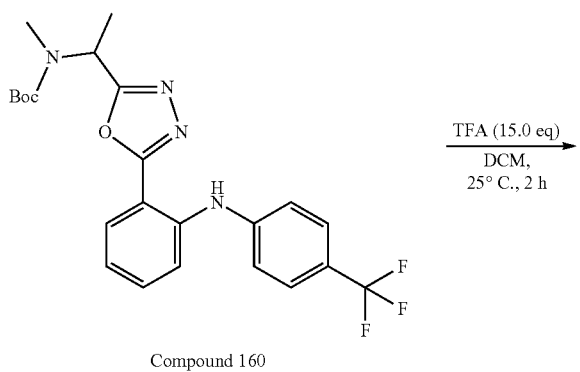

Compound 160

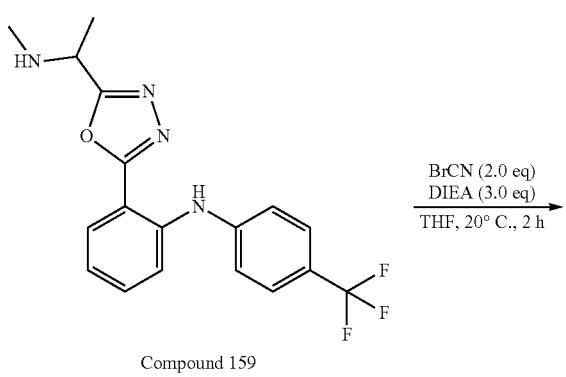

Compound 159

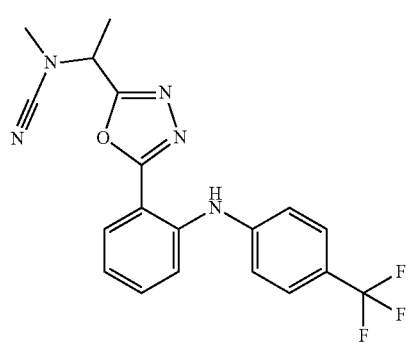

Compound 161

Step 1: Tert-Butyl N-methyl-N-[1-methyl-2-oxo-2-[2-[2-[4-(trifluoromethyl)anilino]benzoyl]hydrazino]ethyl]carbamate To a solution of compound 129-1 (200 mg, 0.67 mmol, 1 eq) and compound 129-1a (165 mg, 0.81 mmol, 1.2 eq) in DMF (2 mL) were added HOBt (137 mg, 1.02 mmol, 1.5 eq), EDCI (194 mg, 1.02 mmol, 1.5 eq) and DIEA (175 mg, 1.35 mmol, 0.24 mL, 2 eq). The mixture was stirred at 25° C. for 16 hr. The reaction mixture was quenched with water (5 mL), extracted with EA (15 mL*3). The combined organic phase was washed with $H_2O$ (5 mL) and brine (5 mL), dried over $Na_2SO_4$, filtered and concentrated in vacuum. The crude product was purified by column chromatography. LCMS confirmed that compound 129-2 (120 mg, 0.23 mmol, 34% yield) was obtained.

Step 2: Tert-Butyl Methyl(1-(5-(2-((4-(trifluoromethyl)phenyl)amino)phenyl)-1,3,4-oxadiazol-2-yl)ethyl)carbamate (Compound 160)

To a solution of compound 129-2 (120 mg, 0.25 mmol, 1 eq) in DCM (2 mL) were added TEA (75 mg, 0.75 mmol, 0.1 mL, 3 eq) and TosCl (57 mg, 0.3 mmol, 1.2 eq). The mixture was stirred at 20° C. for 2 hr. The reaction mixture was concentrated in vacuum. The residue was diluted with EA (20 mL), washed with $H_2O$ (5 mL) and brine (5 mL), dried over $Na_2SO_4$, filtered and concentrated in vacuum. The crude product was purified by column chromatography. LCMS and $^1$HNMR confirmed that Compound 160 (104 mg, 0.22 mmol, 90% yield) was obtained. LCMS (ESI): RT=0.994 min, mass calcd. For $C_{23}H_{25}F_3N_4O_3$, 462.19 m/z found 485.0 [M+Na]$^+$; $^1$H NMR (400 MHz, CDCl$_3$) δ 9.52 (s, 1H), 7.86 (br d, J=7.8 Hz, 1H), 7.58 (d, J=8.5 Hz, 2H), 7.52 (d, J=8.3 Hz, 1H), 7.43-7.34 (m, 3H), 7.00-6.95 (m, 1H), 5.94-5.34 (m, 1H), 2.81 (br s, 3H), 1.71 (br s, 3H), 1.51 (br s, 9H).

Step 3: 2-(5-(1-(methylamino)ethyl)-1,3,4-oxadiazol-2-yl)-N-(4-(trifluoromethyl)phenyl)aniline (Compound 159)

To a solution of Compound 160 (100 mg, 0.22 mmol, 1 eq) in DCM (2 mL) was added TFA (369 mg, 3.24 mmol, 0.24 mL, 15 eq). The mixture was stirred at 20° C. for 2 hr. The reaction mixture was concentrated in vacuum. The residue was diluted with EA (20 mL), washed with saturated aq.$Na_2CO_3$ (10 mL) and brine (10 mL), dried over $Na_2SO_4$, filtered and concentrated in vacuum. The crude product was used for the next step directly. LCMS and $^1$HNMR confirmed that Compound 159 (65 mg, 0.17 mmol, 80% yield) was obtained. LCMS (ESI): RT=0.717 min, mass calcd. For $C_{18}H_{17}F_3N_4O$, 362.14 m/z found 362.9 [M+H]$^+$; $^1$H NMR (400 MHz, CDCl$_3$) δ 9.54 (s, 1H), 7.91 (d, J=7.6 Hz, 1H), 7.59 (d, J=8.5 Hz, 2H), 7.52 (d, J=8.4 Hz, 1H), 7.44-7.35 (m, 3H), 6.98 (t, J=7.5 Hz, 1H), 4.15 (q, J=6.9 Hz, 1H), 2.48 (s, 3H), 1.60 (s, 3H).

Step 4: N-methyl-N-(1-(5-(2-((4-(trifluoromethyl)phenyl)amino)phenyl)-1,3,4-oxadiazol-2-yl)ethyl)cyanamide (Compound 161)

To a solution of Compound 159 (60 mg, 0.16 mmol, 1 eq) in THF (2 mL) were added DIEA (64 mg, 0.5 mmol, 86 uL, 3 eq) and BrCN (35 mg, 0.33 mmol, 24 uL, 2 eq). The mixture was stirred at 20° C. for 2 hr. The reaction mixture was concentrated in vacuum. The residue was diluted with EA (20 mL), washed with H$_2$O (5 mL) and brine (5 mL), dried over Na$_2$SO$_4$, filtered and concentrated in vacuum. The crude product was purified by prep-HPLC. LCMS and $^1$HNMR confirmed that Compound 161 (30 mg, 77 umol, 46% yield) was obtained. LCMS (ESI): RT=0.875 min, mass calcd. For C$_{19}$H$_{16}$F$_3$N$_5$O, 387.13 m/z found 387.9 [M+H]$^+$. $^1$H NMR (400 MHz, CDCl$_3$) δ 9.32 (s, 1H), 7.86 (dd, J=1.5, 8.0 Hz, 1H), 7.52 (d, J=8.5 Hz, 2H), 7.46-7.41 (m, 1H), 7.38-7.26 (m, 3H), 6.96-6.90 (m, 1H), 4.46 (q, J=7.0 Hz, 1H), 2.90 (s, 3H), 1.79 (d, J=7.3 Hz, 3H).

Example 130: 2-methyl-2-(5-(2-((4-(trifluoromethyl)phenyl)amino)phenyl)-1,3,4-oxadiazol-2-yl)propanamide (Compound 162)

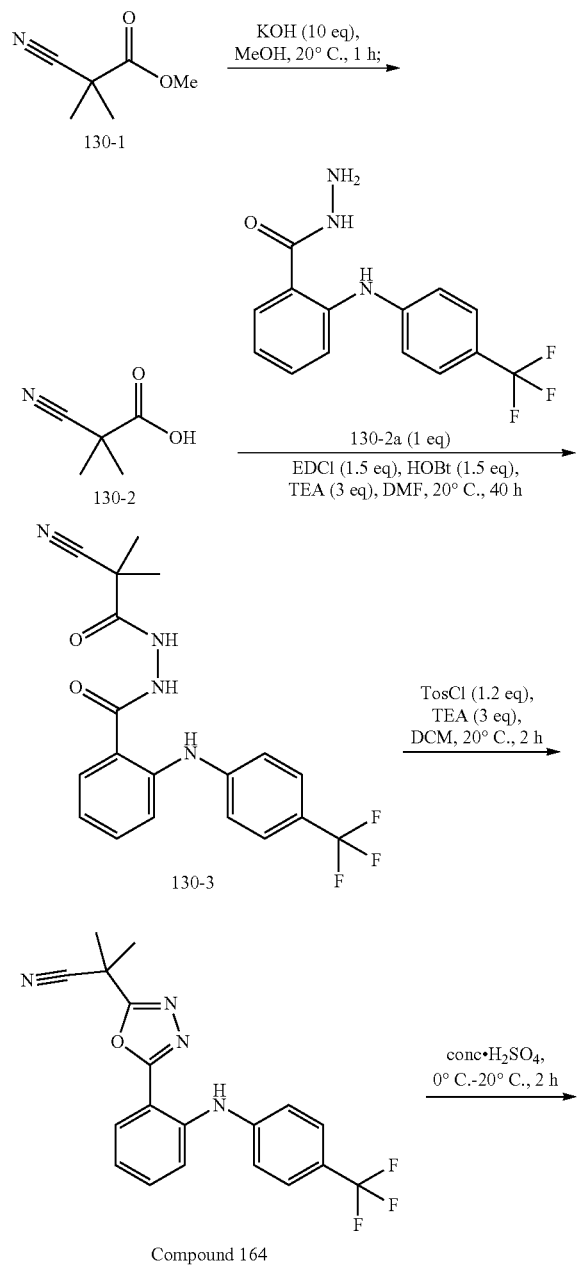

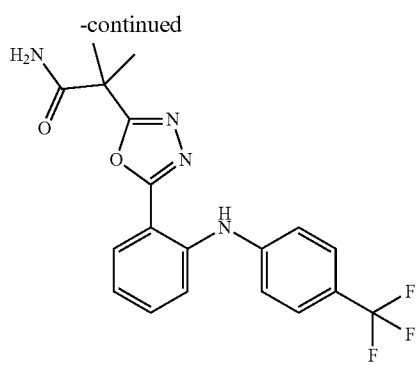

Compound 162

Step 1: 2-cyano-2-methylpropanoic Acid

To a solution of KOH (2.21 g, 39.33 mmol, 10 eq) in MeOH (20 mL) at 20° C. was added 130-1 (500 mg, 3.93 mmol, 1 eq), and the resulting mixture was stirred at 20° C. for 1 h. The reaction mixture was concentrated to remove most of MeOH, and the residue was diluted with water (20 mL), acidified with conc. HCl to pH=1-2, and then extracted with EA (20 mL*3). The combined organic layers were washed with brine (20 mL), dried over anhydrous Na$_2$SO$_4$, filtered and concentrated under reduced pressure to give a residue 130-2 (430 mg, 3.80 mmol, 96.7% yield). $^1$H NMR (400 MHz, CDCl$_3$) δ 1.67 (s, 6H).

Step 2: N'-(2-cyano-2-methylpropanoyl)-2-((4-(trifluoromethyl)phenyl)amino)benzohydrazide To a solution of 130-2 (137.9 mg, 1.22 mmol, 1.2 eq), EDCI (292.2 mg, 1.52 mmol, 1.5 eq) and HOBt (205.9 mg, 1.52 mmol, 1.5 eq) in DMF (4 mL) at 20° C. was added 130-2a (300 mg, 1.02 mmol, 1 eq) and then TEA (308.4 mg, 3.05 mmol, 0.42 mL, 3 eq), and the resulting mixture was stirred at 20° C. for 40 h. The reaction mixture was diluted with water (20 mL), and then extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography to give 130-3 (290 mg, 0.71 mmol, 69.5% yield). LCMS (ESI): RT=0.799 min, mass calc. for C$_{19}$H$_{17}$F$_3$N$_4$O$_2$ 390.13, m/z found 390.9 [M+1]$^+$.

Step 3: 2-methyl-2-(5-(2-((4-(trifluoromethyl)phenyl)amino)phenyl)-1,3,4-oxadiazol-2-yl)propanenitrile (Compound 164)

To a solution of 130-3 (150 mg, 0.38 mmol, 1 eq) and TEA (116.7 mg, 1.15 mmol, 0.16 mL, 3 eq) in DCM (2 mL) at 20° C. was added TosCl (87.9 mg, 0.46 mmol, 1.2 eq), and the resulting mixture was stirred at 20° C. for 2 h. The reaction mixture was diluted with water (20 mL), and then extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography to give Compound 164 (110 mg, 0.29 mmol, 74.3% yield). LCMS (ESI): RT=0.924 min, mass calc. for C$_{19}$H$_{15}$F$_3$N$_4$O 372.12, m/z found 372.9 [M+1]$^+$; $^1$H NMR (400 MHz, CDCl$_3$) δ 9.39 (s, 1H), 7.93 (dd, J=1.3, 8.0

Hz, 1H), 7.60 (d, J=8.5 Hz, 2H), 7.54-7.49 (m, 1H), 7.46-7.41 (m, 1H), 7.36 (d, J=8.5 Hz, 2H), 7.01 (t, J=7.6 Hz, 1H), 1.97 (s, 6H).

Step 4: 2-methyl-2-(5-(2-((4-(trifluoromethyl)phenyl)amino)phenyl)-1,3,4-oxadiazol-2-yl)propanamide (Compound 162)

The sample of Compound 164 (50 mg, 0.13 mmol, 1 eq) was added slowly to $H_2SO_4$ (1 mL) at 0° C., and the resulting mixture was stirred at 20° C. for 2 h. The reaction mixture was added drop-wise into the ice-water (10 mL) under stirring, then basified with saturated $Na_2CO_3$ solution to pH=8-9, and then extracted with EA (20 mL*3). The combined organic layers were washed with brine (20 mL), dried over anhydrous $Na_2SO_4$, filtered and concentrated under reduced pressure to give a residue. The residue was purified by flash silica gel chromatography to give Compound 162 (45.3 mg, 0.12 mmol, 86.4% yield). LCMS (ESI): RT=0.843 min, mass calc. for $C_{19}H_{17}F_3N_4O_2$ 390.13, m/z found 390.1 [M+1]$^+$; $^1$H NMR (400 MHz, CDCl$_3$) δ 9.43 (s, 1H), 7.89 (dd, J=1.4, 7.9 Hz, 1H), 7.59 (d, J=8.5 Hz, 2H), 7.52 (d, J=8.0 Hz, 1H), 7.42 (dt, J=1.4, 7.8 Hz, 1H), 7.36 (d, J=8.5 Hz, 2H), 7.03-6.96 (m, 1H), 6.52 (brs, 1H), 5.50 (brs, 1H), 1.80 (s, 6H).

Example 131: 2-(5-(2-(methylsulfonyl)propan-2-yl)-1,3,4-oxadiazol-2-yl)-N-(4-(trifluoromethyl)phenyl) aniline (Compound 163)

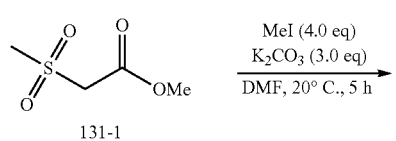

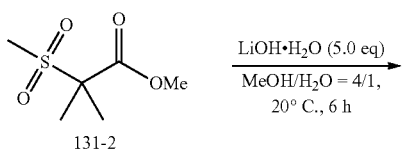

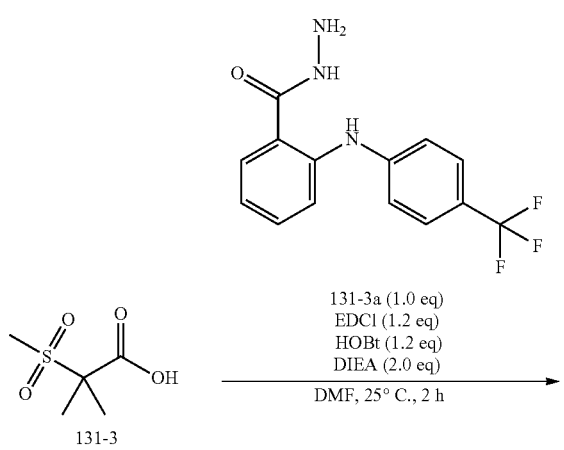

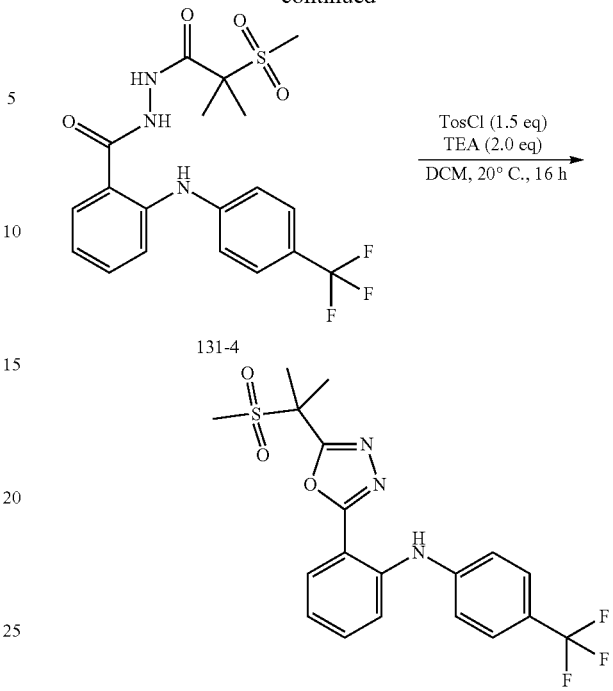

Step 1: Methyl 2-methyl-2-methylsulfonyl-propanoate

To a solution of compound 131-1 (600 mg, 3.94 mmol, 1 eq) and MeI (2.24 g, 15.77 mmol, 1 mL, 4 eq) in DMF (8 mL) was added $K_2CO_3$ (1.63 g, 11.83 mmol, 3 eq). The mixture was stirred at 20° C. for 5 hr. The reaction mixture was quenched with $H_2O$ (10 mL), extracted with EA (15 mL*3). The combined organic phase was washed with $H_2O$ (5 mL) and brine (5 mL*2), dried over $Na_2SO_4$, filtered and concentrated in vacuum. The crude product was used for the next step directly. $^1$HNMR confirmed that compound 131-2 (525 mg, crude) was obtained. $^1$H NMR (400 MHz, CDCl$_3$) δ 3.82 (s, 3H), 3.05 (s, 3H), 1.66 (s, 6H).

Step 2: 2-methyl-2-methylsulfonyl-propanoic Acid

To a solution of compound 131-2 (520 mg, 2.89 mmol, 1 eq) in MeOH (2 mL) and $H_2O$ (0.5 mL) was added LiOH.H$_2$O (605 mg, 14.43 mmol, 5 eq). The mixture was stirred at 20° C. for 6 hr. The reaction mixture was concentrated in vacuum. The aqueous phase was adjusted pH=3 with aqueous solution of citric acid and extracted with EA (15 mL*3). The combined organic phase was washed with $H_2O$ (5 mL) and brine (5 mL), dried over $Na_2SO_4$, filtered and concentrated in vacuum. The crude product was used for the next step directly. $^1$HNMR confirmed that compound 131-3 (230 mg, crude) was obtained. $^1$H NMR (400 MHz, DMSO-d$_6$) δ 3.09 (s, 3H), 1.50 (s, 6H).

Step 3: N'-(2-methyl-2-methylsulfonyl-propanoyl)-2-[4-(trifluoromethyl)anilino]benzohydrazide To a solution of compound 131-3a (325 mg, 1.10 mmol, 1 eq), compound 131-3 (220 mg, 1.32 mmol, 1.2 eq), EDCI (253 mg, 1.32 mmol, 1.2 eq) and HOBt (178 mg, 1.32 mmol, 1.2 eq) in DMF (4 mL) was added DIEA (285 mg, 2.21 mmol, 0.4 mL, 2 eq). The mixture was stirred at 25° C. for 2 hr. The reaction mixture was quenched with H$_2$O (5 mL), extracted with EA (15 mL*3). The combined organic phase was washed with H$_2$O (5 mL) and brine (5 mL*3), dried over Na$_2$SO$_4$, filtered and concentrated in vacuum. The crude product was purified by column chromatography. $^1$HNMR confirmed that compound 131-4 (240 mg, 0.54 mmol, 49% yield) was obtained. $^1$H NMR (400 MHz, CDCl$_3$) δ 9.02 (br d, J=15.1 Hz, 2H), 8.15 (br s, 1H), 7.57-7.40 (m, 3H), 7.40-7.29 (m, 2H), 7.16 (d, J=8.4 Hz, 2H), 6.85 (t, J=7.4 Hz, 1H), 3.08 (s, 3H), 1.66 (s, 6H).

Step 4: 2-(5-(2-(methylsulfonyl)propan-2-yl)-1,3,4-oxadiazol-2-yl)-N-(4-(trifluoromethyl)phenyl)aniline To a solution of compound 131-4 (100 mg, 0.22 mmol, 1 eq) in DCM (2 mL) were added TosCl (64 mg, 0.33 mmol, 1.5 eq) and TEA (45 mg, 0.45 mmol, 62 uL, 2 eq). The mixture was stirred at 20° C. for 16 hr. The reaction mixture was concentrated in vacuum. The residue was diluted with EA (20 mL), washed with brine (5 mL), dried over Na$_2$SO$_4$, filtered and concentrated in vacuum. The crude product was purified by prep-HPLC. LCMS and NMR confirmed that Compound 163 (25 mg, 57 umol, 25% yield) was obtained. LCMS (ESI): RT=0.879 min, mass calcd. For C$_{19}$H$_{18}$F$_3$N$_3$O$_3$S, 425.10 m/z found 425.9 [M+H]$^+$; $^1$H NMR (400 MHz, CDCl$_3$) δ 9.37 (s, 1H), 7.93 (dd, J=1.3, 8.0 Hz, 1H), 7.60 (d, J=8.3 Hz, 2H), 7.54-7.48 (m, 1H), 7.46-7.40 (m, 1H), 7.36 (d, J=8.3 Hz, 2H), 7.04-6.96 (m, 1H), 3.02 (s, 3H), 2.01 (s, 6H).

Example 132: Tert-Butyl 1-(5-(2-((4-(trifluoromethyl)phenyl)amino)phenyl)-1,3,4-oxadiazol-2-yl)cyclopropane-1-carboxylate (Compound 165)

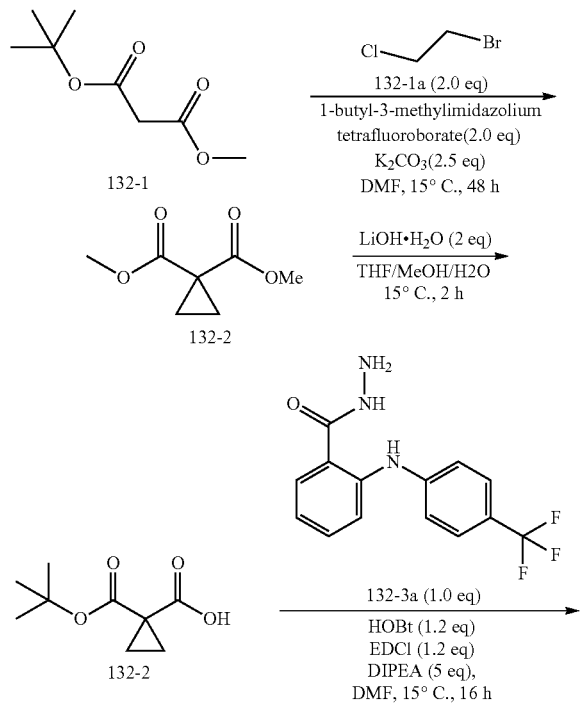

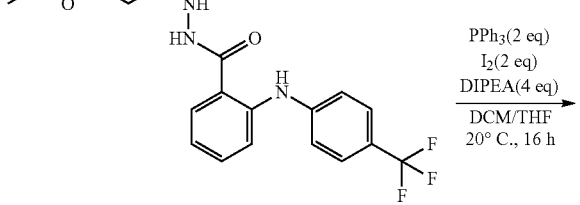

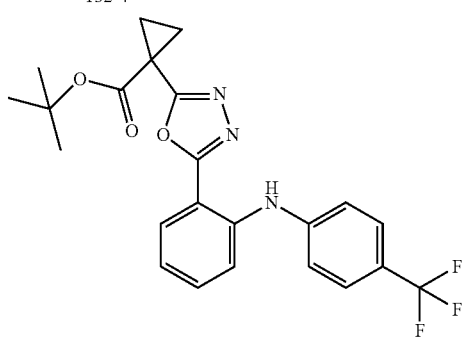

Compound 165

Step 1: O1'-tert-butyl O1-methyl cyclopropane-1,1-dicarboxylate

To a mixture of compound 132-1 (4 g, 23.0 mmol, 3.9 mL, 1.0 eq) in DMF (35 mL) were added 132-1a (6.59 g, 45.9 mmol, 3.8 mL, 2.0 eq), 1-butyl-3-methyl-imidazol-3-ium; tetrafluoroborate (1.04 g, 4.59 mmol, 0.9 mL, 0.2 eq) and K$_2$CO$_3$ (7.93 g, 57.4 mmol, 2.5 eq). Then the resulting mixture was stirred at 15° C. for 48 h. The reaction mixture was diluted with H$_2$O (30 mL) and extracted with EA (100 mL). The combined organic layers were washed with brine (30 mL), dried over Na$_2$SO$_4$, filtered and concentrated under reduced pressure to give compound 132-2 (4.1 g, 20.48 mmol, 89.2% yield). $^1$H NMR (400 MHz DMSO-d$_6$) δ 3.61-3.69 (m, 3H), 1.37-1.45 (m, 9H), 1.21-1.32 (m, 3H).

Step 2: 1-tertbutoxycarbonylcyclopropanecarboxylic Acid

To a mixture of compound 132-2 (3.1 g, 15.48 mmol, 1 eq) in MeOH (10 mL) and THF (25 mL) was drop-wise added a solution of LiOH.H$_2$O (1.3 g, 30.96 mmol, 2.0 eq) in H$_2$O (10 mL) over 2 min at 15° C. The resulting mixture was stirred at 15° C. for 2 h. The solution was concentrated at 15° C. to remove most of organic solvent and extracted with EA (10 mL) twice. The separated aqueous layer was adjusted with cold aq 2 M HCl to pH 2, along with lots of solid formed. Then the suspension was filtered and washed with water (10 mL). The filter cake was collected to give compound 132-3 (1.1 g, 5.91 mmol, 38.2% yield). The filtrate was extracted with EA (15 mL*4). The combined organic layer was washed with brine (15 mL), dried with Na$_2$SO$_4$, filtered and concentrated to give compound 132-3 (500 mg, 2.69 mmol, 17.3% yield). $^1$H NMR (400 MHz, DMSO-d$_6$) δ 1.43-1.36 (m, 9H), 1.26-1.18 (m, 4H).

Step 3: tert-butyl1-[[[2-[4-(trifluoromethyl)anilino]benzoyl]amino]carbamoyl]cyclopropanecarboxylate To a mixture of compound 132-3a (800 mg, 2.71 mmol, 1.0 eq), compound 132-3 (605.4 mg, 3.25 mmol, 1.2 eq), HOBt (439.3 mg, 3.25 mmol, 1.2 eq) and EDCI (623.3 mg, 3.25 mmol, 1.2 eq) in DMF (10 mL) was added DIPEA (1.75 g, 13.55 mmol, 2.4 mL, 5 eq) at 15° C. The resulting mixture was stirred at 15° C. for 16 h. The mixture was concentrated at 40° C. to remove most of organic solvent, diluted with water (30 mL) and extracted with EA (50 mL) twice. The separated aqueous layer was cooled to 0° C. and adjusted with cold aq 2 M HCl to pH~2 and then extracted with EA (15 mL*4). The combined organic layer was washed with brine (15 mL), dried over $Na_2SO_4$, filtered and concentrated to give a residue. The residue was purified by column chromatography to give compound 132-4 (780 mg, 1.65 mmol, 60.9% yield). LCMS (ESI): RT=0.892 min, mass calc. for $C_{23}H_{24}F_3N_3O_4$ 463.17, m/z found 485.9 $[M+23]^+$.

Step 4: Tert-Butyl 1-(5-(2-((4-(trifluoromethyl)phenyl)amino)phenyl)-1,3,4-oxadiazol-2-yl)cyclopropane-1-carboxylate To a mixture of $PPh_3$ (860.3 mg, 3.28 mmol, 2.0 eq) in DCM (10 mL) was added iodine (832.5 mg, 3.28 mmol, 0.7 mL, 2.0 eq) in one portion at 0° C. After the iodine was dissolved completely, DIPEA (847.8 mg, 6.6 mmol, 1.2 mL, 4.0 eq) was added, followed by a solution of compound 132-4 (760 mg, 1.64 mmol, 1.0 eq) in THF (10 mL). The mixture was stirred at 20° C. for 16 h. The reaction mixture was diluted with $H_2O$ (15 mL) and extracted with EA (50 mL*2). The combined organic layers were washed with $NaHCO_3$ (20 mL*2), dried over $Na_2SO_4$, filtered and concentrated under reduced pressure to give a residue. The residue was purified by column chromatography to give Compound 165 (700 mg, 1.5 mmol, 93.9% yield). LCMS (ESI): RT=1.018 min, mass calc. for $C_{23}H_{22}F_3N_3O_3$ 445.16, m/z found 446 $[M+1]^+$; $^1H$ NMR (400 MHz, DMSO-$d_6$) δ 9.22 (s, 1H), 7.84-8.05 (m, 1H), 7.63 (d, J=8.5 Hz, 2H), 7.52-7.60 (m, 2H), 7.35 (d, J=8.3 Hz, 2H), 7.13-7.21 (m, 1H), 1.55-1.66 (m, 4H), 1.28-1.47 (m, 9H).

Example 133: 1-(5-(2-((4-(trifluoromethyl)phenyl)amino)phenyl)-1,3,4-oxadiazol-2-yl)cyclopropane-1-carboxylic Acid (Compound 166)

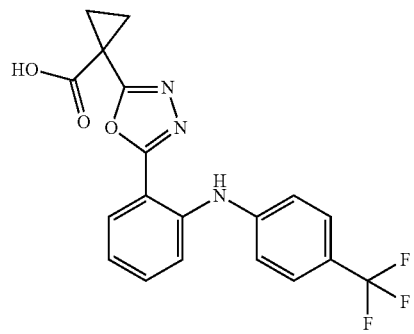

Compound 166

To a mixture of Compound 165 (300 mg, 0.7 mmol, 1 eq) in DCM (2 mL) was added TFA (0.4 mL) in one portion at 15° C. The mixture was stirred at 15° C. for 2 h. The reaction mixture was concentrated at 15° C. to give a residue. The residue was purified by prep-HPLC to give the product (290 mg, 0.75 mmol, 5.5% yield). $^1$HNMR and HPLC showed the product was not pure. 30 mg of the product was repurified by prep-HPLC to give Compound 166 (10.18 mg, 0.03 mmol, 1.94e-1% yield). LCMS (ESI): RT=0.848 min, mass calc. for $C_{19}H_{14}F_3N_3O_3$ 389.10, m/z found 389.9 [M+1]+; $^1H$ NMR (400 MHz, DMSO-$d_6$) δ 9.31 (br s, 1H), 7.88 (d, J=7.5 Hz, 1H), 7.63 (br d, J=8.3 Hz, 2H), 7.59-7.49 (m, 2H), 7.35 (br d, J=8.5 Hz, 2H), 7.13 (br t, J=7.3 Hz, 1H), 1.39 (br s, 2H), 1.22 (br s, 2H).

Example 134: Tert-Butyl Methyl((5-(2-((4-(trifluoromethyl)phenyl)amino)phenyl)-1,3,4-oxadiazol-2-yl)methyl)carbamate (Compound 167) and N-methyl-N-((5-(2-((4-(trifluoromethyl)phenyl)amino)phenyl)-1,3,4-oxadiazol-2-yl)methyl)cyanamide (Compound 168)

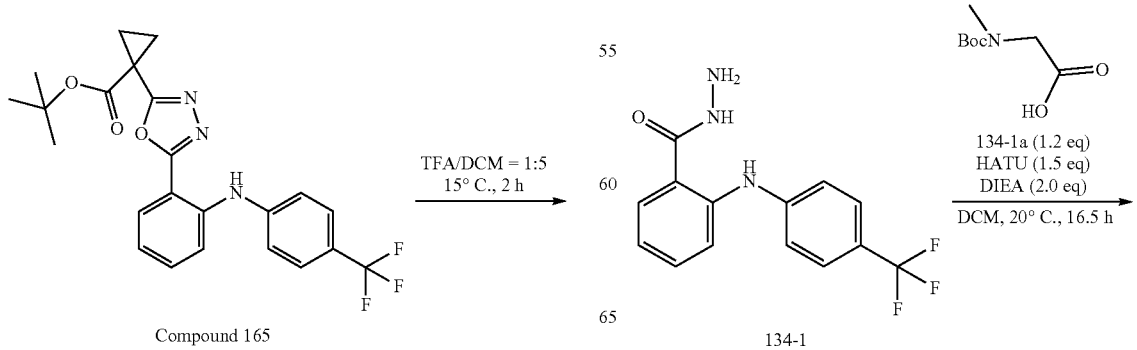

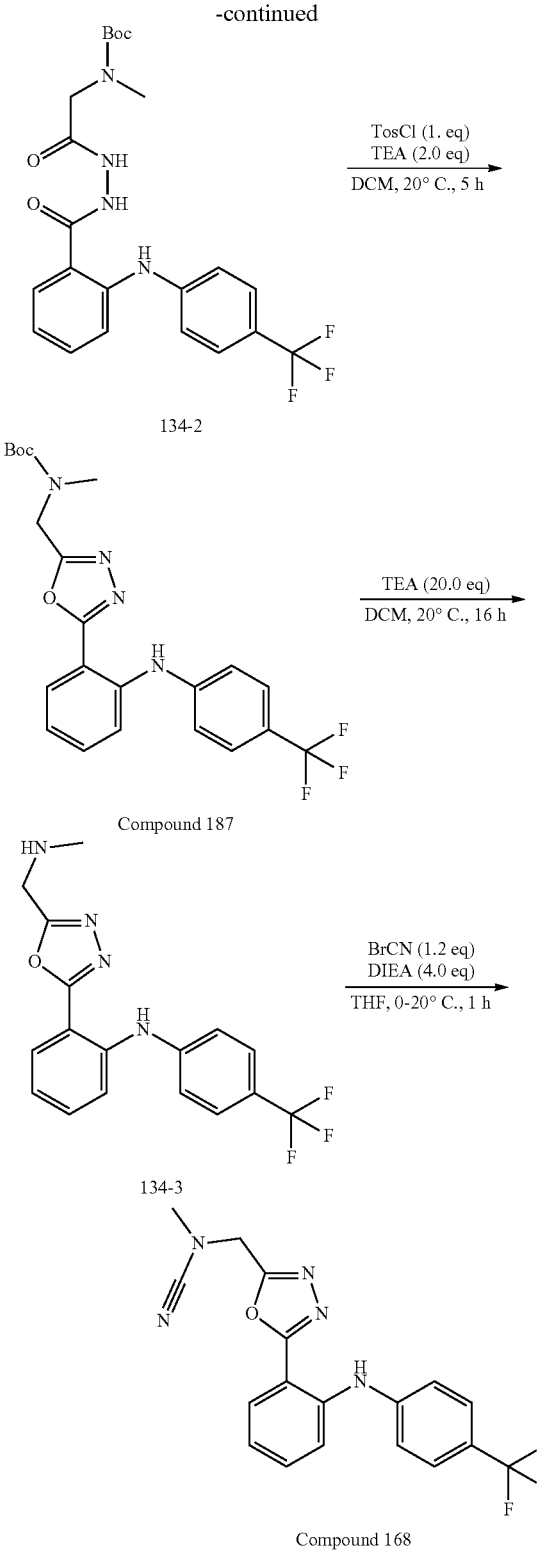

mL) was stirred at 20° C. for 30 min. Then compound 134-1 (200 mg, 0.67 mmol, 1 eq) and DIEA (175 mg, 1.35 mmol, 0.24 mL, 2 eq) were added to the mixture and stirred at 20° C. for 16 hr. The reaction mixture was concentrated in vacuum to give the residue. The residue was diluted with EA (20 mL), washed with $H_2O$ (10 mL*2) and brine (10 mL), dried over $Na_2SO_4$, filtered and concentrated in vacuum. The crude product was purified by column chromatography. LCMS confirmed that compound 134-2 (105 mg, 0.21 mmol, 30.9% yield) was obtained.

Step 2: Tert-Butyl Methyl((5-(2-((4-(trifluoromethyl)phenyl)amino)phenyl)-1,3,4-oxadiazol-2-yl)methyl)carbamate (Compound 167)

To a solution of compound 134-2 (100 mg, 0.21 mmol, 1 eq) in DCM (1 mL) were added TosCl (40.8 mg, 0.21 mmol, 1 eq) and TEA (43 mg, 0.43 mmol, 59 uL, 2 eq). The mixture was stirred at 20° C. for 5 hr. The reaction mixture was concentrated in vacuum to give a residue. Then the residue was diluted with EA (20 mL), washed with $H_2O$ (5 mL) and brine (5 mL), dried over $Na_2SO_4$, filtered and concentrated in vacuum. The crude product was purified by column chromatography. LCMS and $^1$HNMR confirmed that Compound 167 (35 mg, 78 umol, 36.4% yield) was obtained. LCMS (ESI): RT=0.938 min, mass calcd. For $C_{22}H_{23}F_3N_4O_3$, 448.17 m/z found 471.0 [M+H]$^+$. $^1$H NMR (400 MHz, CDCl$_3$) δ 9.49 (s, 1H), 7.87 (br s, 1H), 7.59 (br d, J=8.4 Hz, 2H), 7.52 (d, J=8.4 Hz, 1H), 7.44-7.34 (m, 3H), 6.98 (t, J=7.6 Hz, 1H), 4.83-4.68 (m, 2H), 3.03 (br d, J=11.1 Hz, 3H), 1.51 (br s, 9H).

Step 3: 2-[5-(methylaminomethyl)-1,3,4-oxadiazol-2-yl]-N-[4-(trifluoromethyl)phenyl]aniline To a solution of Compound 167 (30 mg, 66.9 umol, 1 eq) in DCM (1 mL) was added TFA (152 mg, 1.34 mmol, 99 uL, 20 eq). The mixture was stirred at 20° C. for 16 hr. The reaction mixture was concentrated in vacuum. The crude product was used for the next step directly. Compound 134-3 (40 mg, crude) was obtained.

Step 4: N-methyl-N-((5-(2-((4-(trifluoromethyl)phenyl)amino)phenyl)-1,3,4-oxadiazol-2-yl)methyl)cyanamide (Compound 168)

To a solution of compound 134-3 (40 mg, 0.11 mmol, 1 eq) and DIEA (59 mg, 0.46 mmol, 80 uL, 4 eq) in THF (1 mL) was added BrCN (14.6 mg, 0.14 mmol, 10 uL, 1.2 eq) at 0° C. The mixture was stirred at 20° C. for 1 hr. The reaction mixture was concentrated in vacuum to give a residue and the residue was diluted with EA (15 mL), filtered, the filtrate was washed with $H_2O$ (5 mL) and brine (5 mL), dried over $Na_2SO_4$, filtered and concentrated in vacuum. The crude product was purified by prep-HPLC. LCMS and $^1$HNMR confirmed that Compound 168 (14 mg, 37 umol, 32.3% yield) was obtained. LCMS (ESI): RT=0.862 min, mass calcd. For $C_8H_{14}F_3N_5O$, 373.12 m/z found 373.9 [M+H]$^+$. $^1$H NMR (400 MHz, CDCl$_3$) δ 9.39 (s, 1H), 7.94 (dd, J=1.4, 7.9 Hz, 1H), 7.60 (d, J=8.5 Hz, 2H), 7.54-7.49 (m, 1H), 7.46-7.41 (m, 1H), 7.38 (d, J=8.5 Hz, 2H), 7.03-6.97 (m, 1H), 4.53 (s, 2H), 3.03 (s, 3H).

Step 1: Tert-Butyl N-methyl-N-[2-oxo-2-[2-[2-[4-(trifluoromethyl)anilino]benzoyl]hydrazino]ethyl]carbamate A solution of compound 134-1a (153.8 mg, 0.81 mmol, 1.2 eq) and HATU (386 mg, 1.02 mmol, 1.5 eq) in DCM (2

Example 135: 2-(5-(pyrrolidin-2-yl)-1,3,4-oxadiazol-2-yl)-N-(4-(trifluoromethyl)phenyl)aniline (Compound 169), and tert-butyl 2-(5-(2-((4-(trifluoromethyl)phenyl)amino)phenyl)-1,3,4-oxadiazol-2-yl)pyrrolidine-1-carboxylate (Compound 170), and 2-(5-(2-((4-(trifluoromethyl)phenyl)amino)phenyl)-1,3,4-oxadiazol-2-yl)pyrrolidine-1-carbonitrile (Compound 171)

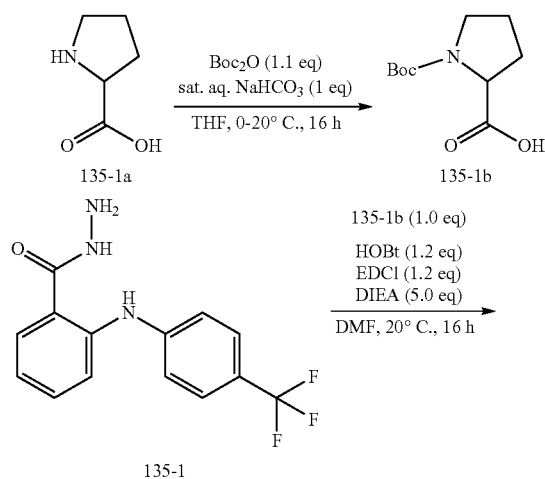

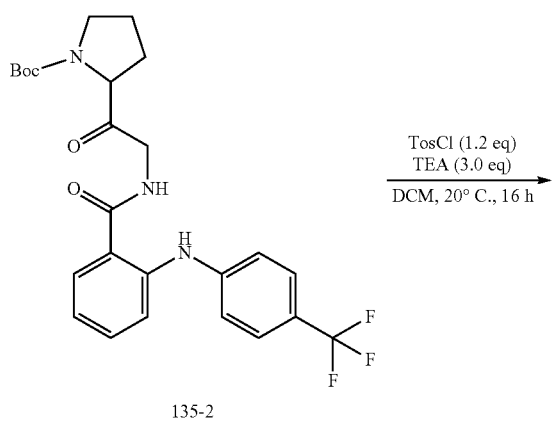

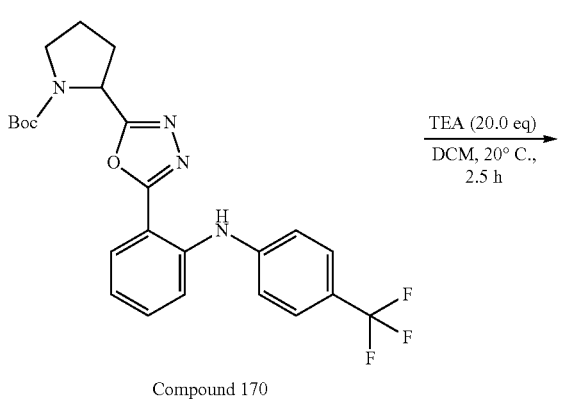

Compound 170

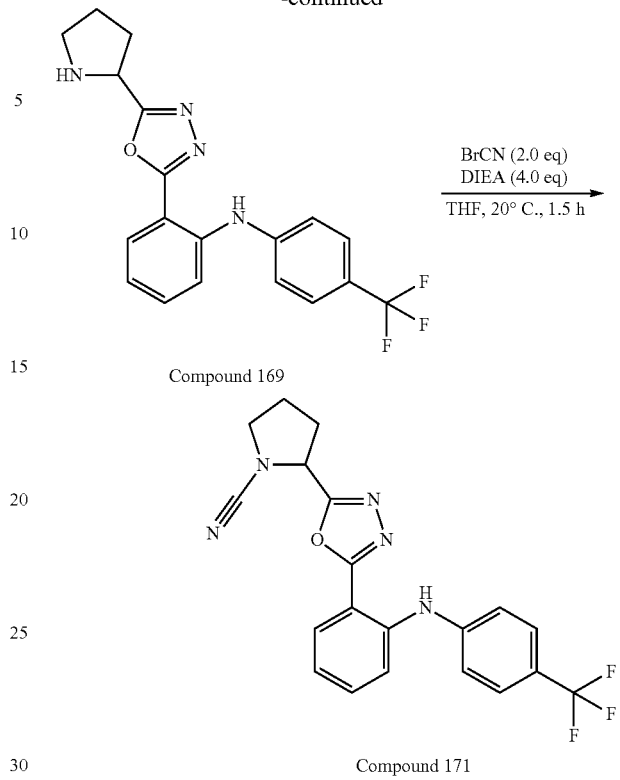

Compound 169

Compound 171

Step 1: 1-tert-butoxycarbonylpyrrolidine-2-carboxylic Acid

To a solution of compound 135-1a (1 g, 8.69 mmol, 1 eq) in NaHCO$_3$ (1 M, 8.7 mL, 1 eq) was added Boc$_2$O (2.1 g, 9.55 mmol, 2.2 mL, 1.1 eq) in THF (5 mL) at 0° C. Then the mixture was stirred at 20° C. for 16 hr. The reaction mixture was concentrated in vacuum to remove THF, then the aqueous phase was adjusted pH=2 with 1M. aq. HCl. The aqueous phase was extracted with EA (20 mL*3), washed with brine (10 mL), dried over Na$_2$SO$_4$, filtered and concentrated in vacuum. The crude product was used for the next step directly. $^1$HNMR confirmed that compound 135-1b (1.8 g, 8.36 mmol, 96.2% yield) was obtained. $^1$H NMR (400 MHz, CDCl$_3$) δ 9.87-7.76 (m, 1H), 4.42-4.21 (m, 1H), 3.63-3.29 (m, 2H), 2.35-2.06 (m, 2H), 2.01-1.85 (m, 2H), 1.51-1.38 (m, 9H).

Step 2: Tert-Butyl 2-[[[2-[4-(trifluoromethyl)anilino]benzoyl]amino]carbamoyl]pyrrolidine-1-carboxylate To a solution of compound 135-1 (300 mg, 1.02 mmol, 1 eq) and compound 135-1b (218 mg, 1.02 mmol, 1 eq) in DMF (3 mL) were added HOBt (164.7 mg, 1.22 mmol, 1.2 eq), EDCI (233.7 mg, 1.22 mmol, 1.2 eq) and DIEA (656 mg, 5.08 mmol, 0.89 mL, 5 eq). The mixture was stirred at 20° C. for 16 hr. The reaction mixture was quenched with H$_2$O (15 mL), extracted with EA (15 mL*3). The combined organic phase was washed with brine (10 mL*3), dried over Na$_2$SO$_4$, filtered and concentrated in vacuum. The crude product was purified by column chromatography. LCMS and $^1$HNMR confirmed that compound 135-2 (300 mg, 0.58 mmol, 56.9% yield) was obtained. $^1$H NMR (400 MHz, CDCl$_3$) δ 9.72 (br s, 1H), 9.22 (br s, 1H), 8.95-8.53 (m, 1H), 7.58 (br d, J=7.3 Hz, 1H), 7.52 (d, J=8.3 Hz, 2H), 7.48-7.42 (m, 1H), 7.41-7.33 (m, 1H), 7.22 (d, J=8.5 Hz, 2H), 6.90 (br t, J=7.4 Hz, 1H), 4.45 (br s, 1H), 3.64-3.32 (m, 2H), 2.50-2.15 (m, 1H), 2.05-1.87 (m, 3H), 1.50 (s, 9H).

Step 3: Tert-Butyl 2-(5-(2-((4-(trifluoromethyl)phenyl)amino)phenyl)-1,3,4-oxadiazol-2-yl)pyrrolidine-1-carboxylate (Compound 170)

To a solution of compound 135-2 (200 mg, 0.4 mmol, 1 eq) in DCM (3 mL) were added TosCl (92.9 mg, 0.48 mmol, 1.2 eq) and TEA (123 mg, 1.22 mmol, 0.17 mL, 3 eq). The mixture was stirred at 20° C. for 16 hr. The reaction mixture was concentrated in vacuum to give a residue and the residue was diluted with EA (20 mL), washed with H$_2$O (5 mL) and brine (5 mL), dried over Na$_2$SO$_4$, filtered and concentrated in vacuum to give the crude product (160 mg). Crude Compound 170 (120 mg, 0.25 mmol, 62% yield) was used for the next step directly. 40 mg of the crude product was purified by prep-HPLC. LCMS and $^1$HNMR confirmed that Compound 170 (10 mg, 21 umol, 5.2% yield) was obtained. LCMS (ESI): RT=0.969 min, mass calcd. For C$_{24}$H$_{25}$F$_3$N$_4$O$_3$, 474.19 m/z found 497.0 [M+Na]$^+$. $^1$H NMR (400 MHz, CDCl$_3$) δ 9.53 (br s, 1H), 7.86 (br d, J=7.5 Hz, 1H), 7.61-7.55 (m, 2H), 7.55-7.48 (m, 1H), 7.44-7.32 (m, 3H), 7.01-6.93 (m, 1H), 5.28-5.09 (m, 1H), 3.78-3.43 (m, 2H), 2.49-2.29 (m, 1H), 2.28-2.11 (m, 2H), 2.11-2.00 (m, 1H), 1.49-1.33 (m, 9H).

Step 4: 2-(5-(pyrrolidin-2-yl)-1,3,4-oxadiazol-2-yl)-N-(4-(trifluoromethyl)phenyl)aniline (Compound 169)

To a solution of Compound 170 (120 mg, 0.25 mmol, 1 eq) in DCM (3 mL) was added TFA (576.7 mg, 5.06 mmol, 0.4 mL, 20 eq). The mixture was stirred at 20° C. for 2.5 hr. The reaction mixture was concentrated in vacuum to give a residue and the residue was diluted with EA (10 mL), the precipitate was collected to give Compound 169 (60 mg, 0.16 mmol, 63.4% yield). The crude product was purified by prep-HPLC. LCMS and $^1$HNMR confirmed that Compound 169 (7.89 mg, 19.8 umol, 7.8% yield) was obtained. LCMS (ESI): RT=0.718 min, mass calcd. For C$_{19}$H$_{17}$F$_3$N$_4$O, 374.14 m/z found 374.9 [M+H]$^+$. $^1$H NMR (400 MHz, DMSO-d$_6$) δ 10.41 (br s, 1H), 9.09 (s, 1H), 8.03-7.95 (m, 1H), 7.62 (d, J=8.5 Hz, 2H), 7.58-7.54 (m, 2H), 7.37 (d, J=8.5 Hz, 2H), 7.18 (m, 1H), 5.09 (t, J=7.4 Hz, 1H), 3.36 (t, J=7.3 Hz, 2H), 2.48-2.29 (m, 2H), 2.20-2.04 (m, 2H).

Step 5: 2-(5-(2-((4-(trifluoromethyl)phenyl)amino)phenyl)-1,3,4-oxadiazol-2-yl)pyrrolidine-1-carbonitrile (Compound 171)

To a solution of Compound 169 (60 mg, 0.16 mmol, 1 eq) in THF (2 mL) were added DIEA (82.8 mg, 0.64 mmol, 0.11 mL, 4 eq) and BrCN (33.9 mg, 0.32 mmol, 23 uL, 2 eq). The mixture was stirred at 20° C. for 1.5 hr. The reaction mixture was concentrated in vacuum to give a residue and the residue was diluted with EA (20 mL), washed with H$_2$O (5 mL) and brine (5 mL), dried over Na$_2$SO$_4$, filtered and concentrated in vacuum. The crude product was purified by prep-HPLC. LCMS and $^1$HNMR confirmed that Compound 171 (31 mg, 76 umol, 47.9% yield) was obtained. LCMS (ESI): RT=0.874 min, mass calcd. For C$_{20}$H$_{16}$F$_3$N$_5$O, 399.13 m/z found 421.9 [M+Na]$^+$. $^1$H NMR (400 MHz, CDCl$_3$) δ 9.41 (s, 1H), 7.92 (dd, J=1.3, 8.0 Hz, 1H), 7.59 (d, J=8.3 Hz, 2H), 7.54-7.49 (m, 1H), 7.46-7.39 (m, 1H), 7.37 (d, J=8.5 Hz, 2H), 7.02-6.97 (m, 1H), 5.05 (dd, J=4.3, 7.8 Hz, 1H), 3.74 (dt, J=5.0, 8.4 Hz, 1H), 3.67-3.59 (m, 1H), 2.58-2.41 (m, 2H), 2.29-2.13 (m, 2H).

Example 136: 2-(5-(2-(methylamino)ethyl)-1,3,4-oxadiazol-2-yl)-N-(4-(trifluoromethyl)phenyl)aniline (Compound 172), tert-butyl methyl(2-(5-(2-((4-(trifluoromethyl)phenyl)amino)phenyl)-1,3,4-oxadiazol-2-yl)ethyl)carbamate (Compound 173), and N-methyl-N-(2-(5-(2-((4-(trifluoromethyl)phenyl)amino)phenyl)-1,3,4-oxadiazol-2-yl)ethyl)cyanamide (Compound 174)

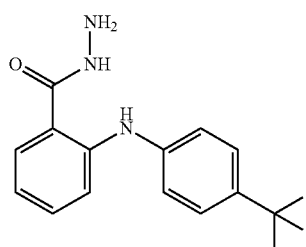
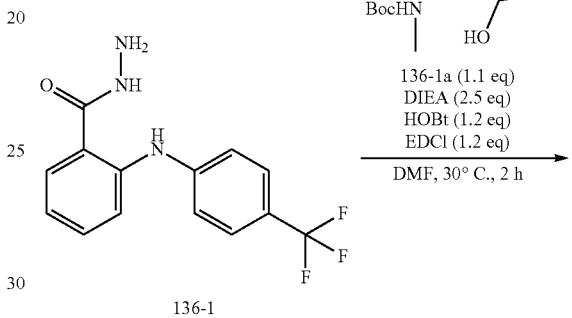

136-1

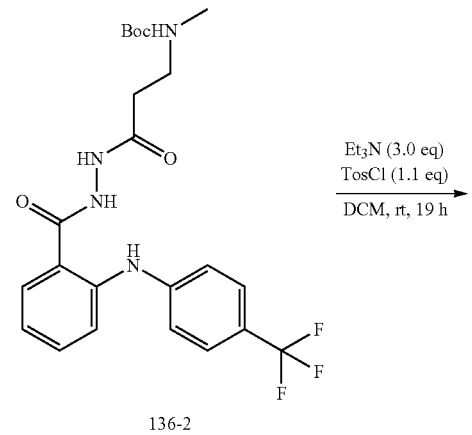

136-2

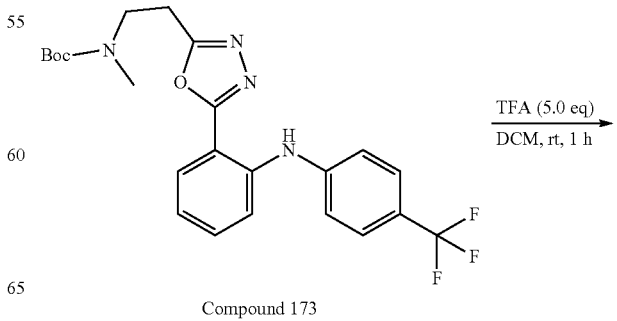

Compound 173

-continued

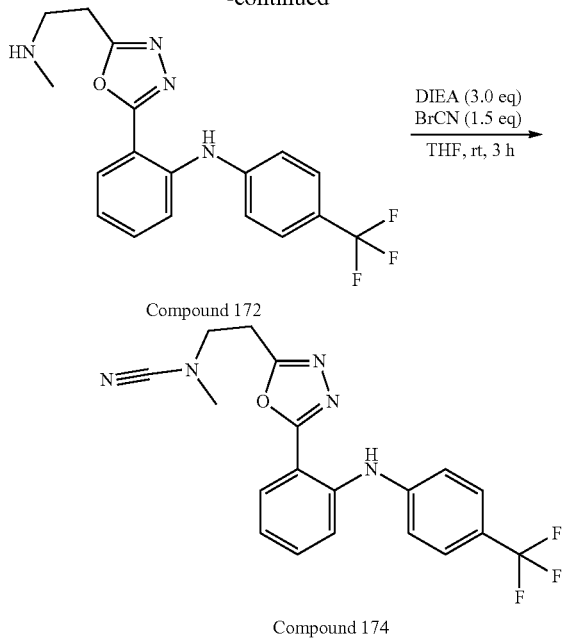

Compound 172

Compound 174

Step 1: Tert-Butyl N-methyl-N-[3-oxo-3-[2-[2-[4-(trifluoromethyl)anilino]benzoyl]hydrazino]propyl]carbamate To a solution of compound 136-1a (151 mg, 0.7 mmol, 1.1 eq), HOBt (109.8 mg, 0.8 mmol, 1.2 eq) and EDCI (155.8 mg, 0.8 mmol, 1.2 eq) in DMF (3 mL) was added compound 136-1 (200 mg, 0.6 mmol, 1 eq) followed by DIEA (218.8 mg, 1.6 mmol, 0.3 mL, 2.5 eq). The reaction was stirred at 30° C. for 2 hr. The reaction was diluted with EA (30 mL) and washed with Sat.NaHCO$_3$ (2*10 mL) and brine (2*10 mL). The organic layer was dried over Na$_2$SO$_4$ and concentrated. The crude compound 136-2 (0.3 g, 0.5 mmol, 73% yield) was used for next step directly. LCMS confirmed that desired product was obtained.

Step 2: Tert-Butyl Methyl(2-(5-(2-((4-(trifluoromethyl)phenyl)amino)phenyl)-1,3,4-oxadiazol-2-yl)ethyl)carbamate (Compound 173)

To a solution of compound 136-2 (0.2 g, 0.3 mmol, 1 eq) and Et$_3$N (101 mg, 0.9 mmol, 0.1 mL, 3 eq) in DCM (2 mL) was added TosCl (25.8 mg, 0.4 mmol, 1.1 eq). The reaction was stirred at 30° C. for 16 hr. Additional TosCl (26 mg) was added. The reaction was continued to stir at 30° C. for 3 hr. The reaction was diluted with DCM (30 mL) and washed with brine (2*10 mL). The organic layer was dried over Na$_2$SO$_4$ and concentrated. The crude product (100 mg, crude) was used for next step directly. 60 mg crude product was purified by prep-HPLC to give Compound 173 (2.88 mg, 6.1 umol, 1.8% yield). LCMS and $^1$HNMR confirmed that desired product was obtained. LCMS (ESI): RT=1.067 min, mass calc. for C$_{23}$H$_{25}$F$_3$N$_4$O$_3$ 462.19, m/z found 463.1 [M+H]$^+$; $^1$H NMR (400 MHz, CDCl$_3$) δ 9.41 (s, 1H), 7.81 (s, 1H), 7.50 (d, J=8.50 Hz, 2H), 7.43 (d, J=8.50 Hz, 1H), 7.25-7.35 (m, 3H), 6.87-6.93 (m, 1H), 3.65 (s, 2H), 3.13 (s, 2H), 2.86 (d, J=10.76 Hz, 3H), 1.33 (s, 9H).

Step 3: 2-(5-(2-(methylamino)ethyl)-1,3,4-oxadiazol-2-yl)-N-(4-(trifluoromethyl)phenyl)aniline (Compound 172)

To a solution of Compound 173 (70 mg, 0.15 mmol, 1 eq) in DCM (1 mL) was added TFA (86 mg, 0.75 mmol, 56 uL, 5 eq). The reaction was stirred at 25° C. for hr. The reaction was adjusted pH to 7-8 with Sat.NaHCO$_3$ and extracted with DCM (3*10 mL). The organic layer was dried over Na$_2$SO$_4$ and concentrated. 10 mg crude product was purified by prep-HPLC to give Compound 172 (4.81 mg, 13.14 umol, 8.68% yield). 30 mg Compound 172 (30 mg, 82 umol, 54% yield) was used for next step directly. HNMR and LCMS confirmed that desired product was obtained. LCMS (ESI): RT=0.892 min, mass calc. for C$_{23}$H$_{25}$F$_3$N$_4$O$_3$ 362.19, m/z found 363.1 [M+H]$^+$; $^1$H NMR (400 MHz, CDCl$_3$) δ 9.45 (s, 1H), 7.80 (dd, J=7.91, 1.38 Hz, 1H), 7.50 (d, J=8.53 Hz, 2H), 7.43 (d, J=8.53 Hz, 1H), 7.25-7.35 (m, 3H), 6.85-6.95 (m, 1H), 2.99-3.13 (m, 4H), 2.43 (s, 3H).

Step 4: N-methyl-N-(2-(5-(2-((4-(trifluoromethyl)phenyl)amino)phenyl)-1,3,4-oxadiazol-2-yl)ethyl)cyanamide (Compound 174)

To a solution of Compound 172 (30 mg, 82 umol, 1 eq) and DIEA (32 mg, 0.25 mmol, 43 uL, 3 eq) in THF (2 mL) was added BrCN (13 mg, 0.12 mmol, 9 uL, 1.5 eq). The reaction was stirred at 25° C. for 3 hr. The reaction was diluted with EA (10 mL) and washed with water (2*5 mL). The organic layer was dried over Na$_2$SO$_4$ and concentrated. The reaction was purified by prep-HPLC to give Compound 174 (14.06 mg, 35 umol, 43% yield). LCMS and $^1$HNMR confirmed that desired product was obtained. LCMS (ESI): RT=0.996 min, mass calc. for C$_{23}$H$_{25}$F$_3$N$_4$O$_3$ 387.13, m/z found 388.0 [M+H]$^+$; $^1$H NMR (400 MHz, CDCl$_3$) δ9.46 (s, 1H), 7.91 (dd, J=7.91, 1.13 Hz, 1H), 7.60 (d, J=8.53 Hz, 2H), 7.52 (d, J=8.53 Hz, 1H), 7.34-7.45 (m, 3H), 7.00 (t, J=7.40 Hz, 1H), 3.54-3.65 (m, 2H), 3.30-3.39 (m, 2H), 3.00 (s, 3H).

Example 137: 2-(5-(pyrrolidin-3-yl)-1,3,4-oxadiazol-2-yl)-N-(4-(trifluoromethyl)phenyl)aniline (Compound 175), tert-butyl 3-(5-(2-((4-(trifluoromethyl)phenyl)amino)phenyl)-1,3,4-oxadiazol-2-yl)pyrrolidine-1-carboxylate (Compound 176), and 3-(5-(2-((4-(trifluoromethyl)phenyl)amino)phenyl)-1,3,4-oxadiazol-2-yl)pyrrolidine-1-carbonitrile (Compound 177)

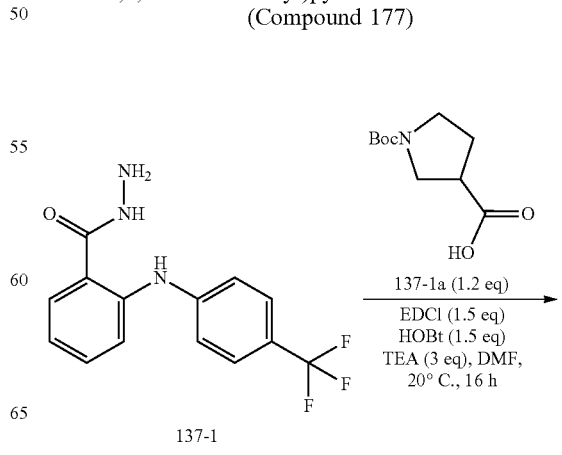

137-1

-continued

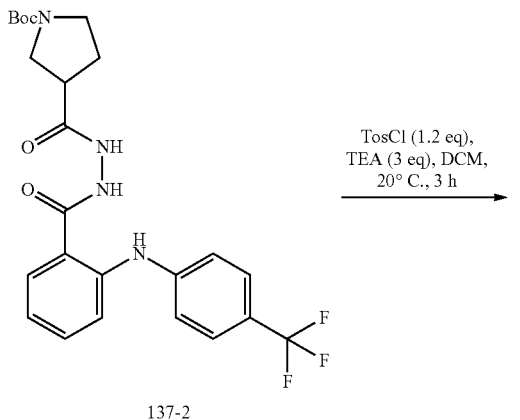
137-2

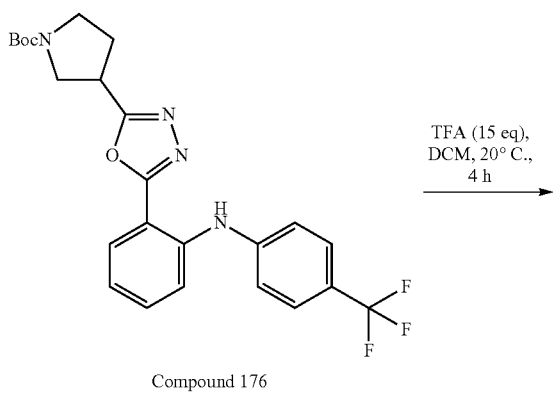
Compound 176

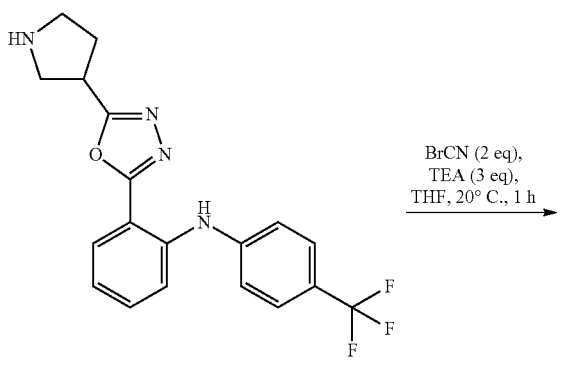
Compound 175

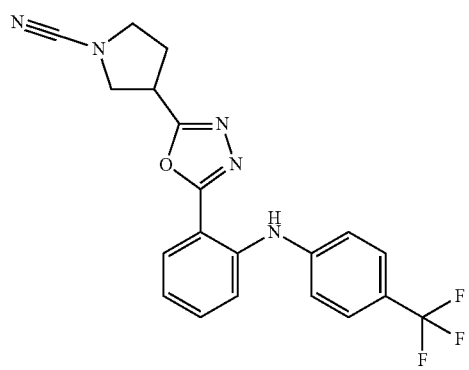
Compound 177

Step 1: Tert-Butyl 3-(2-(2-((4-(trifluoromethyl)phenyl)amino)benzoyl)hydrazinecarbonyl)pyrrolidine-1-carboxylate To a solution of 137-1a (175.0 mg, 0.81 mmol, 1.2 eq), EDCI (194.8 mg, 1.02 mmol, 1.5 eq) and HOBt (137.3 mg, 1.02 mmol, 1.5 eq) in DMF (2 mL) at 20° C. was added 137-1 (200 mg, 0.68 mmol, 1 eq) and TEA (205.6 mg, 2.03 mmol, 0.28 mL, 3 eq), and the resulting mixture was stirred at 20° C. for 16 h. The reaction mixture was diluted with water (20 mL), and then extracted with EA (20 mL*3). The combined organic layers were washed with brine (20 mL), dried over anhydrous $Na_2SO_4$, filtered and concentrated under reduced pressure to give a residue. The residue was purified by flash silica gel chromatography to give 137-2 (250 mg, 0.49 mmol, 72.7% yield). LCMS (ESI): RT=0.826 min, mass calc. for $C_{24}H_{27}F_3N_4O_4$ 492.20, m/z found 515.0 $[M+23]^+$.

Step 2: Tert-Butyl 3-(5-(2-((4-(trifluoromethyl)phenyl)amino)phenyl)-1,3,4-oxadiazol-2-yl)pyrrolidine-1-carboxylate (Compound 176)

To a solution of 137-2 (250 mg, 0.51 mmol, 1 eq) and TEA (154.1 mg, 1.52 mmol, 0.21 mL, 3 eq) in DCM (2 mL) at 20° C. was added TosCl (116.1 mg, 0.61 mmol, 1.2 eq), and the resulting mixture was stirred at 20° C. for 3 h. The reaction mixture was quenched with MeOH (0.5 mL) and concentrated under reduced pressure to give a residue. The residue was purified by flash silica gel chromatography to give Compound 176 (210 mg, 0.44 mmol, 87.2% yield). LCMS (ESI): RT=0.976 min, mass calc. for $C_{24}H_{25}F_3N_4O_3$ 474.19, m/z found 475.0 $[M+1]^+$; $^1$H NMR (400 MHz, $CDCl_3$) δ 9.49 (s, 1H), 7.87 (d, J=7.5 Hz, 1H), 7.58 (d, J=8.3 Hz, 2H), 7.52 (d, J=8.5 Hz, 1H), 7.44-7.38 (m, 1H), 7.36 (d, J=8.5 Hz, 2H), 6.98 (t, J=7.5 Hz, 1H), 3.89 (brs, 1H), 3.81-3.62 (m, 3H), 3.53 (brs, 1H), 2.47-2.33 (m, 2H), 1.49 (s, 9H).

Step 3: 2-(5-(pyrrolidin-3-yl)-1,3,4-oxadiazol-2-yl)-N-(4-(trifluoromethyl)phenyl)aniline (Compound 175)

To a solution of Compound 176 (200 mg, 0.42 mmol, 1 eq) in DCM (4 mL) at 20° C. was added TFA (720.9 mg, 6.32 mmol, 0.47 mL, 15 eq), and the resulting mixture was stirred at 20° C. for 4 h. The reaction mixture was concentrated under reduced pressure to give a residue. The residue was diluted with saturated $Na_2CO_3$ solution (30 mL) and extracted with EA (30 mL*3). The combined organic layers were washed with brine (30 mL), dried over anhydrous $Na_2SO_4$, filtered and concentrated under reduced pressure to give Compound 175 (150 mg, 0.39 mmol, 93.6% yield). LCMS (ESI): RT=0.732 min, mass calc. for $C_{19}H_{17}F_3N_4O$ 374.14, m/z found 374.9 $[M+1]^+$; $^1$H NMR (400 MHz, $CDCl_3$) δ 9.43 (s, 1H), 7.86 (dd, J=1.4, 7.9 Hz, 1H), 7.59 (d, J=8.5 Hz, 2H), 7.54-7.49 (m, 1H), 7.45-7.39 (m, 1H), 7.36 (d, J=8.5 Hz, 2H), 7.02-6.95 (m, 1H), 3.95-3.78 (m, 3H), 3.76-3.60 (m, 2H), 2.54-2.43 (m, 2H).

Step 4: 3-(5-(2-((4-(trifluoromethyl)phenyl)amino)phenyl)-1,3,4-oxadiazol-2-yl)pyrrolidine-1-carbonitrile (Compound 177)

To a solution of Compound 175 (70 mg, 0.19 mmol, 1 eq) and TEA (56.8 mg, 0.56 mmol, 78 uL, 3 eq) in THF (2 mL) at 20° C. was added BrCN (39.6 mg, 0.37 mmol, 27 uL, 2 eq), and the resulting mixture was stirred at 20° C. for 1 h. The reaction mixture was diluted with water (30 mL) and extracted with EA (30 mL*3). The combined organic layers were washed with brine (30 mL), dried over anhydrous Na$_2$SO$_4$, filtered and concentrated under reduced pressure to give a residue. The residue was purified by prep-HPLC to give Compound 177 (62.4 mg, 0.16 mmol, 83.6% yield). LCMS (ESI): RT=0.867 min, mass calc. for C$_{20}$H$_{16}$F$_3$N$_5$O 399.13, m/z found 399.9 [M+1]$^+$; $^1$H NMR (400 MHz, CDCl$_3$) δ 9.52 (s, 1H), 7.88 (dd, J=1.4, 7.9 Hz, 1H), 7.58 (d, J=8.5 Hz, 2H), 7.52 (d, J=8.5 Hz, 1H), 7.43-7.38 (m, 1H), 7.36 (d, J=8.5 Hz, 2H), 6.98 (t, J=7.6 Hz, 1H), 3.67-3.57 (m, 1H), 3.41-3.28 (m, 2H), 3.24 (ddd, J=5.8, 8.1, 11.4 Hz, 1H), 3.12-3.04 (m, 1H), 2.38-2.19 (m, 2H).

Example 138: 2-(5-(2-methyltetrahydrofuran-2-yl)-1,3,4-oxadiazol-2-yl)-N-(4-(trifluoromethyl)phenyl) aniline (Compound 178)

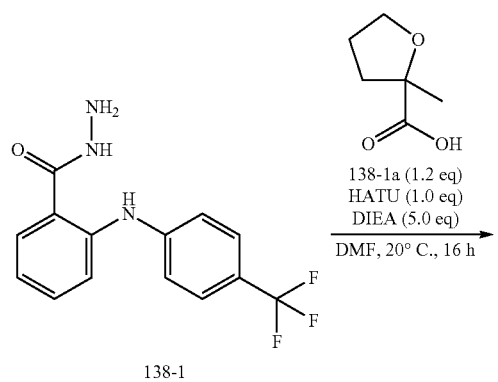

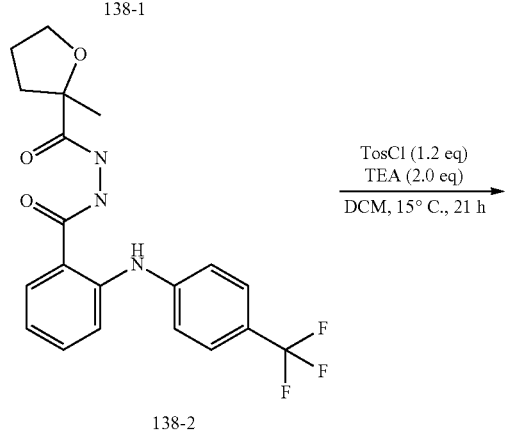

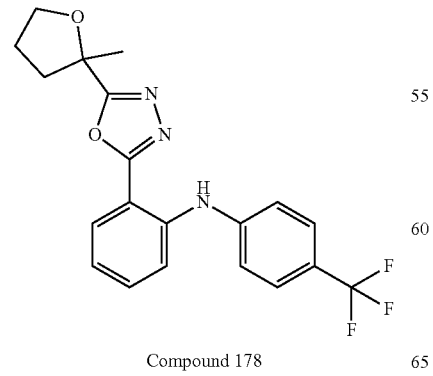

Compound 178

Step 1: 2-methyl-N'-[2-[4-(trifluoromethyl)anilino] benzoyl]tetrahydrofuran-2-carbohydrazide To a solution of compound 138-1 (113 mg, 0.38 mmol, 1 eq), compound 138-1a (60 mg, 0.46 mmol, 1.2 eq) and HATU (146 mg, 0.38 mmol, 1 eq) in DMF (1 mL) was added DIEA (248 mg, 1.92 mmol, 0.3 mL, 5 eq). The mixture was stirred at 20° C. for 16 hr. The reaction mixture was quenched with H$_2$O (10 mL). Then the precipitate was collected. The crude product was used for the next step directly. LCMS confirmed that compound 138-2 (91 mg, 0.21 mmol, 55.8% yield) was obtained.

Step 2: 2-(5-(2-methyltetrahydrofuran-2-yl)-1,3,4-oxadiazol-2-yl)-N-(4-(trifluoromethyl)phenyl)aniline To a mixture of compound 138-2 (60 mg, 0.15 mmol, 1 eq) in DCM (1 mL) were added TosCl (33 mg, 0.17 mmol, 1.2 eq) and TEA (29 mg, 0.30 mmol, 41 uL, 2 eq). The mixture was stirred at 15° C. for 21 hr. The reaction mixture was concentrated in vacuum to give a residue and then the residue was diluted with EA (20 mL), washed with H$_2$O (5 mL) and brine (5 mL), dried over Na$_2$SO$_4$, filtered and concentrated in vacuum. The crude product was purified by prep-HPLC. LCMS and $^1$HNMR confirmed that Compound 178 (26 mg, 67 umol, 45.3% yield) was obtained. LCMS (ESI): RT=0.940 min, mass calcd. For C$_{20}$H$_{18}$F$_3$N$_3$O$_2$, 389.14 m/z found 390.0 [M+H]$^+$; H NMR (400 MHz, CDCl$_3$) δ 9.55 (s, 1H), 7.93 (dd, J=1.4, 7.9 Hz, 1H), 7.58 (d, J=8.5 Hz, 2H), 7.52 (d, J=8.3 Hz, 1H), 7.43-7.38 (m, 1H), 7.36 (d, J=8.5 Hz, 2H), 6.98 (t, J=7.7 Hz, 1H), 4.16-4.06 (m, 1H), 3.99 (q, J=7.6 Hz, 1H), 2.76 (m, 1H), 2.28-2.01 (m, 3H), 1.79 (s, 3H).

Example 139: 3-(5-(2-((4-(trifluoromethyl)phenyl) amino)phenyl)-1,3,4-oxadiazol-2-yl)butane-1,3-diol (Compound 179) and 2-(5-(2-methyloxetan-2-yl)-1, 3,4-oxadiazol-2-yl)-N-(4-(trifluoromethyl)phenyl) aniline (Compound 180)

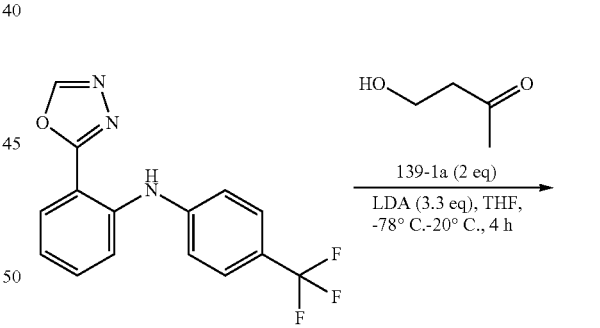

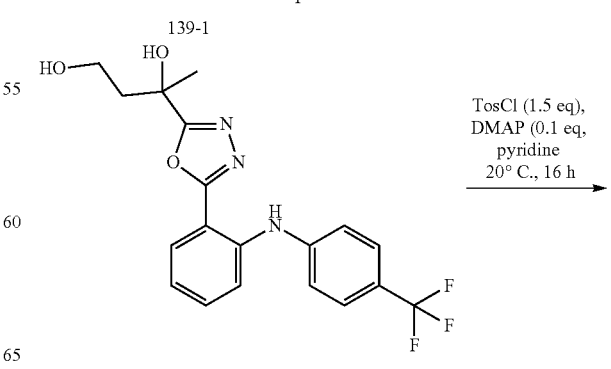

Compound 179

-continued

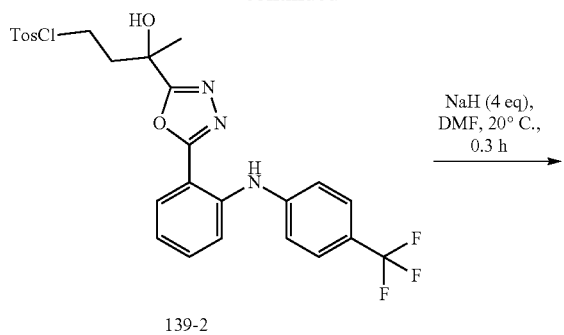

Compound 180

Step 1: 3-(5-(2-((4-(trifluoromethyl)phenyl)amino)phenyl)-1,3,4-oxadiazol-2-yl)butane-1,3-diol (Compound 179)

To a solution of 139-1 (50 mg, 0.16 mmol, 1 eq) in THF (2 mL) at −78° C. was added LDA (2 M, 0.3 mL, 3.3 eq) drop-wise, and the mixture was stirred at −78° C. for 0.5 h. And then the solution of 4-hydroxybutan-2-one (28.9 mg, 0.33 mmol, 28 uL, 2.0 eq) in THF (1 mL) was added at −78° C. into the above solution. The resulting mixture was stirred at 20° C. for 3.5 h. The reaction mixture was quenched with saturated $NH_4Cl$ solution (5 mL), then diluted with water (5 mL) and extracted with EA (10 mL*3). The combined organic layers were washed with brine (10 mL), dried over anhydrous $Na_2SO_4$, filtered and concentrated under reduced pressure to give a residue. The residue was purified by prep-TLC (PE:EA=1:1, UV) to give Compound 179 (10 mg, 24.3 umol, 14.8% yield). LCMS (ESI): RT=0.798 min, mass calc. for $C_{19}H_{18}F_3N_3O_3$ 393.13, m/z found 394.0 [M+1]$^+$; $^1$H NMR (400 MHz, CDCl$_3$) δ 9.48 (s, 1H), 7.93 (dd, J=1.3, 8.0 Hz, 1H), 7.58 (d, J=8.3 Hz, 2H), 7.51 (d, J=8.3 Hz, 1H), 7.44-7.38 (m, 1H), 7.36 (d, J=8.3 Hz, 2H), 7.02-6.94 (m, 1H), 4.53 (s, 1H), 4.09-3.93 (m, 2H), 2.41-2.25 (m, 3H), 1.78 (s, 3H).

Step 2: 3-hydroxy-3-(5-(2-((4-(trifluoromethyl)phenyl)amino)phenyl)-1,3,4-oxadiazol-2-yl)butyl 4-methylbenzenesulfonate To a solution of Compound 179 (90 mg, 0.23 mmol, 1 eq) in pyridine (2 mL) at 20° C. was added TosCl (65.4 mg, 0.34 mmol, 1.5 eq) and DMAP (2.8 mg, 23 umol, 0.1 eq). The resulting mixture was stirred at 20° C. for 16 h. The combined mixture was concentrated under reduced pressure to give a residue. The residue was purified by flash silica gel chromatography to give 139-2 (10 mg, 13 umol, 5.6% yield) was obtained. LCMS (ESI): RT=0.917 min, mass calc. for $C_{26}H_{24}F_3N_3OS$ 547.14, m/z found 570.0 [M+23]$^+$.

Step 3: 2-(5-(2-methyloxetan-2-yl)-1,3,4-oxadiazol-2-yl)-N-(4-(trifluoromethyl)phenyl)aniline (Compound 180)

To a solution of 139-2 (22 mg, 40.2 umol, 1 eq) in DMF (1 mL) at 0° C. was added NaH (6.4 mg, 0.16 mmol, 60% purity, 4 eq). The resulting mixture was stirred at 20° C. for 0.3 h. The reaction mixture was quenched with water (0.5 mL) and concentrated under reduced pressure to give a residue. The residue was purified by prep-HPLC to give Compound 180 (2.27 mg, 6.1 umol, 15.1% yield). LCMS (ESI): RT=0.897 min, mass calc. for $C_{19}H_{16}F_3N_3O_2$ 375.12, m/z found 375.9 [M+1]$^+$; $^1$H NMR (400 MHz, CDCl$_3$) δ 9.54 (s, 1H), 7.97 (dd, J=1.3, 7.9 Hz, 1H), 7.59 (d, J=8.5 Hz, 2H), 7.53 (d, J=8.4 Hz, 1H), 7.42 (t, J=8.6 Hz, 1H), 7.37 (d, J=8.5 Hz, 2H), 7.00 (t, J=7.6 Hz, 1H), 4.89-4.80 (m, 1H), 4.70 (td, J=6.1, 9.0 Hz, 1H), 3.36 (ddd, J=6.3, 8.7, 11.5 Hz, 1H), 2.97-2.87 (m, 1H), 2.00 (s, 3H).

Example 140: 2-(5-(tetrahydrofuran-2-yl)-1,3,4-oxadiazol-2-yl)-N-(4-(trifluoromethyl)phenyl)aniline (Compound 181)

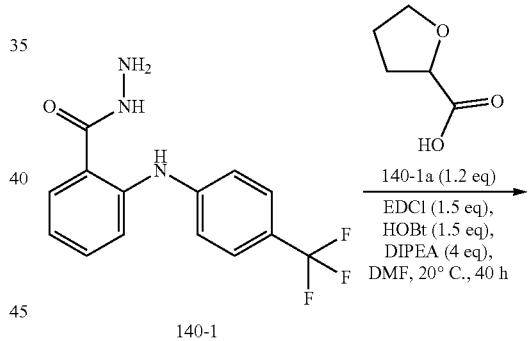

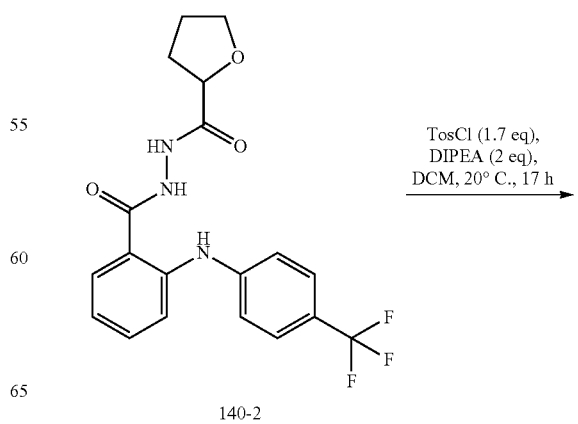

Example 141: 2-(5-(oxetan-2-yl)-1,3,4-oxadiazol-2-yl)-N-(4-(trifluoromethyl)phenyl)aniline (Compound 182)

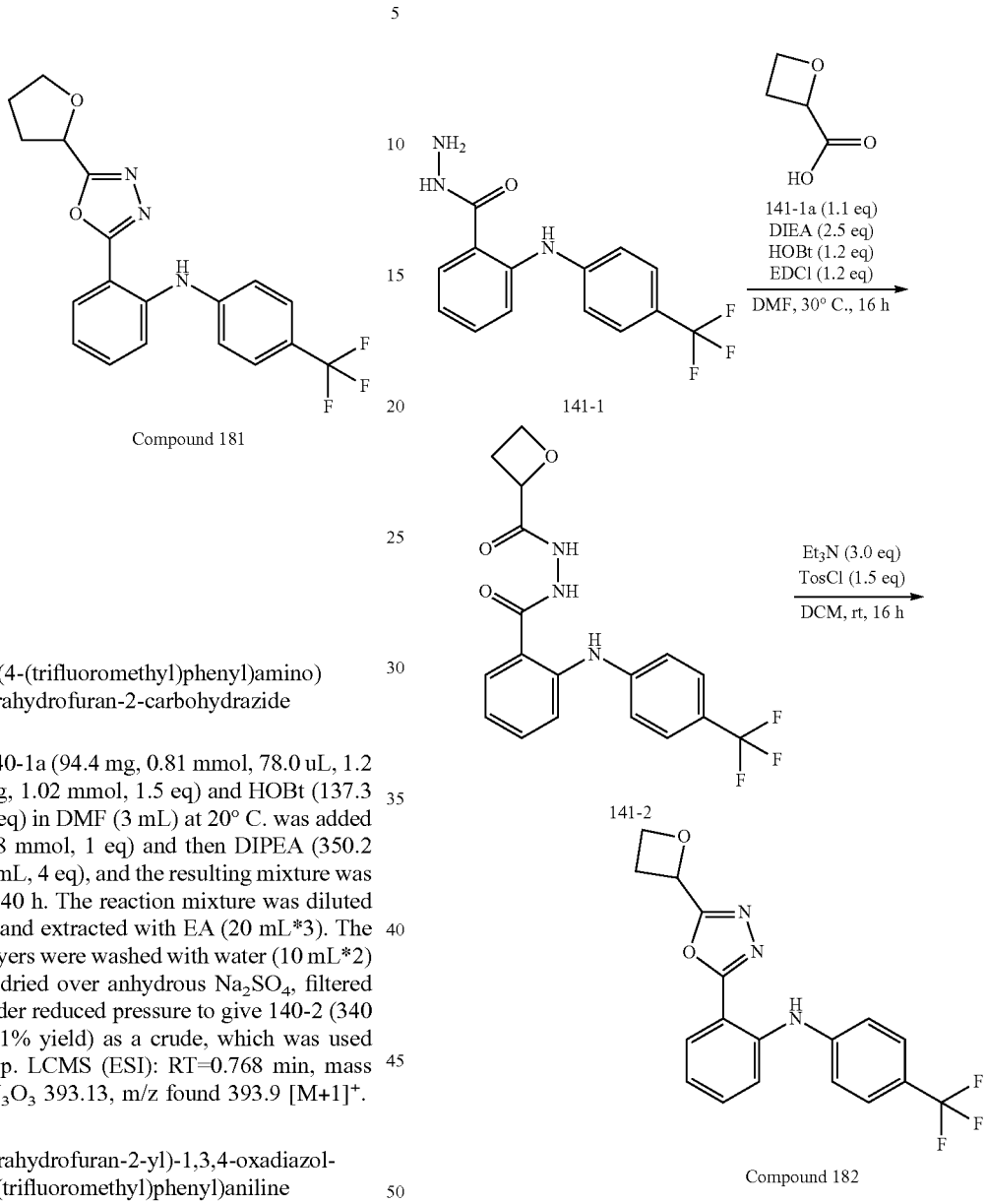

Compound 181

Step 1: N'-(2-((4-(trifluoromethyl)phenyl)amino)benzoyl)tetrahydrofuran-2-carbohydrazide To a solution of 140-1a (94.4 mg, 0.81 mmol, 78.0 uL, 1.2 eq), EDCI (194.8 mg, 1.02 mmol, 1.5 eq) and HOBt (137.3 mg, 1.02 mmol, 1.5 eq) in DMF (3 mL) at 20° C. was added 140-1 (200 mg, 0.68 mmol, 1 eq) and then DIPEA (350.2 mg, 2.71 mmol, 0.5 mL, 4 eq), and the resulting mixture was stirred at 20° C. for 40 h. The reaction mixture was diluted with water (30 mL) and extracted with EA (20 mL*3). The combined organic layers were washed with water (10 mL*2) and brine (20 mL), dried over anhydrous $Na_2SO_4$, filtered and concentrated under reduced pressure to give 140-2 (340 mg, 0.44 mmol, 66.1% yield) as a crude, which was used directly for next step. LCMS (ESI): RT=0.768 min, mass calc. for $C_{19}H_{18}F_3N_3O_3$ 393.13, m/z found 393.9 [M+1]$^+$.

Step 2: 2-(5-(tetrahydrofuran-2-yl)-1,3,4-oxadiazol-2-yl)-N-(4-(trifluoromethyl)phenyl)aniline To a solution of 140-2 (340 mg, 0.45 mmol, 1 eq) and DIPEA (115.7 mg, 0.90 mmol, 0.2 mL, 2 eq) in DCM (4 mL) at 20° C. was added TosCl (102.4 mg, 0.54 mmol, 1.2 eq), and the resulting mixture was stirred at 20° C. for 16 h. After additional 0.5 eq TosCl the reaction was further stirred for 1 h. The mixture was quenched with water (1 mL), and concentrated to give a residue. The residue was purified by prep-HPLC to give Compound 181 (104.96 mg, 0.28 mmol, 62.5% yield). LCMS (ESI): RT=0.912 min, mass calc. for $C_{19}H_{16}F_3N_3O_2$ 375.12, m/z found 375.9 [M+1]$^+$; $^1$H NMR (400 MHz, DMSO-$d_6$) δ 9.20 (s, 1H), 7.95 (d, J=8.0 Hz, 1H), 7.64 (d, J=8.5 Hz, 2H), 7.58 (d, J=3.0 Hz, 2H), 7.33 (d, J=8.5 Hz, 2H), 7.23-7.14 (m, 1H), 5.25 (dd, J=5.3, 7.8 Hz, 1H), 3.94-3.84 (m, 2H), 2.36-2.20 (m, 2H), 2.10-1.93 (m, 2H).

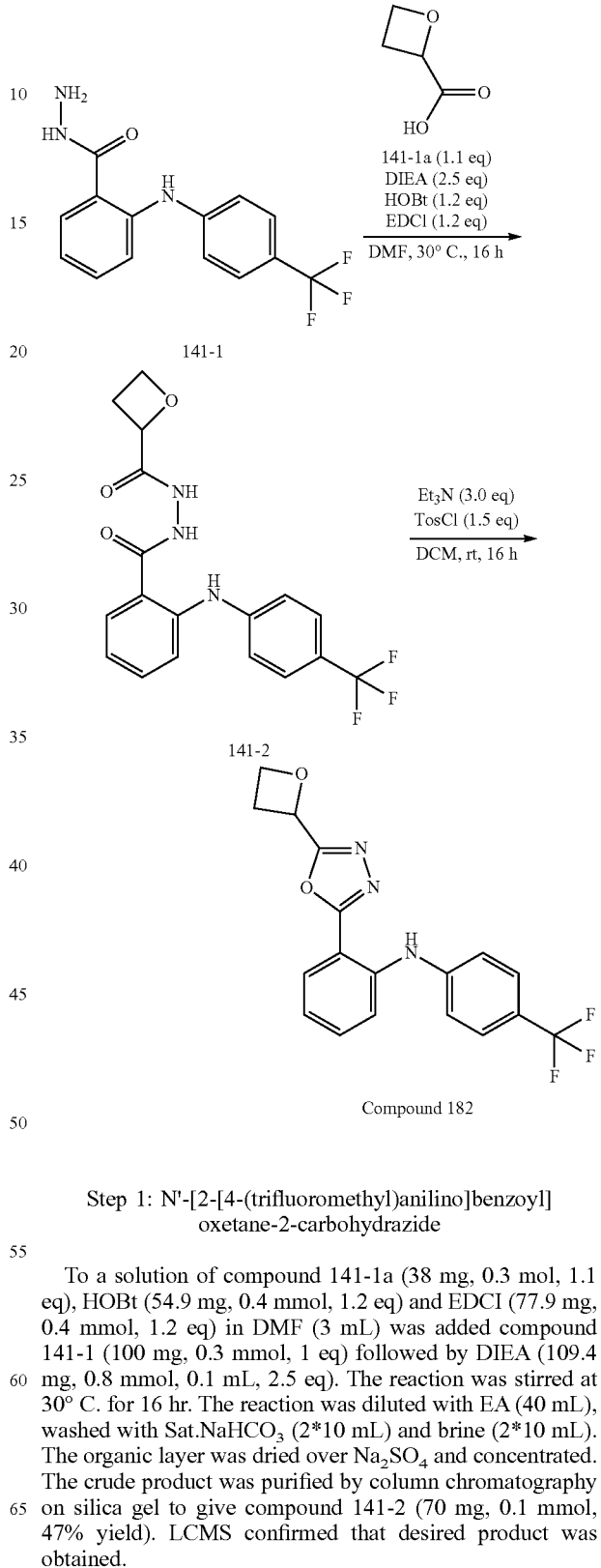

Compound 182

Step 1: N'-[2-[4-(trifluoromethyl)anilino]benzoyl]oxetane-2-carbohydrazide

To a solution of compound 141-1a (38 mg, 0.3 mol, 1.1 eq), HOBt (54.9 mg, 0.4 mmol, 1.2 eq) and EDCI (77.9 mg, 0.4 mmol, 1.2 eq) in DMF (3 mL) was added compound 141-1 (100 mg, 0.3 mmol, 1 eq) followed by DIEA (109.4 mg, 0.8 mmol, 0.1 mL, 2.5 eq). The reaction was stirred at 30° C. for 16 hr. The reaction was diluted with EA (40 mL), washed with Sat.NaHCO$_3$ (2*10 mL) and brine (2*10 mL). The organic layer was dried over Na$_2$SO$_4$ and concentrated. The crude product was purified by column chromatography on silica gel to give compound 141-2 (70 mg, 0.1 mmol, 47% yield). LCMS confirmed that desired product was obtained.

Step 2: 2-(5-(oxetan-2-yl)-1,3,4-oxadiazol-2-yl)-N-(4-(trifluoromethyl)phenyl)aniline To a solution of compound 141-2 (70 mg, 0.1 mmol, 1 eq) and Et₃N (48.7 mg, 0.4 mmol, 67 uL, 3 eq) in DCM (2 mL) was added TosCl (45.9 mg, 0.2 mmol, 1.5 eq). The reaction was stirred at 25° C. for 16 hr. The reaction was diluted with DCM (20 mL) and washed with brine (10 mL). The organic layer was dried over Na₂SO₄ and concentrated. The residue was purified by prep-HPLC to give Compound 182 (18.07 mg, 49 umol, 30% yield). LCMS (ESI): RT=0.999 min, mass calc. for $C_{18}H_{14}F_3N_3O_2$ 361.10, m/z found 362.0 [M+H]⁺; ¹H NMR (400 MHz, CDCl₃) δ 9.44 (s, 1H), 7.91 (dd, J=7.78, 1.51 Hz, 1H), 7.52 (d, J=8.28 Hz, 2H), 7.42-7.48 (m, 1H), 7.25-7.39 (m, 3H), 6.88-6.96 (m, 1H), 5.92 (t, J=7.40 Hz, 1H), 4.75-4.90 (m, 2H), 3.15 (q, J=7.78 Hz, 2H).

Example 142: 2-(5-(3-methyloxetan-3-yl)-1,3,4-oxadiazol-2-yl)-N-(4-(trifluoromethyl)phenyl)aniline (Compound 183)

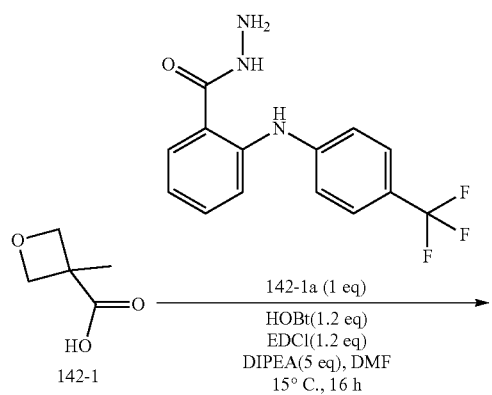

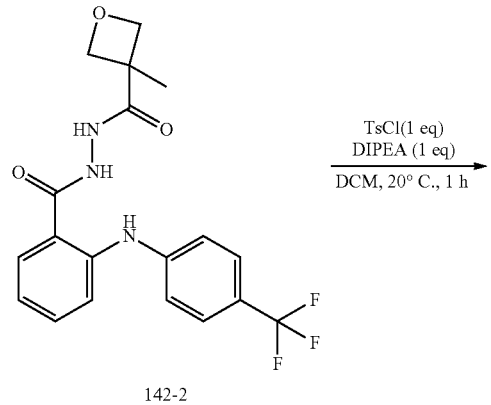

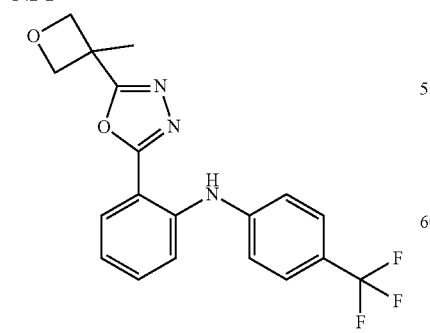

Compound 183

Step 1: 3-methyl-N'-[2-[4-(trifluoromethyl)anilino]benzoyl]oxetane-3-carbohydrazide To a mixture of 142-1a (150 mg, 0.51 mmol, 1.0 eq), compound 142-1 (70.79 mg, 0.61 mmol, 1.2 eq), HOBt (82.4 mg, 0.61 mmol, 1.2 eq) and EDCI (116.9 mg, 0.61 mmol, 1.2 eq) in DMF (3 mL) was added DIPEA (328.3 mg, 2.54 mmol, 0.5 mL, 5 eq) at 15° C. The resulting mixture was stirred at 15° C. for 16 h. The solution was diluted with H₂O (15 mL) and extracted with EA (50 mL) twice. The combined organic layer was washed with Na₂HCO₃ (30 mL), dried with Na₂SO₄, filtered and concentrated to give crude product compound 142-2 (260 mg, crude), which was used directly. LCMS (ESI): RT=0.751 min, mass calc. for $C_{19}H_{18}F_3N_3O_3$ 393.13, m/z found 393.9 [M+1]⁺.

Step 2: 2-(5-(3-methyloxetan-3-yl)-1,3,4-oxadiazol-2-yl)-N-(4-(trifluoromethyl)phenyl)aniline To a mixture of compound 142-2 (240 mg, 0.61 mmol, 1 eq) and DIPEA (78.8 mg, 0.61 mmol, 0.1 mL, 1 eq) in DCM (10 mL) was added TosCl (116.3 mg, 0.61 mmol, 1 eq) at 20° C. The resulting mixture was stirred at 20° C. for 1 h. The reaction mixture was diluted with H₂O (15 mL) and extracted with EA (50 mL*2). The combined organic layers were washed with NaHCO₃ (20 mL*2), dried over Na₂SO₄, filtered and concentrated under reduced pressure to give a residue. The residue was purified by prep-HPLC to give Compound 183 (27.31 mg, 70.6 umol, 11.6% yield). LCMS (ESI): RT=0.889 min, mass calc. for $C_{19}H_{16}F_3N_3O_2$ 375.12, m/z found 375.9 [M+1]⁺; ¹H NMR (400 MHz, CDCl₃) δ 9.22-9.57 (m, 1H), 7.84 (dd, J=7.9, 1.3 Hz, 1H), 7.49 (d, J=8.5 Hz, 2H), 7.43 (d, J=8.4 Hz, 1H), 7.29-7.35 (m, 1H), 7.27 (d, J=8.4 Hz, 2H), 5.08 (d, J=6.0 Hz, 2H), 4.60 (d, J=6.0 Hz, 2H), 1.81-1.88 (m, 3H).

Example 143: 1-(5-(2-((4-(trifluoromethyl)phenyl)amino)phenyl)-1,3,4-oxadiazol-2-yl)cyclopropane-1-carbonitrile (Compound 184)

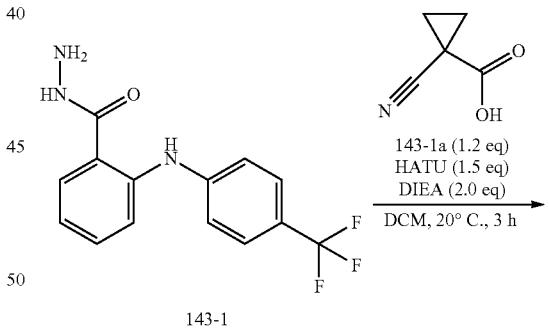

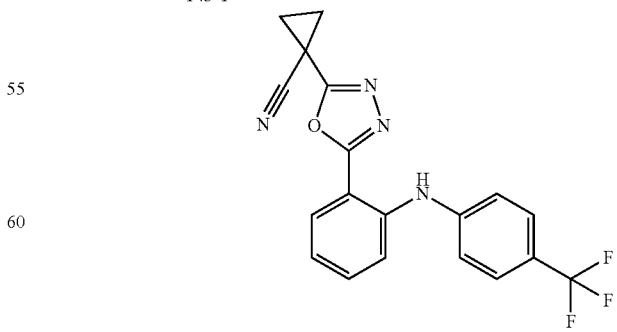

Compound 184

A solution of compound 143-1a (90.3 mg, 0.81 mmol, 1.2 eq) and HATU (386 mg, 1.02 mmol, 1.5 eq) in DCM (6 mL) was stirred at 20° C. for 30 min. Then compound 143-1 (200 mg, 0.68 mmol, 1 eq) and DIEA (175 mg, 1.35 mmol, 0.23 mL, 2 eq) were added to the mixture and stirred at 20° C. for 2.5 hr. The reaction mixture was concentrated in vacuum to give a residue. The residue was diluted with EA (30 mL), washed with H$_2$O (10 mL) and brine (10 mL), dried over Na$_2$SO$_4$, filtered and concentrated in vacuum. The crude product was purified by column chromatography. LCMS and $^1$HNMR confirmed that Compound 184 (28 mg, 74.8 umol, 11% yield) was obtained. LCMS (ESI): RT=1.022 min, mass calcd. For C$_{19}$H$_{13}$F$_3$N$_4$O, 370.10 m/z found 371.1 [M+H]$^+$. $^1$H NMR (400 MHz, CDCl$_3$) δ 9.32 (s, 1H), 7.91 (dd, J=1.3, 8.0 Hz, 1H), 7.59 (d, J=8.3 Hz, 2H), 7.53-7.48 (m, 1H), 7.46-7.39 (m, 1H), 7.35 (d, J=8.3 Hz, 2H), 7.03-6.96 (m, 1H), 2.03-1.98 (m, 4H).

Example 144: N,N-dimethyl-1-(5-(2-((4-(trifluoromethyl)phenyl)amino)phenyl)-1,3,4-oxadiazol-2-yl)cyclopropane-1-carboxamide (Compound 185)

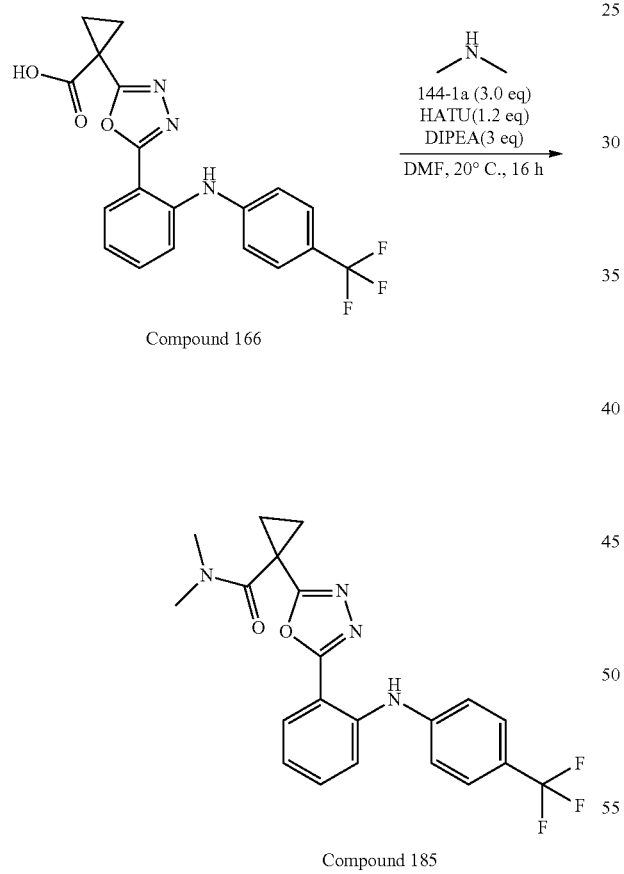

A mixture of Compound 166 (40 mg, 0.1 mmol, 1 eq), HATU (46.9 mg, 0.12 mmol, 1.2 eq), DIPEA (39.8 mg, 0.3 mmol, 0.1 mL, 3 eq) and 144-1a (2 M, 0.15 mL, 3 eq) in DMF (1 mL) was stirred at 20° C. for 15 hr under N$_2$ atmosphere. The mixture was directly purified by prep-HPLC to give Compound 185 (4.20 mg, 10.1 umol, 9.8% yield). LCMS (ESI): RT=0.856 min, mass calc. for C$_{21}$H$_{19}$F$_3$N$_4$O$_2$ 416.15, m/z found 438.9 [M+23]+; $^1$H NMR (400 MHz, DMSO-d$_6$) δ 9.14 (s, 1H), 7.89 (d, J=7.5 Hz, 1H), 7.61 (d, J=8.5 Hz, 2H), 7.54 (d, J=3.8 Hz, 2H), 7.26 (d, J=8.5 Hz, 2H), 7.12-7.20 (m, 1H), 2.90 (br d, J=14.1 Hz, 6H), 1.47-1.65 (m, 4H).

Example 145: N-methyl-1-(5-(2-((4-(trifluoromethyl)phenyl)amino)phenyl)-1,3,4-oxadiazol-2-yl)cyclopropane-1-carboxamide (Compound 186)

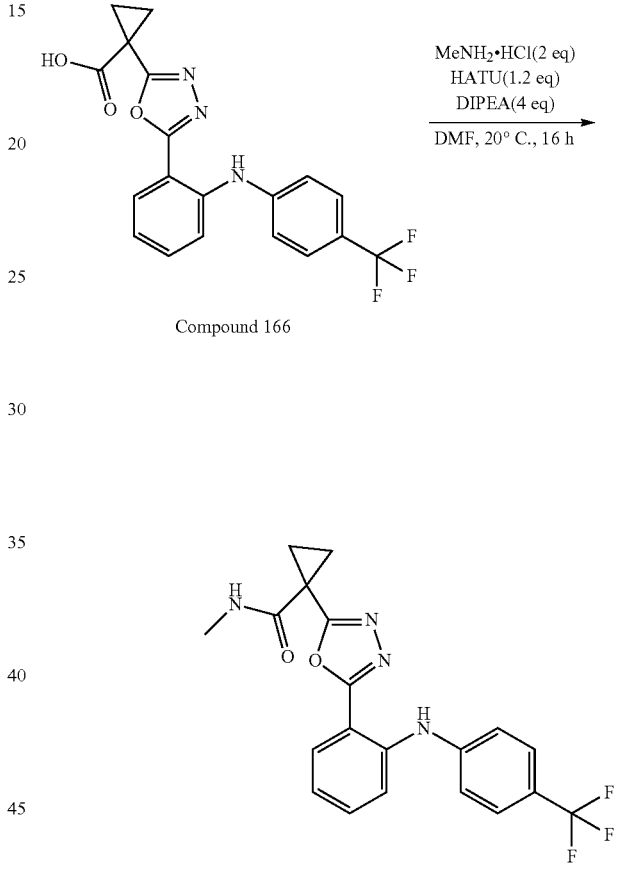

A mixture of Compound 166 (40 mg, 0.1 mmol, 1.0 eq), HATU (46.9 mg, 0.12 mmol, 1.2 eq), DIPEA (53.1 mg, 0.4 mmol, 0.1 mL, 4.0 eq) and methanamine hydrochloride (13.9 mg, 0.2 mmol, 2.0 eq) in DMF (2 mL) was degassed and purged with N$_2$ for 3 times, and then the mixture was stirred at 20° C. for 16 hr under N$_2$ atmosphere. The mixture was directly purified by prep-HPLC to give Compound 186 (18.19 mg, 0.1 mmol, 44.0% yield). LCMS (ESI): RT=0.874 min, mass calc. for C$_{20}$H$_{17}$F$_3$N$_4$O$_2$ 402.13, m/z found 402.9 [M+1]+; $^1$H NMR (400 MHz, DMSO-d$_6$) δ 9.25 (s, 1H), 8.08 (br d, J=4.4 Hz, 1H), 7.91 (d, J=7.6 Hz, 1H), 7.63 (d, J=8.5 Hz, 2H), 7.60-7.51 (m, 2H), 7.33 (d, J=8.4 Hz, 2H), 7.15 (t, J=7.3 Hz, 1H), 2.65 (d, J=4.4 Hz, 3H), 1.58-1.51 (m, 2H), 1.47-1.40 (m, 2H).

Example 146: 1-(5-(2-((4-(trifluoromethyl)phenyl)amino)phenyl)-1,3,4-oxadiazol-2-yl)cyclopropane-1-carboxamide (Compound 187)

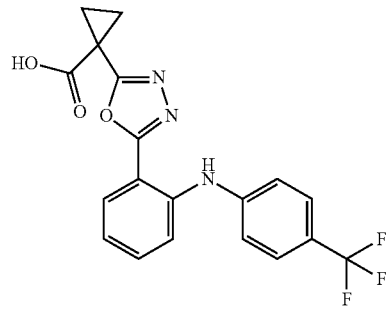

NH₄Cl (3 eq)
HATU (1.2 eq)
DIPEA (3 eq)
―――――――→
DMF, 20° C., 16 h

Compound 166

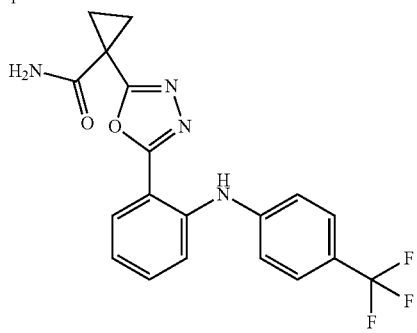

Compound 187

A mixture of Compound 166 (40 mg, 0.1 mmol, 1.0 eq), HATU (46.9 mg, 0.1 mmol, 1.2 eq), DIPEA (39.8 mg, 0.3 mmol, 0.05 mL, 3.0 eq) and NH₄Cl (16.5 mg, 0.3 mmol, 0.01 mL, 3.0 eq) in DMF (1 mL) was degassed and purged with N2 for 3 times, and then the mixture was stirred at 20° C. for 16 hr under N₂ atmosphere. The mixture was directly purified by prep-HPLC to give Compound 187 (28.61 mg, 73.7 umol, 71.7% yield). LCMS (ESI): RT=0.843 min, mass calc. for C₁₉H₁₅F₃N₄O₂ 388.11, m/z found 388.9 [M+1]+; ¹H NMR (400 MHz, DMSO-d₆) δ 9.22 (s, 1H), 7.69 (br s, 1H), 7.63 (d, J=8.5 Hz, 2H), 7.60-7.47 (m, 3H), 7.33 (d, J=8.4 Hz, 2H), 7.15 (t, J=7.2 Hz, 1H), 1.61-1.52 (m, 2H), 1.49-1.42 (m, 2H).

Example 147: N-(1-methoxypropan-2-yl)-5-(2-((4-(trifluoromethyl)phenyl)amino)phenyl)-1,3,4-oxadiazole-2-carboxamide (Compound 188)

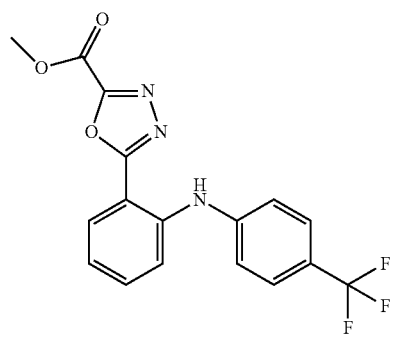

20 eq
―――――――→
MeOH, 60° C., 2 h

-continued

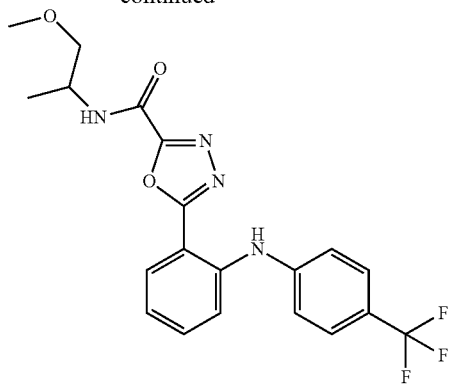

Compound 188

A mixture of compound methyl 5-(2-((4-(trifluoromethyl)phenyl)amino)phenyl)-1,3,4-oxadiazole-2-carboxylate (50 mg, 0.14 mmol, 1 eq) and 1-methoxypropan-2-amine (245.4 mg, 2.75 mmol, 0.3 mL, 20 eq) in MeOH (0.5 mL) was heated at 60° C. for 2 h. The mixture was directly purified by prep-HPLC to give Compound 188 (24.42 mg, 58.1 umol, 42.2% yield). LCMS (ESI): RT=0.880 min, mass calc. for C₂₀H₁₉F₃N₄O₃ 420.14, m/z found 442.9 [M+23]+; H NMR (400 MHz, DMSO-d₆) δ 9.18 (d, J=8.3 Hz, 1H), 9.13 (s, 1H), 8.01 (d, J=7.8 Hz, 1H), 7.64 (d, J=8.5 Hz, 2H), 7.57 (d, J=3.3 Hz, 2H), 7.37 (d, J=8.3 Hz, 2H), 7.21-7.12 (m, 1H), 4.23 (m, 1H), 3.49-3.41 (m, 1H), 3.33 (br d, J=5.5 Hz, 1H), 3.28 (s, 3H), 1.17 (d, J=6.8 Hz, 3H).

Example 148: N-(1-hydroxypropan-2-yl)-5-(2-((4-(trifluoromethyl)phenyl)amino)phenyl)-1,3,4-oxadiazole-2-carboxamide (Compound 189)

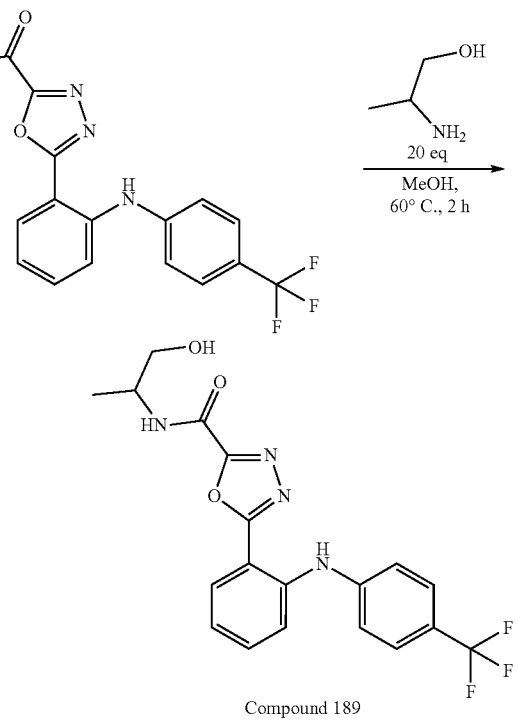

Compound 189

A mixture of methyl compound methyl 5-(2-((4-(trifluoromethyl)phenyl)amino)phenyl)-1,3,4-oxadiazole-2-carboxylate (50 mg, 0.14 mmol, 1.0 eq) and compound 1a (206.8 mg, 2.6 mmol, 0.22 mL, 20 eq) in MeOH (0.5 mL) was heated at 60° C. for 2 h. The residue was directly purified by prep-HPLC to give Compound 189 (28.39 mg, 0.07 mmol, 50.76% yield). LCMS (ESI): RT=0.809 min, mass calc. for $C_{19}H_{17}F_3N_4O_3$ 406.13, m/z found 406.9 [M+1]+; $^1$H NMR (400 MHz, DMSO-$d_6$) δ 9.14 (s, 1H), 9.01 (d, J=8.3 Hz, 1H), 8.03 (d, J=7.9 Hz, 1H), 7.65 (d, J=8.5 Hz, 2H), 7.58 (d, J=3.5 Hz, 2H), 7.38 (d, J=8.4 Hz, 2H), 7.11-7.24 (m, 1H), 4.85 (t, J=5.8 Hz, 1H), 3.84-4.26 (m, 1H), 3.41-3.53 (m, 2H), 1.17 (d, J=6.8 Hz, 3H).

Example 149: N-(2-methoxyethyl)-5-(2-((4-(trifluoromethyl)phenyl)amino)phenyl)-1,3,4-oxadiazole-2-carboxamide (Compound 190)

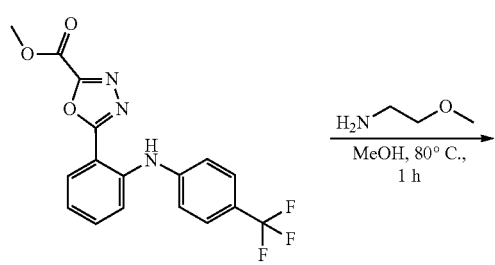

Compound 190

To a mixture of methyl 5-(2-((4-(trifluoromethyl)phenyl)amino)phenyl)-1,3,4-oxadiazole-2-carboxylate (60 mg, 0.17 mmol, 1 eq) in MeOH (3 mL) was added 2-methoxyethan-1-amine (62.0 mg, 0.82 mmol, 5 eq). The mixture was stirred at 80° C. for 1 h. The mixture was concentrated in vacuum. The residue was purified by prep-HPLC. Compound 190 (47.47 mg, 116.82 umol, 70.73% yield) was obtained, which was confirmed by LCMS and $^1$H NMR. LCMS (ESI): RT=0.844 min, mass calcd. for $C_{19}H_{17}F_3N_4O_3$ 406.13, m/z found 406.9 [M+H]$^+$. $^1$H NMR (400 MHz, DMSO-$d_6$) δ 9.38-9.33 (m, 1H), 9.13 (s, 1H), 8.01 (d, J=7.8 Hz, 1H), 7.64 (d, J=8.8 Hz, 2H), 7.59-7.54 (m, 2H), 7.37 (d, J=8.3 Hz, 2H), 7.17 (ddd, J=3.0, 5.3, 8.0 Hz, 1H), 3.52-3.44 (m, 4H), 3.27 (s, 3H).

Example 150: N-(2-hydroxyethyl)-5-(2-((4-(trifluoromethyl)phenyl)amino)phenyl)-1,3,4-oxadiazole-2-carboxamide (Compound 191)

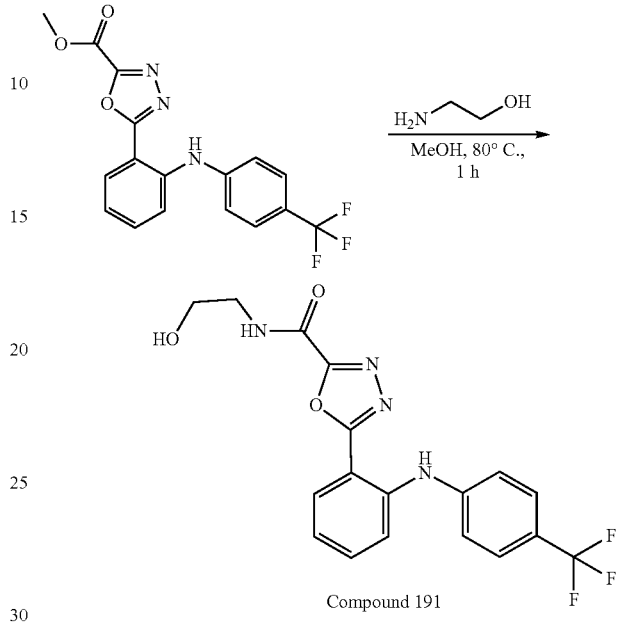

Compound 191

To a mixture of methyl 5-(2-((4-(trifluoromethyl)phenyl)amino)phenyl)-1,3,4-oxadiazole-2-carboxylate (60 mg, 0.17 mmol, 1 eq) in MeOH (3 mL) was added 2-aminoethan-1-ol (50.4 mg, 0.83 mmol, 5 eq). The mixture was stirred at 80° C. for 1 h. The mixture was concentrated in vacuum. The residue was purified by prep-HPLC. Compound 191 (32.95 mg, 83.2 umol, 50.3% yield) was obtained, which was confirmed by LCMS and $^1$H NMR. LCMS (ESI): RT=0.787 min, mass calcd. for $C_{18}H_{15}F_3N_4O_3$ 392.11, m/z found 414.9 [M+Na]$^+$. $^1$H NMR (400 MHz, DMSO-$d_6$) δ 9.26 (t, J=5.5 Hz, 1H), 9.14 (s, 1H), 8.02 (d, J=7.5 Hz, 1H), 7.65 (d, J=8.5 Hz, 2H), 7.60-7.54 (m, 2H), 7.38 (d, J=8.3 Hz, 2H), 7.17 (ddd, J=2.9, 5.3, 7.9 Hz, 1H), 4.83 (t, J=5.6 Hz, 1H), 3.54 (q, J=5.9 Hz, 2H), 3.40-3.36 (m, 2H).

Example 151: N-methoxy-N-methyl-5-(2-((4-(trifluoromethyl)phenyl)amino)phenyl)-1,3,4-oxadiazole-2-carboxamide (Compound 192)

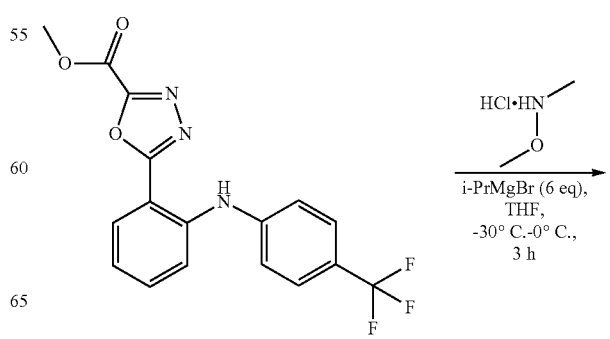

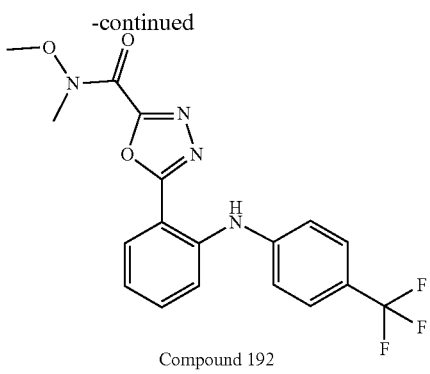

Compound 192

To a solution of methyl 5-(2-((4-(trifluoromethyl)phenyl)amino)phenyl)-1,3,4-oxadiazole-2-carboxylate (60.0 mg, 0.17 mmol, 1 eq) and N,O-dimethylhydroxylamine hydrochloride (48.3 mg, 0.50 mmol, 3 eq) in THF (2 mL) at −30° C. was added i-PrMgBr (0.5 M, 2.0 mL, 6 eq) drop-wise, and the mixture was stirred at 0° C. for 3 h. The reaction mixture was quenched with saturated NH$_4$Cl solution (3 mL) at 0° C., and then diluted with water (20 mL) and extracted with EA (10 mL*3). The combined organic layers were washed with brine (10 mL), dried over anhydrous Na$_2$SO$_4$, filtered and concentrated under reduced pressure to give a residue. The residue was purified by prep-TLC to give Compound 192 (6.84 mg, 16.8 umol, 10.2% yield). LCMS (ESI): RT=0.876 min, mass calc. for C$_{18}$H$_{15}$F$_3$N$_4$O$_3$ 392.11, m/z found 392.9 [M+1]$^+$; $^1$H NMR (400 MHz, CDCl$_3$) δ 9.46 (brs, 1H), 8.02 (d, J=7.8 Hz, 1H), 7.60 (d, J=8.3 Hz, 2H), 7.53-7.49 (m, 1H), 7.46-7.41 (m, 1H), 7.39 (d, J=8.3 Hz, 2H), 7.02-6.97 (m, 1H), 3.97 (s, 3H), 3.45 (s, 3H).

Example 152: N-methoxy-5-(2-((4-(trifluoromethyl)phenyl)amino)phenyl)-1,3,4-oxadiazole-2-carboxamide (Compound 193)

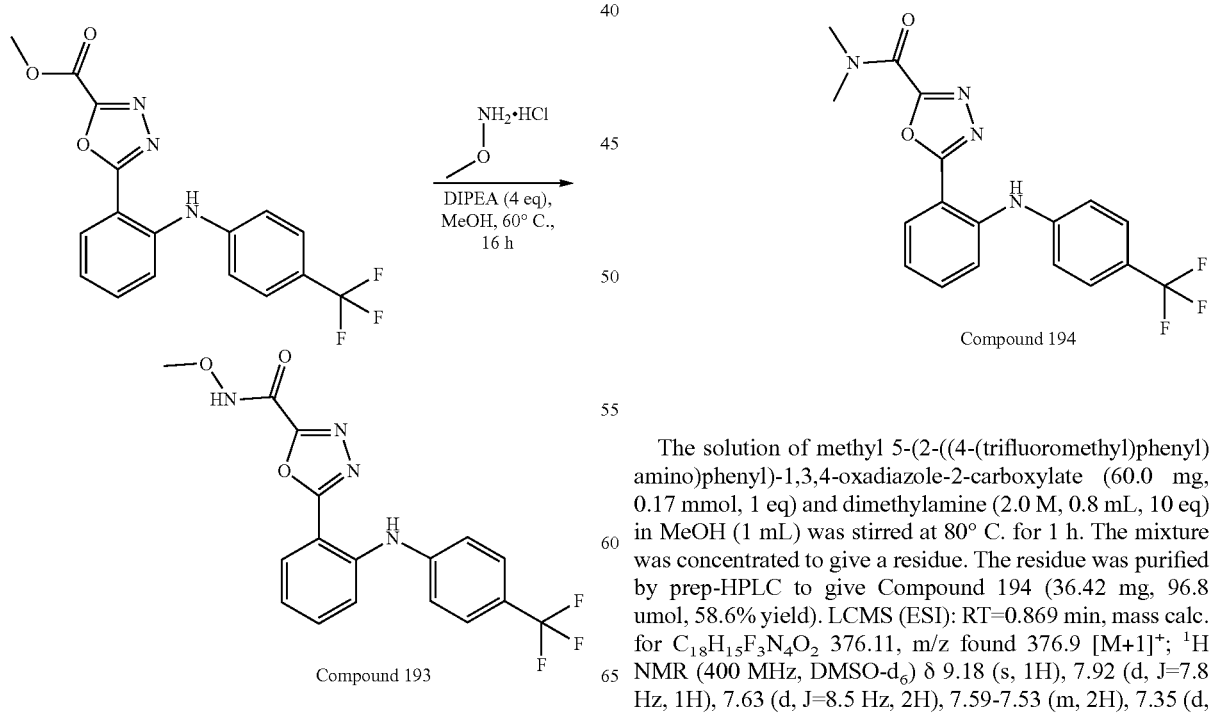

Compound 193

To a solution of methyl 5-(2-((4-(trifluoromethyl)phenyl)amino)phenyl)-1,3,4-oxadiazole-2-carboxylate (60.0 mg, 0.17 mmol, 1 eq) and O-methylhydroxylamine hydrochloride (3 eq) in MeOH (1 mL) at 20° C. was added DIPEA (85.4 mg, 0.66 mmol, 0.1 mL, 4 eq), and the mixture was stirred at 60° C. for 16 h. The mixture was concentrated to give a residue. The residue was purified by prep-HPLC to give Compound 193 (22.02 mg, 58.2 umol, 35.2% yield). LCMS (ESI): RT=0.833 min, mass calc. for C$_{17}$H$_{13}$F$_3$N$_4$O$_3$ 378.09, m/z found 378.8 [M+1]$^+$; $^1$H NMR (400 MHz, DMSO-d$_6$) δ 12.80 (brs, 1H), 9.10 (s, 1H), 7.98 (d, J=7.8 Hz, 1H), 7.64 (d, J=8.5 Hz, 2H), 7.57 (d, J=3.8 Hz, 2H), 7.36 (d, J=8.4 Hz, 2H), 7.17 (td, J=4.1, 8.0 Hz, 1H), 3.76 (s, 3H).

Example 153: N,N-dimethyl-5-(2-((4-(trifluoromethyl)phenyl)amino)phenyl)-1,3,4-oxadiazole-2-carboxamide (Compound 194)

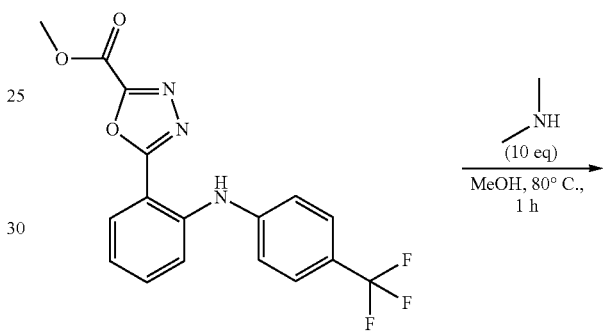

Compound 194

The solution of methyl 5-(2-((4-(trifluoromethyl)phenyl)amino)phenyl)-1,3,4-oxadiazole-2-carboxylate (60.0 mg, 0.17 mmol, 1 eq) and dimethylamine (2.0 M, 0.8 mL, 10 eq) in MeOH (1 mL) was stirred at 80° C. for 1 h. The mixture was concentrated to give a residue. The residue was purified by prep-HPLC to give Compound 194 (36.42 mg, 96.8 umol, 58.6% yield). LCMS (ESI): RT=0.869 min, mass calc. for C$_{18}$H$_{15}$F$_3$N$_4$O$_2$ 376.11, m/z found 376.9 [M+1]$^+$; $^1$H NMR (400 MHz, DMSO-d$_6$) δ 9.18 (s, 1H), 7.92 (d, J=7.8 Hz, 1H), 7.63 (d, J=8.5 Hz, 2H), 7.59-7.53 (m, 2H), 7.35 (d, J=8.5 Hz, 2H), 7.20-7.12 (m, 1H), 3.31 (s, 3H), 3.07 (s, 3H).

Example 154: N-cyclopropyl-5-(2-((4-(trifluoromethyl)phenyl)amino)phenyl)-1,3,4-oxadiazole-2-carboxamide (Compound 195)

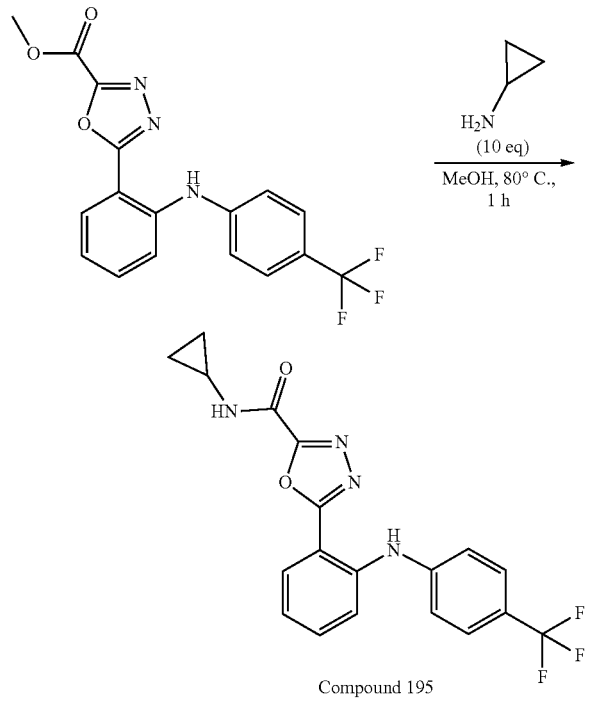

Compound 195

The solution of methyl 5-(2-((4-(trifluoromethyl)phenyl)amino)phenyl)-1,3,4-oxadiazole-2-carboxylate (60.0 mg, 0.17 mmol, 1 eq) and cyclopropylamine (94.3 mg, 1.65 mmol, 0.1 mL, 10 eq) in MeOH (1 mL) was stirred at 80° C. for 1 h. The mixture was concentrated to give a residue. The residue was purified by prep-HPLC to give Compound 195 (45.52 mg, 0.12 mmol, 71.0% yield). LCMS (ESI): RT=0.865 min, mass calc. for $C_{19}H_{15}F_3N_4O_2$ 388.11, m/z found 388.9 [M+1]$^+$; $^1$H NMR (400 MHz, DMSO-d$_6$) δ 9.42 (d, J=4.5 Hz, 1H), 9.13 (s, 1H), 8.01 (d, J=7.8 Hz, 1H), 7.65 (d, J=8.5 Hz, 2H), 7.58 (d, J=3.5 Hz, 2H), 7.37 (d, J=8.5 Hz, 2H), 7.20-7.14 (m, 1H), 2.93-2.88 (m, 1H), 0.79-0.73 (m, 2H), 0.72-0.66 (m, 2H).

Example 155: N-isopropyl-5-(2-((4-(trifluoromethyl)phenyl)amino)phenyl)-1,3,4-oxadiazole-2-carboxamide (Compound 196)

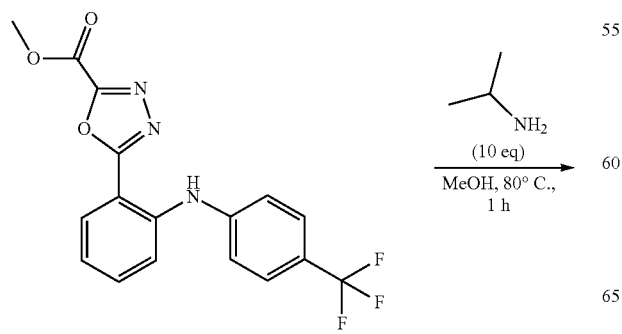

-continued

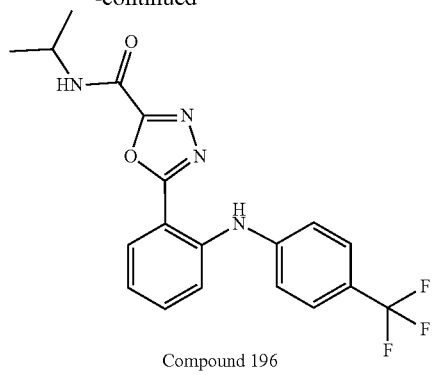

Compound 196

The solution of methyl 5-(2-((4-(trifluoromethyl)phenyl)amino)phenyl)-1,3,4-oxadiazole-2-carboxylate (60.0 mg, 0.17 mmol, 1 eq) and iso-propylamine (97.6 mg, 1.65 mmol, 0.1 mL, 10 eq) in MeOH (1 mL) was stirred at 80° C. for 1 h. The mixture was concentrated to give a residue. The residue was purified by prep-HPLC to give Compound 196 (33.33 mg, 85.4 umol, 51.7% yield). LCMS (ESI): RT=0.890 min, mass calc. for $C_{19}H_{17}F_3N_4O_2$ 390.13, m/z found 390.9 [M+1]$^+$; $^1$H NMR (400 MHz, DMSO-d$_6$) δ 9.20 (d, J=8.3 Hz, 1H), 9.14 (s, 1H), 8.01 (d, J=7.8 Hz, 1H), 7.63 (d, J=8.5 Hz, 2H), 7.59-7.53 (m, 2H), 7.36 (d, J=8.5 Hz, 2H), 7.20-7.12 (m, 1H), 4.18-4.06 (m, 1H), 1.20 (d, J=6.5 Hz, 6H).

Example 156: N-ethyl-5-(2-((4-(trifluoromethyl)phenyl)amino)phenyl)-1,3,4-oxadiazole-2-carboxamide (Compound 197)

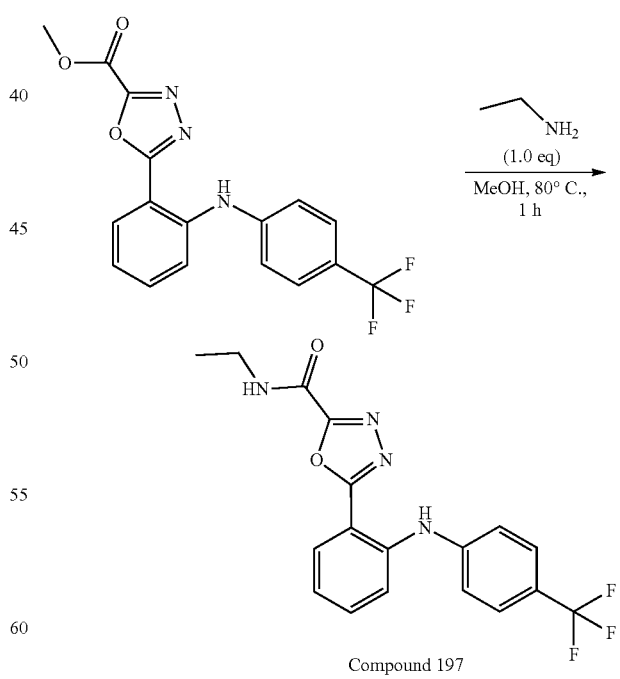

Compound 197

To a solution of methyl 5-(2-((4-(trifluoromethyl)phenyl)amino)phenyl)-1,3,4-oxadiazole-2-carboxylate (60 mg, 0.17 mmol, 1 eq) in MeOH (1 mL) was added ethylamine (7.5 mg, 165.16 umol, 10.8 uL, 1 eq). The mixture was stirred at 80° C. for 1 hr. The reaction mixture was filtered and concentrated under reduced pressure to give a residue. The residue was purified by prep-HPLC to give Compound 197 (19.53 mg, 51.38 umol, 31% yield). LCMS (ESI): RT=0.986 min, mass calc. for $C_{18}H_{15}F_3N_4O_2$ 376.11, m/z found 377.1 [M+H]$^+$; $^1$H NMR (400 MHz, DMSO-d$_6$) δ 9.37 (t, J=5.8 Hz, 1H), 9.14 (s, 1H), 8.00 (d, J=7.8 Hz, 1H), 7.64 (d, J=8.5 Hz, 2H), 7.57 (d, J=2.8 Hz, 2H), 7.37 (d, J=8.5 Hz, 2H), 7.19-7.12 (m, 1H), 3.34-3.27 (m, 2H), 1.15 (t, J=7.2 Hz, 3H).

Example 157: N-methyl-5-(2-((4-(trifluoromethyl)phenyl)amino)phenyl)-1,3,4-oxadiazole-2-carboxamide (Compound 198)

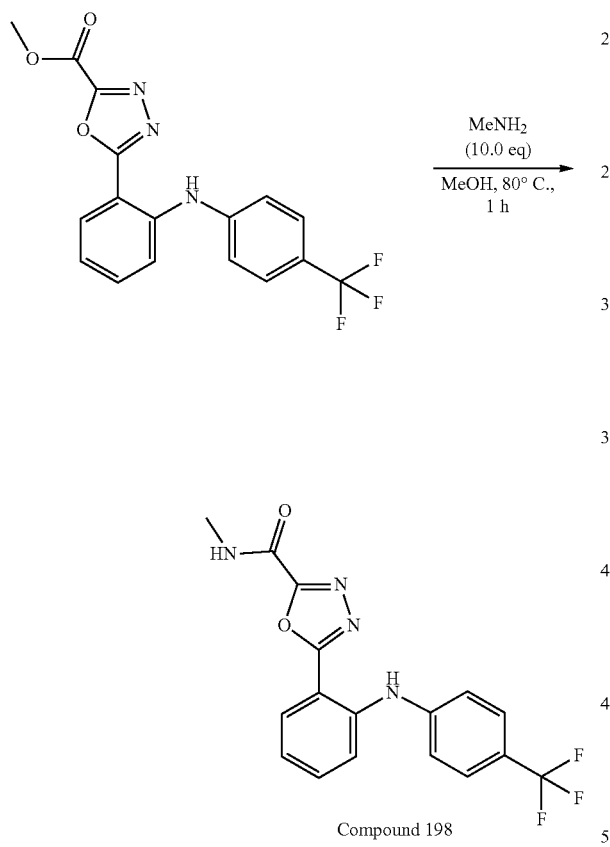

Compound 198

To a solution of methyl 5-(2-((4-(trifluoromethyl)phenyl)amino)phenyl)-1,3,4-oxadiazole-2-carboxylate (60 mg, 0.17 mmol, 1 eq) in MeOH (1 mL) was added MeNH$_2$ (2 M, 0.82 mL, 10 eq). The mixture was stirred at 80° C. for 1 hr. The reaction mixture was concentrated under reduced pressure to give a residue. The residue was purified by prep-HPLC to give Compound 198 (5.24 mg, 14.17 umol, 8% yield). LCMS (ESI): RT=0.953 min, mass calc. for $C_{17}H_{13}F_3N_4O_2$ 362.10, m/z found 363.1 [M+H]$^+$; $^1$H NMR (400 MHz, DMSO-d$_6$) δ 9.28 (d, J=4.8 Hz, 1H), 9.14 (s, 1H), 8.00 (d, J=7.8 Hz, 1H), 7.64 (d, J=8.8 Hz, 2H), 7.57 (d, J=2.5 Hz, 2H), 7.38 (d, J=8.5 Hz, 2H), 7.18-7.14 (m, 1H), 2.84 (d, J=4.8 Hz, 3H).

Example 158: 2,2-dimethyl-5-(5-(2-((4-(trifluoromethyl)phenyl)amino)phenyl)-1,3,4-oxadiazol-2-yl)-1,3-dioxan-5-ol (Compound 199)

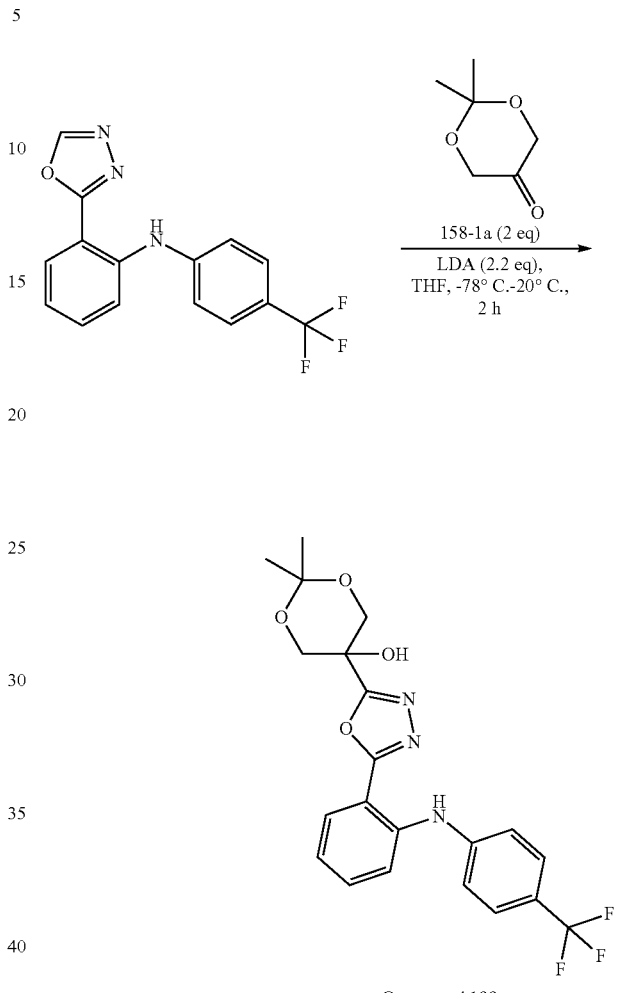

Compound 199

To a solution of 2-(1,3,4-oxadiazol-2-yl)-N-(4-(trifluoromethyl)phenyl)aniline (100 mg, 0.33 mmol, 1 eq) in THF (2 mL) at −78° C. was added LDA (2 M, 0.4 mL, 2.2 eq) drop-wise, and the mixture was stirred at −78° C. for 0.5 h. And then the solution of 158-1a (85.3 mg, 0.66 mmol, 0.2 mL, 2.0 eq) in THF (1 mL) was added at −78° C. into the above solution. The resulting mixture was stirred at 20° C. for 1.5 h. The reaction mixture was quenched with saturated NH4Cl solution (5 mL), then diluted with water (5 mL) and extracted with EA (10 mL*3). The combined organic layers were washed with brine (10 mL), dried over anhydrous Na$_2$SO$_4$, filtered and concentrated under reduced pressure to give a residue. The residue was purified by prep-TLC (PE:EA=2:1, UV) to give Compound 199 (80.13 mg, 0.18 mmol, 56.2% yield). LCMS (ESI): RT=0.861 min, mass calc. for $C_{21}H_{20}F_3N_3O_4$ 435.14, m/z found 436.0 [M+1]$^+$; $^1$H NMR (400 MHz, CDCl$_3$) δ 9.43 (s, 1H), 7.96 (dd, J=1.4, 8.0 Hz, 1H), 7.59 (d, J=8.6 Hz, 2H), 7.54-7.49 (m, 1H), 7.45-7.39 (m, 1H), 7.36 (d, J=8.5 Hz, 2H), 6.99 (t, J=7.6 Hz, 1H), 4.42 (d, J=11.9 Hz, 2H), 4.08 (d, J=11.9 Hz, 2H), 3.70 (s, 1H), 1.57-1.55 (m, 6H).

Example 159: diethyl 2-hydroxy-2-(5-(2-((4-(trifluoromethyl)phenyl)amino)phenyl)-1,3,4-oxadiazol-2-yl)malonate (Compound 200)

Example 160: 2-(5-(2-((4-(trifluoromethyl)phenyl)amino)phenyl)-1,3,4-oxadiazol-2-yl)propane-1,2,3-triol (Compound 201)

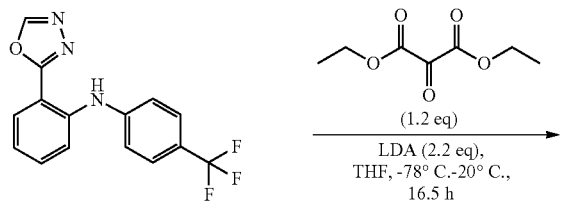

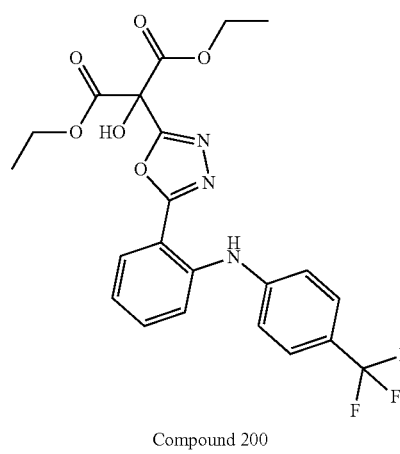

Compound 200

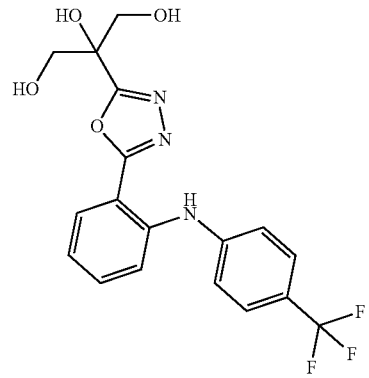

Compound 201

To a solution of 2-(1,3,4-oxadiazol-2-yl)-N-(4-(trifluoromethyl)phenyl)aniline (50 mg, 0.16 mmol, 1 eq) in THF (2 mL) at −78° C. was added LDA (2 M, 0.2 mL, 2.2 eq) drop-wise, and the mixture was stirred at −78° C. for 0.5 h. And then the above solution was added at −78° C. into the solution of diethyl 2-oxopropanedioate (34.2 mg, 0.20 mmol, 30 uL, 1.2 eq) in THF (1 mL). The resulting mixture was stirred at 20° C. for 16 h. The reaction mixture was quenched with saturated NH$_4$Cl solution (5 mL), then diluted with water (5 mL) and extracted with EA (10 mL*3). The combined organic layers were washed with brine (10 mL), dried over anhydrous Na$_2$SO$_4$, filtered and concentrated under reduced pressure to give a residue. The residue was purified by prep-TLC (PE:EA=2:1, UV) to give Compound 200 (25.0 mg, 50.1 umol, 30.6% yield). LCMS (ESI): RT=0.902 min, mass calc. for C$_{22}$H$_{20}$F$_3$N$_3$O$_6$ 479.13, m/z found 480.0 [M+1]$^+$; $^1$H NMR (400 MHz, CDCl$_3$) δ 9.44 (s, 1H), 7.93 (d, J=7.9 Hz, 1H), 7.59 (d, J=8.3 Hz, 2H), 7.54-7.49 (m, 1H), 7.45-7.39 (m, 1H), 7.36 (d, J=8.3 Hz, 2H), 6.98 (t, J=7.0 Hz, 1H), 4.53 (s, 1H), 4.46 (ttd, J=3.6, 7.1, 10.6 Hz, 4H), 1.38 (t, J=7.0 Hz, 6H).

The solution of Compound 199 (70.0 mg, 0.16 mmol, 1 eq) and pyridinium TsOH (16.2 mg, 64.3 umol, 0.4 eq) in MeOH (3 mL) was stirred at 70° C. for 2 h. The reaction mixture was concentrated under reduced pressure to give a residue. The residue was purified by prep-HPLC to give Compound 201 (32.41 mg, 82.0 umol, 51.0% yield). LCMS (ESI): RT=0.742 min, mass calc. for C$_{18}$H$_{16}$F$_3$N$_3$O$_4$ 395.11, m/z found 395.9 [M+1]$^+$; $^1$H NMR (400 MHz, DMSO-d$_6$) δ 9.60-8.75 (m, 1H), 7.95 (d, J=8.0 Hz, 1H), 7.62 (d, J=8.5 Hz, 2H), 7.57-7.48 (m, 2H), 7.37 (d, J=8.5 Hz, 2H), 7.14 (dt, J=1.9, 7.1 Hz, 1H), 3.89-3.78 (m, 4H).

Example 161: 2-hydroxy-1-(5-(2-((4-(trifluoromethyl)phenyl)amino)phenyl)-1,3,4-oxadiazol-2-yl)ethyl acetate (Compound 202) and 2-fluoro-1-(5-(2-((4-(trifluoromethyl)phenyl)amino)phenyl)-1,3,4-oxadiazol-2-yl)ethan-1-ol (Compound 203)

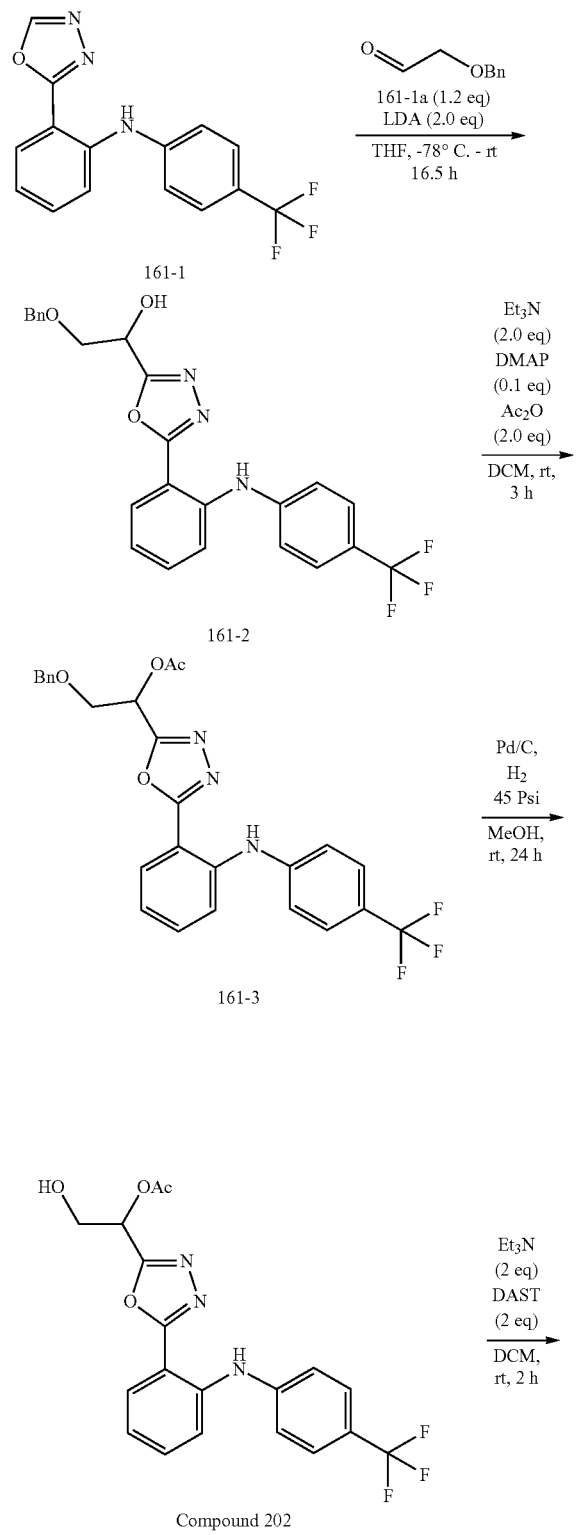

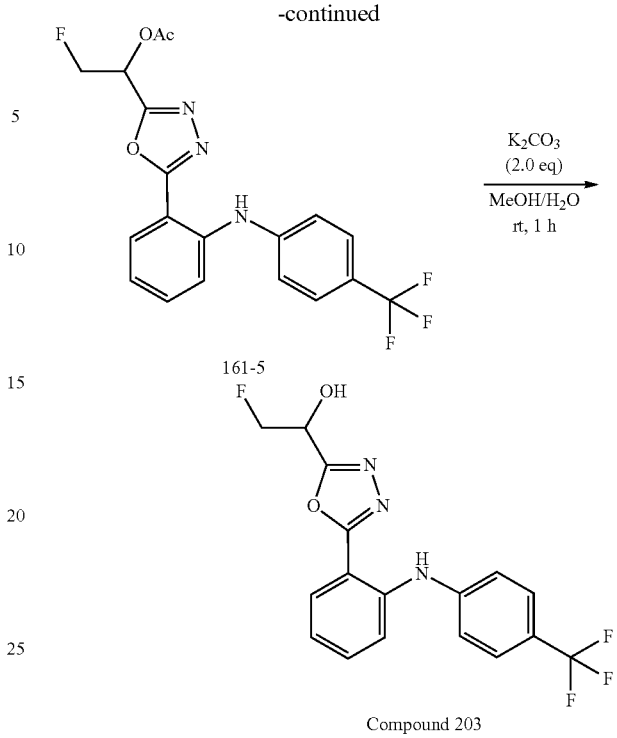

Step 1: 2-benzyloxy-1-[5-[2-[4-(trifluoromethyl)anilino]phenyl]-1,3,4-oxadiazol-2-yl]ethanol To a solution of compound 2-(1,3,4-oxadiazol-2-yl)-N-(4-(trifluoromethyl)phenyl)aniline 161-1 (0.5 g, 1.6 mmol, 1 eq) in THF (8 mL) was added LDA (2 M, 1.6 mL, 2 eq) at −78° C. The mixture was stirred at −78° C. for 30 min. Compound 161-1a (295.1 mg, 1.9 mmol, 0.3 mL, 1.2 eq) in THF (2 mL) was added drop wise to the solution and the reaction was warmed to 20° C. The reaction was stirred at 20° C. for 16 hr. The reaction was quenched by Sat.NH₄Cl (10 mL) and extracted with EA (2*30 mL). The organic layer was dried over Na₂SO₄ and concentrated. The crude product was purified by column chromatography on silica gel to give compound 161-2 (207 mg, 0.4 mmol, 27% yield).

Step 2: [2-benzyloxy-1-[5-[2-[4-(trifluoromethyl)anilino]phenyl]-1,3,4-oxadiazol-2-yl]ethyl]acetate To a solution of compound 161-2 (207 mg, 0.4 mmol, 1 eq), DMAP (5.5 mg, 45 umol, 0.1 eq) and Et₃N (91 mg, 0.9 mmol, 0.1 mL, 2 eq) in DCM (5 mL) was added Ac₂O (92.8 mg, 0.9 mmol, 85 uL, 2 eq). The reaction was stirred at 25° C. for 3 hr. The reaction was diluted with DCM (30 mL) and washed with brine (3*10 mL). The organic layer was dried over Na₂SO₄ and concentrated. The residue was purified by column chromatography on silica gel to give compound 161-3 (160 mg, 0.2 mmol, 61% yield). LCMS confirmed that desired product was obtained.

Step 3: 2-hydroxy-1-(5-(2-((4-(trifluoromethyl)phenyl)amino)phenyl)-1,3,4-oxadiazol-2-yl)ethyl acetate (Compound 202)

To a solution of compound 161-3 (130 mg, 0.2 mmol, 1 eq) in MeOH (20 mL) was added Pd/C (30 mg, 10%) under Ar. The suspension was degassed under vacuum and purged with H₂ 3 times. The mixture was stirred under H$_2$ (50 psi) at 30° C. for 16 hours. The reaction was filtered and concentrated. The residue was purified by prep-HPLC to give Compound 202 (4.63 mg, 10.7 umol, 4.1% yield) and compound 3 (20 mg, 40.2 umol, 15.4% yield). LCMS (ESI): RT=0.825 min, mass calc. for $C_{19}H_{16}F_3N_3O_4$ 407.11, m/z found 407.9 [M+H]⁺; ¹H NMR (400 MHz, CD₃OD) δ7.99 (dd, J=7.91, 1.38 Hz, 1H), 7.56-7.68 (m, 3H), 7.50 (td, J=7.91, 1.51 Hz, 1H), 7.42 (d, J=8.53 Hz, 2H), 7.04-7.12 (m, 1H), 2.02-2.10 (m, 3H).

Step 4: [2-fluoro-1-[5-[2-[4-(trifluoromethyl)an-ilino]phenyl]-1,3,4-oxadiazol-2-yl]ethyl]acetate To a solution of Compound 202 (90 mg, 0.22 mmol, 1 eq) and Et₃N (44 mg, 0.44 mmol, 61 uL, 2 eq) in DCM (3 mL) was added DAST (71 mg, 0.44 mmol, 58 uL, 2 eq). The reaction was stirred at 25° C. for 2 hr. The reaction was diluted with DCM (15 mL) and washed with water (2*5 mL). The organic layer was dried over Na₂SO₄ and concentrated. The reaction was purified by column chromatography on silica gel to give compound 161-5 (20 mg, 46 umol, 21% yield). LCMS confirmed that desired product was obtained. LCMS (ESI): RT=1.027 min, mass calc. for $C_{19}H_{15}F_4N_3O_3$ 409.10, m/z found 410.0 [M+H]⁺.

Step 5: 2-fluoro-1-(5-(2-((4-(trifluoromethyl)phenyl) amino)phenyl)-1,3,4-oxadiazol-2-yl)ethan-1-ol (Compound 203)

To a solution of compound 161-5 (10 mg, 24 umol, 1 eq) in MeOH (1 mL) was added K₂CO₃ (6.7 mg, 48 umol, 2 eq) in H₂O (0.1 mL). The reaction was stirred at 25° C. for 1 hr. The solution was concentrated. The aqueous layer was extracted with EA (2*5 mL). The organic layer was dried over Na₂SO₄ and concentrated. The residue was purified by prep-HPLC to give Compound 203 (1.3 mg, 3.4 umol, 7% yield). LCMS (ESI): RT=0.946 min, mass calc. for $C_{17}H_{13}F_4N_3O_2$ 367.09, m/z found 368.0 [M+H]⁺; ¹H NMR (400 MHz, CDCl₃) δ9.41 (s, 1H), 7.95 (dd, J=7.91, 1.38 Hz, 1H), 7.61 (d, J=8.53 Hz, 2H), 7.49-7.56 (m, 1H), 7.44 (td, J=7.84, 1.38 Hz, 1H), 7.38 (d, J=8.53 Hz, 2H), 6.96-7.05 (m, 1H), 5.72-5.92 (m, 1H), 4.23-4.43 (m, 2H), 2.48 (br s, 1H).

Example 162: 4-bromo-2-(5-cyclopropyl-1,3,4-oxa-diazol-2-yl)-N-(4-(trifluoromethyl)phenyl)aniline (Compound 204)

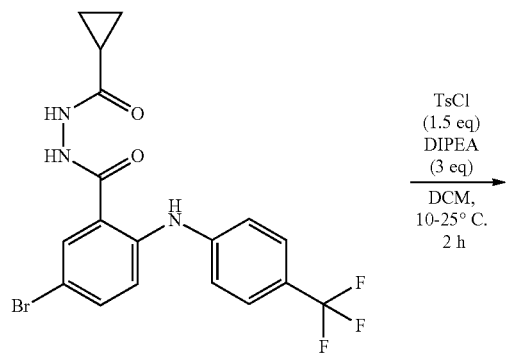

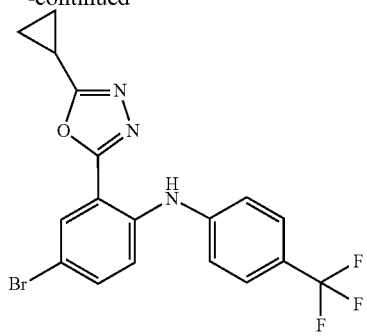

Compound 204

To a mixture of compound 5-bromo-N'-(cyclopropanecarbonyl)-2-((4-(trifluoromethyl)phenyl)amino)benzohydrazide (860 mg, 1.94 mmol, 1 eq) and DIPEA (754.0 mg, 5.83 mmol, 1.0 mL, 3 eq) in DCM (15 mL) was added TsCl (556.1 mg, 2.92 mmol, 1.5 eq) at 10° C. Then the mixture was stirred at 25° C. for 2 h. The mixture was diluted with DCM (200 mL), washed with 1 M HCl (20 mL) and brine (15 mL*2) in turns, dried with Na₂SO₄, filtered and concentrated to give a residue. The residue was purified by column chromatography to give the product (800 mg, 1.89 mmol, 97.2% yield). 50 mg of the crude product was purified by TLC to give Compound 204 (10.64 mg, 24.9 umol, 1.3% yield). MS: mass calc. for $C_{18}H_{13}BrF_3N_3O$ 423.02, m/z found 426.04 [M+1]⁺. ¹H NMR (400 MHz, DMSO-d₆) δ 9.21 (s, 1H), 8.01 (d, J=2.3 Hz, 1H), 7.69-7.59 (m, 3H), 7.48 (d, J=8.8 Hz, 1H), 7.35 (d, J=8.3 Hz, 2H), 2.38-2.27 (m, 1H), 1.21-1.09 (m, 4H).

II. Biological Evaluation

Example A1: YAP Reporter Assay

HEK293T cells stably transfected with 8XTBD luciferase reporter and pRLTK in 384-well plates were treated with the test compounds, starting from 3 μM (final concentration in assay plate), 1:3 dilution, and 10 points in quadruplicates. Post 24-hr incubation with compounds at 37° C. and 5% CO2, cells were lysed and 8XTBD-driven firefly luciferase and control TK-driven *Renilla* luciferase activities were measured using Promega Dual-Luciferase Reporter Assay System.

Reagents: The reagents used for this study are: DMEM: Invitrogen #11960077, Dual-Glo Luciferase Assay System: Promega-E2980, Puromycin Dihydrochloride: Invitrogen-A1113803, 384-well plate: PerkinElmer-6007480, L-GLU-TAMINE: Invitrogen-25030164, Hygromycin B: Invitrogen-10687010, and Penicillin-Streptomycin: Merk-TMS-AB2-C Media: The media used for this assay were: Culture Medium: DMEM+1 ug/mL puromycin+200 ug/mL hygromycin (with 10% FBS+1 mM L-glutamine); and Assay Medium: DMEM (with 10% FBS+1 mM L-glutamine+1× P/S).

Cell Plating: The appropriate media was warmed at 37° C. by water bath: Culture Medium, Assay Medium, 1*D-PBS, 0.05% trypsin-EDTA. The cells were trypsinized after removing all media, then washed with 1*sterile D-PBS and then with 2 ml 0.05% trypsin-EDTA. The cells were then incubated at RT for one minute. Then 10 ml/75 cm2 flask Assay Medium was added to each flask. Using a 10 ml pipette, the cells were then gently resuspended in the media, until the clumps completely disappeared. The cells were then transferred into 50 ml centrifuge tubes and were centrifuged at 800 rpm for 5 mins. The medium was removed and the cells were resuspended with Assay Medium. An aliquot of cells was used to count the cell density (cells/ml). The cell suspension was then diluted with Assay Medium to a concentration of 6×104 cells/ml. 50 ul cells suspension was then plated to 384-well plate (PerkinElmer-6007480), 3×103 cells/well and the cells were incubated in an incubator at 37° C., 5% CO2.

Compound Treatment: In the afternoon (incubation of the plate with 3-4 hrs), the test compounds were added by Echo, starting from 3 uM (final concentration in the assay plate), 1:3 dilution, 10 points, quadruplicates. The plate was placed at 37° C., 5% CO2 incubator for 24 hrs.

Detection: The Dual-Glo Luciferase Reagent was prepared by transferring the contents of one bottle of Dual-Glo Luciferase Buffer to one bottle of Dual-Glo Luciferase Substrate to create the Dual-Glo Luciferase Reagent. Mixing was performed by inversion until the substrate was thoroughly dissolved. After mixing, the reagent was aliquoted into 15 ml tubes. In the afternoon (24 hrs post compound treatment), the DMEM+medium in the 384 well plates were aspirated by Microplate Washer.

Measuring firefly luciferase activity: 20 ul Dual-Glo Luciferase Reagent was added to the 384-well plates. The plates were protected from light to prevent interference with the assay. The plates were shaken for 1 min followed centrifuging plates at 1000 rpm for 30 seconds. After waiting at least 10 minutes, the firefly luminescence was measured by Envision.

Measuring *Renilla* luciferase activity: 20 ul Stop-Glo Reagent was added to the 384-well plates. The plates were shaken for 1 min and then centrifuged at 1000 rpm for 30 seconds. After waiting at least 10 minutes, the *Renilla* luminescence was measured by Envision.

Compound $IC_{50}$ and maximum inhibition on the firefly luciferase and *Renilla* luciferase activities were reported separately. $IC_{50}$ for firefly luciferase activity are shown in the table below.

TABLE 2

| Compound No. | Name | Firefly Luciferase $IC_{50}$ (μM) |
|---|---|---|
| 1 | ethyl 2-(5-(2-((4-(trifluoromethyl)phenyl)amino)phenyl)-1,3,4-oxadiazol-2-yl)acetate | B |
| 2 | 2-(5-(2-((4-(trifluoromethyl)phenyl)amino)phenyl)-1,3,4-oxadiazol-2-yl)ethan-1-ol | A |
| 3 | ethyl 5-(2-((4-(trifluoromethyl)phenyl)amino)phenyl)-1,3,4-oxadiazole-2-carboxylate | A |
| 4 | 5-(2-((4-(trifluoromethyl)phenyl)amino)phenyl)-1,3,4-oxadiazol-2-amine | B |
| 5 | (5-(2-((4-(trifluoromethyl)phenyl)amino)phenyl)-1,3,4-oxadiazol-2-yl)methanol | A |
| 6 | N,N-dimethyl-5-(2-((4-(trifluoromethyl)phenyl)amino)phenyl)-1,3,4-oxadiazol-2-amine | C |
| 8 | methyl 5-(2-((4-(trifluoromethyl)phenyl)amino)phenyl)-1,3,4-oxadiazole-2-carboxylate | B |
| 9 | ethyl (5-(2-((4-(trifluoromethyl)phenyl)amino)phenyl)-1,3,4-oxadiazol-2-yl)glycinate | C |
| 10 | 2-((5-(2-((4-(trifluoromethyl)phenyl)amino)phenyl)-1,3,4-oxadiazol-2-yl)amino)ethan-1-ol | B |
| 11 | ethyl N-methyl-N-(5-(2-((4-(trifluoromethyl)phenyl)amino)phenyl)-1,3,4-oxadiazol-2-yl)glycinate | B |
| 12 | N-methyl-5-(2-((4-(trifluoromethyl)phenyl)amino)phenyl)-1,3,4-oxadiazol-2-amine | B |
| 13 | 5-(5-(2-((4-(trifluoromethyl)phenyl)amino)phenyl)-1,3,4-oxadiazol-2-yl)oxazolidin-2-one | B |
| 14 | N-hydroxy-5-(2-((4-(trifluoromethyl)phenyl)amino)phenyl)-1,3,4-oxadiazole-2-carboxamide | A |
| 15 | 5-(2-((4-(trifluoromethyl)phenyl)amino)phenyl)-1,3,4-oxadiazole-2-carboxamide | A |
| 16 | 3-tosyl-4-(5-(2-((4-(trifluoromethyl)phenyl)amino)phenyl)-1,3,4-oxadiazol-2-yl)oxazolidin-2-one | B |
| 17 | 4-(5-(2-((4-(trifluoromethyl)phenyl)amino)phenyl)-1,3,4-oxadiazol-2-yl)oxazolidin-2-one | A |
| 19 | 2-(methyl(5-(2-((4-(trifluoromethyl)phenyl)amino)phenyl)-1,3,4-oxadiazol-2-yl)amino)ethan-1-ol | B |
| 20 | 2-(1,3,4-oxadiazol-2-yl)-N-[4-(trifluoromethyl)phenyl]aniline | B |
| 22 | 5-[2-[4-(trifluoromethyl)anilino]phenyl]-1,3,4-oxadiazole-2-carbonitrile | A |
| 24 | 2-((5-(2-((4-(trifluoromethyl)phenyl)amino)phenyl)-1,3,4-oxadiazol-2-yl)amino)acetamide | B |
| 25 | 1-[5-[2-[4-(trifluoromethyl)anilino]phenyl]-1,3,4-oxadiazol-2-yl]ethane-1,2-diol | A |
| 26 | 2-oxo-4-(5-(2-((4-(trifluoromethyl)phenyl)amino)phenyl)-1,3,4-oxadiazol-2-yl)oxazolidine-3-carboxylate | A |
| 28 | 2-[5-(aminomethyl)-1,3,4-oxadiazol-2-yl]-N-[4-(trifluoromethyl)phenyl]aniline | B |
| 29 | 4-[5-[2-[4-(trifluoromethyl)anilino]phenyl]-1,3,4-oxadiazol-2-yl]-1,3-dioxolan-2-one | A |
| 30 | 2-amino-2-(5-(2-((4-(trifluoromethyl)phenyl)amino)phenyl)-1,3,4-oxadiazol-2-yl)ethanol | B |

TABLE 2-continued

| Compound No. | Name | Firefly Luciferase IC$_{50}$ (μM) |
|---|---|---|
| 31 | 2-[5-(azidomethyl)-1,3,4-oxadiazol-2-yl]-N-[4-(trifluoromethyl)phenyl]aniline | B |
| 32 | N-(2-hydroxyethyl)-N-(5-(2-((4-(trifluoromethyl)phenyl)amino)phenyl)-1,3,4-oxadiazol-2-yl)methanesulfonamide | B |
| 34 | 1-(5-(2-((4-(trifluoromethyl)phenyl)amino)phenyl)-1,3,4-oxadiazol-2-yl)imidazolidin-2-one | B |
| 35 | 2-(5-(5-methyloxazol-4-yl)-1,3,4-oxadiazol-2-yl)-N-(4-(trifluoromethyl)phenyl)aniline | B |
| 36 | 2-(5-(oxazol-4-yl)-1,3,4-oxadiazol-2-yl)-N-(4-(trifluoromethyl)phenyl)aniline | B |
| 37 | 2-(5-(oxazol-5-yl)-1,3,4-oxadiazol-2-yl)-N-(4-(trifluoromethyl)phenyl)aniline | B |
| 38 | N-(5-(2-((4-(trifluoromethyl)phenyl)amino)phenyl)-1,3,4-oxadiazol-2-yl)methanesulfonamide | B |
| 40 | 2-(5-(5-methylisoxazol-4-yl)-1,3,4-oxadiazol-2-yl)-N-(4-(trifluoromethyl)phenyl)aniline | B |
| 41 | 1-(5-(2-((4-(trifluoromethyl)phenyl)amino)phenyl)-1,3,4-oxadiazol-2-yl)ethanol | A |
| 42 | 2-(5-(2-((4-(trifluoromethyl)phenyl)amino)phenyl)-1,3,4-oxadiazol-2-yl)propan-2-ol | A |
| 44 | 1-(5-(2-((4-(trifluoromethyl)phenyl)amino)phenyl)-1,3,4-oxadiazol-2-yl)cyclopropanol | A |
| 45 | 2-methyl-2-(5-(2-((4-(trifluoromethyl)phenyl)amino)phenyl)-1,3,4-oxadiazol-2-yl)propan-1-ol | A |
| 46 | 2,2,2-trifluoro-1-(5-(2-((4-(trifluoromethyl)phenyl)amino)phenyl)-1,3,4-oxadiazol-2-yl)ethyl 4-methylbenzenesulfonate | B |
| 47 | (1-(5-(2-((4-(trifluoromethyl)phenyl)amino)phenyl)-1,3,4-oxadiazol-2-yl)cyclopropyl)methanol | A |
| 48 | 2-[5-(2H-tetrazol-5-yl)-1,3,4-oxadiazol-2-yl]-N-[4-(trifluoromethyl)phenyl]aniline | C |
| 49 | cyclopropyl(5-(2-((4-(trifluoromethyl)phenyl)amino)phenyl)-1,3,4-oxadiazol-2-yl)methanol | A |
| 50 | 3-[5-[2-[4-(trifluoromethyl)anilino]phenyl]-1,3,4-oxadiazol-2-yl]-4H-1,2,4-oxadiazol-5-one | C |
| 51 | 2,2,2-trifluoro-1-(5-(2-((4-(trifluoromethyl)phenyl)amino)phenyl)-1,3,4-oxadiazol-2-yl)ethanol | A |
| 52 | 1-(5-(2-((4-(trifluoromethyl)phenyl)amino)phenyl)-1,3,4-oxadiazol-2-yl)cyclopentanol | A |
| 53 | 1-(5-(2-((4-(trifluoromethyl)phenyl)amino)phenyl)-1,3,4-oxadiazol-2-yl)cyclopropyl 4-methylbenzenesulfonate | B |
| 54 | 1-(5-(2-((4-(trifluoromethyl)phenyl)amino)phenyl)-1,3,4-oxadiazol-2-yl)cyclobutanol | A |
| 55 | 3-(5-(2-((4-(trifluoromethyl)phenyl)amino)phenyl)-1,3,4-oxadiazol-2-yl)oxetan-3-ol | A |
| 56 | 3-(5-(2-((4-(trifluoromethyl)phenyl)amino)phenyl)-1,3,4-oxadiazol-2-yl)tetrahydrofuran-3-ol | A |
| 57 | (1-(5-(2-((4-(trifluoromethyl)phenyl)amino)phenyl)-1,3,4-oxadiazol-2-yl)cyclopropyl)carbamate | B |
| 58 | 2-(5-(1-aminocyclopropyl)-1,3,4-oxadiazol-2-yl)-N-(4-(trifluoromethyl)phenyl)aniline | B |
| 59 | N-(1-(5-(2-((4-(trifluoromethyl)phenyl)amino)phenyl)-1,3,4-oxadiazol-2-yl)cyclopropyl)acetamide | B |
| 60 | 2,2-difluoro-1-(5-(2-((4-(trifluoromethyl)phenyl)amino)phenyl)-1,3,4-oxadiazol-2-yl)ethanol | A |
| 62 | 1-(1-(5-(2-((4-(trifluoromethyl)phenyl)amino)phenyl)-1,3,4-oxadiazol-2-yl)cyclopropyl)urea | B |
| 63 | 2-(5-(1-fluorocyclopropyl)-1,3,4-oxadiazol-2-yl)-N-(4-(trifluoromethyl)phenyl)aniline | C |
| 66 | 2-[5-(1-methylsulfonylcyclopropyl)-1,3,4-oxadiazol-2-yl]-N-[4-(trifluoromethyl)phenyl]aniline | A |
| 67 | 2-(5-(1-methoxycyclopropyl)-1,3,4-oxadiazol-2-yl)-N-(4-(trifluoromethyl)phenyl)aniline | A |
| 68 | 2-(5-(2-methylbut-3-yn-2-yl)-1,3,4-oxadiazol-2-yl)-N-(4-(trifluoromethyl)phenyl)aniline | A |
| 69 | 2-(5-(but-3-yn-2-yloxy)-1,3,4-oxadiazol-2-yl)-N-(4-(trifluoromethyl)phenyl)aniline | A |
| 70 | 2-(5-(but-2-yn-1-yloxy)-1,3,4-oxadiazol-2-yl)-N-(4-(trifluoromethyl)phenyl)aniline | C |
| 71 | 2-(5-(methylsulfonyl)-1,3,4-oxadiazol-2-yl)-N-(4-(trifluoromethyl)phenyl)aniline | B |
| 72 | 2-(5-(methylthio)-1,3,4-oxadiazol-2-yl)-N-(4-(trifluoromethyl)phenyl)aniline | B |
| 73 | 2-(5-methoxy-1,3,4-oxadiazol-2-yl)-N-(4-(trifluoromethyl)phenyl)aniline | A |

TABLE 2-continued

| Compound No. | Name | Firefly Luciferase IC$_{50}$ (μM) |
|---|---|---|
| 75 | (S)-3-methyl-3-(5-(2-((4-(trifluoromethyl)phenyl)amino)phenyl)-1,3,4-oxadiazol-2-yl)pyrrolidin-2-one | A |
| 76 | (R)-3-methyl-3-(5-(2-((4-(trifluoromethyl)phenyl)amino)phenyl)-1,3,4-oxadiazol-2-yl)pyrrolidin-2-one | A |
| 77 | (R)-4-(5-(2-((4-(trifluoromethyl)phenyl)amino)phenyl)-1,3,4-oxadiazol-2-yl)oxazolidin-2-one | A |
| 78 | (S)-4-(5-(2-((4-(trifluoromethyl)phenyl)amino)phenyl)-1,3,4-oxadiazol-2-yl)oxazolidin-2-one | B |
| 79 | 1-chloro-3-(5-(2-((4-(trifluoromethyl)phenyl)amino)phenyl)-1,3,4-oxadiazol-2-yl)propan-2-ol | A |
| 80 | 3-chloro-1-(5-(2-((4-(trifluoromethyl)phenyl)amino)phenyl)-1,3,4-oxadiazol-2-yl)propan-1-ol | A |
| 81 | 2-chloro-1-(5-(2-((4-(trifluoromethyl)phenyl)amino)phenyl)-1,3,4-oxadiazol-2-yl)ethan-1-ol | A |
| 82 | (E)-2-(5-((3-bromoallyl)oxy)-1,3,4-oxadiazol-2-yl)-N-(4-(trifluoromethyl)phenyl)aniline | B |
| 83 | 2-(5-(prop-2-yn-1-yloxy)-1,3,4-oxadiazol-2-yl)-N-(4-(trifluoromethyl)phenyl)aniline | A |
| 84 | 2-(5-(allyloxy)-1,3,4-oxadiazol-2-yl)-N-(4-(trifluoromethyl)phenyl)aniline | B |
| 85 | 1-(5-(2-((4-(trifluoromethyl)phenyl)amino)phenyl)-1,3,4-oxadiazol-2-yl)ethan-1-one | A |
| 86 | 2-(5-(2-methyl-1,3-dioxolan-2-yl)-1,3,4-oxadiazol-2-yl)-N-(4-(trifluoromethyl)phenyl)aniline | A |
| 87 | N-methoxy-N,2-dimethyl-2-(5-(2-((4-(trifluoromethyl)phenyl)amino)phenyl)-1,3,4-oxadiazol-2-yl)propanamide | A |
| 88 | 1-((5-(2-((4-(trifluoromethyl)phenyl)amino)phenyl)-1,3,4-oxadiazol-2-yl)methyl)cyclopropane-1-carbonitrile | B |
| 89 | 2,2-dimethyl-3-(5-(2-((4-(trifluoromethyl)phenyl)amino)phenyl)-1,3,4-oxadiazol-2-yl)propanenitrile | B |
| 90 | 2-(5-ethyl-1,3,4-oxadiazol-2-yl)-N-(4-(trifluoromethyl)phenyl)aniline | B |
| 91 | 2-(5-(2-(isopropylamino)ethyl)-1,3,4-oxadiazol-2-yl)-N-(4-(trifluoromethyl)phenyl)aniline | C |
| 93 | N-isopropyl-N-(2-(5-(2-((4-(trifluoromethyl)phenyl)amino)phenyl)-1,3,4-oxadiazol-2-yl)ethyl)cyanamide | B |
| 94 | 2-(5-(2-(ethylamino)ethyl)-1,3,4-oxadiazol-2-yl)-N-(4-(trifluoromethyl)phenyl)aniline | C |
| 96 | N-ethyl-N-(2-(5-(2-((4-(trifluoromethyl)phenyl)amino)phenyl)-1,3,4-oxadiazol-2-yl)ethyl)cyanamide | A |
| 97 | 2-(5-((isopropylamino)methyl)-1,3,4-oxadiazol-2-yl)-N-(4-(trifluoromethyl)phenyl)aniline | C |
| 99 | N-isopropyl-N-((5-(2-((4-(trifluoromethyl)phenyl)amino)phenyl)-1,3,4-oxadiazol-2-yl)methyl)cyanamide | B |
| 100 | 2-(5-((ethylamino)methyl)-1,3,4-oxadiazol-2-yl)-N-(4-(trifluoromethyl)phenyl)aniline | B |
| 102 | N-ethyl-N-((5-(2-((4-(trifluoromethyl)phenyl)amino)phenyl)-1,3,4-oxadiazol-2-yl)methyl)cyanamide | A |
| 103 | 2-methyl-2-(5-(2-((4-(trifluoromethyl)phenyl)amino)phenyl)-1,3,4-oxadiazol-2-yl)propanoic acid | B |
| 104 | 2-(5-(2-aminoethyl)-1,3,4-oxadiazol-2-yl)-N-(4-(trifluoromethyl)phenyl)aniline | C |
| 108 | N-((5-(2-((4-(trifluoromethyl)phenyl)amino)phenyl)-1,3,4-oxadiazol-2-yl)methyl)acrylamide | A |
| 110 | N-(cyanomethyl)-2-methyl-2-(5-(2-((4-(trifluoromethyl)phenyl)amino)phenyl)-1,3,4-oxadiazol-2-yl)propanamide | C |
| 112 | 2-methyl-N-(prop-2-yn-1-yl)-2-(5-(2-((4-(trifluoromethyl)phenyl)amino)phenyl)-1,3,4-oxadiazol-2-yl)propanamide | C |
| 113 | N-(2-cyanoethyl)-5-(2-((4-(trifluoromethyl)phenyl)amino)phenyl)-1,3,4-oxadiazole-2-carboxamide | A |
| 114 | N-(cyanomethyl)-5-(2-((4-(trifluoromethyl)phenyl)amino)phenyl)-1,3,4-oxadiazole-2-carboxamide | A |
| 115 | N-(but-3-yn-1-yl)-5-(2-((4-(trifluoromethyl)phenyl)amino)phenyl)-1,3,4-oxadiazole-2-carboxamide | A |
| 116 | N-(prop-2-yn-1-yl)-5-(2-((4-(trifluoromethyl)phenyl)amino)phenyl)-1,3,4-oxadiazole-2-carboxamide | A |
| 117 | (E)-2-(5-(prop-1-en-1-yl)-1,3,4-oxadiazol-2-yl)-N-(4-(trifluoromethyl)phenyl)aniline | B |
| 119 | 2-(5-(2-((4-(trifluoromethyl)phenyl)amino)phenyl)-1,3,4-oxadiazol-2-yl)acetic acid | B |
| 120 | 1-(5-(2-((4-(trifluoromethyl)phenyl)amino)phenyl)-1,3,4-oxadiazol-2-yl)but-3-yn-2-ol | A |
| 121 | 2-bromo-1-(5-(2-((4-(trifluoromethyl)phenyl)amino)phenyl)-1,3,4-oxadiazol-2-yl)ethan-1-ol | A |

TABLE 2-continued

| Compound No. | Name | Firefly Luciferase IC$_{50}$ (μM) |
|---|---|---|
| 122 | 2-(5-(oxiran-2-yl)-1,3,4-oxadiazol-2-yl)-N-(4-(trifluoromethyl)phenyl)aniline | A |
| 123 | N-(4-(trifluoromethyl)phenyl)-2-(5-vinyl-1,3,4-oxadiazol-2-yl)aniline | A |
| 124 | 1-(5-(2-((4-(trifluoromethyl)phenyl)amino)phenyl)-1,3,4-oxadiazol-2-yl)but-3-yn-1-ol | A |
| 126 | 3-(5-(2-((4-(trifluoromethyl)phenyl)amino)phenyl)-1,3,4-oxadiazol-2-yl)propanenitrile | B |
| 129 | N-methyl-N-(3-(5-(2-((4-(trifluoromethyl)phenyl)amino)phenyl)-1,3,4-oxadiazol-2-yl)propyl)cyanamide | A |
| 130 | 3-hydroxy-3-(5-(2-((4-(trifluoromethyl)phenyl)amino)phenyl)-1,3,4-oxadiazol-2-yl)butanenitrile | A |
| 132 | 2-(5-(2-methyloxiran-2-yl)-1,3,4-oxadiazol-2-yl)-N-(4-(trifluoromethyl)phenyl)aniline | A |
| 133 | 2-(5-(prop-1-en-2-yl)-1,3,4-oxadiazol-2-yl)-N-(4-(trifluoromethyl)phenyl)aniline | B |
| 134 | 1-amino-2-(5-(2-((4-(trifluoromethyl)phenyl)amino)phenyl)-1,3,4-oxadiazol-2-yl)propan-2-ol | B |
| 135 | 2-(5-(2-((4-(trifluoromethyl)phenyl)amino)phenyl)-1,3,4-oxadiazol-2-yl)butan-2-ol | A |
| 136 | 2-(5-((1-aminocyclopropyl)methyl)-1,3,4-oxadiazol-2-yl)-N-(4-(trifluoromethyl)phenyl)aniline | B |
| 137 | 2-(5-(2-((4-(trifluoromethyl)phenyl)amino)phenyl)-1,3,4-oxadiazol-2-yl)acetonitrile | B |
| 140 | N-methyl-N-((1-(5-(2-((4-(trifluoromethyl)phenyl)amino)phenyl)-1,3,4-oxadiazol-2-yl)cyclopropyl)methyl)cyanamide | A |
| 143 | N-methyl-N-(2-methyl-1-(5-(2-((4-(trifluoromethyl)phenyl)amino)phenyl)-1,3,4-oxadiazol-2-yl)propan-2-yl)cyanamide | C |
| 144 | 2-(5-(2-methyl-1-(methylamino)propan-2-yl)-1,3,4-oxadiazol-2-yl)-N-(4-(trifluoromethyl)phenyl)aniline | B |
| 146 | N-methyl-N-(2-methyl-2-(5-(2-((4-(trifluoromethyl)phenyl)amino)phenyl)-1,3,4-oxadiazol-2-yl)propyl)cyanamide | A |
| 147 | 2-(5-(2-(methylamino)propyl)-1,3,4-oxadiazol-2-yl)-N-(4-(trifluoromethyl)phenyl)aniline | C |
| 149 | N-methyl-N-(1-(5-(2-((4-(trifluoromethyl)phenyl)amino)phenyl)-1,3,4-oxadiazol-2-yl)propan-2-yl)cyanamide | A |
| 150 | 2-(5-(1-(methylamino)propan-2-yl)-1,3,4-oxadiazol-2-yl)-N-(4-(trifluoromethyl)phenyl)aniline | B |
| 152 | N-methyl-N-(2-(5-(2-((4-(trifluoromethyl)phenyl)amino)phenyl)-1,3,4-oxadiazol-2-yl)propyl)cyanamide | A |
| 153 | 2-(5-(1-(methylamino)cyclopropyl)-1,3,4-oxadiazol-2-yl)-N-(4-(trifluoromethyl)phenyl)aniline | B |
| 155 | N-methyl-N-(1-(5-(2-((4-(trifluoromethyl)phenyl)amino)phenyl)-1,3,4-oxadiazol-2-yl)cyclopropyl)cyanamide | A |
| 156 | 2-(5-(2-(methylamino)propan-2-yl)-1,3,4-oxadiazol-2-yl)-N-(4-(trifluoromethyl)phenyl)aniline | B |
| 158 | N-methyl-N-(2-(5-(2-((4-(trifluoromethyl)phenyl)amino)phenyl)-1,3,4-oxadiazol-2-yl)propan-2-yl)cyanamide | A |
| 159 | 2-(5-(1-(methylamino)ethyl)-1,3,4-oxadiazol-2-yl)-N-(4-(trifluoromethyl)phenyl)aniline | B |
| 161 | N-methyl-N-(1-(5-(2-((4-(trifluoromethyl)phenyl)amino)phenyl)-1,3,4-oxadiazol-2-yl)ethyl)cyanamide | A |
| 162 | 2-methyl-2-(5-(2-((4-(trifluoromethyl)phenyl)amino)phenyl)-1,3,4-oxadiazol-2-yl)propanamide | A |
| 163 | 2-(5-(2-(methylsulfonyl)propan-2-yl)-1,3,4-oxadiazol-2-yl)-N-(4-(trifluoromethyl)phenyl)aniline | B |
| 164 | 2-methyl-2-(5-(2-((4-(trifluoromethyl)phenyl)amino)phenyl)-1,3,4-oxadiazol-2-yl)propanenitrile | A |
| 166 | 1-(5-(2-((4-(trifluoromethyl)phenyl)amino)phenyl)-1,3,4-oxadiazol-2-yl)cyclopropane-1-carboxylic acid | A |
| 167 | tert-butyl methyl((5-(2-((4-(trifluoromethyl)phenyl)amino)phenyl)-1,3,4-oxadiazol-2-yl)methyl)carbamate | C |
| 168 | N-methyl-N-((5-(2-((4-(trifluoromethyl)phenyl)amino)phenyl)-1,3,4-oxadiazol-2-yl)methyl)cyanamide | A |
| 169 | 2-(5-(pyrrolidin-2-yl)-1,3,4-oxadiazol-2-yl)-N-(4-(trifluoromethyl)phenyl)aniline | B |
| 171 | 2-(5-(2-((4-(trifluoromethyl)phenyl)amino)phenyl)-1,3,4-oxadiazol-2-yl)pyrrolidine-1-carbonitrile | A |
| 172 | 2-(5-(2-(methylamino)ethyl)-1,3,4-oxadiazol-2-yl)-N-(4-(trifluoromethyl)phenyl)aniline | C |
| 174 | N-methyl-N-(2-(5-(2-((4-(trifluoromethyl)phenyl)amino)phenyl)-1,3,4-oxadiazol-2-yl)ethyl)cyanamide | A |
| 175 | 2-(5-(pyrrolidin-3-yl)-1,3,4-oxadiazol-2-yl)-N-(4-(trifluoromethyl)phenyl)aniline | B |

TABLE 2-continued

| Compound No. | Name | Firefly Luciferase IC$_{50}$ (μM) |
|---|---|---|
| 177 | 3-(5-(2-((4-(trifluoromethyl)phenyl)amino)phenyl)-1,3,4-oxadiazol-2-yl)pyrrolidine-1-carbonitrile | B |
| 178 | 2-(5-(2-methyltetrahydrofuran-2-yl)-1,3,4-oxadiazol-2-yl)-N-(4-(trifluoromethyl)phenyl)aniline | A |
| 179 | 3-(5-(2-((4-(trifluoromethyl)phenyl)amino)phenyl)-1,3,4-oxadiazol-2-yl)butane-1,3-diol | A |
| 180 | 2-(5-(2-methyloxetan-2-yl)-1,3,4-oxadiazol-2-yl)-N-(4-(trifluoromethyl)phenyl)aniline | A |
| 181 | 2-(5-(tetrahydrofuran-2-yl)-1,3,4-oxadiazol-2-yl)-N-(4-(trifluoromethyl)phenyl)aniline | B |
| 182 | 2-(5-(oxetan-2-yl)-1,3,4-oxadiazol-2-yl)-N-(4-(trifluoromethyl)phenyl)aniline | A |
| 183 | 2-(5-(3-methyloxetan-3-yl)-1,3,4-oxadiazol-2-yl)-N-(4-(trifluoromethyl)phenyl)aniline | B |
| 184 | 1-(5-(2-((4-(trifluoromethyl)phenyl)amino)phenyl)-1,3,4-oxadiazol-2-yl)cyclopropane-1-carbonitrile | A |
| 185 | N,N-dimethyl-1-(5-(2-((4-(trifluoromethyl)phenyl)amino)phenyl)-1,3,4-oxadiazol-2-yl)cyclopropane-1-carboxamide | B |
| 186 | N-methyl-1-(5-(2-((4-(trifluoromethyl)phenyl)amino)phenyl)-1,3,4-oxadiazol-2-yl)cyclopropane-1-carboxamide | B |
| 187 | 1-(5-(2-((4-(trifluoromethyl)phenyl)amino)phenyl)-1,3,4-oxadiazol-2-yl)cyclopropane-1-carboxamide | A |
| 188 | N-(1-methoxypropan-2-yl)-5-(2-((4-(trifluoromethyl)phenyl)amino)phenyl)-1,3,4-oxadiazole-2-carboxamide | B |
| 189 | N-(1-hydroxypropan-2-yl)-5-(2-((4-(trifluoromethyl)phenyl)amino)phenyl)-1,3,4-oxadiazole-2-carboxamide | B |
| 190 | N-(2-methoxyethyl)-5-(2-((4-(trifluoromethyl)phenyl)amino)phenyl)-1,3,4-oxadiazole-2-carboxamide | A |
| 191 | N-(2-hydroxyethyl)-5-(2-((4-(trifluoromethyl)phenyl)amino)phenyl)-1,3,4-oxadiazole-2-carboxamide | A |
| 192 | N-methoxy-N-methyl-5-(2-((4-(trifluoromethyl)phenyl)amino)phenyl)-1,3,4-oxadiazole-2-carboxamide | B |
| 194 | N,N-dimethyl-5-(2-((4-(trifluoromethyl)phenyl)amino)phenyl)-1,3,4-oxadiazole-2-carboxamide | C |
| 195 | N-cyclopropyl-5-(2-((4-(trifluoromethyl)phenyl)amino)phenyl)-1,3,4-oxadiazole-2-carboxamide | B |
| 196 | N-isopropyl-5-(2-((4-(trifluoromethyl)phenyl)amino)phenyl)-1,3,4-oxadiazole-2-carboxamide | B |
| 197 | N-ethyl-5-(2-((4-(trifluoromethyl)phenyl)amino)phenyl)-1,3,4-oxadiazole-2-carboxamide | A |
| 198 | N-methyl-5-(2-((4-(trifluoromethyl)phenyl)amino)phenyl)-1,3,4-oxadiazole-2-carboxamide | A |
| 199 | 2,2-dimethyl-5-(5-(2-((4-(trifluoromethyl)phenyl)amino)phenyl)-1,3,4-oxadiazol-2-yl)-1,3-dioxan-5-ol | C |
| 200 | diethyl 2-hydroxy-2-(5-(2-((4-(trifluoromethyl)phenyl)amino)phenyl)-1,3,4-oxadiazol-2-yl)malonate | B |
| 201 | 2-(5-(2-((4-(trifluoromethyl)phenyl)amino)phenyl)-1,3,4-oxadiazol-2-yl)propane-1,2,3-triol | A |
| 202 | 2-hydroxy-1-(5-(2-((4-(trifluoromethyl)phenyl)amino)phenyl)-1,3,4-oxadiazol-2-yl)ethyl acetate | A |
| 203 | 2-fluoro-1-(5-(2-((4-(trifluoromethyl)phenyl)amino)phenyl)-1,3,4-oxadiazol-2-yl)ethan-1-ol | A |
| 204 | 4-bromo-2-(5-cyclopropyl-1,3,4-oxadiazol-2-yl)-N-(4-(trifluoromethyl)phenyl)aniline | B |

Note:
Biochemical assay IC$_{50}$ data are designated within the following ranges:
A: ≤0.100 μM
B: >0.100 μM to ≤1.000 μM
C: >1.000 μM to ≤5.000 μM
D: >5.000 μM Example A2: Tumor Suppression Assay The procedures described herein for the tumor suppression assay is as described in PCT/US2013/043752 (WO 2013/188138). Mouse procedures are performed according to the guidelines of approved animal protocol and based on the methods. After the cells are grown to 90%>confluence, these cells are harvested by trypsinization, washed in phosphate-buffered saline (PBS), and resuspended in PBS supplemented with 50% matrigel (BD Biosciences). An appropriate amount of cells is prepared for administration, such as 200 μL per injection site. Immuno-compromised mice are injected on the dorsolateral sites subcutaneously. Any one of the compounds described herein is formulated accordingly and is then administered at a suitable dose. Control mice received vehicle alone. The average tumor diameter (two perpendicular axes of the tumor are measured) are recorded. The data are expressed in tumor volume estimated by ([width]2×length/2). Paired, two-tailed Student's t-test is performed to access the statistical significance.

Example A3: Cell Proliferation Assay

Cancer cell lines are plated in 384-well plates 24 h before drug treatment. Post incubation for various time periods with the test compounds, starting from 3 µM (final concentration in assay plate), 1:3 dilution, and 10 points in duplicates, the number of viable cells and proliferative cells are determined using CellTiter-Glo® Luminescent Cell Viability Assay Kit (Promega) and Click-iT EdU HCS Assay Kit (Invitrogen) according to the manufacturers' protocols. The $IC_{50}$ values and maximum % inhibition of the test compounds are calculated using the dose response curves.

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt thereof:

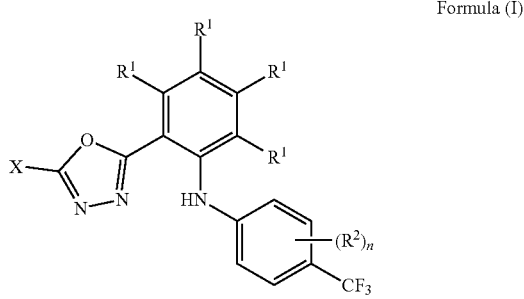

Formula (I)

wherein:
X is H, —CN, halogen, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, -$L^1$-$Y^1$, -$L^2$-$L^3$-$Y^2$, -$L^2$-$L^3$-$L^4$-$Y^2$, -$L^5$-$L^6$-$L^3$-$Y^2$, or -$L^6$-$L^5$-$L^3$-$Y^2$;

$L^1$ is substituted or unsubstituted $C_1$-$C_6$alkylene;

$Y^1$ is —$N_3$, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

$L^2$ is absent, substituted or unsubstituted $C_1$-$C_6$alkylene, substituted or unsubstituted $C_3$-$C_{10}$cycloalkylene, or substituted or unsubstituted $C_2$-$C_{10}$heterocycloalkylene;

$L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —O—$NR^3$(C=O)—, —$NR^3$(C=O)—, —$NR^3$(C=O)$NR^3$—, —O(C=O)$NR^3$—, —$NR^3$(C=O)O—, —$NR^3$($SO_2$)$NR^3$—, —($SO_2$)$NR^3$—, —($SO_2$)$NR^3$—, —($SO_2$)$NR^3$—(C=O)—, —(C=O)—$NR^3$($SO_2$)$NR^3$—, —(C=O)—$NR^3$($SO_2$)—, —$NR^3$(C=O)O—, —O(C=O)—$NR^3$($SO_2$)—, —$NR_3$($SO_2$)$NR^3$—(C=O)—, —(C=O)—$NR^3$($SO_2$)$NR^3$—, —O(C=O)—$NR^3$($SO_2$)—$NR^3$—, —$NR^3$($SO_2$)$NR^3$—(C=O)O—, —O—($SO_2$)—, or —($SO_2$)—O—;

each $R^3$ is independently H, —CN, —S(=O)$_2$($C_1$-$C_4$alkyl), or substituted or unsubstituted $C_1$-$C_6$alkyl;

$L^4$ is substituted or unsubstituted $C_1$-$C_6$alkylene;

$L^5$ is substituted or unsubstituted $C_1$-$C_6$alkylene;

$L^6$ is substituted or unsubstituted $C_3$-$C_{10}$cycloalkylene;

$Y^2$ is H, —CN, —$N_3$, halogen, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, —$OR^6$, —(C=O)$OR^6$, —N($R^6$)$_2$, or (C=O)N($R^6$)$_2$;

or $R^3$ and $Y^2$ on the same N atom are taken together with the N atom to which they are attached to form a substituted or unsubstituted N-containing heterocycle;

each $R^6$ is independently H or substituted or unsubstituted $C_1$-$C_6$alkyl;

or two $R^6$ on the same N atom are taken together with the N atom to which they are attached to form a substituted or unsubstituted N-containing heterocycle;

each $R^1$ is independently H, halogen, —CN, —$OR^4$, —$SR^4$, —N($R^4$)$_2$, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or -$L^7$-$Y^3$;

$L^7$ is substituted or unsubstituted $C_1$-$C_6$alkylene;

$Y^3$ is —Si($R^7$)$_2$;

each $R^7$ is independently substituted or unsubstituted $C_1$-$C_6$alkyl;

n is 0, 1, 2, 3, or 4;

each $R^2$ is independently H, halogen, —$N_3$, —CN, —$OR^5$, —$SR^5$, —($SO_2$)$R^5$, —N($R^5$)$_2$, —$CO_2R^5$, substituted or unsubstituted $C_1$-$C_6$alkyl, substituted or unsubstituted $C_1$-$C_6$haloalkyl, substituted or unsubstituted $C_2$-$C_6$alkenyl, substituted or unsubstituted $C_2$-$C_6$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

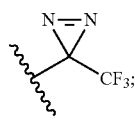 [SMILES: *C1(C(F)(F)F)N=N1]

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;

or two R$^4$ on the same N atom are taken together with the N atom to which they are attached to form a substituted or unsubstituted N-containing heterocycle; and each R$^5$ is independently H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;

or two R$^5$ on the same N atom are taken together with the N atom to which they are attached to form a substituted or unsubstituted N-containing heterocycle.

2. The compound, or pharmaceutically acceptable salt thereof, of claim 1, wherein:

X is substituted or unsubstituted C$_1$-C$_6$alkyl, substituted or unsubstituted C$_1$-C$_6$haloalkyl, substituted or unsubstituted C$_3$-C$_{10}$cycloalkyl, substituted or unsubstituted C$_2$-C$_{10}$heterocycloalkyl, or substituted or unsubstituted heteroaryl.

3. The compound, or pharmaceutically acceptable salt thereof, of claim 2, wherein:

X is substituted or unsubstituted C$_1$-C$_4$alkyl.

4. The compound, or pharmaceutically acceptable salt thereof, of claim 2, wherein:

X is substituted or unsubstituted C$_2$-C$_6$heterocycloalkyl.

5. The compound, or pharmaceutically acceptable salt thereof, of claim 4, wherein:

X is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl.

6. The compound, or pharmaceutically acceptable salt thereof, of claim 1, wherein:

X is -L$^2$-L$^3$-Y$^2$.

7. The compound, or pharmaceutically acceptable salt thereof, of claim 6, wherein:

L$^2$ is substituted or unsubstituted C$_1$-C$_4$alkylene;

L$^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —NR$^3$(C=O)O—, —NR$^3$(SO$_2$)—, —(SO$_2$)NR$^3$—, or —O—(SO$_2$)—;

Y$^2$ is independently H, —CN, —N$_3$ substituted or unsubstituted C$_1$-C$_4$alkyl, substituted or unsubstituted C$_1$-C$_4$haloalkyl, substituted or unsubstituted C$_1$-C$_4$heteroalkyl, substituted or unsubstituted C$_3$-C$_6$cycloalkyl, substituted or unsubstituted C$_2$-C$_6$heterocycloalkyl, substituted or unsubstituted benzyl, substituted or unsubstituted phenyl, substituted or unsubstituted monocyclic heteroaryl, —OR$^6$, —(C=O)OR$^6$, —N(R$^6$)$_2$, or —(C=O)N(R$^6$)$_2$; and each R$^6$ is independently H or substituted or unsubstituted C$_1$-C$_4$alkyl.

8. The compound, or pharmaceutically acceptable salt thereof, of claim 1, wherein:

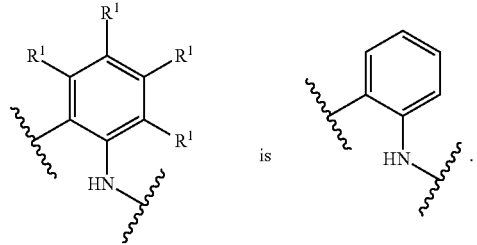

9. The compound, or pharmaceutically acceptable salt thereof, of claim 1, wherein:

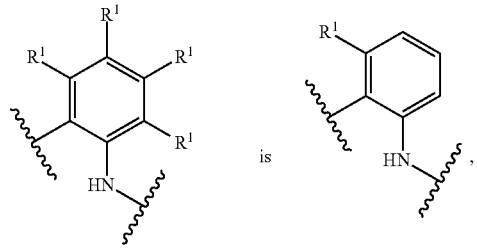

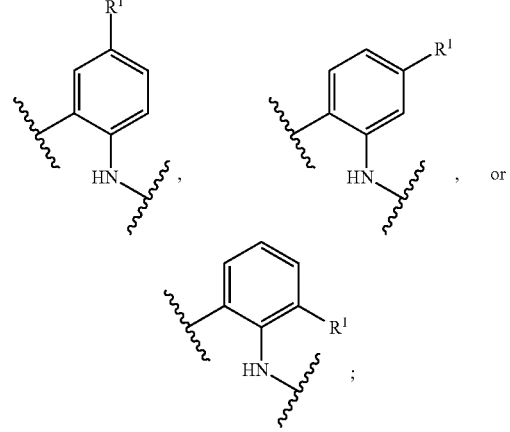

R$^1$ is halogen, —CN, —OR$^4$, —SR$^4$, —N(R$^4$)$_2$, substituted or unsubstituted C$_1$-C$_4$alkyl, substituted or unsubstituted C$_1$-C$_4$haloalkyl, substituted or unsubstituted C$_1$-C$_4$heteroalkyl, substituted or unsubstituted C$_3$-C$_6$cycloalkyl, substituted or unsubstituted C$_2$-C$_6$heterocycloalkyl, substituted or unsubstituted benzyl, substituted or unsubstituted phenyl, or substituted or unsubstituted monocyclic heteroaryl.

10. The compound, or pharmaceutically acceptable salt thereof, of claim 9, wherein:

R$^1$ is halogen, substituted or unsubstituted C$_1$-C$_4$alkyl, or substituted or unsubstituted C$_1$-C$_4$haloalkyl.

11. The compound, or pharmaceutically acceptable salt thereof, of claim 10, wherein:

R$^1$ is F, Cl, Br, I, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$F, —CHF$_2$, —CF$_3$, or —CH$_2$CF$_3$.

12. The compound, or pharmaceutically acceptable salt thereof, of claim 1, wherein the compound has the structure of Formula (Ia), or a pharmaceutically acceptable salt thereof:

Formula (Ia)

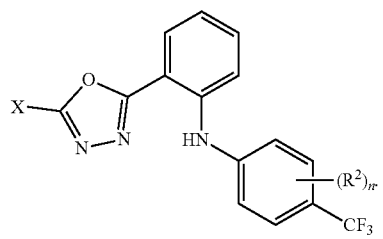

13. The compound, or pharmaceutically acceptable salt thereof, of claim 1, wherein the compound has the structure of Formula (Ib), or a pharmaceutically acceptable salt thereof:

Formula (Ib)

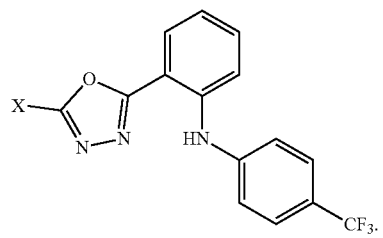

14. A compound that has one of the following structures:

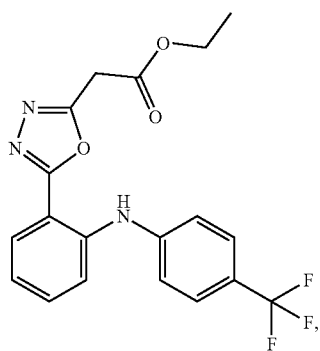

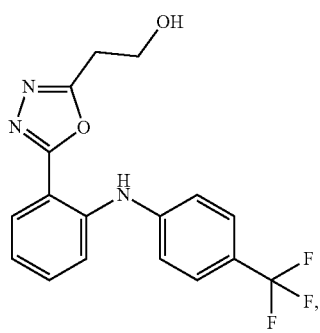

-continued

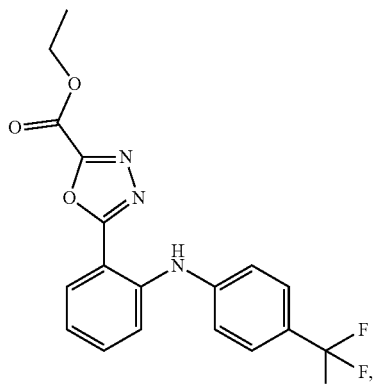

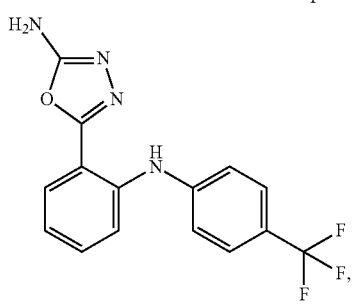

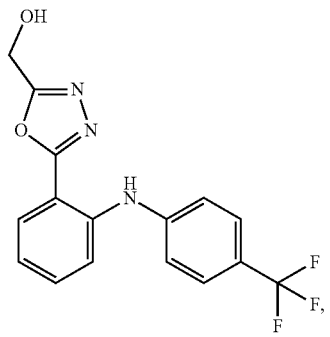

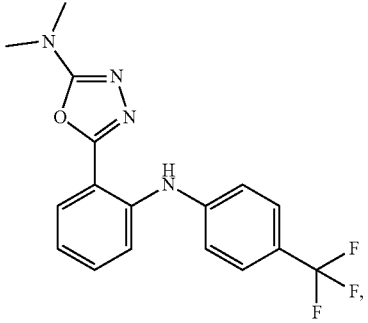

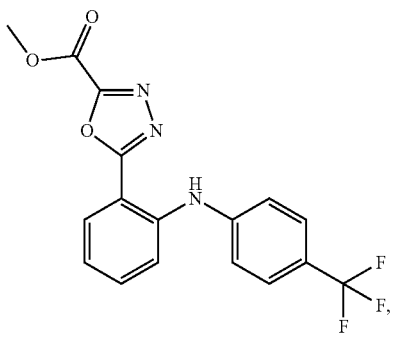

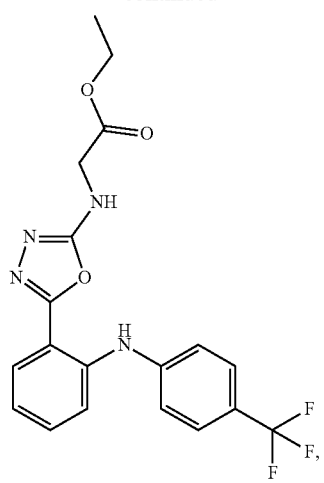
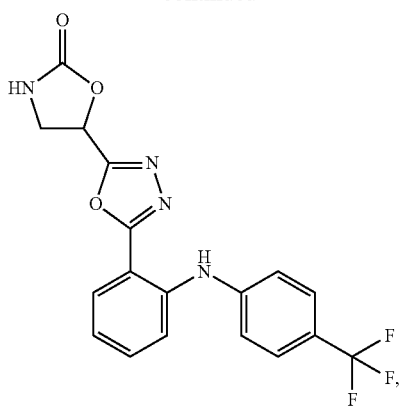
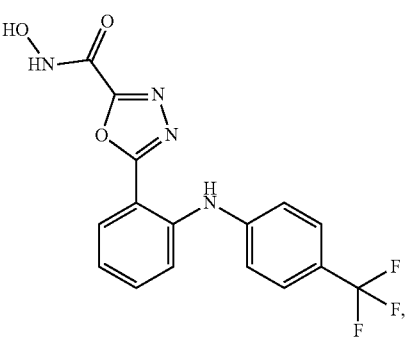
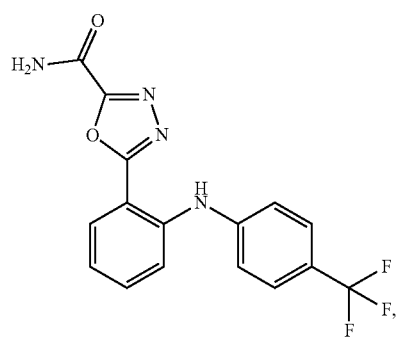
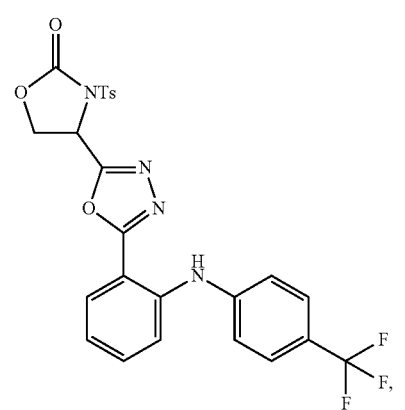

413
-continued
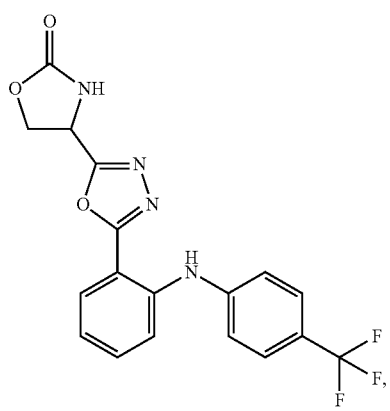
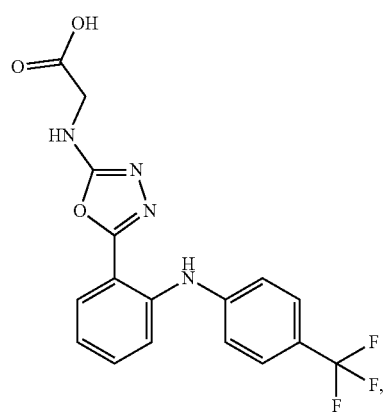
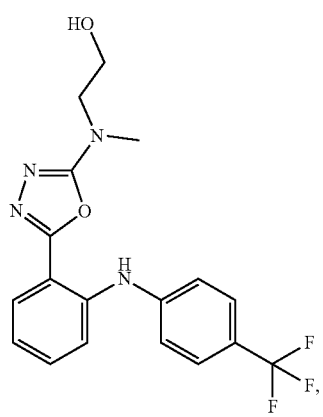
414
-continued
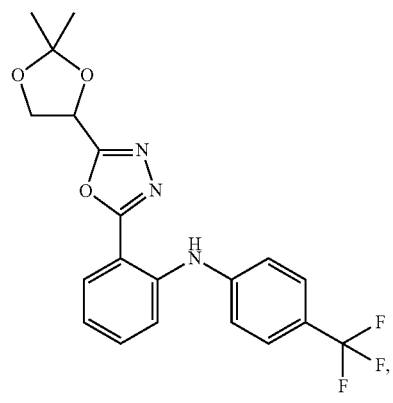
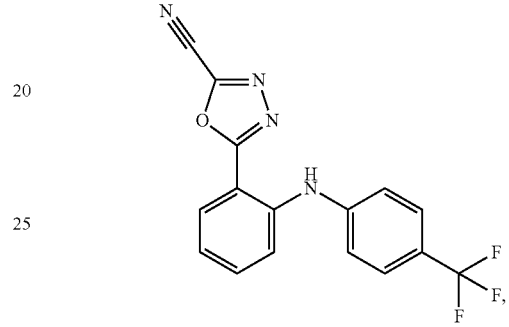
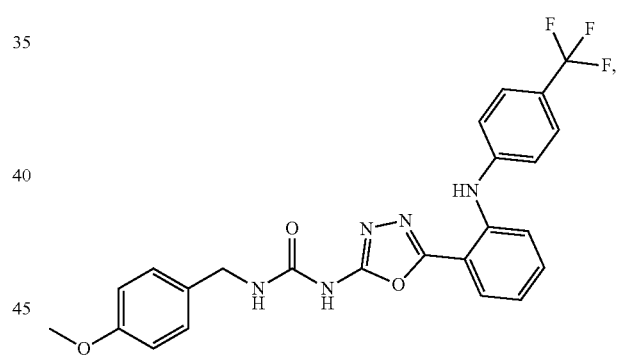
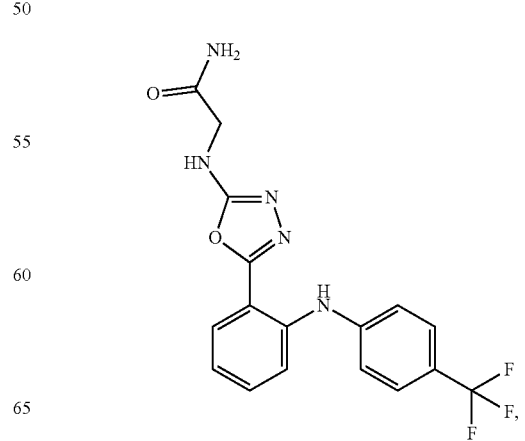
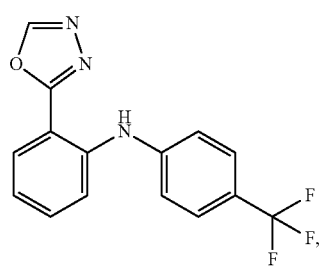

-continued
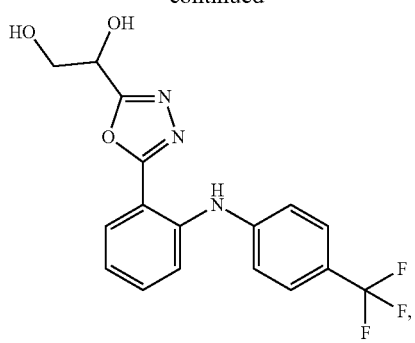
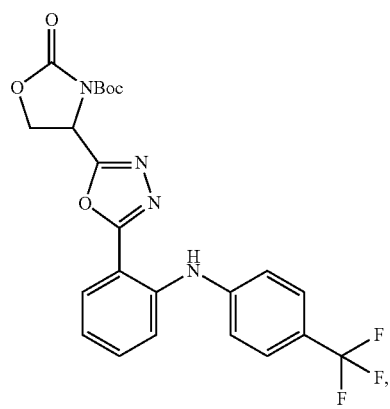
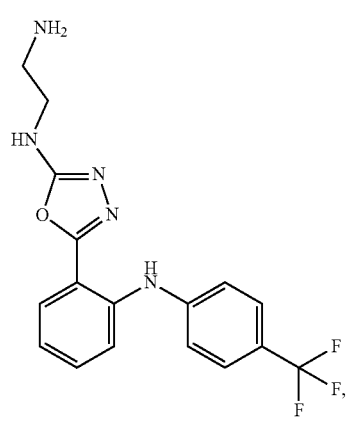
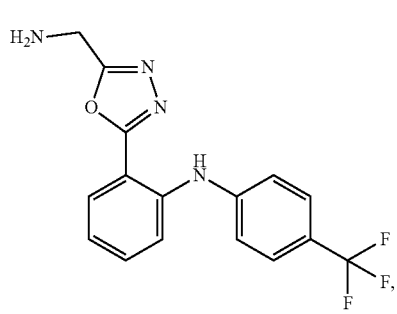
-continued
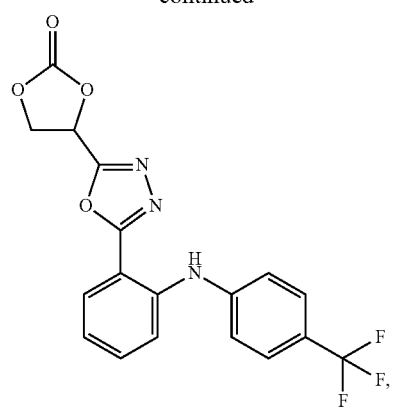
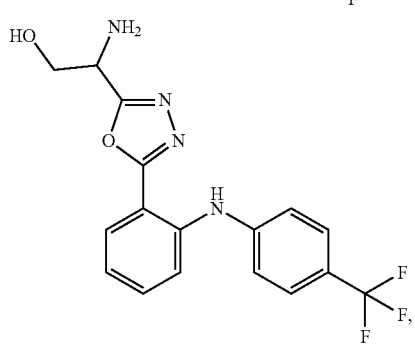
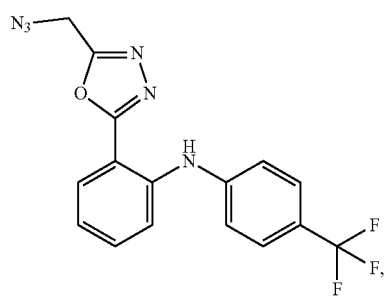
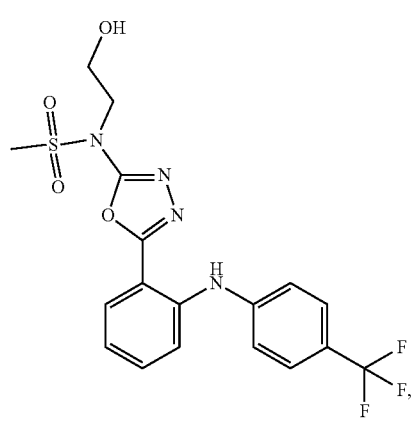

417
-continued
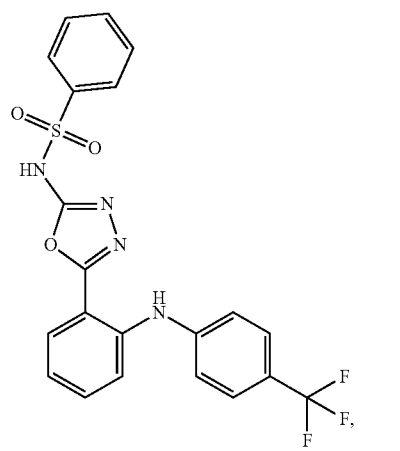
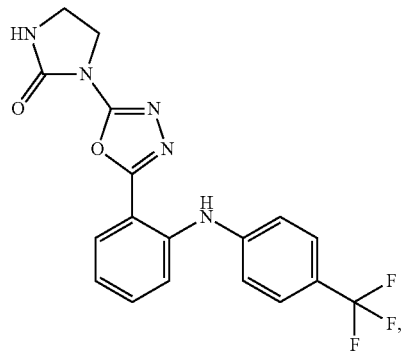
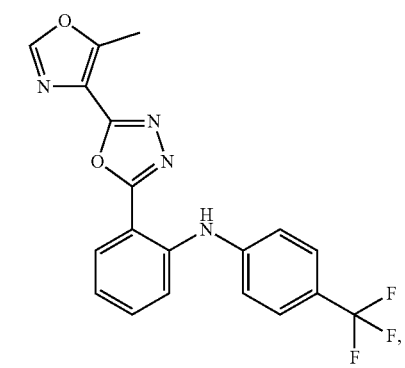
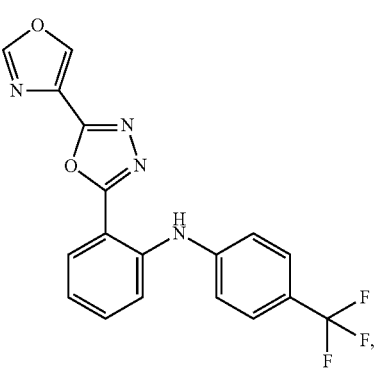
418
-continued
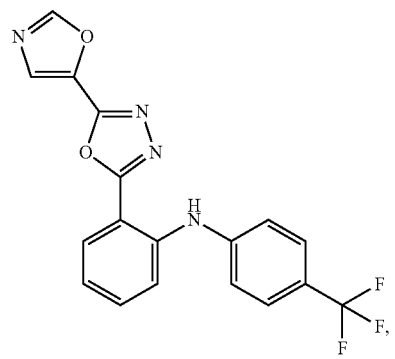
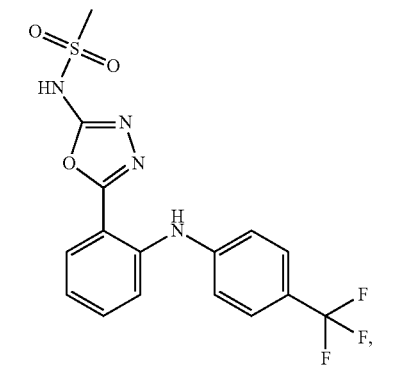
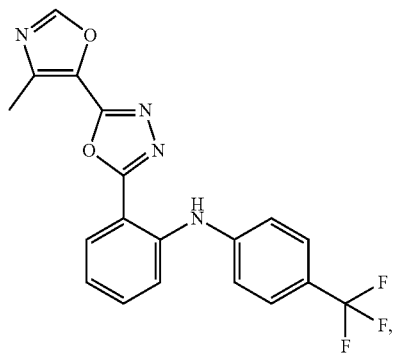
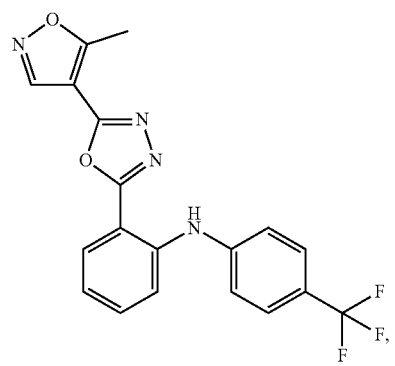

-continued
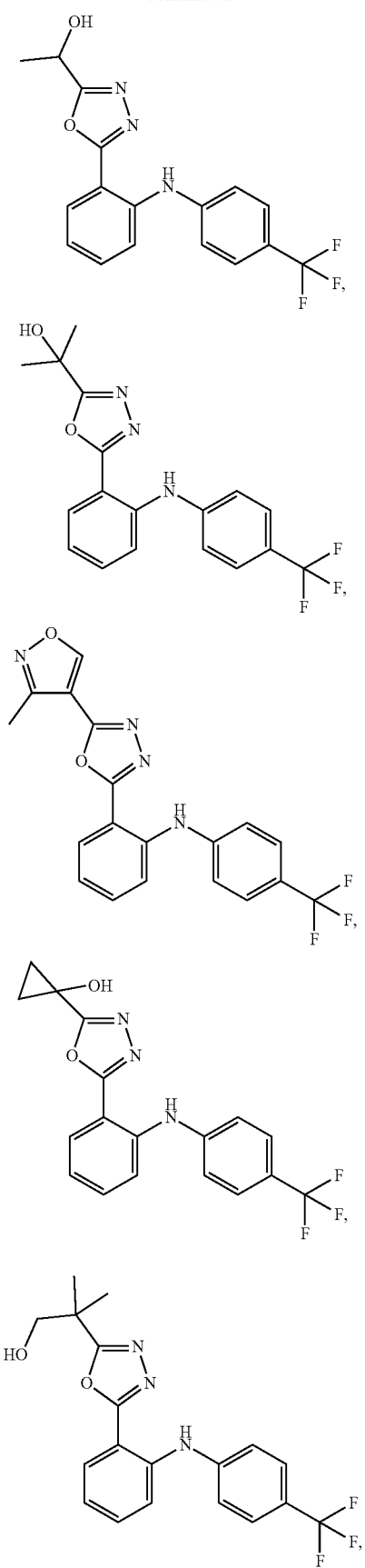
-continued
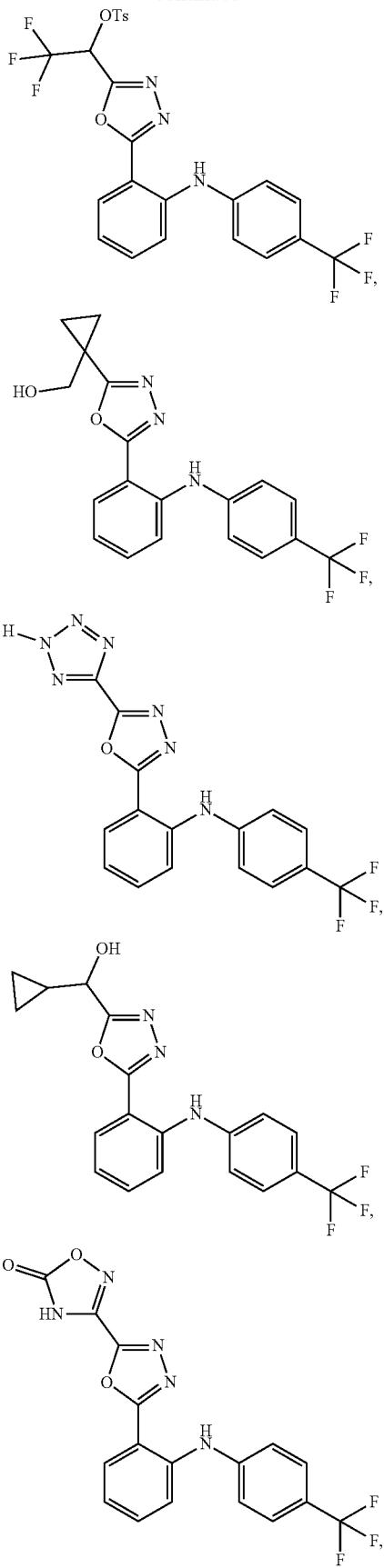 [SMILES: Cc1ccc(S(=O)(=O)OC(c2nnc(-c3ccccc3Nc3ccc(C(F)(F)F)cc3)o2)C(F)(F)F)cc1 ; OCC1(c2nnc(-c3ccccc3Nc3ccc(C(F)(F)F)cc3)o2)CC1 ; FC(F)(F)c1ccc(Nc2ccccc2-c2nnc(-c3nn[nH]n3)o2)cc1 ; OC(c1nnc(-c2ccccc2Nc2ccc(C(F)(F)F)cc2)o1)C1CC1 ; O=c1[nH]c(-c2nnc(-c3ccccc3Nc3ccc(C(F)(F)F)cc3)o2)no1]

421
-continued
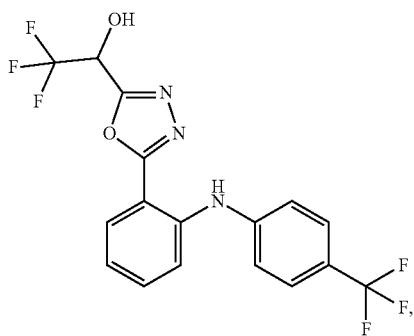
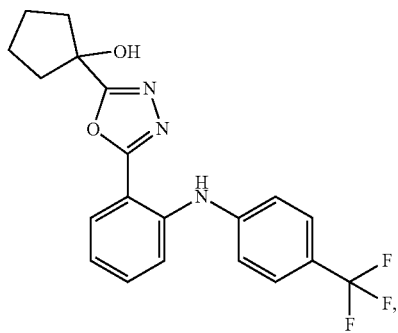
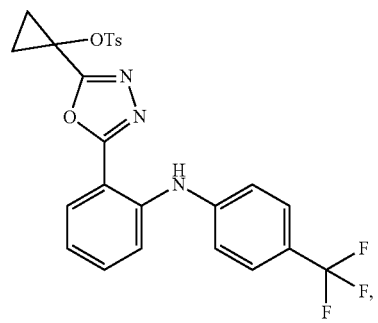
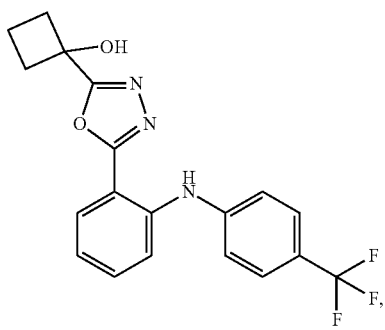
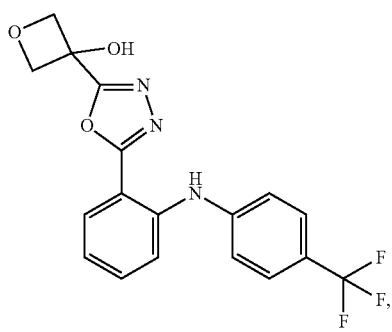
422
-continued
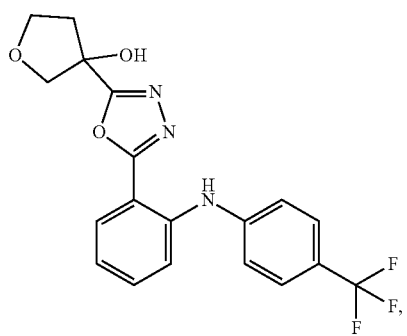
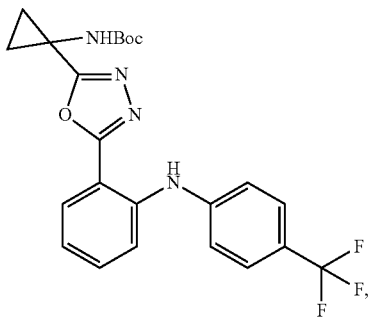
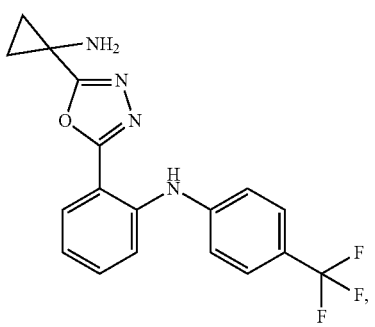
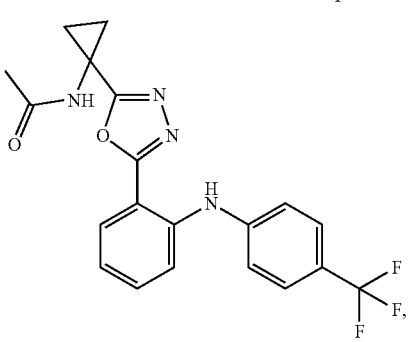
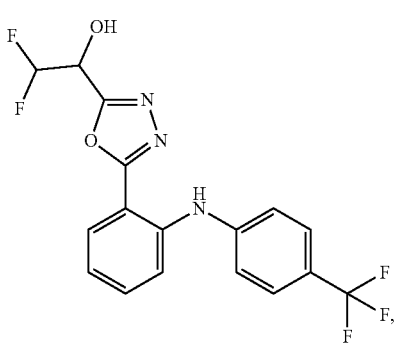

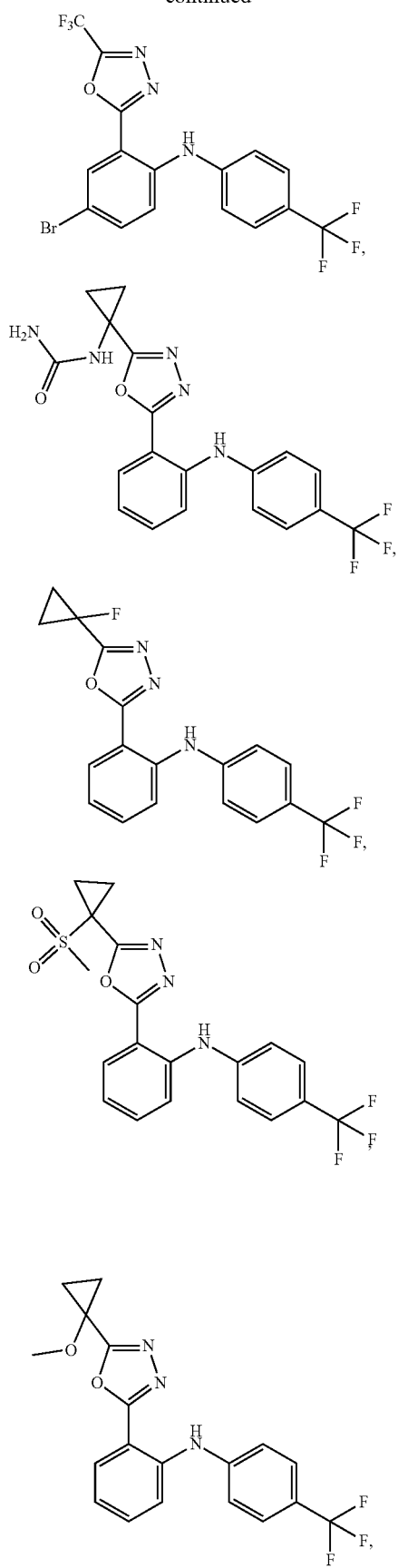
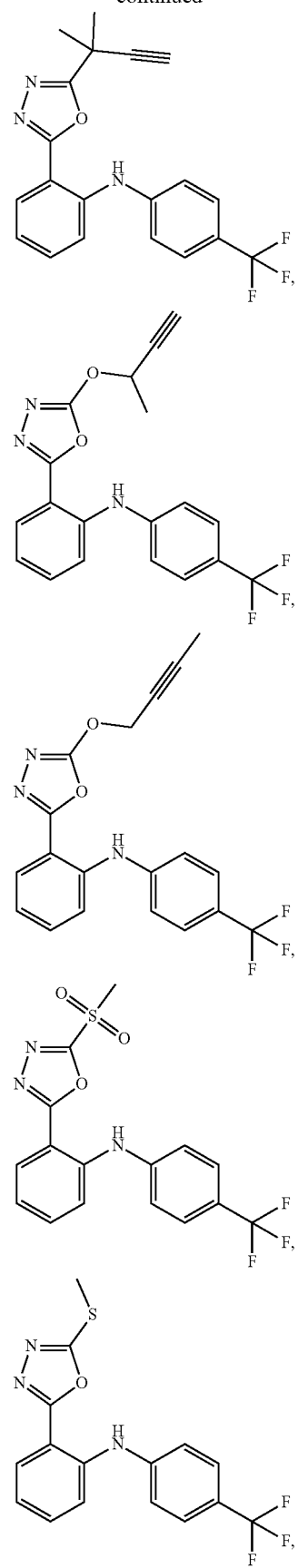

425
-continued
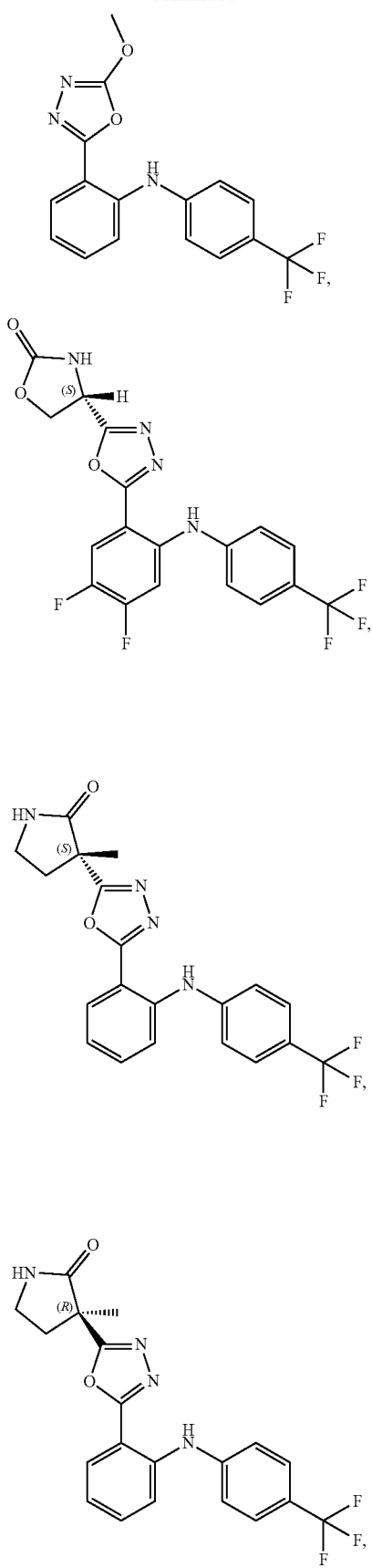
426
-continued
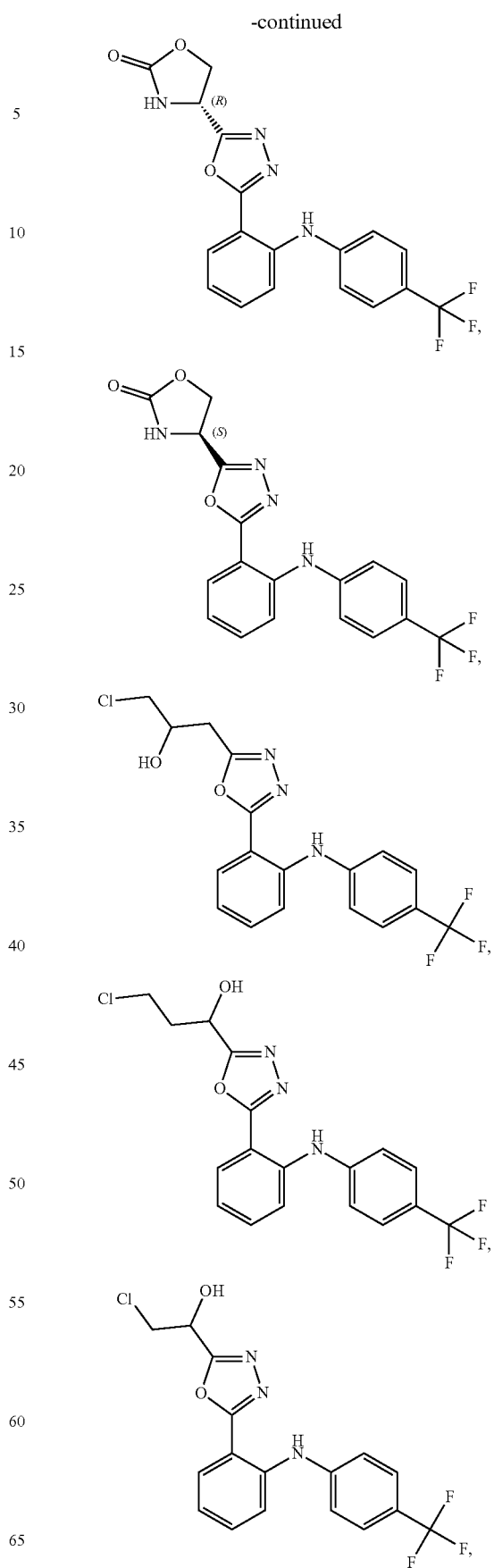

427
-continued
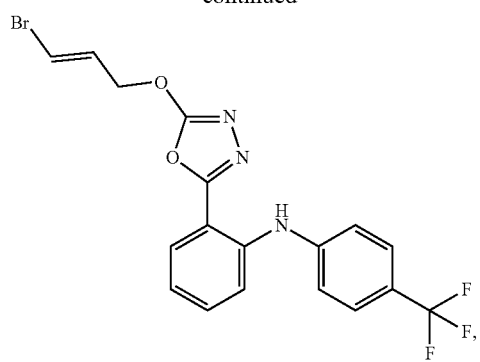
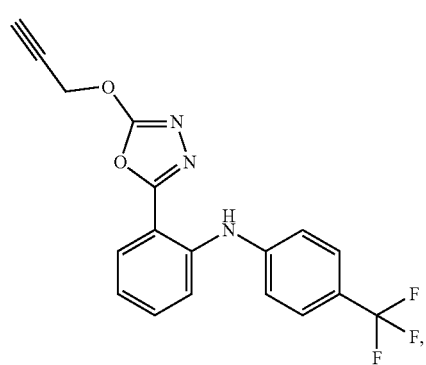
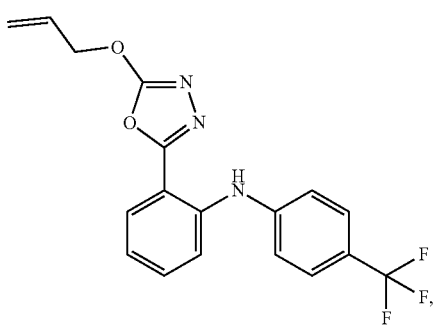
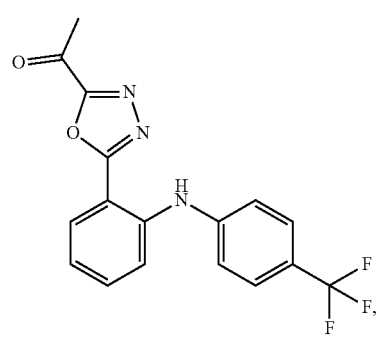
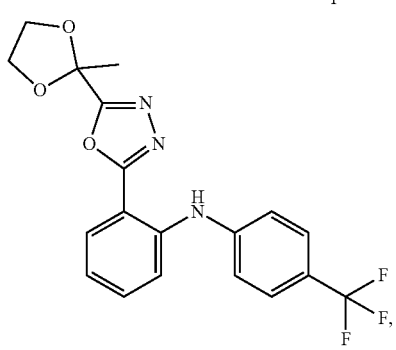
428
-continued
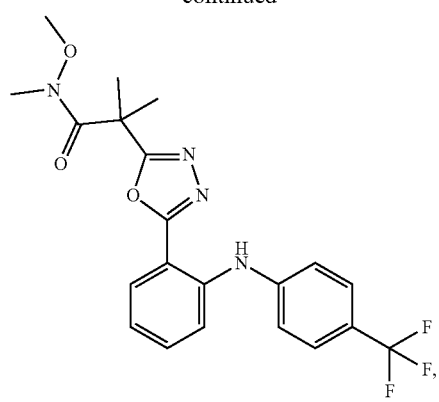
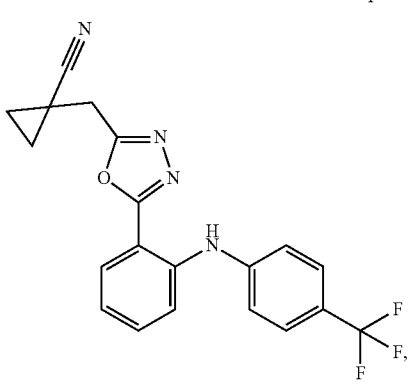
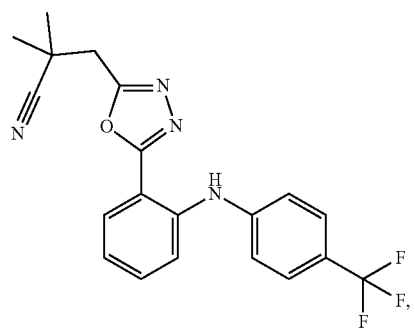
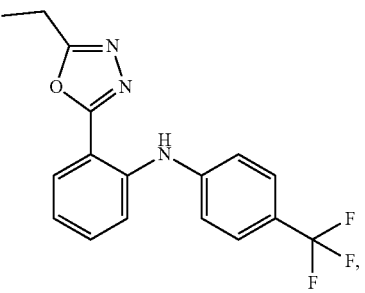

429
-continued
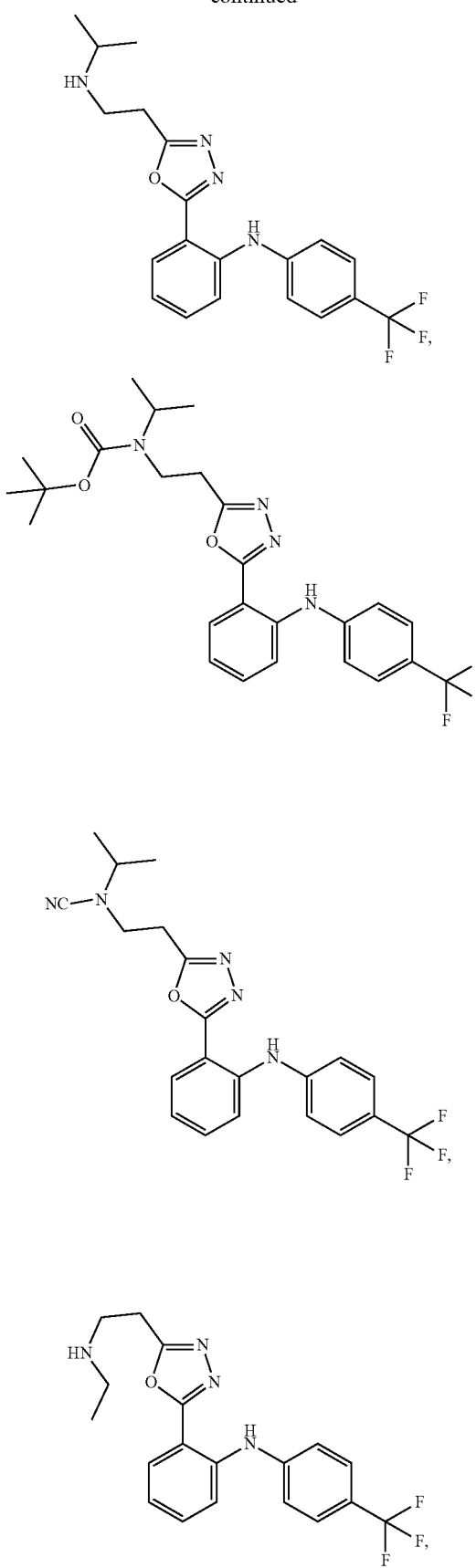
430
-continued
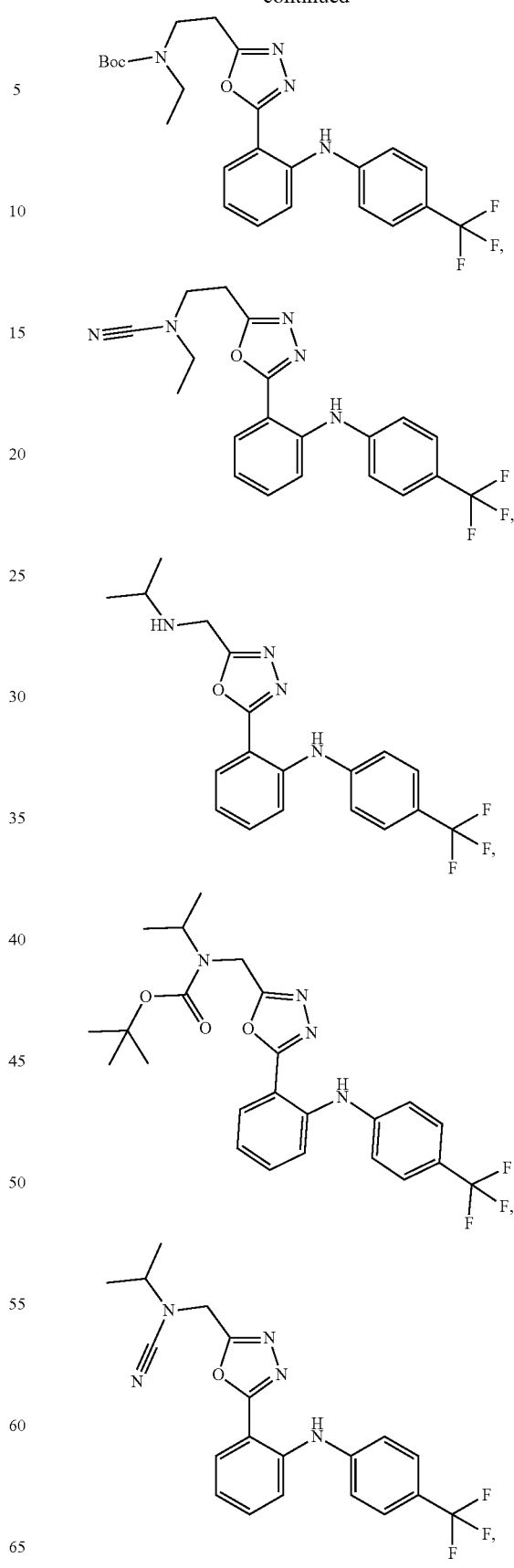

431
-continued
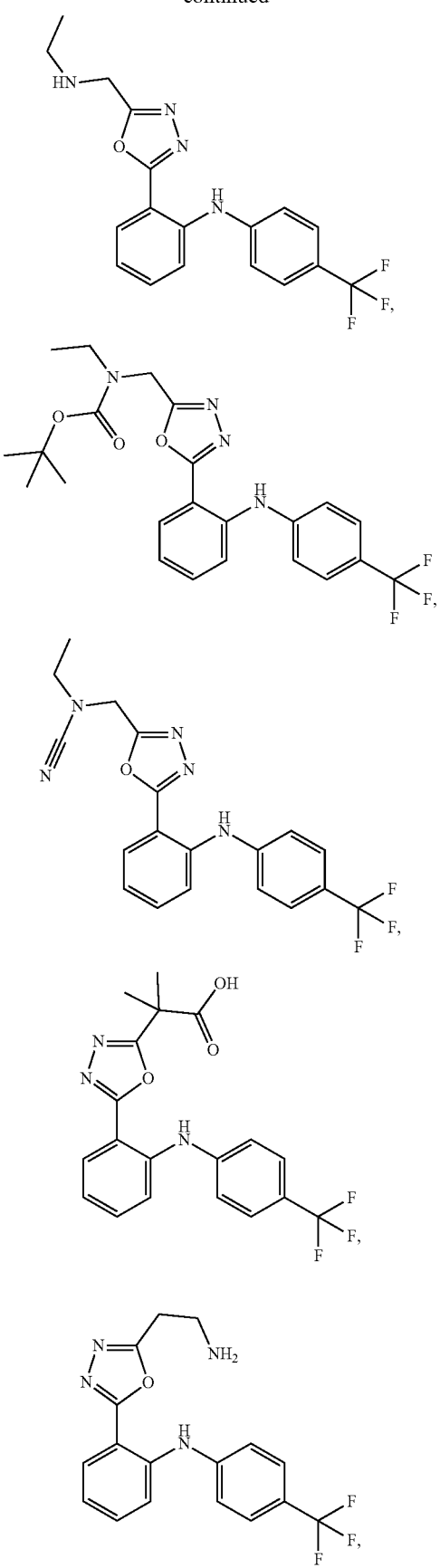
432
-continued
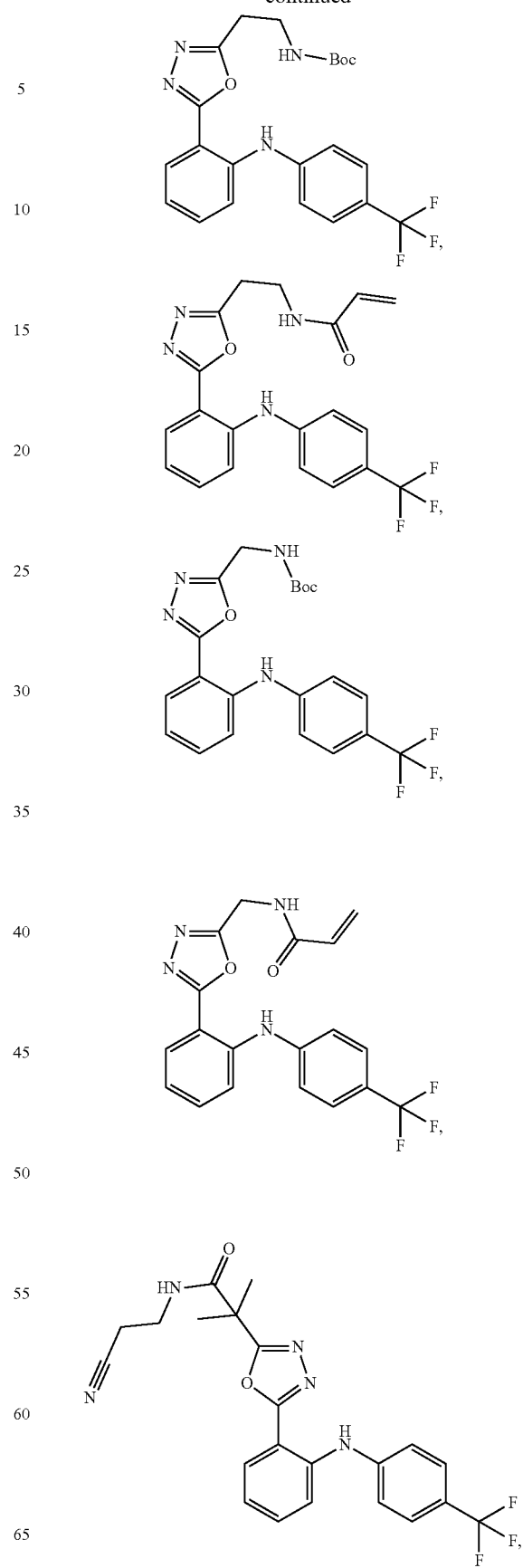

433
-continued
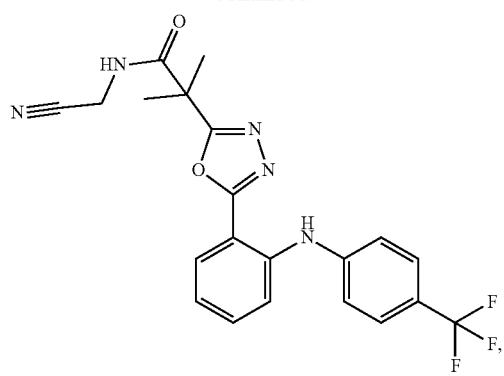
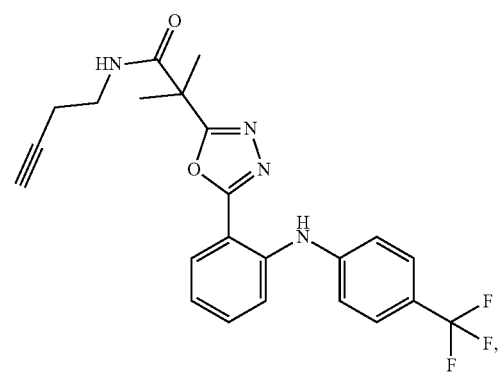
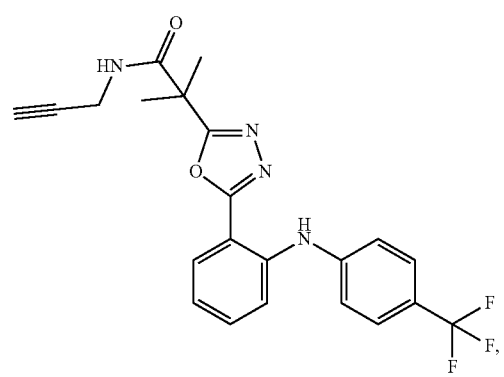
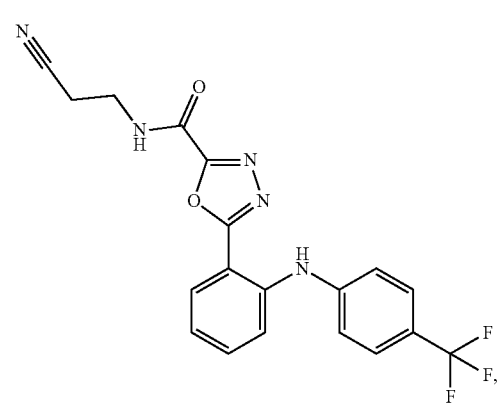
434
-continued
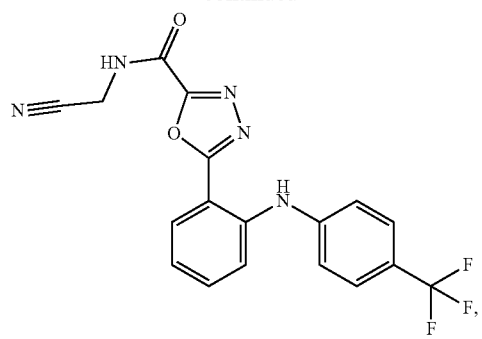
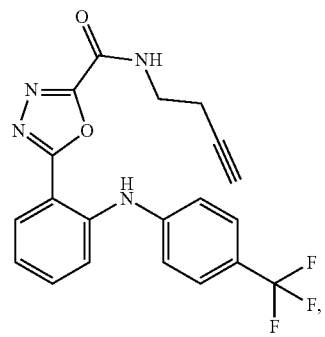
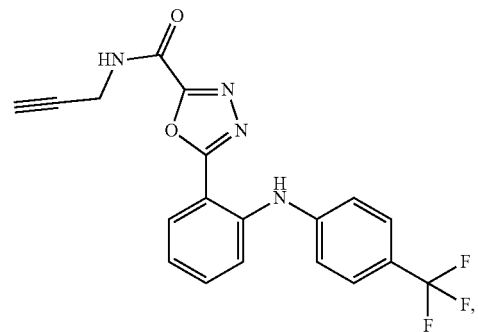
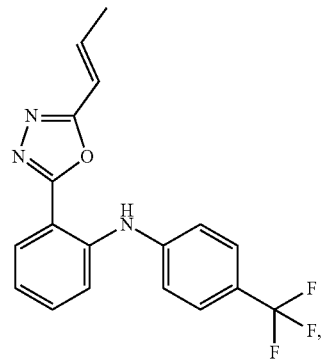
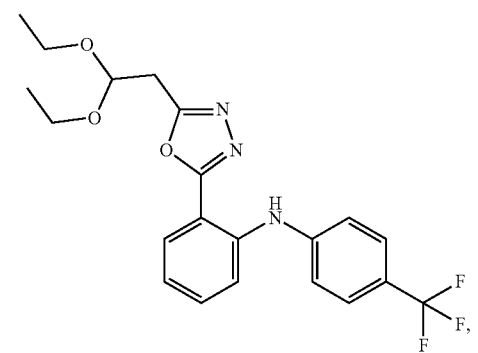

435
-continued
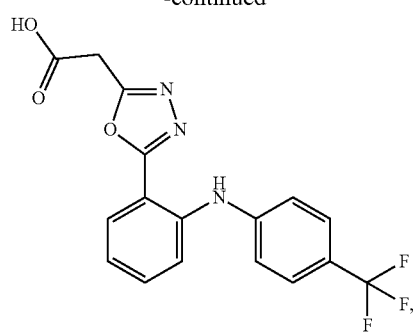
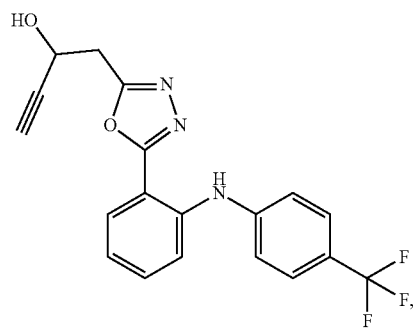
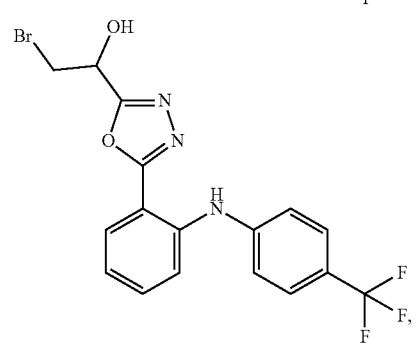
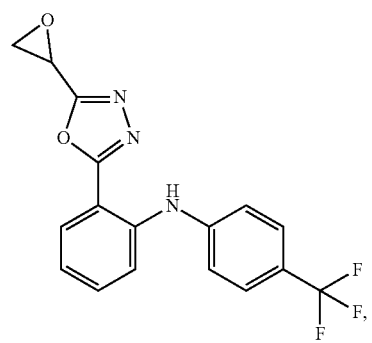
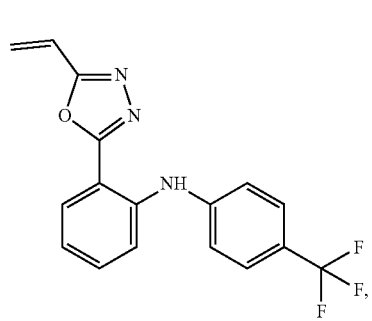
436
-continued
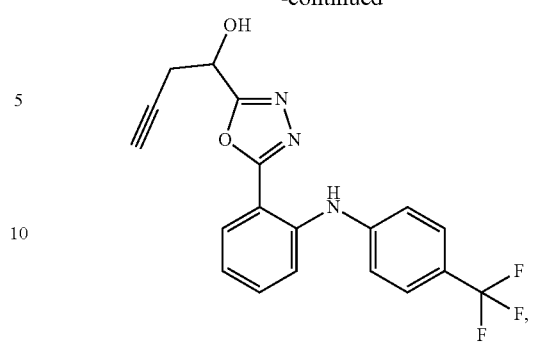
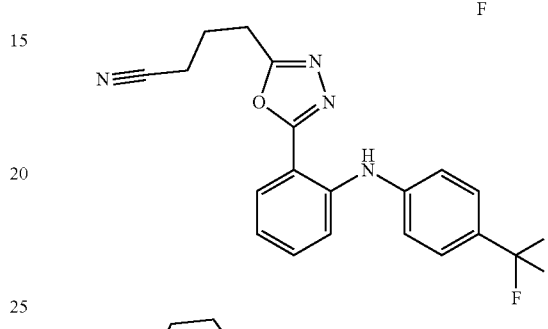
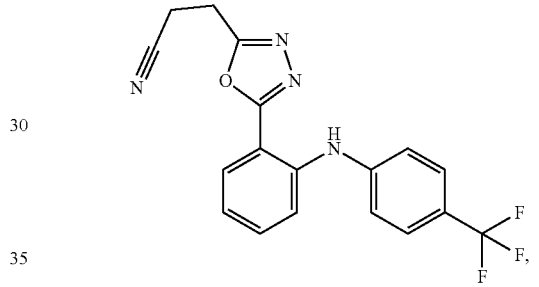
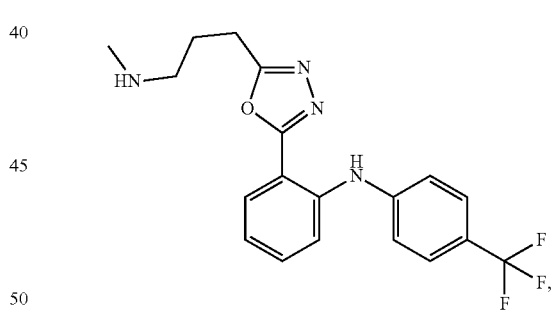
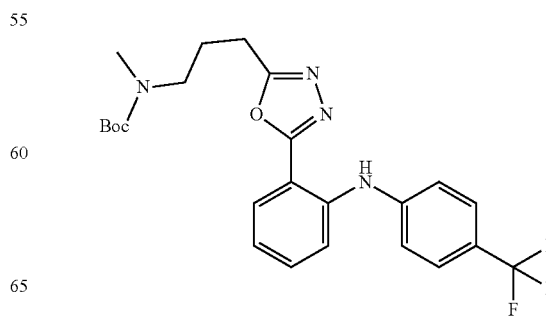

437
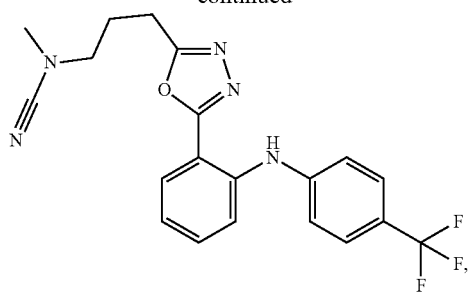
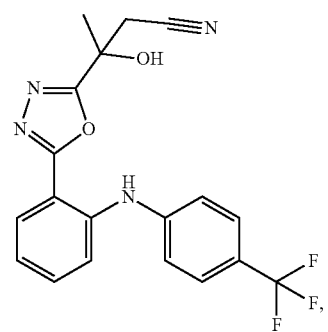
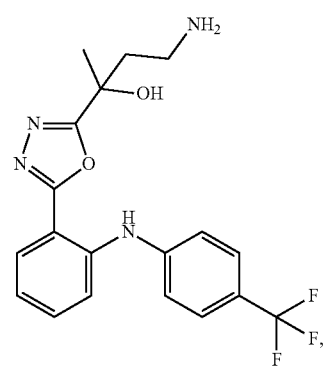
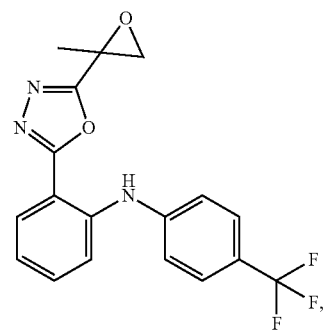
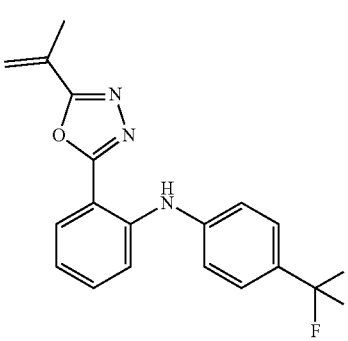
438
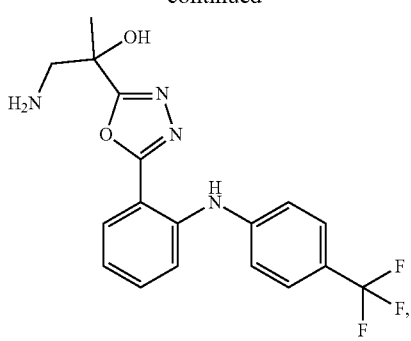
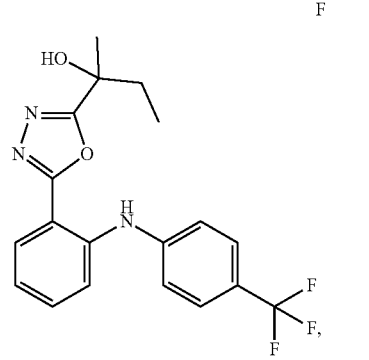
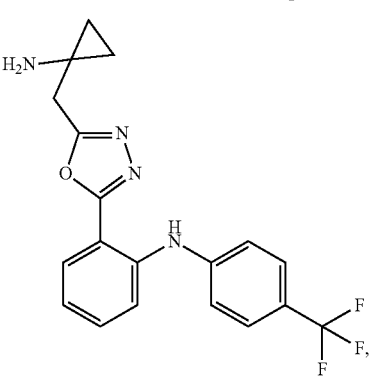
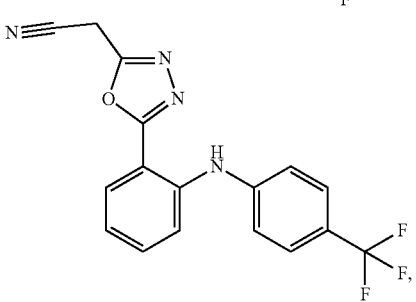
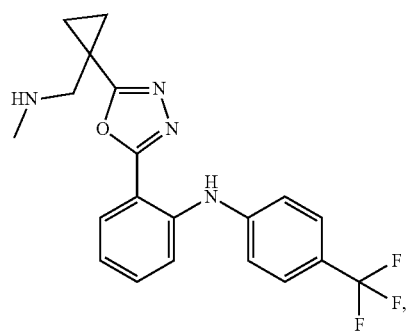

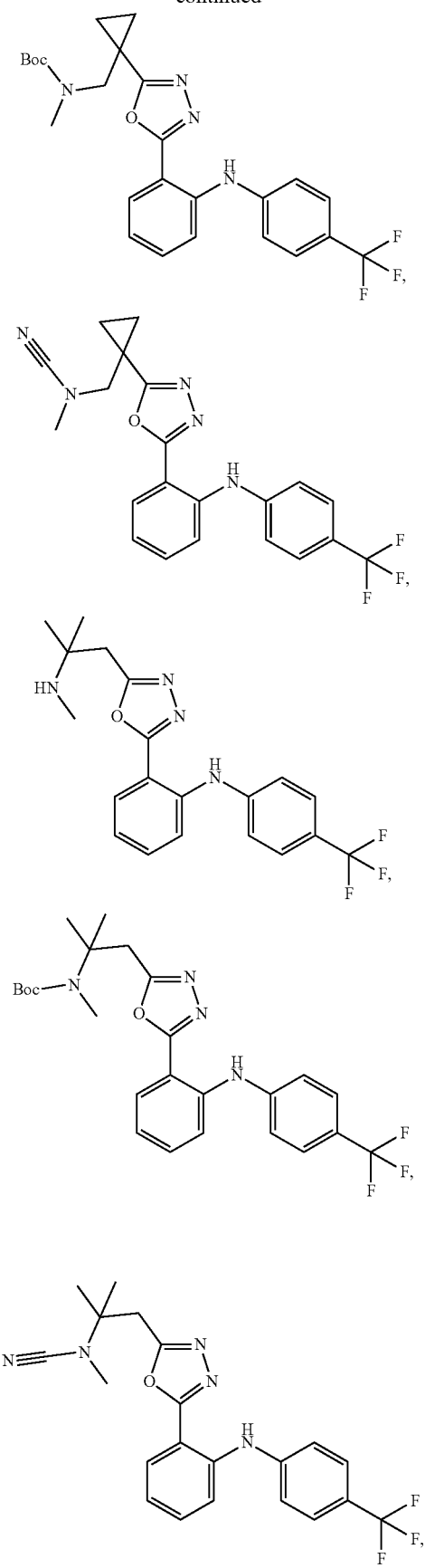

441
-continued
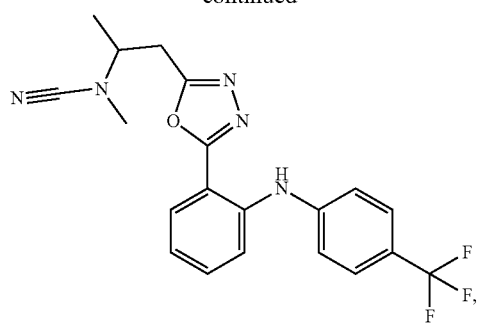
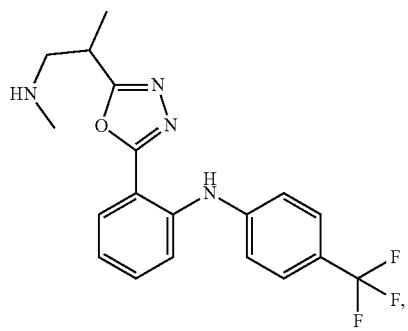
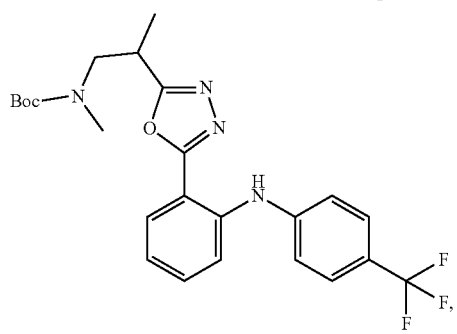
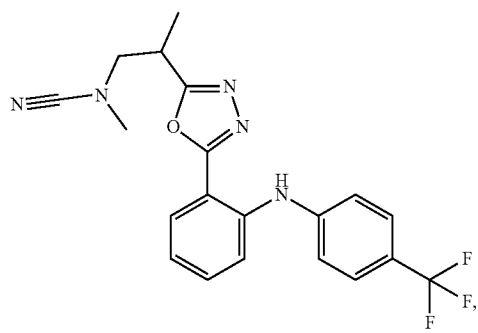
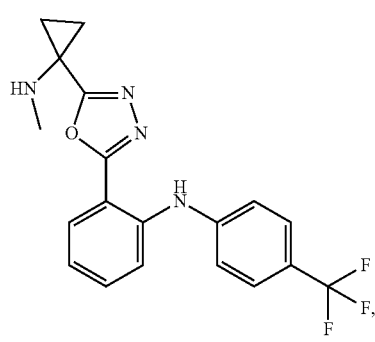
442
-continued
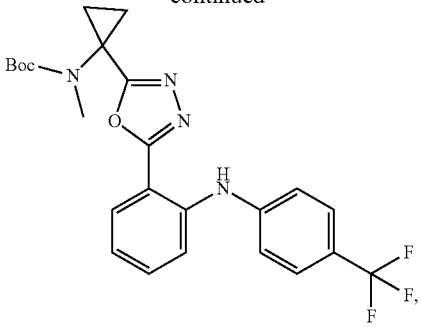
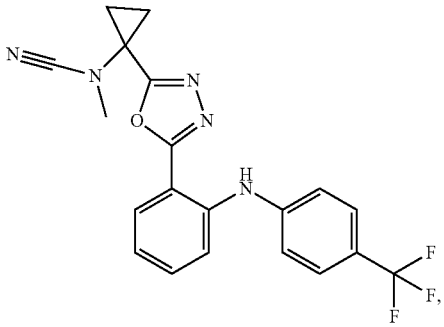
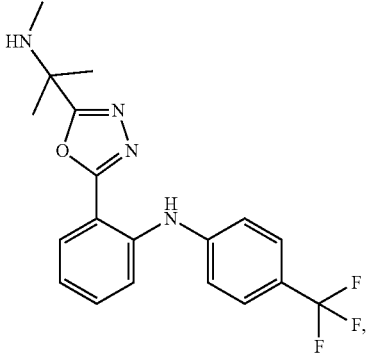
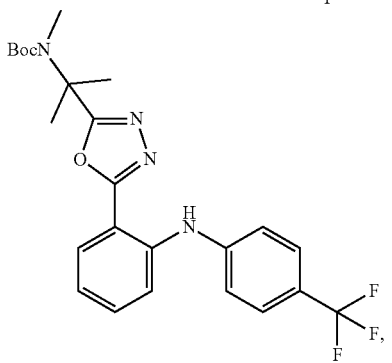
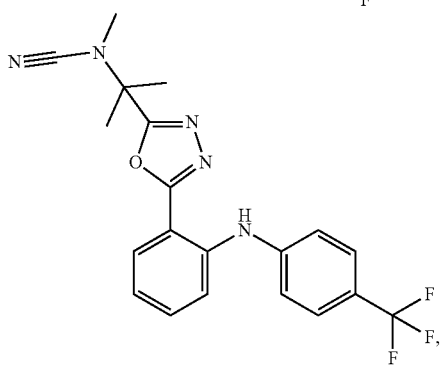

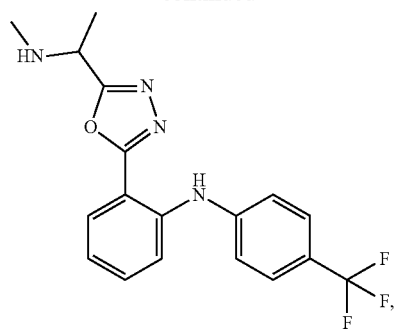
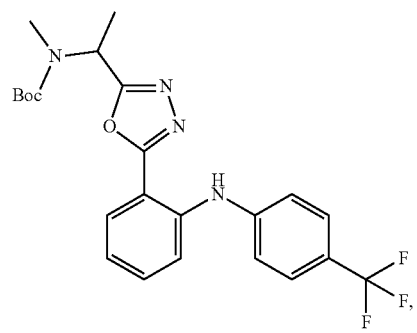
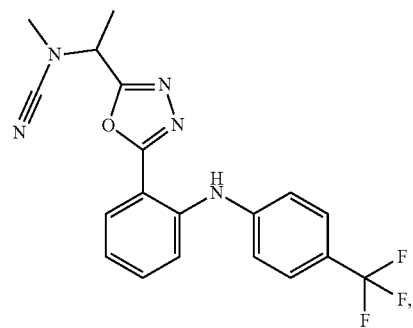
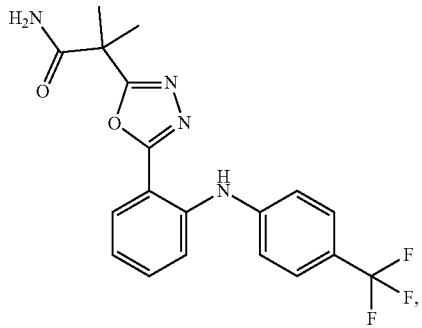
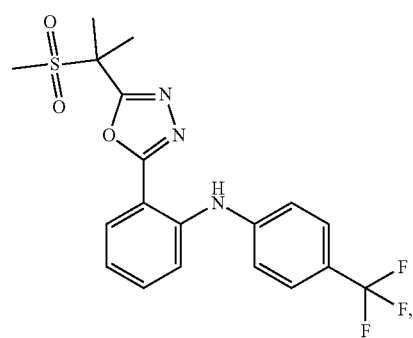
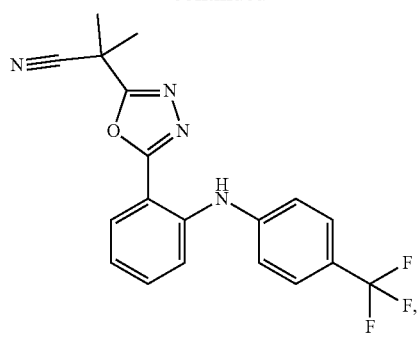
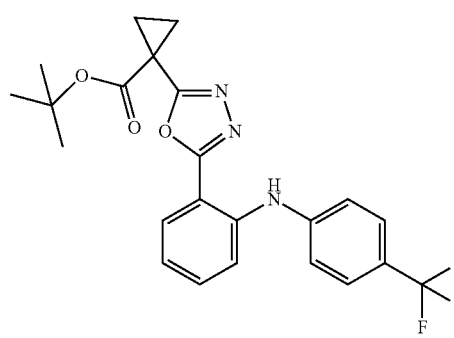
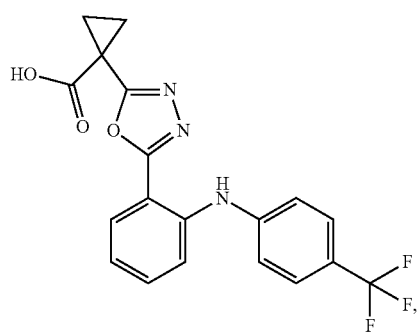
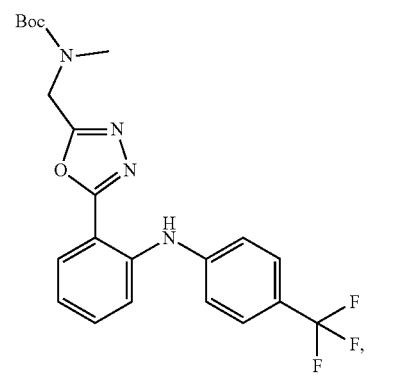
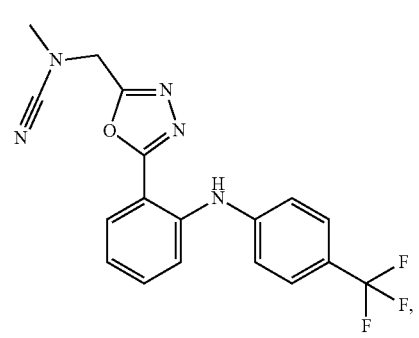

445
-continued
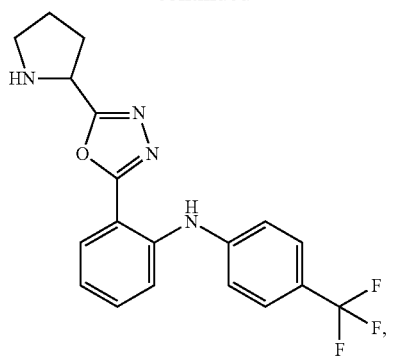
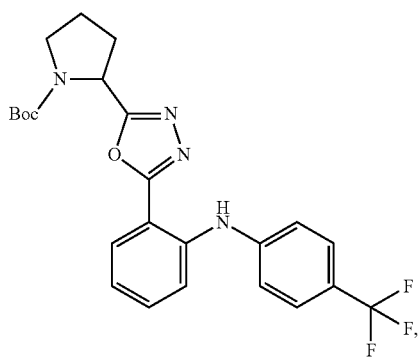
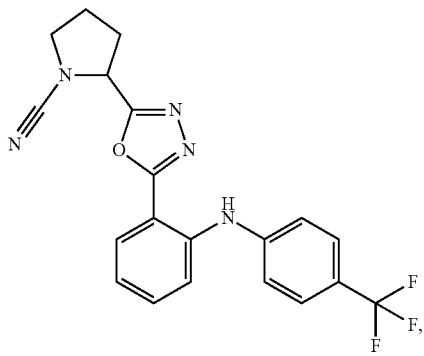
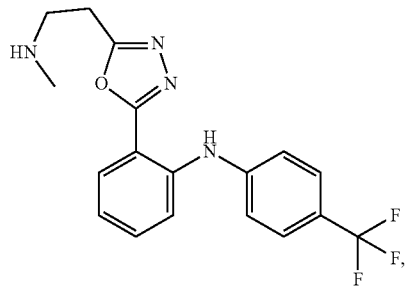
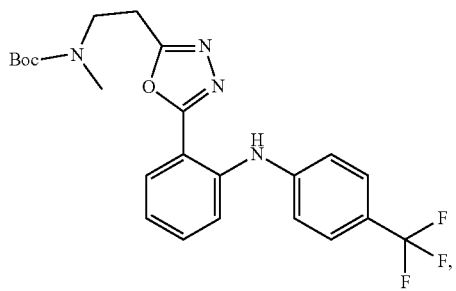
446
-continued
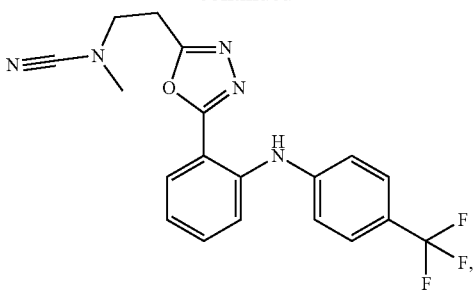
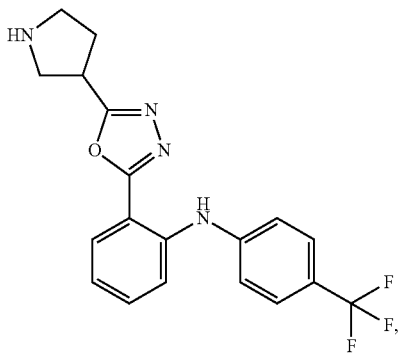
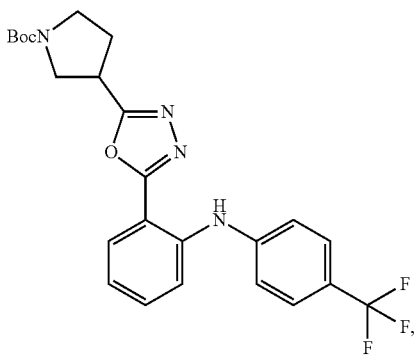
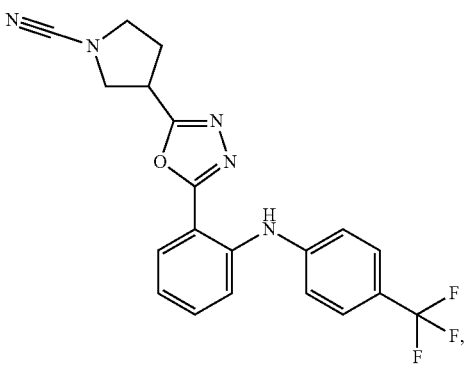
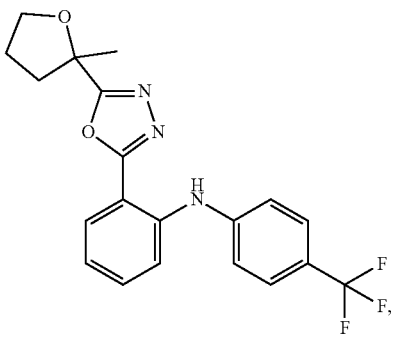

447
-continued
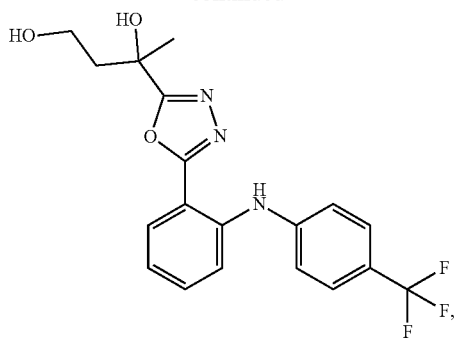
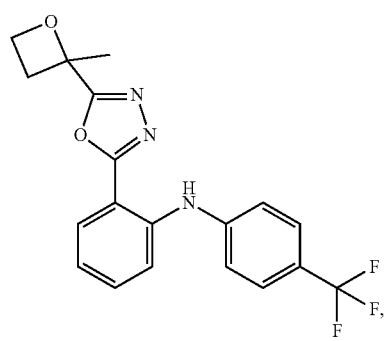
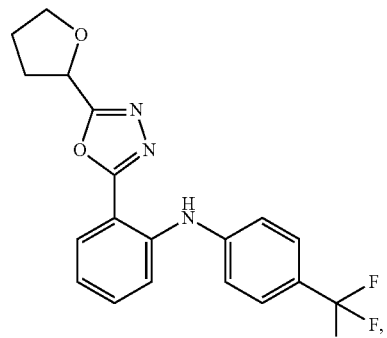
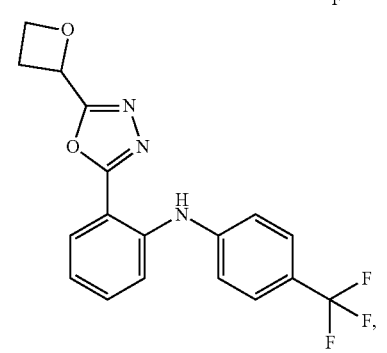
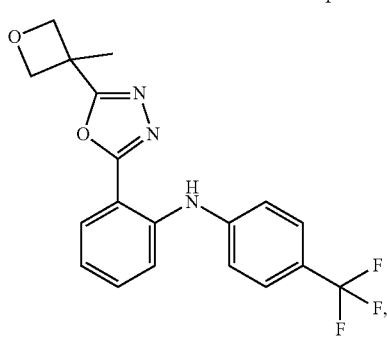
448
-continued
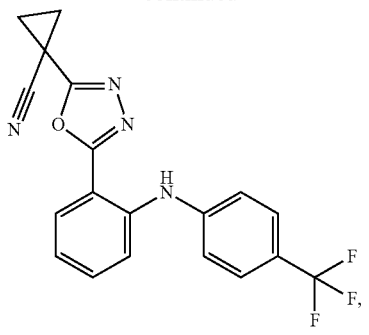
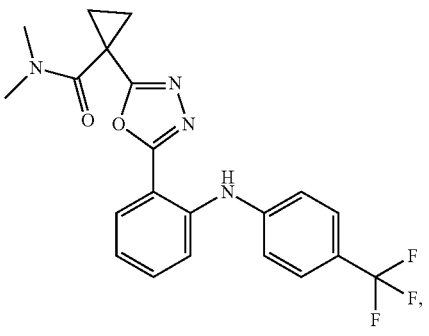
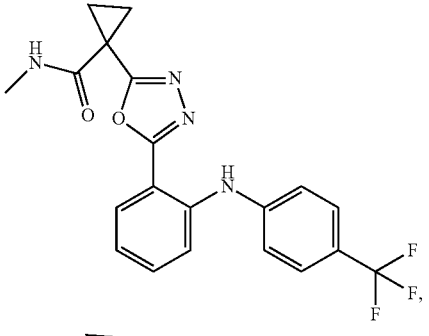
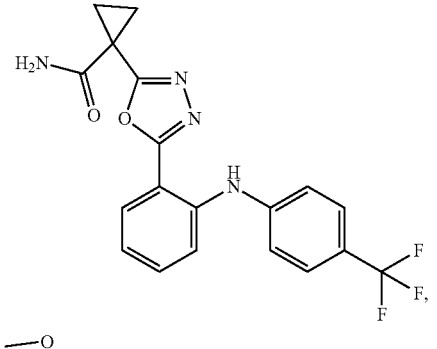
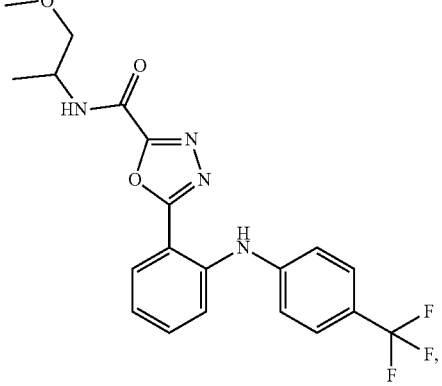

449
-continued
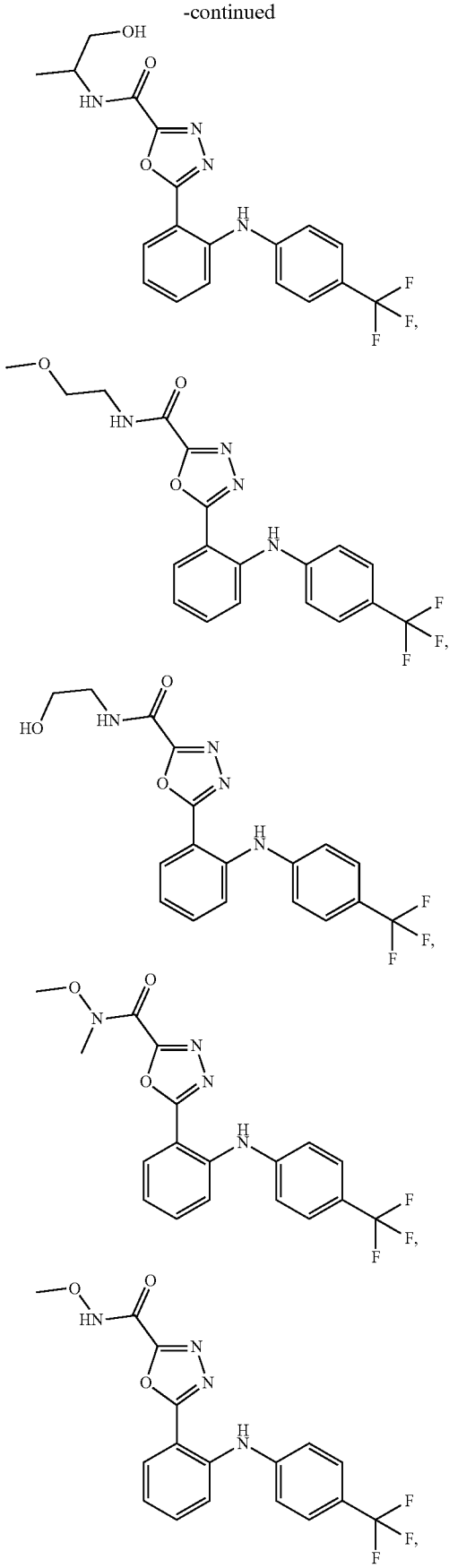
450
-continued
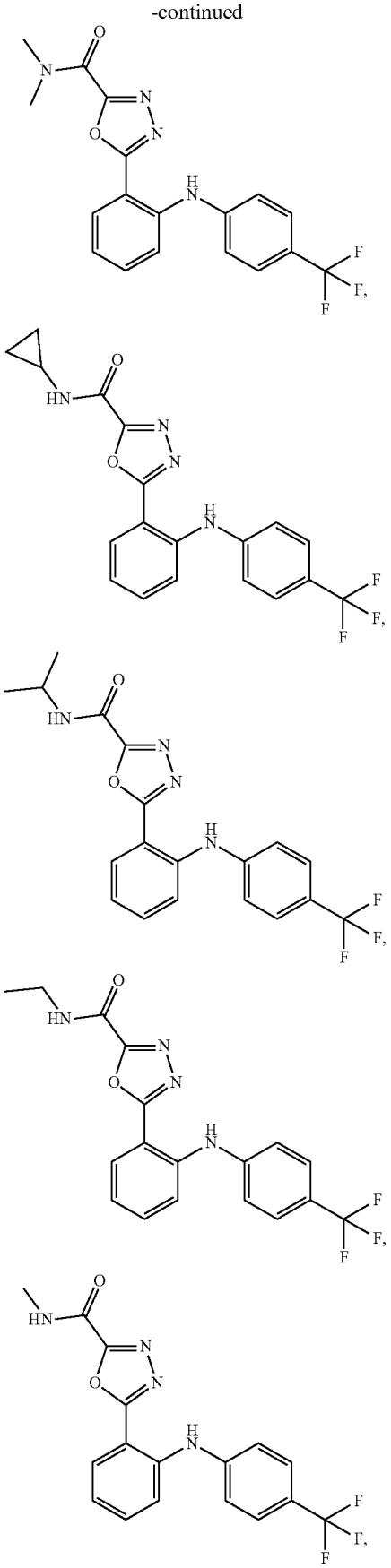

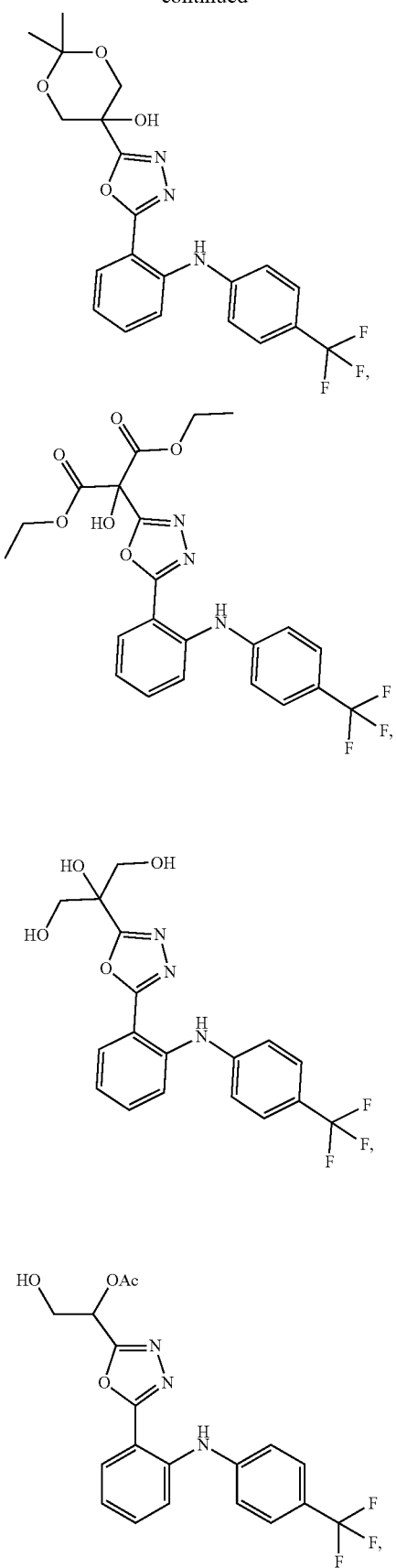

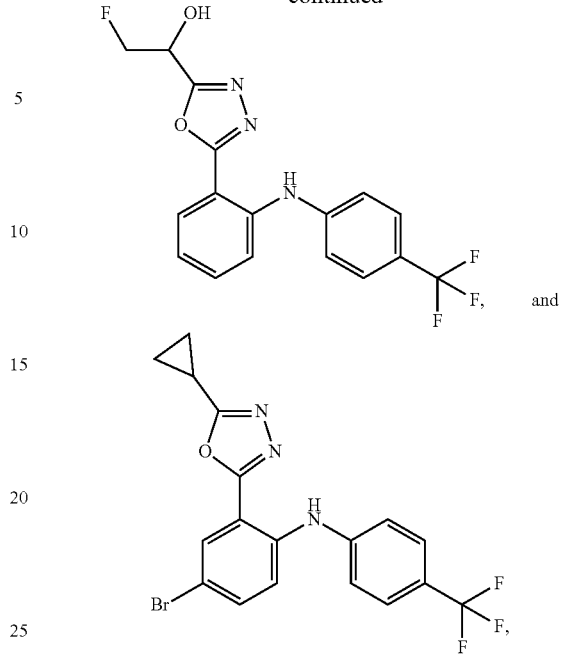

or a pharmaceutically acceptable salt thereof.

15. A pharmaceutical composition comprising a pharmaceutically acceptable excipient and a compound of claim 1, or a pharmaceutically acceptable salt thereof.

16. A method for treating a cancer in a subject in need thereof comprising administering a therapeutically effective amount of a compound of claim 1, or a pharmaceutically acceptable salt thereof; wherein the cancer is selected from mesothelioma, hepatocellular carcinoma, meningioma, malignant peripheral nerve sheath tumor, lung cancer, prostate cancer, pancreatic cancer, adenosquamous carcinoma, thyroid cancer, gastric cancer, esophageal cancer, ovarian cancer, melanoma, and breast cancer.

17. A method of inhibiting transcriptional coactivator with PDZ binding motif/Yes-associated protein transcriptional coactivator (TAZ/YAP) in a subject, comprising administering to the subject a compound of claim 1, or a pharmaceutically acceptable salt thereof.

18. The compound, or pharmaceutically acceptable salt thereof, of claim 13, wherein:
   X is substituted or unsubstituted $C_1$-$C_6$alkyl or substituted or unsubstituted $C_2$-$C_{10}$heterocycloalkyl.

19. The compound, or pharmaceutically acceptable salt thereof, of claim 13, wherein:
   X is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted 1,3-dioxolan-2-onyl, substituted or unsubstituted oxazolidinonyl, substituted or unsubstituted imidazolidin-2-onyl, or substituted or unsubstituted oxadiazolonyl.

* * * * *